US008372860B2

(12) United States Patent
Moon et al.

(10) Patent No.: US 8,372,860 B2
(45) Date of Patent: *Feb. 12, 2013

(54) CARBOLINE DERIVATIVES USEFUL IN THE INHIBITION OF ANGIOGENESIS

(75) Inventors: Young-Choon Moon, Belle Mead, NJ (US); Liangxian Cao, Parlin, NJ (US); Nadarajan Tamilarasu, Edison, NJ (US); Hongyan Qi, Plainsboro, NJ (US); Soongyu Choi, Skillman, NJ (US); William Joseph Lennox, South Plainfield, NJ (US); Donald Thomas Corson, Annandale, NJ (US); Seongwoo Hwang, Edison, NJ (US); Thomas Davis, South Orange, NJ (US)

(73) Assignee: PTC Therapeutics, Inc., South Plainfield, NJ (US)

( * ) Notice: Subject to any disclaimer, the term of this patent is extended or adjusted under 35 U.S.C. 154(b) by 285 days.

This patent is subject to a terminal disclaimer.

(21) Appl. No.: 12/715,651

(22) Filed: Mar. 2, 2010

(65) Prior Publication Data

US 2010/0179132 A1     Jul. 15, 2010

Related U.S. Application Data

(63) Continuation of application No. 11/107,783, filed on Apr. 18, 2005, now Pat. No. 7,767,689, which is a continuation-in-part of application No. 11/079,420, filed on Mar. 15, 2005, now Pat. No. 7,601,840.

(60) Provisional application No. 60/552,725, filed on Mar. 15, 2004.

(30) Foreign Application Priority Data

Mar. 15, 2005    (WO) ................ PCT/US2005/008481

(51) Int. Cl.
*A61K 31/437*    (2006.01)
*C07D 471/04*    (2006.01)
(52) U.S. Cl. ........................................ 514/292; 546/117
(58) Field of Classification Search ................. 514/292; 546/117
See application file for complete search history.

(56) References Cited

U.S. PATENT DOCUMENTS

| 3,492,304 A | 1/1970 | Shavel et al. |
| 4,014,890 A | 3/1977 | Welch, Jr. |
| 4,720,484 A | 1/1988 | Vincent et al. |
| 4,754,038 A | 6/1988 | Abou-Gharbia |
| 5,039,801 A | 8/1991 | Brossi et al. |

(Continued)

FOREIGN PATENT DOCUMENTS

| CA | 2099060 A1 | 12/1993 |
| EP | 0 008 249 | 8/1981 |

(Continued)

OTHER PUBLICATIONS

Advisory Action mailed Oct. 7, 2009 from the United States Patent and Trademark Office for U.S. Appl. No. 11/107,783, filed Apr. 18, 2005.

(Continued)

*Primary Examiner* — Rita Desai
(74) *Attorney, Agent, or Firm* — Jones Day

(57) ABSTRACT

In accordance with the present invention, compounds that inhibit the expression of VEGF post-transcriptionally have been identified, and methods for their use provided. In one aspect of the invention, compounds useful in the inhibition of VEGF production, in the treatment of solid tumor cancer, and in reducing plasma and/or tumor VEGF levels, are provided. In another aspect of the invention, methods are provided for the inhibition of VEGF production, the treatment of cancer, and the reduction of plasma and/or tumor VEGF levels, using the compounds of the invention.

21 Claims, 13 Drawing Sheets

U.S. PATENT DOCUMENTS

| | | | |
|---|---|---|---|
| 5,120,543 A | 6/1992 | Hagin et al. | |
| 5,166,204 A | 11/1992 | Nagai et al. | |
| 5,206,377 A | 4/1993 | McAfee | |
| 5,314,908 A | 5/1994 | McAfee | |
| 5,382,569 A | 1/1995 | Cody et al. | |
| 5,403,851 A | 4/1995 | D'Orlando et al. | |
| 5,451,600 A | 9/1995 | Banner et al. | |
| 5,580,878 A | 12/1996 | D'Orlando et al. | |
| 5,622,960 A | 4/1997 | Pommier et al. | |
| 5,633,388 A | 5/1997 | Diana et al. | |
| 5,760,051 A | 6/1998 | Audia et al. | |
| 5,866,587 A | 2/1999 | De Nanteuil et al. | |
| 6,043,252 A | 3/2000 | Bombrun | |
| 6,048,868 A | 4/2000 | Fourtillan et al. | |
| 6,175,015 B1 | 1/2001 | Yuan et al. | |
| 6,235,718 B1 | 5/2001 | Balasubramanium et al. | |
| 6,306,870 B1 | 10/2001 | Bombrun | |
| 6,331,543 B1 | 12/2001 | Garvey et al. | |
| 6,350,757 B1 | 2/2002 | Goldstein et al. | |
| 6,376,529 B1 | 4/2002 | Tang et al. | |
| 6,514,981 B1 | 2/2003 | Tang et al. | |
| 6,552,017 B1 | 4/2003 | Robichaud et al. | |
| 6,630,589 B1 | 10/2003 | Giordano et al. | |
| 6,635,638 B2 | 10/2003 | Sui et al. | |
| 6,653,132 B1 | 11/2003 | Keshet et al. | |
| 6,667,152 B2 | 12/2003 | Miles et al. | |
| 6,706,750 B1 | 3/2004 | Bentley et al. | |
| 6,890,933 B1 | 5/2005 | Feng et al. | |
| 7,115,621 B2 | 10/2006 | Sawyer et al. | |
| 7,601,840 B2 * | 10/2009 | Moon et al. | 546/117 |
| 7,767,689 B2 * | 8/2010 | Moon et al. | 514/292 |
| 7,872,133 B2 | 1/2011 | Ohmoto et al. | |
| 8,076,352 B2 * | 12/2011 | Cao et al. | 514/292 |
| 8,076,353 B2 * | 12/2011 | Cao et al. | 514/292 |
| 2002/0016298 A1 | 2/2002 | Hay et al. | |
| 2002/0091125 A1 | 7/2002 | Hay et al. | |
| 2002/0128206 A1 | 9/2002 | Hay et al. | |
| 2002/0173503 A1 | 11/2002 | Robichaud et al. | |
| 2003/0023087 A1 | 1/2003 | Garvey et al. | |
| 2003/0040527 A1 | 2/2003 | Yeh et al. | |
| 2003/0130171 A1 | 7/2003 | Schoenhard | |
| 2003/0158168 A1 | 8/2003 | Massimini et al. | |
| 2003/0220377 A1 | 11/2003 | Chesworth | |
| 2004/0023947 A1 | 2/2004 | Martin et al. | |
| 2004/0058877 A1 | 3/2004 | Hay et al. | |
| 2004/0116458 A1 | 6/2004 | Sawyer et al. | |
| 2004/0127482 A1 | 7/2004 | Robichaud et al. | |
| 2004/0157834 A1 | 8/2004 | Hay et al. | |
| 2004/0186094 A1 | 9/2004 | Robichaud et al. | |
| 2004/0209864 A1 | 10/2004 | Robichaud et al. | |
| 2004/0214223 A1 | 10/2004 | Cao | |
| 2004/0214848 A1 | 10/2004 | Schoenhard | |
| 2004/0229864 A1 | 11/2004 | Bourrain et al. | |
| 2005/0004156 A1 | 1/2005 | Feng et al. | |
| 2005/0054568 A1 | 3/2005 | Ling et al. | |
| 2005/0054634 A1 | 3/2005 | Busch et al. | |
| 2005/0143371 A1 | 6/2005 | Meyers et al. | |
| 2005/0267018 A1 | 12/2005 | Blatt et al. | |
| 2005/0272759 A1 | 12/2005 | Moon et al. | |
| 2008/0103213 A1 | 5/2008 | Kurzrock et al. | |
| 2008/0293766 A1 | 11/2008 | Diamond et al. | |
| 2009/0017021 A1 | 1/2009 | Davis et al. | |
| 2010/0125065 A1 | 5/2010 | Moon et al. | |
| 2010/0158858 A1 | 6/2010 | Cao et al. | |
| 2011/0160190 A1 | 6/2011 | Moon et al. | |
| 2012/0129841 A1 | 5/2012 | Cao et al. | |

FOREIGN PATENT DOCUMENTS

| | | |
|---|---|---|
| EP | 0 357 122 A2 | 3/1990 |
| EP | 0 406 734 A2 | 1/1991 |
| EP | 0 468 789 | 1/1992 |
| EP | 0 491 943 | 7/1992 |
| EP | 0 549 916 A2 | 2/1993 |
| EP | 0 549 916 A3 | 8/1993 |
| EP | 0 719 837 A2 | 12/1995 |
| EP | 0 300 541 | 3/1996 |
| EP | 1 348 434 A1 | 10/2003 |
| EP | 1 512 397 | 3/2005 |
| EP | 1 383 765 | 12/2006 |
| FR | 2 432 025 B1 | 2/1980 |
| FR | 2 662 940 A1 | 12/1991 |
| JP | 3-287586 | 12/1991 |
| JP | 4-275221 | 9/1992 |
| WO | WO 91/18604 | 12/1991 |
| WO | WO 94/10175 A1 | 5/1994 |
| WO | WO 94/11378 | 5/1994 |
| WO | WO 96/26207 | 8/1996 |
| WO | WO 96/32003 | 10/1997 |
| WO | WO 97/37658 | 10/1997 |
| WO | WO 97/43287 | 11/1997 |
| WO | WO 99/06390 | 2/1999 |
| WO | WO 00/39314 | 7/2000 |
| WO | WO 01/21584 | 3/2001 |
| WO | WO 01/21589 | 3/2001 |
| WO | WO 01/47887 | 7/2001 |
| WO | WO 01/87038 | 11/2001 |
| WO | WO 02/051805 | 7/2002 |
| WO | WO 02/088123 | 11/2002 |
| WO | WO 03/020279 A2 | 3/2003 |
| WO | WO 03/033496 A1 | 4/2003 |
| WO | WO 03/051841 | 6/2003 |
| WO | WO 03/087815 | 10/2003 |
| WO | WO 03/099821 A1 | 12/2003 |
| WO | WO 03/103656 | 12/2003 |
| WO | WO 2004/035047 | 4/2004 |
| WO | WO 2004/069831 | 8/2004 |
| WO | WO 2004/096766 | 11/2004 |
| WO | WO 2004/110999 | 12/2004 |
| WO | WO 2004/113300 A1 | 12/2004 |
| WO | WO 2004/113336 A1 | 12/2004 |
| WO | WO 2005/000246 | 1/2005 |
| WO | WO 2005/005386 | 1/2005 |
| WO | WO 2005/007672 A2 | 1/2005 |
| WO | WO 2005/009370 A2 | 2/2005 |
| WO | WO 2005/014543 | 2/2005 |
| WO | WO 2005/037791 | 4/2005 |
| WO | WO 2005/070930 A2 | 8/2005 |
| WO | WO 2005/089764 A1 | 9/2005 |
| WO | WO 2005/097162 | 10/2005 |
| WO | WO 2005/113003 | 12/2005 |
| WO | WO 2006/015035 A1 | 2/2006 |
| WO | WO 2006/058088 A2 | 6/2006 |
| WO | WO 2006/113703 A2 | 10/2006 |
| WO | WO 2007/002051 | 1/2007 |
| WO | WO 2008/127714 | 10/2008 |
| WO | WO 2008/127715 | 10/2008 |
| WO | WO 2010/138644 | 12/2010 |
| WO | WO 2010/138652 | 12/2010 |
| WO | WO 2010/138659 | 12/2010 |
| WO | WO 2010/138685 | 12/2010 |
| WO | WO 2010/138695 | 12/2010 |
| WO | WO 2010/138706 | 12/2010 |
| WO | WO 2010/138758 | 12/2010 |

OTHER PUBLICATIONS

Amendment filed Jan. 29, 2010 for U.S. Appl. No. 11/107,783, filed Apr. 18, 2005.

Amendment filed May 1, 2009 for U.S. Appl. No. 11/079,420, filed Mar. 15, 2005.

Amendment filed Oct. 21, 2009 for U.S. Appl. No. 11/107,783, filed Apr. 18, 2005.

Amendment filed Oct. 8, 2009 for U.S. Appl. No. 11/107,783, filed Apr. 18, 2005.

Calabresi et al., "Section IX Chemotherapy of Neoplastic Diseases—Introduction," Goodman & Gilman's The Pharmacological Basis of Therapeutics 10th ed., 2001, Hardman JG, Limbird LE, and Gilman AG, Eds, McGraw-Hili, New York 2001,1381-1388 (pp. 1381,1383-1385, and 1388 provided).

Dorwald F.A., 2005, Side Reactions in Organic Synthesis, Wiley: VCH, Weinheim p. IX of Preface.

Final Office Action mailed May 14, 2009 from the United States Patent and Trademark Office for U.S. Appl. No. 11/107,783, filed Apr. 18, 2005.

International Search Report for International Application No. PCT/US10/36287, filed May 27, 2010.

International Search Report for International Application No. PCT/US10/36300, filed May 27, 2010.
International Search Report for International Application No. PCT/US10/36345, filed May 27, 2010.
International Search Report for International Application No. PCT/US10/36364, filed May 27, 2010.
International Search Report for International Application No. PCT/US10/36387, filed May 27, 2010.
International Search Report for International Application No. PCT/US10/36467, filed May 27, 2010.
Kuldo et al., 2005, "Molecular Pathways of Endothelial Cell Activation for (Targeted) Pharmacological Intervention of Chronic Inflammatory Diseases," Current Vascular Pharmacology, 3:11-39.
Non-Final Office Action mailed Jan. 2, 2008 from the United States Patent and Trademark Office for U.S. Appl. No. 11/079,420, filed Mar. 15, 2005.
Non-Final Office Action mailed Jul. 6, 2010 from the United States Patent and Trademark Office for U.S. Appl. No. 11/735,069, filed Apr. 13, 2007.
Non-Final Office Action mailed Mar. 11, 2008 from the United States Patent and Trademark Office for U.S. Appl. No. 11/107,783, filed Apr. 18, 2005.
Non-Final Office Action mailed Nov. 23, 2010 from the United States Patent and Trademark Office for U.S. Appl. No. 11/785,871, filed Jun. 6, 2007.
Non-Final Office Action mailed Oct. 9, 2008 from the United States Patent and Trademark Office for U.S. Appl. No. 11/107,783, filed Apr. 18, 2005.
Non-Final Office Action mailed Sep. 29, 2008 from the United States Patent and Trademark Office for U.S. Appl. No. 11/079,420, filed Mar. 15, 2005.
Notice of Allowance mailed Apr. 8, 2009 from the United States Patent and Trademark Office for U.S. Appl. No. 11/079,420, filed Mar. 15, 2005.
Notice of Allowance mailed Oct. 30, 2009 from the United States Patent and Trademark Office for U.S. Appl. No. 11/107,783, filed Apr. 18, 2005.
Preliminary Amendment filed Aug. 18, 2005 for U.S. Appl. No. 11/107,783, filed Apr. 18, 2005.
Preliminary Amendment filed Aug. 3, 2007 for U.S. Appl. No. 11/735,069, filed Apr. 13, 2007.
Preliminary Amendment filed Dec. 30, 2009 for U.S. Appl. No. 12/506,485, filed Jul. 21, 2009.
Response filed Apr. 26, 2010 to Restriction Requirement mailed Mar. 26, 2010 from the United States Patent and Trademark Office for U.S. Appl. No. 11/735,069, filed Apr. 13, 2007.
Response filed Dec. 29, 2008 to Non-Final Office Action mailed Sep. 29, 2008 from the United States Patent and Trademark Office for U.S. Appl. No. 11/079,420, filed Mar. 15, 2005.
Response filed Feb. 19, 2009 to Non-Final Office Action mailed Oct. 9, 2008 from the United States Patent and Trademark Office for U.S. Appl. No. 11/107,783, filed Apr. 18, 2005.
Response filed Jul. 1, 2008 to Non-Final Office Action mailed Jan. 2, 2008 from the United States Patent and Trademark Office for U.S. Appl. No. 11/079,420, filed Mar. 15, 2005.
Response filed Jul. 11, 2008 to Non-Final Office Action mailed Mar. 11, 2008 from the United States Patent and Trademark Office for U.S. Appl. No. 11/107,783, filed Apr. 18, 2005.
Response filed Sep. 28, 2009 to Final Office Action mailed May 14, 2009 from the United States Patent and Trademark Office for U.S. Appl. No. 11/107,783, filed Apr. 18, 2005.
Response filed Sep. 7, 2010 to Restriction Requirement mailed Jun. 7, 2010 from the United States Patent and Trademark Office for U.S. Appl. No. 11/765,871, filed Jun. 20, 2007.
Restriction Requirement mailed Jun. 7, 2010 from the United States Patent and Trademark Office for U.S. Appl. No. 11/765,871, filed Jun. 20, 2007.
Restriction Requirement mailed Mar. 26, 2010 from the United States Patent and Trademark Office for U.S. Appl. No. 11/735,069, filed Apr. 13, 2007.
Roodink et al., 2010, "Targeted Therapies of cancer: Angiogenesis inhibition seems not enough," Cancer Letters, 299:1-10.
Ruoslahti et al., "Targeting of drugs and nanoparticles to tumors," Journal of Cell Biology, Mar. 2010, 188(6), 759-768.
Supplemental Response filed Sep. 25, 2008 to Non-Final Office Action mailed Jan. 2, 2008 from the United States Patent and Trademark Office for U.S. Appl. No. 11/079,420, filed Mar. 15, 2005.
Written Opinion of the International Search Authority for International Application No. PCT/US2006/01547, filed Apr. 17, 2006.
Written Opinion of the International Searching Authority for International Application No. PCT/US10/36287, filed May 27, 2010.
Written Opinion of the International Searching Authority for International Application No. PCT/US10/36300, filed May 27, 2010.
Written Opinion of the International Searching Authority for International Application No. PCT/US10/36345, filed May 27, 2010.
Written Opinion of the International Searching Authority for International Application No. PCT/US10/36364, filed May 27, 2010.
Written Opinion of the International Searching Authority for International Application No. PCT/US10/36387, filed May 27, 2010.
Written Opinion of the International Searching Authority for International Application No. PCT/US10/36467, filed May 27, 2010.
Written Opinion of the International Searching Authority for International Application No. PCT/US2005/008481, filed Mar. 15, 2005.
Written Opinion of the International Searching Authority for International Application No. PCT/US2008/004809, filed Apr. 12, 2008.
Written Opinion of the International Searching Authority for International Application No. PCT/US2008/004810, filed Apr. 12, 2008.
Final Office Action mailed Mar. 16, 2011 from the United States Patent and Trademark Office for U.S. Appl. No. 11/735,069, filed Apr. 13, 2007.
U.S. Appl. No. 10/592,761, filed Sep. 14, 2006, Moon.
U.S. Appl. No. 11/720,055, filed May 23, 2007, Lennon.
U.S. Appl. No. 11/720,057, filed May 23, 2007, Cao.
U.S. Appl. No. 11/720,061, filed May 23, 2007, Choi.
U.S. Appl. No. 11/735,069, filed Apr. 13, 2007, Cao.
U.S. Appl. No. 11/765,871, filed Jun. 20, 2007, Cao et al.
Abou-Gharbia et al., "Antipsychotic activity of substituted γ-carbolines," J. Med. Chem., 30:1818-1823 (1987).
Akiri et al., "Regulation of vascular endothelial growth factor (VEGF) expression is mediated by internal initiation of translation and alternative initiation of transcription," Oncogene, 17:227-236 (1998).
Asano et al., "Wide spectrum of antitumor activity of a neutralizing monoclonal antibody to human vascular endothelial growth factor," Jpn. J. Cancer Res., 90:93-100 (1999).
Avastin® Product Insert (2008).
Babbs Copyright 2006 Beilstein MDL on STN, AN 5523540, Abstract of .Massiot, G. "Synthesis of indole alkaloids and related molecules along non biogenetic routes," Bull. Soc. Chem. Belg., 99(9): 717-728 (1990).
Babbs Copyright 2006 Beilstein MDL on STN, AN 5669242, Abstract of Piper et al., "Pictet-spengier reaction of biogenic amines with carbohydrates. Synthesis of novel C-nucleosides," Can. J. Chem., 61:2721-2728 (1983).
Babbs Copyright 2006 Beilstein MDL on STN, AN 5702218, Abstract of Pogosyan et al., Synthesis and biological activity of 3-R-1,2,3,4-tetrahydro-4β-carboline derivatives, Pharm. Chem. J. (Engl. Transl.), 21(6):414-417 (1987).
Babbs Copyright 2006 Beilstein MDL on STN, AN 5776298, Abstract of Moehrie et al., "Fused dihydro-1,2,4-triazines," Arch. Pharm. (Weinheim Ger.), 320(3):198-202 (1987).
Babbs Copyright 2006 Beilstein MDL on STN, AN 6010011, Abstract of Waldmann et al., "Asymmetrische pictet-spengler-reaktionen mit N,N-phthaloyl-aminosaeuren als chiralen hilfsgruppen," Angew. Chem, 107(21):2608-2610 (1995).
Babbs Copyright 2006 Beilstein MDL on STN, AN 6236596, Abstract of Lu et al., "stereoselective synthesis of phosphorothioate and alkylphosphinate analogsusing a l-tryptophan derived chiral auxiliary," Tetrahedron, 56(26):4355-4366 (2000).
Bergsland et al., "A randomized phase II trail comparing rhuMab VEGF (Recombinant humanized monoclonal antibody to vascular endothelial cell growth factor) plus 5-fluorouracil/leucovorin (FU/LV) to FU/LV alone in patients with metastatic colorectal cancer," American Society of Clinical Oncology 36th Annual Meeting, May 2000, New Orleans, LA, USA, Abstract No. 939.

Birman et al., "A novel route to the geissoschizine skeleton: the influence of ligands on the diastereoselectivity of the Heck cyclization," Tetrahedeon Letters, 39(40):7219-7222 (1998).

Borgstrom et al. "Neutralizing anti-vascular endothelial growth factor antibody completely inhibits angiogenesis and growth of human prostate carcinoma micro tumors in vivo," Prostate, 35:1-10 (1998).

Bornes et al., :Control of the vascular endothelial growth factor internal ribosome entry side (IRESA) activity and translation initiation by alternatively splice coding sequences, J. Biol. Chem., 279(18):18717-18726 (2004).

Boyer, S.J., "Small molecule inhibitors of KDR (VEGFR-2) kinase: An overview of structure activity relationships," Current Topics in Medicinal Chemistry, 2:973-1000 (2002).

Brekken et al., "Selective inhibition of vascular endothelial growth factor (VEGF) receptor 2 (KDR/Flk-1) activity by a monoclonal anti-VEGF antibody blocks tumor growth in mice," Cancer Res., 60:5117-5124 (2000).

Cao et al. "Synthesis and in vitro cytotoxic evaluation of 1,3-bisubstituted and 1,3,9-trisubstituted β-carboline derivatives," European Journal of Medicinal Chemistry, 40:249-257 (2005).

Cao et al., "PTC299 inhibits VEGF expression through its 5' UTR," Poster submitted at EORTC in 2006.

Carmeliet et al., "Angiogenesis in cancer and other diseases," Nature, 407:249-257 (2000).

Carmeliet et al., "Abnormal blood vessel development and lethality in embryos lacking a single VEGF allele," Nature, 380:435-439 (1996).

Carmeliet, Peter, "Angiogenesis in health and disease," Nature Medicine, 9(6):653-660 (2003).

Chomczynski et al., "Single-step method of RNA isolation by acid guanidinium thiocyanate-phenol-chloroform extraction," Anal. Biochem., 162-156-159 (1987).

Claffey et al, "Identification of a human VPF/VEGF 3' untranslated region mediating hypoxia-induced mRNA stability," Molecular Biology of the Cell, 9:469-481 (1998).

Clark et al., "Opthalmic drug delivery," Nat. Rev. Drug Discovery, 2:448-459 (2003).

Cleaveland et al., "Identification of a novel inhibitor (NSC 665564) of dihydroorotate dehydrogenase with a potency equivalent to brequinar," Biochemical and Biophysical Research Communications, 223(3):654-659 (1996).

Connolly et al., "Human vascular permeability factor," J. Biol. Chem., 264(33):20017-20024 (1989).

Daugan et al., "The discovery of tadalafil: A novel and highly selectively PDE5 inhibitor: 2:2,3,6,7,12,12a-hexahydropyrazino[1',2':1,6][pyrido[3,4-b]indole-1,4-dione analogues," J. Med. Chem., 46(21):4533-4542 (2003).

Daugan et al., "The discovery of tadalafil: A novel and highly selectively PDE5 inhibitor: 1: 5,6,11,11a-Tetrahydro-1H-imidazo[1',5':1,6]pyrido[3,4-b]indole-1,3(2H)-dione analogues," J. Med. Chem., 46:4525-4532 (2003).

DeJong et al., "RNA and RNA-protein complexes as targets for therapeutic intervention," Current Topics in Medicinal Chemistry, 2(3):289-302 (2002).

David et al., "Preclinical development of PTC299: an orally bioavailable small molecule drug that selectively inhibits VEGF protein production, tumor growth, and microvessel density," Poster submitted at EORTC in 2006.

Davis T., et al., "Discovery and preclinical efficacy of PTC299, an antiagiogenic candidate in clinical development for the treatment of cancer," Presented at 10th International Symposium on Anti-Angiogenic Agents in 2008.

Davis et al., "Abstract 3870 Post-transcriptional control as a novel approach to anti-angiogenesis: development of a small molecule that reduces the production of tumor vascular endothelial growth factor A (VEGF)," Abstract presented at 96th annual meeting of American Association for Cancer Research, Apr. 16-20, 2005.

Davis et al., Post-transcriptional control as a novel approach to anti-angiogenesis: development of a small molecule that reduces the production of tumor vascular endothelial growth factor A (VEGF), Poster presented at 96th annual meeting of American Association for Cancer Research, Apr. 16-20, 2005.

DeVore et al., "A randomized phase 11 trial comparing rhumab VEGF (recombinant humanized monoclonal antibody to vascular endothelial cell growth factor) plus carboplatin/paclitaxel (CP) to CP alone in patients with stage IIIB/IV NSCLC," American Society of Clinical Oncology 36th Annual Meeting, May 2000, New Orleans, LA, USA, Abstract No. 1896.

Dirix et al., "Elevated levels of the angiogenic cytokines basic fibroblast growth factor and vascular endothelial growth factor in sera of cancer patients," Br. J. Cancer, 76(2):238-243 (1997).

Dreyfuss et al., "Messenger-RNA-binding proteins and the messages they carry," Nature Reviews Molecular Cell Biology, 3:195-205 (2002).

Ellis et al., "Down-regulation of vascular endothelial growth factor in human colon carcinoma cell lines by antisense transfection decreases endothelial cell proliferation," Surgery, 120(5):871-878 (1996).

Eyetech Study Group, "Preclinical and phase 1A clinical evaluation of an anti-VEGF pegylated aptamer (EYE001) for the treatment of exudative age-related macular degeneration," 22(2):143-52 (2002).

Ferrara et al., "Clinical applications of angiogenic growth factors and their inhibitors," Nat. Med., 5(12):1359-64 (1999).

Ferrara et al., "The biology of vascular endothelial growth factor," Endocr. Rev., 18(1):4-25 (1997).

Ferrara et al., "Vascular endothelial growth factor is essential for corpus luteum angiogenesis," Nat. Med., 4(3):336-340 (1998).

Ferrara, "Role of vascular endothelial growth factor in physiologic and pathologic angiogenesis: Therapeutic implications," Scmin. Oncol., 29(6 Suppl 16):10-14 (2002).

Filleur et al., "SiRnA-Mediated inhibition of vascular endothelial growth severely limits tumor resistance to antiangiogenic thrombospondin-1 and slows tumor vascularization and growth," Cancer Res., 63:3912-22 (2003).

Folkman, "Tumor angiogenesis: Therapeutic implications," N. Engl. J. Med., 285(21):1182-6 (1971).

Folkman, 1996, "Fighting Cancer by Attacking Its Blood Supply," Scientific American 275(3):150-154.

Fong et al., "Role of the Flt-1 receptor tyrosine kinase in regulating the assembly of vascular endothelium," Nature, 376:66-70 (1995).

Fong etal., "SU5416 is a potent and selective inhibitor of the vascular endothelial growth factor receptor (Flk-1/KDR) that inhibits tyrosine kinase catalysis, tumor vascularization, and growth of multiple tumor types," Cancer Res., 59:99-106 (1999).

Freter et al., "Reactions of 1-aryl-1,2,3,4,-tetrahydro-β-carbolines in acid solution," Justus Liebigs Annalen der Chemie, 684:159-87 (1965).

Funatsu et al., "Angiotensin II and vascular endothelial growth factor in the vitreous fluid of patients with diabetic macular edema and other retinal disorders," Am. J. Opthalmol., 133(4):537-43 (2002).

Fuhrmann-Benzaakein et al., "Elevated levels of angiogenic cytokines in the plasma of cancer patients," Int. J. Cancer, 85:40-45 (2000).

Gasparini et al., "Prognostic significance of vascular endothelial growth factor protein in node-negative breast carcinoma," J. natl. Cancer Inst., 89(2):139-147 (1997).

Ge et al., "Regulation of promoter activity of the APP gene by cytokines and growth factors," Ann NY Acad Sci., 973:463-467 (2002).

Geng et al., "Inhibition of vascular endothelial growth factor receptor signaling leads to reversal of tumor resistance to radiotherapy," Cancer Res., 61:2413-2419 (2001).

Giles et al., "Phase II study of SU5416—a small-molecule, vascular endothelial growth factor tyrosine-kinase receptor inhibitor-in patients with refractory myeloproliferative diseases," Cancer, 97z(8):1920-8 (2000).

Goldberg et al., "A 40-bp RNA element that mediates stabilization of vascular endothelial growth factor mRNA by HuR," J. Biol. Chem., 277(16):13635-40 (2002).

Gordon et al., "Phase I safety and pharmacokinetic study of recombinant human anti-vascular endothelial growth factor in patients with advanced cancer," J Clin Oncol., 19(3):843-850 (2001).

Hanahan et al., Patterns and emerging mechanisms of the angiogenic switch during tumorigenesis, Cell, 86:353-364 (1996).

Henry et al., "Aromatic isocyanates as reagents for the identification of some heterocyclic compounds," J. Am. Chem. Soc., pp. 2297-3000 (1949).

Hicklin et al., "Monoclonal antibody strategies to block angiogenesis," Drug Discovery Today, 6(10):517-528 (2001).

Hirawat et al, "51 Poster phase 1 single-dose safety, PK, and food-effect study of PTC299, a novel VEGF expression inhibitor for treatment of solid tumors," European J. of Cancer, Supplement, Pergamon (Oxford, Great Britain), 4(12):19-20 (Nov. 1, 2006).

Hirawat et al., "PTC299: A novel post-transcriptional VEGF expression inhibitor," Poster presented at 5th International Colorectal Cancer Congress, Oct. 2006.

Hirawat et al., "Phase 1 single-dose safety, PK, and food-effect study of PTC299, a novel VEGF expression inhibitor for treatment of solid tumors," Poster presented at EORTC in 2006.

Hirawat, "Phase 1 single-dose safety, PK and food-effect study of PTC299, a novel VEGF expression inhibitor for treatment of solid tumors," Abstract submitted for 19th Meeting of the European Association for Cancer Research on Jun. 12, 2006.

Hirawat et al., "Phase 1 multiple dose safety, pharmacokinetic, pharmacodynamic study of PTC299, a novel VEGF expression inhibitor for the treatment of solid tumors," Poster presented at American Association for Cancer Research, Apr. 14-18, 2007.

Hirawat et al., "Phase 1 studies assessing the safety, PK and VEGF-modulating effects of PTC299, a novel, VEGF expression inhibitor," Submitted to American Society of Clinical Oncology on Jan. 9, 2007, Tracking No. 07-AB-33792-ASCO.

Hirawat et al., "A phase 1 multiple-dose safety, pharmacokinetic, and pharmacodynamic study of PTC299, a novel VEGF expression inhibitor for treatment of solid tumor," Abstract submitted Nov. 28, 2006 for 2007 meeting of American Association for Cancer Research, Tracking No. 07-AB-4295-AACR.

Hirawat et al., "Phase 1 studies assessing the safety, PK and VEGF-modulating effects of PTC299, a novel, VEGF expression inhibitor," J. of Clinical Oncology, ASCO Annual Meeting Proceedings, Part 1, vol. 25, No. 18S, (Jun. 20, 2007) (URRL: http://www.asco.org/ASCO/Abstracts+%26+Virtual+Meeting/Abstracts?&vmview=abst_detail_view&confID=47abstract1D=33792>) (abstract 3562).

Holash et al., "Vessel cooption, regression, and growth in tumors mediated by angiopoientins and VEGF," Science, 284:1994-1998 (1999).

Honda et al., "Experimental subretinal neovascularization is inhibited by adenovirus-mediated soluble VEGF/flt-1 receptor gene trasfection: A role of VEGF and possible treatment for SRN in age-related macular degeneration," Gene Ther., 7:978-85 (2000).

Huez et al., "Two independent internal ribosome entry sites are involved in translation initiation of vascular endothelial growth factor mRNA," Mol. Cell. Biol., 18(11):6178-6190 (1998).

Ichihara et al., "Enhancer for carcinostatic effect," Derwent AN—1992-376264 (Sep. 30, 1992).

Ikeda et al., "Hypoxia-induced transcriptional activation and increased mRNA stability of vascular endothelial growth in C6 glioma cells," J/ Biol. Chem., 270(34):19761-19766 (1995).

International Search Report issued in PCT/US/2005/042484 on Oct. 4, 2006.

International Search Report issued on Aug. 4, 2008, in corresponding International Application No. PCT/US/2008/004809.

International Search Report issued on Jul. 25, 2008, in corresponding International Application No. PCT/US2008/004810.

International Search Report issued on Feb. 26, 2007 in corresponding International Application PCT/US2006/014547.

International Search Report mailed Jun. 16, 2006, issued in International Application No. PCT/US05/042483.

International Search Report mailed Jun. 16, 2006, issued in International Application No. PCT/US05/042482.

International Search Report mailed Oct. 24, 2005, issued in International Application No. PCT/US05/008452.

International Search Report PCT/US2005/008481, mailed Mar. 8, 2005.

Ishida et al., "Antitumor agents 201. Cytotoxicity of harmine and β-carboline analogs," Bioorganic & Medicinal Chemistry Letters, 9:3319-3324 (1999).

Jiang etal., "Potassium superoxide as an alternative reagent for winterfeldt oxidation of β-carbolines," Organic Letters, 5(1):43-46 (2003).

Kedersha et al., "Stress granules: sites of mRNA triage that regulate mRNA stability and translatability," Biochemical Society Transactions, 30(6):963-969 (2002).

Kerbal et al., "Clinical translation of angiogenesis inhibitors," Nat. Rev. Cancer, 2:727-39 (2002).

Kim et al., "Inhibition of vascular endothelial growth factor-induced angiogenesis suppresses tumor growth in vivo," Nature, 362:841-844 (1993).

Kozak, "Influences of mRNA secondary structure on initiation by eukaryotic ribosomes," PNAS, 83:2850-2854.

Kraggerud et al., Regulation of protein synthesis in human cells exposed to extreme hypoxia,: Anticancer Res., 15:683-686 (1995).

Krzystolik et al., "Prevention of experimental choroidal neovascularization with intravitreal anti-vascular endothelial growth factor antibody fragment," Arch. Ophthalmol., 120:338-46 (2002).

Lai et al., "Evidence that tristetraprolin binds to AU-rich elements and promotes the deadenylation and destabilization of tumor necrosis factor alpha mRNA," Molecular and Cellular Biology, 19(6):4311-4323 (1999).

Laird et al., "SU6668 is a potent antiangiogenic and antitumor agent that induces regression of established tumors," Cancer Res., 60:4152-60 2000).

LeClerc et al., "Folypoly-γ-glutamate synthetase gene mRNA splice variants and protein expression in primary human leukemia cells, cells lines, and normal human tissues," Clin. Cancer Res., 7:942-951 (2001).

Leung et al., "Vascular endothelial growth factor is a secreted angiogenic mitogen," Science, 246:1306-1309 (1989).

Levy et al., "Post-transcriptional regulation of vascular endothelial growth factor by hypoxia," J. Biol. Chem., 271(5):2746-2753 (1996).

Lin et al., "Inhibition of tumor growth by targeting tumor endothelium using a soluble vascular endothelial growth factor receptor," Cell Growth Differ., 9:49-58 (1998).

Lip et al., "Age-related macular degeneration is associated with increased vascular endothelial growth factor, hemorheology and endothelial dysfunction," Opthalmology, 108(4):705-10 (2001.

Liu et al., "Hypoxia regulates vascular endothelial growth factor gene expression in endothelial cells identification of a 5' enhancer," Circ. Res., 77(3):638-643 (1995).

Matter, "Tumor angiogenesis as a therapeutic target," Drug Discovery Today, 6(19):1005-1024 (2001).

Maxwell et al., "The tumour suppressor protein VHL targets hypoxia-inducible factors for oxygen-dependent proteolysis," Nature, 399:271-275 (1999).

Miao et al., "Preclinical and phase 1 study results of PTC299, an oral inhibitor of VEGF expression," Poster, presented Feb. 7-9, 2008.

Millauer et al., "Glioblastoma growth inhibited in vivo by a dominant-negative Flk-1 mutant," Nature, 367:576-579 (1994).

Miller et al., "The vascular endothelial growth factor mRNA contains an internal ribosome entry site," FEBS Letters, 434:417-420 (1998).

Mohan et al., Pictet-Spengler reaction of solid support: synthesis of 1,2,3,4-tetrahydro-β-carboline libraries, Tetrahedron Letters, 37(23):3963-3966 (1996).

Moulder et al., "Epidermal growth factor receptor (HER!) tyrosine kinase inhibitor ZD1839 (Iressa) inhibits HER2/neu (erbB2)-overexpressing breast cancer cells in vitro and in vi vo ," cancer Res., 61:8887-95 (2001).

Neipp et al., "Synthesis of bridged azabicyclic structures via ring-closing olefin metathesis," J. Org. Chem.., 68:8867-8878 (2003).

Nexavar® Product Insert (2005).

Nicolaus, "Symbiotic approach to drug design," Deceision Making in Drug Research (F. Gross, ed. Raven Press, New York, NY), pp. 173-186 (1983).

Ohno-Matsui et al., "Inducible expression of vascular endothelial growth factor in adult mice causes severe proliferative retinopathy and retinal detachment," Am. J. Pathol., 160(2):711-719 (2002).

Ortega et al., "Signal relays in the VEGF system," Front. Biosci., 4:d141:152 (1999).

Ozaki et al., "Blockage of vascular endothelial cell growth factor receptor signaling is sufficient to completely prevent retinal neovascularization," Am. J. Pathol., 156(2):697-707 (2000).

PTC299 Phase 1 Study in healthy volunteers (Study 002) power point presentatin presented at American Association for Cancer Research Meeting 2007.

Parry et al., "Bioactivity of anti-angiogenic ribozymes targeting Flt-1 and KDR mRNA," Nucleic Aids Res., 27(13):2569-2577 (1999).

Plouet et al., "Isolation and characterization of a newly identified endothelial cell mitogen produced by ArT-20 cells," EMBDO J., 8(12):3801-3806 (1989).

Rak et al., "Oncogenes and tumor angiogeneiss: differential modes of vascular endothelial growth factor up-regulation in ras-transformed epitheliam cells and fibrolasts," Cancer Res., 60:490-498 (2000).

Reich et al., "Small interfering RNA (siRNA) targeting VEGF effectively inhibits ocular neovascularization in a mouse model.,"Mol. Vis., 9:210-216 (2003).

Rofstad et al., "Vascular endothelial growth factor, interleukin 8, platelet-derived endothelial cell growth factor, and basis fibroblast growth factor promote angiogenesis and metastasis in human melanoma xenografts," Cancer Res., 60:4932-4938 (2000).

Ryan et al., "Toxicologic pathology of unique biotechnology agents and biotherapies," Toxicol. Pathol., 27(1):78-86 (1999).

Saishin et al., "VEGF-TRAP$_{R1R2}$ suppresses choroidal neovascularization and VEGF-induced breakdown of the blood-retinal barrier," J. Cell Physiol., 195:241-8 (2003).

Sato et al., "Properties of two VEGF receptors, Flk-1 and KDR, in signal transduction," Annals of New York Academy of Sciences, 902:201-207 (2000).

Schwesinger et al., "Intrachoroidal neovascularization in transgenic mice overexpresing vascular endothelial growth factor in the retinal pigment epithelium," Am. J. Pathol., 158(3):1161-1172 (2001).

Semenza, "Regulation of mammalian $O_2$ homeostasis by hypoxia-inducible factor 1," Annu. Re. Cell. Dev. Biol., 15:551-578 (1999).

Shalaby et al., "Failure of blood-island formation and vasculogenesis in Flk-l-deficient mice," Nature, 376:62-66 (1995).

Shanmugasundaram et al., "Synthesis and biological activity of pyrazino[3,2,1-j,k]carbazoles," Indian Journal of Chemistry, 37b;1133-1136 (1998).

Shanmugasundaram et al., "Synthesis of 3-phenylisoxazolo[3,4-a]carbzaoles," Zeitschrift Für Naturforschung, 54b:1202-1204 (1999).

Shen et al., "Preclinical evaluation of a phosphorothioate oligonucleotide in the retina of rhesus monkey," Lab. Invest., 82(2):167-82 (2002).

Song et al., "β-carbolines as specific inhibitors of cyclin-dependent kinases," Bioorg. Med. Chem. Lett., 12:1129-1132 (2002).

Stein et al., "Translation of vascular endothelial growth factor mRNA by internal ribosome entry: Implications for translation under hypoxia," Mol. Cell. Biol., 18(6):3112-3119 (1998).

Stoecklin et al., "A constitutive decay element promotes tumor necrosis factor alpha mRNA degradation via an AU-rich element-independent pathway," Molecular and Cellular Biology, 23(10):3506-3515 (2003).

Sugimoto et al., "Neutralization of circulating vascular endothelial growth factor (VEGF) by anti-VEGF antibodies and soluble VEGF receptor 1 (sFlt-1) induces proteinuria," J. Biol. Chem., 278(15):12605-8 (2003).

Sun et al., "4-(2-pyridl)piperazine-1-carboxamides: potent vanilloid receptor 1 antagonists," Bioorganic & Medicinal Chem. Lett., 13:3611-3616 (2003).

Sutent® Product Insert (2006).

Taylor et al., "Highly enantioselective catalytic acyl-Pieter-Spengler reactions," Journal of the American Chemical Society, 126(34):10558-10559 (2004).

Tischer et al., "The human gene for vascular endothelial growth factor," J. Biol. Chem., 266(18):11947-11954 (1991).

Trotta et al., "BCR/AB:L activates mdm2 mRNA translation via the la antigen," Cancer Cell, 3:145-160 (2003).

Trotta et al., PTC299 inhibits expression of VEGF through the 5'untranslated region of its mRNA, Poster presented at 10th International Symposium on Anti-Angiogenic Agents, Feb. 2008.

Ullner et al., "Abstract 3857 Post-transcriptional inhibition of vascular endothelial growth factor (VEGF) expression arrests tumor growth at a prevascular stage," Abstract presented at American Association for Cancer Research, Apr. 16-20, 2005.

Verheul et al., "Platelet and coagulation activation with vascular endothelial growth factor generation in soft tissue sarcomas," Clin. Cancer Res., 6:166-171 (2000).

Wedge et al., "ZD4190: an orally active inhibitor of vascular endothelial growth factor signaling with broad-spectrum antitumor efficacy," Cancer Res., 60:970-5 (2000).

Witmer et al., "Vascular endothelial growth factors and angiogenesis in eye disease," Prog. Retin Eye Res., 22:1-29 (2003).

Yamanaka et al., "A development of Pictet-Spengler reaction in aprotic media using chloroflormates; a short synthesis of borrerine," Heterocycles, 22(2):371-4 (1984).

Yoshida et al., "Oxidation of cycloalkan[b]indoles with iodine pentoxide ($I_2O_5$)," Chem. Pharm. Bull., 35(12):4700-4704 (1987).

Yuan et al., "Time-dependent vascular regression and permeability changes in established human tumor xenografts induced by an anti-vascular endothelial growth factor/vascular permeability factor antibody," Proc. Natl. Acad. Sci. USA, 93:14765-14770 (1996).

Zhang et al., "Concise enantioselective syntheses of quinolactacins A2 and B through alternative winterfeldt oxidation," Journal of Organic Chemistry, 68(11):4523-4526 (2003).

Zhu et al., "Inhibition of tumor growth and metastasis by targeting tumor-associated angiogenesis with antagonists to the receptors of vascular endothelial growth factor," Invest. New Drugs, 17:195-212 (1999).

Beilstein Copyright 2006 Beilstein MDL on STN, Beilstein Records (BRN): 9976380.

Beilstein Copyright 2006 Beilstein MDL on STN, Beilstein Records (BRN): 9975229.

Beilstein Copyright 2006 Beilstein MDL on STN, Beilstein Records (BRN): 9974267.

Beilstein Copyright 2006 Beilstein MDL on STN, Beilstein Records (BRN): 9973640.

Beilstein Copyright 2006 Beilstein MDL on STN, Beilstein Records (BRN): 9817157.

Beilstein Copyright 2006 Beilstein MDL on STN, Beilstein Records (BRN): 9802212.

Beilstein Copyright 2006 Beilstein MDL on STN, Beilstein Records (BRN): 9793124.

Beilstein Copyright 2006 Beilstein MDL on STN, Beilstein Records (BRN): 9792788.

Beilstein Copyright 2006 Beilstein MDL on STN, Beilstein Records (BRN): 9790084.

Beilstein Copyright 2006 Beilstein MDL on STN, Beilstein Records (BRN): 9784177.

Beilstein Copyright 2006 Bcilstcin MDL on STN, Bcilstcin Records (BRN): 9781935.

Beilstein Copyright 2006 Bcilstcin MDL on STN, Bcilstcin Records (BRN): 9778052.

Beilstein Copyright 2006 Beilstein MDL on STN, Beilstein Records (BRN): 9715971.

Beilstein Copyright 2006 Beilstein MDL on STN, Beilstein Records (BRN): 9713454.

Beilstein Copyright 2006 Beilstein MDL on STN, Beilstein Records (BRN): 9666272.

Beilstein Copyright 2006 Beilstein MDL on STN, Beilstein Records (BRN): 9664783.

Beilstein Copyright 2006 Beilstein MDL on STN, Beilstein Records (BRN): 9664782.

Beilstein Copyright 2006 Beilstein MDL on STN, Beilstein Records (BRN): 9662877.

Beilstein Copyright 2006 Beilstein MDL on STN, Beilstein Records (BRN): 9662875.

Beilstein Copyright 2006 Beilstein MDL on SRN, Beilstein Records (BRN): 9656936.

Beilstein Copyright 2006 Beilstein MDL on STN, Beilstein Records (BRN): 9530614.

Beilstein Copyright 2006 Beilstein MDL on STN, Beilstein Records (BRN): 9529248.

Beilstein Copyright 2006 Beilstein MDL on STN, Beilstein Records (BRN): 9526693.

Beilstein Copyright 2006 Beilstein MDL on STN, Beilstein Records (BRN): 9525620.

Beilstein Copyright 2006 Beilstein MDL on STN, Beilstein Records (BRN): 9525619.
Beilstein Copyright 2006 Beilstein MDL on STN, Beilstein Records (BRN): 9525032.
Beilstein Copyright 2006 Beilstein MDL on STN, Beilstein Records (BRN): 9523521.
Beilstein Copyright 2006 Beilstein MDL on STN, Beilstein Records (BRN): 9520875.
Beilstein Copyright 2006 Beilstein MDL on STN, Beilstein Records (BRN): 9520142.
Beilstein Copyright 2006 Beilstein MDL on STN, Beilstein Records (BRN): 9517212.
Beilstein Copyright 2006 Beilstein MDL on STN, Beilstein Records (BRN): 9504026.
Beilstein Copyright 2006 Beilstein MDL on STN, Beilstein Records (BRN): 9446639.
Beilstein Copyright 2006 Beilstein MDL on STN, Beilstein Records (BRN): 9374742.
Beilstein Copyright 2006 Beilstein MDL on STN, Beilstein Records (BRN): 9371916.
Beilstein Copyright 2006 Beilstein MDL on STN, Beilstein Records (BRN): 9370648.
Beilstein Copyright 2006 Beilstein MDL on STN, Beilstein Records (BRN): 9370647.
Beilstein Copyright 2006 Beilstein MDL on STN, Beilstein Records (BRN): 9370056.
Beilstein Copyright 2006 Beilstein MDL on STN, Beilstein Records (BRN): 9370055.
Beilstein Copyright 2006 Beilstein MDL on STN, Beilstein Records (BRN): 9367542.
Beilstein Copyright 2006 Beilstein MDL on STN, Beilstein Records (BRN): 9364536.
Beilstein Copyright 2006 Beilstein MDL on STN, Beilstein Records (BRN): 9364535.
Beilstein Copyright 2006 Beilstein MDL on STN, Beilstein Records (BRN): 9363589.
Beilstein Copyright 2006 Beilstein MDL on STN, Beilstein Records (BRN): 9362270.
Beilstein Copyright 2006 Beilstein MDL on STN, Beilstein Records (BRN): 9361560.
Beilstein Copyright 2006 Beilstein MDL on STN, Beilstein Records (BRN): 9359112.
Beilstein Copyright 2006 Beilstein MDL on STN, Beilstein Records (BRN): 9345640.
Beilstein Copyright 2006 Beilstein MDL on STN, Beilstein Records (BRN): 9344461.
Beilstein Copyright 2006 Beilstein MDL on STN, Beilstein Records (BRN): 9342433.
Beilstein Copyright 2006 Beilstein MDL on STN, Beilstein Records (BRN): 9230699.
Beilstein Copyright 2006 Beilstein MDL on STN, Beilstein Records (BRN): 9162855.
Beilstein Copyright 2006 Beilstein MDL on STN, Beilstein Records (BRN): 9147336.
Beilstein Copyright 2006 Beilstein MDL on STN, Beilstein Records (BRN): 9145027.
Beilstein Copyright 2006 Beilstein MDL on STN, Beilstein Records (BRN): 9102751.
Beilstein Copyright 2006 Beilstein MDL on STN, Beilstein Records (BRN): 9101976.
Beilstein Copyright 2006 Beilstein MDL on STN, Beilstein Records (BRN): 9100379.
Beilstein Copyright 2006 Beilstein MDL on STN, Beilstein Records (BRN): 9100313.
Beilstein Copyright 2006 Beilstein MDL on STN, Beilstein Records (BRN): 9099224.
Beilstein Copyright 2006 Beilstein MDL on STN, Beilstein Records (BRN): 9097021.
Beilstein Copyright 2006 Beilstein MDL on STN, Beilstein Records (BRN): 9096422.
Beilstein Copyright 2006 Beilstein MDL on STN, Beilstein Records (BRN): 9093081.
Beilstein Copyright 2006 Beilstein MDL on STN, Beilstein Records (BRN): 8871444.
Beilstein Copyright 2006 Beilstein MDL on STN, Beilstein Records (BRN): 8870325.
Beilstein Copyright 2006 Beilstein MDL on STN, Beilstein Records (BRN): 8866741.
Beilstein Copyright 2006 Beilstein MDL on STN, Beilstein Records (BRN): 8817881.
Beilstein Copyright 2006 Beilstein MDL on STN, Beilstein Records (BRN): 8816950.
Beilstein Copyright 2006 Beilstein MDL on STN, Beilstein Records (BRN): 8816625.
Beilstein Copyright 2006 Beilstein MDL on STN, Beilstein Records (BRN): 8816426.
Beilstein Copyright 2006 Beilstein MDL on STN, Beilstein Records (BRN): 8816097.
Beilstein Copyright 2006 Beilstein MDL on STN, Beilstein Records (BRN): 8816032.
Beilstein Copyright 2006 Beilstein MDL on STN, Beilstein Records (BRN): 8816007.
Beilstein Copyright 2006 Beilstein MDL on STN, Beilstein Records (BRN): 8815946.
Beilstein Copyright 2006 Beilstein MDL on STN, Beilstein Records (BRN): 8815858.
Beilstein Copyright 2006 Beilstein MDL on STN, Beilstein Records (BRN): 8815758.
Beilstein Copyright 2006 Beilstein MDL on STN, Beilstein Records (BRN): 8815143.
Beilstein Copyright 2006 Beilstein MDL on STN, Beilstein Records (BRN): 8813808.
Beilstein Copyright 2006 Beilstein MDL on STN, Beilstein Records (BRN): 8813211.
Beilstein Copyright 2006 Beilstein MDL on STN, Beilstein Records (BRN): 8813188.
Beilstein Copyright 2006 Beilstein MDL on STN, Beilstein Records (BRN): 8813024.
Beilstein Copyright 2006 Beilstein MDL on STN, Beilstein Records (BRN): 8813017.
Beilstein Copyright 2006 Beilstein MDL on STN, Beilstein Records (BRN): 8812495.
Beilstein Copyright 2006 Beilstein MDL on STN, Beilstein Records (BRN): 8812493.
Beilstein Copyright 2006 Beilstein MDL on STN, Beilstein Records (BRN): 8811818.
Beilstein Copyright 2006 Beilstein MDL on STN, Beilstein Records (BRN): 8811580.
Beilstein Copyright 2006 Beilstein MDL on STN, Beilstein Records (BRN): 8811014.
Beilstein Copyright 2006 Beilstein MDL on STN, Beilstein Records (BRN): 8808882.
Beilstein Copyright 2006 Beilstein MDL on STN, Beilstein Records (BRN):8808569.
Beilstein Copyright 2006 Beilstein MDL on STN, Beilstein Records (BRN): 8807751.
Beilstein Copyright 2006 Beilstein MDL on STN, Beilstein Records (BRN): 8806692.
Beilstein Copyright 2006 Beilstein MDL on STN, Beilstein Records (BRN): 8800981.
Beilstein Copyright 2006 Beilstein MDL on STN, Beilstein Records (BRN): 8665535.
Beilstein Copyright 2006 Beilstein MDL on STN, Beilstein Records (BRN): 8665534.
Beilstein Copyright 2006 Beilstein MDL on STN, Beilstein Records (BRN): 8644848.
Beilstein Copyright 2006 Beilstein MDL on STN, Beilstein Records (BRN): 8626861.
Beilstein Copyright 2006 Beilstein MDL on STN, Beilstein Records (BRN): 8462875.
Beilstein Copyright 2006 Beilstein MDL on STN, Beilstein Records (BRN): 8455070.
Beilstein Copyright 2006 Beilstein MDL on STN, Beilstein Records (BRN): 8454267.

Beilstein Copyright 2006 Beilstein MDL on STN, Beilstein Records (BRN): 8454265.
Beilstein Copyright 2006 Beilstein MDL on STN, Beilstein Records (BRN): 8454264.
Beilstein Copyright 2006 Beilstein MDL on STN, Beilstein Records (BRN): 8453888.
Beilstein Copyright 2006 Beilstein MDL on STN, Beilstein Records (BRN): 8453887.
Beilstein Copyright 2006 Beilstein MDL on STN, Beilstein Records (BRN): 8453886.
Beilstein Copyright 2006 Beilstein MDL on STN, Beilstein Records (BRN): 8453110.
Beilstein Copyright 2006 Beilstein MDL on STN, Beilstein Records (BRN): 8450993.
Beilstein Copyright 2006 Beilstein MDL on STN, Beilstein Records (BRN): 8448477.
Beilstein Copyright 2006 Beilstein MDL on STN, Beilstein Records (BRN): 8448341.
Beilstein Copyright 2006 Beilstein MDL on STN, Beilstein Records (BRN): 8445916.
Beilstein Copyright 2006 Beilstein MDL on STN, Beilstein Records (BRN): 8442395.
Beilstein Copyright 2006 Beilstein MDL on STN Beilstein Records (BRN): 8439487.
Beilstein Copyright 2006 Beilstein MDL on STN, Beilstein Records (BRN): 8437234.
Beilstein Copyright 2006 Beilstein MDL on STN, Beilstein Records (BRN): 8434528.
Beilstein Copyright 2006 Beilstein MDL on STN, Beilstein Records (BRN): 8432032.
Beilstein Copyright 2006 Beilstein MDL on STN, Beilstein Records (BRN): 8372543.
Beilstein Copyright 2006 Beilstein MDL on STN, Beilstein Records (BRN): 8372542.
Beilstein Copyright 2006 Beilstein MDL on STN, Beilstein Records (BRN): 8360332.
Beilstein Copyright 2006 Beilstein MDL on STN, Beilstein Records (BRN): 8355677.
Beilstein Copyright 2006 Beilstein MDL on STN, Beilstein Records (BRN): 8228273.
Beilstein Copyright 2006 Beilstein MDL on STN, Beilstein Records (BRN): 8222993.
Beilstein Copyright 2006 Beilstein MDL on STN, Beilstein Records (BRN): 8081712.
Beilstein Copyright 2006 Beilstein MDL on STN, Beilstein Records (BRN): 8079036.
Beilstein Copyright 2006 Beilstein MDL on STN, Beilstein Records (BRN): 8075760.
Beilstein Copyright 2006 Beilstein MDL on STN, Beilstein Records (BRN): 8021716.
Beilstein Copyright 2006 Beilstein MDL on STN, Beilstein Records (BRN): 8019500.
Beilstein Copyright 2006 Beilstein MDL on STN, Beilstein Records (BRN): 8016588.
Beilstein Copyright 2006 Beilstein MDL on STN, Beilstein Records (BRN): 8011654.
Beilstein Copyright 2006 Beilstein MDL on STN, Beilstein Records (BRN): 7866702.
Beilstein Copyright 2006 Beilstein MDL on STN, Beilstein Records (BRN): 7866701.
Beilstein Copyright 2006 Beilstein MDL on STN, Beilstein Records (BRN): 7755570.
Beilstein Copyright 2006 Beilstein MDL on STN, Beilstein Records (BRN): 7742795.
Beilstein Copyright 2006 Beilstein MDL on STN, Beilstein Records (BRN): 7742792.
Beilstein Copyright 2006 Beilstein MDL on STN, Beilstein Records (BRN): 7742791.
Beilstein Copyright 2006 Beilstein MDL on STN, Beilstein Records (BRN): 7679040.
Beilstein Copyright 2006 Beilstein MDL on STN, Beilstein Records (BRN): 7676206.
Beilstein Copyright 2006 Beilstein MDL on STN, Beilstein Records (BRN): 7675004.
Beilstein Copyright 2006 Beilstein MDL on STN, Beilstein Records (BRN): 7674764.
Beilstein Copyright 2006 Beilstein MDL on STN, Beilstein Records (BRN): 7671562.
Beilstein Copyright 2006 Beilstein MDL on STN, Beilstein Records (BRN): 7662538.
Beilstein Copyright 2006 Beilstein MDL on STN, Beilstein Records (BRN): 7659004.
Beilstein Copyright 2006 Beilstein MDL on STN, Beilstein Records (BRN): 7652157.
Beilstein Copyright 2006 Beilstein MDL on STN, Beilstein Records (BRN): 7470167.
Beilstein Copyright 2006 Beilstein MDL on STN, Beilstein Records (BRN): 7470143.
Beilstein Copyright 2006 Beilstein MDL on STN, Beilstein Records (BRN): 7470039.
Beilstein Copyright 2006 Beilstein MDL on STN, Beilstein Records (BRN): 7469940.
Beilstein Copyright 2006 Beilstein MDL on STN, Beilstein Records (BRN): 7402634.
Beilstein Copyright 2006 Beilstein MDL on STN, Beilstein Records (BRN): 7398947.
Beilstein Copyright 2006 Beilstein MDL on STN, Beilstein Records (BRN): 7148211.
Beilstein Copyright 2006 Beilstein MDL on STN, Beilstein Records (BRN): 7145754.
Beilstein Copyright 2006 Beilstein MDL on STN, Beilstein Records (BRN): 7071896.
Beilstein Copyright 2006 Beilstein MDL on STN, Beilstein Records (BRN): 7071895.
Beilstein Copyright 2006 Beilstein MDL on STN, Beilstein Records (BRN): 7071528.
Beilstein Copyright 2006 Beilstein MDL on STN, Beilstein Records (BRN): 7066532.
Beilstein Copyright 2006 Beilstein MDL on STN, Beilstein Records (BRN): 7066215.
Beilstein Copyright 2006 Beilstein MDL on STN, Beilstein Records (BRN): 7065599.
Beilstein Copyright 2006 Beilstein MDL on STN, Beilstein Records (BRN): 7062671.
Beilstein Copyright 2006 Beilstein MDL on STN, Beilstein Records (BRN): 7061800.
Beilstein Copyright 2006 Beilstein MDL on STN, Beilstein Records (BRN): 6885612.
Beilstein Copyright 2006 Beilstein MDL on STN, Beilstein Records (BRN): 6490207.
Beilstein Copyright 2006 Beilstein MDL on STN, Beilstein Records (BRN): 5915066.
Beilstein Copyright 2006 Beilstein MDL on STN, Beilstein Records (BRN): 5914990.
Beilstein Copyright 2006 Beilstein MDL on STN, Beilstein Records (BRN): 5897211.
Beilstein Copyright 2006 Beilstein MDL on STN, Beilstein Records (BRN): 5891878.
Beilstein Copyright 2006 Beilstein MDL on STN, Beilstein Records (BRN): 5679522.
Beilstein Copyright 2006 Beilstein MDL on STN, Beilstein Records (BRN): 5176764.
Beilstein Copyright 2006 Beilstein MDL on STN, Beilstein Records (BRN): 5140134.
Beilstein Copyright 2006 Beilstein MDL on STN, Beilstein Records (BRN): 5134348.
Beilstein Copyright 2006 Beilstein MDL on STN, Beilstein Records (BRN): 4895148.
Beilstein Copyright 2006 Beilstein MDL on STN, Beilstein Records (BRN): 4762626.
Beilstein Copyright 2006 Beilstein MDL on STN, Beilstein Records (BRN): 4635034.
Beilstein Copyright 2006 Beilstein MDL on STN, Beilstein Records (BRN): 4620668.

Beilstein Copyright 2006 Beilstein MDL on STN, Beilstein Records (BRN): 4617494.
Beilstein Copyright 2006 Beilstein MDL on STN, Beilstein Records (BRN): 4604797.
Beilstein Copyright 2006 Beilstein MDL on STN, Beilstein Records (BRN): 4213069.
Beilstein Copyright 2006 Beilstein MDL on STN, Beilstein Records (BRN): 1206456.
Beilstein Copyright 2006 Beilstein MDL on STN, Beilstein Records (BRN): 1206372.
Beilstein Copyright 2006 Beilstein MDL on STN, Beilstein Records (BRN): 942566.
Beilstein Copyright 2006 Beilstein MDL on STN, Beilstein Records (BRN): 850369.
Beilstein Copyright 2006 Beilstein MDL on STN, Beilstein Records (BRN): 845560.
Beilstein Copyright 2006 Beilstein MDL on STN, Beilstein Records (BRN): 843324.
Beilstein Copyright 2006 Beilstein MDL on STN, Beilstein Records (BRN): 592929.
Beilstein Copyright 2006 Beilstein MDL on STN, Beilstein Records (BRN): 382858.
Beilstein Copyright 2006 Beilstein MDL on STN, Beilstein Records (BRN): 382697.
Beilstein Copyright 2006 Beilstein MDL on STN, Beilstein Records (BRN): 382603.
Beilstein Copyright 2006 Beilstein MDL on STN, Beilstein Records (BRN): 382449.
Beilstein Copyright 2006 Beilstein MDL on STN, Beilstein Records (BRN): 360771.
Beilstein Copyright 2006 Beilstein MDL on STN, Beilstein Records (BRN): 356831.
Beilstein Copyright 2006 Beilstein MDL on STN, Beilstein Records (BRN): 326903.
Beilstein Copyright 2006 Beilstein MDL on STN, Beilstein Records (BRN): 309045.
Beilstein Copyright 2006 Beilstein MDL on STN, Beilstein Records (BRN): 297782.
Beilstein Copyright 2006 Beilstein MDL on STN, Beilstein Records (BRN): 264050.
Beilstein Copyright 2006 Beilstein MDL on STN, Beilstein Records (BRN): 263250.
Beilstein Copyright 2006 Beilstein MDL on STN, Beilstein Records (BRN): 9977461.
Beilstein Copyright 2006 Beilstein MDL on STN, Beilstein Records (BRN): 9977460.
Beilstein Copyright 2006 Beilstein MDL on STN, Beilstein Records (BRN): 930285.
Beilstein Copyright 2006 Beilstein MDL on STN, Beilstein Records (BRN): 927125.
Beilstein Copyright 2006 Beilstein MDL on STN, Beilstein Records (BRN): 900708.
Beilstein Copyright 2006 Beilstein MDL on STN, Beilstein Records (BRN): 720845.
Beilstein Copyright 2006 Beilstein MDL on STN, Beilstein Records (BRN): 697548.
Beilstein Copyright 2006 Beilstein MDL on STN, Beilstein Records (BRN): 264804.
Beilstein Copyright 2006 Beilstein MDL on STN, Beilstein Records (BRN): 315587.
Beilstein Copyright 2006 Beilstein MDL on STN, Beilstein Records (BRN): 368153.
Beilstein Copyright 2006 Beilstein MDL on STN, Beilstein Records (BRN): 678238.
Beilstein Copyright 2006 Beilstein MDL on STN, Beilstein Records (BRN): 689657.
Beilstein Copyright 2006 Beilstein MDL on STN, Beilstein Records (BRN): 694521.
Beilstein Copyright 2006 Beilstein MDL on STN, Beilstein Records (BRN): 723806.
Beilstein Copyright 2006 Beilstein MDL on STN, Beilstein Records (BRN): 730528.
Beilstein Copyright 2006 Beilstein MDL on STN, Beilstein Records (BRN): 941361.
Caplus Copyright 2006 ACS on STN, Accession No. 1964:404361, Abstract of Antonaccio et al., "Recent progress in aspiodosperma alkaloids," Anais da Associacao Brasileira de Quimica, 21:31-7 (1962).
Caplus Copyright 2006 ACS on STN, Accession No. 1964:52704, Abstract of Taborsky et al., "Synthesis and preliminary pharmacology of some 9H-pyrido [3,4-b] indoles (β-carbolines) and tryptamines related to serotonin and melatonin," Journal of Medicinal Chemistry, 7(2):135-41 (1964).
Caplus Copyright 2006 ACS on STN, Accession No. 1981:84336, Abstract of Afza et al., "Some new derivatives of tetrahydroharmine," Pakistan Journal of Scientific and Industrial Research, 22(6):290-2 (1979).
Caplus Copyright 2006 ACS on STN, Accession No. 1988:5744, Abstract of O'Malley et al., "Tremorgenic mycotoxins, synthesis of 6-demethoxyfumitremorgin β," Tetrahedron Letters, 28(11):1131-4 (1987).
Caplus Copyright 2006 ACS on STN, Accession No. 1991:471974, Abstract of Jean etal., "Heteroyohimbine-type indole alkaloids: synthesis of a key intermediate of (+)-ajmalicine from carbohydrates and tryptamine," Discovery and innovation, 2(3):42-50 (1990).
Caplus Copyright 2006 ACS on STN, Accession No. 1994:481198, Abstract of Herraiz et al., "Separationi and characteriziation of 1,2,3,,4-tetrahydro-β-carboline-3-carboxylic acids by HPLC and GC-MS. Identification in wine samples," American Journal of Enology and Viticulture, 45(1):92-101 (1994).
Caplus Copyright 2006 ACS on STN, Accession No. 1995:957085, Abstract of Peters et al., "Endogenous alkaloids in man. Part 24. 2-Trifluoroacetyl-1-methyl-1,2,3,4-tetrahydro-β-carboline, a gas chromatographically useful derivative of the mammalian alkaloid eleagnine," Zeitschrift fuer Naturforschung, B: Chemical Sciences, 50(10):1564-5 (1995).
Caplus Copyright 2006 ACS on STN, Accession No. 1996:127543, Abstract of Pellegrini et al., "Total synthesis of (+)-elacomine and (−)-isoelacomine, two hithereto unnamed oxindole alkaloids from Elaeagnus commutata," Helvetica Chimica Acts, 79(1):151-68 (1996).
Caplus Copyright 2006 ACS on STN, Accession No. 1997:311459, Abstract of Herraiz, T., "Analysis of tetrahydro-β-carbolines and their precursors by electron ionization mass spectrometry. Identification in foods stuffs by gas chromatography/mass spectrometry," Rapid Communications in Mass Spectrometry, 11(7):762-768 (1997).
Caplus Copyright 2006 ACS on STN, Accession No. 1997:303146, Abstract of Tietze et al., "Efficient biomimetic synthesis of indole alkaloids of the vallesiachotamine group by domino Knoevenagel hetero Diels-Adler hydrogenation sequence," Liebigs Annalen/Recueil, 5:881-886 (1997).
Caplus Copyright 2006 ACS on STN, Accession No. 1998:229659, Abstract of Madrigal et al. "Stererocontrolled synthesis of 3,6-dimethyl-1,2,3,6,7,12,12a-hexahydropyrazino[1,2-b]β- carboline-1,4-diones," Journal of Organic Chemistry, 63(8):2724-2727 (1998).
Caplus Copyright 2006 ACS on STN, Accession No. 1999:726418, Abstract of Itoh et al., "A novel synthesis of chiral 1-alllyl-1,2,3,4-tetrahydro-β-carboline employing allytributyltin and chiral acyl chlorides," Synlett, 11:1799-1801 (1999).
Caplus Copyright 2006 ACS on STN, Accession No. 2003:829870, Abstract of Itoh et al., "Proline-Catalyzed asymmetric addition reaction of 9-tosyl-3,4-didhydro-β-carboline with ketones," Organic Letters, 5(23):4301-4304 (2003.
Caplus Copyright 2006 ACS on STN, Accession No. 2003:689601, Abstract of Santos et al., "A novel asymmetric reduction of didhydro-β-carboline derivatives using calyx[6]arene/chiral amine as a host complex," Tetrahedron: Asymmetry, 14(17):2515-2519 (2003.
Caplus Copyright 2006 ACS on STN, Accession No. 2003:545316, Abstract of Takayama et al., "First asymmetric total synthesis of Us-7 and -8, novel D-seco corynanthe-type oxindole alkaloids from uncaria attenuate: structure revision of Us-7 and determination of absolute stereochemistry," Organic Lletters, 5(16):2967-2970 (2003).

Caplus Copyright 2006 ACS on STN, Accession No. 2004:164526, Abstract of Itoh et al., "Syntheses of 1,2,3,4,6,7,12,12b-octahydroindolo [2,3,a]quinolizine and harmicine using a chiral 1-allyl-1,2,3,4-tetrahydro-β-carboline as the starting material," Heterocyles, 63(3):655-661 (2004).

Caplus Copyright 2006 ACS on STN, Accession No. 2004:752104, Abstract of Toscano et al., "Alkaloids and diterpenes from croton moritibensis," Pharmaceutical Biology (Lisse, Netherlands), 42(1):62-67 (2004).

Caplus Copyright 2006 ACS on STN, Accession No. 2005:208078, Abstract of Milen et al., "Studies on stereoselective approaches to β-carboline derivatives," Central European Journal of Chemistry, 3(1):118-136.

Caplus Copyright 2006 ACS on STN, Accession No. 1960:103442, Abstract of Kanaok, Yuichi, "Applications of the Robinson dehydrogenation reaction. IV. Oxidation of some tetrahydro-β-carboline derives," Chemical & Pharmaceutical Bulletin 7:597-601 (1959).

Caplus Copyright 2006 ACS on STN, Accession No. 1980:586630, Abstract of Campos et al., "Selenium dioxide oxidations in the β-carboline areas," Heterocycles, 14(7):975-84 (1980).

Caplus Copyright 2006 ACS on STN, Accession No. 1981:567018, Beck et al., "Analysis of 1-methyl-,2,3,4-tetrahydero-β-carboline in alcoholic beverages," Food and cosmetics Toxicology, 19(2):173-7 (1981).

Caplus Copyright 2006 ACS on STN, Accession No. 1982:523372, Abstract of Allen et al., "Analysis of 1-methyl-1,2,3,4-tetrahydro-β-carboline by GC/MS using deuterium-labeled internal standards," Analytical Chemistry Symposia Series, 11(Stable Isot.):611-16 (1982).

Caplus Copyright 2006 ACS on STN, Accession No. 1982:598438, Abstract of Cain et al. "Dichlorodicyanoquinone oxidations in the indole area. Synthesis of crenatine," Journal of Organic Chemistry, 47(25):4933-6 (1982).

Caplus Copyright 2006 ACS on STN, Accession No. 1983:160991, Abstract of Cain et al., "Selenium dioxide oxidations in the indole area. Synthesis of β-carboline alkaloids," Journal of the American Chemical Society, 105(4):907-13 (1983).

Caplus Copyright 2006 ACS on STN, Accession No. 1983:198514, Abstract of Siddiqui et al., "Studies in harmine series of alkaloids. Part 1. Derivatives of tetrahydroharmine," Pakistan Journal of Scientific and Industrial Research, 25(5):147-52 (1982).

Caplus Copyright 2006 ACS on STN, Accession No. 1996:494549, Abstract of Nakamura et al., "Enantioselective allylzincation of cyclic aldimines in the presence of anionic bis-oxazoline ligand," Journal of the American Chemistry Society, 118(35):8489-8490 (1996).

Caplus Copyright 2006 ACS on STN, Accession No. 2005:240075, Abstract of Roszkowski et al., "Enantioselective synthesis of 1-substituted tetrahydro-β-carboline derivatives via asymmetric transfer hydrogenation," Journal of Molecular Catalysis A: Chemical, 232(1-2):143-149 (2005).

Caplus Copyright 2006 ACS on STN, Accession No. 1930:788, Abstract of Tatsui, G., "Synthesis of carboline derivatives," Yakugaku Zasshi, 49:749-58 (1929).

Caplus Copyright 2006 ACS on STN, Accession No. 1930:789, Abstract of Zelinski et al., "Decomposition of cholesterylene and of cholesteryl ether with aluminum chloride," Ber. 62b:2199-2202 (1929).

Caplus Copyright 2006 ACS on STN, Accession No. 1964:16683, deStevens et al., "Heterocycles. XIV. 2- and 3-Azaoctahydroindole [2,3-al]quinolizines," Journal of Organic Chemistry,,, 28(11):3210-12 (1963).

Caplus Copyright 2006 ACS on STN, Accession No. 1964:404362 Abdusalamov et al., "Some derivatives of tetrahydroharman," Uzbekskii Khimicheskii Zhumal, 8(1):48-50 (1964).

Caplus Copyright 2006 ACS on STN, Accession No. 1965:23665, Abstract of Lefer et al., "Potentiation of the cardiovascular effects of norepinephrine by a tetrahydro-β-carboline," Archives Internationales de Pharmacodynamie et de Therapie, 151(3-4):383-93 (1964).

Caplus Copyright 2006 ACS on STN, Accession No. 1965:446445, Abstract of Trojanek etal., "Absolute configuration of vincamine and some of other alkaloids of the ebumamine type," Chemistry & Industry (London, UK), 28:1261 (1965).

Caplus Copyright 2006 ACS on STN, Accession No. 1966:499526, Abstract of Potier et al., "Alkaloids of cinchona ledgeriana leaves. II. Structure of cinschophyllamine and isocinchophyllamine," Bulletin de la Societe Chimique de France, 7:2309-15 (1966).

Caplus Copyright 2006 ACS on STN, Accession No. 1967:473734, Abstract of Abdusalamov et al., "Some tetrahydrohaman derivatives," Nauchnye Trudy-Tashkentaskii Gosudarstvennyi Universitet im. V.I. Lenina, 286:76-9 (1966).

Caplus Copyright 2006 ACS on STN, Accession No. 1968:95725 McIsaac et al., "Chromatography of β-carbolines," Journal of Chromatography, 31(2):446-54 (1967).

Caplus Copyright 2006 ACS on STN, Accession No. 1979:152436, Abstract of Oikawa et al., "Synthesis of oxidized diketopiperazine alkaloids by the selective oxidation of C-3 side chains of indoles," Tennen Yuki Kagobutsu Toronkai Koen Yoshishu, $21^{st}$, 22-7 (1978).

Caplus Copyright 2006 ACS on STN, Accession No. 1988:56414, Abstract of Bailey et al., "Synthesis of 3-(2-indolyl)propenoate derivatives of tryptamine, valuable intermediates for the preparation of indole alkaloids," Tetrahedron Letters, 28(25):2879-82 (1987).

Caplus Copyright 2006 ACS on STN, Accession No. 1989:173526, Abstract of Sonnei et al., "The chemistry of indoles. XLV. A convenient synthetic method of 2-substituted indoles and its application for the synthesis of natural alkaloid, borrerine," Heterocycles, 27(7):1585-7 (1988).

Caplus Copyright 2006 ACS on STN, Accession No. 1998:710496, Abstract of Ottoni et al., "Efficient and simple methods for the introduction of the sulfonyl, acyl, and alkyl protecting groups on the nitrogen of indole and its derivatives," Tetrahedron, 54(46):13915-13928 (1998).

Caplus Copyright 2006 ACS on STN, Accession No. 1999:655036, Abstract of Zhao et al., "Synthesis of 6-amino-acid-substituted 4,6,7,12-tetrahydro-4-oxoindolo [2,3-α]quinolizines," Journal fuer Praktische Chemie (weinheim, Germany) 341(7):691-694 (1999).

Caplus Copyright 2006 ACS on STN, Accession No. 2000:659238, Abstract of Bringmann et al., "Endogeneous alkaloids in man Part 36, chemical modification of the mitochondrial complex I inhibitor 1-trichloromethyl-1,2,3,4-tetrahydro-β-carboline: synthesis and evaluation of N-alkanoyl derivatives," Zeitschrift fuer Naturforschung, C: Journal of Biosciences, 55(7/8):620-630 (2000).

Caplus Copyright 2006 ACS on STN, Accession No. 2001:615283, Abstract of Itoh et al., "Preparation of bothe enantiomers of 1-alk\yl-1,2,3,4-tetrahydro-β-carboline using allyltin reagents and a chiral auxiliary derived from L:-proline," Tetrahedron, 57(34):7277-7289 (2001.

Caplus Copyright 2006 ACS on STN, Accession No. 2002:928751, Abstract of Itoh et al., "Concise syntheses of harmicine and a pyrrolidino-isoquinoline derivatives using chiral 1-allyl adducts of β-carboline and isoquinoline as starting materials," Heterocycles, 58:115-118 (2002).

Caplus Copyright 2006 ACS on STN, Accession No. 2003:190790, Abstract of Fekete et al, "Comparative study on separation of diastereomers by HPLC," Chromatographia, 57(3/4):147-153 (2003).

Caplus Copyright 2006 ACS on STN, Accession No. 2004:1128008, Abstract of Ohba et al., "Synthesis of Na-demthyl-20-deethylsuaveoline, the structure proposed for sellowine," Heterocycles, 63(12):2845-2850 (2004).

Caplus Copyright 2006 ACS on STN, Accession No. 2005:226859, Abstract of Danieli et al., "Combinatorial solid-phase synthesis of 6-hydroxy-1,2,3,4-tetrahydro-β-carbolines from L-5-hydroxytroptophan," Journal of Combinatorial Chemistry, 7(3):458-462 (2005).

Caplus Copyright 2006 ACS on STN, Accession No. 2005:443867, Abstract of Kinderman et al., "Catalytic N-sulfonyliminium ion-mediated cyclizations to a α-vinyl-substituted isoquinolines and β-carbolines and applications in metathesis," Journal of organic Chemistry, 70(14):5519-5527 (2005).

Caplus Copyright 2006 ACS on STN, Accession No. 2005:502638, Abstract of Nagata et al., "Cross-metathesis of 1-allylated β-carboline and isoquinoline derivatives," Heterocycles, 65(6):1283-1287.

Caplus Copyright 2006 ACS on STN, Accession No. 2005:640103, Abstract of Takasu et al., "Synthesis and evaluation of β-carbolinium cations as new antimalarial agents based on pi-delocalized lipophilic cation (DLC) hypothesis," Chemical & Pharmaceutical Bulletin, 53(6):653-661 (2005).
Caplus printout for CAS Reg. No. 252916-29-3, 2009.
Caplus printout for CAS Reg. No. 341031-54-7, 2009.
Caplus printout for CAS Reg. No. 259188-38-0, 2009.
Caplus printout for CAS Reg. No. 15866-90-7, 2009.
Caplus printout for CAS Reg. No. 862124-26-3, 2009.
Caplus printout for CAS Reg. No. 365253-37-8, 2009.
Caplus printout for CAS Reg. No. 443913-73-3, 2009.
Chemcats Copyright 2006 ACS on STN, Accession No. 2006:455990.
Chemcats Copyright 2006 ACS on STN, Accession No. 1999:170837.
Chemcats Copyright 2006 ACS on STN, Accession No. 2004:1704901.
Chemcats Copyright 2006 ACS on STN, Accession No. 2004:2860460.
Chemcats Copyright 2006 ACS on STN, Accession No. 2004:3826780.
Chemcats Copyright 2006 ACS on STN, Accession No. 2005:1150844.
Chemcats Copyright 2006 ACS on STN, Accession No. 2005:1418898.
Chcmcats Copyright 2006 ACS on STN, Accession No. 2005:1937218.
Chemcats Copyright 2006 ACS on STN, Accession No. 2005:2670194.
Chemcats Copyright 2006 ACS on STN, Accession No. 2005:3598258.
Chemcats Copyright 2006 ACS on STN, Accession No. 2005:464357.
Chemcats Copyright 2006 ACS on STN, Accession No. 2005:691695.
HCA Copyright 2006 ACS on STN, Accession No. 134:311102, Abstract of WO 2001/026644, Curis, Inc. (Apr. 19, 2001).
HCA Copyright 2006 ACS on STN, Accession No. 114:42770, Abstract of EP 0 380 155 A1, Duphar International Reseaerch B.V. (Aug. 1, 1990).
HCA Copyright 2006 ACS on STN, Accession No. 116:207832, Abstract of EP 0 468 789 A2, Merck Frosst Canada Inc. (Jan. 29, 1992).
HCA Copyright 2006 ACS on STN, Accession No. 127:149080, Abstract of WO 1997/023458 A1, Warner-Lambert Company et al., (Jul. 3, 1997).
HCA Copyright 2006 ACS on STN, Accession No. 136:325823, Abstract of WO 2002/030421, Curis, Inc (Apr. 18, 2002).
HCA Copyright 2006 ACS on STN, Accession No. 136:64122, Abstract of WO 2001/098344 A2, Biogen, Inc. (Dec. 27, 2001).
Hcaplus Copyright 2006 ACS on STN, AN 1982:143144, Abstract of Cloudsdale et al., "Synthetic studies in the ajmaline series," J. Org. Chem., 47(6):919-928 (1982).
Hcaplus Copyright 2006 ACSon STN, AN 1980:22200, Abstract of Kluge et al., "Phosphonate reagents for the synthesis of enol ethers and one-carbon homologation to aldehydes," J. Org. Chem., 44(26):4847-4852 (1979).
Hcaplus Copyright 2006 ACS on STN, Accession No. 1995:188469, Abstract of Waldmann et al., "Asymmetric steering of the Picter-Spengler reaction by means of amino acid esters as chiral auxiliary groups," Tetrahedron, 50(41):11865-84 (1994).
Hcaplus Copyright 2006 ACS on STN, Accession No. 1995:470885, Abstract of Soe et al.,"Asymmetric Pictet-Spengler reaction with a chiral N-(β-3-indolyl) ethyl-1-methylbenzylamine," Tetrahedron Letters, 36(11):1857-60 ( 1995).
Hcaplus Copyright 2006 ACS on STN, Accession No. 1995:741637, Abstract of Kawashima et al., "Synthesis and pharmacological evaluation of 1,2,3,4-tetrahydro-β-carboline derivatives," Chemical & Pharmaceutical Bulletin, 43(5):783-7 (1995).

Hcaplus Copyright 2006 ACS on STN, Accession No. 1996:94639, Abstractof Soe et al., "Asymmetrin Pictet-Spengler reaction using a methylbenzylamine as achiral auxiliary group," Heterocycles, 42(1):347-58 (1996).
Hcaplus Copyright 2006 ACS on STN, Accession No. 1999:241413, Abstract of Kawate etal., "Chiral auxiliary approach to the asymmetricPictet-Spengler reaction of tryptamines," Heterocycles, 50(2):1033-1039 (1999).
Hcaplus Copyright 2006 ACS on STN, Accession No. 2002:862393, Abstract of Jiang et al., "Synthesis of optically pure pyrroloquinolones via Pictet-Spengler and Wintwerfeldt reactions," Tetrahedron Letters, 43(49):8941-8945 (2002).
Hcaplus Copyright 2006 ACS on STN, Accession No. 2003:67259, Abstract of Tsuji et al., "An efficient synthetic approach to optically active β-carboline derivatives via Picter-Spengler reaction promoted by trimethylchlorosilane," Tetrahedron: Asymmetry, 14(2):177-180 (2003.
Hcaplus Copyright 2006 ACS on STN, Accession No. 1990:198356, Abstract of CZ 261296 B1, Protiva et al. (Jan. 12, 1989).
Hcaplus Copyright 2006 ACS on STN, Accession No. 1990:77229, Abstract of CZ 262100 B1, Protiva, et al. (Feb. 10, 1989).
Hcaplus Copyright 2006 ACS on STN, Accession No. 1999:131592, Abstract of Venko et al., "Synthesis of 2-acyltetrahydro-β-carbolines by an intramolecular α-amidoalkylation reaction," Synthetic Communications, 29(3):487-494 (1999).
Hcaplus Copyright 2006 ACS on STN, Accession No. 1928:29116, Abstract of Tatsui, U., "Synthesis of carboline derivativies," Yakugaku Zasshi, 48:453-9 (1928).
Hcaplus Copyright 2006 ACS on STN, Accession No. 1952:57257, Abstracto f Groves et al.,"Constitution of yohimbine and related alkaloids. Vi. The synthesis of 1,2,3,4,6,7,12,12b-octahydro-2-ketoindole-2[2,3,-a]-pyridocoline and 1,2,3,4-tetrahydro [2,3-a] pyridocoline," Journal of the Chemical Society, 650-61 (1952).
Hcaplus Copyright 2006 ACS on STN, Accession No. 1958:98075, Abstract of Prasad et al., "Consittution of yohimbine and related alkaloids, XII. Unsuccessful synthetic approaches to yohimbine and alstonline," Journal of Chemical Society, 2045-51 (1958).
Hcaplus Copyright 2006 ACS on STN, Accession No. 1959:122350, Abstract of Bartlett et al., "The alkaloids of tabemanthe iboga. VIII." Journal of the American Chemical Society, 81:1932-5 (1959).
Hcaplus Copyright 2006 ACS on STN, Accession No. 1959:122351, Abstract of Kline, G. Bruce, "Indole alkaloids. A study of the Dieckmann considensation of 1-carbethoxymethyl-2-(2-carbethoxyethyl)-1,2,3,4-tetrahydro-β-carboline. A synthesis of 20-carbethoxy-15(16)-yohimben-17-one," Journal of the American Chemical Society, 81:2251-5 (1959).
Hcaplus Copyright 2006 ACS on STN, Accession No. 1961:112225, Abstract of Vejdelek et al., "Synthetic experiments in the group of hypotensive alkaloids. XXI. Chemistry of 1,2,3,4-tetrahydronorhaman-1-carboxylic acid and derivatives," J. or Medicinal & Pharmaceutical Chemistry, 3:427-40 (1961).
Hcaplus Copyright 2006 ACS on STN, Accession No. 1961:99570, Abstract of Mndzhoyan et al., "Syntheses based on harmine and tetrahydroharmine. III. Cyanoethylation of harmine and tetrahydroharmine," Izvest. Akad. Nauk Armyan. 13(14):297-304 (1960).
Hcaplus Copyright 2006 ACS on STN, Accession No. 1962:45986, Abstractof Agbalyan, S.F., "Decyanoethylation in 1,2,3,4-tetrahydro-β-carbolines," Izvest. Akad, najk, Armyan, S.S.R., Khim Nauki, 14:277-82 (1961).
Hcaplus Copyright 2006 ACS on STN, Accession No. 1963:27125, Abstact of Agbalyan S.G., "Cyanoethylation of harmine and tetrahydroharmine," Izvestiya Akademii Nauk Armyanskoi SSR, Khimicheskie Nauki, 14:611-16 (1961).
Hcaplus Copyright 2006 ACS on STN, Accession No. 1963:415546, Wells et al., "Synthesis of 1,2,3,4,6,7-hexaydroindolo [2,3-1]-1,3-trimethylenequinolizine and its intermediates," Bol. Inst. Quim. Univ. Nal. Anton. Mex., 14:32-47 (1962).
Hcaplus Copyright 2006 ACS on STN, Accession No. 1964:30874, Abstract of Henecka et al., "Synthesis in the β-carboline series," Med. Chem. Abhandl. Med-Chem. Forschugsstaetten Farbenfabriken Bayer.-G., 7:277-86 (1963).

Hcaplus Copyright 2006 ACS on STN, Accession No. 1967:115626, Abstract of Elliott et al., "New synthetic approaches to the benz[h]indole[2,3,-a] quinolizine ring system," J. of Heterocyclic Chemistry, 4(1):127-9 (1967).

Hcaplus Copyright 2006 ACS on STN, Accession No. 1967:65442, Abstract of Szantay et al., "Synthesis of substituted octahydroindolo '2,3,-1]-quinolizines. The formation of a new type of ring system," J. of Organic Chemistry, 32(2):423-7 (1967).

Hcaplus Copyright 2006 ACS on STN, Accession No. 1969:11546, Abstract of Von Strandtmann et al.,"Azecino [2,1-α] tetrahydroisoquinolines and related compounds. I. Reaction of 3,4-dihydroisoquinolines with nonemolizable β-diketones," J. of Organic Chemistry, 33(11):4010-15 (1968).

Hcaplus Copyright 2006 ACS on STN, Accession No. 1971:53396, Abstract of Mukerdzhli et al., Indole derivatives. LX. Synthesis of β-lactamsofthe indole series, Khimiya Geterotsiklicheskikh Soedinenii, 12:1626-30 (1970).

Hcaplus Copyright 2006 ACS on STN, Accession No. 1971:551703, Abstract of Novak et al., "Synthesis of an analog of Quantril containing the indolouinolizidine ring," Acta Cheimica Academia Scientiarum Hungaricae, 70(1-2):91-6 (1971).

Hcaplus Copyright 2006 ACS on STN, Accession No. 1973:438449, Abstrat of Velichkova, St., "MAO (monoamine oxidasc)—inhibiting effect of some simplified structural analogs of reserpine," Trudove na Nauchnoizsledovatelksiya Khimikofarmatsevtichen Institut, 8:321-6 (1972).

Hcaplus Copyright 2006 ACS on STN, Accession No. 1975:479451, Abstracat of Bilova et al., "Synthesis and pharmacological study of new pyridine-N-(acetylamido)-β-carboline derivatives," Trudove na Nauchnoizsledovatelksiya Khimikofarmatsevtichen Institut, 9:141-53 (1974).

Hcaplus Copyright 2006 ACS on STN, Accession No. 1978:540332, Abstract of Rehse et al., "Neuropsychotropic activity of reserpine analogs, 1,2,3,4-tretrahydro-β-carbolines," Archiv der Pharmazie (Weinheim, Germany), 311(3):228-35 (1978).

Hcaplus Copyright 2006 ACS on STN, Accession No. 1981:30596, Abstract of Bikova et al., "Synthesis and pharmacological testing β-carbolines with basis substitutes," Trudove na Nauchnoizsledovatelksiya Khimikofarmatsevtichen Institut, 10:65-84 (1978).

Hcaplus Copyright 2006 ACS on STN, Accession No. 1983-16659, Abstract of Kumar et al., "Agents acting on CNS. Part XXIX. Synthesis of seco analog of centbutindole, a potent neuroleptic," European Journal of Medicianl Chemistry, 17(4):312-16 (1982).

Hcaplus Copyright 2006 ACS on STN, Accession No. 1983:53150, Abstract of Massiot et al., "α,, α'-Bis(phenylthio) carbonls in organic synthesis," Bulletin de la Societe Chimique de France, (7-8, Pt. 2):241-8 (1982).

Hcaplus Copyright 2006 ACS on STN, Accession No. 1985:184894, Abstract of Flecker et al., "Reactions with indole derivatives, LI. Seco-aldehydes from didrovaltratum," Tetrahedron, 40(23):4843-52 (1984).

Hcaplus Copyright 2006 ACS on STN, Accession No. 1985:406574, Abstract of Mandal et al., "Synthesis of 3-acetyl-1,4,6,7,12,12b-hexahydroindole [2,3-a] quinolizine," Heterocycles, 23(4):931-4 (1985).

Hcaplus Copyright 2006 ACS on STN, Accession No. 1985:6903, Abstract of Massiot et al., "Synthesis of (−)-ajmalicine from (−)-tryptophan," J. of the Chemical Society, Chemical Communications, 11:715-16 (1984).

Hcaplus Copyright 2006 ACS on STN, Accession No. 1987:138281, Abstract of Bobowski et al., "1,1-disubstituted-2,3,4,9-tetrahydro-1H-pyrido [3,4,-b] indolecarboxylic acid esters and ketones. The base catalyzed transformation of 1-(2',3',4',9'-tetrahydrospiro [cyclohexane-1,1'-[1H] pyrido [3,4-b] indol]-2-yl) alkanones into 2-(4,9-dihydro-3H-pyrido[3,4-b]indol-1-yl)-1-alkylcyclohexanls," J. of Heterocyclic Chemistry, 22(6):1679-88 (1985).

Hcaplus Copyright 2006 ACS on STN, Accession No. 1987:509062, Abstract of Blasko et al., "Octahydroindolo [2,3-a] quinolizines and 3,4-dihydro-β-carbolines as new inhibitors of human platelet aggregation," Arzneimittel-Forschung, 37(6):667-9 (1987).

Hcaplus Copyright 2006 ACS on STN, Accession No. 1987:568626, Misztal et al., "Synthesis and pharmacological properties ofsome 2-substituted 1-(3-pyridyl)1-2,3,4-tetrahydro-β-carbolines," Polish Journal of Pharmacology and Pharmacy, 39(1):97-103 (1987).

Hcaplus Copyright 2006 ACS on STN, Accession No. 1987:590347, Abstract of Pogosyan et al., "Synthesis and biological activity of 3-substituted-1,2,3,4-tetrahydro-β-carbolines derivatives," Khimiko-Farmatsevticheskii Zhumai, 21(6):678-81 (1987).

Hcaplus Copyright 2006 ACS on STN, Accession No. 1988:131668, Abstract of Moehrie et al., Tetracyclic imidazoles, Monatschefte fluer Chemie, 118(4):477-83 (1987).

Hcaplus Copyright 2006 ACS on STN, Accession No. 1988:21850, Abstract of Moehrie et al., "Methylhydrazone function as a neighboring group in amine dehydrogenation," Archiv der Pharmazie (Weinheim, Germany), 320(3):258-63 (1987).

Hcaplus Copyright 2006 ACS on STN, Accession No. 1988:400244, Abstract of Hulinska et al., "1-Methyl-, 1-phenyl-, and 1-[2-(2-dimethylaminoethoxy)phenyl]-2,3,4,9-tetrahydro-1II-pyrido[3,4-] indole and their 2-substituted derivatives. Synthesis and pharmacological screening," Collection of Czechoslovak Chemical Communications, 53(2):373-80 (1988).

Hcaplus Copyright 2006 ACS on STN, Accession No. 1989-107998, Abstract of Misztal et al., "Synthesis and pharmacological properties of some 2-(3-aminopropionyl)-and 2-(3-aminopropyl)-1-(3-pyridyl)-1,2,3,4-tetrahydro-β-carbolines," Polish Journal of Pharmacology and Pharmacy, 40(4):413-22 (1988).

Hcaplus Copyright 2006 ACS on STN, Accession No. 1989:477876, Abstract of Grigg et al., "A dehydration route to azomethine ylides and isoindoles," Journal of the Chemical Society, Perkin Transactions 1: Organic and Bio-Organic Chemistry, (1972-1999), (1):198-200 (1989).

Hcaplus Copyright 2006 ACS on STN, Accession No. 1989:595214, Abstract of Wasserman et al., "The chemistry of vicinal tricarbonyl compounds. Applications in the synthesis of vincamine-rlated alkaloids," Tetrahedron Letters, 30(7):873-6 (1989).

Hcaplus Copyright 2006 ACS on STN, Accession No. 1990:440504, Abstract of Fuji et al., "Synthesis of 1-(pentafluorophenyl)-β-carboline," Journal of Fluorine Chemistry, 46(3):479-89 (1990).

Hcaplus Copyright 2006 ACS on STN, Accession No. 1990:552798, Abstract of Rosenmund et al., "Stereoselective synthesis of rac-yohimb-15-enone," Liebigs Annalen der Chemie, 9:857-62 (1990).

Hcaplus Copyright 2006 ACS on STN, Accession No. 1991:492679, Abstract of Huizenga et al., "Models of folate cofactors. 22. Lewis acid catalyzed cyclization of carbob-fragment transfer products of folate cofactor models. Synthesis of enantiomerically pure tetracyclic (ABCE) ring system of Aspidosperma alkaloids," Tetrahedron, 47(24):4155-64 (1991).

Hcaplus Copyright 2006 ACS on STN, Accession No. 1991:558999, Abstract of Zhang et al., "Stereoselective synthesis of enantiomerically pure 3-acetyl-1,4,6,7,12,12b-hexahydroindolo-2,3-quinolizine," Hauxue Tongbao, 6:31-3 (1991).

Hcaplus Copyright 2006 ACS on STN, Accession No. 1991:583240, Abstract of Miszatl et al., "Structure and spectral properties of β-carbolines. Parpt 4. Synthesis of the new ring system: 9,10,15,15b-tetrahydroindole [1',2': 4,3] pyrazino [2,1-1] carbolin-7 (6H)-one," Journal of the Chemical Society, Perkin Transactions 1: Organic and Bio-Organic Chemistry (1972-1999), 8:1871-4 (1991).

Hcaplus Copyright 2006 ACS on STN, Accession No. 1991:62055, Abstract of Miszati et al., "Structure and spectral properties of β-carbolines. Part 3. Synethesis and stereochemistry of 1,2,3,,4,6,7,9,10,15b,15c-decahydropyrido '1", 2": 1', 2'] pyrazino [4', 3':1,2] pyrido [3,4-b] indoles," J. of the Chemical Society, Perkin Transactions 1: Organic and Bio-Organic Chemistry (1972-1999), 8:2311-15 (1990).

Hcaplus Copyright 2006 ACS on STN, Accession No. 1992:448375, Abstracat of Kawate et al., "New evidencefor the presence of a *Spiroindolenium* species in the Pictet-Spengler reaction," Heterocycles, 33(2):801-11 (1992).

Hcaplus Copyright 2006 ACS on STN, Accession No. 1992:470107, Abstract of Qais et al., "Asymmetric syntheses of 1-alkyltetrahydro-β-carbolines and a 9-thio analog," Chemical & Pharmaceutical Bulletin, 39(12):3338-40 (1991).

Hcaplus Copyright 2006 ACS on STN, Accession No. 1992:634323, Abstract of Wasserman et al., "Oxidation of yide precursors to vicinal tricarbonyls. Applications in vincamine alkaloid synthesis," Tetrahedron, 48(34):7071-7082.

Hcaplus Copyright 2006 ACS on STN, Accession No. 1992:83990, Abstract of McNulty et al., "Diastereoselective Pictet-Spengler reaction of L-(Boc) prolinal: a biomimetic synthesis of eudistomins H and I, and woodinine," Tetrahedron Letters, 32(37):4875-8 (1991).

Hcaplus Copyright 2006 ACS on STN, Accession No. 1993:409022, Abstract of Peng etal., "Synthesis of enantiomerically pure indoloquinolizine derivatives," Liebigs Annalen der Chemie, 2:141-6 (1993).

Hcaplus Copyright 2006 ACS on STN, Accession No. 1993: 603331, Abstract of Kawate et al., "Alkylation of 3,4-dihydro-β-carboline," Chemical & Pharmaceutical Bulletin, 41(2):287-91 (1993).

Hcaplus Copyright 2006 ACS on STN, Accession No. 1994:135090, Abstract of Waldmann et al., "Asymmetric Pictet-Spengler reactions employing amino acid esters as mediators of selectivity," Tetrahedron Letters, 34(37):5867-70 (1993).

Hcaplus Copyright 2006 ACS on STN, Accession No. 1994:298503, Abstract of Lehmann et al., "Indoles. X. Synthesis, structure and D2-affinity of the β-carboline analog of flutroline," Archiv der Pharmazie (Weinhein, Germany), 326(12):947-51 (1993).

Hcaplus Copyright 2006 ACS on STN, Accession No. 1994:557928, Abstract of McNulty et al., "Diastereoselective Pictet-Spengler reactions of L-(Boc) phenylalaninal and L-(Boc) prolinal: biomimetic syntheses of eudistomin T and (−)-Woodinine," J. of Chemical Society, Perkin Transactions 1: Organic and Bio-Organic Chemistry, (1972-1999), 10:1329-37 (1994).

Hcaplus Copyright 2006 ACS on STN, Accession No. 1995:202652, Abstract of Lehnert et al., "DNA topoisomerase II inhibition by substituted 1,2,3,4-tetrahydro-β-carboline derivatives," Bioorganic & Medicinal Chemistry Letters, 4(20):2411-16 (1994).

Hcaplus Copyright 2006 ACS on STN, Accession No. 1995:347689, Abstract of Zhao et al., Proton NMR and stereochemistry of synthetic indole alkaloids, Bopuxue Zazhi, 12(1):71-8 (1995).

Hcaplus Copyright 2006 ACS on STN, Accession No. 1995:764144, Abstracat of Loegers et al.,"Mannich biscyclizations. Total synthesis of (−)-ajmalicine," J. of the American Chemical Society, 117(36):9139-50 (1995).

Hcaplus Copyright 2006 ACS on STN, Accession No. 1995:957191, Abstract of Waldmann et al., "Asymmetric Pictet-Spengler reactions employing N, N-phthaloyl amino acids as chiral auxiliary groups," Angewandte Chemie, International Edition in English, 34(21):2402-3 (1995).

Hcaplus Copyright 2006 ACS on STN, Accession No. 1996:268475, Abstract of Uematsu et al., "Asymmetric transfer hydrogenation of imines," J. of the American Chemical Society, 118(20):4916-17 (1996).

Hcaplus Copyright 2006 ACS on STN, Accession No. 1996:512657, Abstract of Legsier et al., "Synthesis of optically active tetrahydro-β-carbolines by the Pictet-Spengler reaction." J. de la Society Algerienne de Chimie, 6(1):17-27 (1996).

Hcaplus Copyright 2006 ACS on STN, Accession No. 1997:55320, Abstract of Schmidt et al., "Asymmetric control in the Pictet-Spengler reaction by means of N-protected amino acids as chiral auxiliary groups," Chemistry-A European Journal, 2(12):1566-1571 (1999) Published in: Agnew. Chem., Int. Ed. Engl., 35(23/24).

Hcaplus Copyright 2006 ACS on STN, Accession No. 1998:355721, Abstract of Bienayme, H., "Reagent Explosion: and efficient method to increase library size and diversity," Tetrahedron Letters, 39(24):4255-4258 (1998).

Hcaplus Copyright 2006 ACS on STN, Accession No. 1999:767765, Abstract of Zhao et al., "Easy generation of an enantiopure general indol alkaloid building block by kinetic resolution," Tetrahedron: Asymmetry, 10(20):3899-3905 (1999).

Hcaplus Copyright 2006 ACS on STN, Accession No. 1999:799056, Abstract of Boumendjet et al., "Synthesis of ajmalicine derivatives using Wittig-Horner and Knovenagel reactions," Tetrahedron Letters, 40(51):9033-9036 (1999).

Hcaplus Copyright 2006 ACS on STN, Accession No. 2000:337953, Abstract of You et al., "Applciation of DDQ in the synthesis of β-carboline alkaloid," Hecheng Huaxue, 8(1):83-86 (2000). Only English STN Abstract provided.

Hcaplus Copyright 2006 ACS on STN, Accession No. 2002:637676, Abstract of WO 2002/064590, Lilly Icos LLC (0822/2002).

Hcaplus Copyright 2006 ACS on STN, Accession No. 2002:659480, Abstract of Bonnefont-Rousselot et al., "Melatonin related compounds inhibit lipid peroxidation during copper or free radical-induced LDL oxidation," J. of Pineal Research, 32(2):109-117 (2002).

Hcaplus Copyright 2006 ACS on STN, Accession No. 2002:861062, Abstract of Joule, J.A., "Product class 13: indole and its derivatives," Science of Synthesis, 10:361-652 (2001).

Hcaplus Copyright 2006 ACS on STN, Accession No. 2003:431047, Abstract of Cheve et al., "Antioxidant activity of pinoline analogues in the LDL oxidation model," MedicinalChemistry Research, 11(7):361-379 (2002).

Hcaplus Copyright 2006 ACS on STN, Accession No. 2004:611809, Abstract of Donova et al., "N-Acyliminum reagents of 3,4-dihydro-β-carboline and acyl chlorides in the reaction of intermolecular α-amidoalkylation toward heteroaromatics," Synthetic Communications, 34(15):2813-2821 (2004).

Hcaplus Copyright 2006 ACS on STN, Accession No. 2005:580707, Abstract of Zhuang et al., "Enantioselective Friedel-Crafts type additionto indoles to nitro-olefina using achiral hydrogen-bonding catalyst—a synthesis of optically active tetrahydro-β-carbolines," Organic & Biomolecular Chemistry, 3(14):2566-2571 (2005).

Hcaplus Copyright 2006 ACS on STN, Accession No. 2005:643328, Abstrat of Mekhloufi et al., "Antioxidant activity of melatonin and a pinoline derivative on linoleate model system," J. of Pineal Research, 39(1):27-33 (2005).

Hcaplus Copyright 2006 ACS on STN, Accession No. 2005:886847, Abstract of Taileux et al., "Increased susceptibility of low-density lipoprotein to ex vivo oxidation in mice transgenic for human apolipoprotein B treated with 1-melatonin-related compound is not associated with atherosclerosis progression," J. of Cardiovasculer Pharmacology, 46(3):241-249 (2005).

Hcaplus Copyright 2006 ACS on STN, Accession No. 1980:22200, Abstract of Kluge et al., "Phosphate reagents for the synthesis of enol ethers and one-carbon homologation toaldehydes," J. of Organic Chemistry, 44(26):4847-52 (1979).

Hcaplus Copyright 2006 ACS on STN, Accession No. 1982:143144, Abstract of Cloudsdale et al., "Synthetic studies in the ajmaline series," J. of Organic Chemistry, 47(6):919-28 (1982).

Hcaplus Copyright 2006 ACS on STN, Accession No. 1965:498671, Abstract of NL 6413518, Omnium Chimique, Societe Anon. (May 24, 1965).

Hcaplus Copyright 2006 ACS on STN, Accession No. 1966:420748, Abstract of NL 6512087, Imperial Chemical Industries Ltd., (Mar. 17, 1966).

Hcaplus Copyright 2006 ACS on STN, Accession No. 1972:501562, Abstract of DE 20 61 359 A, Badische Anilin- & Soda-Fabrik AG (Jun. 22, 1972).

Hcaplus Copyright 2006 ACS on STN, Accession No. 1972:526602, Abstractof DE 20 62 828 A, Boehringer, C.H., (Jun. 22, 1972).

Hcaplus Copyright 2006 ACS on STN, Accession No. 1977:423246, Abstract of DE 26 37 503 A1, Endo Laboratories Inc. (Mar. 3, 1977).

Hcaplus Copyright 2006 ACS on STN, Accession No. 1977:468520, Abstract of JP 52031097 A1, Oki et al., (Mar. 9, 1977).

Hcaplus Copyright 2006 ACS on STN, Accession No. 1980:471821, Abstract of EP 0 008 249, Synthelabo S.A. (Feb. 20, 1980).

Hcaplus Copyright 2006 ACS on STN, Accession No. 1981:121318, Abstractof JP 55145687 A2, Synthelabo S.A. (Nov. 13, 1980).

Hcaplus Copyright 2006 ACS on STN, Accession No. 1981:139775, Abstract of EP 0 017 727 A1, Ciba-Geigy A-G (Oct. 29, 1980).

Hcaplus Copyright 2006 ACS on STN, Accession No. 1981:175153,Abstract of EP 0 018 857 A1, Synthelabo S.A. (Nov. 12, 1980).

Hcaplus Copyright 2006 ACS on STN, Accession No. 1981:497842, Abstract of FR 2456743 A1, Synthelabo S.A. *Dec. 12, 1980).

Hcaplus Copyright 2006 ACS on STN, Accession No. 1982:35284, Abstractof FR 2460301 A2, Synthelabo S.A. (Jan. 23, 1981).

Hcaplus Copyright 2006 ACS on STN, Accession No. 1982:550721, Abstract of FR 2486801 A1, Synthelabo S.A. (Jan. 22, 1982).
Hcaplus Copyright 2006 ACS on STN, Accession No. 1984:490905, Abstract of EP 0 101 574 A1, BASF A.-G. (Feb. 29, 1984).
Hcaplus Copyright 2006 ACS on STN, Accession No. 1985:24611, Abstractof DE 33 02 126 A1, Boehringer Ingelheim K.-G. (Jul. 26, 1984).
Hcaplus Copyright 2006 ACS on STN, Accession No. 1986:207248, Abstract of JP 60246385 A2, Sankyo Co., Ltd. (Dec. 6, 1985).
Hcaplus Copyright 2006 ACS on STN, Accession No. 1988:630991, Abstractof EP 0 273 321 A1, Kawaken Fine Chemicals Co., Ltd. (Jul. 6, 1988).
Hcaplus Copyright 2006 ACS on STN, Accession No. 1989:205701, Abstract of DE 37 05 220 A1, Boehringer Ingelheim K-G (Sep. 1, 1988).
Hcaplus Copyright 2006 ACS on STN, Accession No. 1989:407060, Abstract of WO 1989/000159 A1, Richter, Gedeon, Veyeszeti Gyar Rt. (Jan. 12, 1989).
Hcaplus Copyright 2006 ACS on STN, Accession No. 1989:477986, Abstract of EP 0 300 541 A1, Duphar International Research B.V. (Jan. 25, 1989).
Hcaplus Copyright 2006 ACS on STN, Accession No. 1989:554290, Abstract of HU 46032 A2, Gyogynoveny Kutato Intezet (Sep. 28, 1988).
Hcaplus Copyright 2006 ACS on STN, Accession No. 1990:235665, Abstract of JP 01319482 A2, Kawaken Fine Chemicals Co., Ltd (Dec. 25, 1989).
Hcaplus Copyright 2006 ACS on STN, Accession No. 1990:441332, Abstractof EP 0 346 847 A2, Hoffman-LaRoche, F. und Co. A-G (Dec. 20, 1989).
Hcaplus Copyright 2006 ACS on STN, Accession No. 1992:235613, Abstract of JP 03287586, Taisho Pharmaceutical Co., Ltd. (Dec. 18, 1991).
Hcaplus Copyright 2006 ACS on STN, Accession No. 1993:175782, Abstract of JP 04275221 A2, Taisho Pharmaceutical Co.,Ltd. (Sep. 30, 1992).
Hcaplus Copyright 2006 ACS on STN, Accession No. 1994:54535, Abstracat of HU 63164 A2, Richter Gedeon, Vegyeszeti Gyar Rt. (Jul. 28, 1993).
Hcaplus Copyright 2006 ACS on STN, Accession No. 1995:861292, Abstract of JP 07179467, Nippon Shoji Kk (Jul. 18, 1995).
Hcaplus Copyright 2006 ACS on STN, Accession No. 1996:311402, Abstract of DE 44 36 190 A1, Bringham et al., (Apr. 11, 1996).
Hcaplus Copyright 2006 ACS on STN, Accession No. 1996:425286, Abstract of WO 1996/008490 A1, Cemaf et al. (Mar. 21, 1996).
Hcaplus Copyright 2006 ACS on STN, Accession No. 1997:244196, Abstract of EP 0 758 021 A2, Polifarma S.P.A. (Feb. 12, 1997).
Hcaplus Copyright 2006 ACS on STN, Accession No. 1997:618080, Abstract of WO 1997/032860 A1, James Black Foundation Ltd., et al. (Sep. 12, 1997).
Hcaplus Copyright 2006 ACS on STN, Accession No. 1997:752957, Abstract of WO 1997/043287 A1, Icos Corporation e tal., (Nov. 20, 1997).
Hcaplus Copyright 2006 ACS on STN, Accession No. 2000:191086, Abstracatof WO 2000/015639 A1, Icos Corp. (Mar. 23, 2000).
Hcaplus Copyright 2006 ACS on STN, Accession No. 2000:755247, Abstract of EP 1 046 627 A2, Solvay (Societe Anonyme) (Oct. 25, 2000).
Hcaplus Copyright 2006 ACS on STN, Accession No. 2000:772630, Abstract of WO 2000/064897 A1, Macef et al., (Nov. 2, 2000).
Hcaplus Copyright 2006 ACS on STN, Accession No. 2001:12443, Abstract of WO 2001/000610 A1, Aventis Pharma Deutschland GmbII (Jan. 4, 2001).
Hcaplus Copyright 2006 ACS on STN, Accession No. 2001:338479, Abstract of WO 2001/032604 A1, University College London (May 10, 2001).
Hcaplus Copyright 2006 ACS on STN, Accession No. 2001:62384, Abstract of EP 1 070 716 A1, Adir et Compagnie (Jan. 24, 2001).
Hcaplus Copyright 2006 ACS on STN, Accession No. 2001:851157, Abstract of WO 2001/087882, Ortho-McNeil Pharmaceutical, Inc. (Nov. 22, 2001).
Hcaplus Copyright 2006 ACS on STN, Accession No. 2002:275987, Abstract of WO 2002/028858 A2, Lilly Icos LLC (Apr. 11, 2002).

Hcaplus Copyright 2006 ACS on STN, Accession No. 2002:408517, Abstract of WO 2002/041884, Pain Therapeutics, Inc. (May 30, 2002).
Hcaplus Copyright 2006 ACS on STN, Accession No. 2002:615404, Abstracat of WO 2002/62339 A1, SmithKline Beecham Corporation (Aug. 15, 2002).
Hcaplus Copyright 2006 ACS on STN, Accession No. 2002:637677, Abstract of WO 2002/064591, Lilly Icos LLC, USA (Aug. 22, 2002).
Hcaplus Copyright 2006 ACS on STN, Accession No. 2002:946116, Abstract of WO 2002/098428 A1, Lilly Icos LLC (Dec. 12, 2002).
Hcaplus Copyright 2006 ACS on STN, Accession No. 2003:356232, Abstract of WO 2003/037310 A2, Pain Therapeutics, Inc. (May 8, 2003).
Hcaplus Copyright 2006 ACS on STN, Accession No. 2003:356260, Abstract of WO 2003/037340 A1, Pain Therapeutics, Inc. (May 8, 2003).
Hcaplus Copyright 2006 ACS on STN, Accession Number: 2003:5960, Abstract of WO 2003/000691 A1, Lilly Icos LLC (Jan. 3, 2003).
Hcaplus Copyright 2006 ACS on STN, Accession No. 2003:76556, Abstract of WO 2003/007888 A2, Adipogenix, Inc. (Jan. 30, 2003).
Hcaplus Copyright 2006 ACS on STN, Accession No. 2004:1154677, Abstract of WO 2004/113300 A1, Ono Pharmaceutical Co., Ltd. (Dec. 29, 2004).
Hcaplus Copyright 2006 ACS on STN, Accession No. 2004:41506, Abstract of WO 2004/005328 A2, Sigma-Tau Industrie Farmaceutiche Riunitc S.p. A. (Jan. 15, 2004).
Hcaplus Copyright 2006 ACS on STN, Accession No. 2004:965248, Abstracat of WO 2004/096802, Oscient Pharmaceuticals et al. (Nov. 11, 2004).
Hcaplus Copyright 2006 ACS on STN, Accession No. 2005:1106860, Abstract of WO 2005/095403, Intermune, Inc. (Oct. 13, 2005).
Hcaplus Copyright 2006 ACS on STN, Accession No. 2005:371064, Abstract of WO 2005/037214, Intermune, Inc. (Apr. 28, 2005).
Hcaplus Copyright 2006 ACS on STN, Accession No. 2005:696910, Abstract of WO 2005/070930 A2, Chiron Corporation (Aug. 4, 2005).
Hcaplus Copyright 2006 ACS on STN, Accession No. 2005:902862, Abstract of WO 2005/077912 A1, Mitsubishi Pharma Corporation (Aug. 25, 2005).
Hcaplus Copyright 2006 ACS on STN, AN 1965:480584, Abstract of Freter et al., "Reactions of 1-aryl-1,2,3,4-tetrahydro-β-carbolines in acid solution," Justus Liebigs Annalen der Chemie, 684:159-87 (1965).
List of Compounds from Registry Copyright 2006 ACS on STN.
Marpat Copyright 2006 ACS on STN, Accession No. 109:129416, Abstract of EP 0 272 056 A1, Harbor Branch Oceanographic Institution, Inc. (Jun. 22, 1988).
Marpat Copyright 2006 ACS on STN, Accession No. 116:235610, Abstract of EP 0 466 548 A1, Adir et Cie. (Jan. 15, 1992).
Marpat Copyright 2006 ACS on STN, Accession No. 116:256054, Abstract of WO 1992/000295 A1, Rorer International (Holdings), Inc. (Jan. 9, 1992).
Marpat Copyright 2006 ACS on STN, Accession No. 117:212969, Abstract of WO 1992/006108 A1, PolifarmaS.p.A. (Apr. 16, 1992).
Marpat Copyright 2006 ACS on STN, Accession No. 117:234001, Abstract of JP 04173786 A2, Kawaken Fine Chemicals Co., Ltd. (Jun. 22, 1992).
Marpat Copyright 2006 ACS on STN, Accession No. 121:179566, Abstract of WO 1994/010175 A1, United States Dept. of Health and Human Services et al. (May 11, 1994).
Marpat Copyright 2006 ACS on STN, Accession No. 121:301326, Abstract of DE 42 43 496 A1, Boehringer Ingelheim KG (Mar. 10, 1994).
Marpat Copyright 2006 ACS on STN, Accession No. 122:106542, Abstract of WO 1994/014843 A1, Warner-Lambert Co. (Jul. 7, 1994).
Marpat Copyright 2006 ACS on STN, Accession No. 124:117997, Abstract of EP 0 675 112 A1, Bristol-Myers Squibb Co. (Oct. 4, 1995).

Marpat Copyright 2006 ACS on STN, Accession No. 124:203106, Abstract of WO 1995/030687, Boehringer Ingelheim KG et al. (Nov. 16, 1995).
Marpat Copyright 2006 ACS on STN, Accession No. 124:233150, Abstract of DE 44 45 939 A1, Boehringer Ingelheim KG (Nov. 9, 1995).
Marpat Copyright 2006 ACS on STN, Accession No. 124:290283, Abstract of CA 2143588, Bhide et al. (Sep. 25, 1995).
Marpat Copyright 2006 ACS on STN, Accession No. 124:344109, Abstract of EP 0 696 593 A2, Bristol-Myers Squibb Company (Feb. 14, 1996).
Marpat Copyright 2006 ACS on STN, Accession No. 125:33473, Abstract of WO 1996/003377 A1, Sankyo Co., Ltd. (Feb. 8, 1995).
Marpat Copyright 2006 ACS on STN, Accession No. 125:33651, Abstract of CA 2157998, Lilly Industries Ltd. (Mar. 13, 1996).
Marpat Copyright 2006 ACS on STN, Accession No. 129:260346, Abstract of WO 1998/040385 A1, Novo Nordisk A/S (Sep. 17, 1998).
Marpat Copyright 2006 ACS on STN, Accession No. 132:35702, Abstract of WO 1999/064420 A1, Societe De Conseils De Recherches Et D'applications Scientifiques S.A. (Dec. 16, 1999).
Marpat Copyright 2006 ACS on STN, Accession No. 132:88209, Abstract of WO 2000/002878 A1, University of Bristol (Jan. 20, 2000).
Marpat Copyright 2006 ACS on STN, Accession No. 133:247280, Abstract of WO 2000/056304, Harbor Branch Oceanographic Institution, Inc. et al. (Sep. 28, 2000).
Marpat Copyright 2006 ACS on STN, Accession No. 134:252660, Abstract of EP 1 086 947 A1, Pfizer Products Inc. (Mar. 28, 2001).
Marpat Copyright 2006 ACS on STN, Accession No. 134:56654, Abstract of WO 2000/077001 A1, Du Pont Pharmaceuticals Company (Dec. 21, 2000).
Marpat Copyright 2006 ACS on STN, Accession No. 134:56655, Abstract of WO 2000/077002 A1, Du Pont Pharmaceuticals Company (Dec. 21, 2000).
Marpat Copyright 2006 ACS on STN, Accession No. 134:56657, Abstract of WO 2000/077010 A2, Du Pont Pharmaceuticals Company (Dec. 21, 2000).
Marpat Copyright 2006 ACS on STN, Accession No. 135:371735, Abstract of WO 2001/087038, Ortho-McNeil Pharmaceutical, Inc. (Nov. 22, 2001).
Marpat Copyright 2006 ACS on STN, Accession No. 137:140432, Abstract of WO 2002/059129 A2, Bristol-Myers Squibb Company (Aug. 1, 2002).
Marpat Copyright 2006 ACS on STN, Accession No. 137:353008, Abstract of WO 2002/088123 A1, Lilly Icos LLC (Nov. 7, 2002).
Marpat Copyright 2006 ACS on STN, Accession No. 137:78864, Abstract of WO 2002/051842 A1, F. Hoffmann-LaRoche A.-G (Jul. 4, 2002).
Marpat Copyright 2006 ACS on STN, Accession No. 138:11447, Abstract of WO 2002/098875 A1, Lilly Icos LLC (Dec. 12, 2002).
Marpat Copyright 2006 ACS on STN, Accession No. 138:338490, Abstract of WO 2003/033496 A1, Transtech Pharma, Inc. (Apr. 24, 2003).
Marpat Copyright 2006 ACS on STN, Accession No. 139:395821, Abstract of WO 2003/095427 A1, Taisho Pharmaceutical Co., Ltd. (Nov. 20, 2003).
Marpat Copyright 2006 ACS on STN, Accession No. 141:379919, Abstract of WO 2004/092123, Microbia, Inc. (Oct. 28, 2004).
Marpat Copyright 2006 ACS on STN, Accession No. 142:162053, Abstract of FR 2857581 A1, Institut Europeen Biologie Cellulaire (Jan. 21, 2005).
Marpat Copyright 2006 ACS on STN, Accession No. 142:411220, Abstract of CN 1472209, Fuda University (Feb. 4, 2004).
Marpat Copyright 2006 ACS on STN, Accession No. 94:139825, Abstract of JP 55104282 A2, Synthelabo S.A. (Aug. 9, 1980).
Marpat Accession No. 114:37805, Abstract of US 5120543, Hagin et al. (Jun. 9, 1992).
Registry Copyright 2006 ACS on STN, Registry No. 97405-15-7.
Registry Copyright 2006 ACS on STN, Registry No. 865678-67-7.
Registry Copyright 2006 ACS on STN, Registry No. 289656-58-2.
Registry Copyright 2006 ACS on STN, Registry No. 289656-60-6.
Registry Copyright 2006 ACS on STN, Registry No. 334490-33-4.
Registry Copyright 2006 ACS on STN, Registry No. 334490-34-5.
Registry Copyright 2006 ACS on STN, Registry No. 334490-35-6.
Registry Copyright 2006 ACS on STN, Registry No. 335094-02-5.
Registry Copyright 2006 ACS on STN, Registry No. 335094-03-6.
Registry Copyright 2006 ACS on STN, Registry No. 335094-04-7.
Registry Copyright 2006 ACS on STN, Registry No. 335094-06-9.
Registry Copyright 2006 ACS on STN, Registry No. 335094-07-0.
Registry Copyright 2006 ACS on STN, Registry No. 335094-08-1.
Registry Copyright 2006 ACS on STN, Registry No. 335094-09-2.
Registry Copyright 2006 ACS on STN, Registry No. 335094-11-6.
Registry Copyright 2006 ACS on STN, Registry No. 335094-12-7.
Registry Copyright 2006 ACS on STN, Registry No. 335094-13-8.
Registry Copyright 2006 ACS on STN, Registry No. 335094-14-9.
Registry Copyright 2006 ACS on STN, Registry No. 335094-15-0.
Registry Copyright 2006 ACS on STN, Registry No. 335094-17-2.
Registry Copyright 2006 ACS on STN, Registry No. 335094-20-7.
Registry Copyright 2006 ACS on STN, Registry No. 335094-21-8.
Registry Copyright 2006 ACS on STN, Registry No. 335094-22-9.
Registry Copyright 2006 ACS on STN, Registry No. 335094-23-0.
Registry Copyright 2006 ACS on STN, Registry No. 335094-24-1.
Registry Copyright 2006 ACS on STN, Registry No. 335094-25-2.
Registry Copyright 2006 ACS on STN, Registry No. 335094-26-3.
Registry Copyright 2006 ACS on STN, Registry No. 335094-27-4.
Registry Copyright 2006 ACS on STN, Registry No. 335094-29-6.
Registry Copyright 2006 ACS on STN, Registry No. 335094-31-0.
Registry Copyright 2006 ACS on STN, Registry No. 335120-54-2.
Registry Copyright 2006 ACS on STN, Registry No. 335120-56-4.
Registry Copyright 2006 ACS on STN, Registry No. 335120-58-6.
Registry Copyright 2006 ACS on STN, Registry No. 335120-60-0.
Registry Copyright 2006 ACS on STN, Registry No. 335120-62-2.
Registry Copyright 2006 ACS on STN, Registry No. 335120-64-4.
Registry Copyright 2006 ACS on STN, Registry No. 335120-66-6.
Registry Copyright 2006 ACS on STN, Registry No. 335120-68-8.
Registry Copyright 2006 ACS on STN, Registry No. 335120-70-2.
Registry Copyright 2006 ACS on STN, Registry No. 335120-72-4.
Registry Copyright 2006 ACS on STN, Registry No. 335120-74-6.
Registry Copyright 2006 ACS on STN, Registry No. 335120-76-8.
Registry Copyright 2006 ACS on STN, Registry No. 335120-78-0.
Registry Copyright 2006 ACS on STN, Registry No. 335120-82-6.
Registry Copyright 2006 ACS on STN, Registry No. 335120-84-8.
Registry Copyright 2006 ACS on STN, Registry No. 335120-87-1.
Registry Copyright 2006 ACS on STN, Registry No. 335120-89-3.
Registry Copyright 2006 ACS on STN, Registry No. 335120-91-7.
Registry Copyright 2006 ACS on STN, Registry No. 335120-93-9.
Registry Copyright 2006 ACS on STN, Registry No. 335120-95-1.
Registry Copyright 2006 ACS on STN, Registry No. 335120-97-3.
Registry Copyright 2006 ACS on STN, Registry No. 335120-99-5.
Registry Copyright 2006 ACS on STN, Registry No. 335121-01-2.
Registry Copyright 2006 ACS on STN, Registry No. 335121-03-4.
Registry Copyright 2006 ACS on STN, Registry No. 335121-05-6.
Registry Copyright 2006 ACS on STN, Registry No. 335121-07-8.
Registry Copyright 2006 ACS on STN, Registry No. 335121-11-4.
Registry Copyright 2006 ACS on STN, Registry No. 335121-13-6.
Registry Copyright 2006 ACS on STN, Registry No. 335121-23-8.
Registry Copyright 2006 ACS on STN, Registry No. 335121-25-0.
Registry Copyright 2006 ACS on STN, Registry No. 335121-27-2.
Registry Copyright 2006 ACS on STN, Registry No. 335121-31-8.
Registry Copyright 2006 ACS on STN, Registry No. 335121-33-0.
Registry Copyright 2006 ACS on STN, Registry No. 335121-35-2.
Registry Copyright 2006 ACS on STN, Registry No. 335121-39-6.
Registry Copyright 2006 ACS on STN, Registry No. 335121-41-0.
Registry Copyright 2006 ACS on STN, Registry No. 335121-43-2.
Registry Copyright 2006 ACS on STN, Registry No. 335121-45-4.
Registry Copyright 2006 ACS on STN, Registry No. 335121-49-8.
Registry Copyright 2006 ACS on STN, Registry No. 336120-14-0.
Registry Copyright 2006 ACS on STN, Registry No. 336120-15-1.
Registry Copyright 2006 ACS on STN, Registry No. 336120-16-2.
Registry Copyright 2006 ACS on STN, Registry No. 336120-17-3.
Registry Copyright 2006 ACS on STN, Registry No. 336120-19-5.
Registry Copyright 2006 ACS on STN, Registry No. 336120-20-8.
Registry Copyright 2006 ACS on STN, Registry No. 336120-21-9.
Registry Copyright 2006 ACS on STN, Registry No. 336120-22-0.
Registry Copyright 2006 ACS on STN, Registry No. 336120-23-1.
Registry Copyright 2006 ACS on STN, Registry No. 336120-24-2.

Registry Copyright 2006 ACS on STN, Registry No. 336120-25-3.
Registry Copyright 2006 ACS on STN, Registry No. 336120-26-4.
Registry Copyright 2006 ACS on STN, Registry No. 336120-27-5.
Registry Copyright 2006 ACS on STN, Registry No. 336120-28-6.
Registry Copyright 2006 ACS on STN, Registry No. 336120-29-7.
Registry Copyright 2006 ACS on STN, Registry No. 336120-30-0.
Registry Copyright 2006 ACS on STN, Registry No. 336120-31-1.
Registry Copyright 2006 ACS on STN, Registry No. 336120-33-3.
Registry Copyright 2006 ACS on STN, Registry No. 337317-89-2.
Registry Copyright 2006 ACS on STN, Registry No. 337317-92-7.
Registry Copyright 2006 ACS on STN, Registry No. 337317-95-0.
Registry Copyright 2006 ACS on STN, Registry No. 337317-98-3.
Registry Copyright 2006 ACS on STN, Registry No. 337318-01-1.
Registry Copyright 2006 ACS on STN, Registry No. 337318-07-7.
Registry Copyright 2006 ACS on STN, Registry No. 337318-10-2.
Registry Copyright 2006 ACS on STN, Registry No. 337318-13-5.
Registry Copyright 2006 ACS on STN, Registry No. 337318-16-8.
Registry Copyright 2006 ACS on STN, Registry No. 337318-22-6.
Registry Copyright 2006 ACS on STN, Registry No. 337318-25-9.
Registry Copyright 2006 ACS on STN, Registry No. 337318-28-2.
Registry Copyright 2006 ACS on STN, Registry No. 337318-31-7.
Registry Copyright 2006 ACS on STN, Registry No. 337318-34-0.
Registry Copyright 2006 ACS on STN, Registry No. 337318-37-3.
Registry Copyright 2006 ACS on STN, Registry No. 337318-43-1.
Registry Copyright 2006 ACS on STN, Registry No. 337318-46-4.
Registry Copyright 2006 ACS on STN, Registry No. 337318-49-7.
Registry Copyright 2006 ACS on STN, Registry No. 337318-55-5.
Registry Copyright 2006 ACS on STN, Registry No. 337318-58-8.
Registry Copyright 2006 ACS on STN, Registry No. 337318-64-6.
Registry Copyright 2006 ACS on STN, Registry No. 337318-67-9.
Registry Copyright 2006 ACS on STN, Registry No. 337318-70-4.
Registry Copyright 2006 ACS on STN, Registry No. 337318-85-1.
Registry Copyright 2006 ACS on STN, Registry No. 337318-88-4.
Registry Copyright 2006 ACS on STN, Registry No. 337318-91-9.
Registry Copyright 2006 ACS on STN, Registry No. 337318-94-2.
Registry Copyright 2006 ACS on STN, Registry No. 337318-97-5.
Registry Copyright 2006 ACS on STN, Registry No. 337319-03-6.
Registry Copyright 2006 ACS on STN, Registry No. 337319-09-2.
Registry Copyright 2006 ACS on STN, Registry No. 337319-12-7.
Registry Copyright 2006 ACS on STN, Registry No. 337319-21-8.
Registry Copyright 2006 ACS on STN, Registry No. 337319-24-1.
Registry Copyright 2006 ACS on STN, Registry No. 337319-30-9.
Registry Copyright 2006 ACS on STN, Registry No. 337319-33-2.
Registry Copyright 2006 ACS on STN, Registry No. 337319-36-5.
Registry Copyright 2006 ACS on STN, Registry No. 33 73 19-42-3.
Registry Copyright 2006 ACS on STN, Registry No. 337319-48-9.
Registry Copyright 2006 ACS on STN, Registry No. 337331-00-7.
Registry Copyright 2006 ACS on STN, Registry No. 337332-12-4.
Registry Copyright 2006 ACS on STN, Registry No. 337333-42-3.
Registry Copyright 2006 ACS on STN, Registry No. 337334-25-5.
Registry Copyright 2006 ACS on STN, Registry No. 337338-22-4.
Registry Copyright 2006 ACS on STN, Registry No. 337338-52-0.
Registry Copyright 2006 ACS on STN, Registry No. 400867-22-3.
WPINDEX Copyright 2006 The Thomson Corp on STN, Accession No. 1995-275237, Abstract of WO 1995/019978 A1, (Icos-N) Icos Corp, et al., (Jul. 27, 1995).
WPINDEX Copyright 2006 The Thomson Corp on STN, Accession No. 1997-528820, Abstract of EP 0 803 505 A1, (Adir) Adir & Cic, et al. (Oct. 29, 1997).
WPINDEX Copyright 2006 The Thomson Corp on STN, Accession No. 1990-068877, Abstract of EP 357122 A, (Duin) Duphar Int Res BV (Sep. 28, 1993).
Ardill, et al., 1990, "X=Y-ZH compounds as potential 1,3-dipoles, Part 29. The iminium ion route to azomethine ylides. Reaction of cyclic secondary amines with mono- and bi-functional aldehydes," Tetrahedron 46(18):6449-6466.
Audia et al., 1996, "Potent, selective tetrahydro-beta-carboline antagonists of the serotonin B contractile receptor in the rat stomach fundus," J. Med. Chem. 39:2773-2780.
Database Accession No. 84862, 570837, 578504, 585452, 690268 (XRN) accompanied by Aghbalian et al., 1972, "Synthesis Based on Harmine and Tetrahydroharmine," Armyanskii Khimicheskii Zhurnal 25:689-692; Partial European Search Report for EP 11178488 dated May 9, 2012, p. 4.
Database REAXYS [Online], Elsevier Information Systems GmbH, Frankfurt/Main: XP002675485, Database Accession No. 84862, 230057, 306267 (XRN), accompanied by Fischer, 1897, "Über Harmin und Harmalin," Ber. Dtsch. Chem. Ges, 30(3):2481-2489; Fischer, 1901, "Chemische Studien der Alkaloide der Steppenrante (Peganum Harmala)," Chem. Zentralbl. 72(1):957-959; Partial European Search Report for EP11178488 dated May 9, 2012, p. 2.
Database REAXYS [Online], Elsevier information Systems GmbH, Frankfurt/Main XP002675486, Database Accession No. 207280, 3918373 (XRN), accompanied by Fischer, 1914, "Über Harmin mid Harmalin," Ber. Dtsch. Chem. Ges. 47:99-107 ; Partial European Search Report for EP11178488 dated May 9, 2012, p. 3.
Final Office Action mailed Jul. 26, 2012 from the United States Patent and Trademark Office for U.S. Appl. No. 13/040,614, filed Mar. 4, 2011.
Hino et al., 1990, "2-Hydroxy-1-substituted-1,2,3,4-Tetrahydro-β-carbolines. The Pictet-Spengler Reaction of N-Hydroxytryptamine with Aldehydes," Chem. & Pharm. Bull. 38(1):59-64.
Iakhontov et al., 1958, "Reduction of Derivatives of Harmine with Sodium Borohydride to Derivatives of Py-Tetrahydroharmine" Zhurnal Obshchei Khimii 28(11):3139-3141.
Kawashima et al., 1995, "Synthesis and pharmacological evaluation of 1,2,3,4-tetrahydro-β-carboline derivatives," Chem. Pharm. Bull. 43(5):783-787.
Kawate et al., 1999, "Chiral Auxiliary Approach to the Asymmetric Pictet-Spengler Reaction of Tryptamines," Heterocycles 50(2):1033-1039.
Lehmann et al., 1997, "Lactamisation of 4,9-Dihydropyrano [3,4-b] indol-1(3H)-ones. A New Synthetic Route to the beta-Carboline Ring System," Archiv der Pharmazie 320(1):30-36.
Lehnert et al., 1994, "DNA topoisomerase II inhibition by substituted 1,2,3,4-tetrahydro-β-carboline derivatives," Bioorganic & Medicinal Chemistry Letters 4(20):2411-2416.
McNulty et al., 1991, "Diastereoselective Pictet-Spengler reaction of E-(Boc) prolinal: a biomimetic synthesis of eudistomins H and I, and woodinine," Tetrahedron Letters 32(37):4875-4878.
Non-Final Office Action mailed Apr. 4, 2012 from the United States Patent and Trademark Office for U.S. Appl. No. 12/506,485, filed Jul. 21, 2009.
Non-Final Office Action mailed Jan. 9. 2012 from the United States Patent and Trademark Office for U.S. Appl. No. 13/040,614, filed Mar. 4, 2011.
Response filed Aug. 22, 2012 to Non-Final Office Action mailed Apr. 4, 2012 from the United States Patent and Trademark Office for U.S. Appl. No. 12/506,485, filed Jul. 21, 2009.
Response filed Jul. 6, 2012 to Non-Final Office Action mailed Jan. 9, 2012 from the United States Patent and Trademark Office for U.S. Appl. No. 13/040,614, filed Mar. 4, 2011.
Rubtsov et al., 1959, "Synthesis of Py-N-Alkyltetrahydroharmines" Zhurnal Obshehei Khimii 29:3232-3235.
Saiga et al., 1987, "Synthesis of 1,2,3,4-tetrahydro-beta-carboline derivatives as hepatoprotective agents. III. Introduction of substituents onto methyl 1,2,3,4-tetrahydro-beta-carboline-2-carbodithioate," Chem. Pharm. Bull. 35(8), 3284-3291.
Schonenberger et al., 1986, "Fragmentation of Optically Active (1-Phenylethyl)- and (1-Naphthylethyl) ureas in Refluxing Alcohols: Easy Preparation of Optically Active Amines of High Optical Purity," Helvetica Chimica Acta 69(6):1486-1497.
Siddiqui et al., 1992, "Preparation of Tetrahydroharmine Analogues—Their Antibacterial, Bronchodilator and Cytotoxic Activity and Effect on Central Nervous System," Proc. Pakistan Acad. Sci. 29(4):285-298.
Soe et al., 1995, "Asymmetric Pictet-Spengler reaction with a chiral N-(β-3-indolyl) ethyl-l-methylbenzulamine," Tetrahedron Letters 36(11):1857-1860.
Solomina et al., 1990, "Synthesis and Pharmacological Properties of 1-R-2-[3'-R'-Amino-2-Hydroxypropyl]- 1,2,3,4-Tetrahydro-β-Carbolines," Chem. Pharm. Bull. 24(4):272-275.
Tsuji et al., 2002, "Pictet-Spengler Reaction of Nitrones and Imines Catalyzed by Yb(OTf)3-TMSCI," Chem. Lett. 4: 428-429.

Wu et al., 2002, "A Versatile Linkage Strategy for Solid-Phase Synthesis of N,N-Dimethyltryptamines and β-Carbolines," Organic Letters 4(23):4033-4036.

Yamada et al., 1998, "Chiral Lewis Acid-Mediated Enantioselective Pictet-Spengler Reaction of $N_b$-Hydroxytryptamine with Aldehydes," J. Org. Chem. 63(18):6348-6354.

American Macular Degeneration Foundation (AMDF)—Wet Type AMD, http://www.macular.org/wet.html (last visited May 19, 2011).

Boulton et al., 1998, "VEGF localisation in diabetic retinopathy," Br. J. Ophthalmol. 82:561-568.

D'Amato et al., 1995, "Angiogenesis Inhibition in Age-Related Macular Degeneration," Ophthalmology 102(9):1261-1262.

Honda et al., 2000, "Experimental subretinal neovascularization is inhibited by adenovirus-mediated soluble VEGF/flt-1 receptor gene transfection: a role of VEGF and possible treatment for SRN in age-related macular degeneration." Gene Therapy 7:978-985.

Inoue et al., 1998, "Vascular Endothelial Growth Factor (VEGF) Expression in Human Coronary Atherosclerotic Lesions: Possible Pathophysiological Significance of VEGF in Progression of Atherosclerosis," Circulation 98:2108-2116.

Kvanta et al., 1996, "Subfoveal Fibrovascular Membranes in Age-Related Macular Degeneration Express Vascular Endothelial Growth Factor," Ophthalmol. Vis. Sci. 37:1929-1934.

Notice of Allowance mailed Jul. 13, 2011 from the United States Patent and Trademark Office for U.S. Appl. No. 11/735,069, filed Apr. 13, 2007.

Notice of Allowance mailed Jul. 21, 2011 from the United States Patent and Trademark Office for U.S. Appl. No. 11/765,871, filed Jun. 20, 2007.

Ray et al., Mar. 2004, "Association of the VEGF Gene With Proliferative Diabetic Retinopathy But Not Proteinuria in Diabetes," Diabetes 53:861-864.

Response filed Jan. 5, 2011 to Non-Final Office Action mailed Jun. 6, 2010 from the United States Patent and Trademark Office for U.S. Appl. No. 11/735,069, filed Apr. 13, 2007.

Response filed Jun. 3, 2011 to Final Office Action mailed Mar. 16, 2011 from the United States Patent and Trademark Office for U.S. Appl. No. 11/735,069, filed Apr. 13, 2007.

Response filed May 23, 2011 to Non-Final Office Action mailed Nov. 11, 2010 from the United States Patent and Trademark Office for U.S. Appl. No. 11/765,871, filed Jun. 20, 2007.

Stompor et al., 2002, "Selected Growth Factors in Peritoneal Dialysis: Their Relationship to Markers of Inflammation. Dialysis Adequacy, Residual Renal Function, and Peritoneal Membrane Transport," Perit. Dial. Int. 22:670-676.

Taichmann et al., 1997, "Human neutrophils secrete vascular endothelial growth factor," J. Leukoc. Biol. 62:397-400.

Venkov et al., 1999 "Synthesis of 2-Acyltetrahydro-β-Carbolines by an Intramolecular α-Amidoalkylation Reaction," Synthetic Communications 29(3):487-494.

Xia et al., 2003, "Transgenic delivery of VEGF to mouse skin leads to an inflammatory condition resembling human psoriasis," Blood 102:161-168.

* cited by examiner

CARBOLINE DERIVATIVES USEFUL IN THE INHIBITION OF ANGIOGENESIS

CROSS REFERENCE TO RELATED APPLICATION

This application is a continuation of U.S. application Ser. No. 11/107,783, filed Apr. 18, 2005, now U.S. Pat. No. 7,767,689 currently allowed, which is a continuation-in-part of U.S. application Ser. No. 11/079,420, filed Mar. 15, 2005, now U.S. Pat. No. 7,601,840, issued Oct. 13, 2009, which claims the benefit of and priority to U.S. Provisional Application No. 60/552,725, filed Mar. 15, 2004, which applications are incorporated herein by reference in their entireties. This application also claims priority to International Application No. PCT/US2005/08481, filed Mar. 15, 2005, which application is incorporated herein by reference in its entirety.

STATEMENT REGARDING FEDERALLY SPONSORED RESEARCH OR DEVELOPMENT

This invention was made with government support under Federal Award ID 1R43CA108330-01 awarded by the National Institutes of Health. The government has certain rights in the invention.

FIELD OF THE INVENTION

The present invention relates to methods and compounds for inhibiting angiogenesis. More particularly, the present invention relates to methods and compounds for inhibiting angiogenesis.

BACKGROUND OF THE INVENTION

Aberrant angiogenesis plays a critical role in the pathogenesis of numerous diseases, including malignant, ischemic, inflammatory and immune disorders (Carmeliet, *Nat. Med.*, 9(6):653-60 (2003), Ferrara, *Semin. Oncol.*, 29(6 Suppl 16): 10-4 (2002)). The best-known of these disorders are cancer, exudative macular degeneration and diabetic retinopathy (DR), the last two of which are leading cause of blindness in the United States (Witmer et al., *Prog. Retin Eye Res.*, 22(1): 1-29 (2003), Clark et al., *Nat. Rev. Drug Discovery*, 2:448-459 (2003)). During the last decade our understanding of the molecular basis of angiogenesis has grown considerably. Numerous cytokines and growth factors that stimulate angiogenesis, such as VEGF, FGF-2, PDGF, IGF-1, TGF, TNF-α, G-CSF have been identified (Ferrara et al., *Nat. Med.*, 5(12): 1359-64 (1999), Kerbel et al., *Nat. Rev. Cancer*, 2(10):727-39 (2002), Rofstad et al., *Cancer Res.*, 60(17):4932-8 (2000)). Among these growth factors, Vascular Endothelial Growth Factor (VEGF) plays a central role in angiogenesis (Ferrara, *Semin. Oncol.*, 29(6 Suppl 16): 10-4 (2002)).

VEGF, also known as VEGF-A, was initially identified for its ability to induce vascular permeability and to promote vascular endothelial cell proliferation (Leung et al., *Science*, 246:1306-1309 (1989), Plouet et al., *EMBO J.*, 8:3801-3806 (1989), Connolly et al., *J. Biol. Chem.*, 264:20017-20024 (1989)). VEGF is encoded by a single gene that gives rise to four isoforms by alternative splicing (Tischer et al., *J. Biol. Chem.*, 266:11947-11954 (1991)). All four isoforms share the same unusually long and GC rich 5'-UTR, as well as a 3'-UTR that includes multiple RNA stability determinants. The receptors VEGFR-2 (also known as KDR or Flk-1) and VEGFR-1 (previously known as Flt1) recognize the dimeric form of VEGF (Ortega et al., *Front. Biosci.*, 4:D141-52 (1999), Sato et al., *Annals of New York Academy of Science*, 902:201-207, (2000)). The highly specific VEGFR-2 receptor is expressed on endothelial cells. VEGF binding to the VEGFR-2 receptor activates the receptor's tyrosine kinase activity, leading to endothelial cell proliferation, differentiation and primitive vessel formation (Shalaby et al., *Nature*, 376:62-66, (1995)). VEGFR-1 inhibits endothelial cell growth either by acting as a decoy or by suppressing signaling pathways through VEGFR-2 (Fong et al., *Nature*, 376:66-70 (1995)).

Over 30 years ago, it was proposed that inhibition of tumor angiogenesis could be an effective approach for the treatment of cancer (Folkman, *N. Engl. J. Med.*, 285(21):1182-6 (1971)). VEGF and its receptor have been demonstrated to have a central role in tumor angiogenesis, especially in the early stages of tumor growth (Hanahan et al., *Cell*, 86:353-364, 1996)). Indeed, increased levels of VEGF expression have been correlated with microvessel density in primary tumor tissues (Gasparini et al., *J. Natl. Cancer Inst.*, 89:139-147 (1997)). Moreover, increased levels of the VEGF transcript are found in virtually all of the common solid tumors (Ferrara et al., *Endocr. Rev.*, 18:4-25, 1997)). In general, tumor-bearing patients have higher levels of VEGF compared to those in tumor-free individuals, and high VEGF levels in serum/plasma are associated with poor prognosis (Dirix et al., *Br. J. Cancer*, 76:238-243 (1997)). Consistent with the role of VEGF in tumor angiogenesis, VEGF null embryonic stem cells showed a dramatically reduced ability to form tumors in nude mice (Carmeliet et al., *Nature*, 380:435-439 (1996)). Direct evidence for the involvement of VEGF in tumorgenesis was demonstrated by using specific antibodies against VEGF in human xenografts implanted in nude mice (Kim et al., *Nature*, 362:841-844 (1993), Hichlin et al., *Drug Discovery Today*, 6:517-528 (2001)). In these studies, the inhibition of tumor growth correlated positively with decreased vessel formation in the antibody-treated tumors. Subsequent experiments using the soluble receptors substantiated the importance of VEGF activity in tumor growth (Lin et al., *Cell Growth Differ.*, 9(1):49-58 (1998)), and demonstrated that inactivation of VEGF by specific antibody treatment directly resulted in a nearly complete suppression of tumor-associated neovascularization (Borgstrom et al., *Prostate*, 35:1-10 (1998), Yuan et al., *Proc. Natl. Acad. Sci. USA*, 93:14765-14770 (1996)).

In exudative macular degeneration and diabetic retinopathy, pre-clinical experiments and clinical trials have demonstrated that over production of VEGF is critical for aberrant retinal or choroidal neovascularization (reviewed in Witmer et al., *Prog. Retin Eye Res.*, 22(1):1-29 (2003)). Evidence has been obtained that intra-ocular VEGF levels are strongly correlated with active retinal/choroidal neovascularization (CNV) in patients with diseases such as diabetic retinopathy and wet form macular degeneration (Funatsu et al., *Am. J. Ophthalmol.*, 133(4):537-43 (2002), Lip et al., *Ophthalmology*, 108(4):705-10 (2001)). In addition, studies using transgenic mice demonstrated that overexpression of VEGF in retinal pigment epithelial cells or photoreceptor cells results in choroidal or retinal neovasucularization (Schwesinger et al., *Am. J. Pathol.*, 158(3):1161-72 (2001), Ohno-Matsui et al., *Am. J. Pathol.*, 160(2):711-9 (2002)). In recent studies neutralizing antibodies, soluble receptor, receptor antagonists, or siRNA have proven efficacious in reducing VEGF-mediated blood vessel formation in animal models and in the clinic. (Eyetech Study Group, 22(2):143-52 (2002), Krzystolik et al., *Arch. Ophthalmol.*, 120(3):338-46 (2002), Shen et al., *Lab Invest.*, 82(2):167-82 (2002), Honda et al., *Gene Ther.*, 7(11):978-85 (2000), Saishin et al., *J. Cell Physiol.*, 195(2):241-8 (2003)).

VEGF expression is regulated by a number of factors and agents including cytokines, growth factors, steroid hormones and chemicals, and mutations that modulate the activity of oncogenes such as ras or the tumor suppressor gene VHL (Maxwell et al., *Nature*, 399:271-275 (1999), Rak et al., *Cancer Res.*, 60:490-498 (2000)). Nevertheless, hypoxia is the most significant physiologic signal for regulating VEGF expression. Hypoxia results in enhanced VEGF expression by increasing both the transcription rate and stability of the VEGF transcript (Ikeda et al., *J. Biol. Chem.* 270:19761-19766 (1995), Stein et al., *Mol. Cell. Biol.* 18:3112-3119 (1998), Levy et al., *J. Biol. Chem.* 271:2746-2753 (1996)). Hypoxia-inducible factor 1α (HIF-1α) is a transcription factor that increases VEGF gene expression in cells undergoing hypoxia by binding to the hypoxia response element (HRE) located in the VEGF promoter (Liu et al., *Circ. Res.*, 77:638-643 (1995), Semenza, *Annu. Rev. Cell. Dev. Biol.*, 5:551-578 (1999)). Both the stability and translation efficiency of the VEGF transcript is influenced by sequences in the 5'- and 3'-untranslated regions (UTRs). The 5'-UTR contains an internal ribosomal entry site (IRES) and mediates cap-independent translation initiation while the 3'-UTR harbors multiple AU-rich (AUR) stability determinants that have been previously shown to regulate turnover of VEGF mRNA. In addition, the translation initiation of the VEGF transcript is uniquely regulated. Under hypoxic conditions, translation of most cellular transcripts mediated by cap-dependent translation initiation process is greatly impaired (Kraggerud et al., *Anticancer Res.*, 15:683-686 (1995)). Initiation of translation of the VEGF mRNA, however, is unique under hypoxic conditions in that it is mediated via an internal ribosome entry site (IRES) within the VEGF 5'UTR (Stein et al., *Mol. Cell. Biol.* 18:3112-3119 (1998), Levy et al., *J. Biol. Chem.* 271:2746-2753 (1996), Huez et al., *Mol. Cell. Biol.*, 18:6178-6190 (1998), Akiri et al., *Oncogene*, 17:227-236 (1998)). Thus, this form of post-transcriptional regulation permits cells to produce large amounts of VEGF protein to support either further tumor growth or aberrant neovascularization in ocular diseases under hypoxic conditions. The stability of VEGF mRNA is also greatly enhanced as a consequence of the binding of factors to elements in the 3'-UTR (Goldberg et al., *J. Biol. Cell. J. Biol. Chem.*, 277(16):13635-40 (2002)).

There is a large body of experimental evidence indicating that tumor growth can be inhibited by the prevention of neovascularization (Lin et al., *Cell Growth Differ.*, 9(1):49-58 (1998), Zhu et al., *Invest. New Drugs*, 17:195-212 (1999)). Tumor vessels are generally immature and constantly undergo remodeling (Carmeliet, *Nat. Med.*, 9(6):653-60 (2003), Carmeliet et al., *Nature*, 407:249-257 (2000)). Active and aberrant angiogenesis is the result of a disruption in the normal balance of proangiogenic and anti-angiogenic factors, including various cytokines, growth factors and steroid hormones. Despite the complexity of the regulation of tumor angiogenesis, accumulated evidence indicates that targeting a single proangiogenic factor might be sufficient to inhibit tumor angiogenesis and suppress tumor growth (Kim et al., *Nature*, 362:841-844 (1993), Millauer et al., *Nature*, 367:576-579 (1994), Fong et al., *Cancer Res.*, 59:99-106 (1999)). Among many angiogenesis targets, VEGF and its receptor are most attractive (Carmeliet, *Nat. Med.*, 9(6):653-60 (2003), Ortega et al., *Front. Biosci.*, 4:D141-52 (1999)). As noted above, treatment with a monoclonal antibody specifically targeting VEGF inhibited the growth of tumors in human xenografts implanted in nude mice. Subsequently, various approaches designed to inactivate VEGF signaling have been tested in tumor models and have proven to be highly effective in a broad range of tumor cell lines including carcinomas, sarcomas and gliomas (Ferrara et al., *Endocr. Rev.*, 18:4-25, 1997), Kim et al., *Nature*, 362:841-844 (1993), Millauer et al., *Nature*, 367:576-579 (1994), Fong et al., *Cancer Res.*, 59:99-106 (1999), Geng et al., *Cancer Res.*, 61:2413-2419 (2001)). In addition, inhibition of VEGF by anti-VEGF antibody did not result in significant side effects in fully developed rodents or primates (Ryan et al, *Toxicol. Pathol.*, 27:78-86 (1999), Ferrara et al., *Nat. Med.*, 4:336-340 (1998)). Taken together, these results indicate that VEGF is a valid target for the development of tumor therapy. Indeed, a number of clinical trials are underway using VEGF inhibitors (Matter, *Drug Discovery Today*, 6:1005-1024 (2001), Hichlin et al., *Drug Discovery Today*, 6:517-528 (2001)).

Although several pro-angiogenic factors are implicated in the pathology of exudative age-related macular degeneration, VEGF appears to be the most critical in the pathogenesis and development of this disease (Witmer et al., *Prog. Retin Eye Res.*, 22(1):1-29 (2003), Holash et al., *Science*, 284:1994-1998 (1999)). Data from preclinical experiments and clinical trials have demonstrated that blockade of VEGF alone is sufficient to alleviate or stabilize disease progression (Eyetech Study Group, 22(2):143-52 (2002), Krzystolik et al., *Arch. Ophthalmol.*, 120(3):338-46 (2002), Shen et al., *Lab Invest.*, 82(2):167-82 (2002), Honda et al., *Gene Ther.*, 7(11): 978-85 (2000), Saishin et al., *J. Cell Physiol.*, 195(2):241-8 (2003)). For example, inhibition of VEGFR signaling by a specific tyrosine kinase inhibitor is sufficient to completely prevent retinal neovascularization in a murine retinopathy of prematurity model (Ozaki H, Seo M S, Ozaki et al., *Am. J. Pathol.*, 156(2):697-707 (2000)). Furthermore, it has recently been demonstrated that small interfering RNAs (siRNA) directed against murine VEGF significantly inhibited ocular neovascularization after laser photocoagulation in a mouse model (Reich et al., *Mol. Vis.* 30; 9:210-6 (2003)). These results indicate that selective inhibition of VEGF expression is achievable and offers validation of this approach for the treatment of ocular neovascular diseases such as exudative macular degeneration and diabetic retinopathy.

Three approaches have been used to inhibit VEGF activity, including (1) neutralization of VEGF activity by using a specific antibody, soluble VEGF receptor or aptamer oligos against the VEGF/VEGFR interaction (Kim et al., *Nature*, 362:841-844 (1993), Lin et al., *Cell Growth Differ.*, 9(1):49-58 (1998), Borgstrom et al., *Prostate*, 35:1-10 (1998), Zhu et al., *Invest. New Drugs*, 17:195-212 (1999), Millauer et al., *Nature*, 367:576-579 (1994), Asano et al., *Jpn. J. Cancer Res.*, 90(1):93-100 (1999), Brekken et al., *Cancer Res.*, 60(18):5117-24 (2000)); (2) inhibition of VEGFR mediated signal transduction by specific small molecule tyrosine kinase inhibitors (Fong et al., *Cancer Res.*, 59:99-106 (1999), Wedge et al., *Cancer Res.*, 60(4):970-5 (2000), Laird et al., *Cancer Res.*, 60(15):4152-60 (2000)); and (3) inhibition of VEGF/VEGFR expression by using antisense, siRNA or ribozyme (Reich et al., *Mol. Vis.* 30; 9:210-6 (2003), Parry et al., *Nucleic Acids Res.*, 27:2569-2577 (1999), Ellis et al., *Surgery*, 120:871-878 (1996), Filleur et al., *Cancer Res.*, 63(14):3919-22 (2003)). Although all of these approaches show significant inhibition of angiogenesis in vivo, they all possess significant limitations. For example, therapeutic proteins (antibody and soluble receptors) or oligos (antisense, siRNA and ribozyme) are large molecules with poor permeability that usually require parenteral administration and are costly to produce. For treatment of chronic ocular neovascularization, multiple injections may be impractical due to potential complications such as retinal detachment and procedure related infection. Moreover, tyrosine kinase inhibitors have the potential for limited specificity. VEGF is constitutively expressed at a low level in normal eyes and other tissues and thus it may be harmful to completely suppress VEGF function by administration of antibody or tyrosine kinase inhibitors systemically, especially for patients with AMD and RD many of whom are also hypertensive (Giles et al., *Cancer*, 97(8):1920-8 (2003), Sugimoto et al., *J. Biol. Chem.*, 278 (15):12605-8 (2003), Bergsland et al., American Society of Clinical Oncology 36th Annual Meeting, 20-23 May, 2000, New Orleans, La., USA, Abstract 939), DeVore et al., American Society of Clinical Oncology 36th Annual Meeting, 20-23 May, 2000, New Orleans, La., USA, Abstract 1896).

Thus, there remains a need to develop, characterize and optimize lead molecules for the development of novel anti-angiogenesis drugs. Accordingly, it is an object of the present invention to provide such compounds.

All documents referred to herein are incorporated by reference into the present application as though fully set forth herein.

SUMMARY OF THE INVENTION

In accordance with the present invention, compounds that inhibit the expression of VEGF post-transcriptionally have been identified, and methods for their use provided.

In one aspect of the invention, compounds of Formulas (I), (II) and (III), including Formulas (I-a) to (I-l), are provided which are useful in the inhibition of VEGF production, in the inhibition of angiogenesis, and/or in the treatment of cancer, diabetic retinopathy or exudative macular degeneration.

In another aspect of the invention, methods are provided for the inhibition of VEGF production, the inhibition of angiogenesis, and/or the treatment of cancer, diabetic retinopathy, rheumatoid arthritis, psoriasis, atherosclerosis, chronic inflammation, other chronic inflammation-related diseases and disorders, obesity, or exudative macular degeneration using the compounds described herein.

In one embodiment, the invention is directed to methods for inhibiting VEGF production comprising administering a VEGF-expression inhibiting amount of at least one compound of the invention to a subject in need thereof.

In another embodiment, methods for inhibiting angiogenesis are provided comprising administering an anti-angiogenic amount of at least one compound of the invention to a subject in need thereof.

The present invention also provides methods for treating a solid tumor cancer comprising administering a therapeutically effective amount of a compound of Formula (I), or a pharmaceutically acceptable salt, hydrate, solvate, clathrate, polymorph, racemate or stereoisomer of said compound, to a subject in need thereof.

Solid tumor cancers that can be treated by the present invention include solid tumor carcinomas and solid tumor sarcomas. Solid tumor carcinomas include, but are not limited to, pediatric solid tumors, such as Wilms tumor and neuroblastoma, and carcinomas of the epidermis, such as malignant melanomas, as well as lung cancers, cervical cancers, colon cancers and renal cancers. Solid tumor sarcomas include, but are not limited to, fibrosarcomas.

The present invention also provides methods for treating a Wilms tumor comprising administering a therapeutically effective amount of a compound of Formula (I), or a pharmaceutically acceptable salt, hydrate, solvate, clathrate, polymorph, racemate or stereoisomer of said compound, to a subject in need thereof.

The present invention also provides methods for treating a neuroblastoma comprising administering a therapeutically effective amount of a compound of Formula (I), or a pharmaceutically acceptable salt, hydrate, solvate, clathrate, polymorph, racemate or stereoisomer of said compound, to a subject in need thereof.

The present invention further provides methods of treating a malignant melanoma comprising administering a therapeutically effective amount of a compound of Formula (I), or a pharmaceutically acceptable salt, hydrate, solvate, clathrate, polymorph, racemate or stereoisomer of said compound, to a subject in need thereof.

The present invention yet further provides methods for treating cervical cancer comprising administering a therapeutically effective amount of a compound of Formula (I), or a pharmaceutically acceptable salt, hydrate, solvate, clathrate, polymorph, racemate or stereoisomer of said compound, to a subject in need thereof.

The present invention also provides methods for treating lung cancer comprising administering a therapeutically effective amount of a compound of Formula (I), or a pharmaceutically acceptable salt, hydrate, solvate, clathrate, polymorph, racemate or stereoisomer of said compound, to a subject in need thereof.

The present invention also provides methods for treating colon cancer comprising administering a therapeutically effective amount of a compound of Formula (I), or a pharmaceutically acceptable salt, hydrate, solvate, clathrate, polymorph, racemate or stereoisomer of said compound, to a subject in need thereof.

The present invention further provides methods for treating a solid tumor cancer by post-transcriptionally modifying VEGF expression comprising administering a therapeutically effective amount of a compound of Formula (I), or a pharmaceutically acceptable salt, hydrate, solvate, clathrate, polymorph, racemate or stereoisomer of said compound, to a subject in need thereof.

The present invention yet further provides methods for treating a solid tumor cancer by slowing tumorigenesis at a pre-vascular stage comprising administering a therapeutically effective amount of a compound of Formula (I), or a pharmaceutically acceptable salt, hydrate, solvate, clathrate, polymorph, racemate or stereoisomer of said compound, to a subject in need thereof.

The present invention also provides methods for treating a solid tumor cancer by reducing tumor VEGF levels comprising administering a therapeutically effective amount of a compound of Formula (I), or a pharmaceutically acceptable salt, hydrate, solvate, clathrate, polymorph, racemate or stereoisomer of said compound, to a subject in need thereof.

The present invention further provides methods for treating a solid tumor cancer by reducing perivascularly sequestered VEGF comprising administering a therapeutically effective amount of a compound of Formula (I), or a pharmaceutically acceptable salt, hydrate, solvate, clathrate, polymorph, racemate or stereoisomer of said compound, to a subject in need thereof.

The present invention also provides methods of blocking VEGF mRNA translation comprising administering a therapeutically effective amount of a compound of Formula (I), or a pharmaceutically acceptable salt, hydrate, solvate, clathrate, polymorph, racemate or stereoisomer of said compound, to a subject in need thereof.

The present invention further provides methods of slowing tumorigenesis at a pre-vascular stage comprising administering a therapeutically effective amount of a compound of Formula (I), or a pharmaceutically acceptable salt, hydrate, solvate, clathrate, polymorph, racemate or stereoisomer of said compound, to a subject in need thereof.

The present invention yet further provides methods of reducing tumor VEGF levels comprising administering a therapeutically effective amount of a compound of Formula (I), or a pharmaceutically acceptable salt, hydrate, solvate, clathrate, polymorph, racemate or stereoisomer of said compound, to a subject in need thereof.

The present invention also provides methods of reducing plasma VEGF levels comprising administering a therapeutically effective amount of a compound of Formula (I), or a pharmaceutically acceptable salt, hydrate, solvate, clathrate, polymorph, racemate or stereoisomer of said compound, to a subject in need thereof.

The present invention further provides methods of reducing perivascularly sequestered VEGF comprising administering a therapeutically effective amount of a compound of Formula (I), or a pharmaceutically acceptable salt, hydrate, solvate, clathrate, polymorph, racemate or stereoisomer of said compound, to a subject in need thereof.

The present invention yet further provides methods of treating a solid tumor cancer comprising measuring plasma levels of VEGF, tumor levels of VEGF, or both, and administering administering a therapeutically effective amount of a compound of Formula (I), or a pharmaceutically acceptable salt, hydrate, solvate, clathrate, polymorph, racemate or stereoisomer of said compound, to a subject in need thereof.

The present invention also provides methods of diagnosing solid tumor cancers comprising measuring plasma levels of VEGF.

The present invention further provides methods of diagnosing solid tumor cancers comprising measuring tumor levels of VEGF.

The present invention yet further provides methods of treating a solid tumor cancer comprising administering a therapeutically effective amount of a compound of Formula (I), or a pharmaceutically acceptable salt, hydrate, solvate, clathrate, polymorph, racemate or stereoisomer thereof, together with one or more additional cancer agents to a subject in need thereof.

These and other aspects of the invention will be more clearly understood with reference to the following preferred embodiments and detailed description.

DETAILED DESCRIPTION OF THE INVENTION

Figure 1:
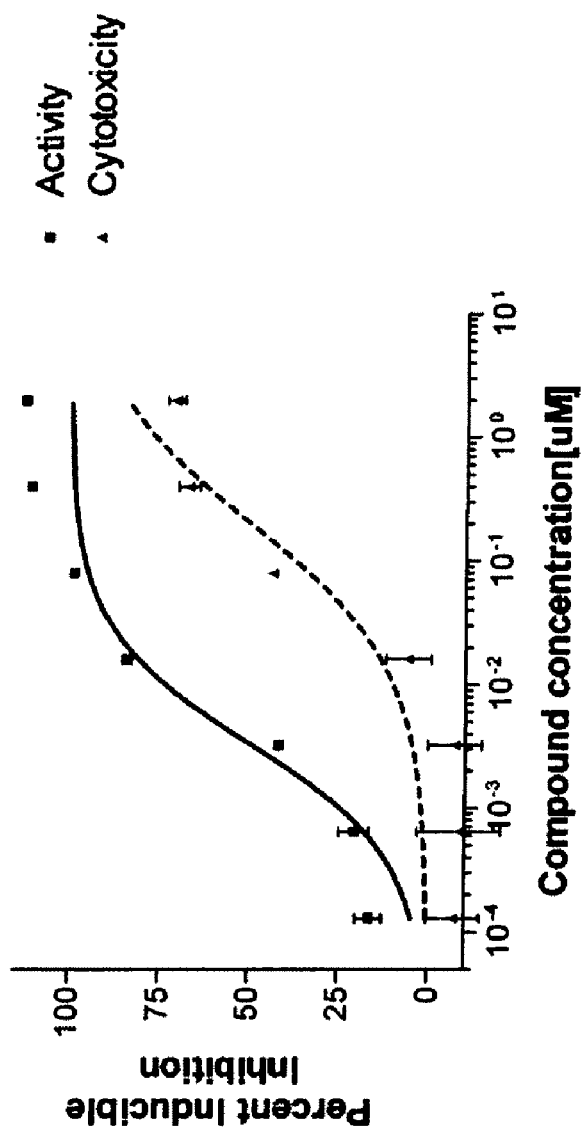
FIG. 1 illustrates inhibition of VEGF expression in a cervical cancer tumor by a certain compound of the invention.

Aberrant up-regulation of Vascular Endothelial Growth Factor (VEGF), a key factor for angiogenesis, is an important contributor to the pathogenesis of disease states such as cancer, diabetic retinopathy, rheumatoid arthritis, psoriasis, atherosclerosis, chronic inflammation, other chronic inflammation-related diseases and disorders, obesity, or exudative macular degeneration. In accordance with the present invention, compounds that inhibit the expression of VEGF post-transcriptionally have been identified, and methods for their use provided. The compounds of the invention have nanomolar to sub-nanomolar activity for the inhibition of VEGF expression.

A. Compounds of the Invention

In one aspect of the invention, compounds are provided which are useful in the inhibition of VEGF production, in the inhibition of angiogenesis, and/or in the treatment of cancer, diabetic retinopathy or exudative macular degeneration. In certain embodiments, the compounds of the invention specifically inhibit VEGF production, while in other embodiments, the compounds of the invention inhibit VEGF expression as well as that of other angiogenesis factors such as FGF-2. In this regard, pan-angiogenic inhibitor may be preferred in methods of inhibiting tumor growth, while VEGF specific inhibitors may be preferred for the treatment of ocular neovascular disorders (Eyetech Study Group, 22(2):143-52 (2002)).

The compounds of the invention generally include one or more chiral centers, and as such may exist as racemic mixtures (R/S) or as enantiomerically pure compositions. The compounds may exist as (R) or (S) isomers (when one chiral center is present) in enantiomerically pure compositions. In a preferred embodiment, the compounds of the invention are the (S) isomers and may exist as enantiomerically pure compositions comprising only the (S) isomer. As one of skill will recognize, when more than one chiral center is present, the compounds of the invention may exist as (R,R), (R,S), (S,R), (S,S), etc. isomer. Preferred compounds included (S,S) and (S,R) isomers.

As used herein, "racemic mixture" refers to compositions consisting substantially of greater than 50%, 70%, 90%, or 99% of one of the isomers.

As used herein, "enantiomerically pure" refers to compositions consisting substantially of a single isomer, preferably consisting of 90%, 92%, 95%, 98%, 99%, or 100% of a single isomer.

Preferred compounds of the present invention useful in the inhibition of VEGF production include those of Formula (I) as shown below.

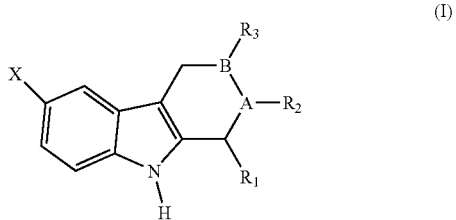

(I)

wherein,

X is hydrogen; a $C_1$ to $C_6$ alkyl, optionally substituted with one or more halogens; a hydroxyl group; a halogen; a $C_1$ to $C_5$ alkoxy, optionally substituted with a $C_6$ to $C_{10}$ aryl group;

A is C or N;

B is C or N, with the proviso that at least one of A or B is N, and that when A is N, B is C;

$R_1$ is a hydroxyl group; a $C_1$ to $C_8$ alkyl group, optionally substituted with an alkylthio group, a 5 to 10 membered heteroaryl, a $C_6$ to $C_{10}$ aryl group optionally substituted with at least one independently selected $R_o$ group; a $C_2$ to $C_8$ alkyenyl group; a $C_2$ to $C_8$ alkynyl group; a 3 to 12 membered heterocycle group, wherein the heterocycle group is optionally substituted with at least one independently selected halogen, oxo, amino, alkylamino, acetamino, thio, or alkylthio group; a 5 to 12 membered heteroaryl group, wherein the heteroaryl group is optionally substituted with at least one independently selected halogen, oxo, amino, alkylamino, acetamino, thio, or alkylthio group; or a $C_6$ to $C_{10}$ aryl group, optionally substituted with at least one independently selected $R_o$ group;

$R_o$ is a halogen; a cyano; a nitro; a sulfonyl, wherein the sulfonyl is optionally substituted with a $C_1$ to $C_6$ alkyl or a 3 to 10 membered heterocycle; an amino group, wherein the amino group is optionally substituted with a $C_1$ to $C_6$ alkyl, —C(O)—$R_b$, —C(O)O—$R_b$, a sulfonyl, an alkylsulfonyl, a 3 to 10 membered heterocycle group optionally substituted with a —C(O)O—$R_a$; —C(O)—NH—$R_b$; a 5 to 6 membered heterocycle; a 5 to 6 membered heteroaryl; a $C_1$ to $C_6$ alkyl group, wherein the alkyl group is optionally substituted with at least one independently selected hydroxyl, halogen, amino, or 3 to 12 membered heterocycle group, wherein the amino group and heterocycle group are optionally substituted with at least one independently selected $C_1$ to $C_4$ alkyl group, which $C_1$ to $C_4$ alkyl group is optionally substituted with at least one independently selected $C_1$ to $C_4$ alkoxy group, amino group, alkylamino group, or 5 to 10 membered heterocycle group; a —C(O)—$R_n$ group; or an —O$R_a$ group;

$R_a$ is hydrogen; $C_2$ to $C_8$ alkylene; a —C(O)O—$R_b$ group; a —C(O)—NH—$R_b$; a $C_1$ to $C_8$ alkyl, wherein the alkyl group is optionally substituted with at least one independently selected hydroxyl, halogen, $C_1$ to $C_4$ alkoxy, amino, alkylamino, acetamide, —C(O)—$R_b$, —C(O)O—$R_b$, $C_6$ to $C_{10}$ aryl, 3 to 12 membered heterocycle, or 5 to 12 heteroaryl group, further wherein the alkylamino is optionally substituted with a hydroxyl, a $C_1$ to $C_4$ alkoxy, or a 5 to 12 membered heteroaryl optionally substituted with a $C_1$ to $C_4$ alkyl, further wherein the acetamide is optionally substituted with a $C_1$ to $C_4$ alkoxy, sulfonyl, or alkylsulfonyl, further wherein and the heterocycle group is optionally substituted with a $C_1$ to $C_4$ alkyl optionally substituted with a hydroxyl group, —C(O)—$R_n$, —C(O)O—$R_n$, or an oxo group;

$R_b$ is hydroxyl; an amino; an alkylamino, wherein the alkylamino is optionally substituted with a hydroxyl, an amino, an alkylamino, a $C_1$ to $C_4$ alkoxy, a 3 to 12 membered heterocycle optionally substituted with at least one independently selected $C_1$ to $C_6$ alkyl, oxo, —C(O)O—$R_a$, or a 5 to 12 membered heteroaryl optionally substituted with a $C_1$ to $C_4$ alkyl; a $C_1$ to $C_4$ alkoxy; a $C_2$ to $C_8$ alkenyl; a $C_2$ to $C_8$ alkynyl; a $C_6$ to $C_{10}$ aryl, wherein the aryl is optionally substituted with at least one independently selected halogen or $C_1$ to $C_4$ alkoxy; a 5 to 12 membered heteroaryl; 3 to 12 membered heterocycle group, wherein the heterocycle is optionally substituted with at least one independently selected acetamide, —C(O)O—$R_n$, 5 to 6 membered heterocycle, or $C_1$ to $C_6$ alkyl optionally substituted with a hydroxyl, $C_1$ to $C_4$ alkoxy, amino group, or alkylamino group; or a $C_1$ to $C_8$ alkyl, wherein the alkyl is optionally substituted with at least one independently selected $C_1$ to $C_4$ alkoxy, $C_6$ to $C_{10}$ aryl, amino, or 3 to 12 membered heterocycle group, wherein the amino and heterocycle groups are optionally substituted with at least one independently selected $C_1$ to $C_6$ alkyl, oxo, or —C(O)O—$R_n$ group;

$R_2$ is a hydrogen; a hydroxyl; a 5 to 10 membered heteroaryl group; a $C_1$ to $C_8$ alkyl group, wherein the alkyl group is optionally substituted with a hydroxyl, a $C_1$ to $C_4$ alkoxy, a 3 to 10 membered heterocycle, a 5 to 10 membered heteroaryl, or $C_6$ to $C_{10}$ aryl group; a —C(O)—$R_c$ group; a —C(O)O—$R_d$ group; a —C(O)—N($R_dR_d$) group; a —C(S)—N($R_dR_d$) group; a —C(S)—O—$R_e$ group; a —S(O$_2$)—$R_e$ group; a —C(N$R_e$)—S—$R_e$ group; or a —C(S)—S—$R_f$ group;

$R_c$ is hydrogen; an amino, wherein the amino is optionally substituted with at least one independently selected $C_1$ to $C_6$ alkyl or $C_6$ to $C_{10}$ aryl group; a $C_6$ to $C_{10}$ aryl, wherein the aryl is optionally substituted with at least one independently selected halogen, haloalkyl, hydroxyl, $C_1$ to $C_4$ alkoxy, or $C_1$ to $C_6$ alkyl group; —C(O)—$R_n$; a 5 to 6 membered heterocycle, wherein the heterocycle is optionally substituted with a —C(O)—$R_n$ group; a 5 to 6 membered heteroaryl; a thiazoleamino group; a $C_1$ to $C_8$ alkyl group, wherein the alkyl group is optionally substituted with at least one independently selected halogen, a $C_1$ to $C_4$ alkoxy, a phenyloxy, a $C_6$ to $C_{10}$ aryl, —C(O)—$R_n$, —O—C(O)—$R_n$, hydroxyl, or amino group, optionally substituted with a —C(O)O—$R_n$ group;

$R_d$ is independently hydrogen; a $C_2$ to $C_8$ alkenyl group; a $C_2$ to $C_8$ alkynyl group; a $C_6$ to $C_{10}$ aryl group, wherein the aryl is optionally substituted with at least one independently selected halogen, nitro, $C_1$ to $C_6$ alkyl, —C(O)O—$R_e$, or —O$R_e$; or a $C_1$ to $C_8$ alkyl group, wherein the alkyl group is optionally substituted with at least one independently selected halogen, $C_1$ to $C_4$ alkyl, $C_1$ to $C_4$ alkoxy, phenyloxy, $C_6$ to $C_{10}$ aryl, 5 to 6 membered heteroaryl, —C(O)—$R_n$, —O—C(O)—$R_n$, or hydroxyl group, wherein the $C_6$ to $C_{10}$ aryl group is optionally substituted with at least one independently selected halogen or haloalkyl group;

$R_e$ is a hydrogen; a $C_1$ to $C_6$ alkyl group, wherein the alkyl group is optionally substituted with at least one independently selected halogen or alkoxy group; or a $C_6$ to $C_{10}$ aryl group, wherein the aryl group is optionally substituted with at least one independently selected halogen or alkoxy group;

$R_f$ is a $C_1$ to $C_6$ alkyl group, optionally substituted with at least one independently selected halogen, hydroxyl, $C_1$ to $C_4$ alkoxy, cyano, $C_6$ to $C_{10}$ aryl, or —C(O)—$R_n$ group, wherein the alkoxy group may be optionally substituted with at least one $C_1$ to $C_4$ alkoxy group and the aryl group may be optionally substituted with at least one independently selected halogen, hydroxyl, $C_1$ to $C_4$ alkoxy, cyano, or $C_1$ to $C_6$ alkyl group;

$R_n$ is a hydroxyl, $C_1$ to $C_4$ alkoxy, amino, or $C_1$ to $C_6$ alkyl group;

$R_3$ is hydrogen or —C(O)—$R_g$;

$R_g$ is a hydroxyl group; an amino group, wherein the amino is optionally substituted with a $C_6$ to $C_{10}$ cycloalkyl group or a 5 to 10 membered heteroaryl group; or a 5 to 10 membered heterocycle group, wherein the heterocycle group is optionally substituted with a —C(O)—$R_n$ group; and n is 0, 1, 2, or 3.

As will be evident to one of skill in the art, the compounds of Formula (I) comprise at least one stereocenter (e.g., at the $R_1$ substituent), and may exist as a racemic mixture or as an enantiomerically pure composition. In a preferred embodiment, the compounds of Formula (I) are the (S) isomer, in an enantiomerically pure composition.

As used herein, the term "alkyl" generally refers to saturated hydrocarbyl radicals of straight, branched or cyclic configuration including methyl, ethyl, n-propyl, isopropyl, n-butyl, isobutyl, sec-butyl, tert-butyl, n-pentyl, n-hexyl, cyclohexyl, n-heptyl, octyl, n-octyl, and the like. In some embodiments, alkyl substituents may be include $C_1$ to $C_8$, $C_1$ to $C_6$, or $C_1$ to $C_4$ alkyl groups. The alkyl group may be optionally substituted with one or more halogen or alkoxy groups. For instance, the alkyl group may be a haloalkyl, dihaloalkyl, or trihaloalkyl.

As used herein, "alkenyl" generally refers to linear, branched or cyclic alkene radicals having one or more carbon-carbon double bonds, such as $C_2$ to $C_8$ and $C_2$ to $C_6$ alkenyl groups, including 3-prop enyl.

As used herein, "alkynyl" generally refers to linear, branched or cyclic alkyne radicals having one or more carbon-carbon triple bonds, such as $C_2$ to $C_8$ and $C_2$ to $C_6$ alkynyl groups, including hex-3-yne.

As used herein, "aryl" refers to a carbocyclic aromatic ring structure. Included in the scope of aryl groups are aromatic rings having from five to twenty carbon atoms. Aryl ring structures include compounds having one or more ring structures, such as mono-, bi-, or tricyclic compounds. Examples of aryl groups that include phenyl, tolyl, anthracenyl, fluorenyl, indenyl, azulenyl, phenanthrenyl (i.e., phenanthrene), and napthyl (i.e., napthalene) ring structures. In certain embodiments, the aryl group may be optionally substituted.

As used herein, "heteroaryl" refers to cyclic aromatic ring structures in which one or more atoms in the ring, the heteroatom(s), is an element other than carbon. Heteroatoms are typically O, S or N atoms. Included within the scope of heteroaryl, and independently selectable, are O, N, and S heteroaryl ring structures. The ring structure may include compounds having one or more ring structures, such as mono-, bi-, or tricyclic compounds. In some embodiments, the heteroaryl groups may be selected from heteroaryl groups that contain one or more heteroatoms, two or more heteroatoms, three or more heteroatoms, or four or more heteroatoms. Heteroaryl ring structures may be selected from those that contain five or more atoms, six or more atoms, or eight or more atoms. Examples of heteroaryl ring structures include: acridine, benzimidazole, benzoxazole, benzodioxole, benzofuran, dihydro-chromen-4-only, 1,3-diazine, 1,2-diazine, 1,2-diazole, 1,4-diazanaphthalene, furan, furazan, imidazole, indole, isoxazole, isoquinoline, isothiazole, isoindolyl, oxazole, purine, pyridazine, pyrazole, pyridine, pyrazine, pyrimidine, pyrrole, quinoline, quinoxaline, thiazole, thiophene, 1,3,5-triazine, 1,2,4-triazine, 1,2,3-triazine, tetrazole and quinazoline. In certain embodiments, the heteroaryl may be optionally substituted.

As used herein, "heterocycle" refers to cyclic ring structures in which one or more atoms in the ring, the heteroatom(s), is an element other than carbon. Heteroatoms are typically O, S or N atoms. Included within the scope of heterocycle, and independently selectable, are O, N, and S heterocycle ring structures. The ring structure may include compounds having one or more ring structures, such as mono-, bi-, or tricyclic compounds. In some embodiments, the heterocycle groups may be selected from heterocycle groups that contain one or more heteroatoms, two or more heteroatoms, three or more heteroatoms, or four or more heteroatoms. Example of heterocycle groups include morpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl or tetrahydrothiopyranyl and the like. In certain embodiments, the heterocycle may optionally be substituted.

As used herein, "alkanoyl" generally refers to a group with the structure —C(O)—R. In certain embodiments, R may be a hydrogen, an alkyl, an 4-morpholinyl group, or a thiazoleamino group.

As used herein, "alkoxy" generally refers to a group with the structure —O—R. In certain embodiments, R may be an alkyl group, such as a $C_1$ to $C_5$ alkyl group.

For the purposes of this invention, halo substituents may be independently selected from the halogens such as fluorine, chlorine, bromine, iodine, and astatine.

In certain preferred embodiments, X may be hydrogen, methoxy, hydroxyl, benzoxy, or a halogen, preferably bromide or chloride. In other embodiments, X may preferably be a $C_1$ to $C_4$ alkyl or a haloalkyl.

$R_1$ may preferably be a $C_6$ to $C_8$ aryl group, optionally substituted with at least one $R_0$ group. $R_0$ may then preferably be methoxy, benzoxy, a $C_1$ to $C_6$ alkyl, a 5 to 6 membered heteroaryl (such as furyl or imidazole), cyano, nitro, tri-fluro methyl, or a halogen, more preferably methoxy, benzoxy, iso-butyl or a halogen, and more preferably methoxy, iso-butyl, bromide or chloride. Alternatively, $R_1$ may be a 5 to 10 membered heteroaryl or 3 to 12 membered heterocycle, such as a pyridinyl group, a thiophene group, a furyl group, a tetrahydro furyl group, and a thiazole group dihydrochromen-4-onyl group, a 1H-isoindolyl group, or a benzodioxole group.

$R_2$ may preferably be a —$CH_2$-furyl group, a pyrimidyl group, or a —C(O)O—$R_d$ group. $R_d$ may preferably then be a $C_1$ to $C_6$ alkyl, optionally substituted with at least one halogen; or a $C_5$ to $C_6$ aryl, optionally substituted with at least one methyl, methoxy, or halogen.

Preferred $R_1$ substituents also include the following, where the * indicates the bond of attachment to the carboline scaffold molecule.

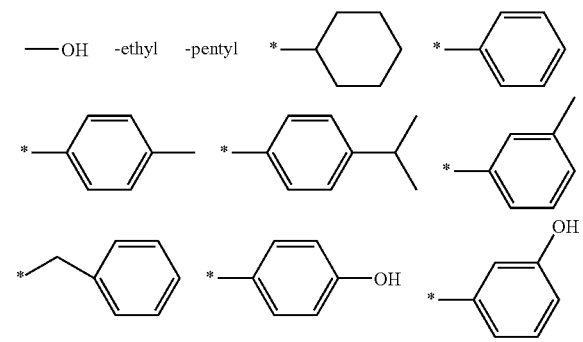

-continued
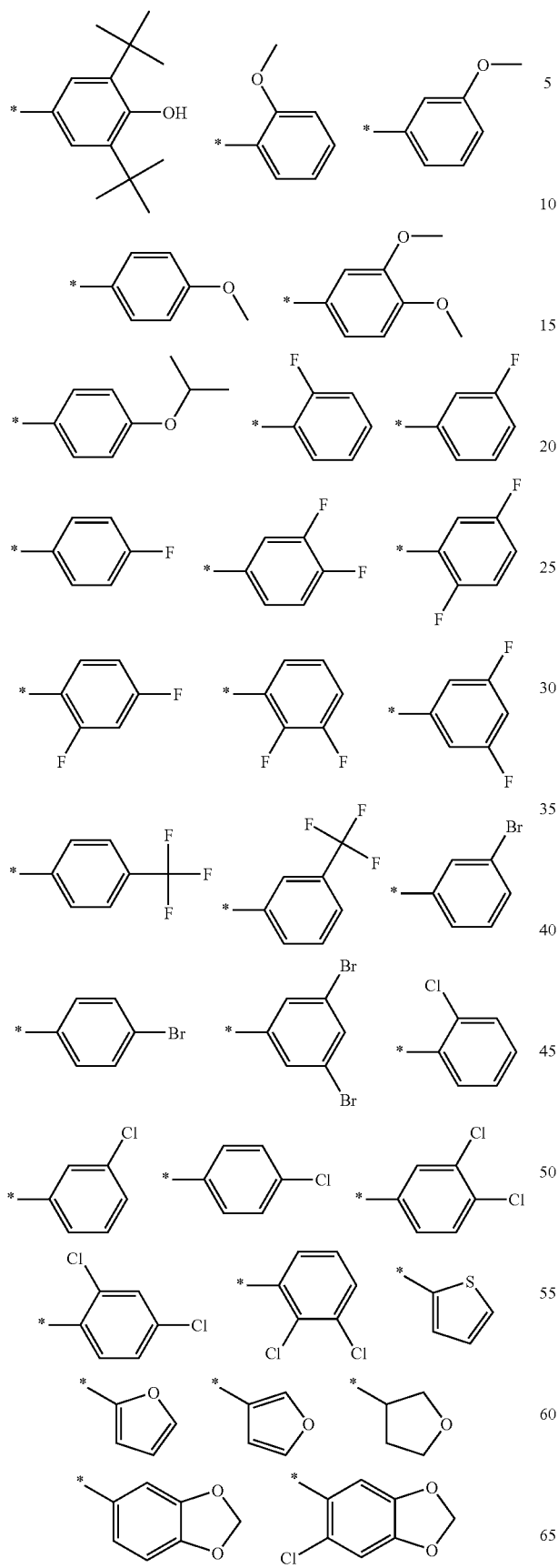
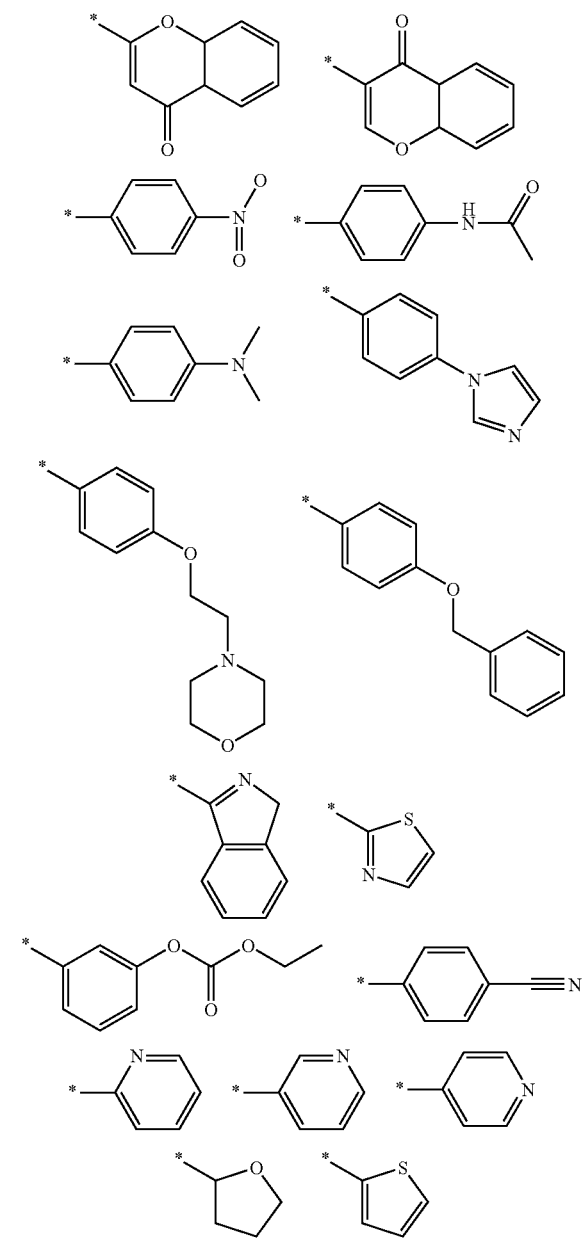
Other preferred $R_1$ substituents include the following, where the * indicates the bond of attachment to the carboline scaffold molecule.
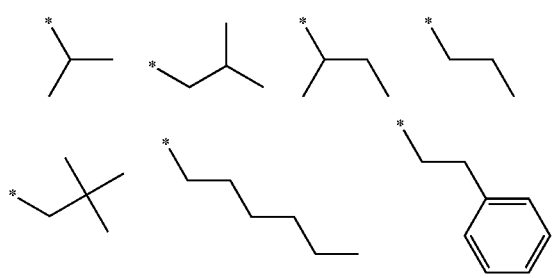

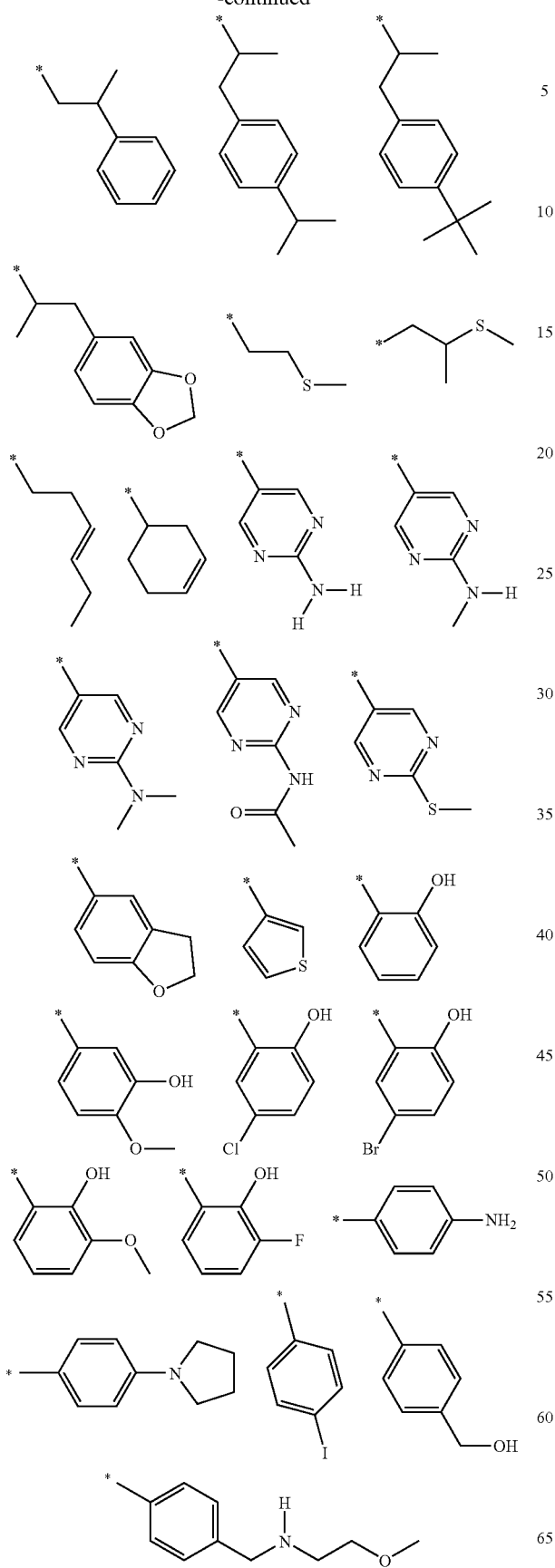
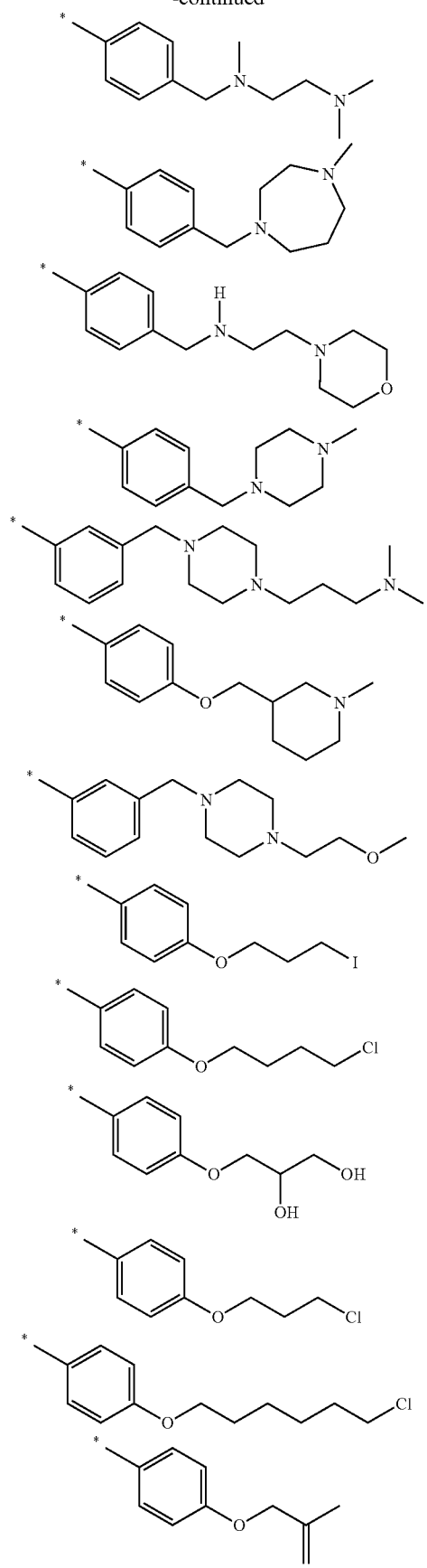

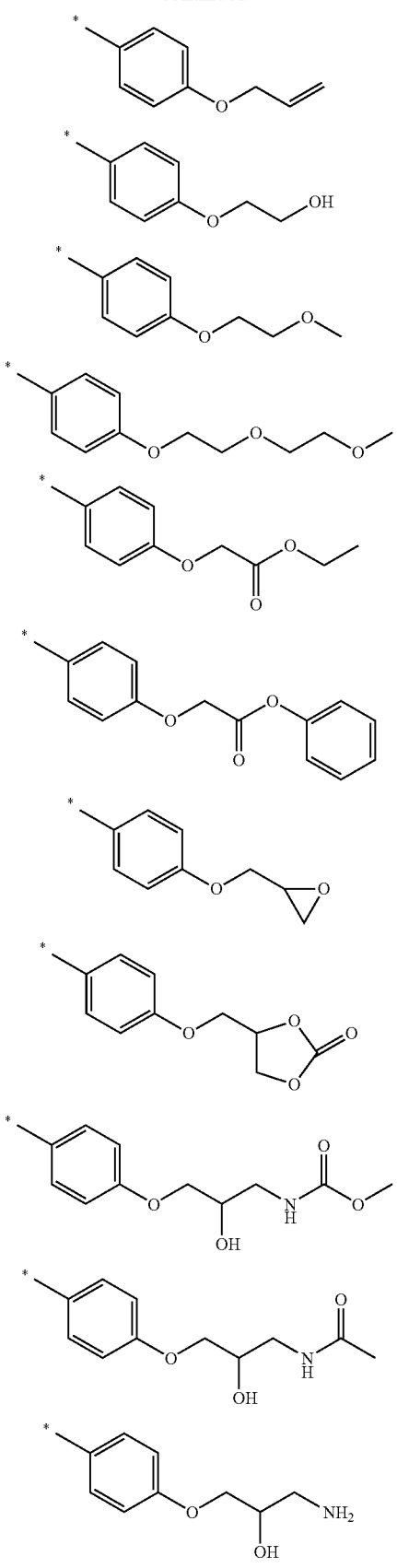
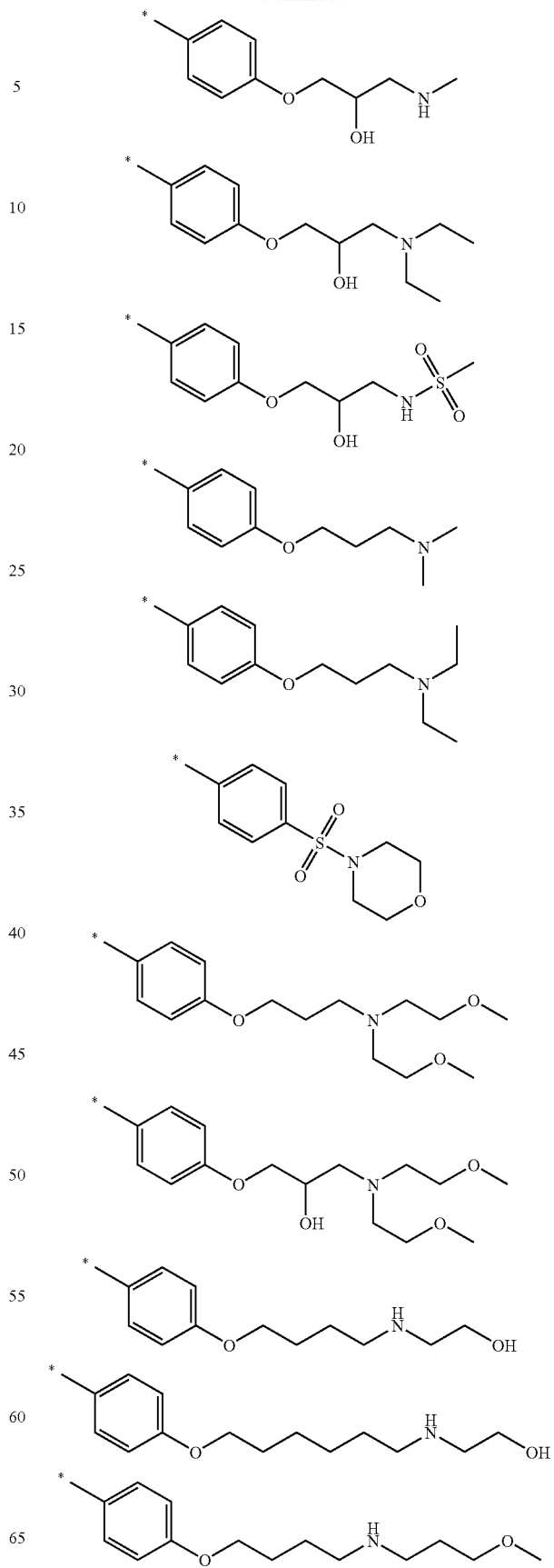

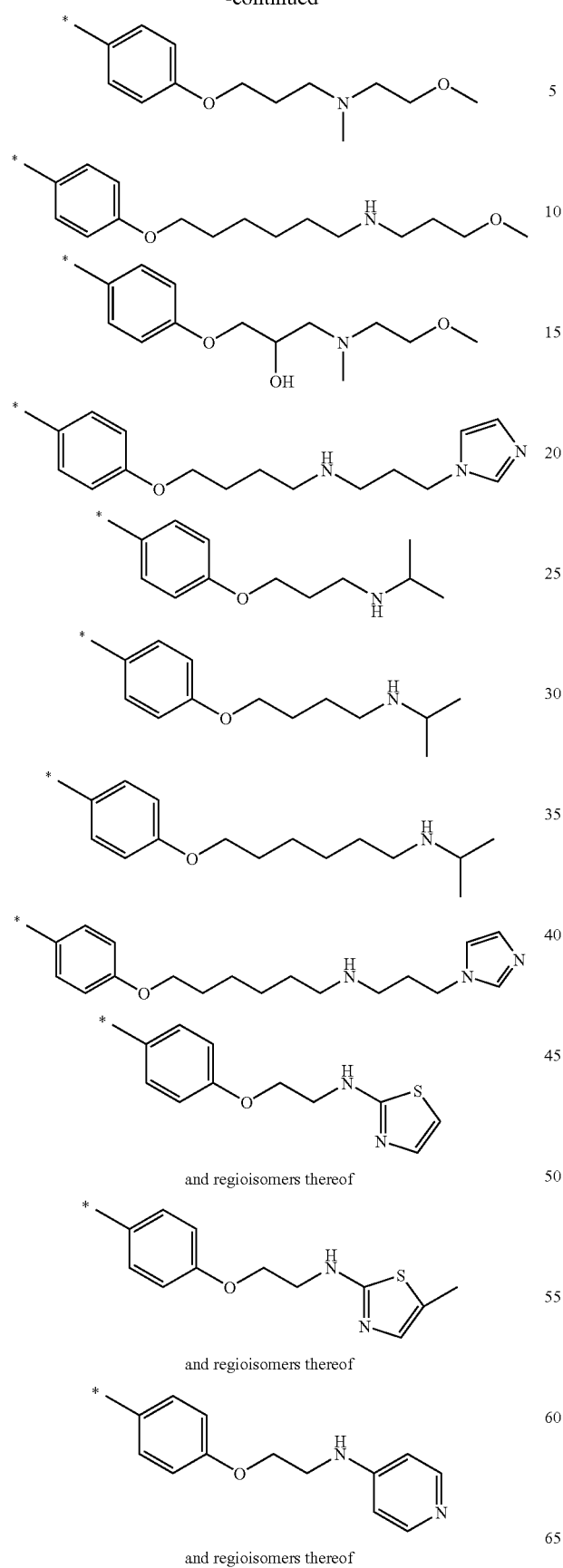
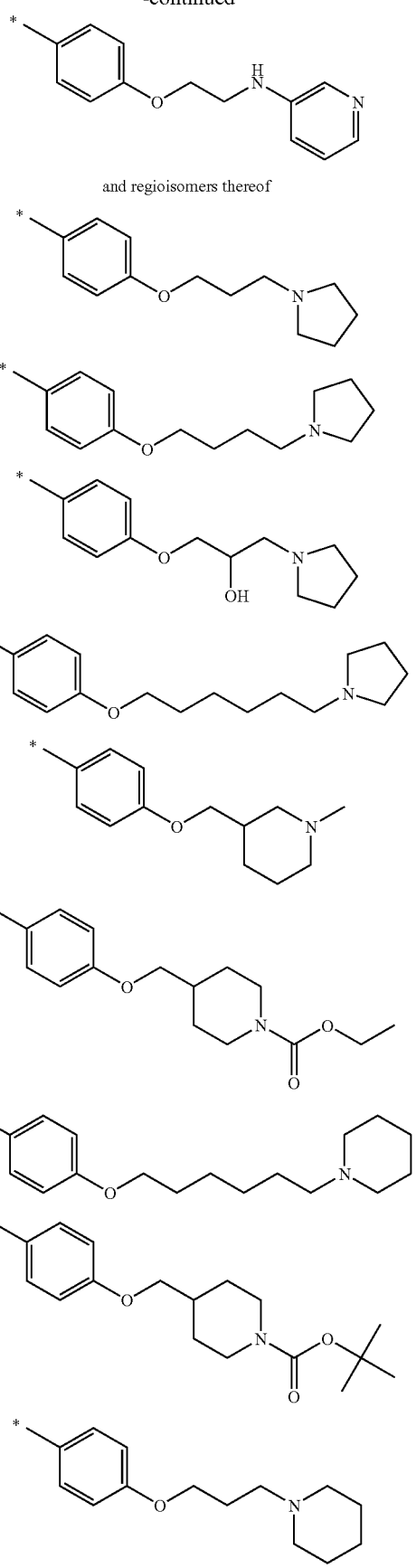
and regioisomers thereof

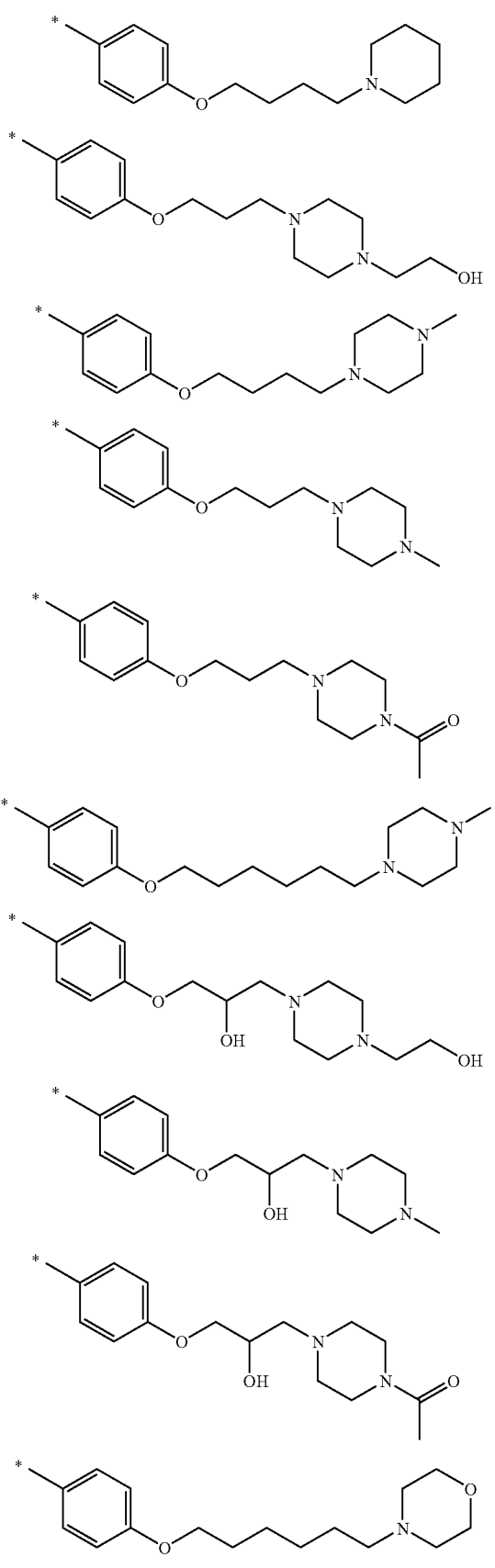
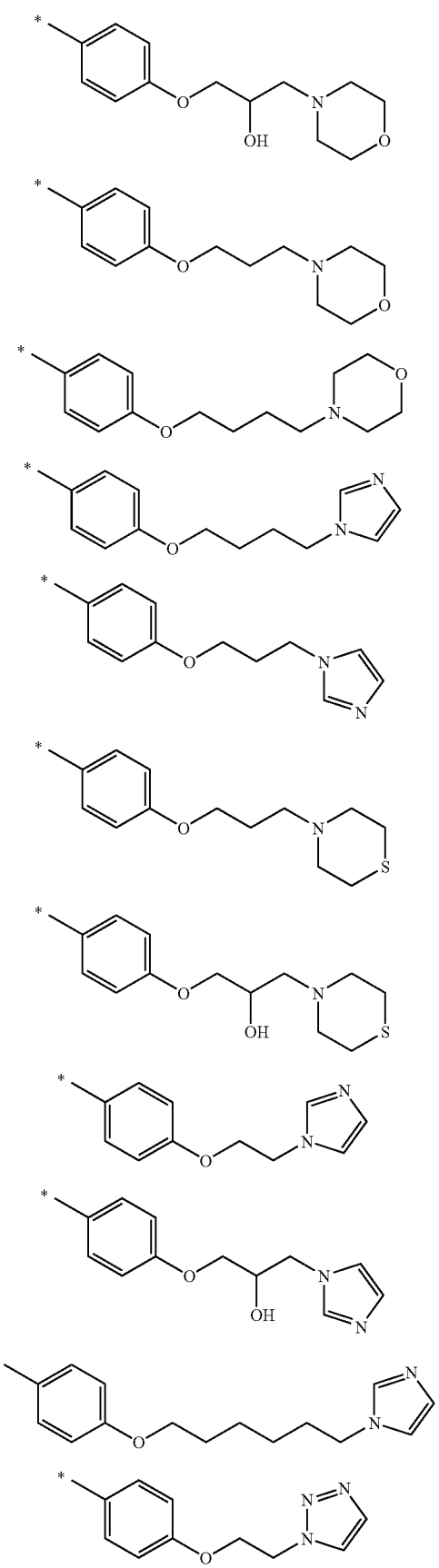

23
-continued
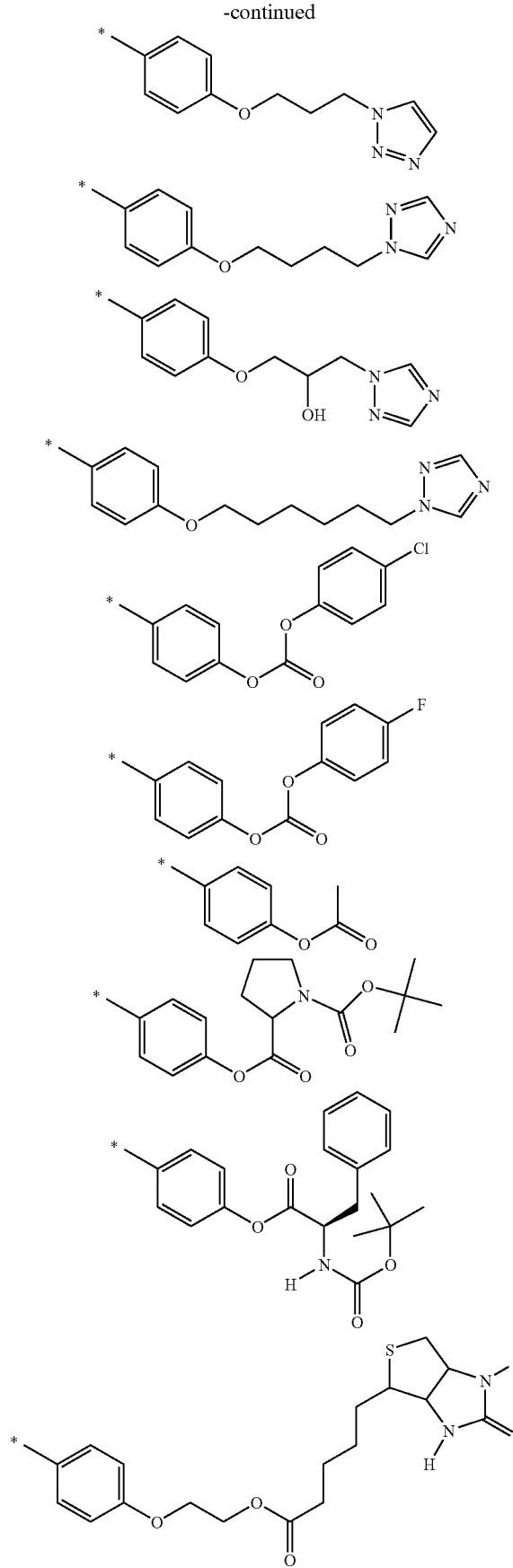
24
-continued
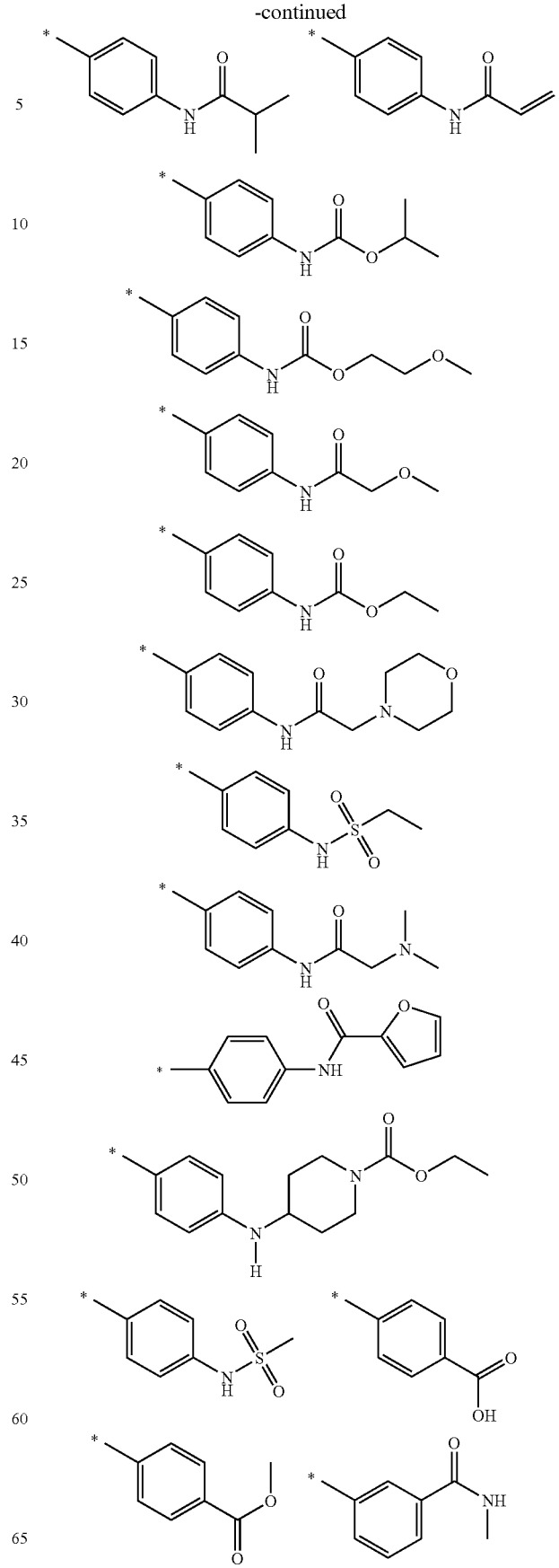

-continued
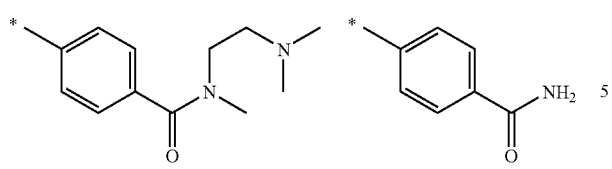
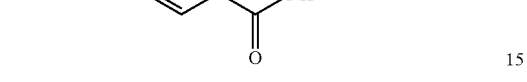
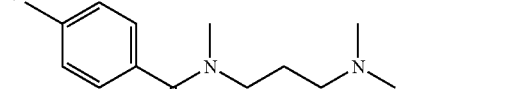
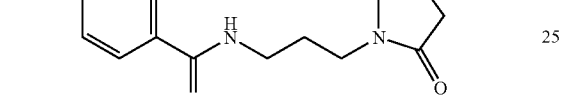

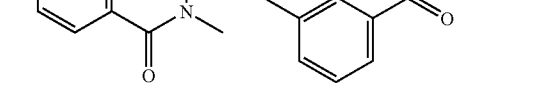

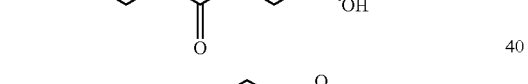
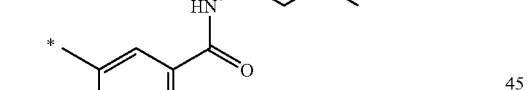
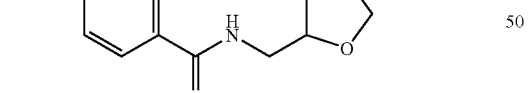
-continued
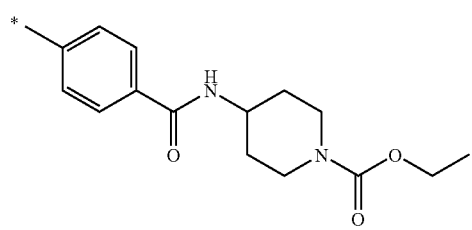
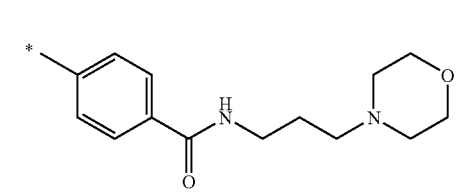
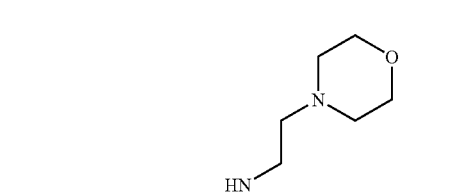
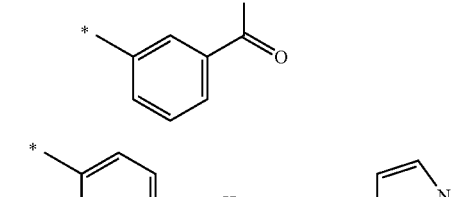
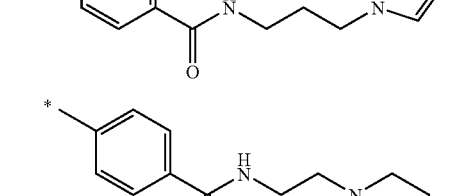
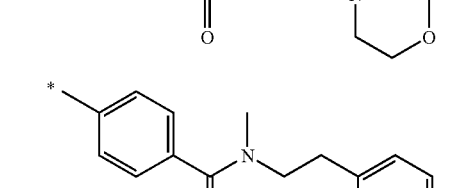
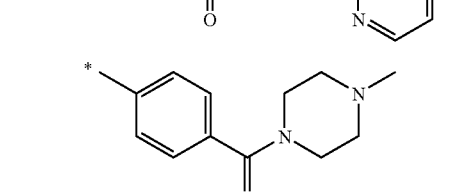
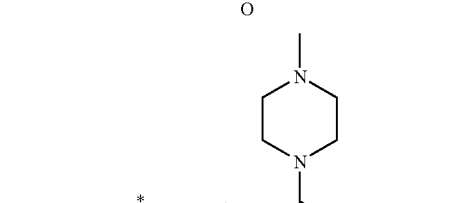
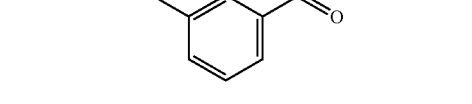

27
-continued
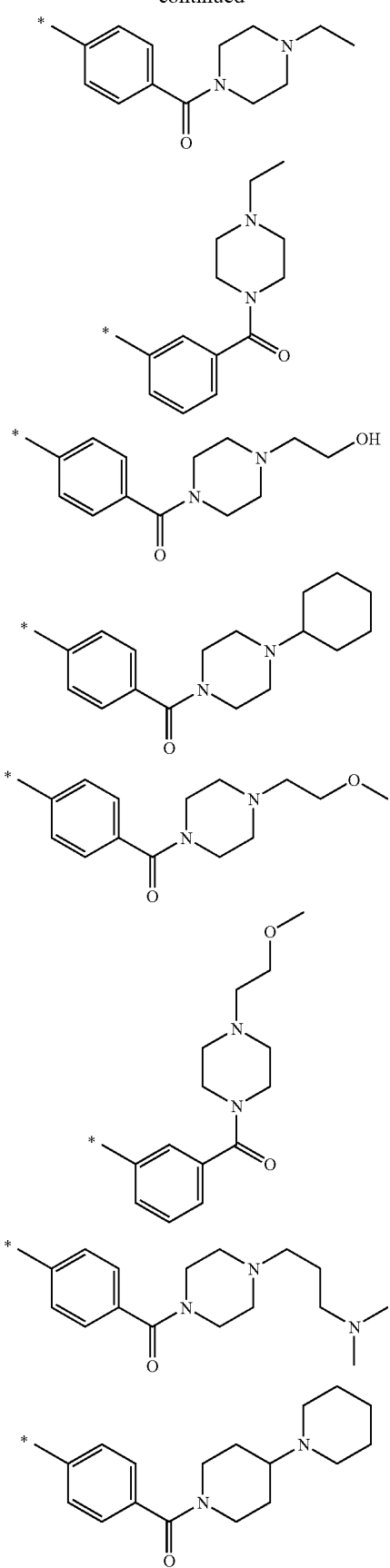
28
-continued
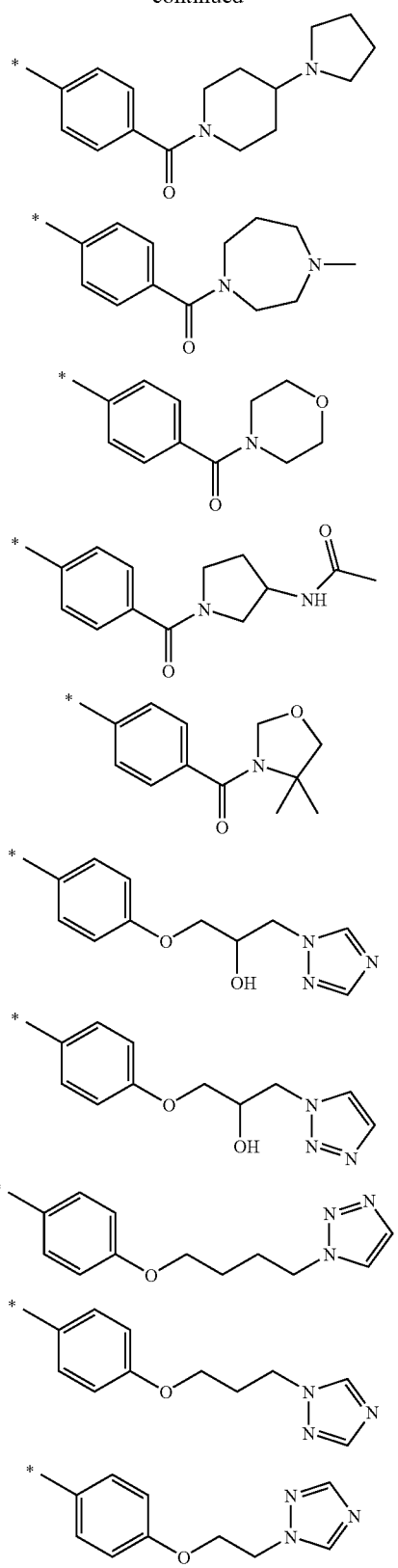
Preferred $R_2$ substituents also include the following, where the * indicates the bond of attachment to the carboline scaffold molecule.

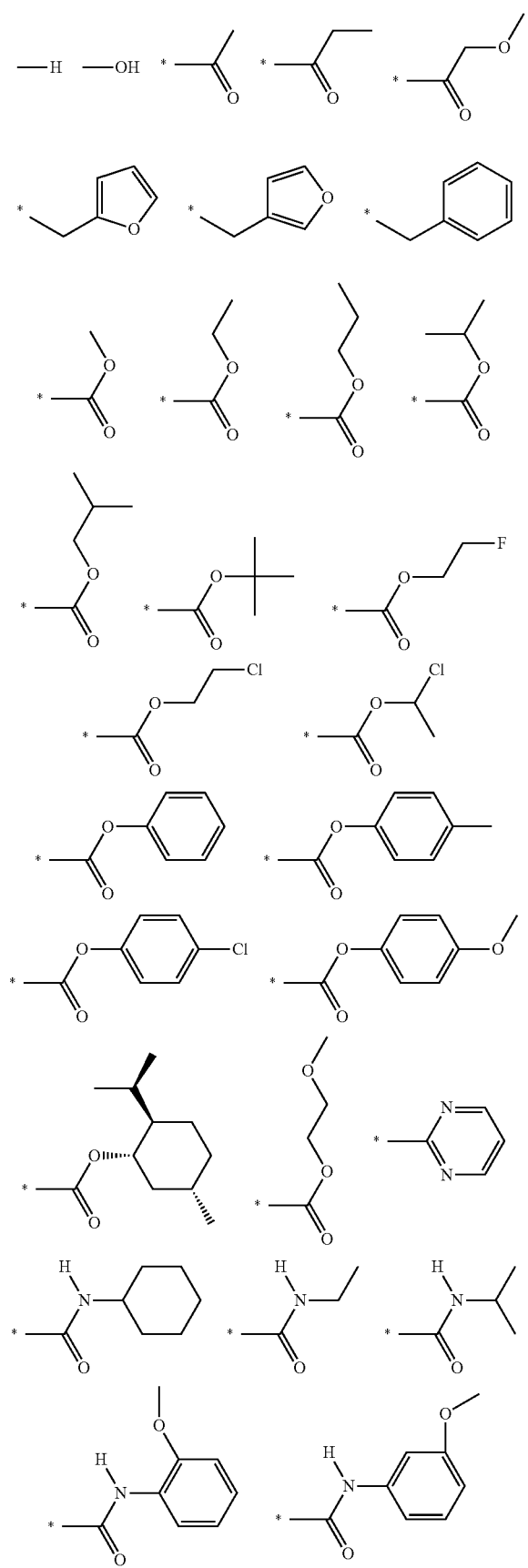
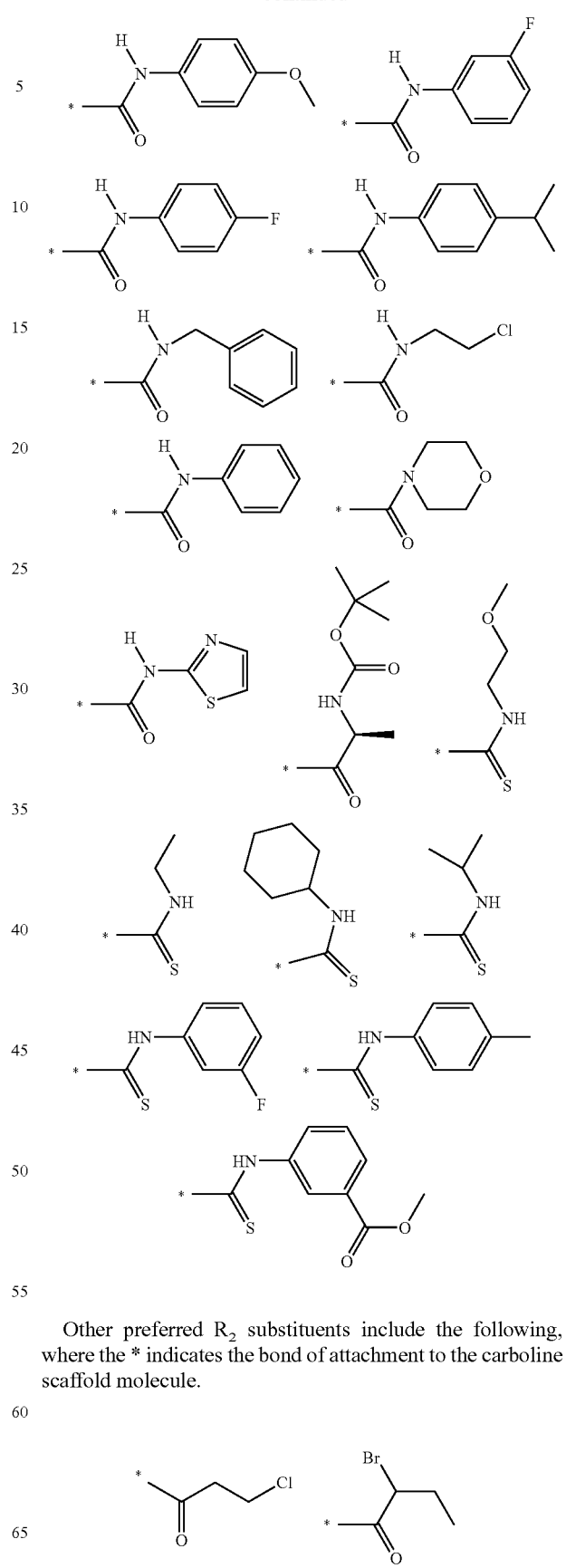
Other preferred $R_2$ substituents include the following, where the * indicates the bond of attachment to the carboline scaffold molecule.
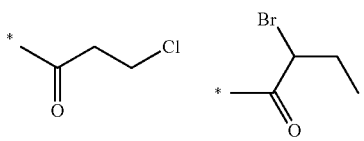

-continued
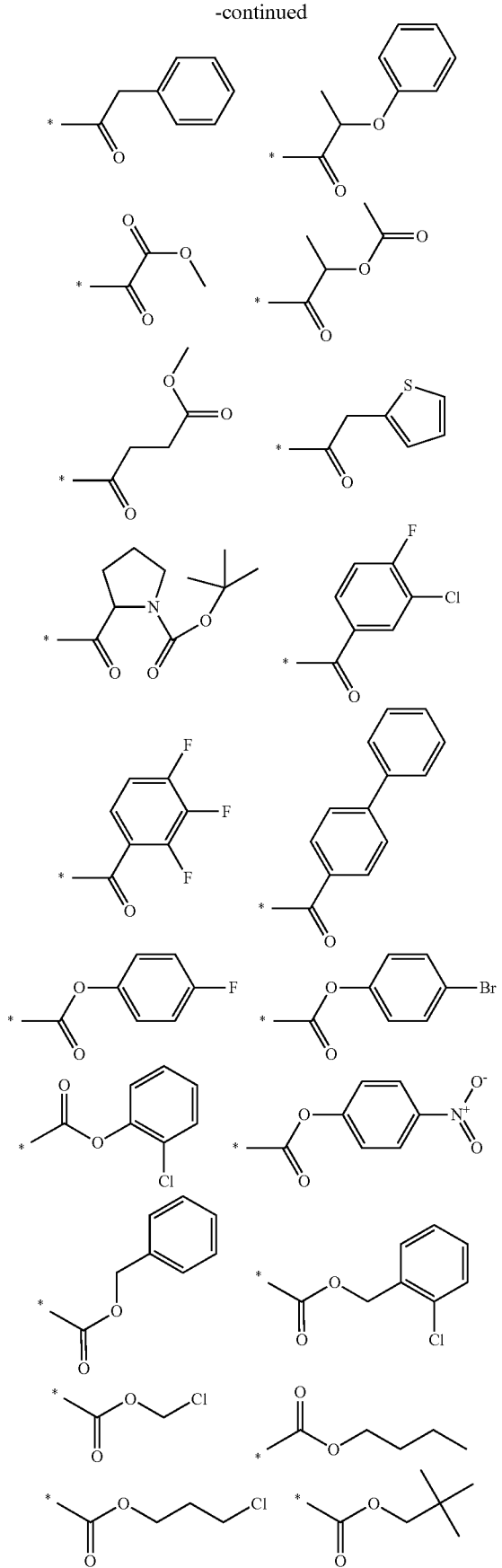
-continued
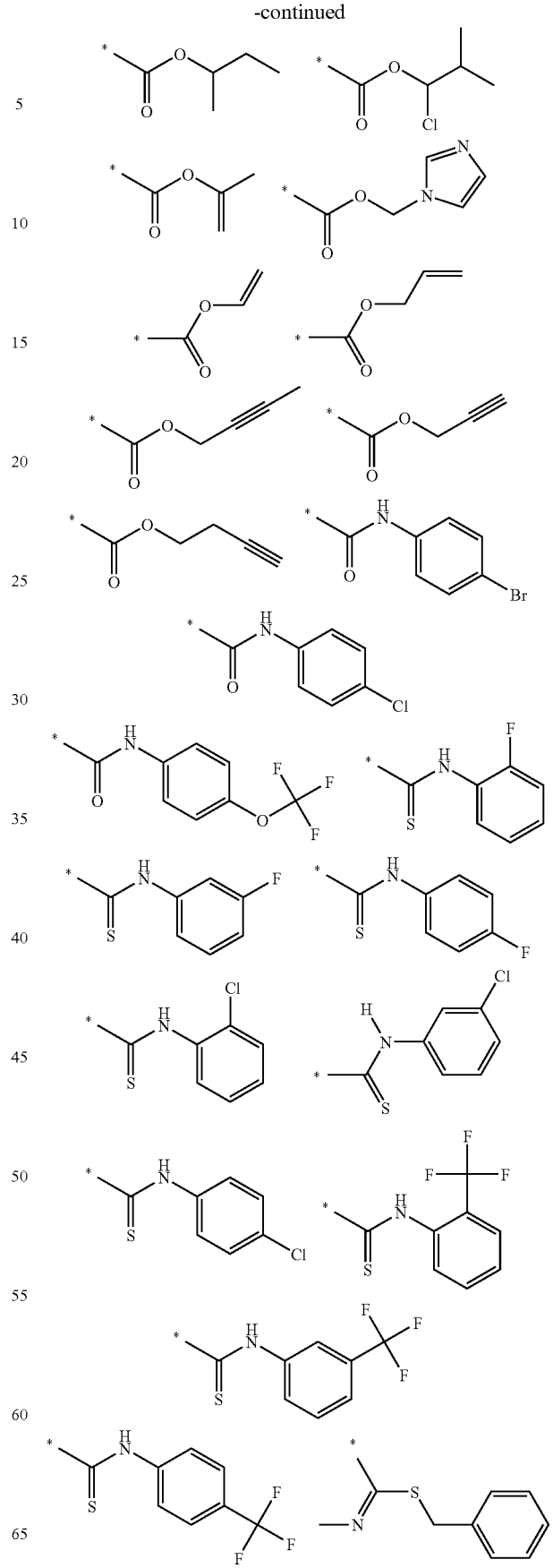

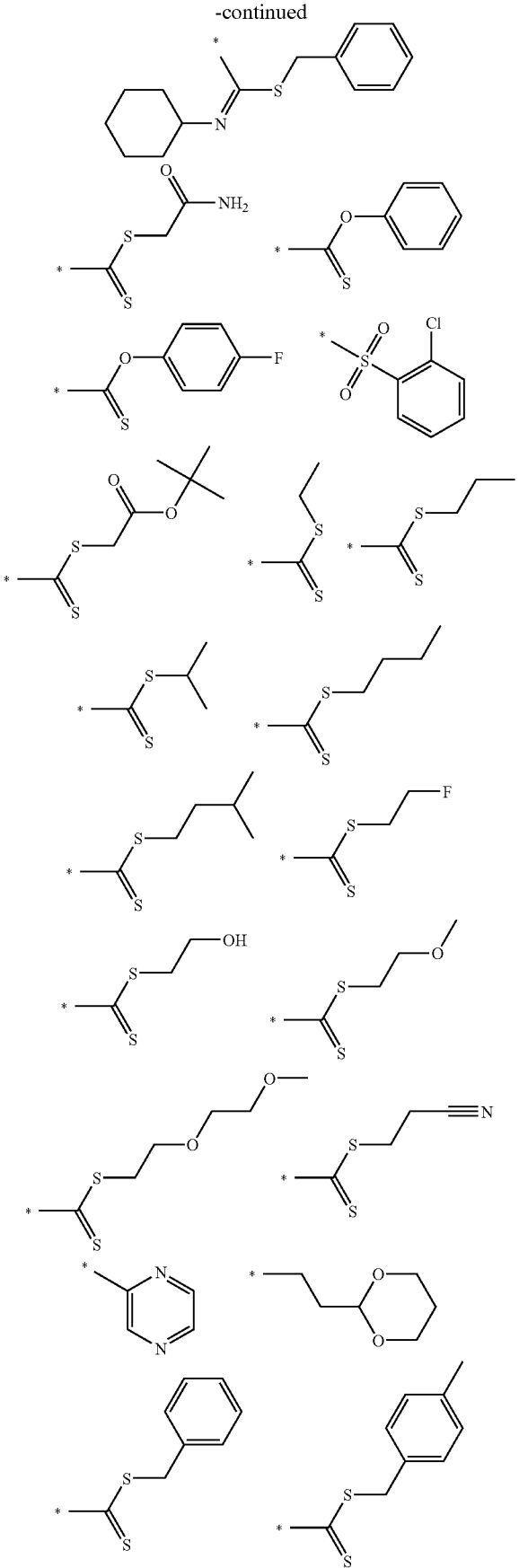
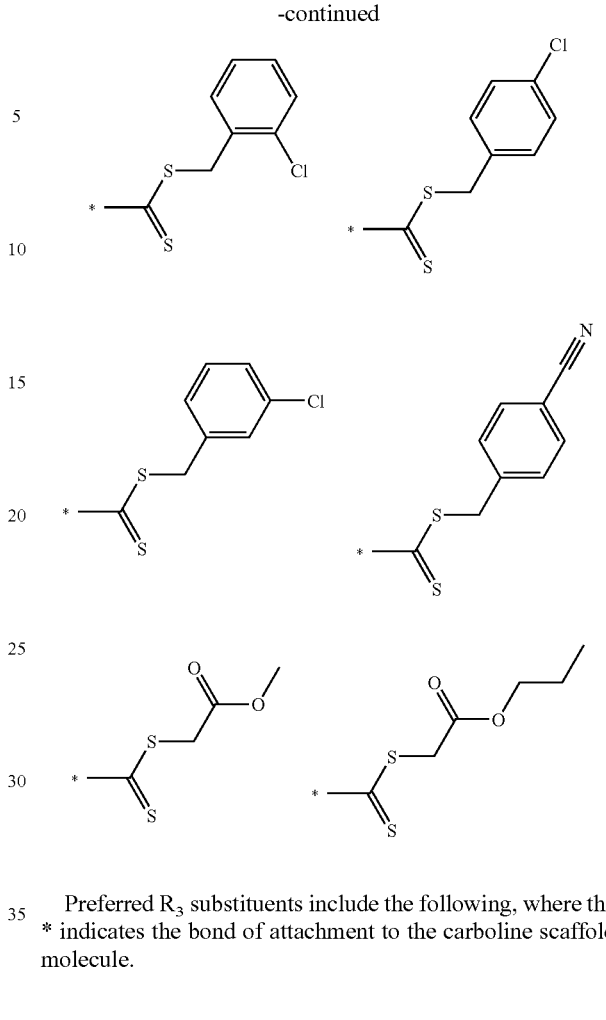

Preferred R₃ substituents include the following, where the * indicates the bond of attachment to the carboline scaffold molecule.

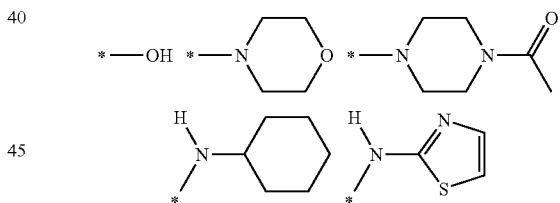

A preferred class of compounds within Formula (I) include those compounds of Formula (I-a) as shown below.

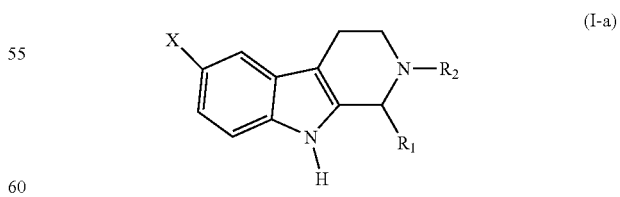

wherein X, R₁ and R₂ are defined as described with regard to Formula (I) and the preferred embodiments described above.

Another preferred class of compounds within Formula (I) include those compounds of Formula (I-b) as shown below.

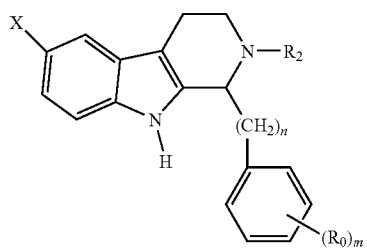
(I-b)

wherein:
X is a halogen;
R$_2$ is as described above with regard to Formula (I);
R$_0$ is as described above with regard to Formula (I);
m is 0, 1, 2, or 3; and
n is 0, 1, 2, or 3.

Other preferred classes of compounds within Formula (I) include the following.

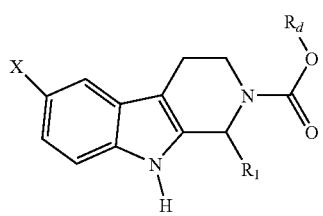
(I-c)

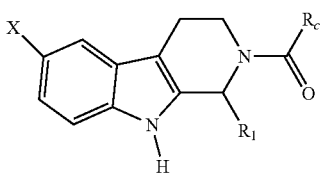
(I-d)

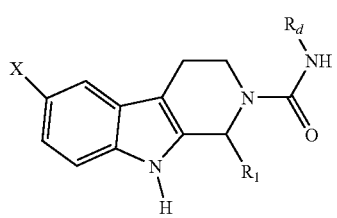
(I-e)

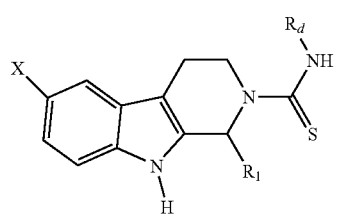
(I-f)

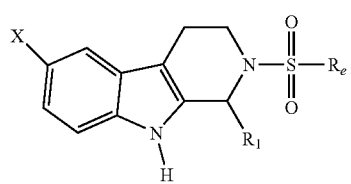
(I-g)

-continued

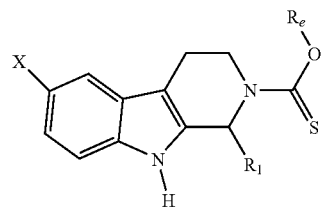
(I-h)

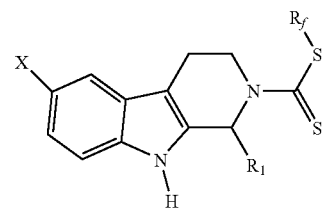
(I-i)

It is understood that substituents X and R$_1$, R$_c$, R$_d$, and R$_e$ of the compounds of Formulas (I-c) to (I-i) are defined as in Formula (I).

In other embodiments, preferred compounds of the present invention useful in the inhibition of VEGF production include those of Formulas (I-i) through (I-l), as shown below. In the embodiments of Formulas (I-j) through (I-l), substituents X, R$_1$, R$_2$, R$_3$, etc. are defined as in Formula (I), as well as Formulas (I-a) to (I-i).

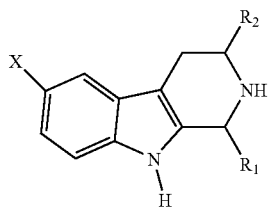
(I-j)

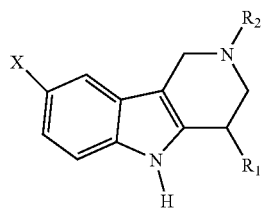
(I-k)

Also included within the scope of the invention are pharmaceutically acceptable salts, hydrates, solvates, calthrates, polymorphs, racemates and stereoisomers of the compounds described herein.

In another aspect of the invention, preferred compounds of the present invention useful in the inhibition of VEGF production include those of Formula (I-l) as shown below.

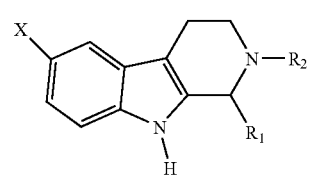
(I-l)

wherein,

X is hydrogen; a hydroxyl group; a halogen; a $C_1$-$C_4$ alkyl; a $C_1$ to $C_5$ alkoxy, optionally substituted with a $C_6$ to $C_8$ aryl group;

$R_1$ is a hydroxyl group; a $C_1$ to $C_8$ alkyl group, optionally substituted with a $C_6$ to $C_8$ aryl group, wherein the $C_6$ to $C_8$ aryl group is optionally substituted with at least one $R_0$ group; a heterocycle group; a heteroaryl group; and a $C_6$ to $C_8$ aryl group, optionally substituted with at least one $R_0$ group;

$R_0$ is a halogen; a $C_1$ to $C_6$ alkyl, optionally substituted with one or more halogen groups; a cyano group; a nitro group; an amino group; an aminoalkyl group; an acetamide group; an imidazole group; or $OR_a$;

$R_a$ is hydrogen; a $C_1$ to $C_6$ alkyl, optionally substituted with a heterocycle group or a $C_6$ to $C_8$ aryl group; or a —C(O)O—$R_b$;

$R_b$ is $C_1$ to $C_4$ alkyl group;

$R_2$ is a hydrogen; a hydroxyl; a heteroaryl group; a $C_1$ to $C_8$ alkyl group, optionally substituted with an alkoxy, hydroxyl, heteroaryl, or $C_6$ to $C_8$ aryl group; a —C(O)—$R_e$ group; a —C(O)O—$R_d$ group; a —C(O)NH—$R_d$ group; a —C(S)NH—$R_d$ group; a —S($O_2$)—$R_e$ group; or (1S)-isopropyl-carbamic acid tert-butyl ester;

$R_c$ is hydrogen; a 4-morpholinyl group; a thiazoleamino group; a piperazinyl group, optionally substituted with a —C(O)$CH_3$ group; a $C_1$ to $C_6$ alkyl group, optionally substituted with a halogen, an alkoxy, or hydroxyl group;

$R_d$ is hydrogen; a benzyl group; a $C_1$ to $C_8$ alkyl group, optionally substituted with a halogen or an alkoxy group; a $C_6$ to $C_8$ aryl group, optionally substituted with at least one halogen, $C_1$ to $C_5$ alkyl, —C(O)$OR_e$, or $OR_e$;

$R_e$ is a hydrogen; a $C_1$ to $C_6$ alkyl group, optionally substituted with at least one halogen or alkoxy group; or a $C_6$ to $C_8$ aryl group; and n is 0, 1, 2, or 3.

In another embodiment, compounds of Formulas (II), (III) and (IV) are provided, which are useful for inhibiting VEGF production, and treating cancer.

(II)

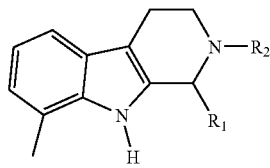

(III)

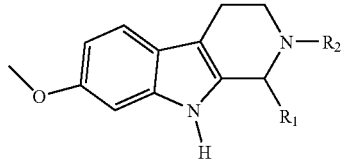

(IV)

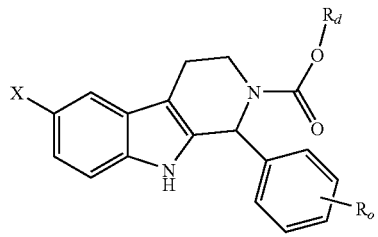

Wherein X, $R_1$, $R_2$, $R_o$ and $R_d$ are defined as described above with regard with Formula (I).

For the purposes of this invention, where one or more functionalities encompassing X $R_1$, $R_2$, $R_0$, $R_a$, $R_b$, $R_c$, $R_d$, and $R_e$, are incorporated into a molecule of Formulas (I), (II), and (III), including Formulas (I-a) to (I-k), each of the functionalities appearing at any location within the disclosed may be independently selected, and as appropriate, independently substituted. Further, where a more generic substituent is set forth for any position in the molecules of the present invention, it is understood that the generic substituent may be replaced with more specific substituents, and the resulting molecules are within the scope of the molecules of the present invention.

Preferred compounds of the invention include the following.

1

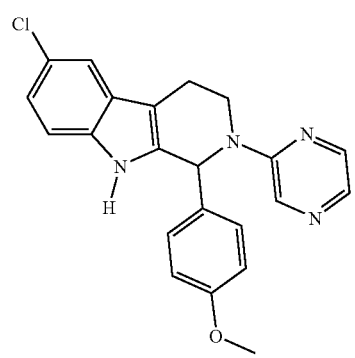

2

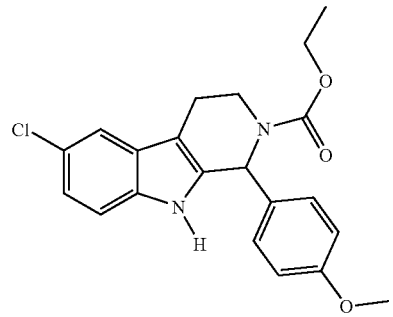

3

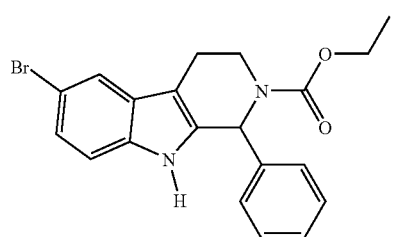

4

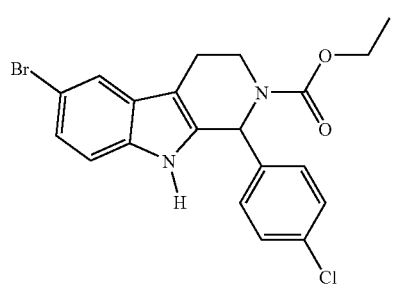

5
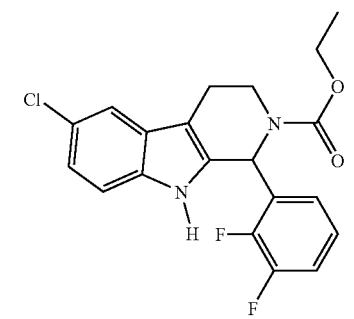
6
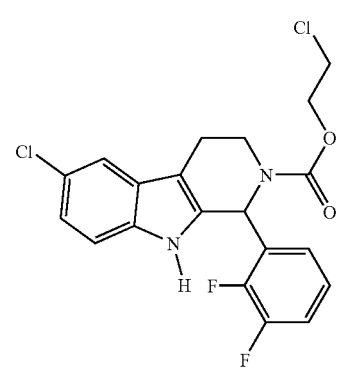
7
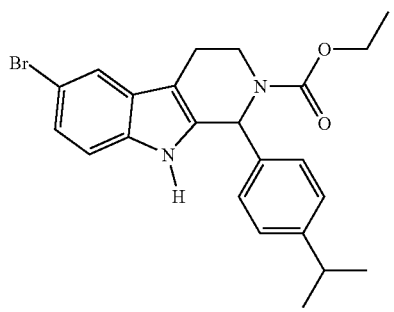
8
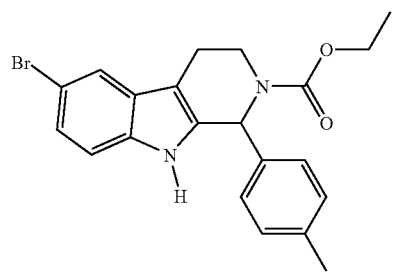
9
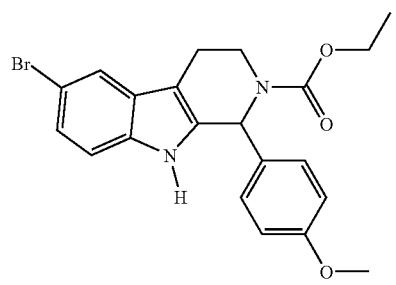
10
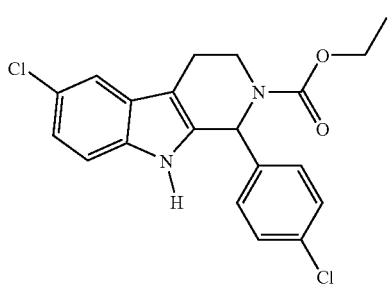
11
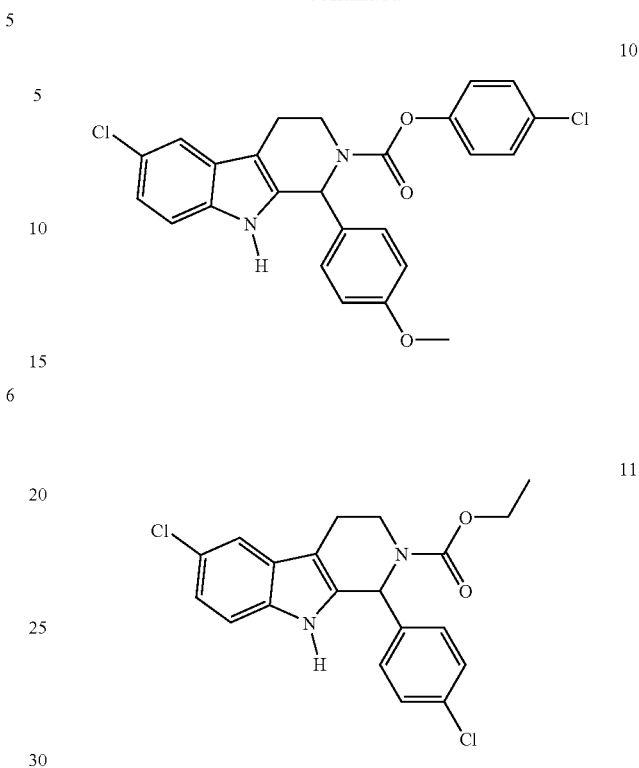
12
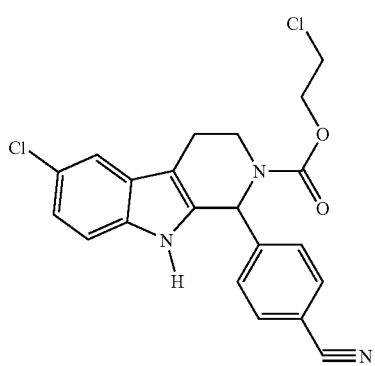
13
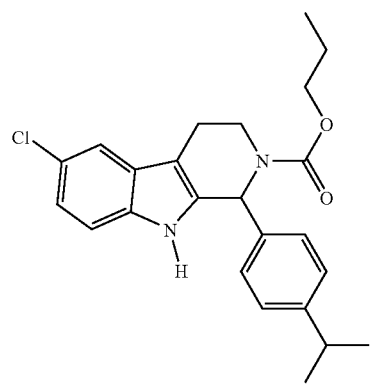

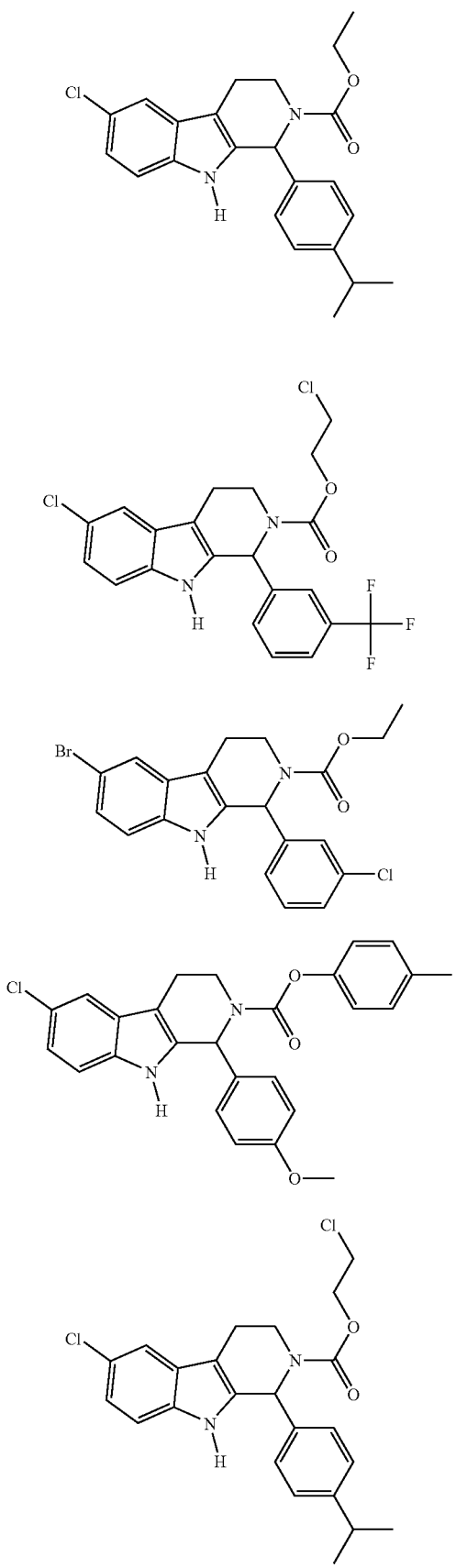
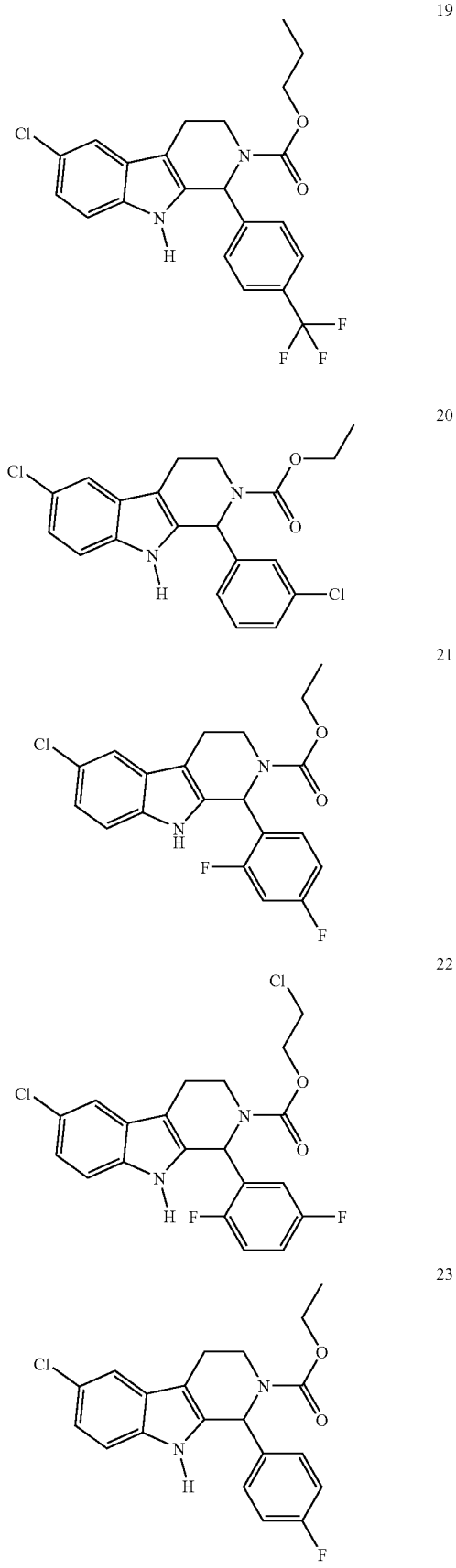

24
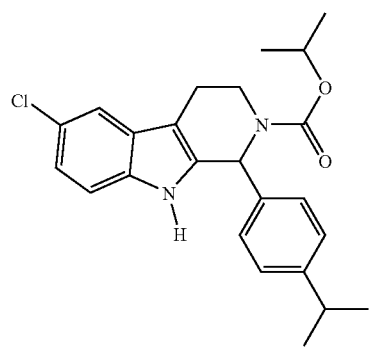
25
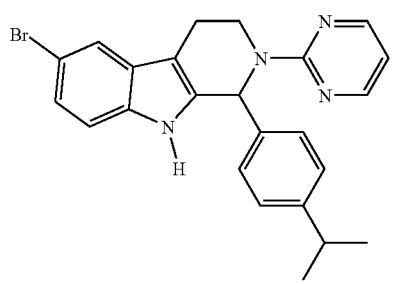
26
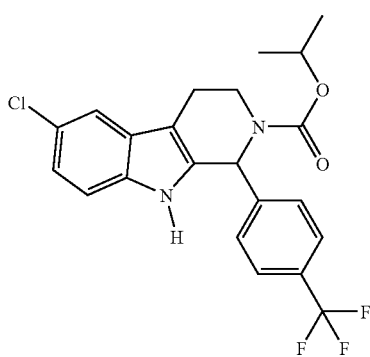
27
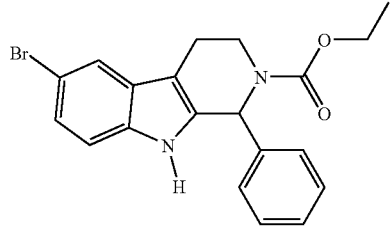
28
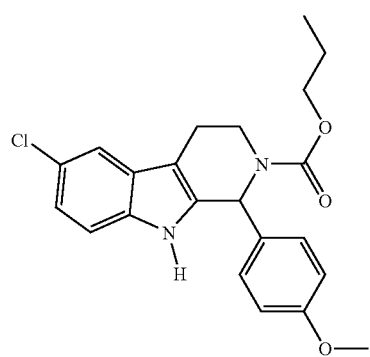
29
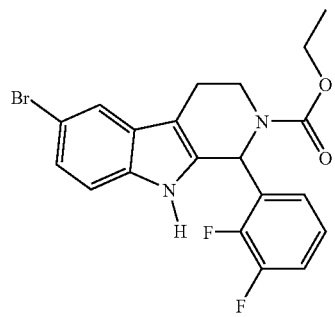
30
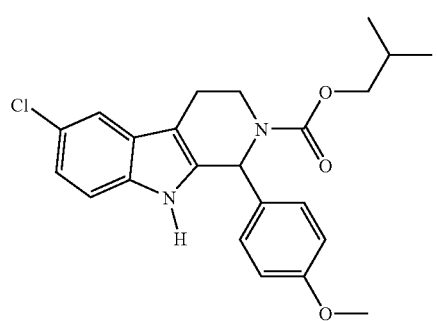
31
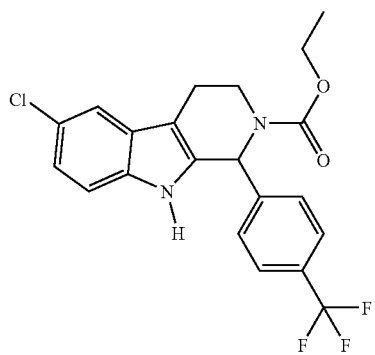
32
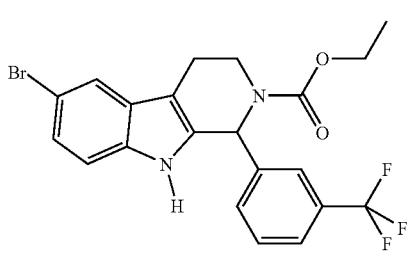
33
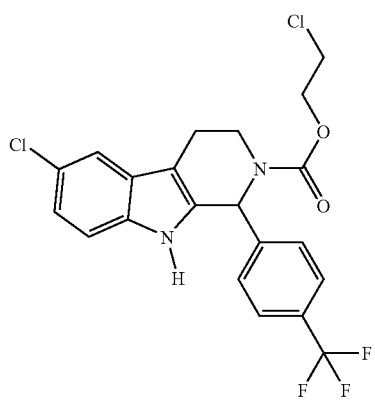

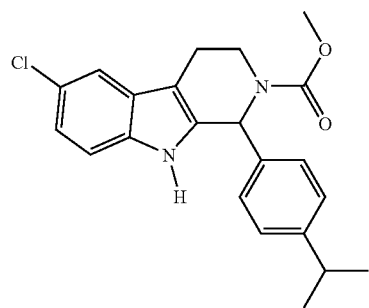
34
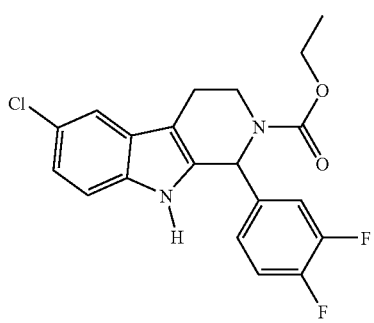
39
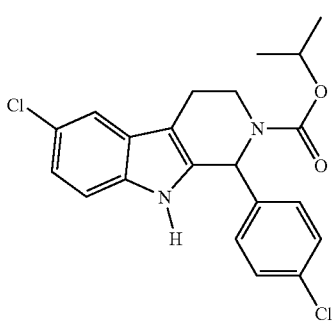
35
40
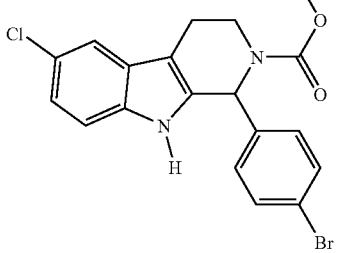
36
41
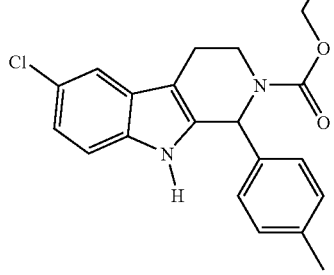
37
42
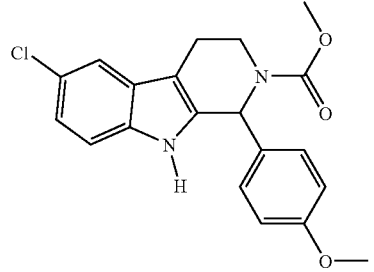
38
43

44
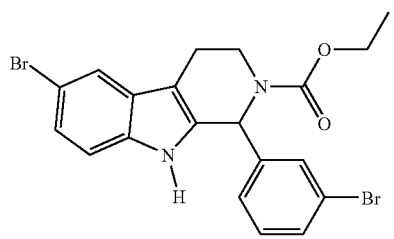
45
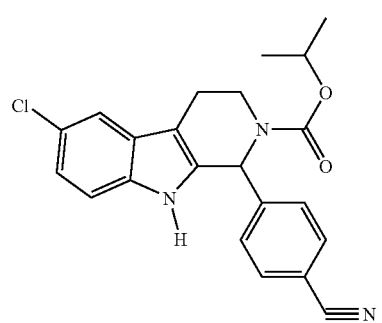
46
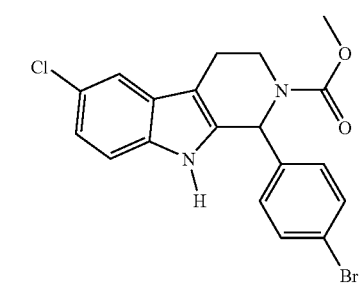
47
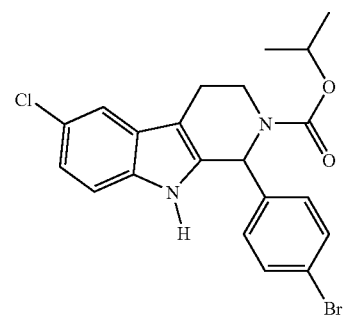
48
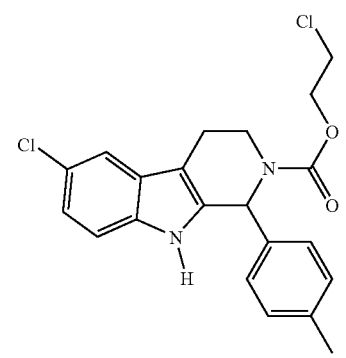
49
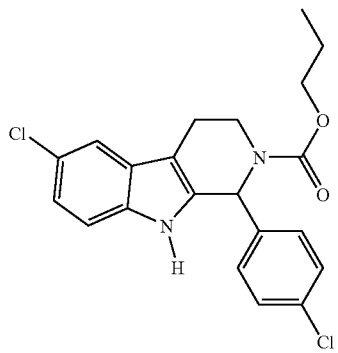
50
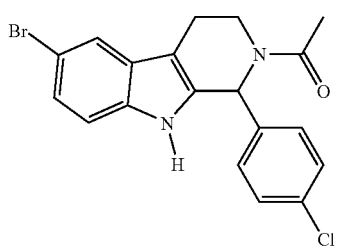
51
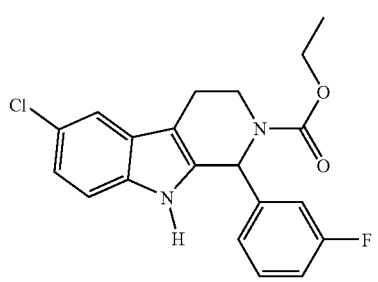
52
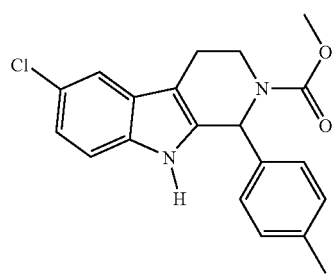
53
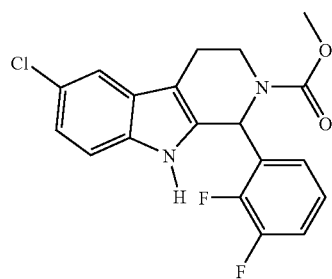

54
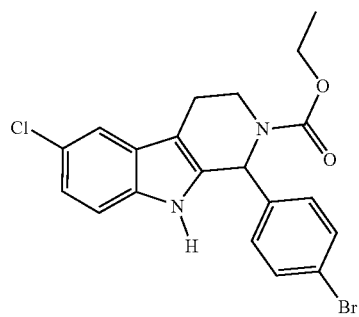
55
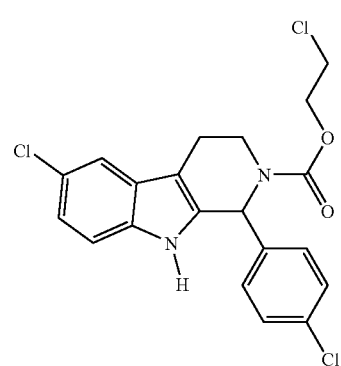
56
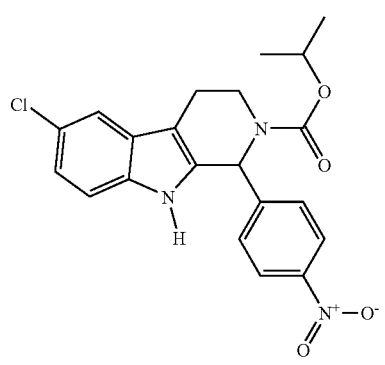
57
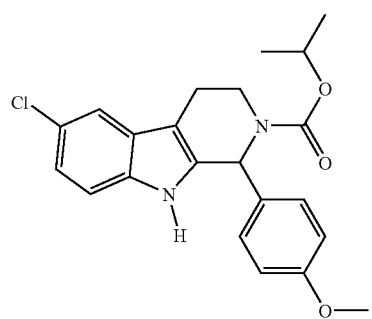
58
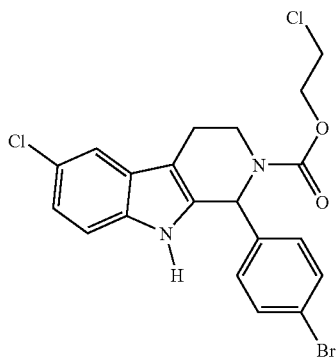
59
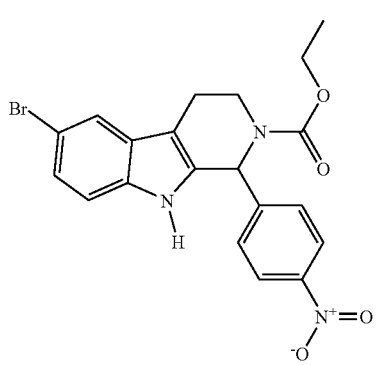
60
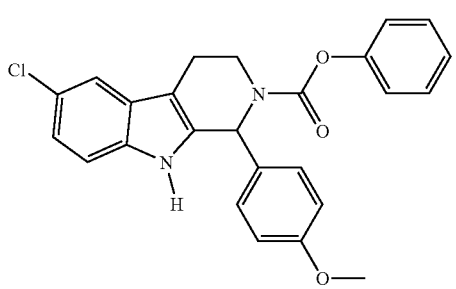
61
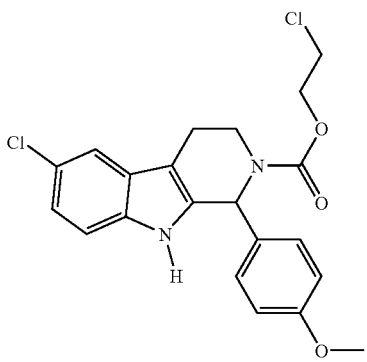

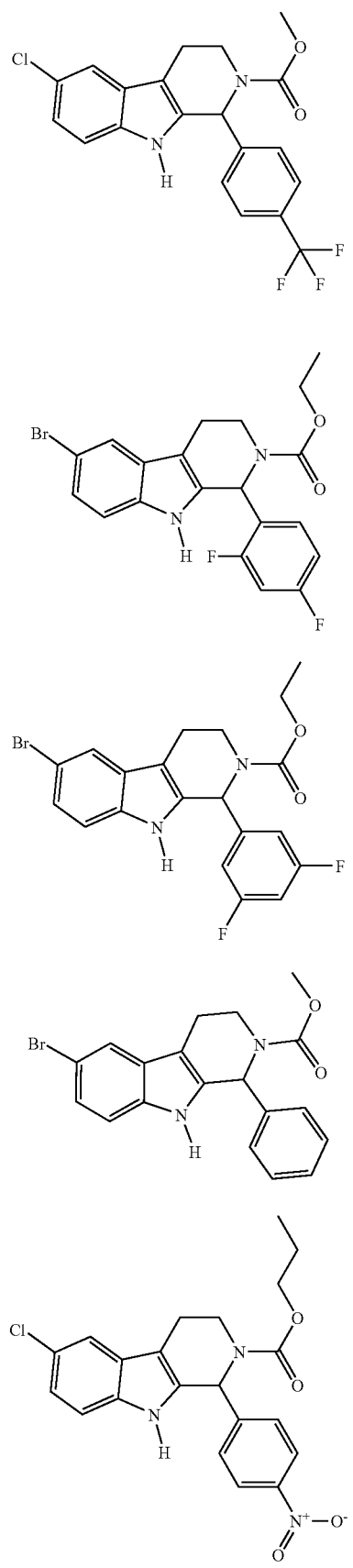
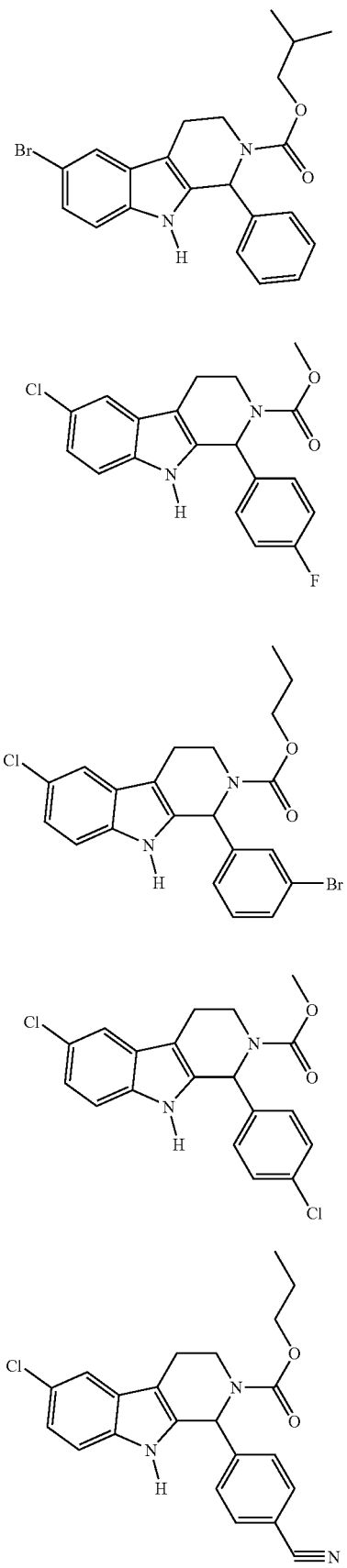

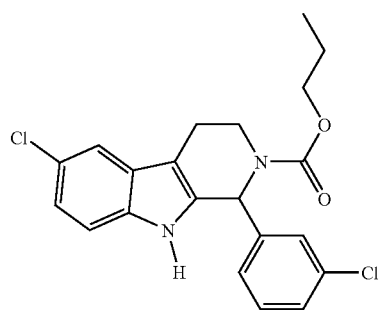
72
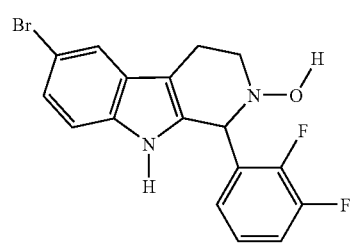
73
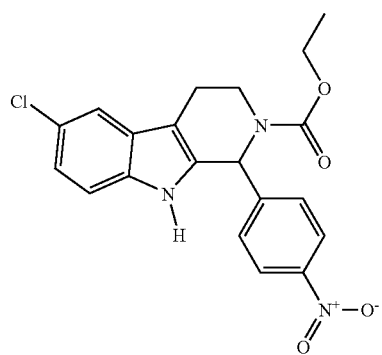
74
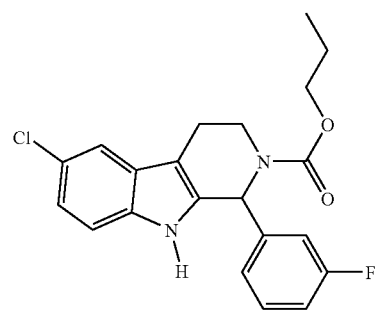
75
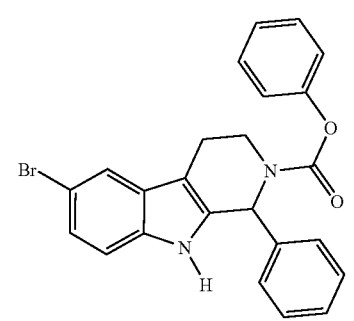
76
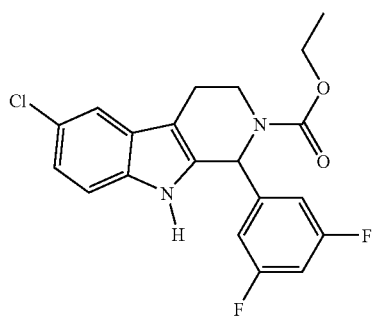
77
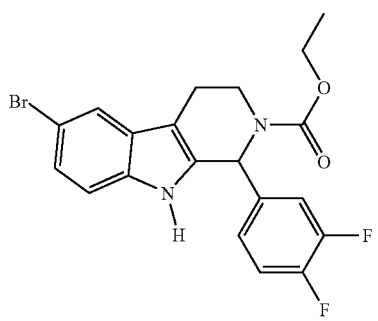
78
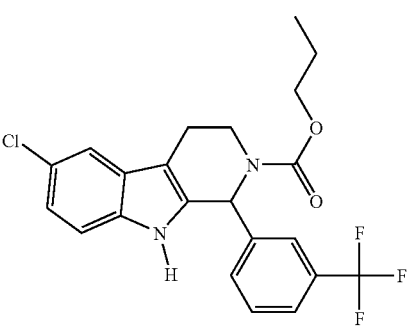
79
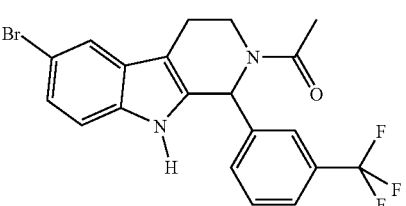
80
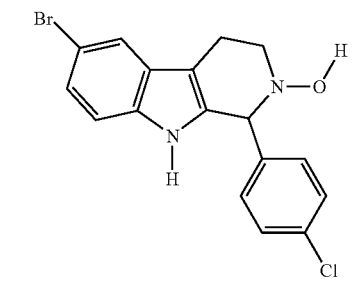
81

82 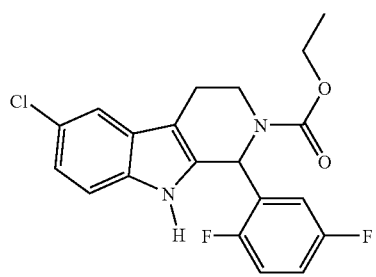
83 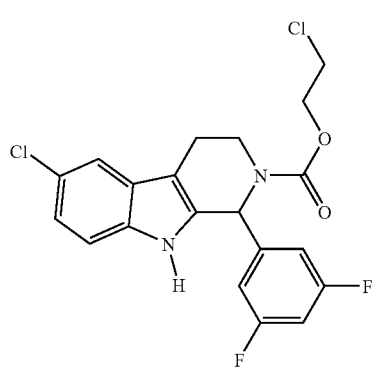
84 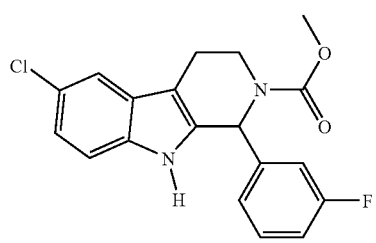
85 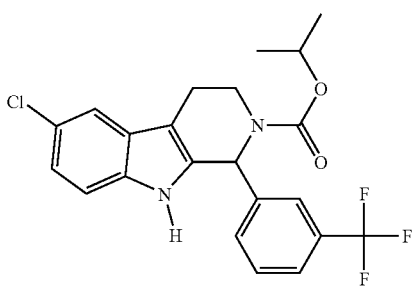
86 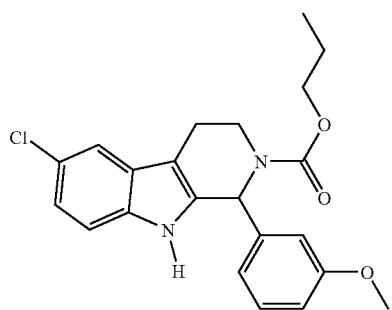
87 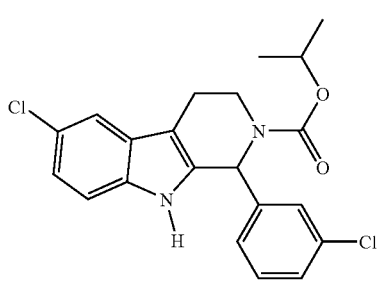
88 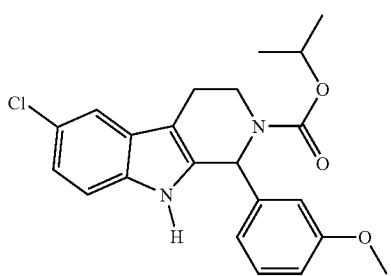
89 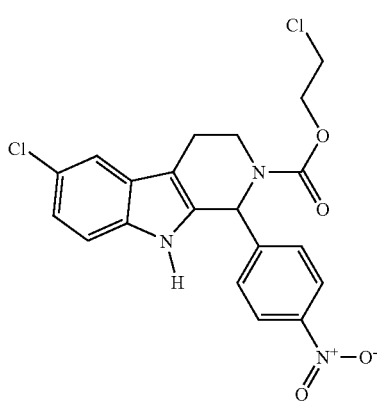
90 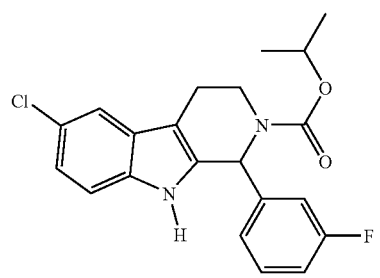
91 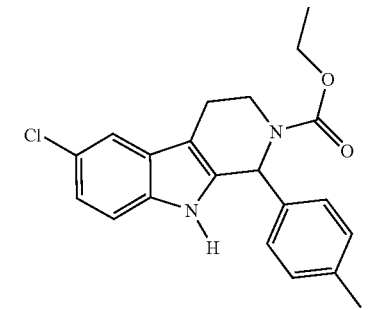

92
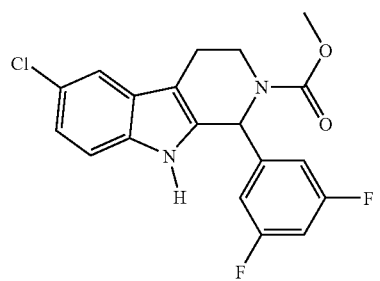
93
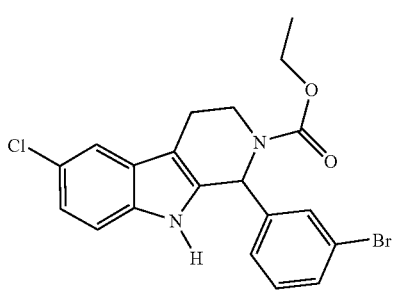
94
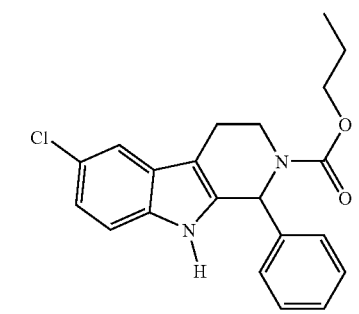
95
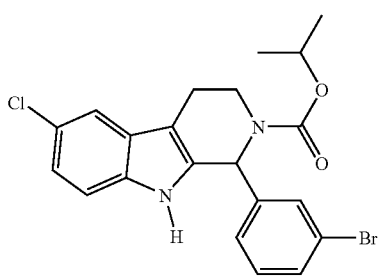
96
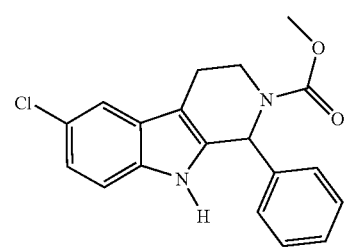
97
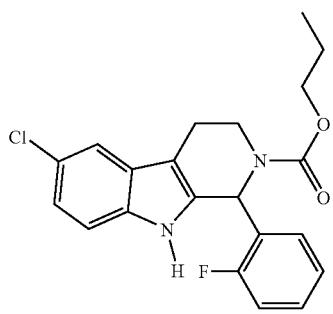
98
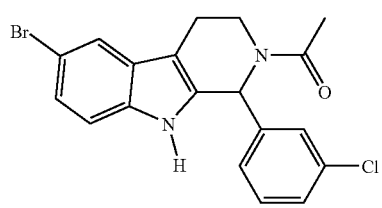
99
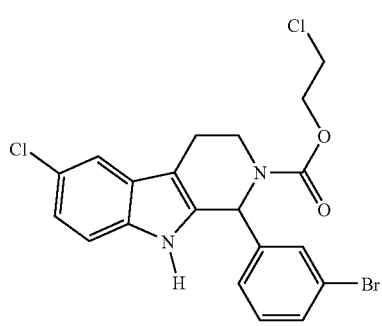
100
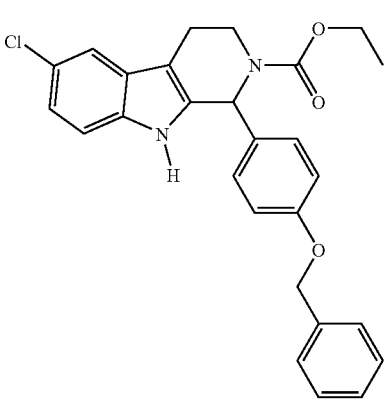
101
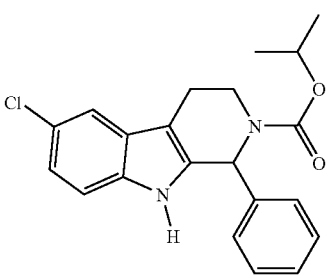

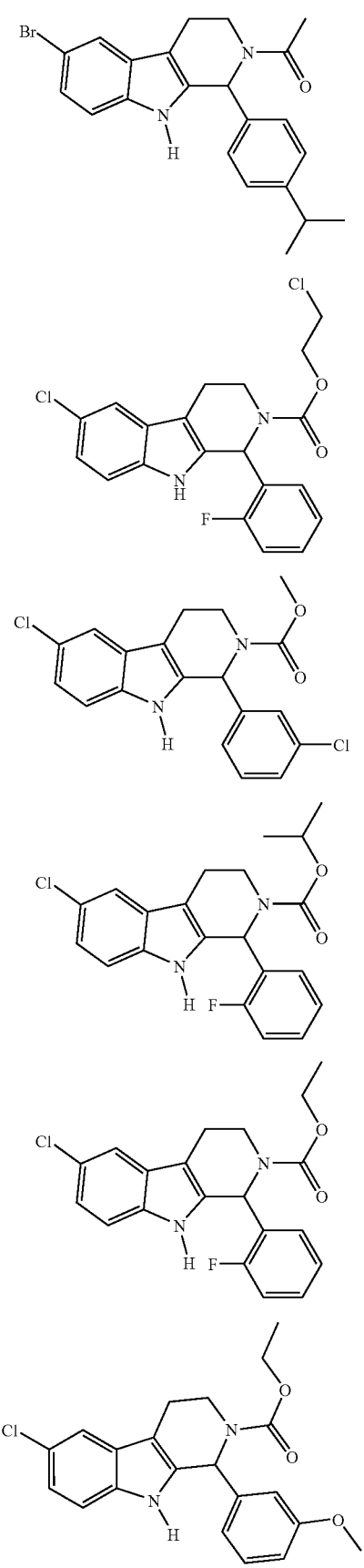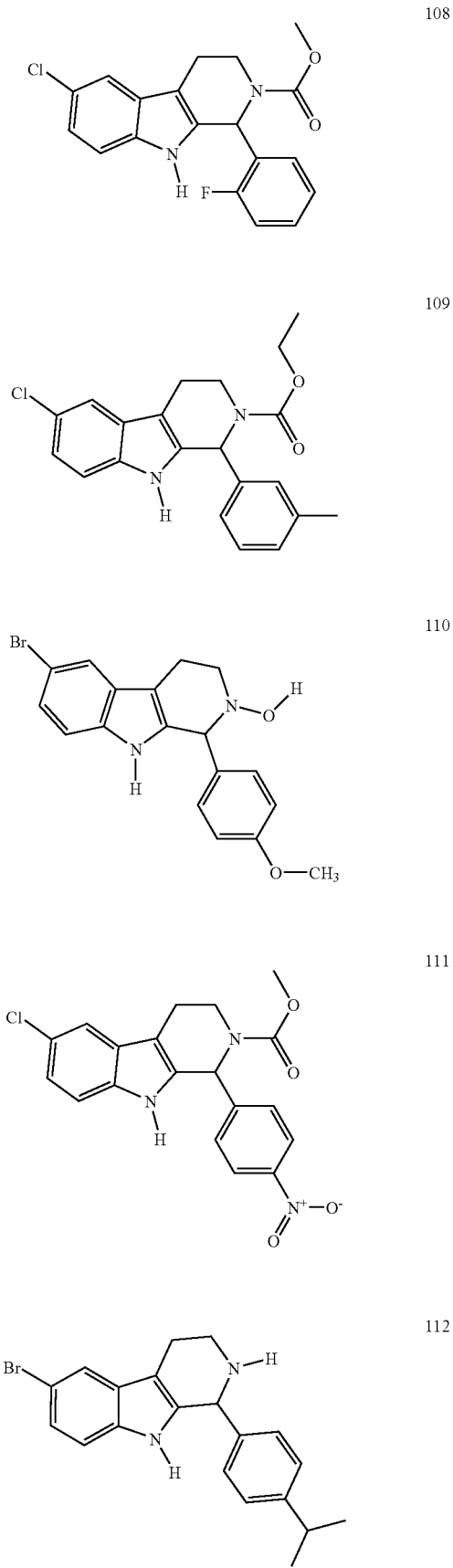 [SMILES: COC(=O)N1CCc2c([nH]c3ccc(Cl)cc23)C1c1ccccc1F ; CCOC(=O)N1CCc2c([nH]c3ccc(Cl)cc23)C1c1cccc(C)c1 ; COc1ccc(C2c3[nH]c4ccc(Br)cc4c3CCN2O)cc1 ; COC(=O)N1CCc2c([nH]c3ccc(Cl)cc23)C1c1ccc([N+](=O)[O-])cc1 ; CC(C)c1ccc(C2NCCc3c2[nH]c2ccc(Br)cc32)cc1]

113 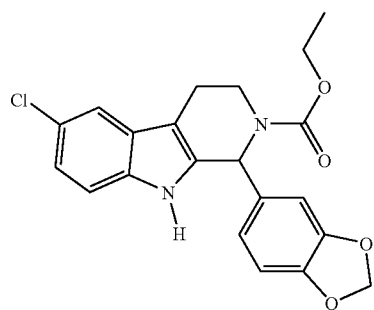
114 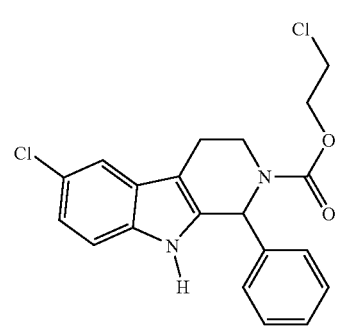
115 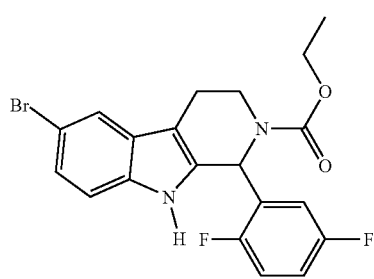
116 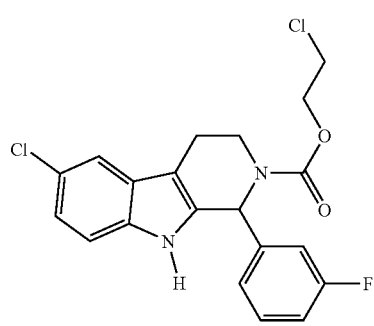
117 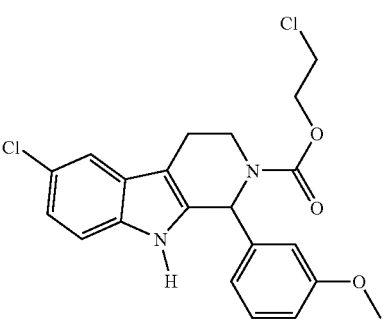
118 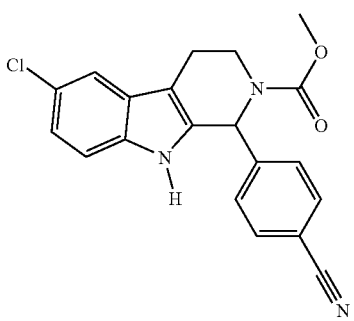
119 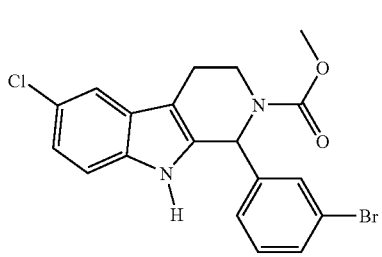
120 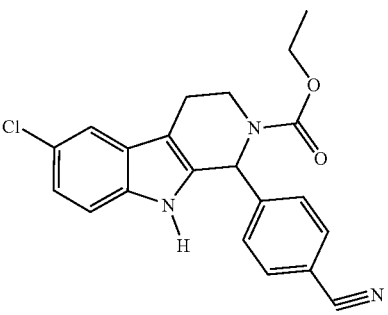
121 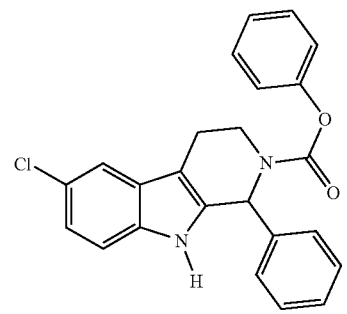
122 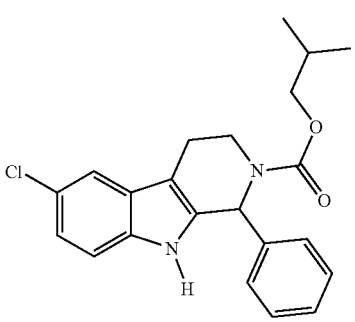

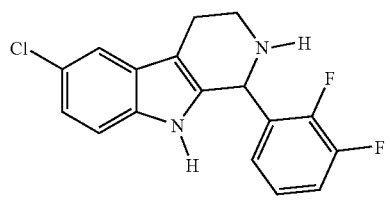
123
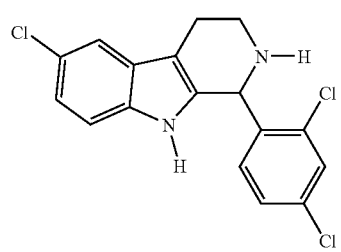
124
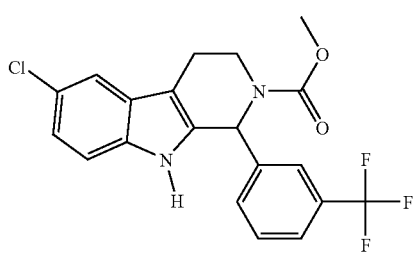
125
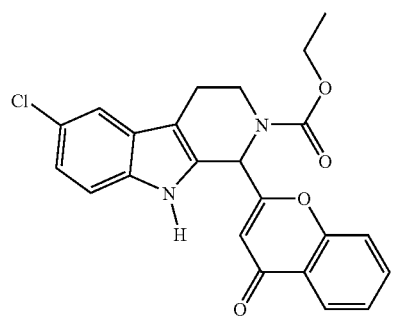
126
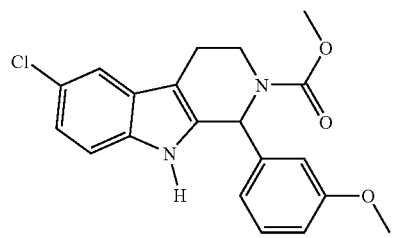
127
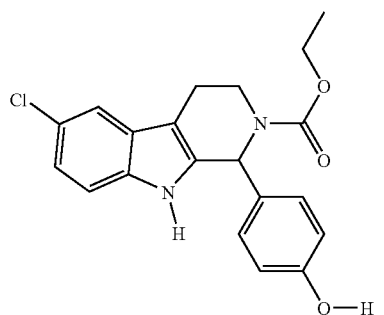
128
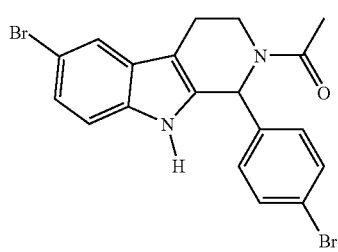
129
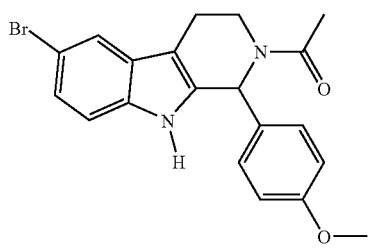
130
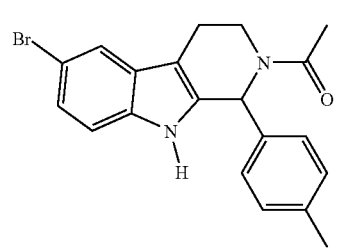
131
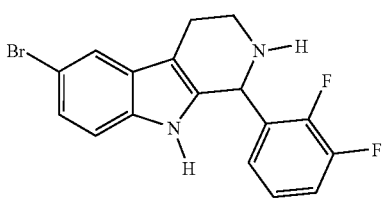
132
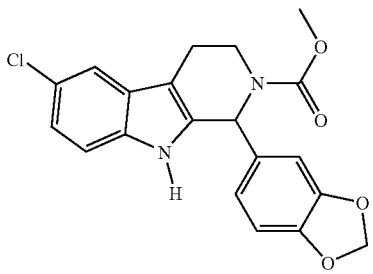
133
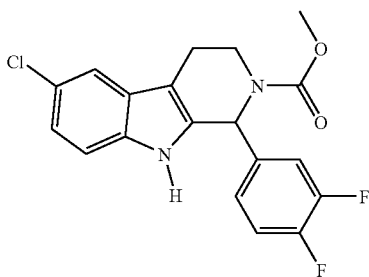
134

135
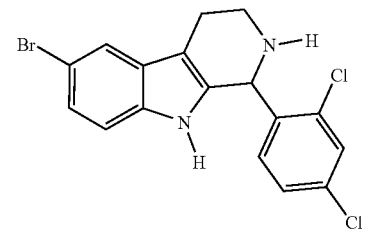
136
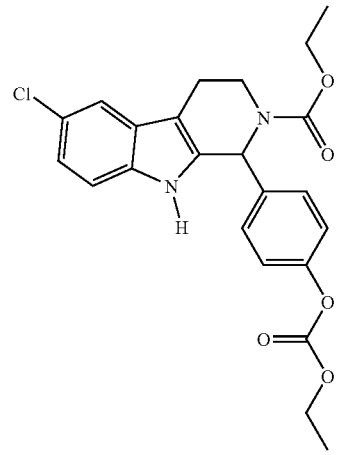
137
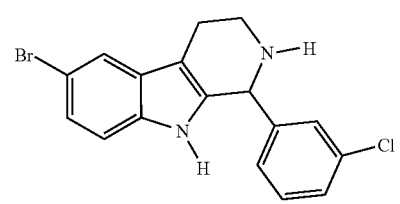
138
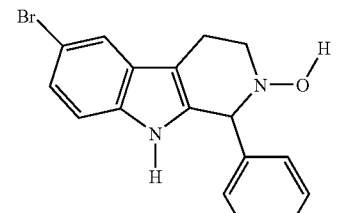
139
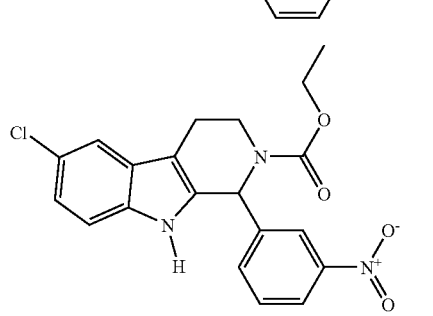
140
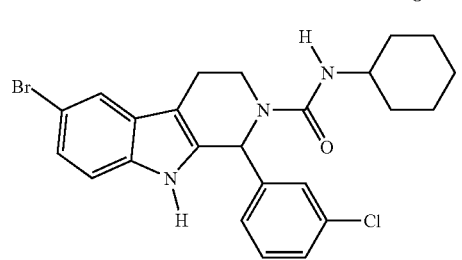
141
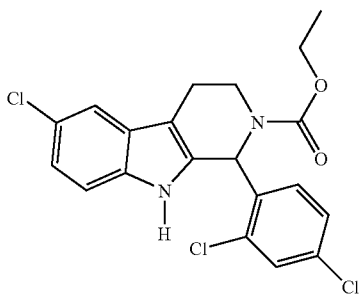
142
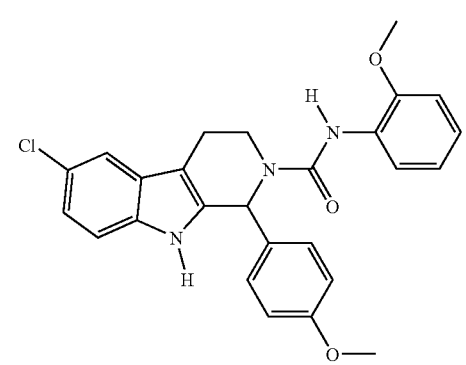
143
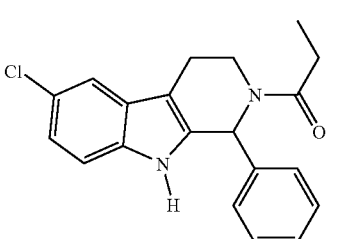
144
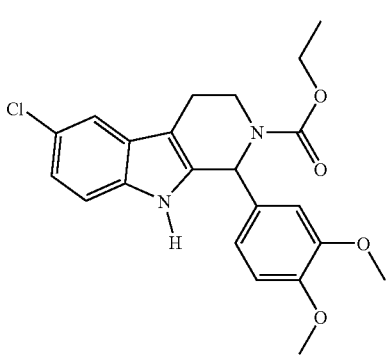
145
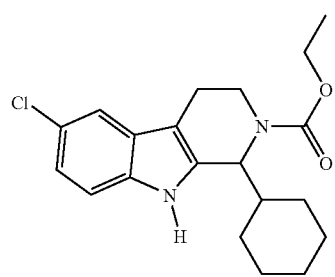

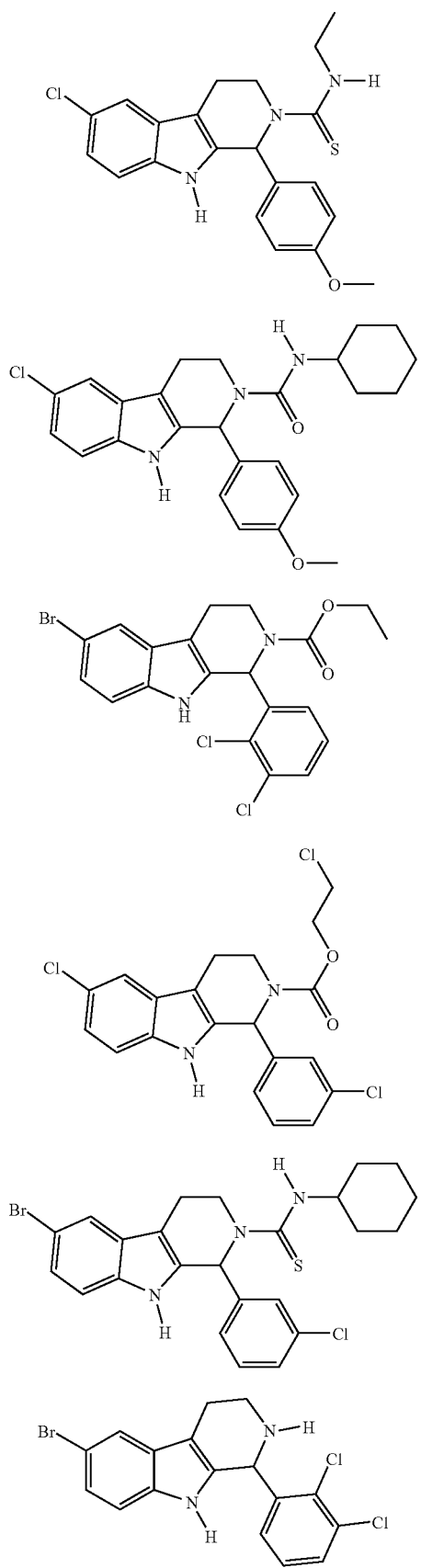
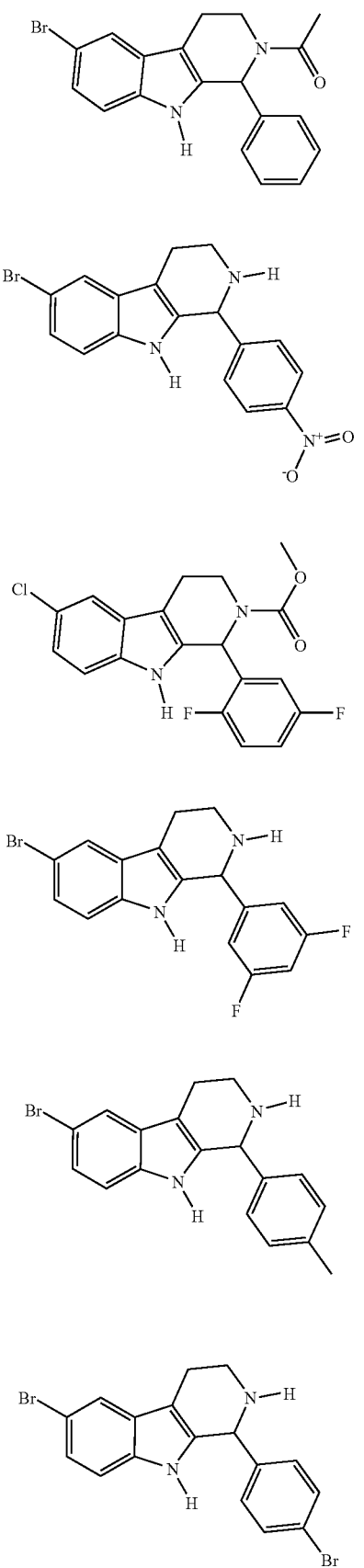

158 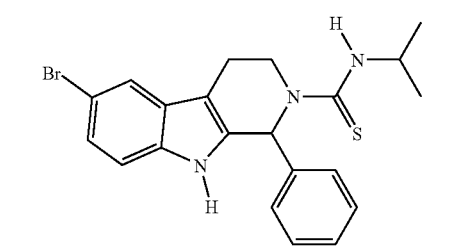
159 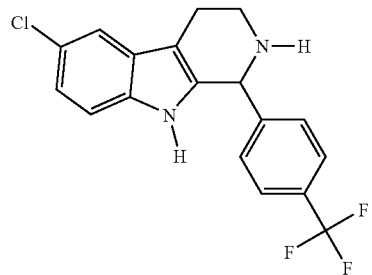
160 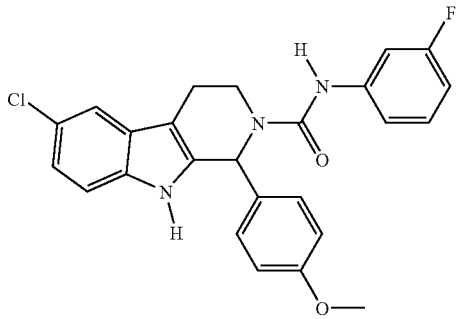
161 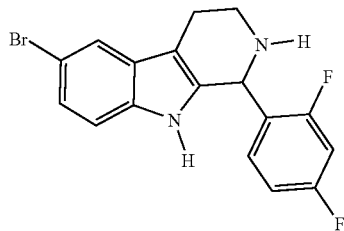
162 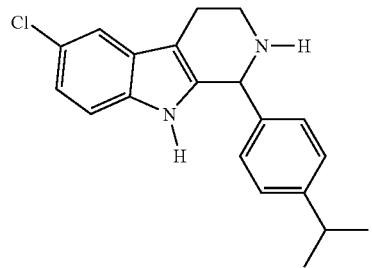
163 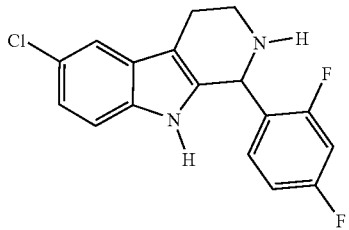
164 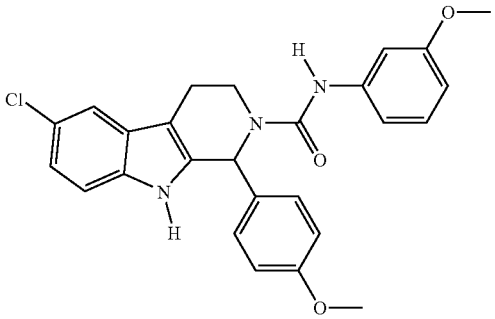
165 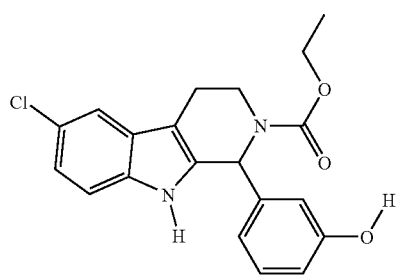
166 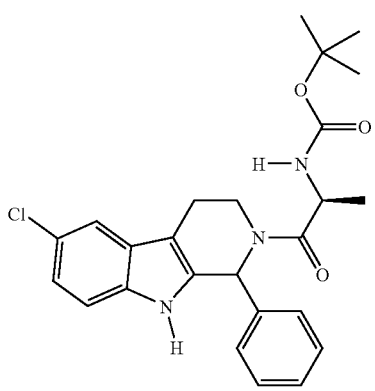
167 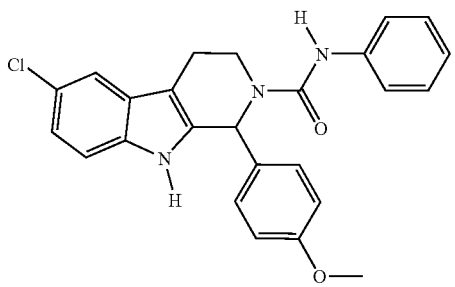
168 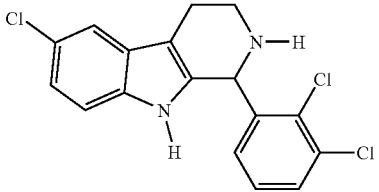

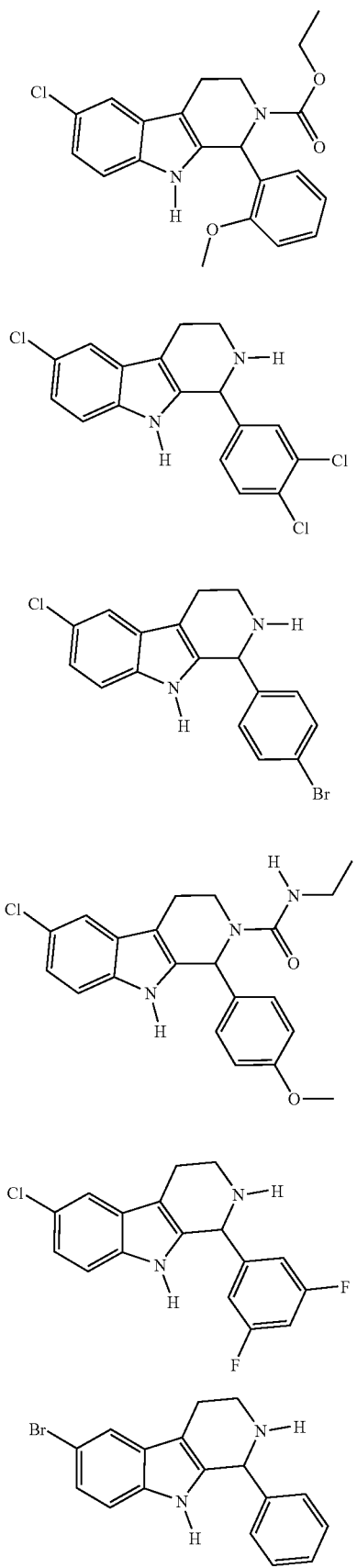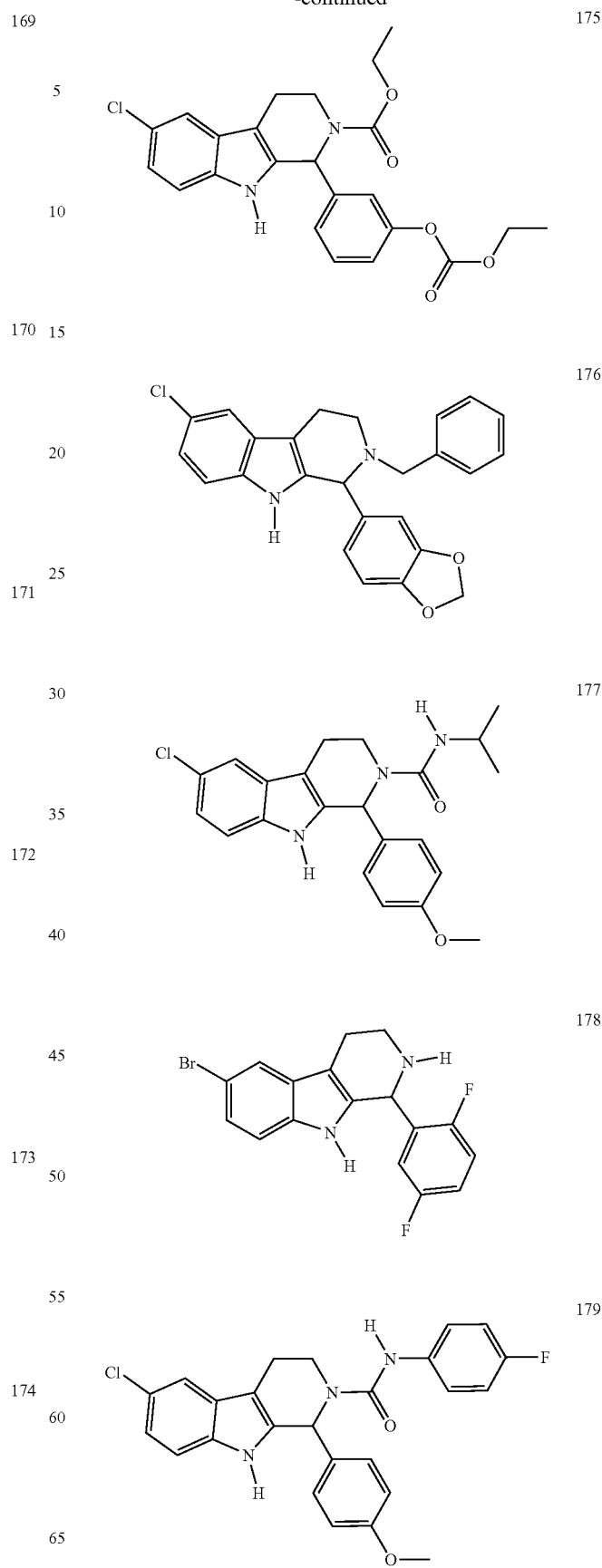

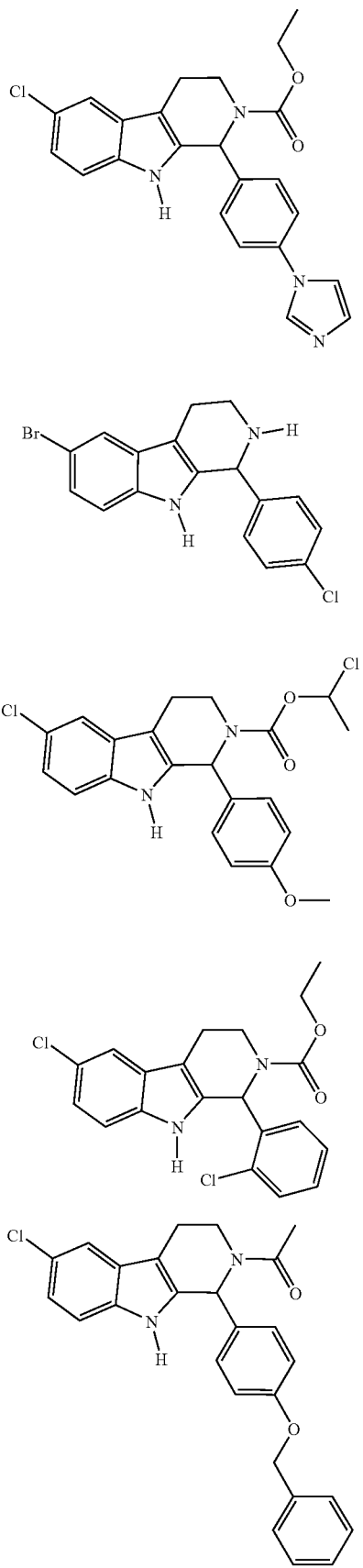
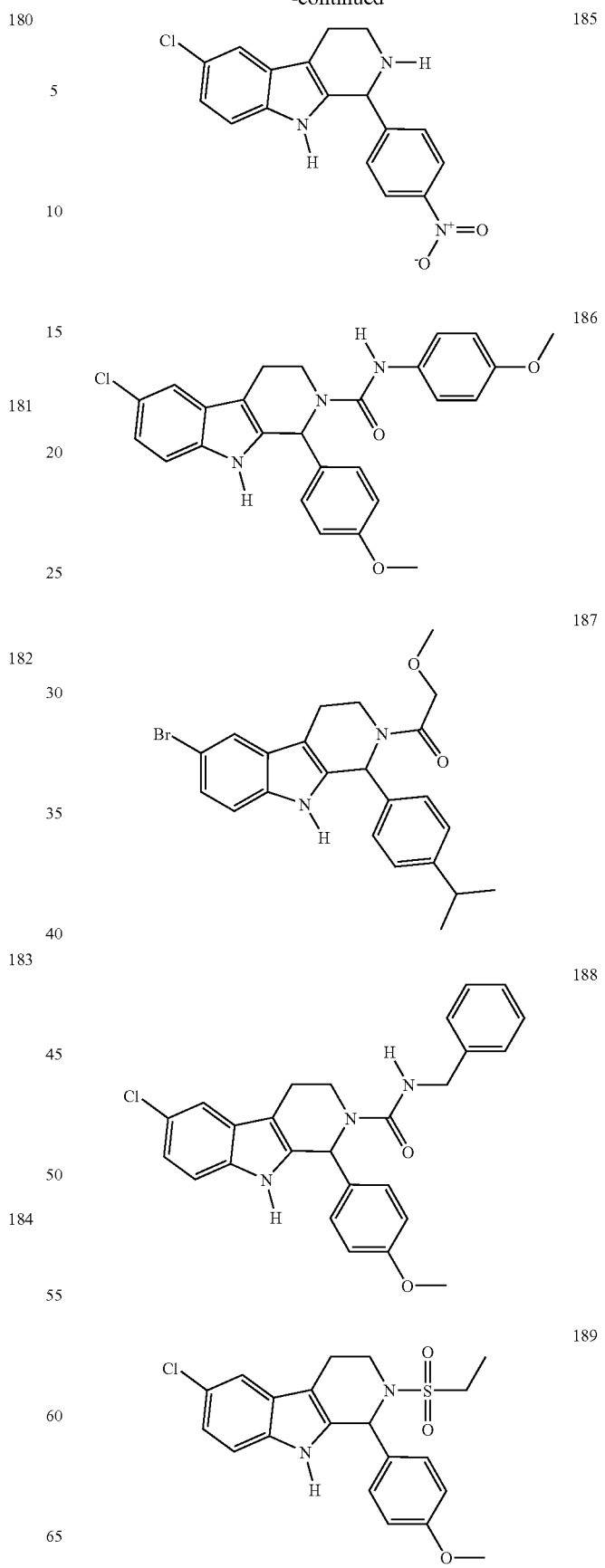

190 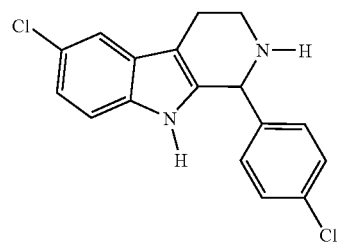
191 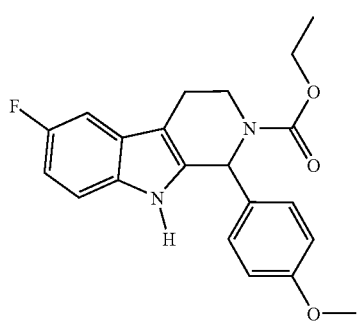
192 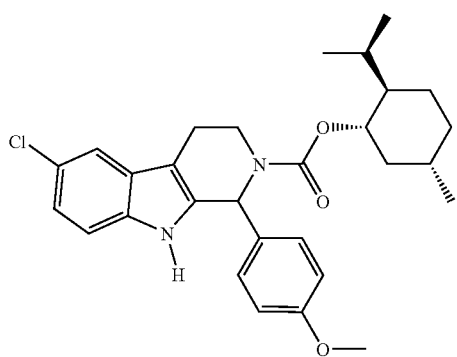
193 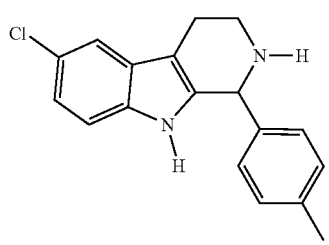
194 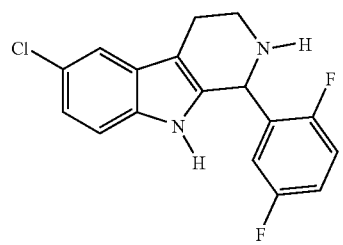
195 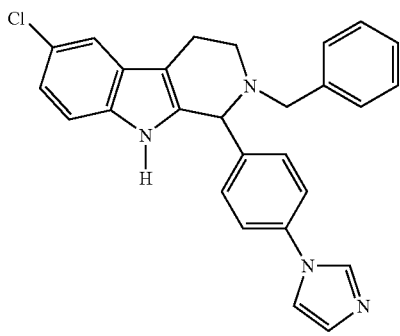
196 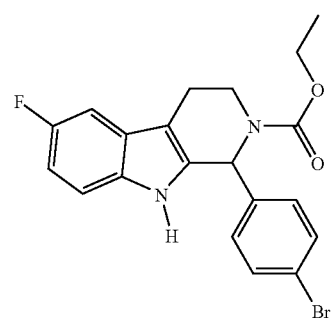
197 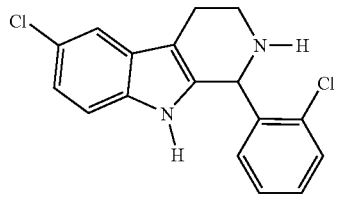
198 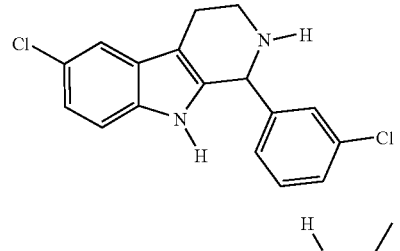
199 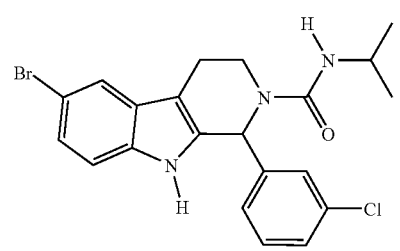
200 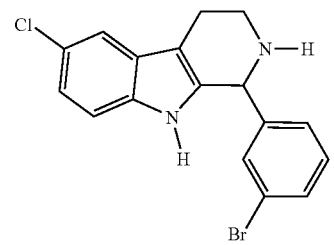

201 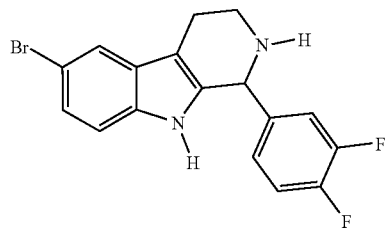
202 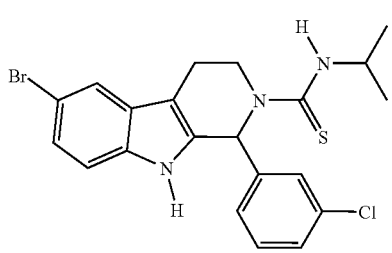
203 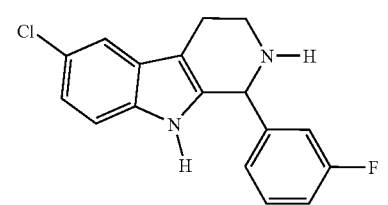
204 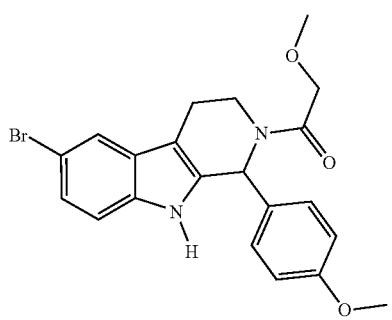
205 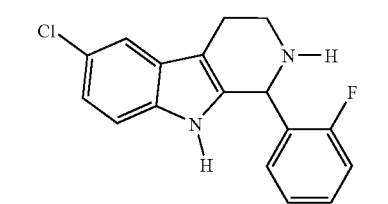
206 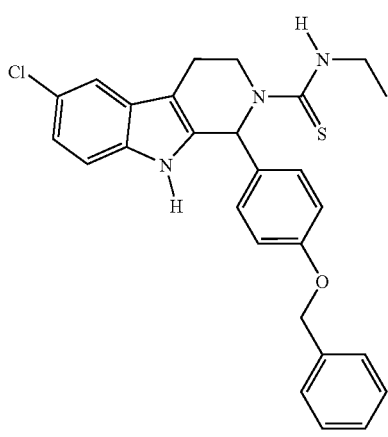
207 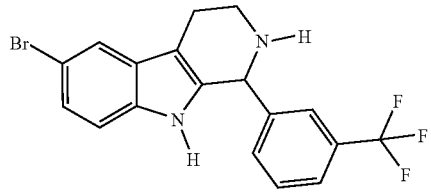
208 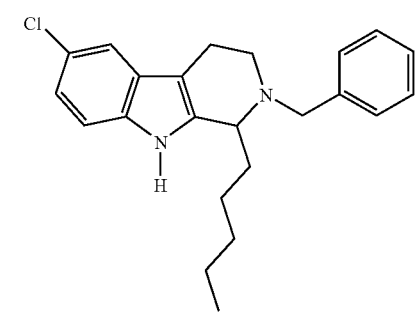
209 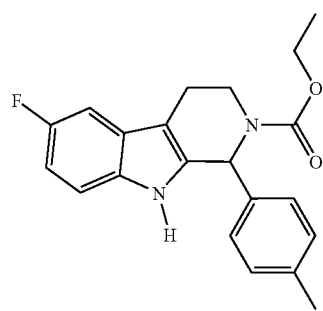
210 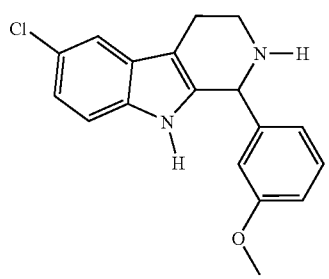
211 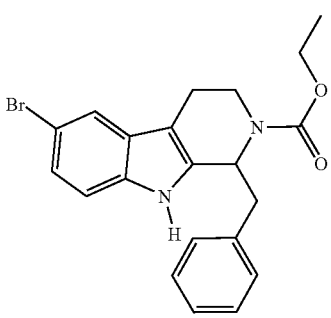

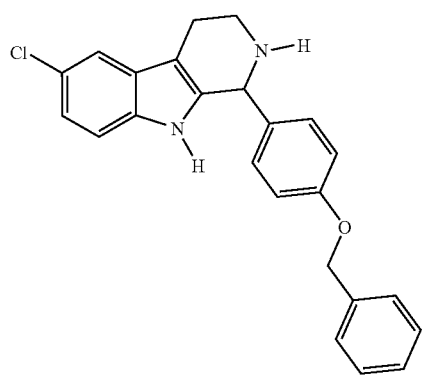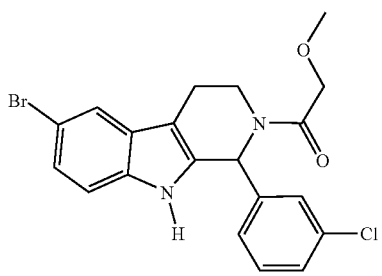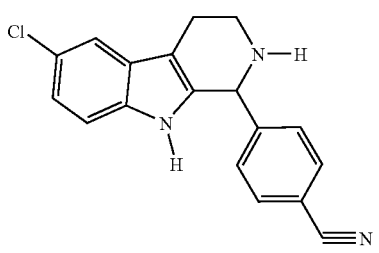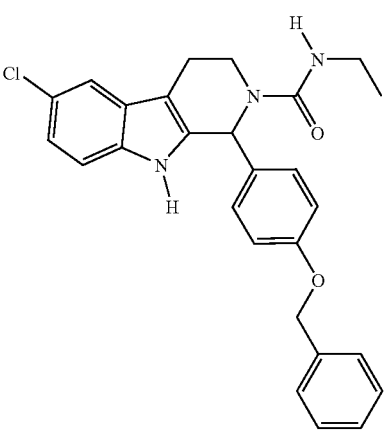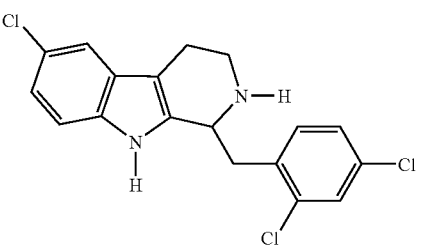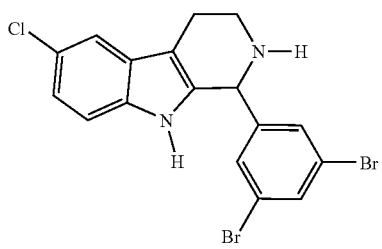

224
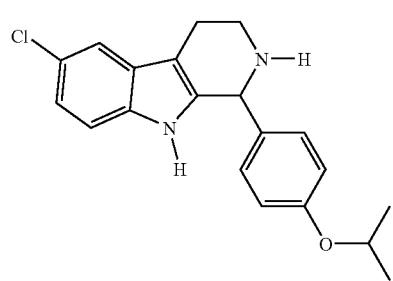
225
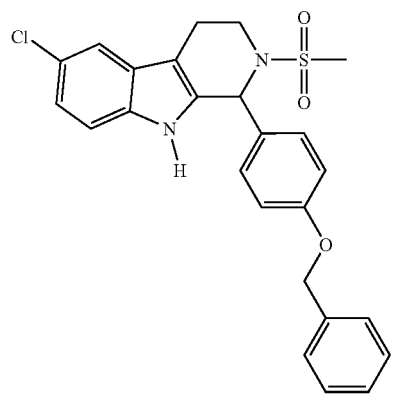
226
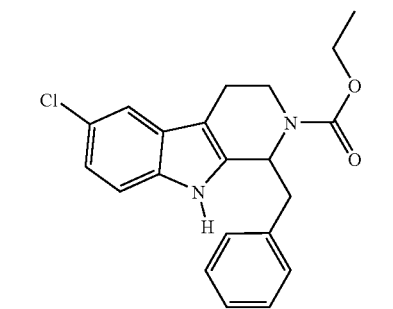
227
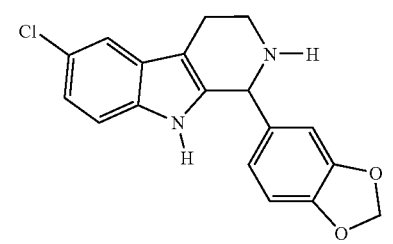
228
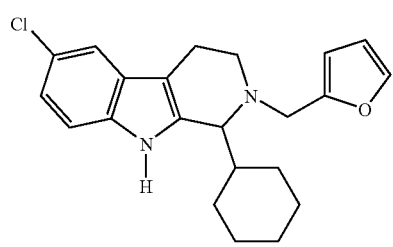
229
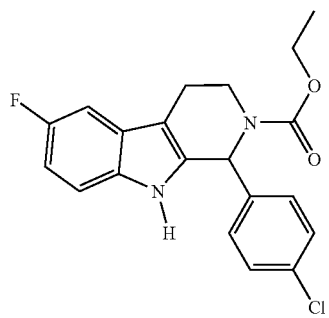
230
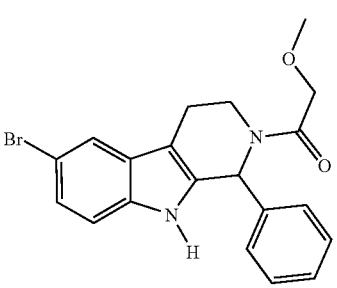
231
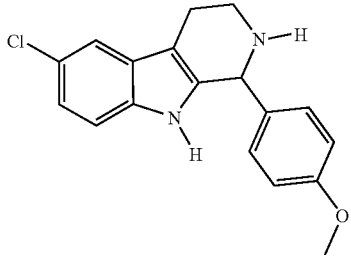
232
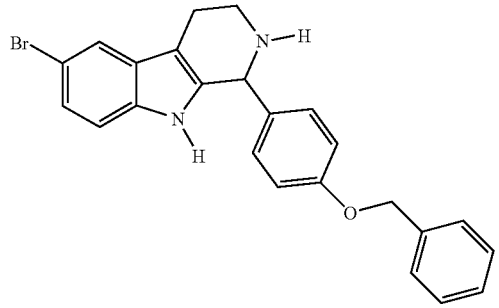
233
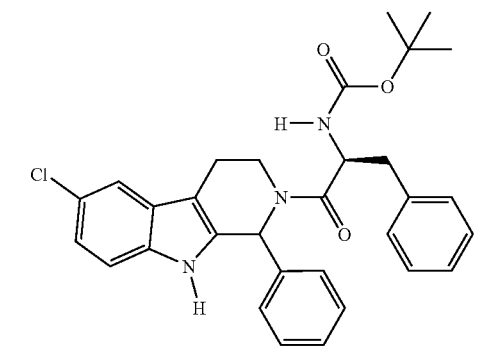

234
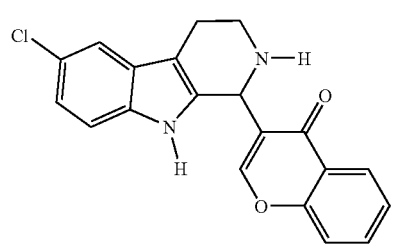
235
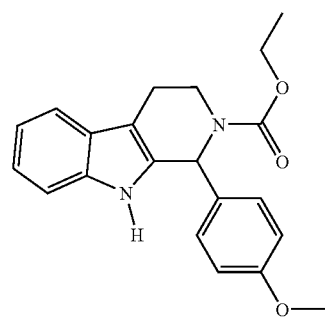
236
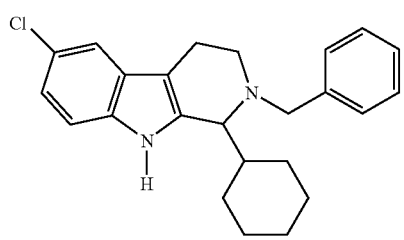
237
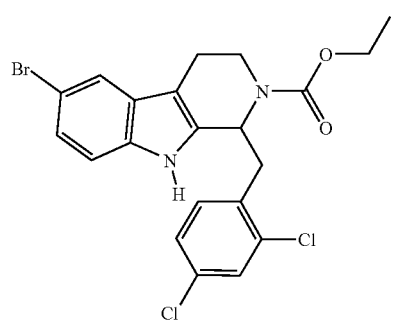
238
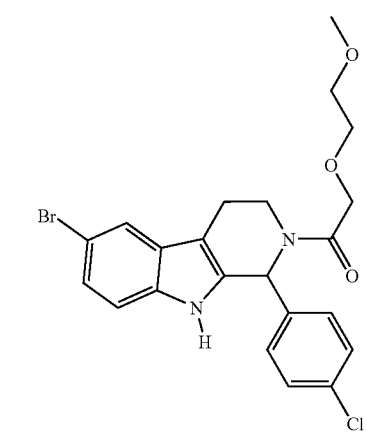
239
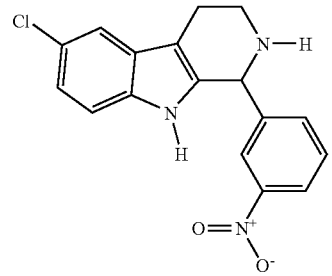
240
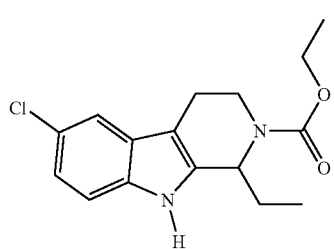
241
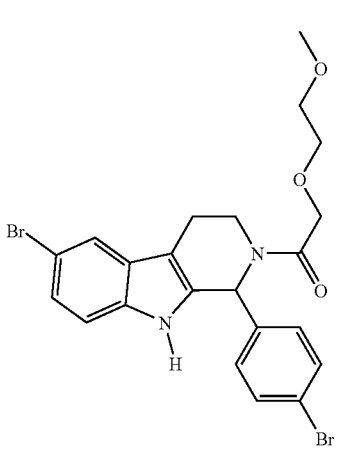
242
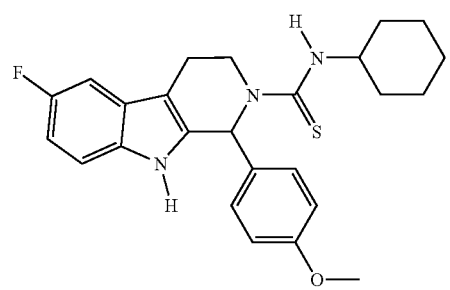
243
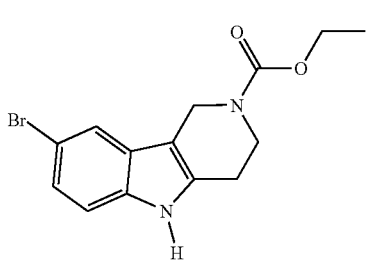

| 244 | 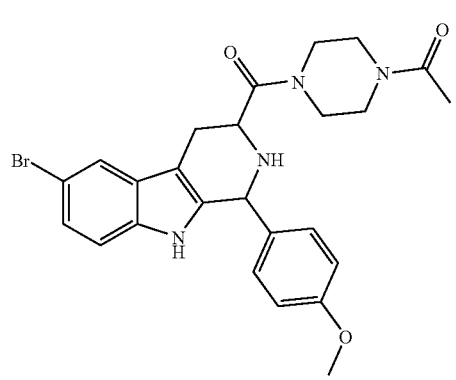 |
| 245 | 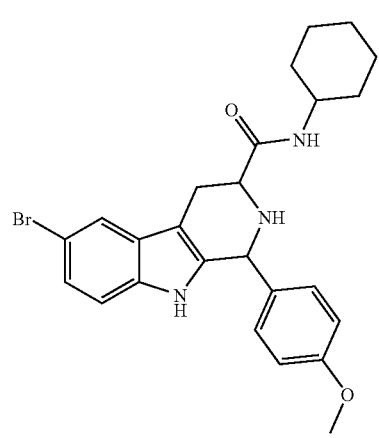 |
| 246 | 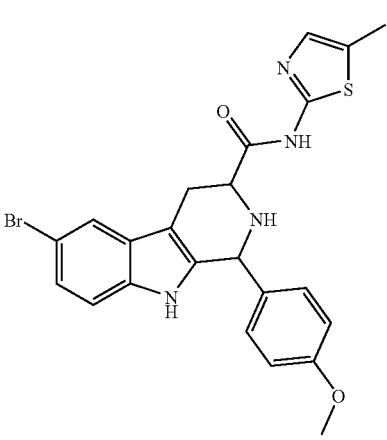 |
| 247 | 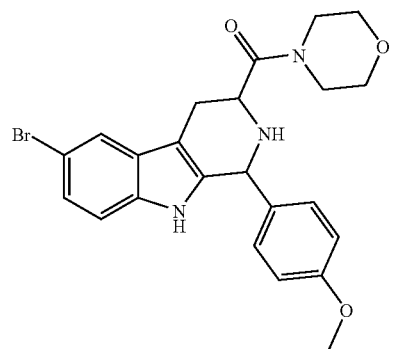 |
| 248 | 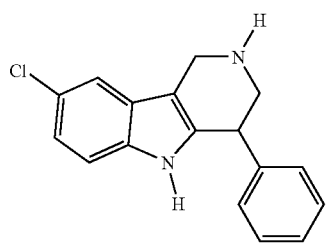 |
| 249 | 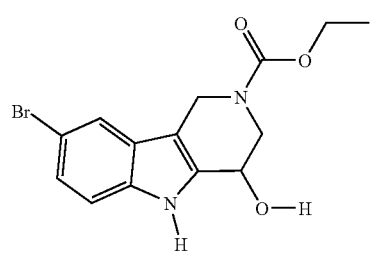 |
| 250 | 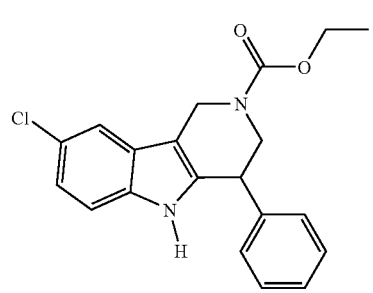 |
| 251 | 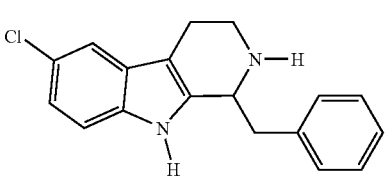 |
| 252 | 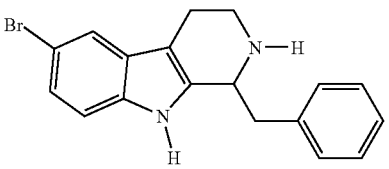 |
| 253 | 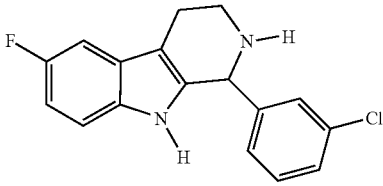 |
| 254 | 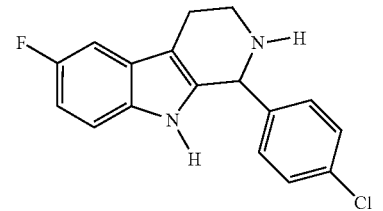 |

255
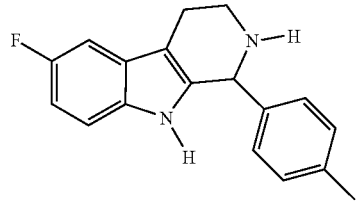
256
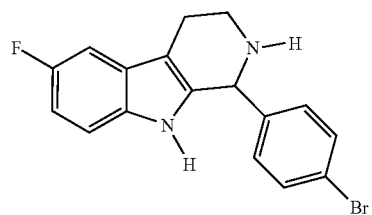
257
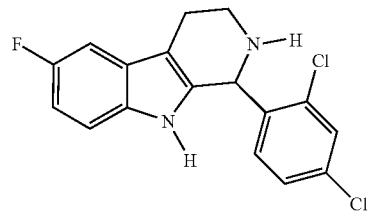
258
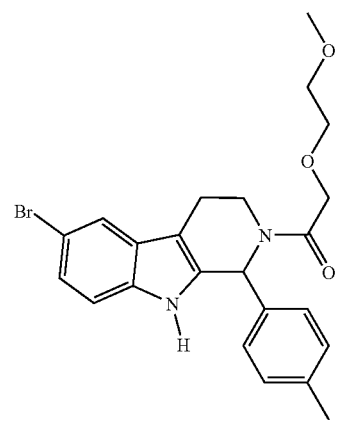
259
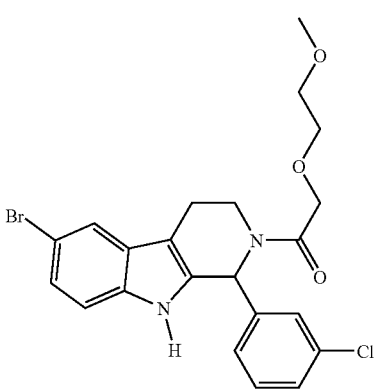
260
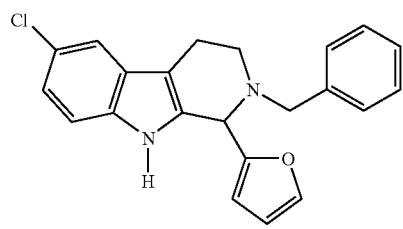
261
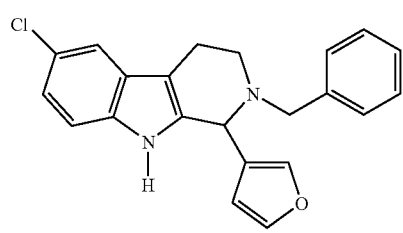
262
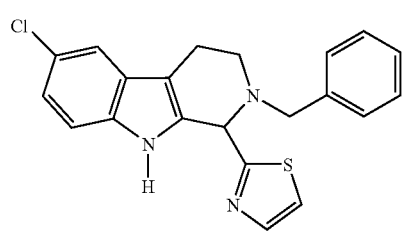
263
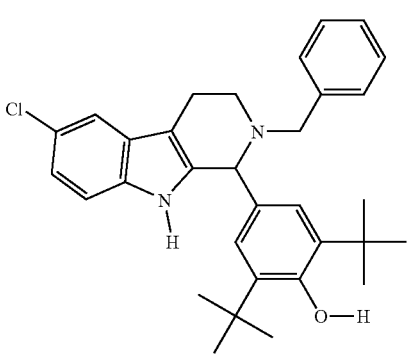
264
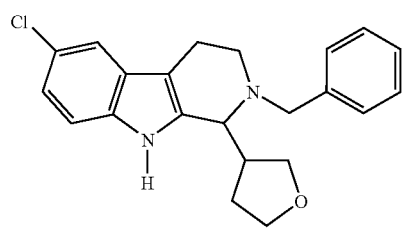
265
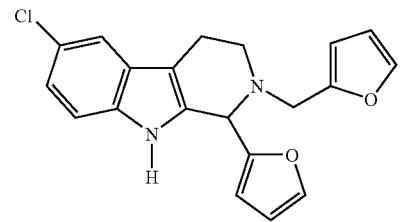

266 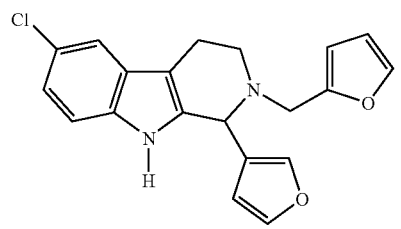
267 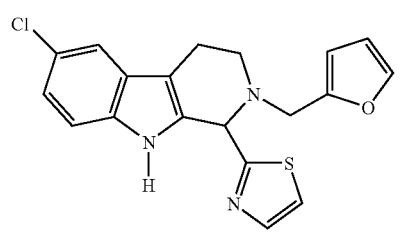
268 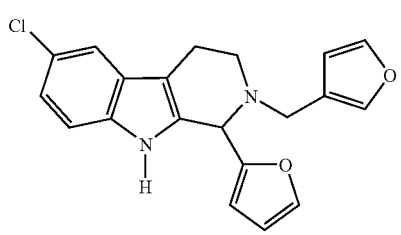
269 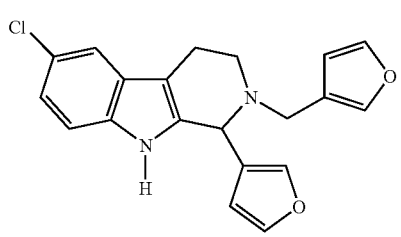
270 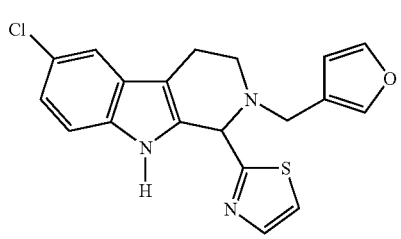
271 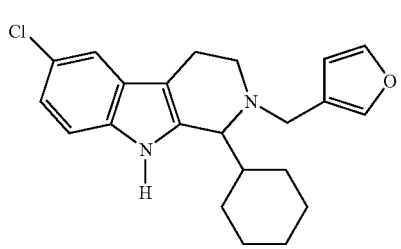
272 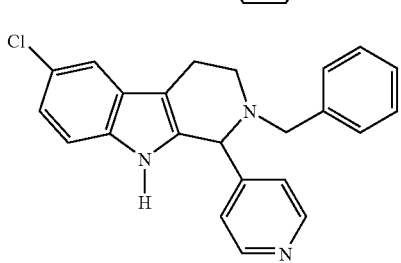
273 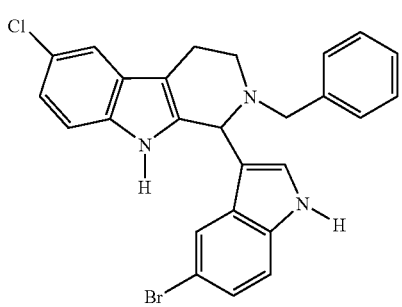
274 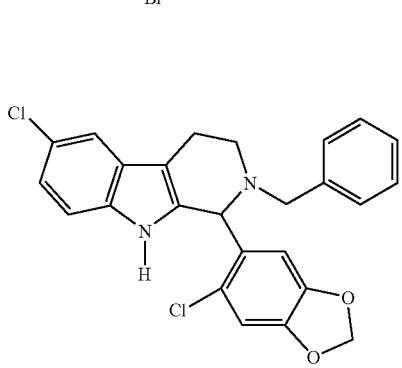
275 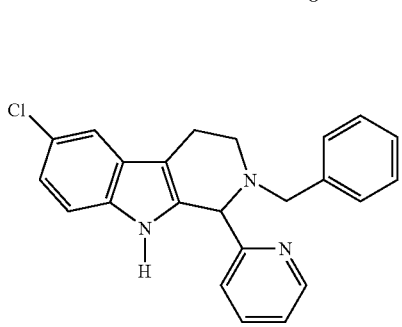
276 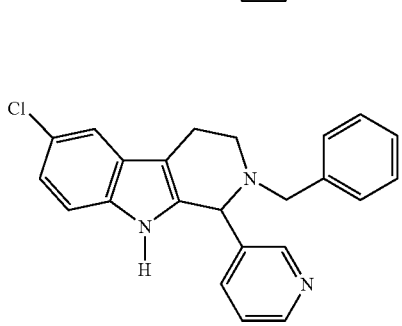
277 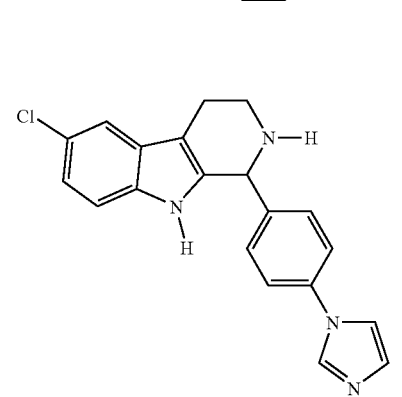

278
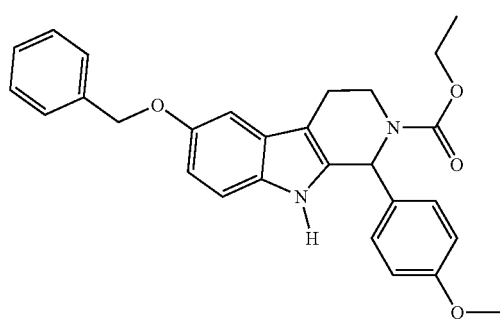
279
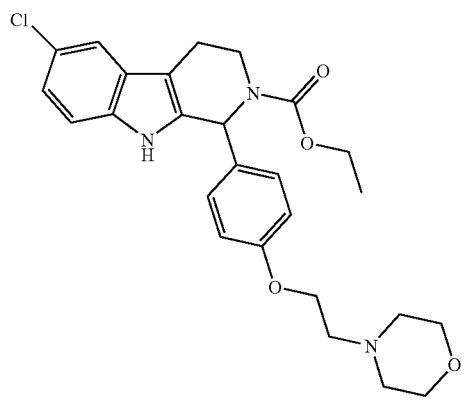
280
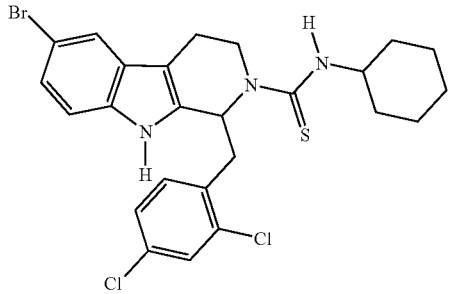
281
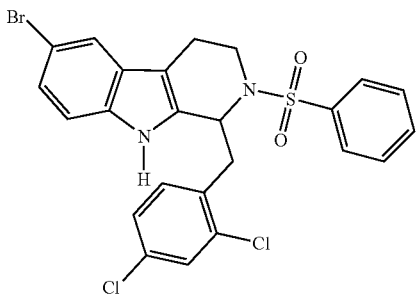
282
283
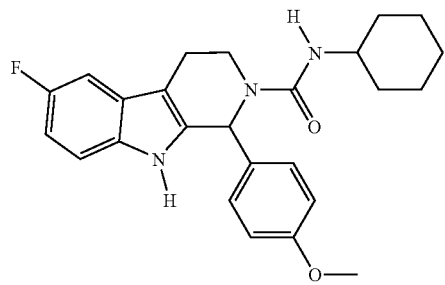
284
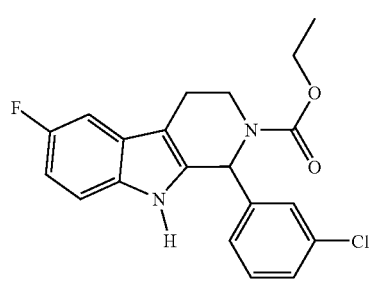
285
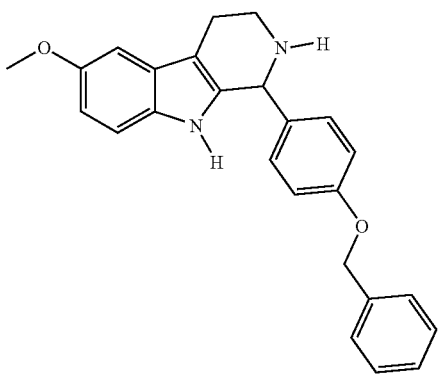
286
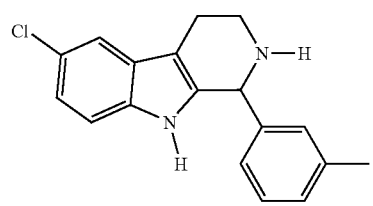
287
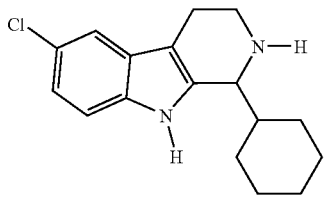

288
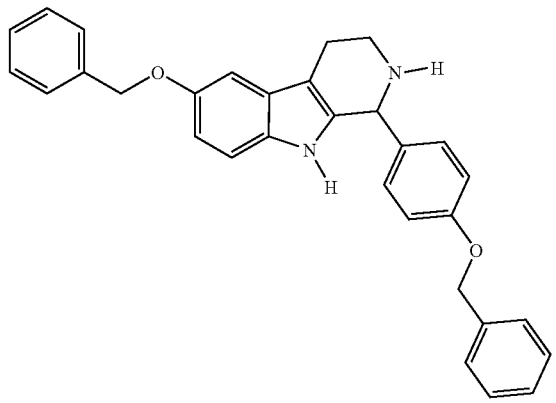
289
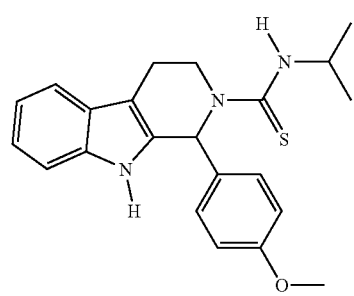
290
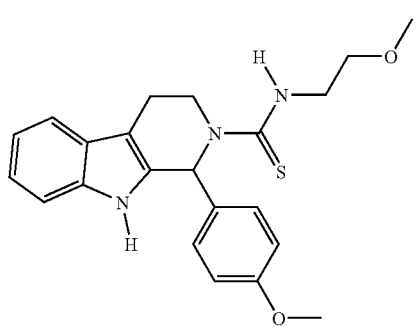
291
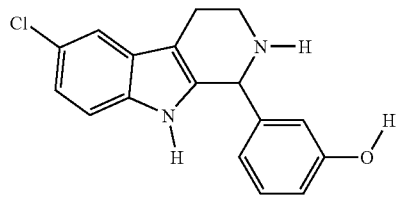
292
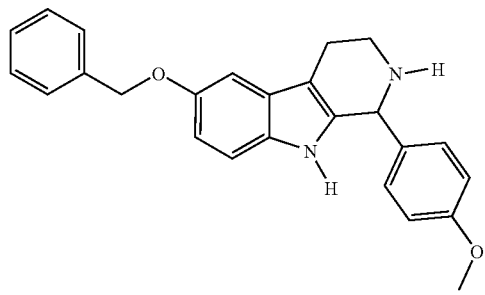
293
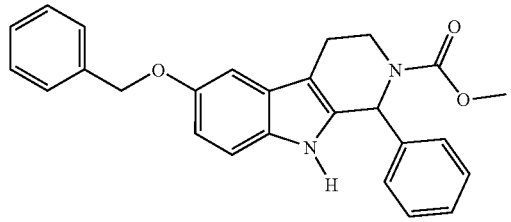
294
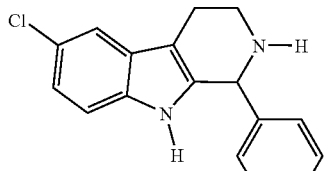
295
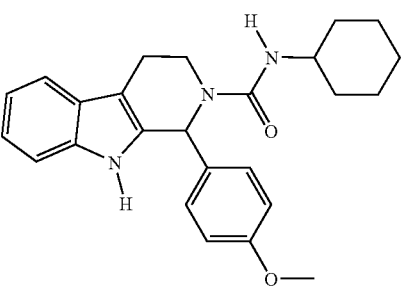
296
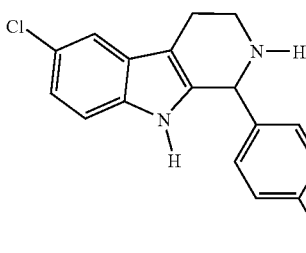
297
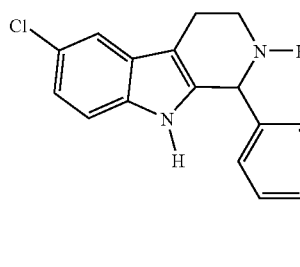
298
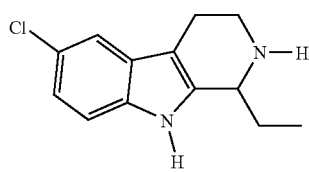

299
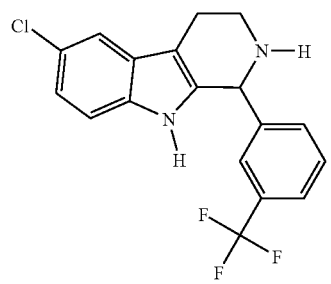
300
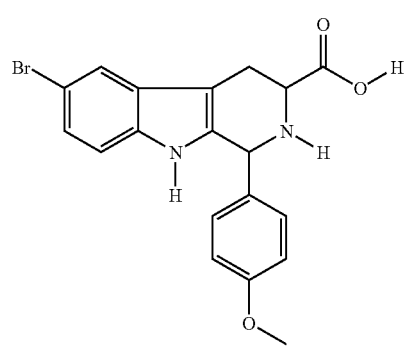
301
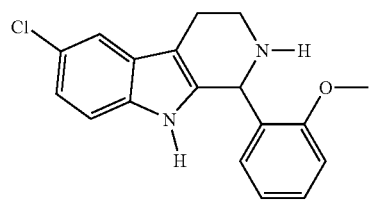
302
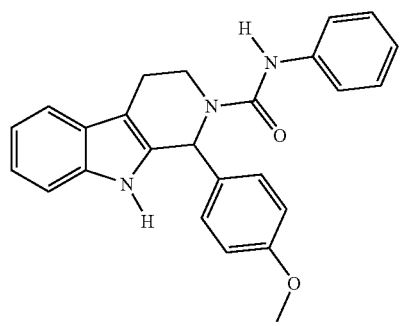
303
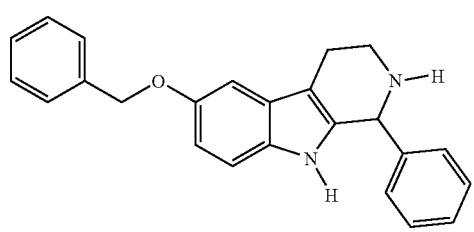
304
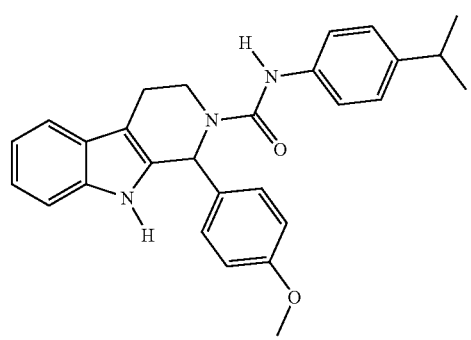
305
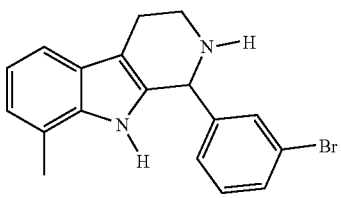
306
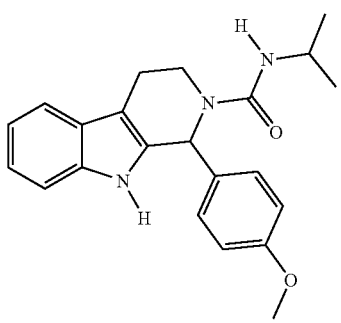
307
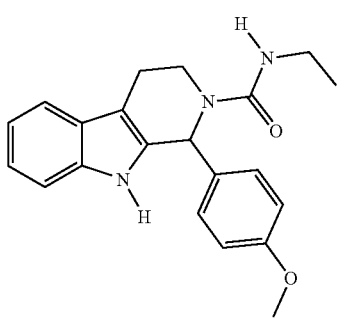
308
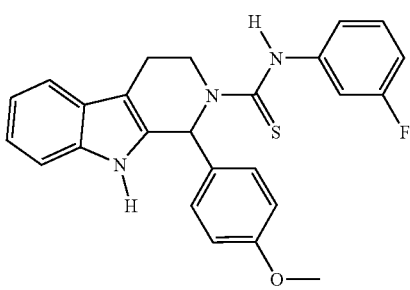

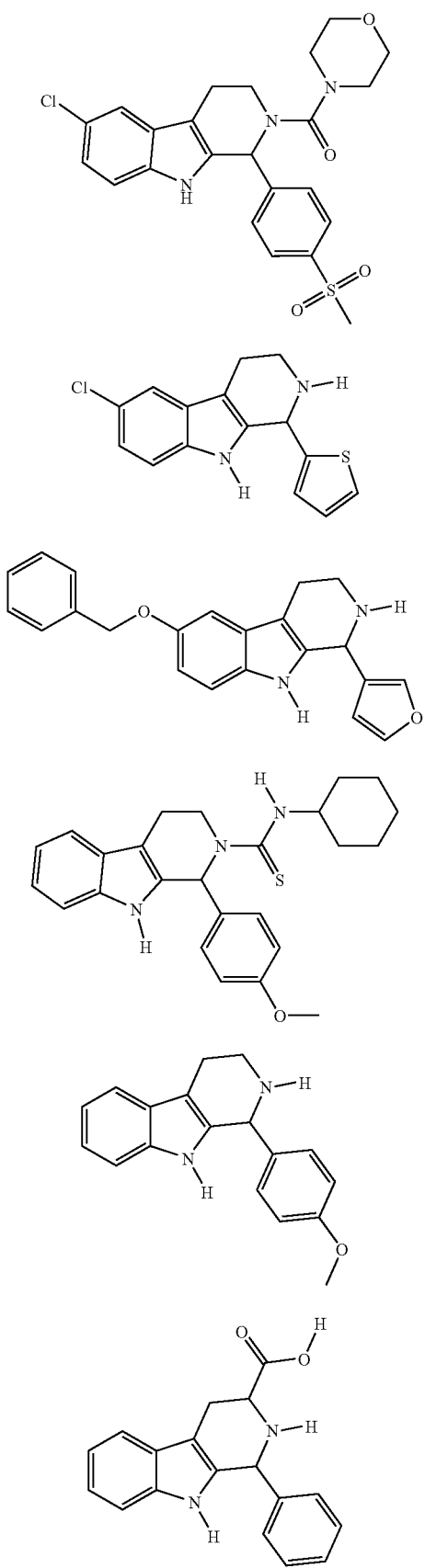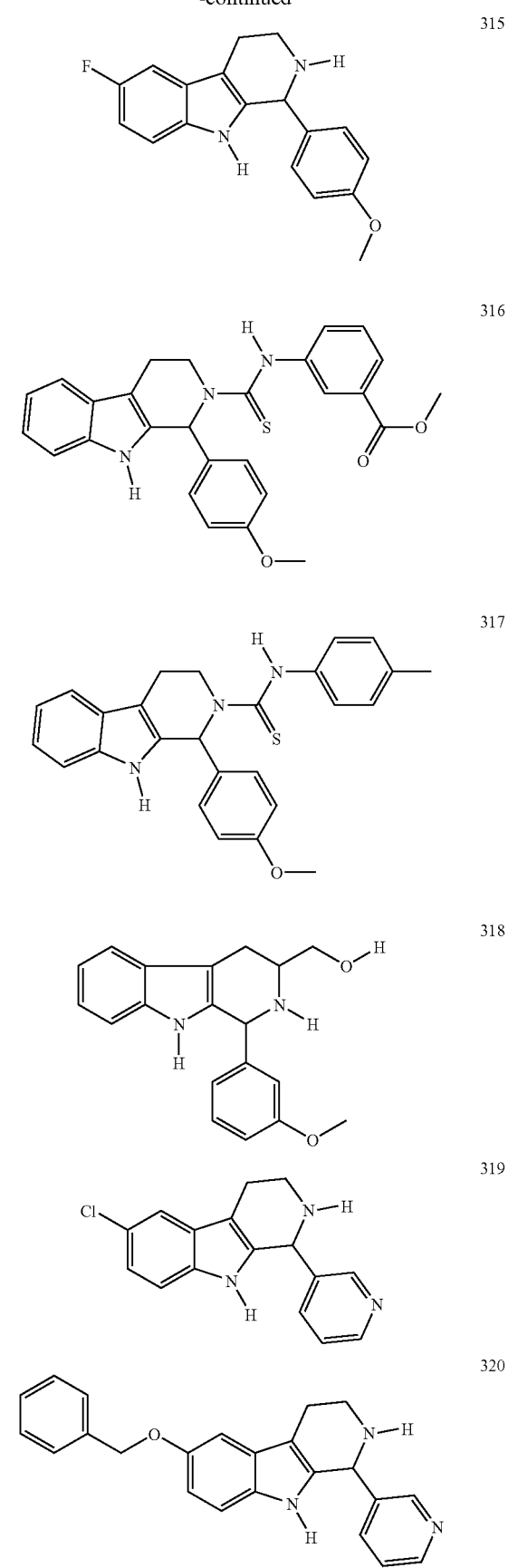

321 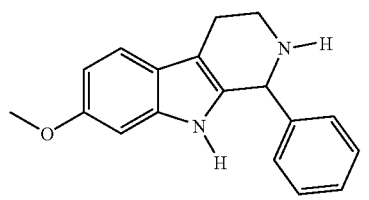
322 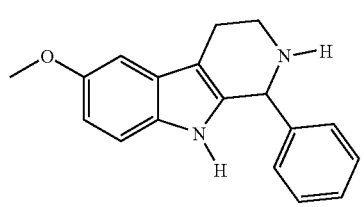
323 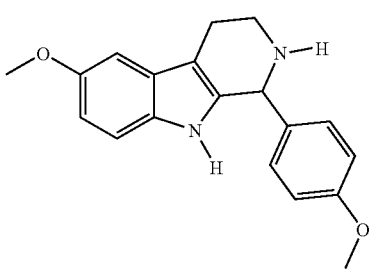
324 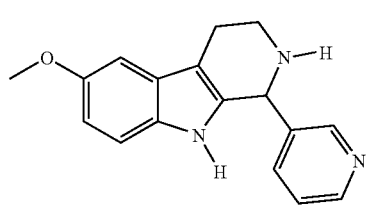
325 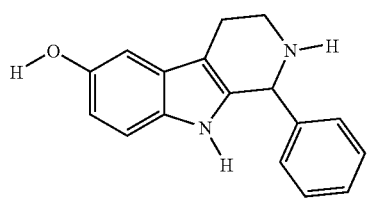
326 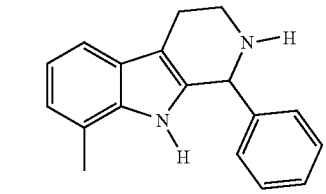
327 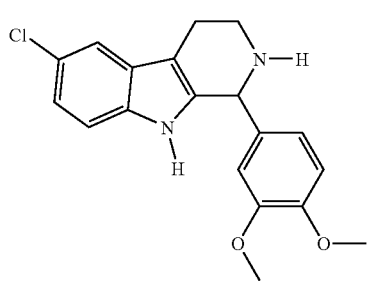
328 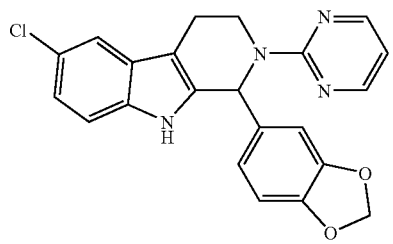
329 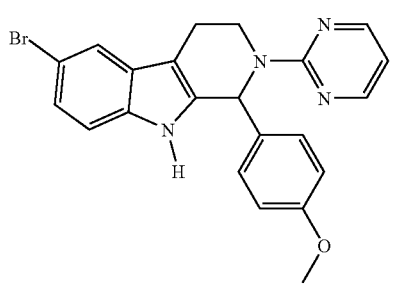
330 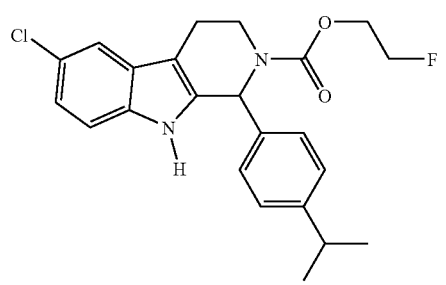
331 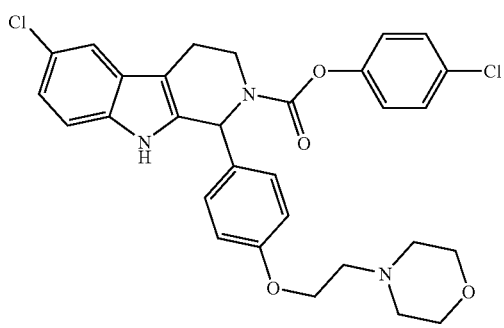
332 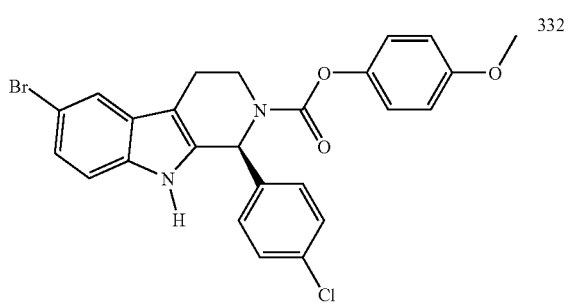

-continued
333
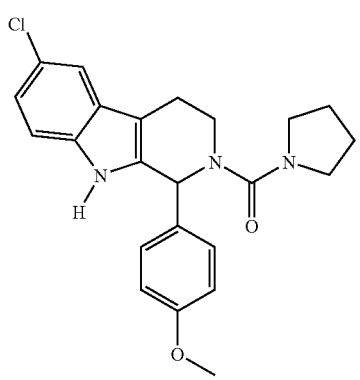
334
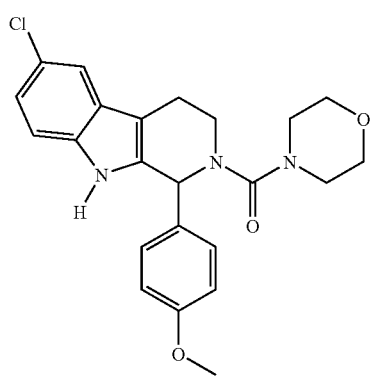
335
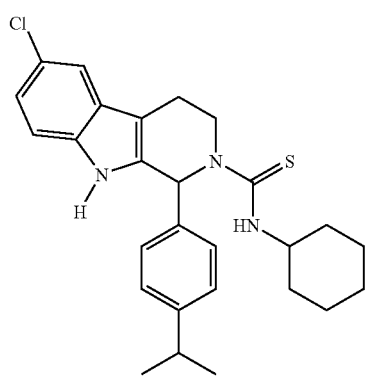
336
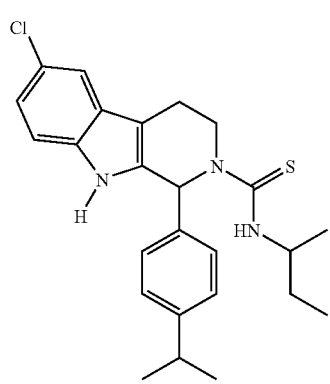
-continued
337
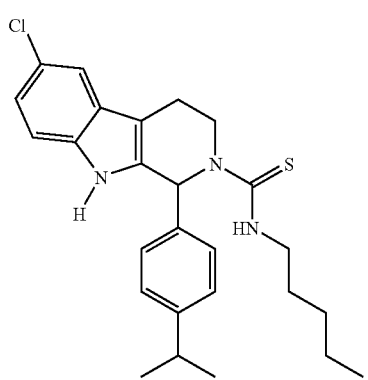
338
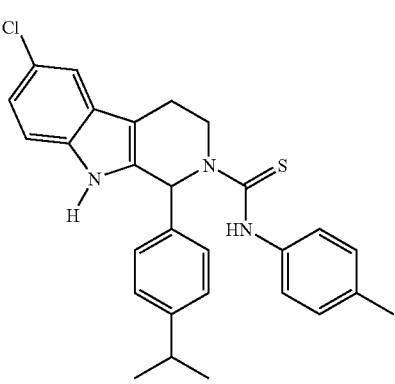
339
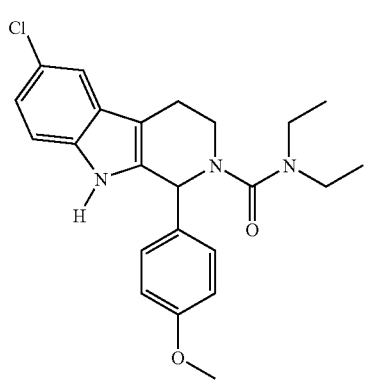
340
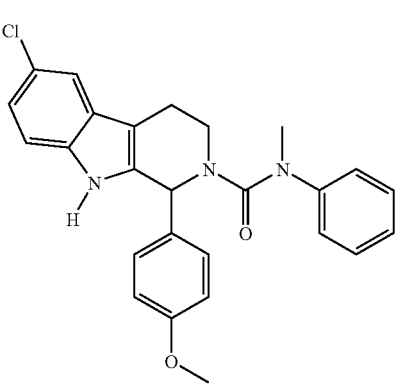

103
-continued
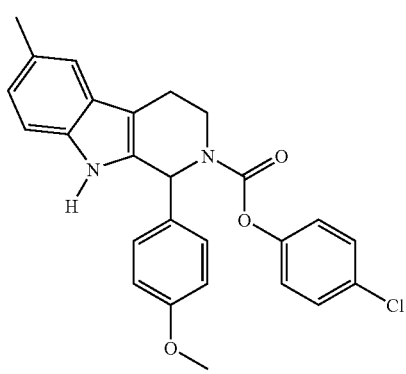
341
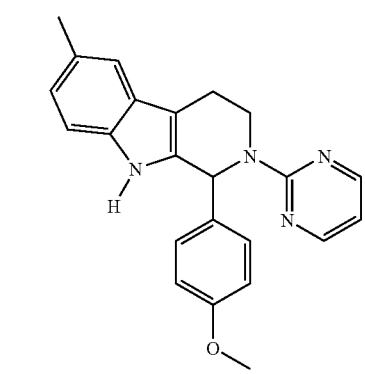
342
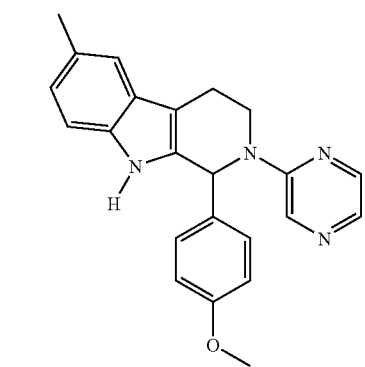
343
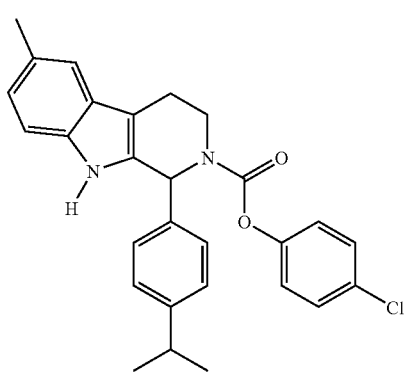
344
104
-continued
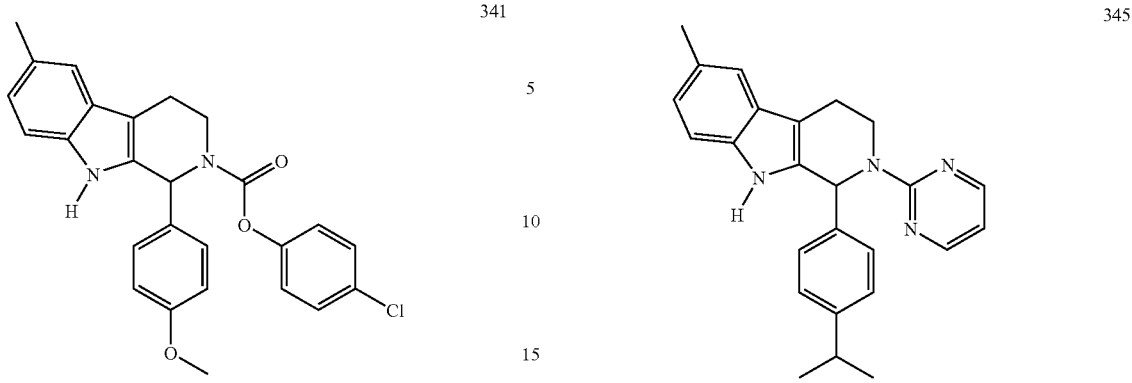
345
346
347
348
349

-continued
350
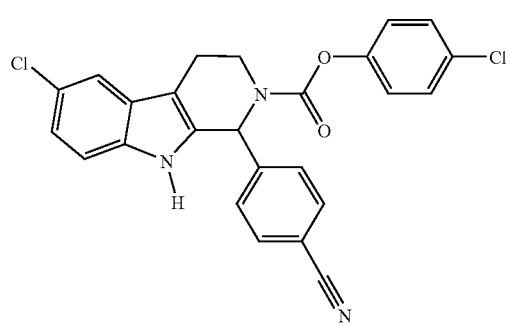
351
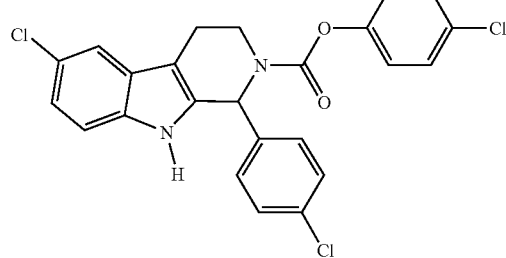
352
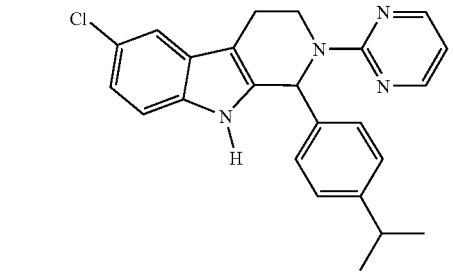
353
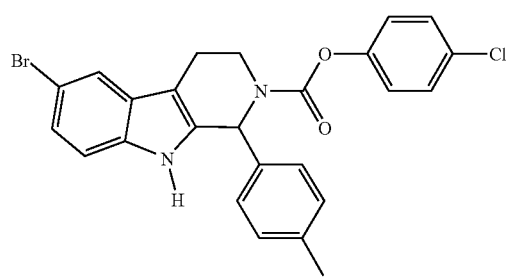
354
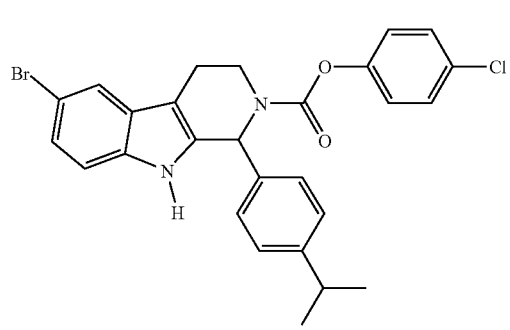
-continued
355
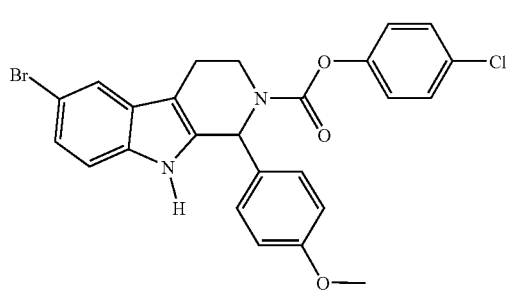
356
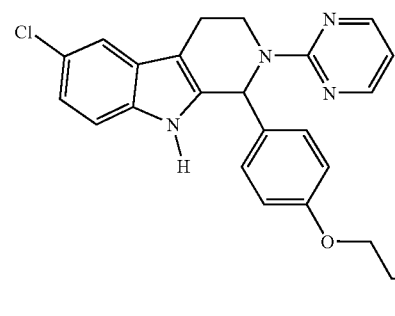
357
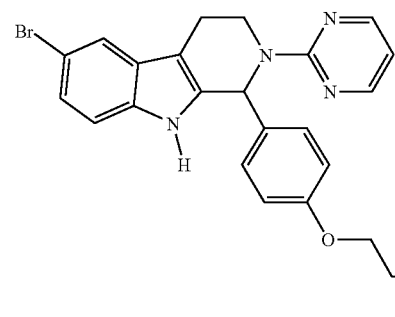
358
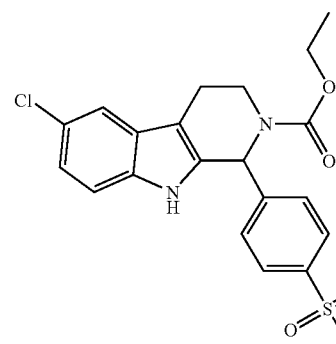
359
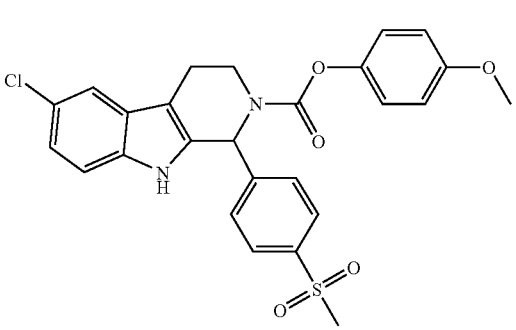

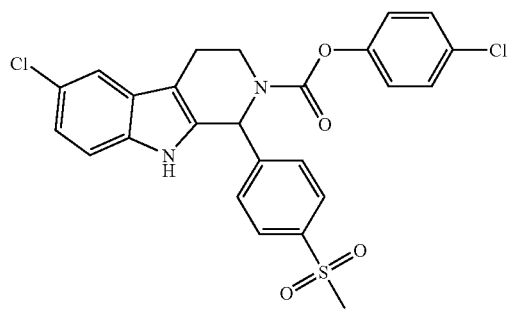
360
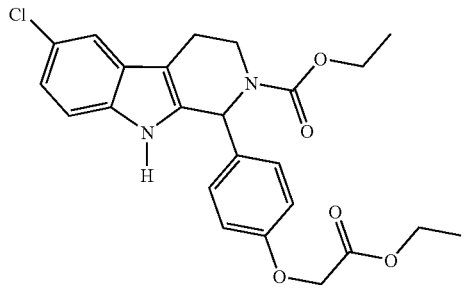
365
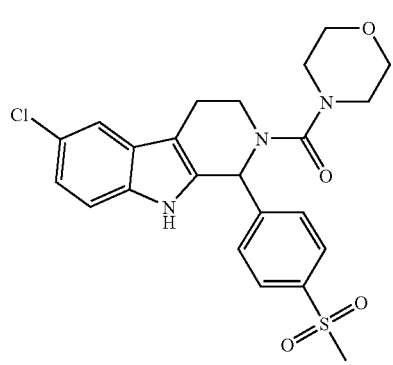
361
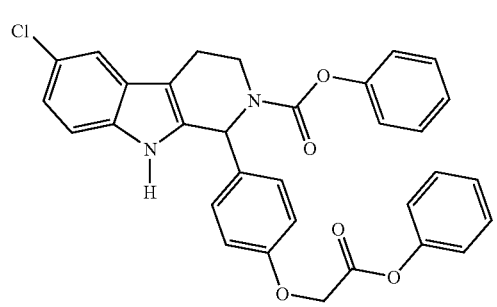
366
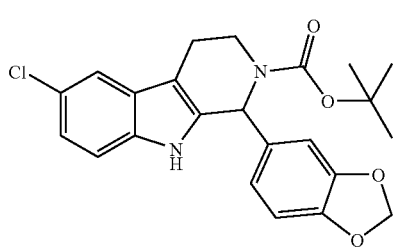
362
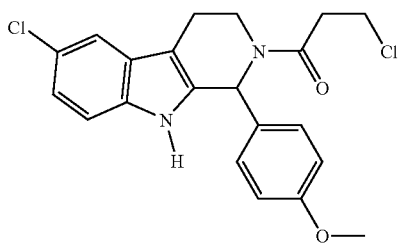
367
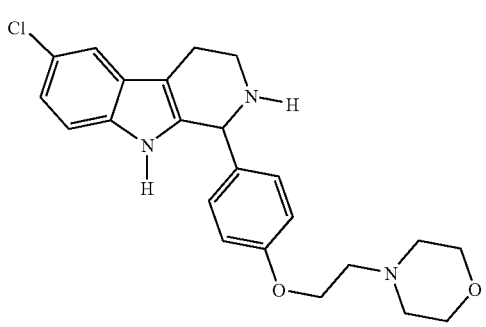
363
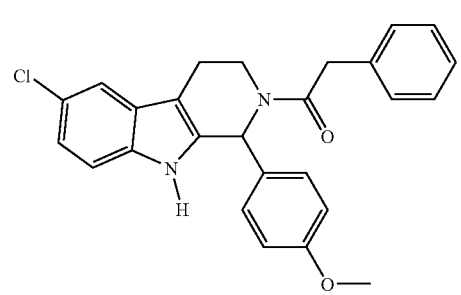
368
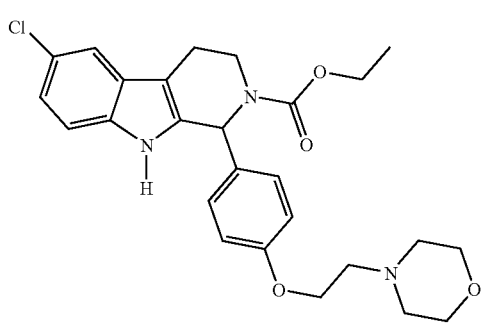
364
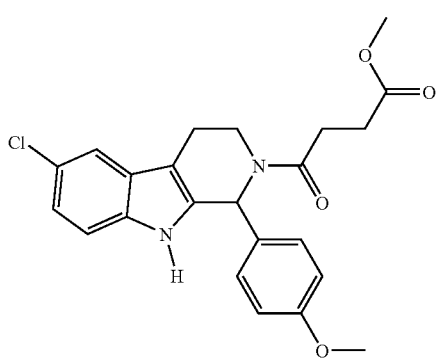
369

-continued
| | |
|---|---|
| 370 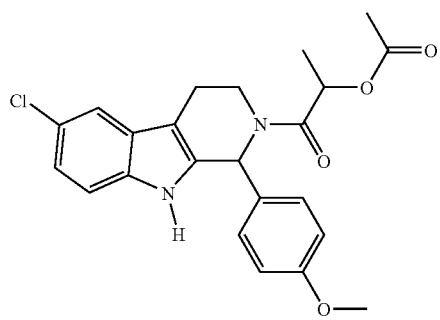 | 374 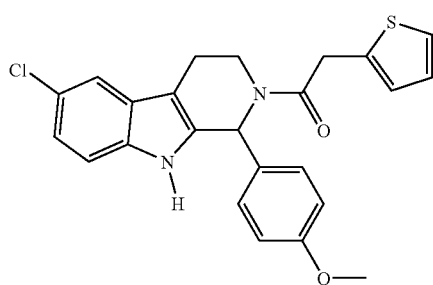 |
| 371 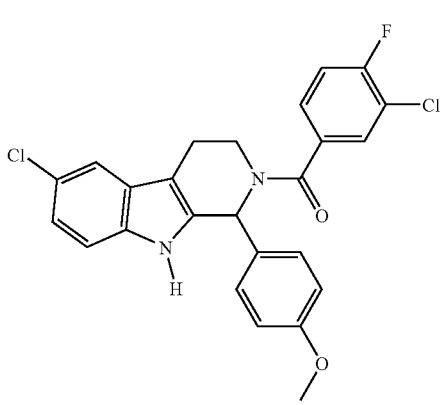 | 375 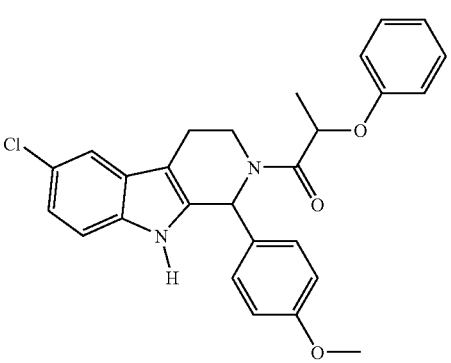 |
| 372 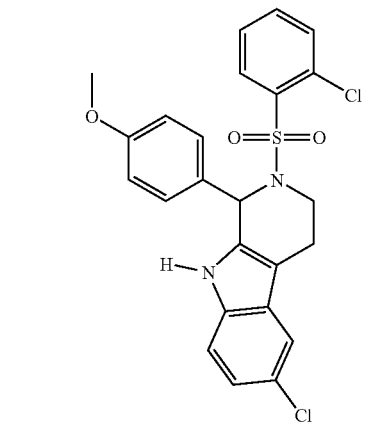 | 376 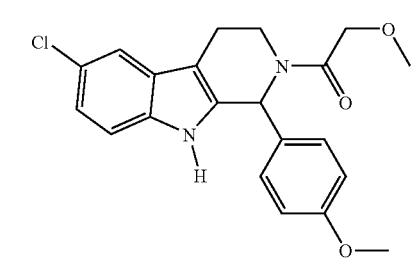 |
| | 377 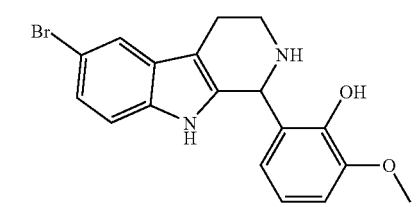 |
| | 378 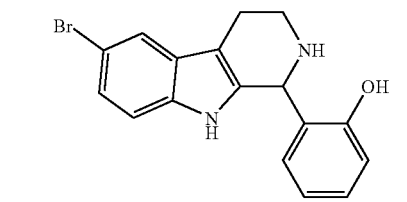 |
| 373 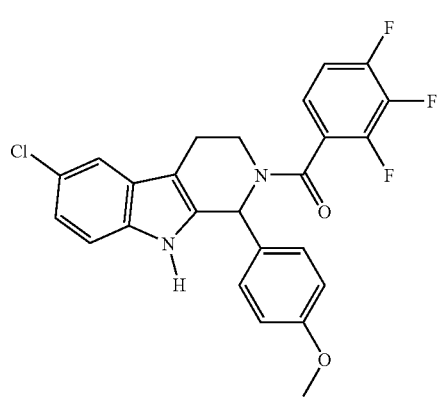 | 379 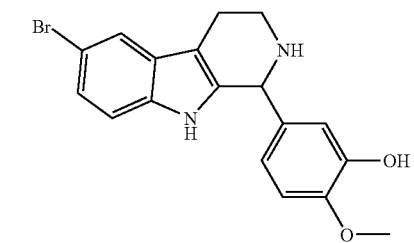 |

380 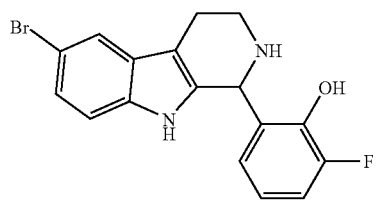
381 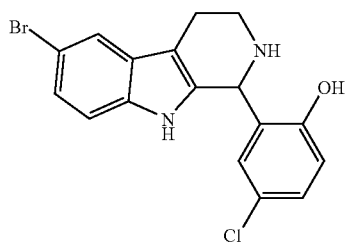
382 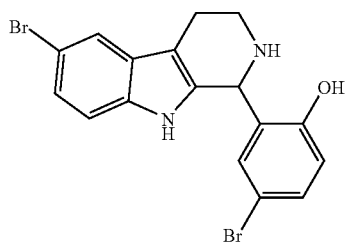
383 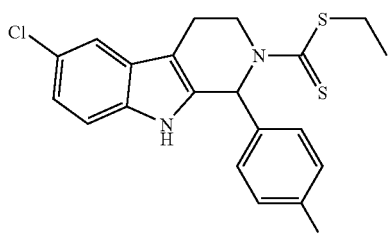
384 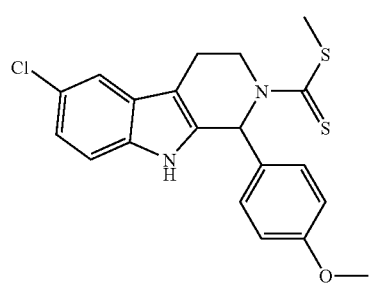
385 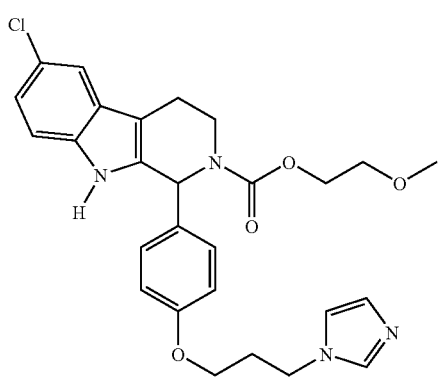
386 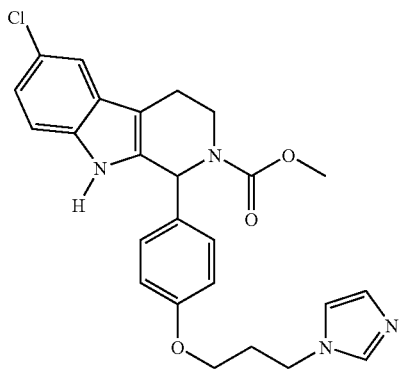
387 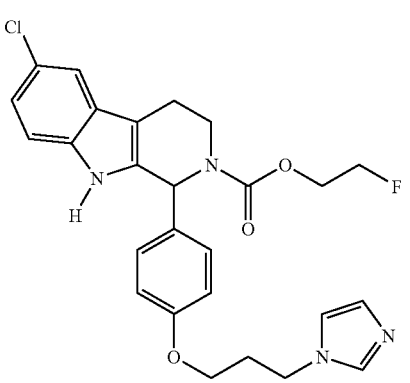
388 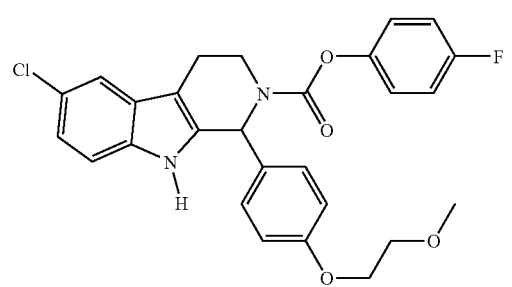
389 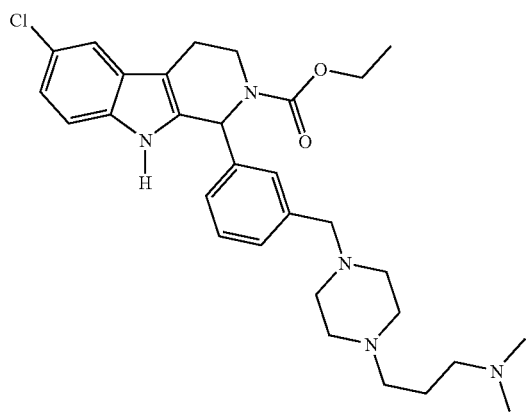

| | |
|---|---|
| 390 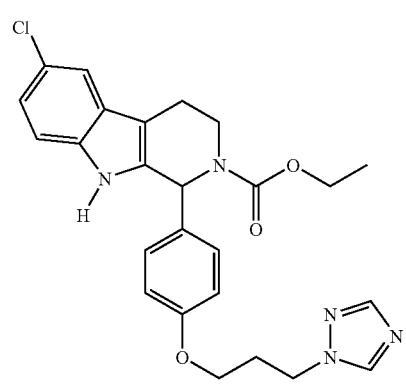 | 395 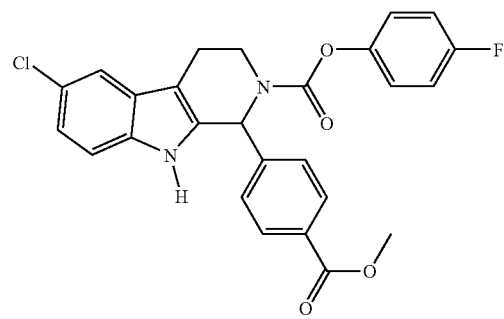 |
| 391 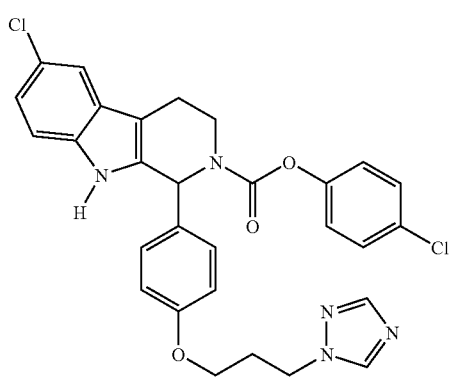 | 396 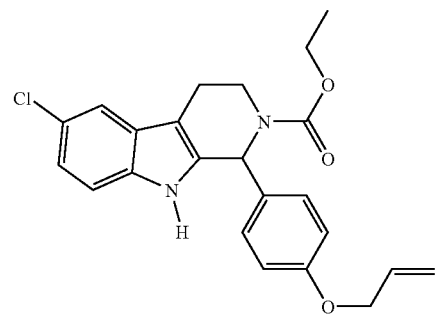 |
| 392 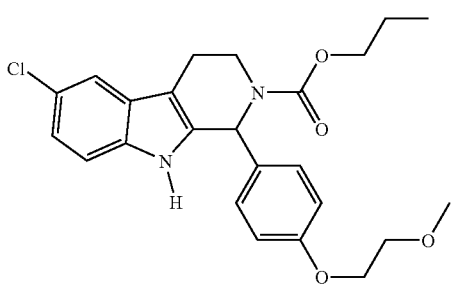 | 397 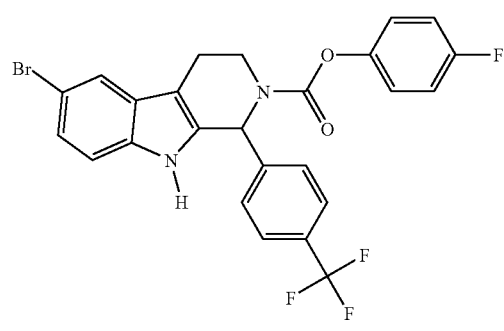 |
| 393 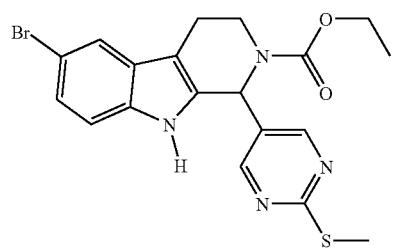 | 398 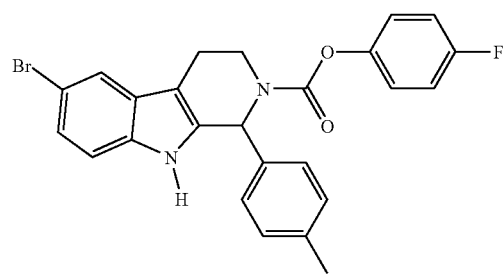 |
| 394 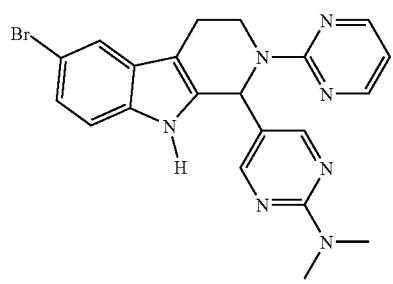 | 399 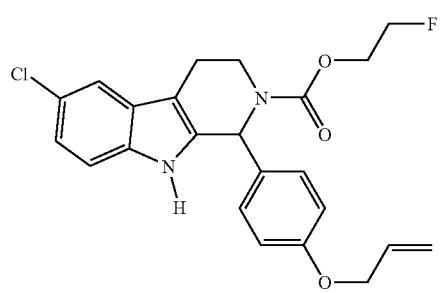 |

400
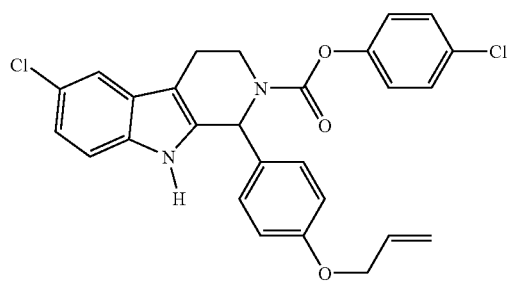
401
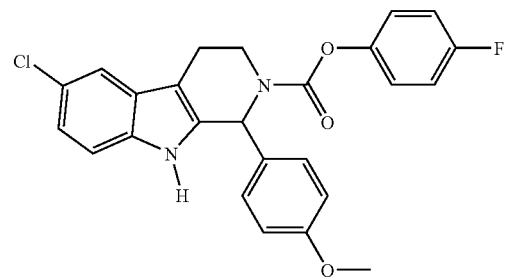
402
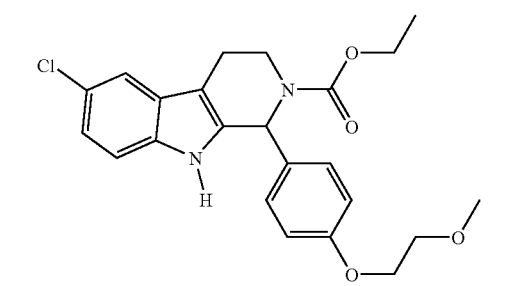
403
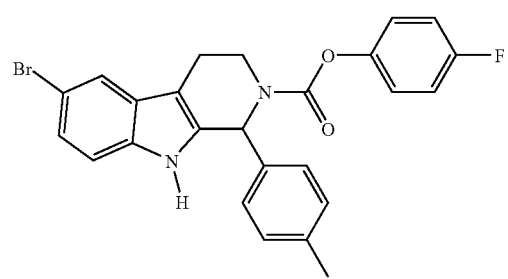
404
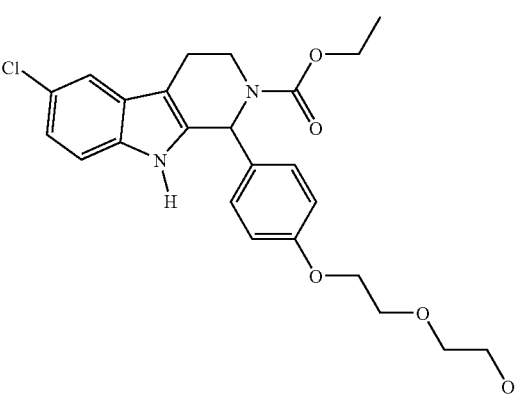
405
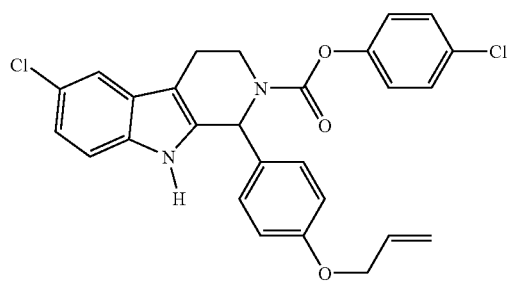
406
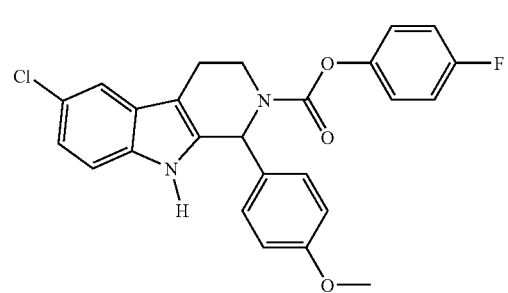
407
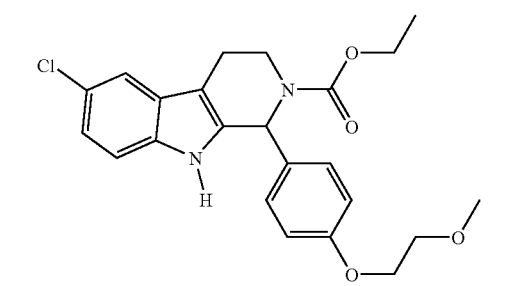
408
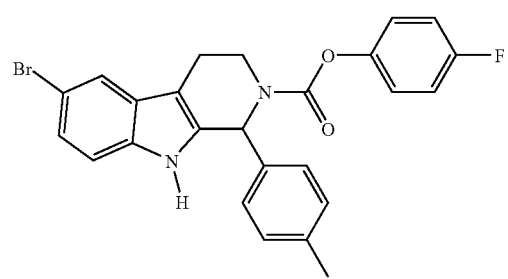
409
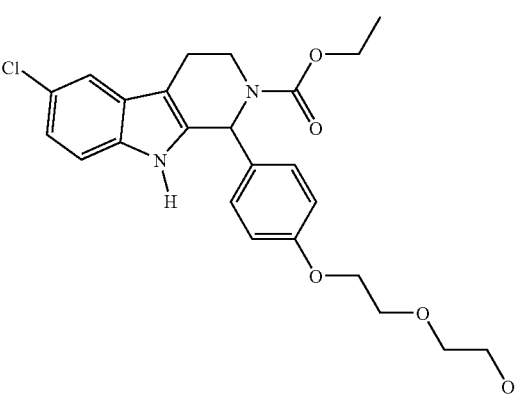

410
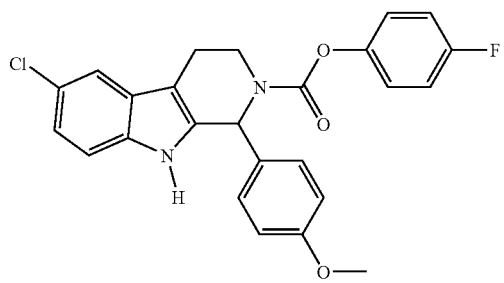
411
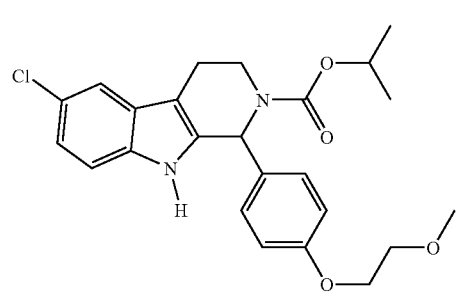
412
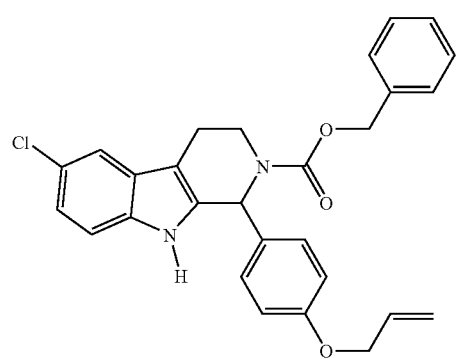
413
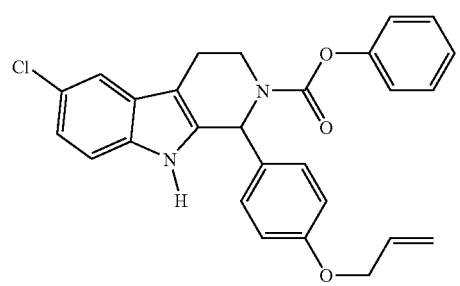
414
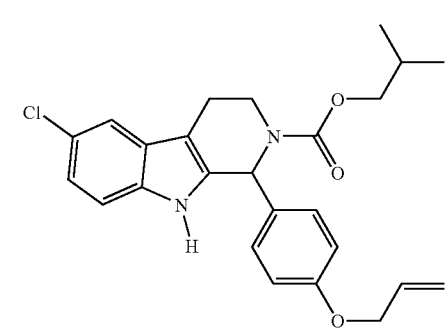
415
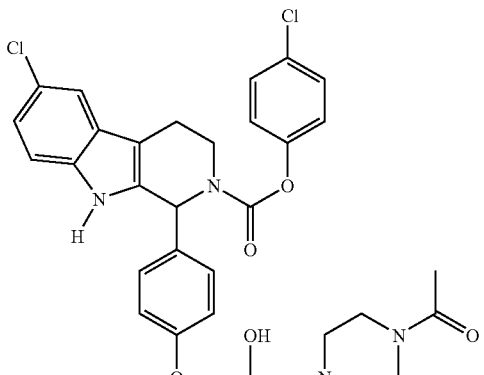
416
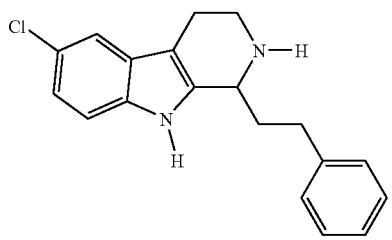
417
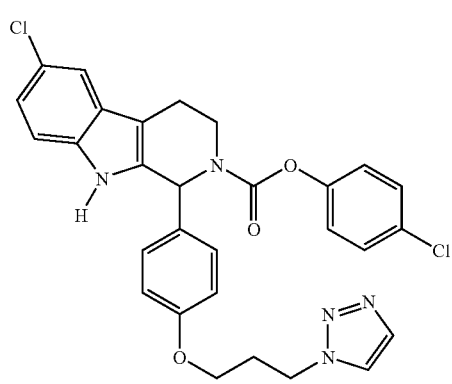
418
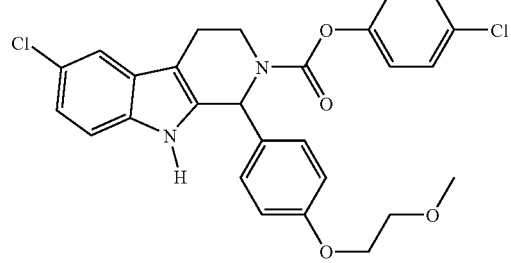
419
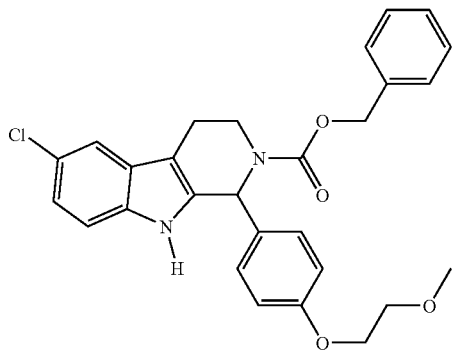

119
-continued
| | |
|---|---|
| 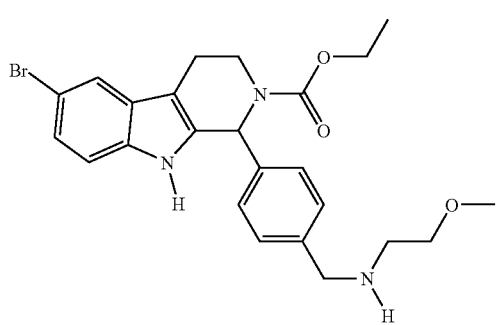 | 420 |
| 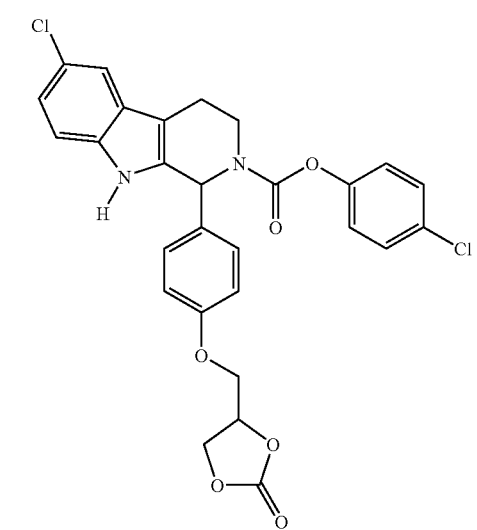 | 421 |
| 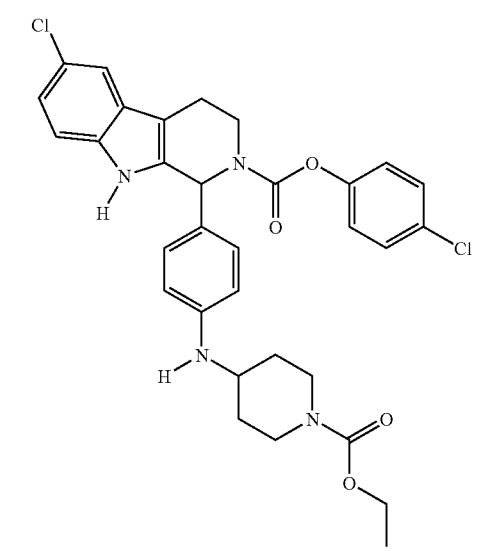 | 422 |
| 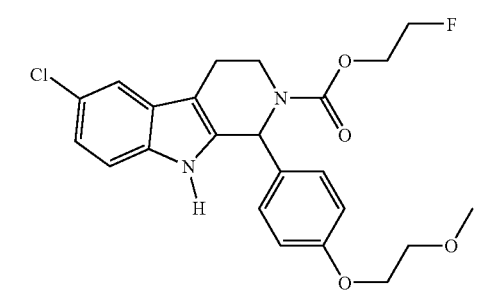 | 423 |
120
-continued
| | |
|---|---|
| 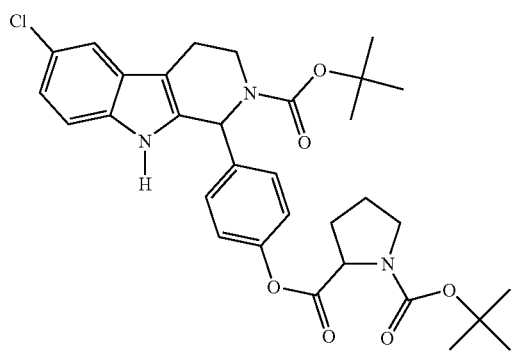 | 424 |
| 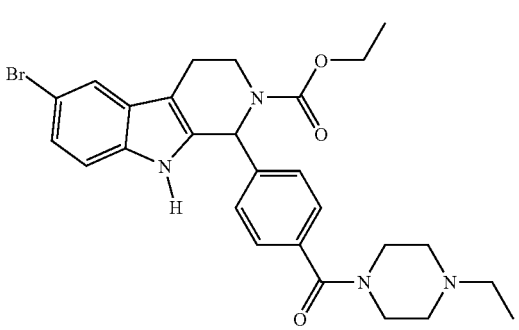 | 425 |
| 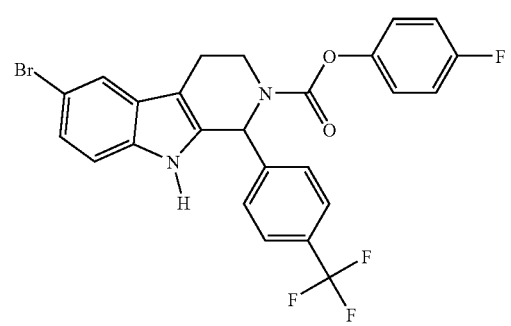 | 426 |
| 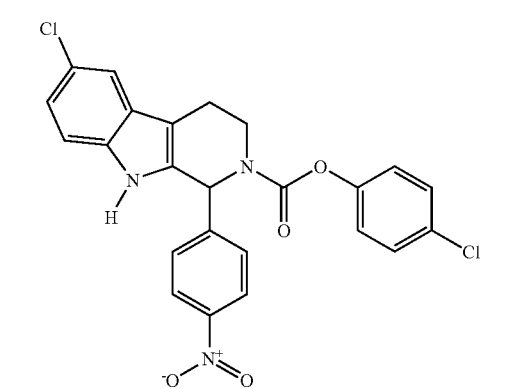 | 427 |

428
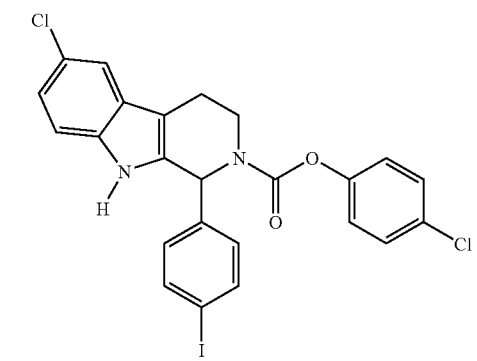
429
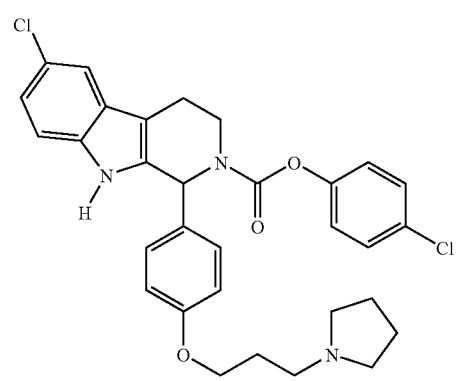
430
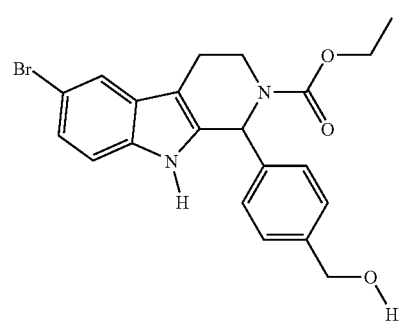
431
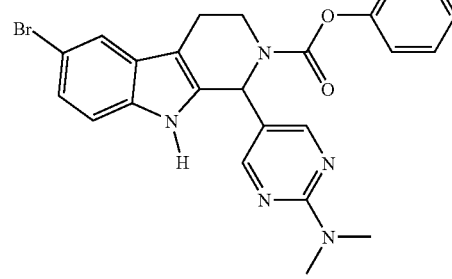
432
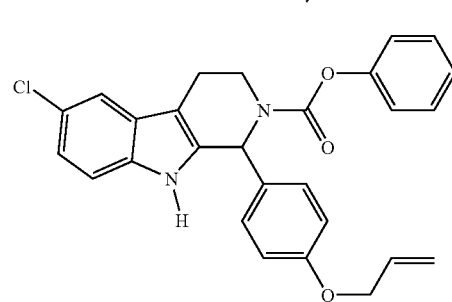
433
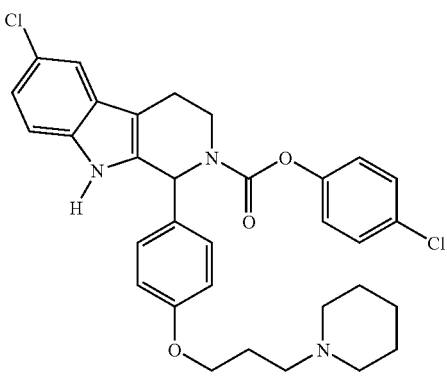
434
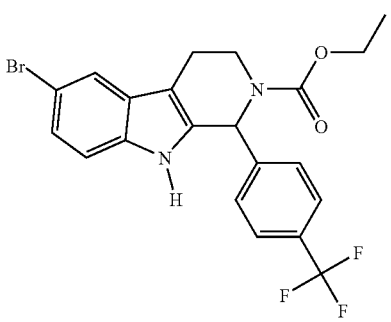
435
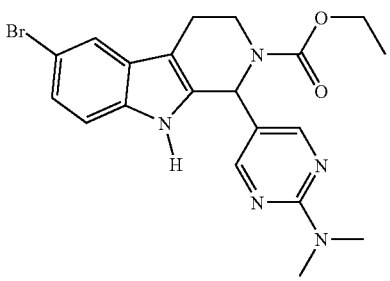
436
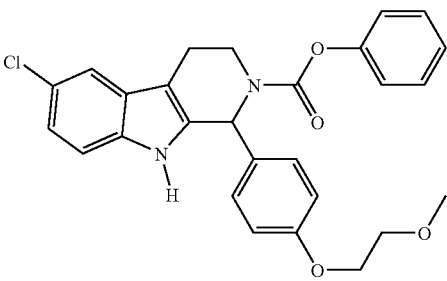

123
-continued
437
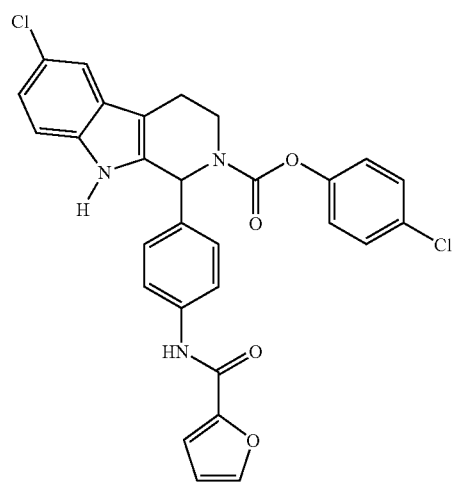
438
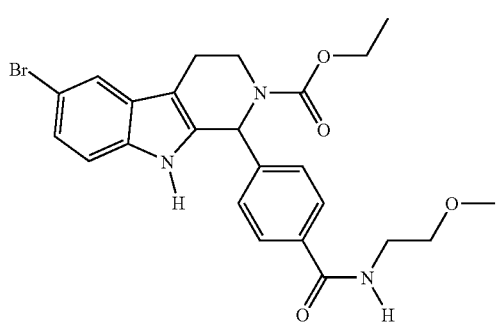
439
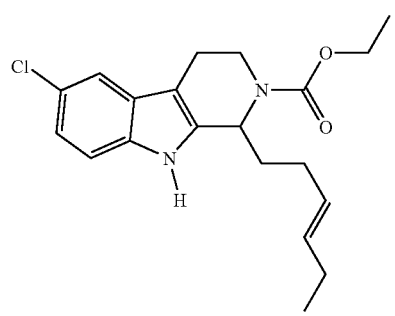
440
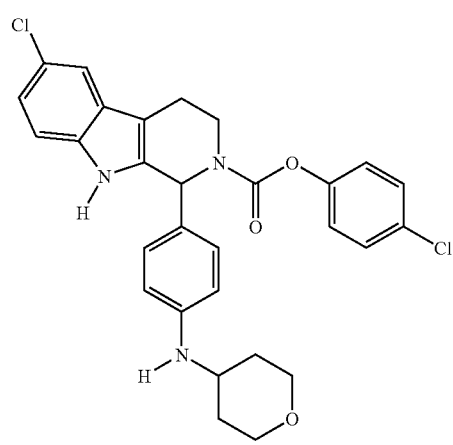
124
-continued
441
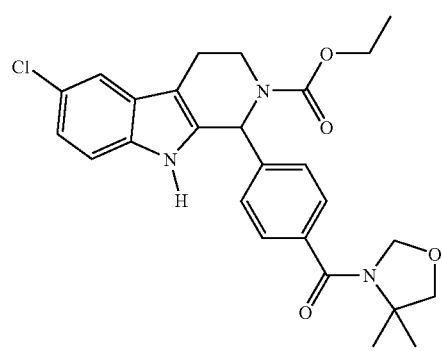
442
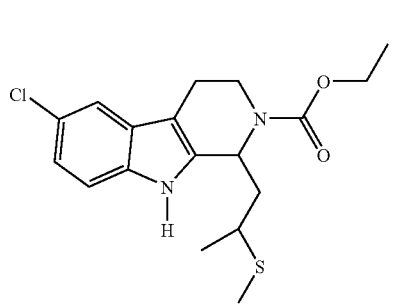
443
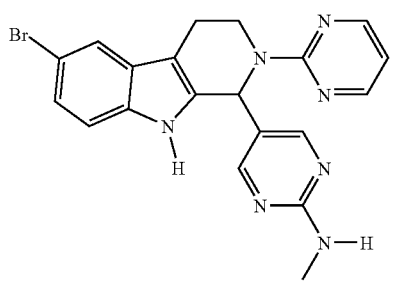
444
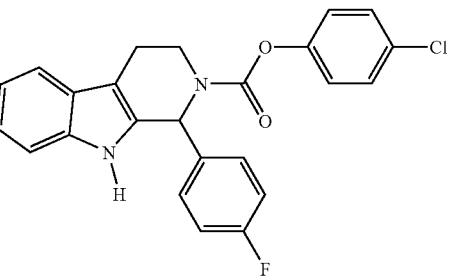
445
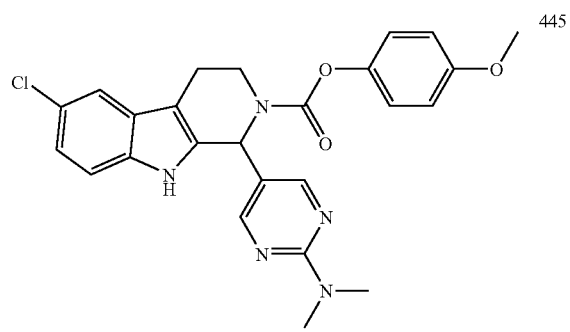

446
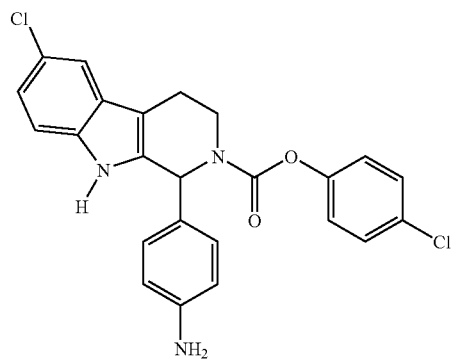
447
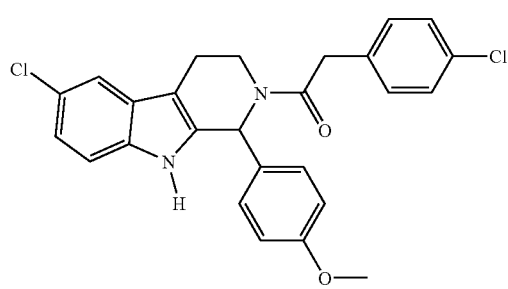
448
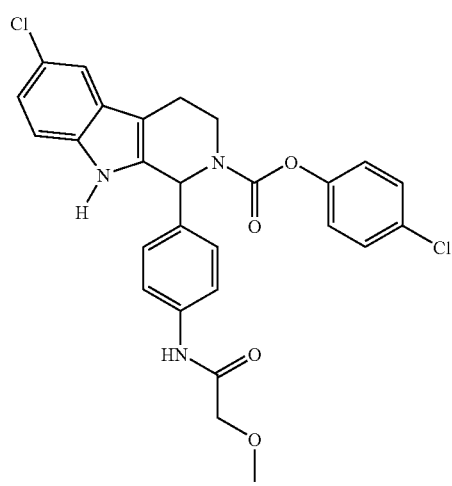
449
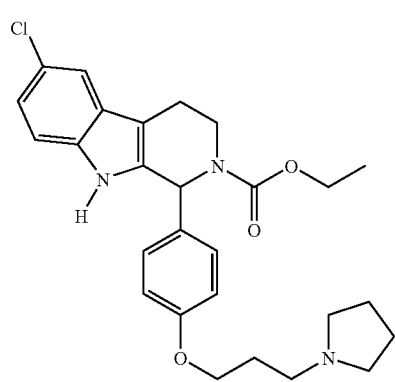
450
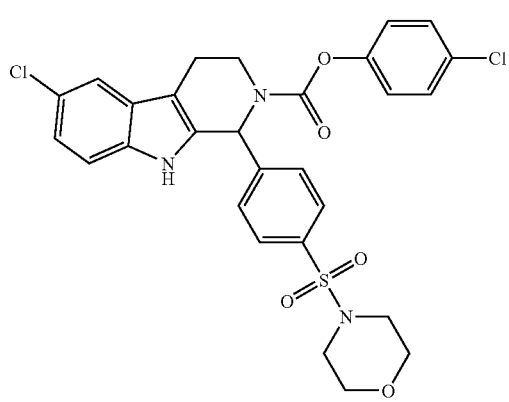
451
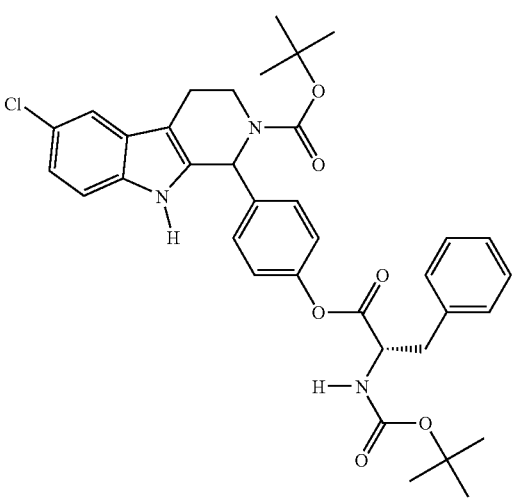
452
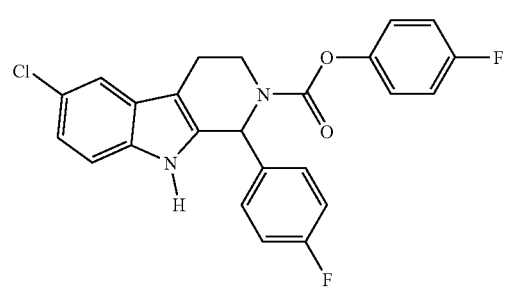

453
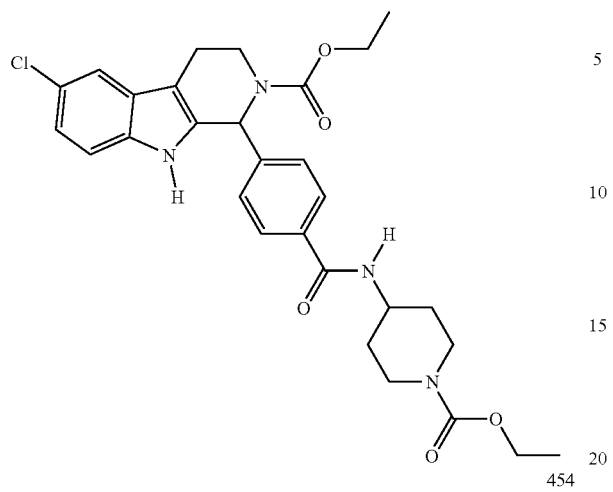
454
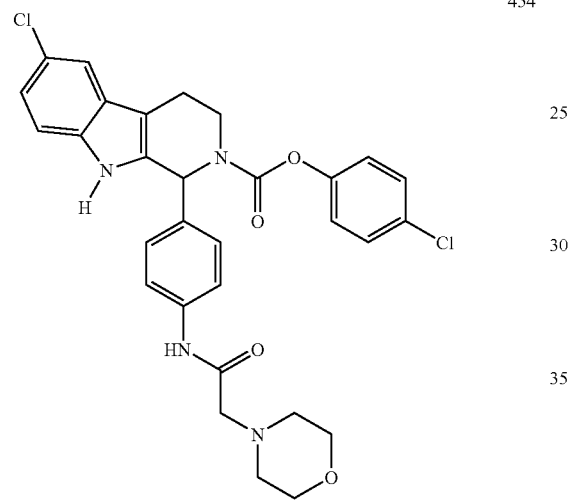
455
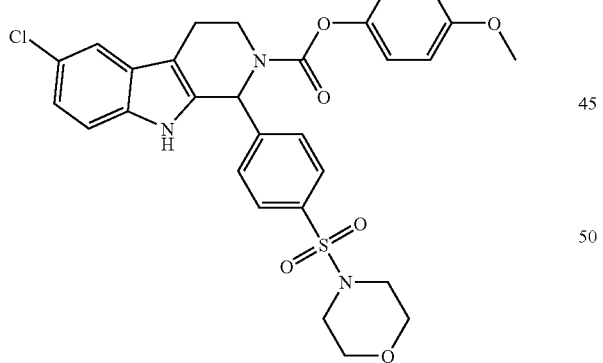
456
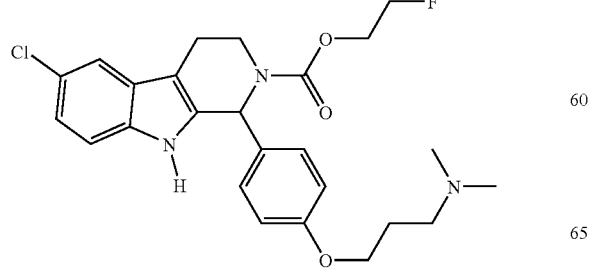
457
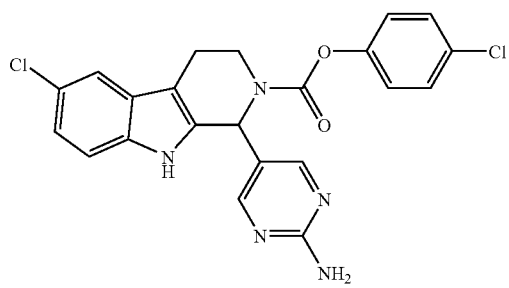
458
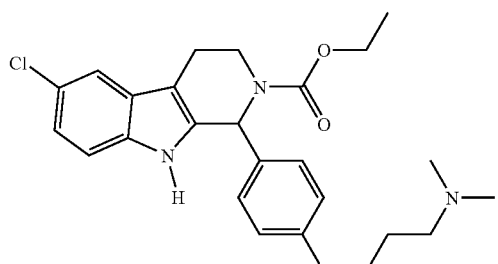
459
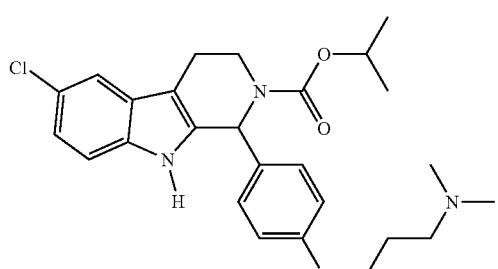
460
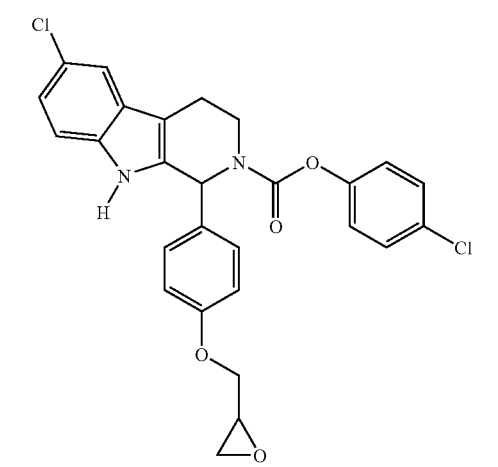

-continued
461
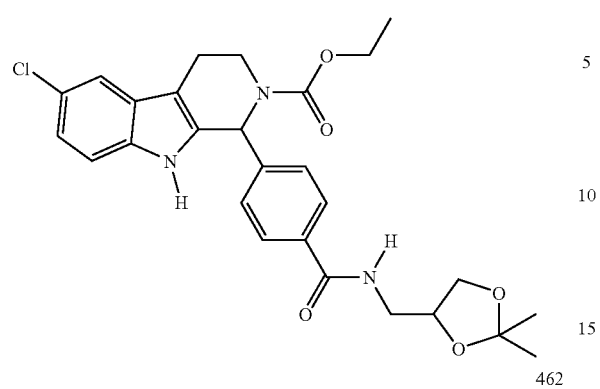
462
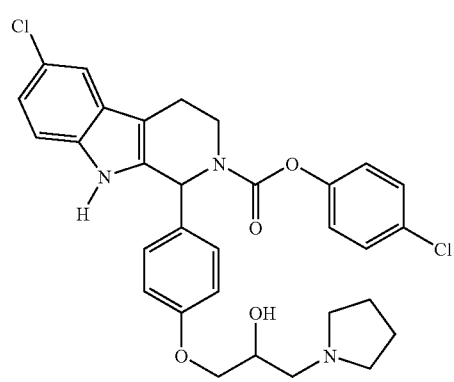
463
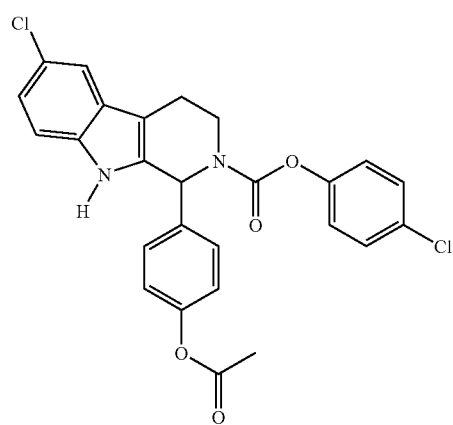
464
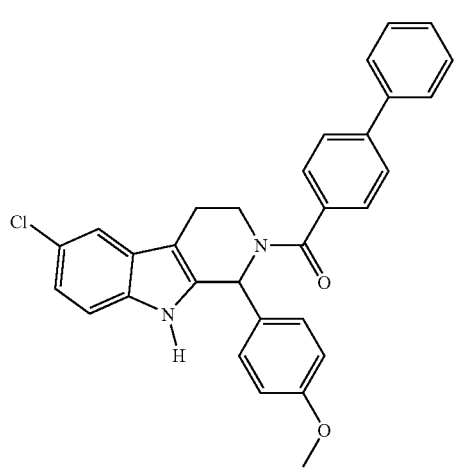
-continued
465
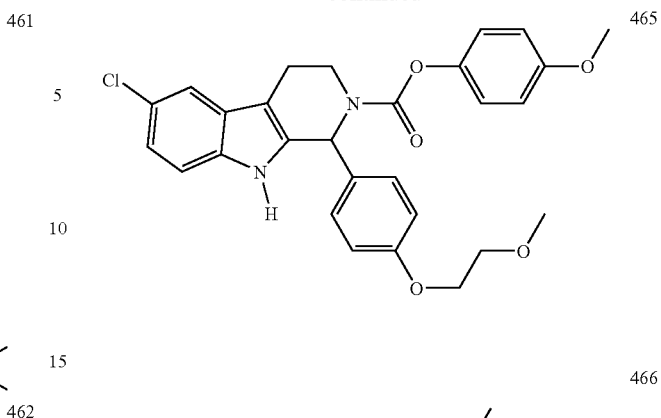
466
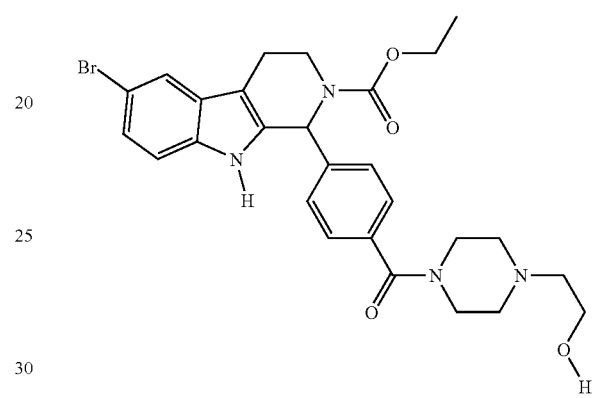
467
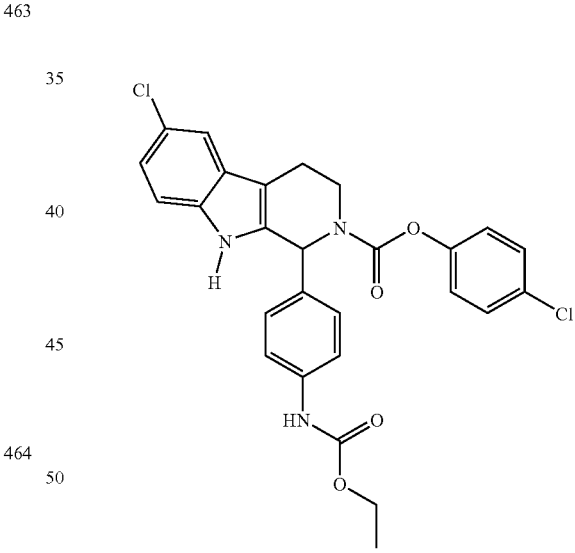
468
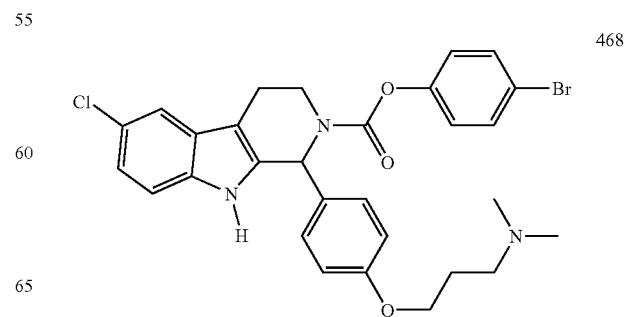

131
-continued
469
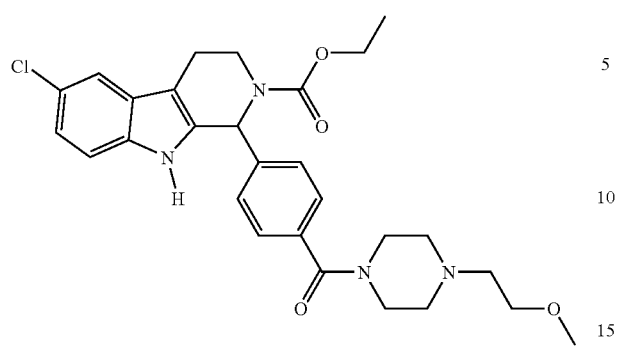
470
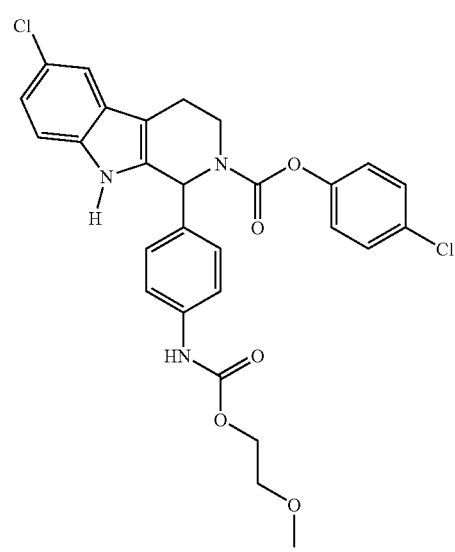
471
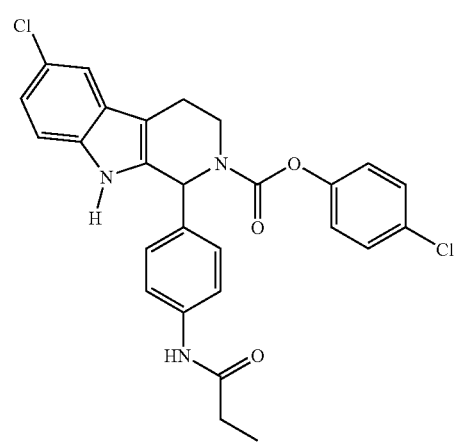
472
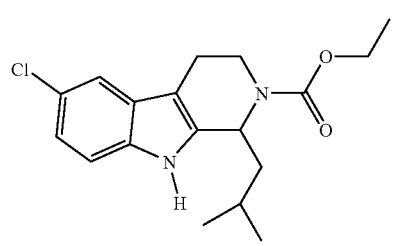
132
-continued
473
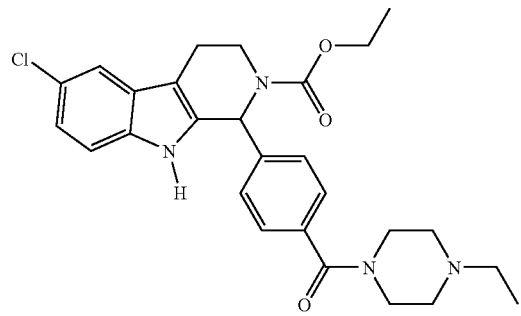
474
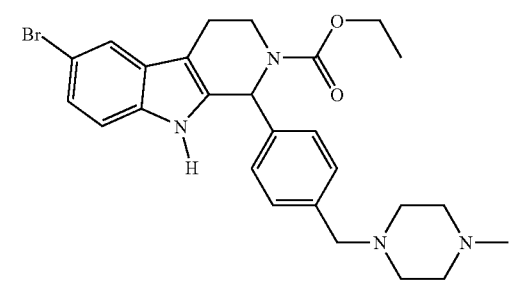
475
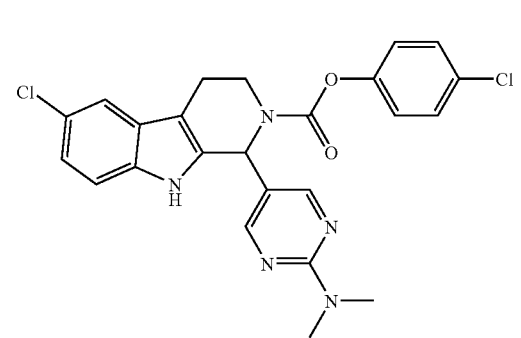
476
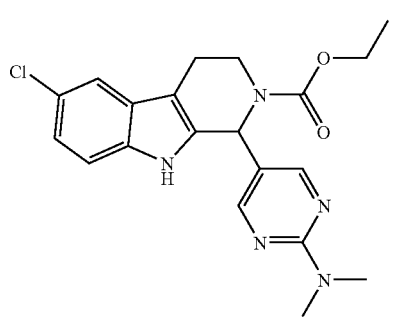
477
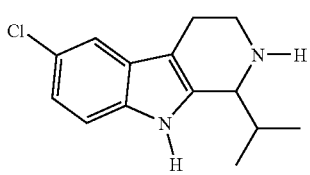

478
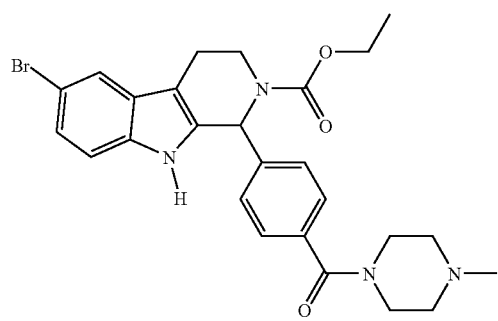
479
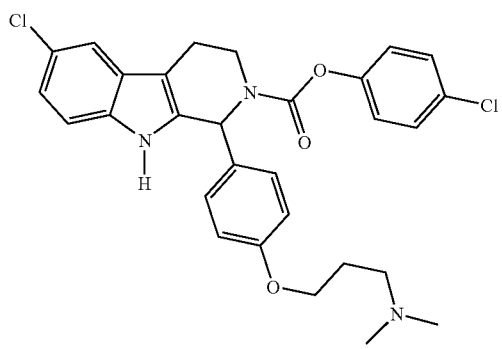
480
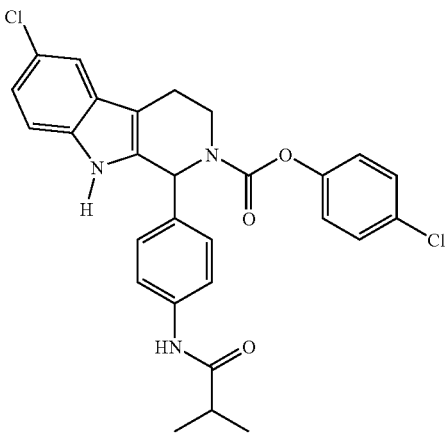
481
482
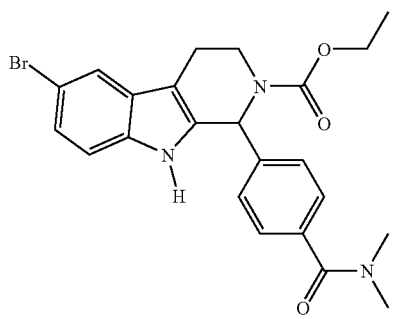
483
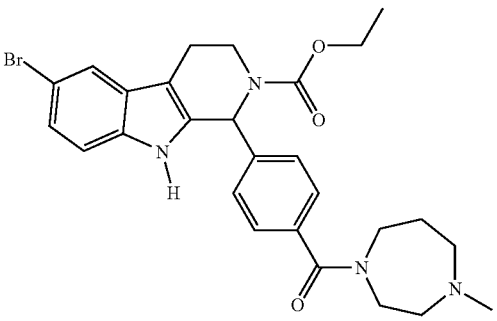
484
485
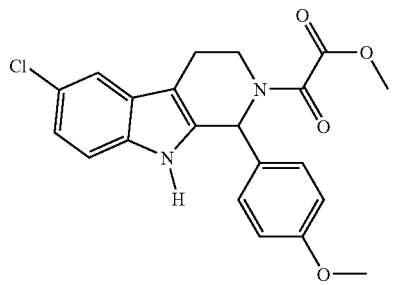
486
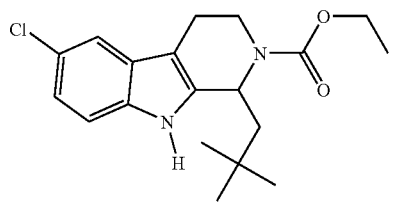

487 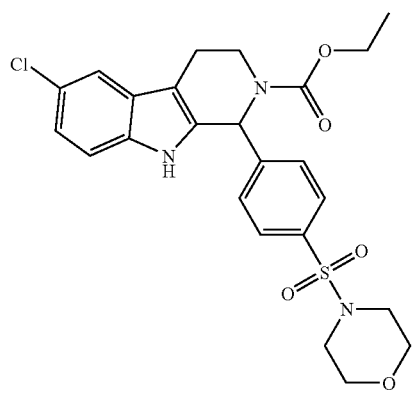
488 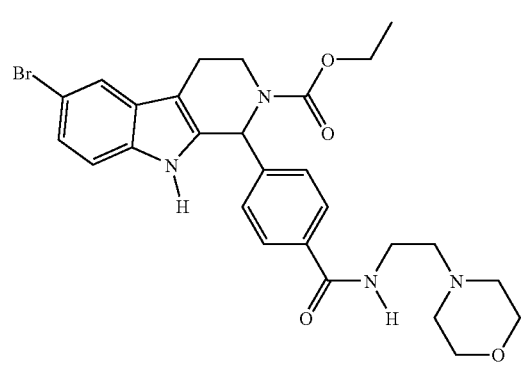
489 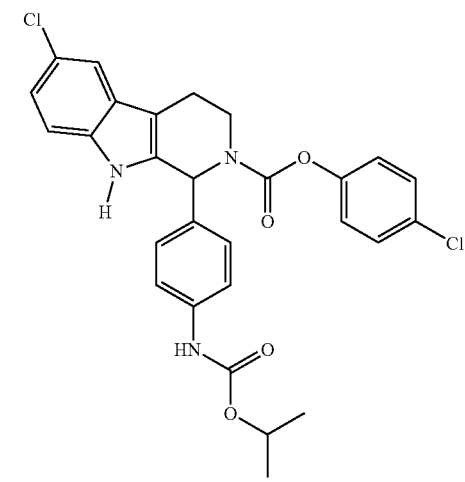
490 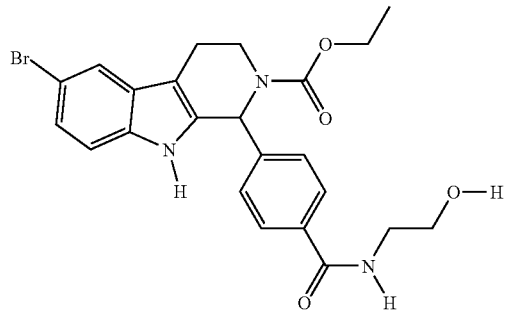
491 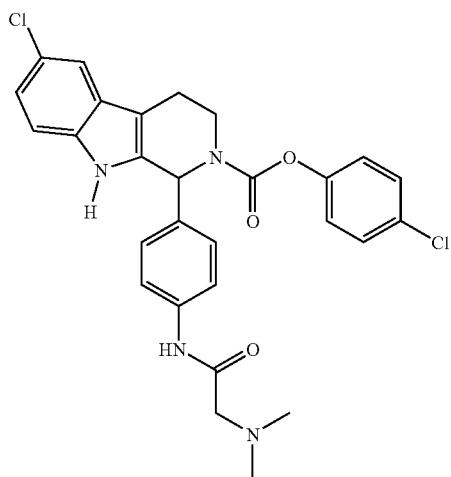
492 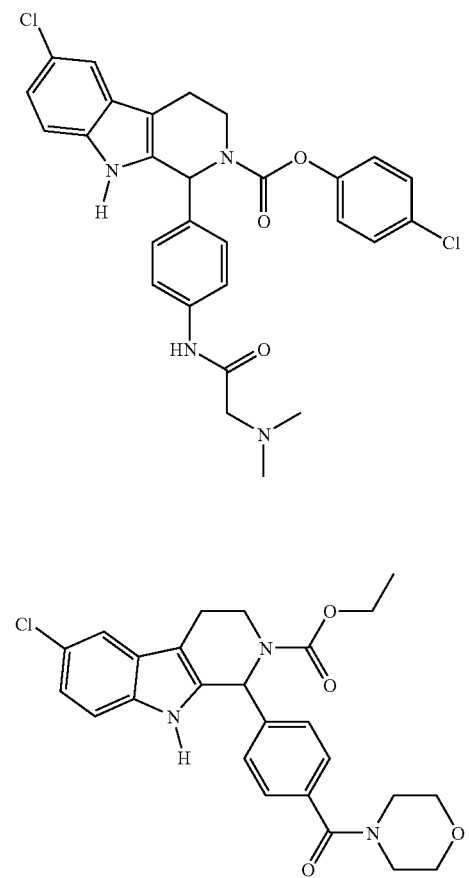
493 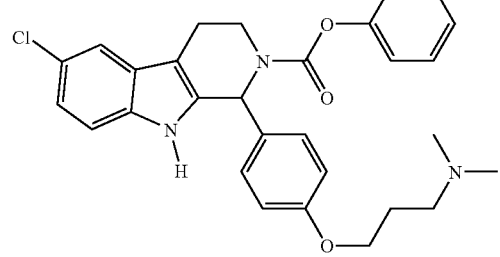
494 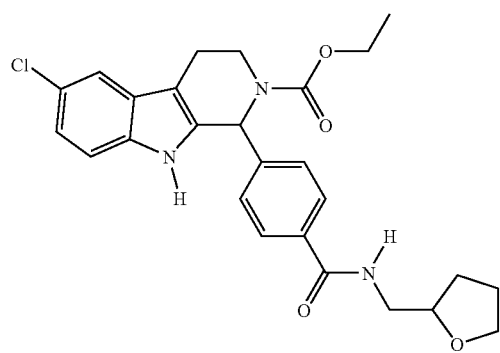

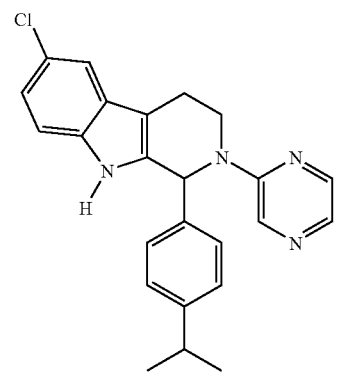
495
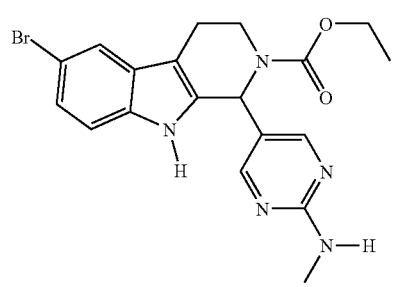
496
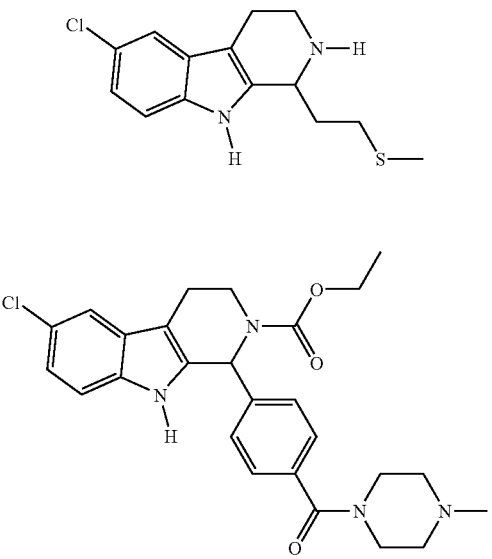
497
498
499
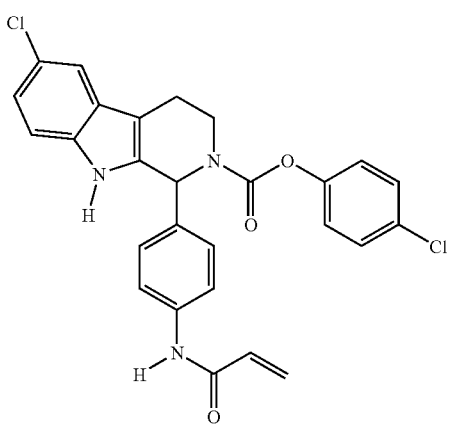
500
501
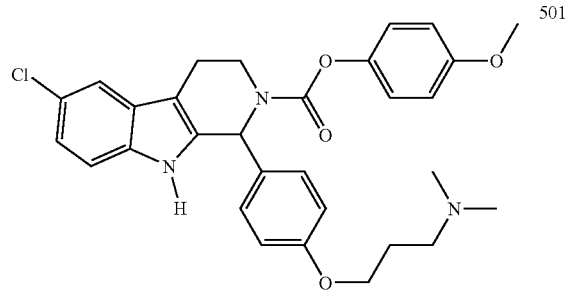
502
503
504

139
-continued
505
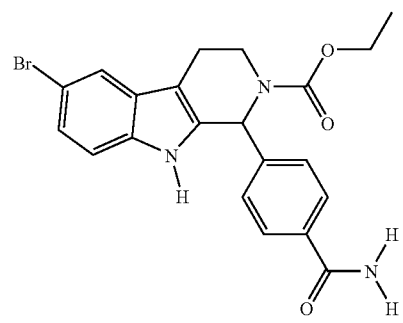
506
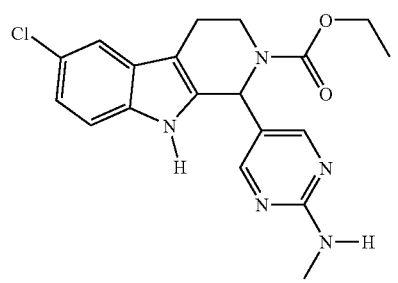
507
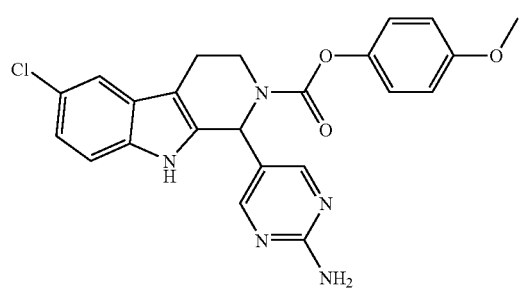
508
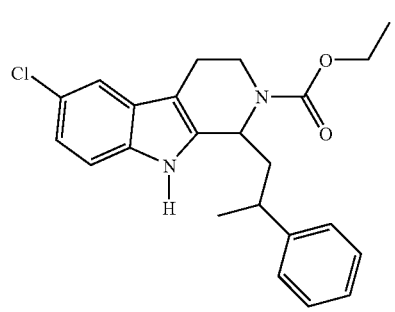
509
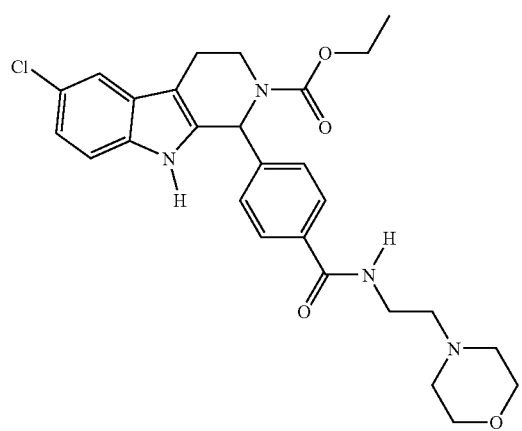
140
-continued
510
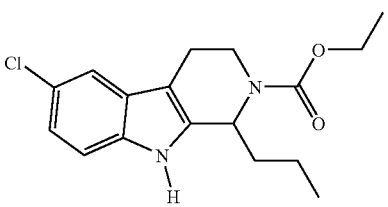
511
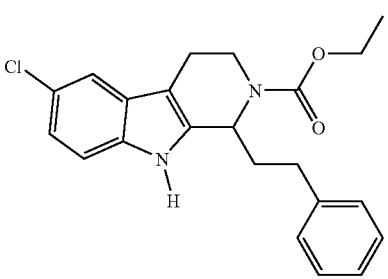
512
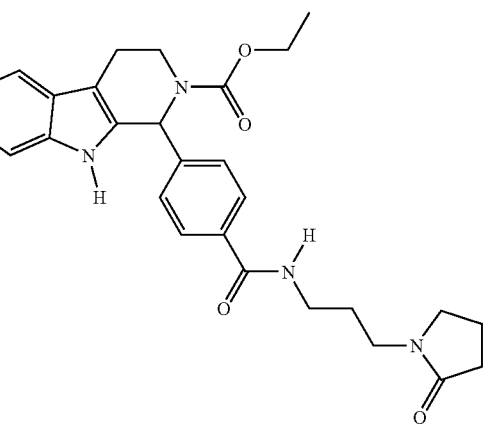
513
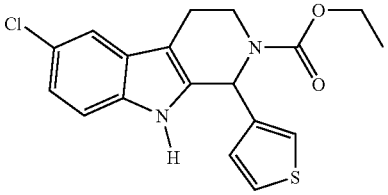
514
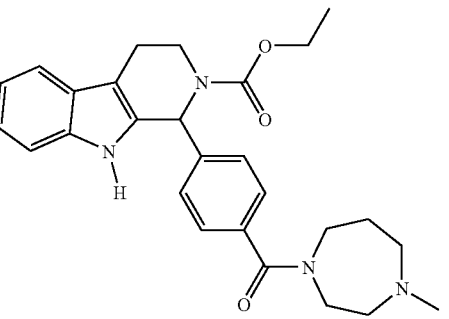

515 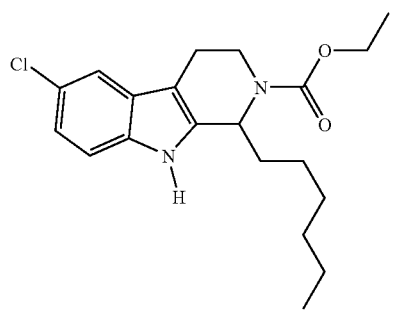
516 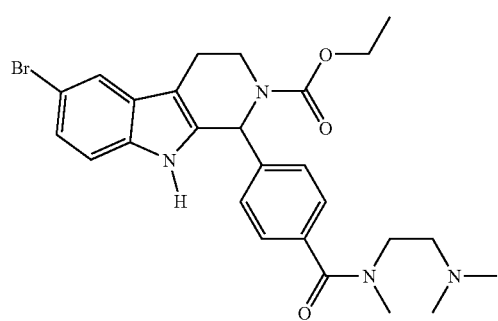
517 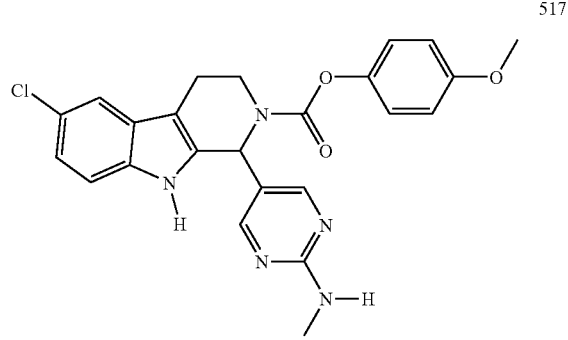
518 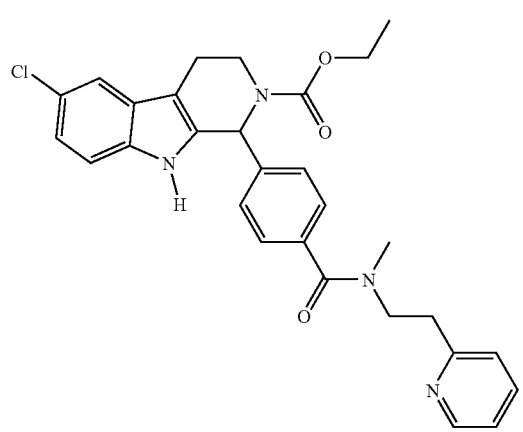
519 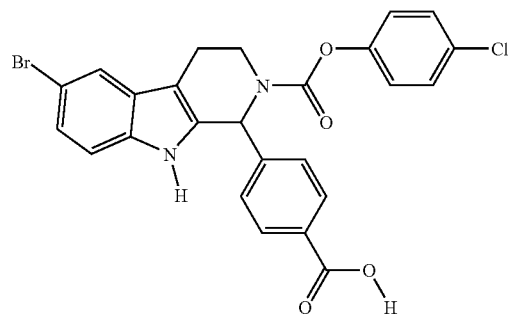
520 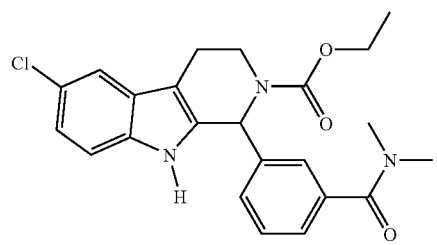
521
522 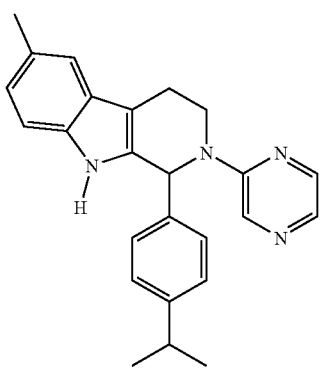

| 523 | 528 |
|---|---|
| 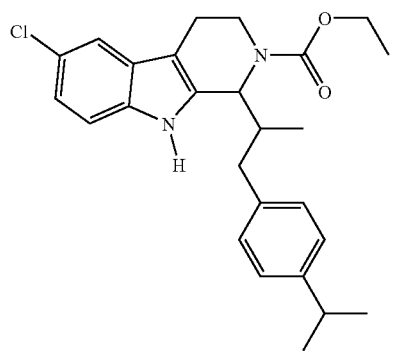 | 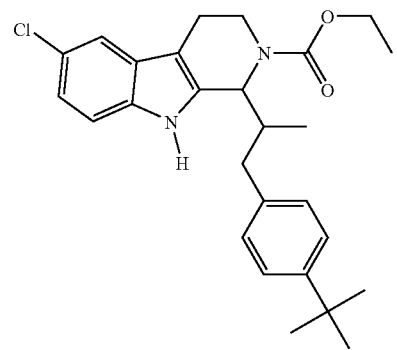 |
| 524 | 529 |
| 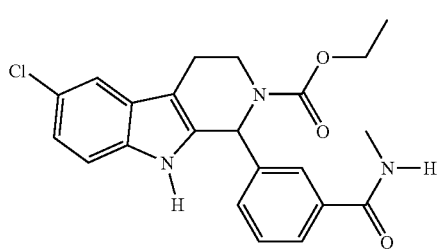 | 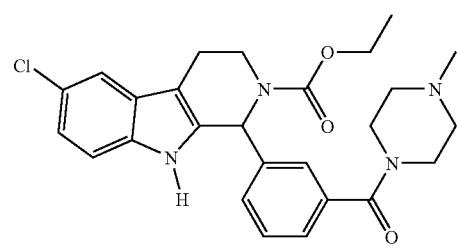 |
| 525 | 530 |
| 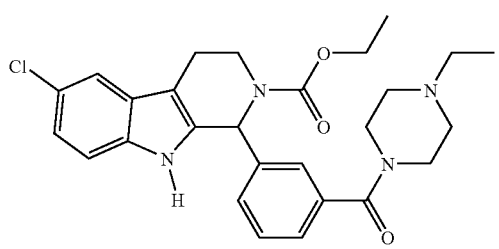 | 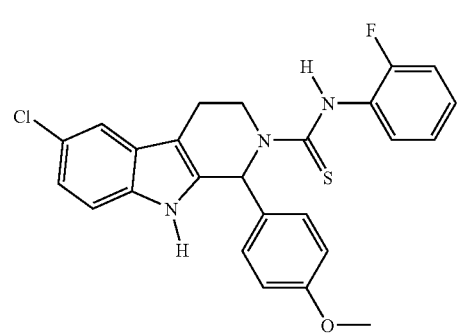 |
| 526 | 531 |
| 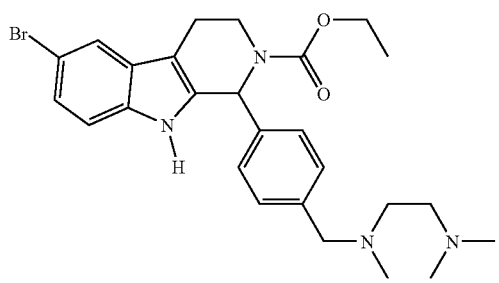 | 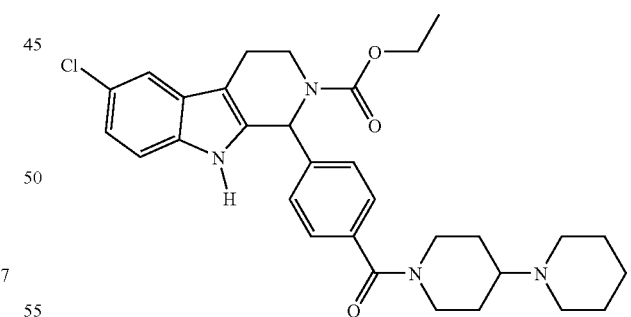 |
| 527 | 532 |
| 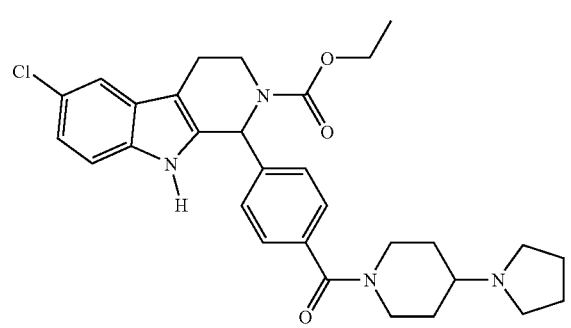 | 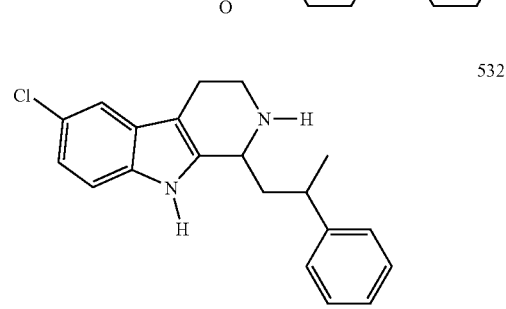 |

145
-continued
533
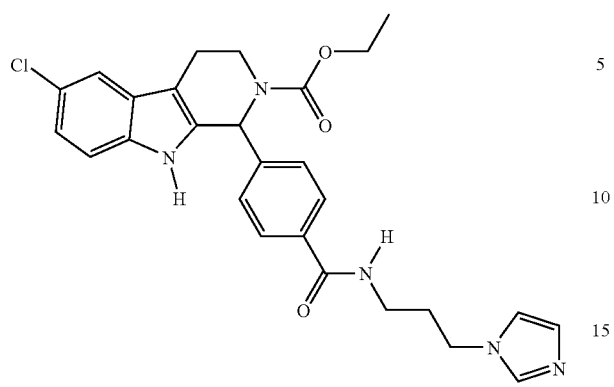
534
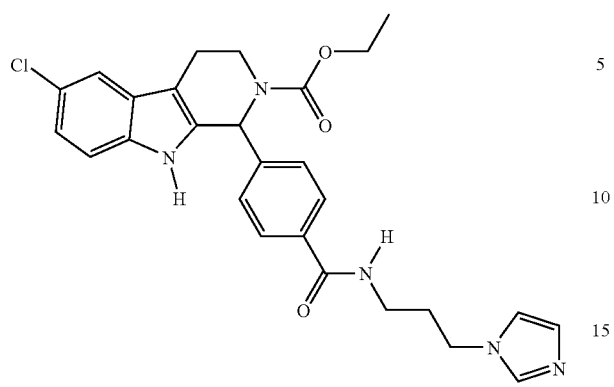
535
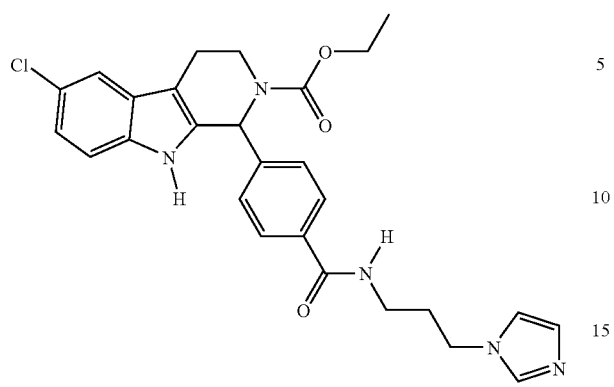
536
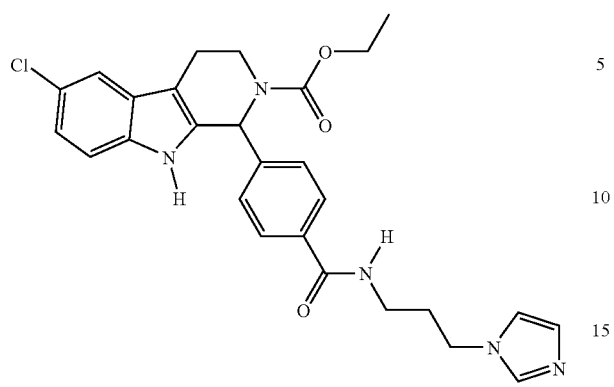
146
-continued
537
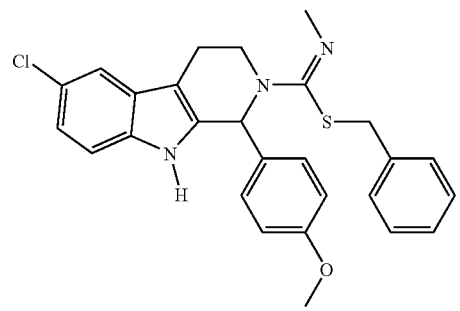
538
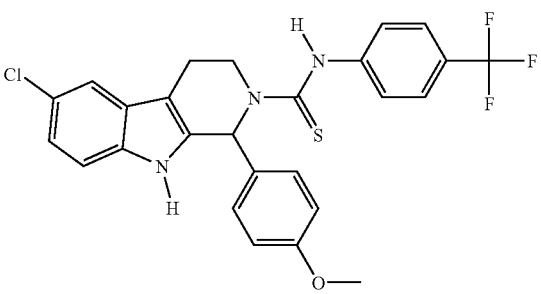
539
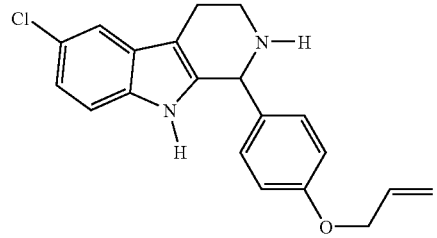
540
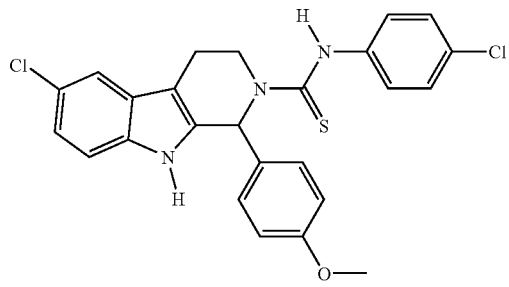
541
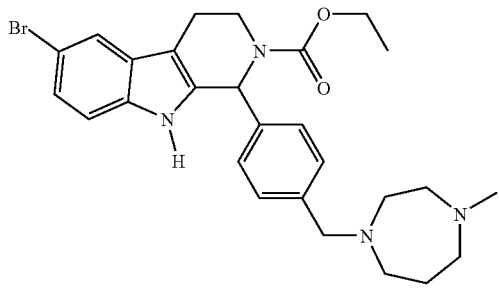

147
-continued
542
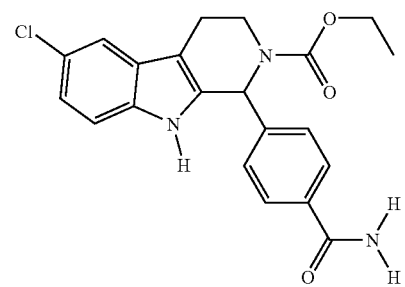
543
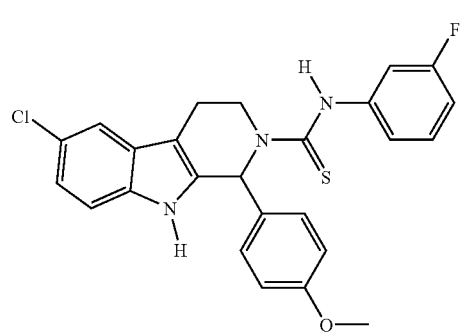
544
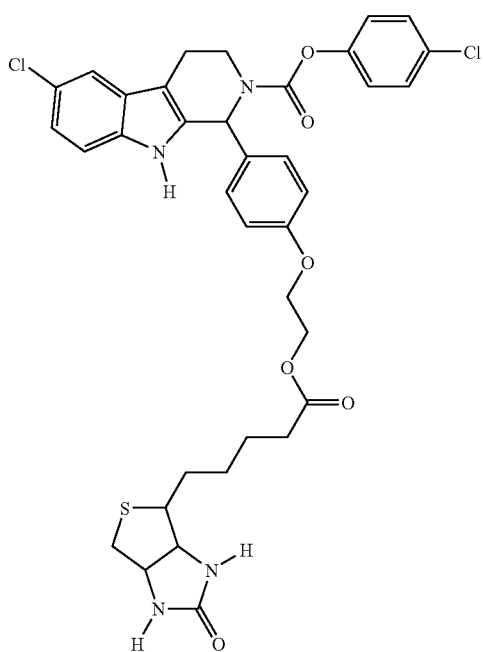
545
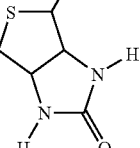
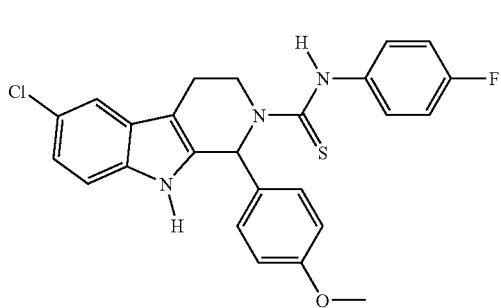
148
-continued
546
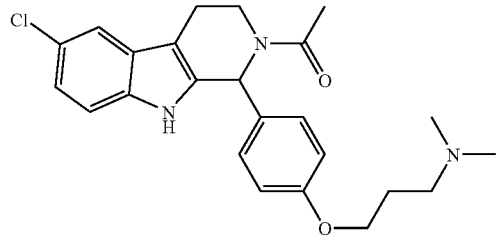
547
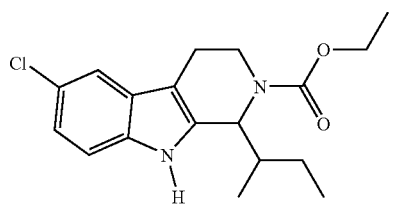
548
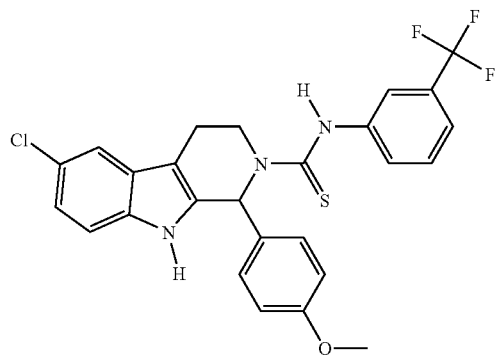
549
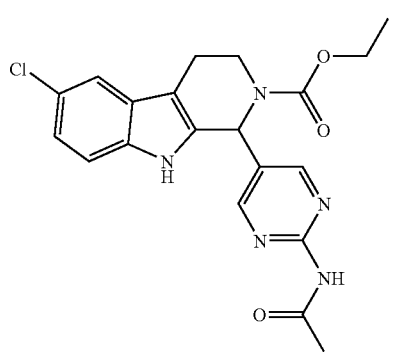
550
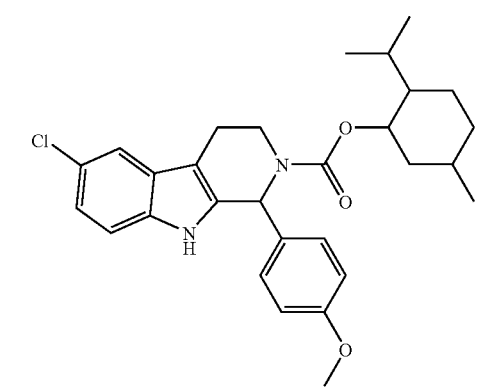

551
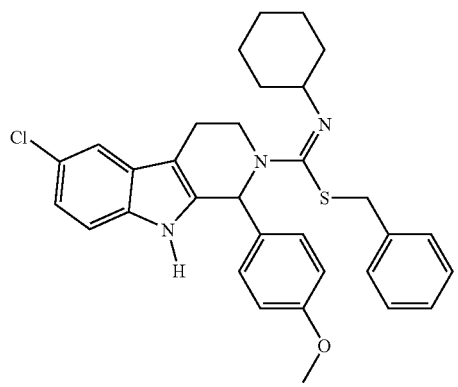
552
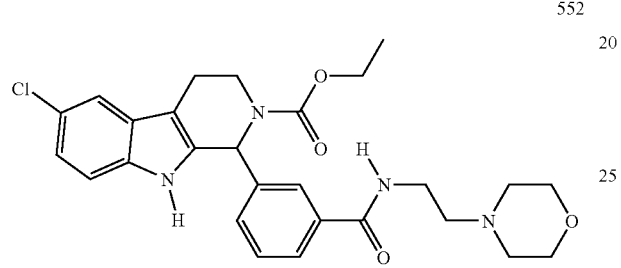
553
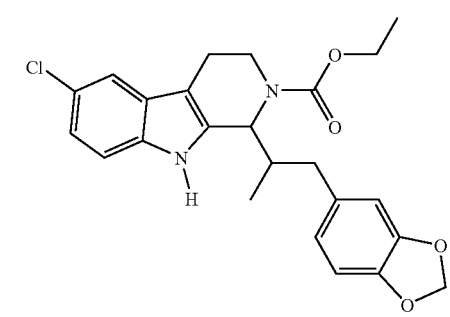
554
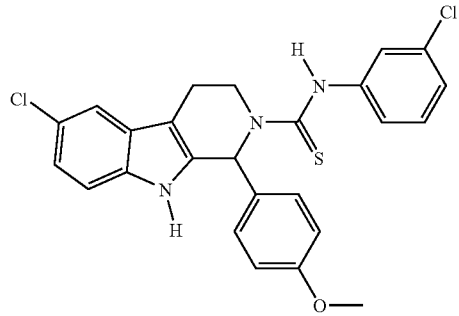
555
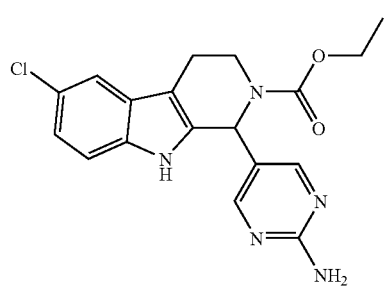
556
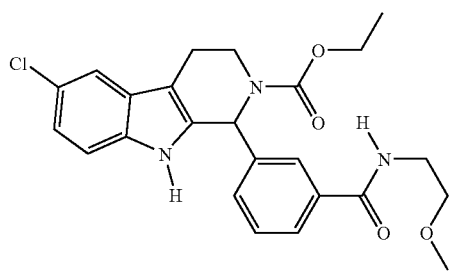
557
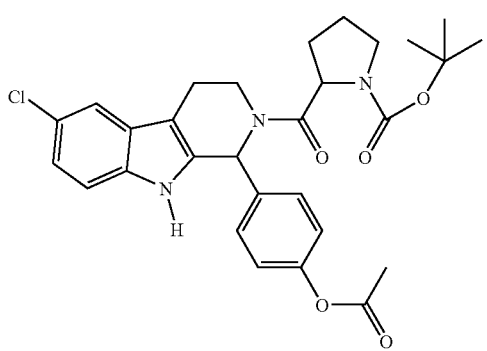
558
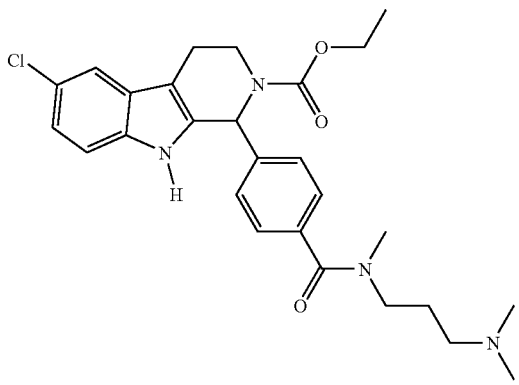
559
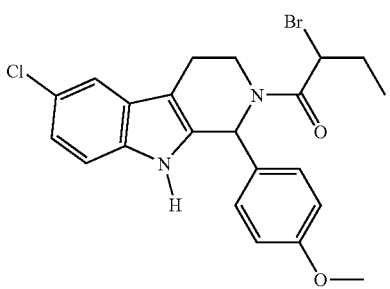

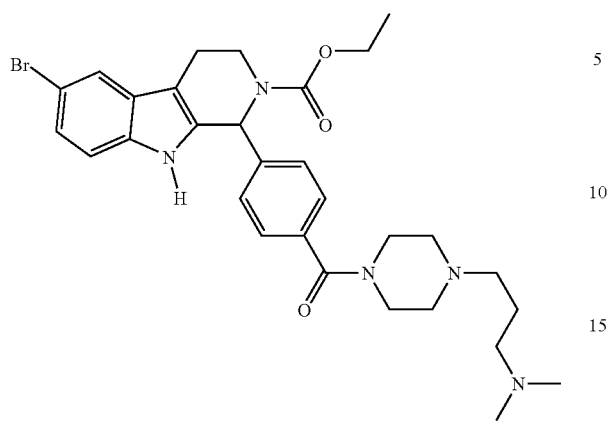
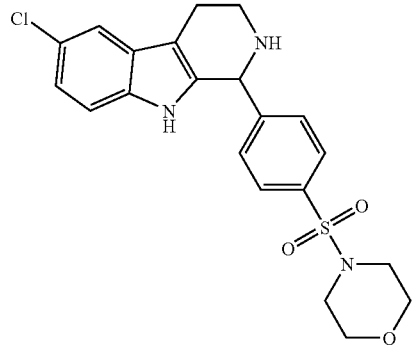
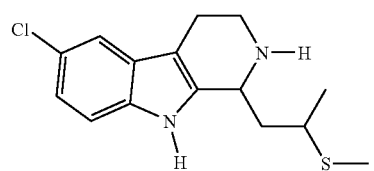

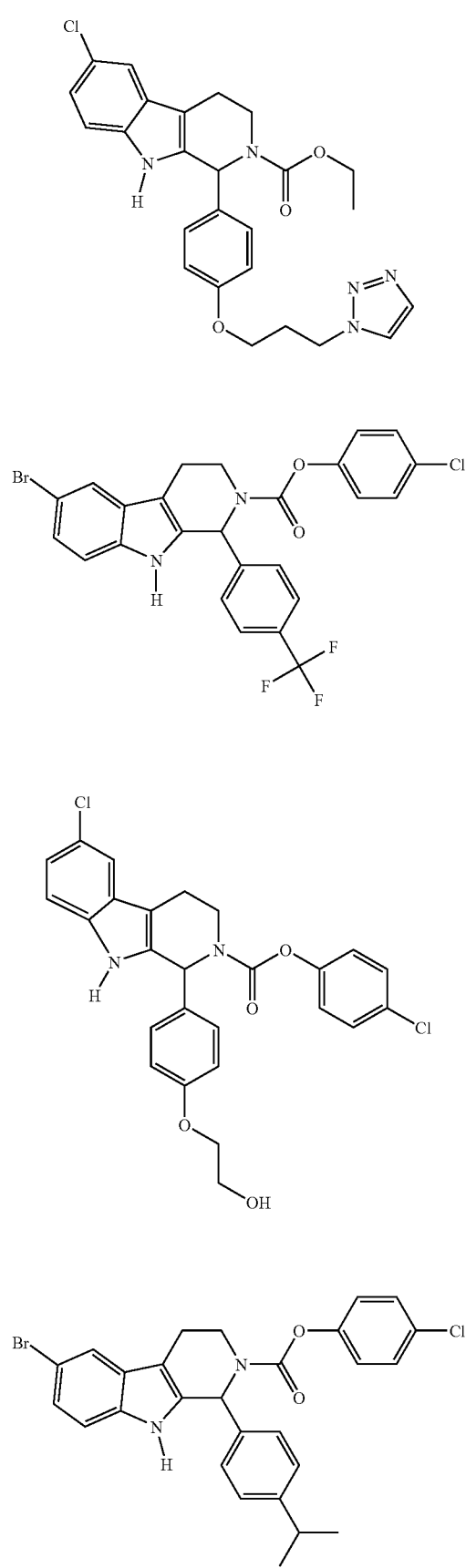

578 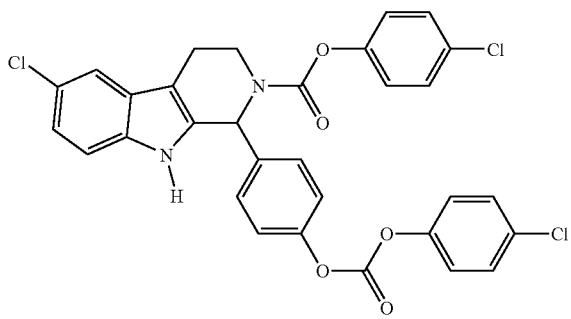
579 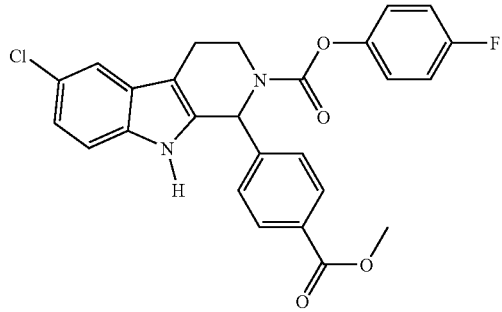
580 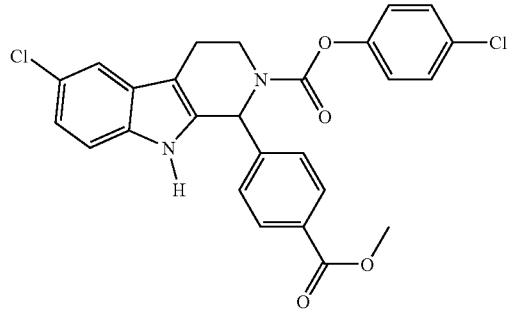
581 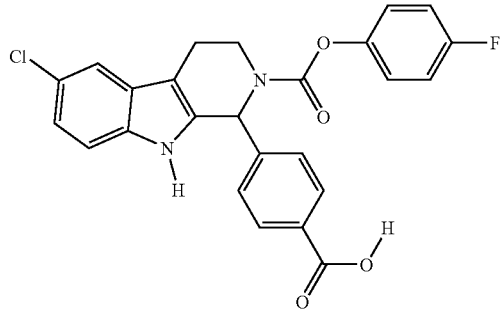
582 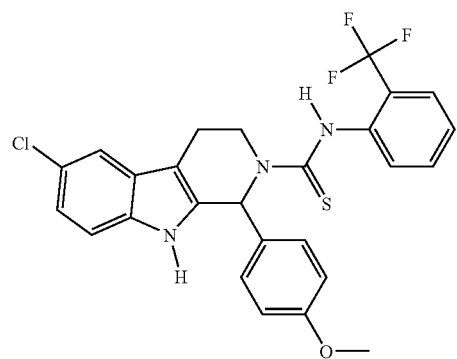
583 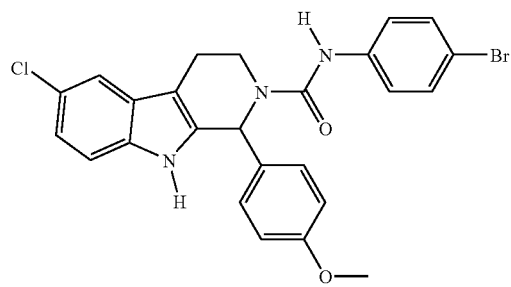
584 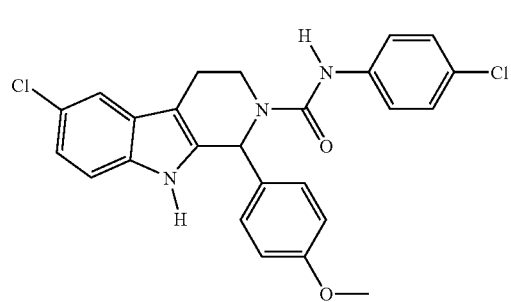
585 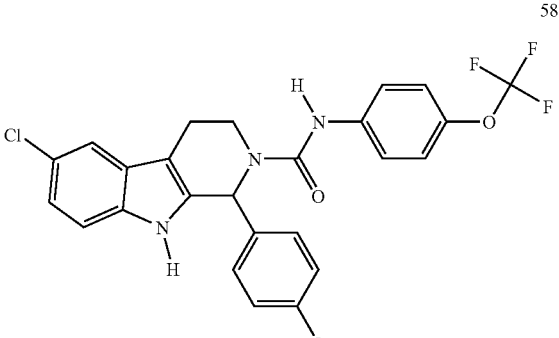
586 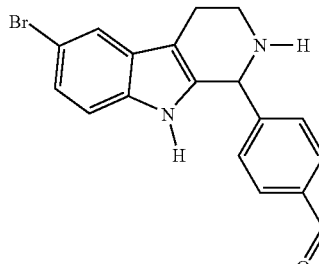
587 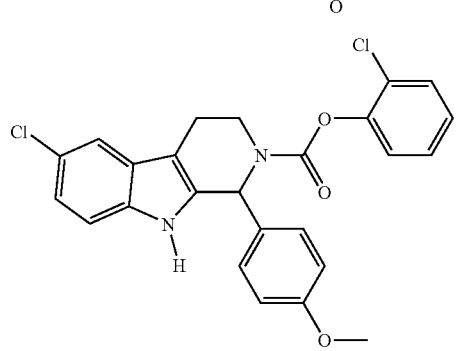

588
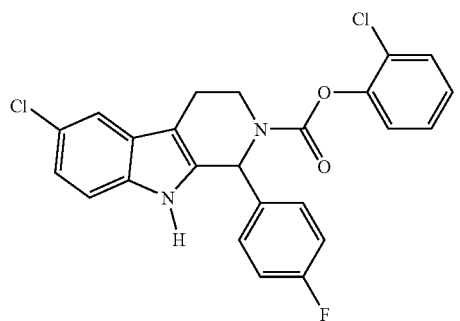
589
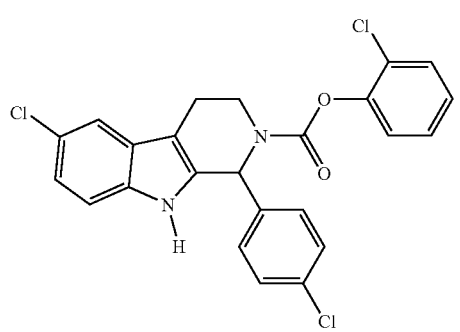
590
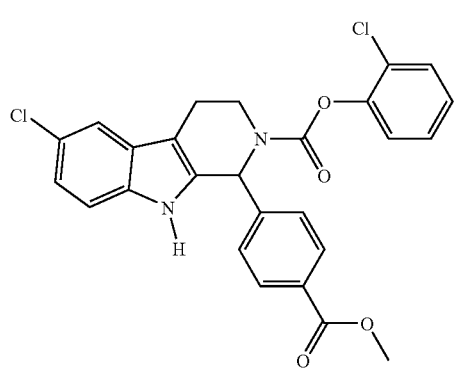
591
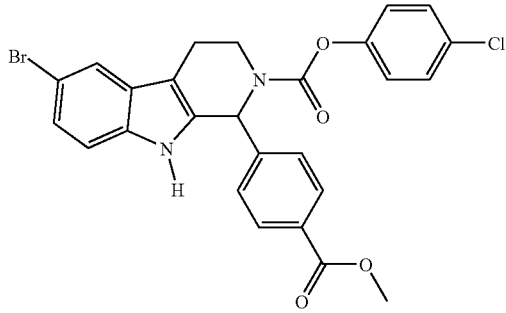
592
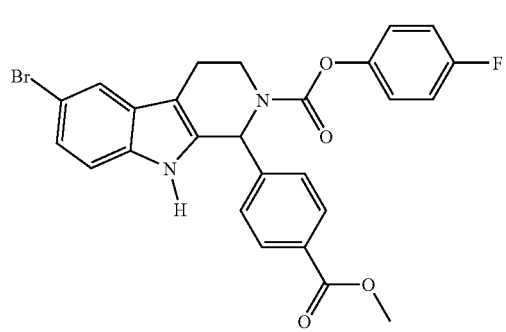
593
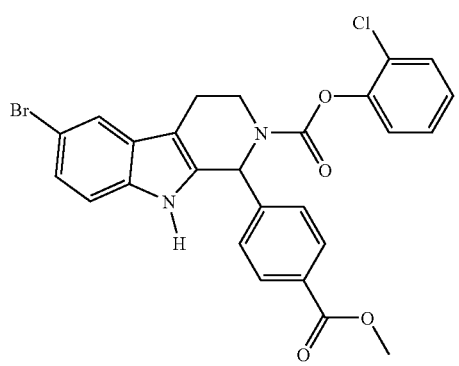
594
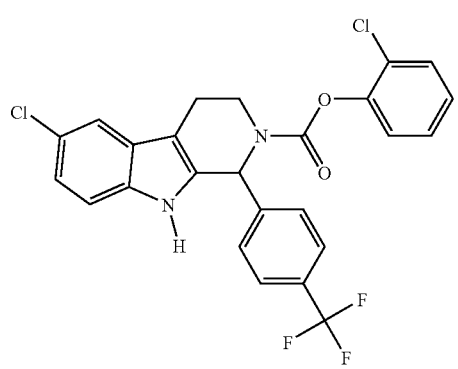
595
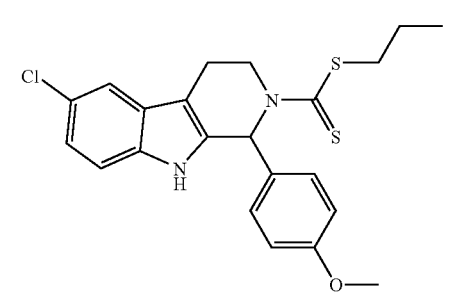
596
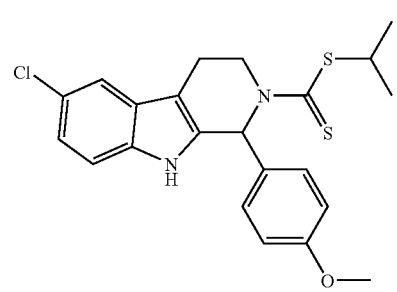
597
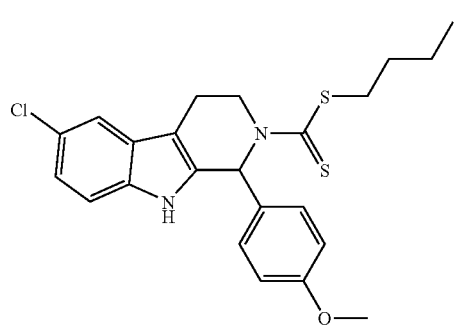

598
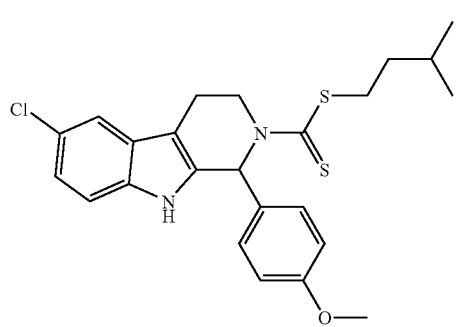
599
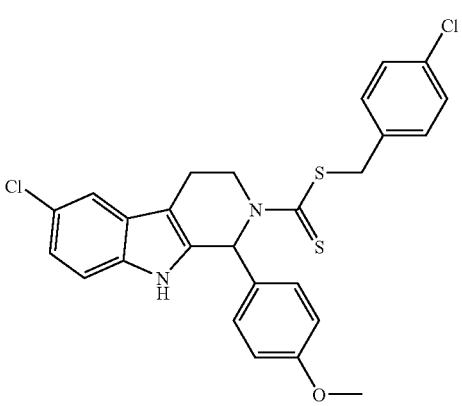
600
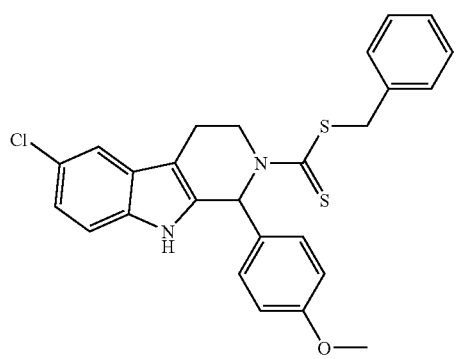
601
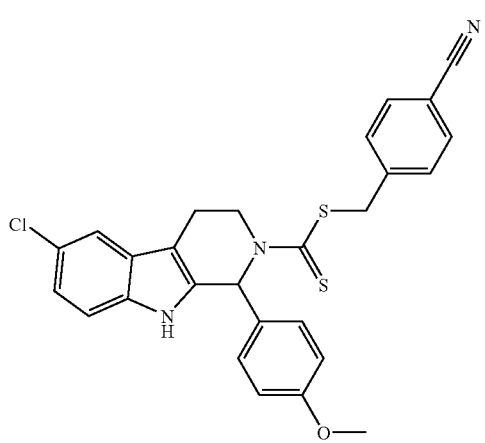
602
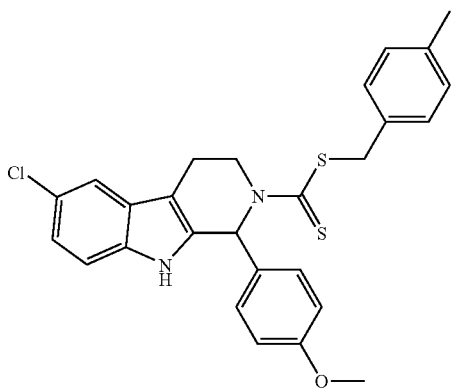
603
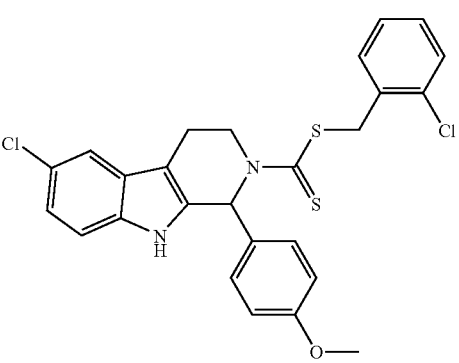
604
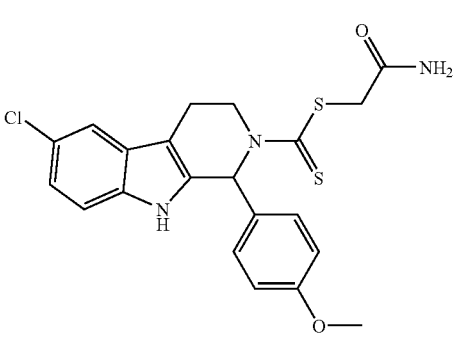
605
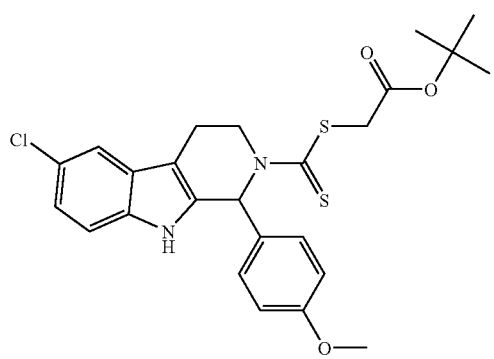

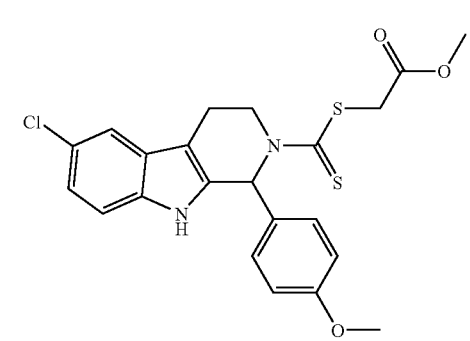
606
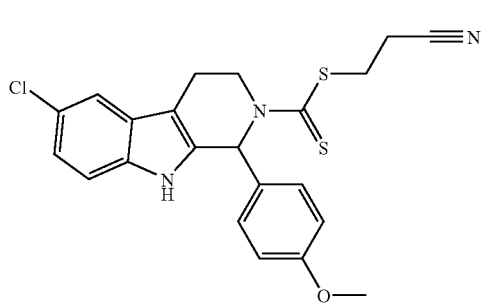
607
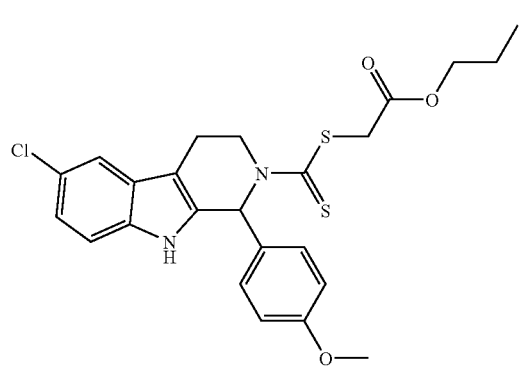
608
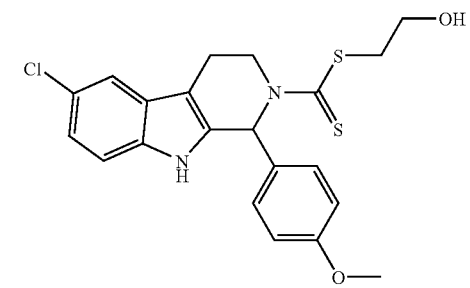
609
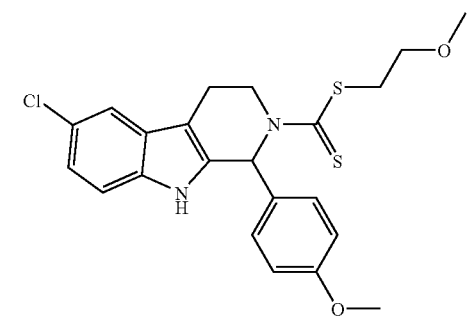
610
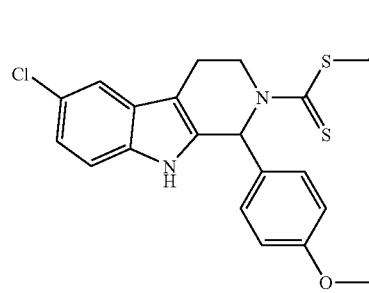
611
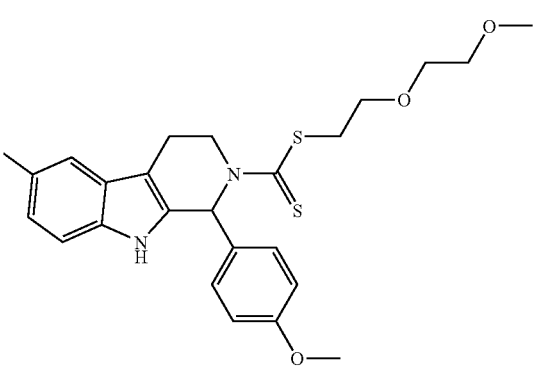
612
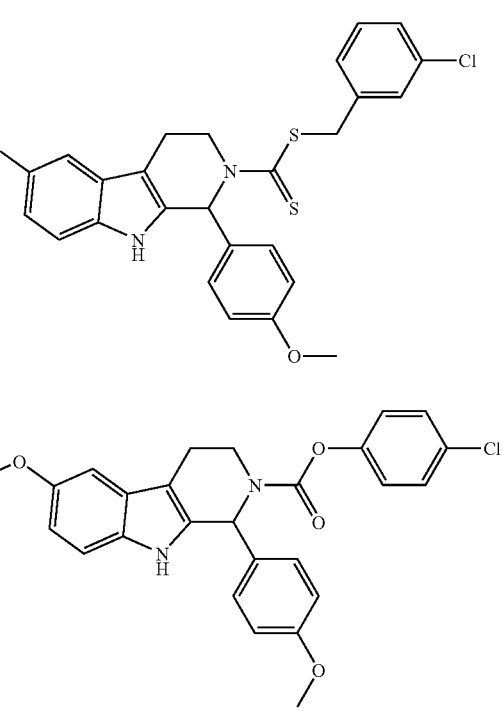
613
614
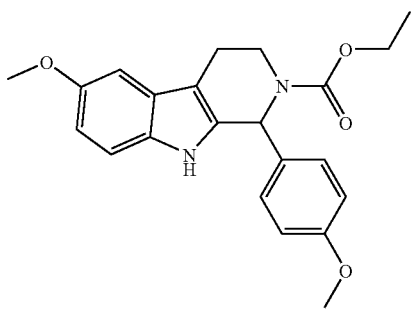
615

616 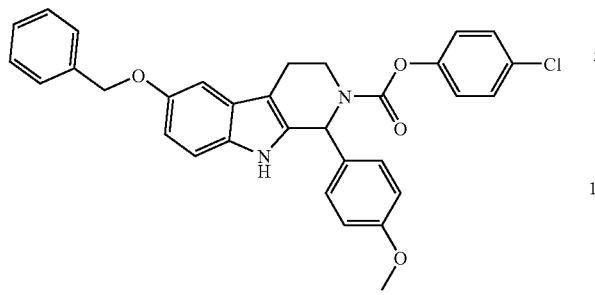
617 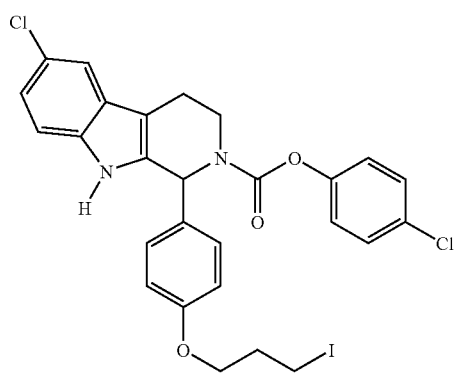
618 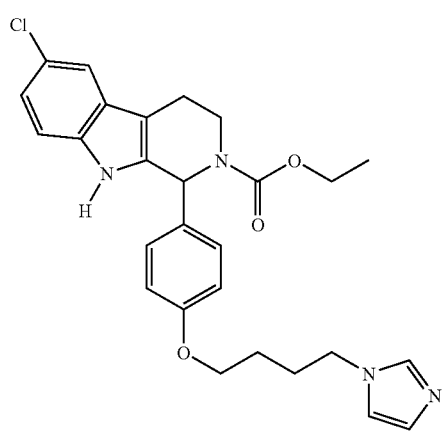
619 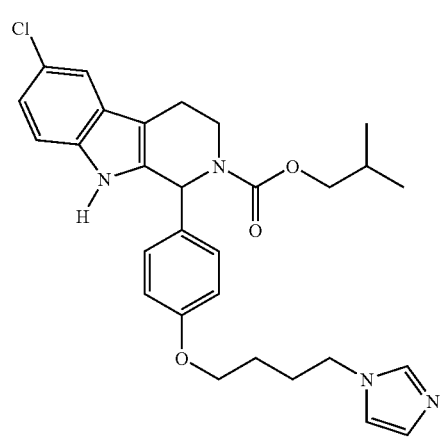
620 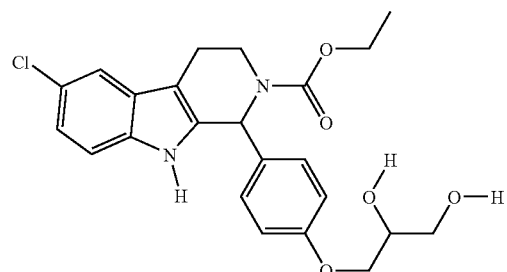
621 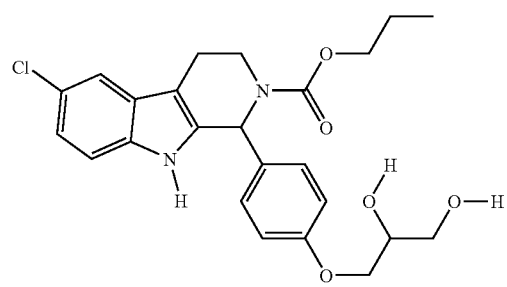
622 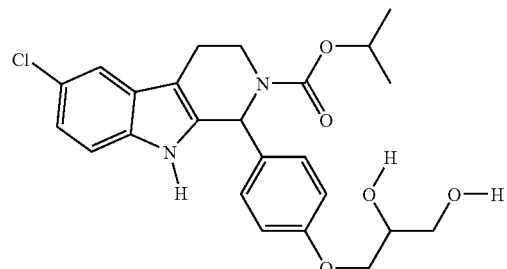
623 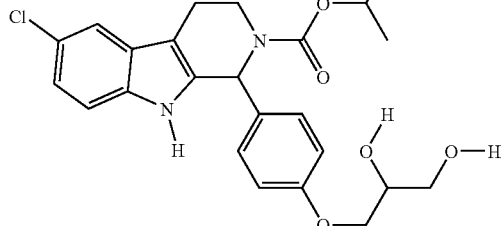
624 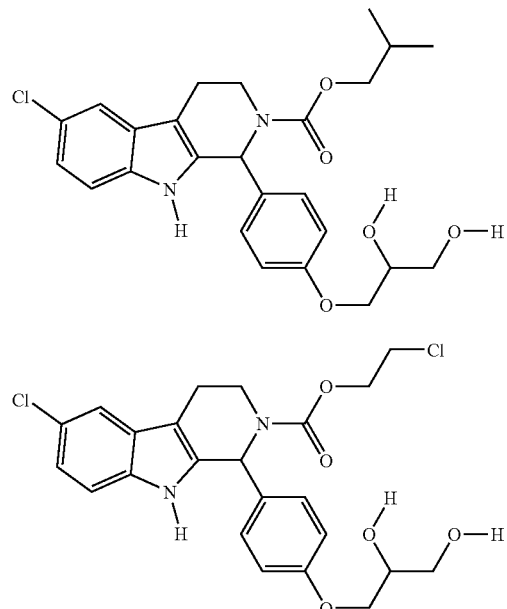

625
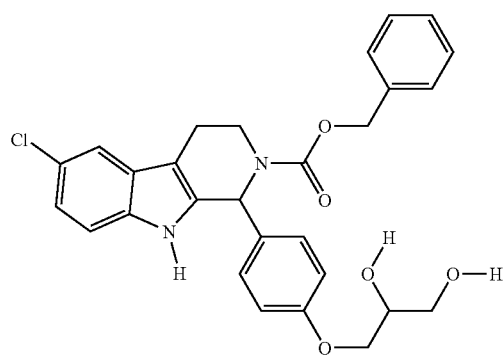
626
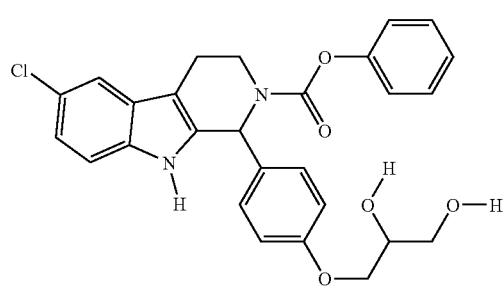
627
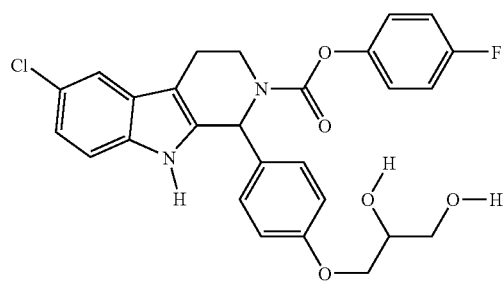
628
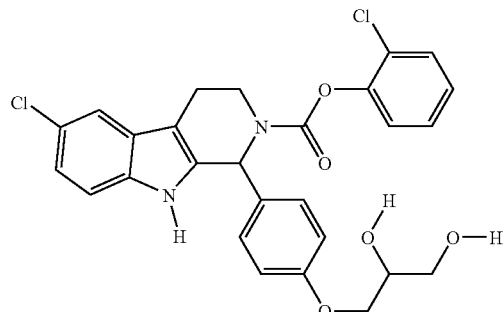
629
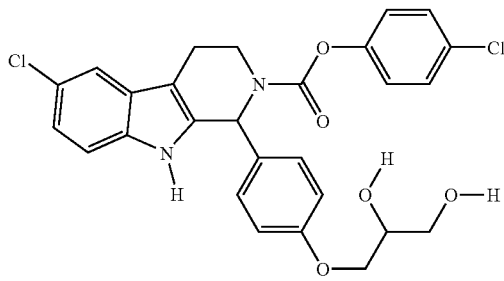
630
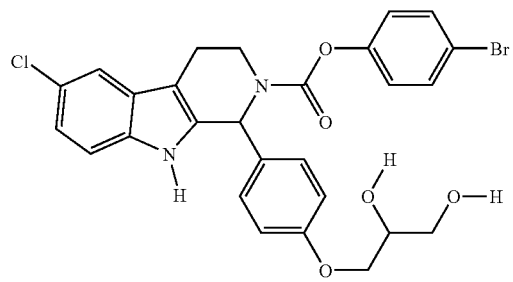
631
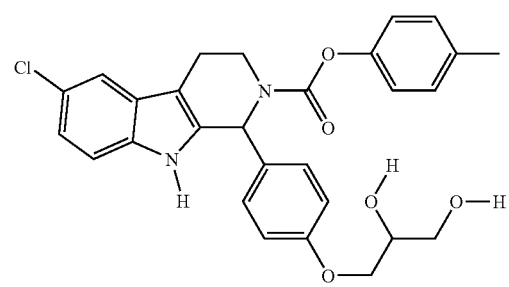
632
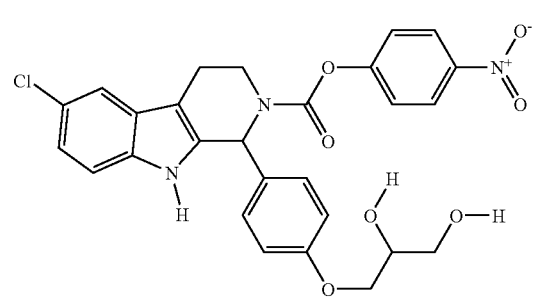
633
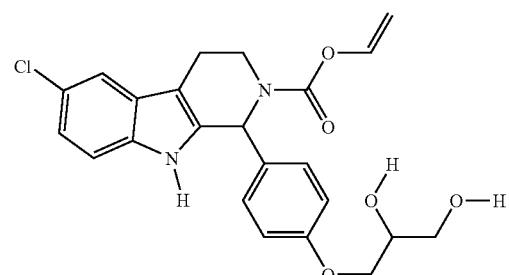
634
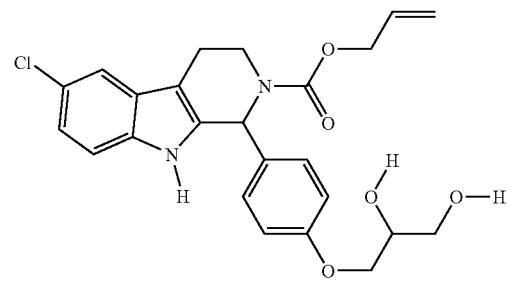

635
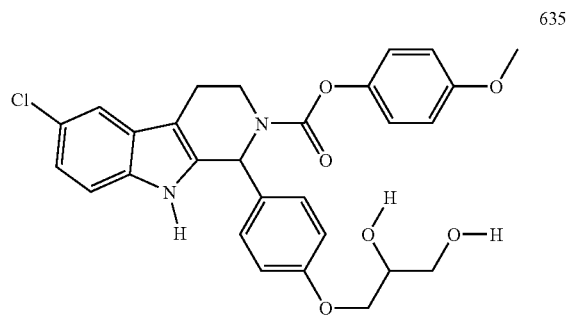
636
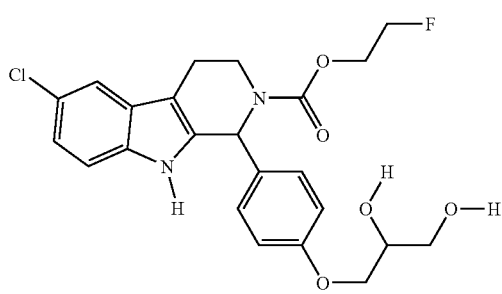
637
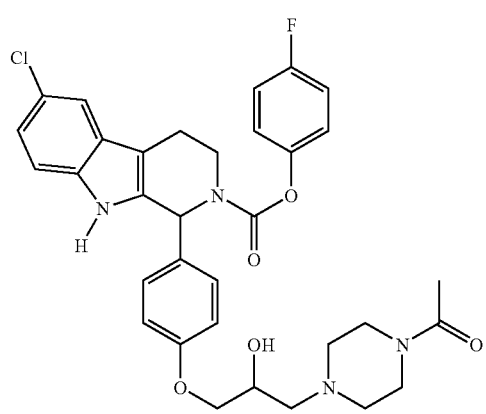
638
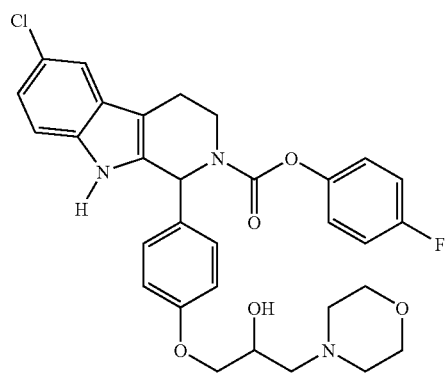
639
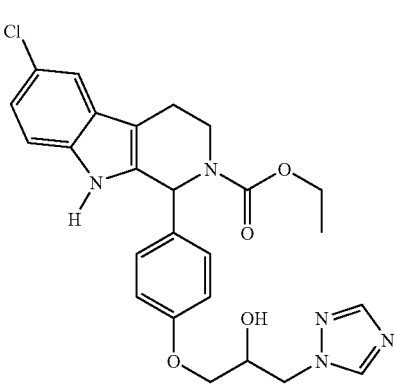
640
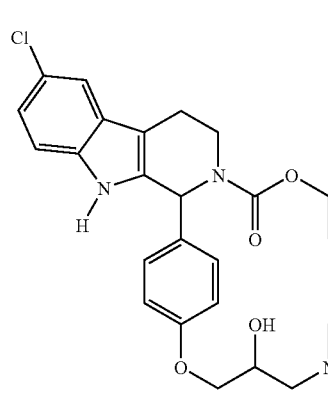
641
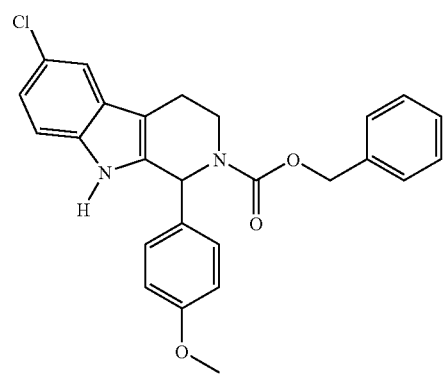
642
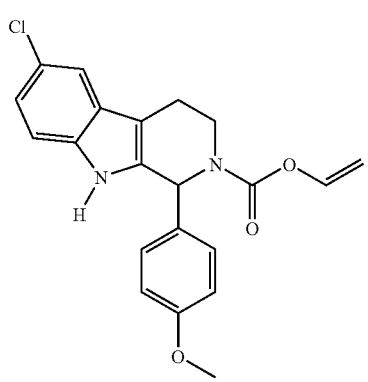

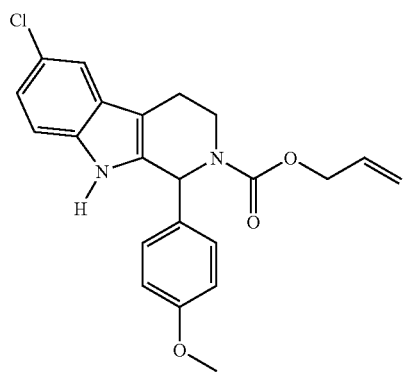
643
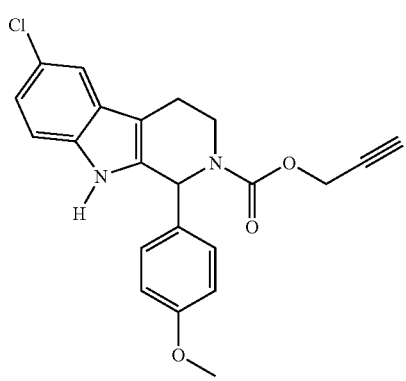
644
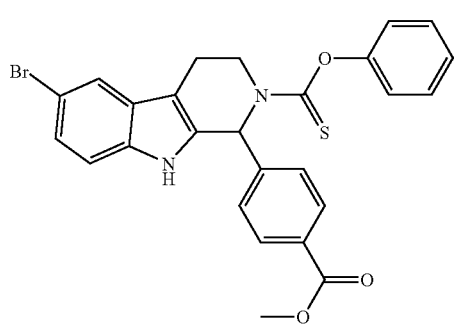
645
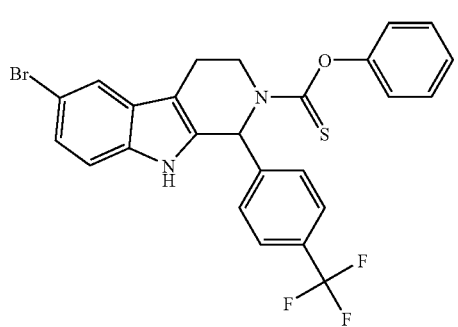
646
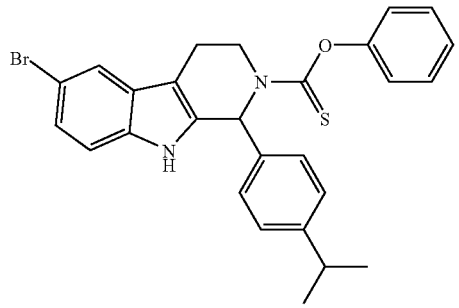
647
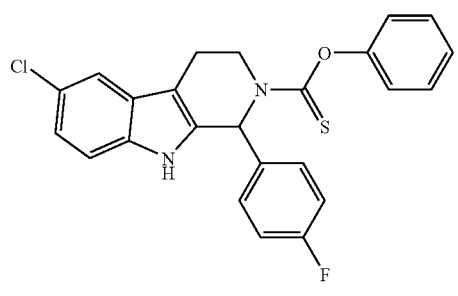
648
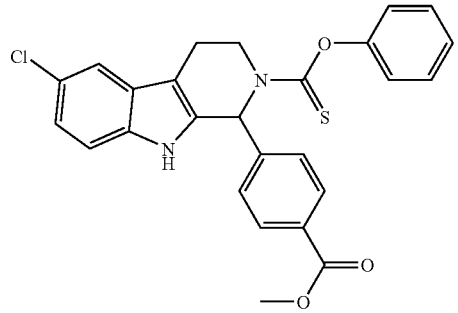
649
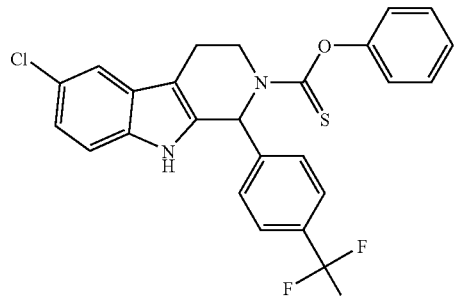
650
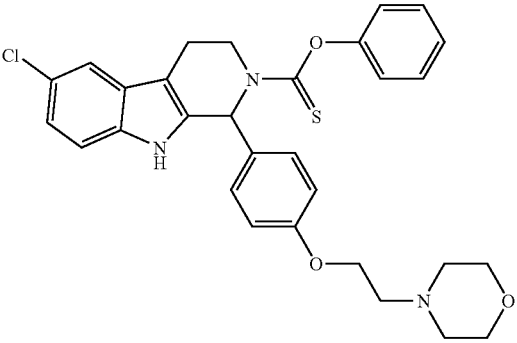
651

652
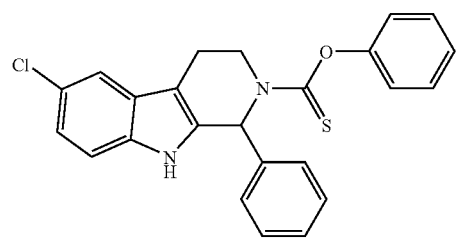
653
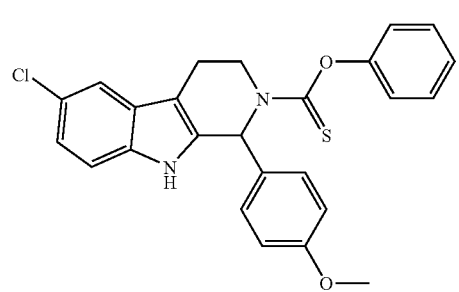
654
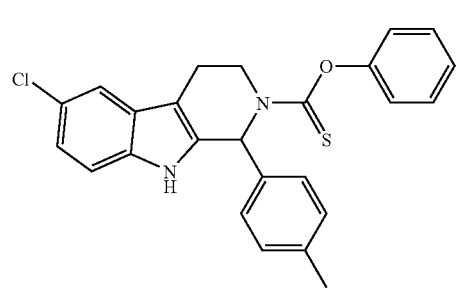
655
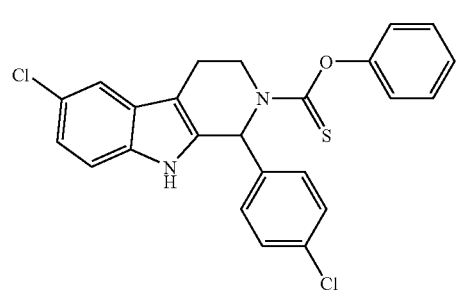
656
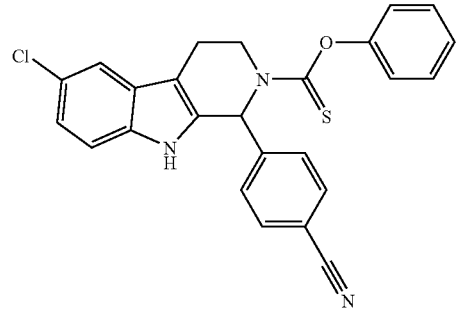
657
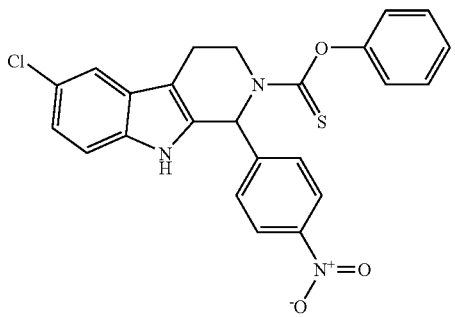
658
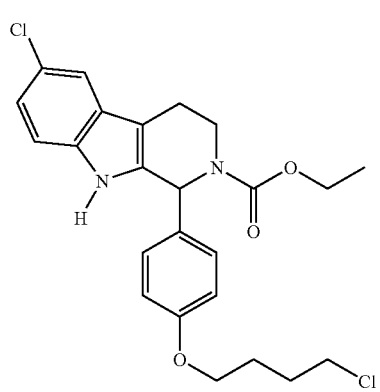
659
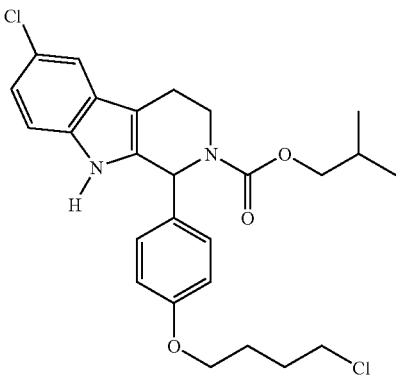
660
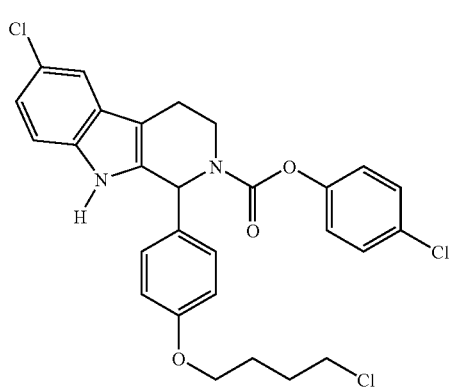

661 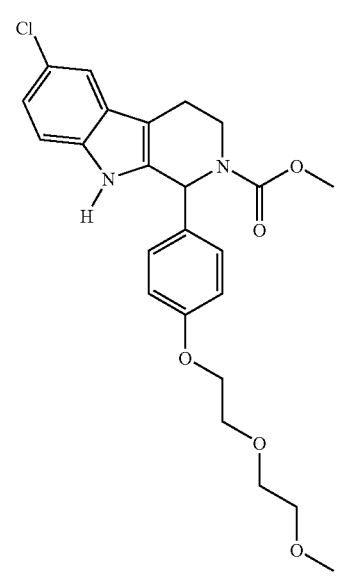
662 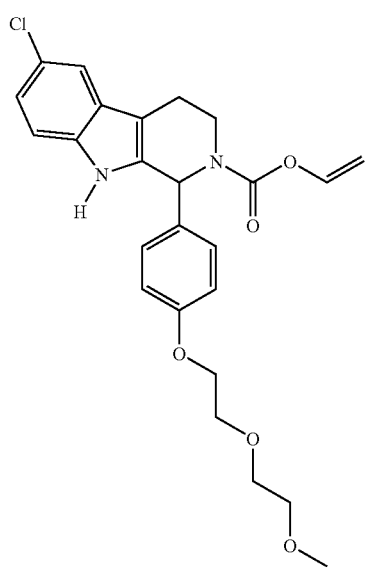
663 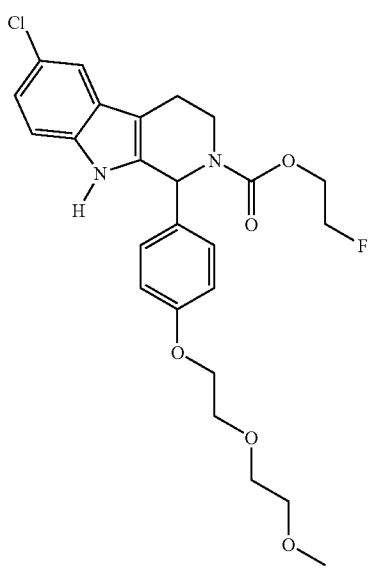
664 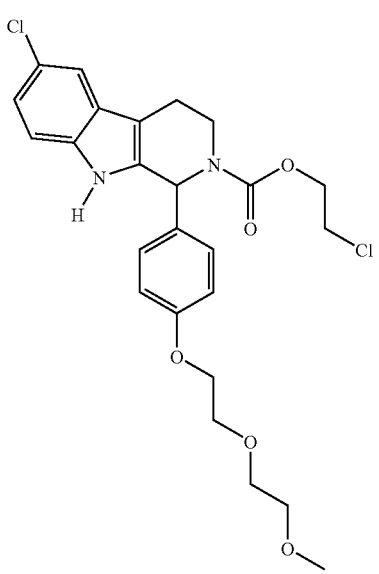
665 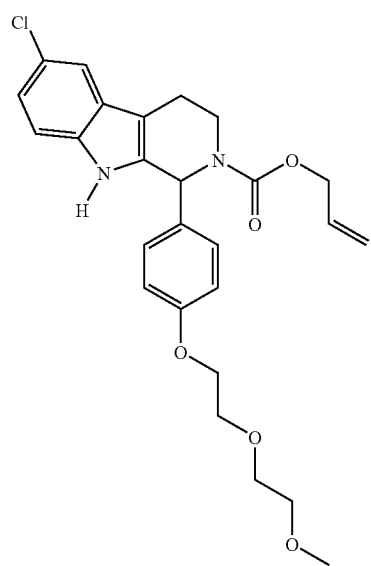
666 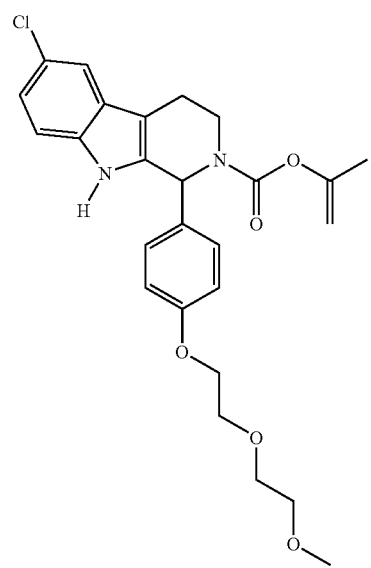

-continued

667

668

669

-continued

670

671

672

673 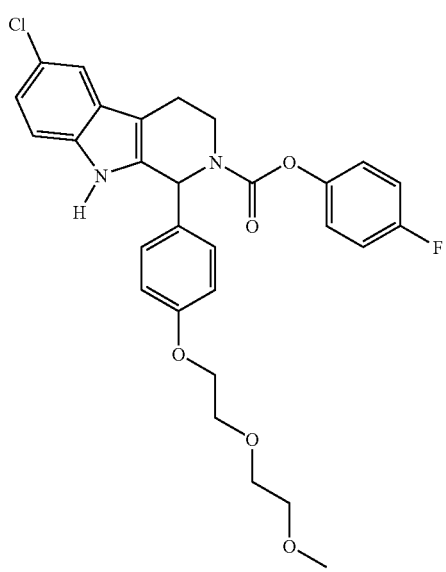
674 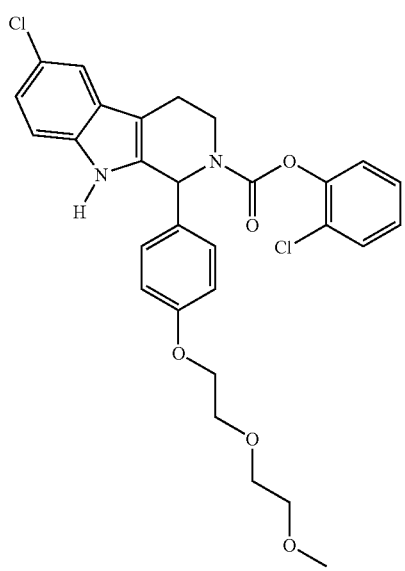
675 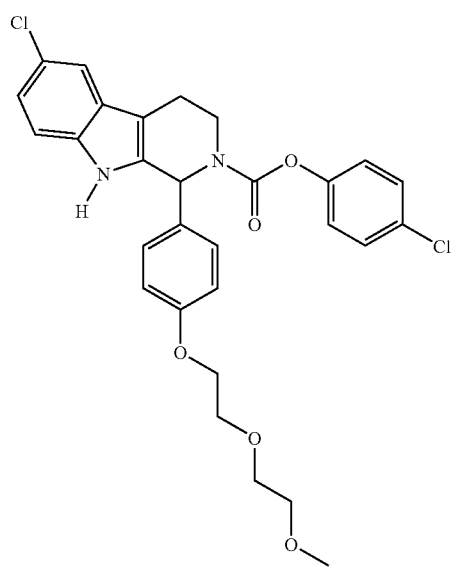
676 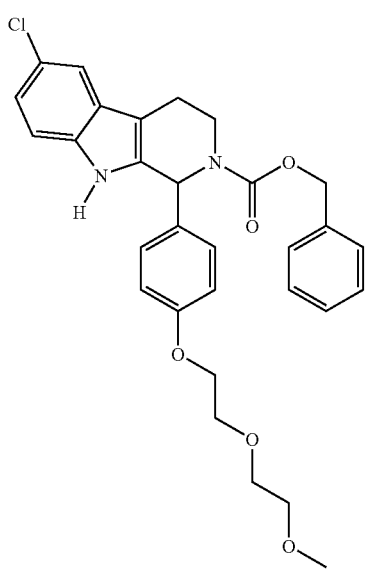
677 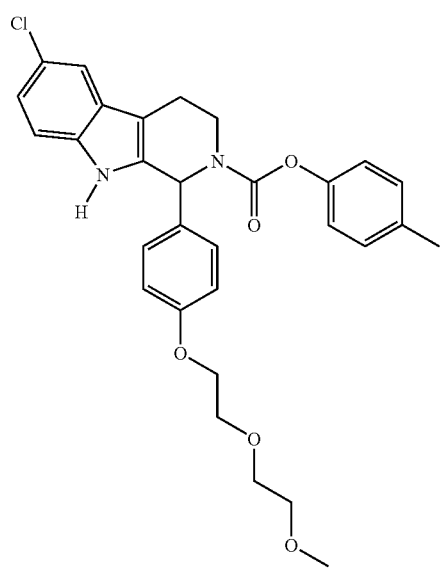
678 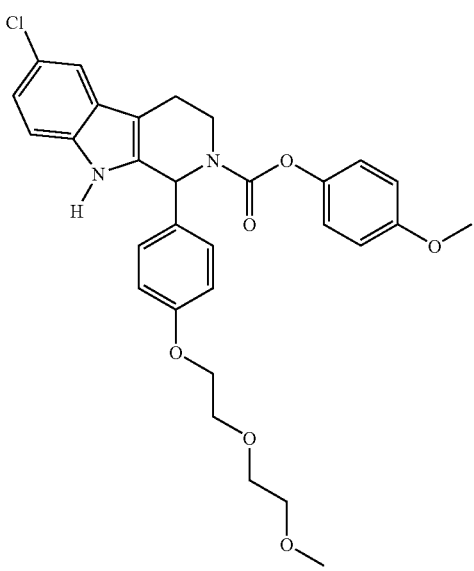

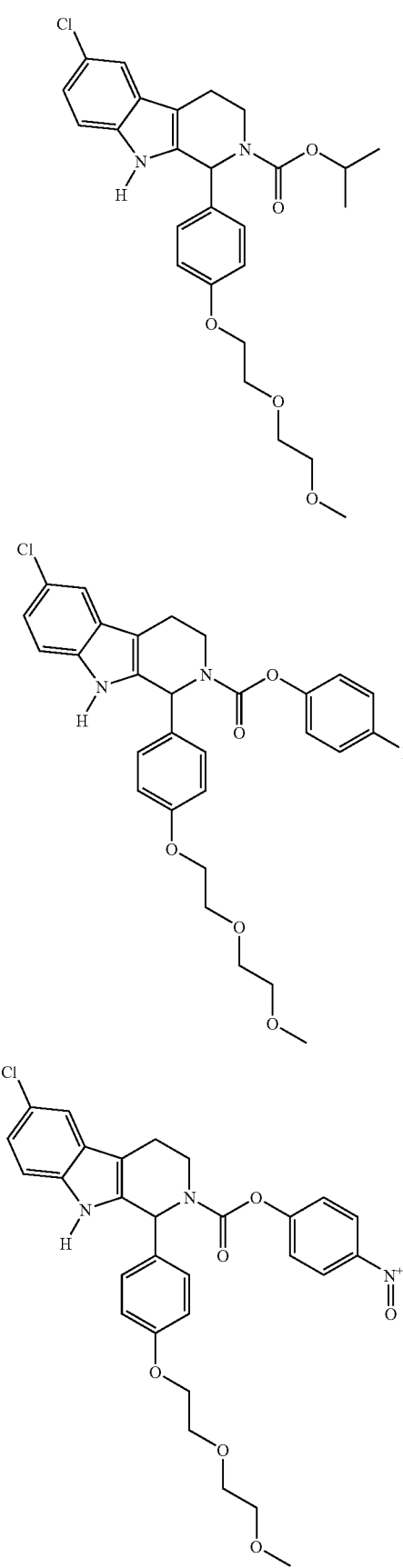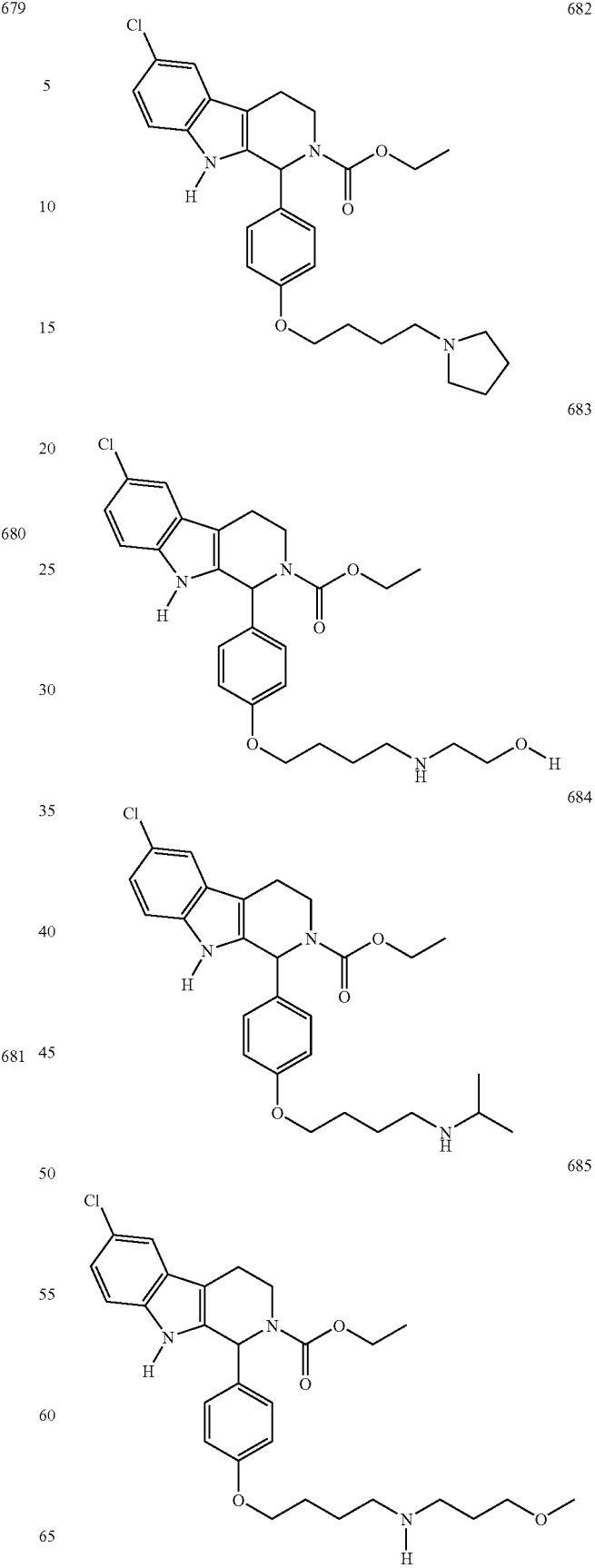

686 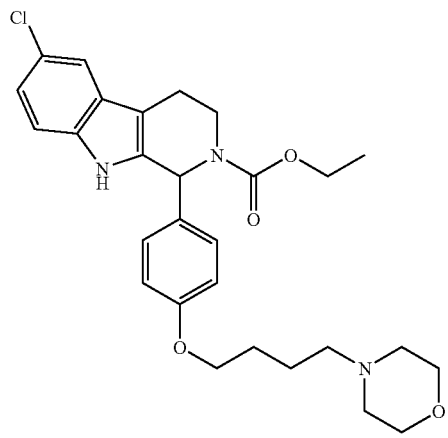
687 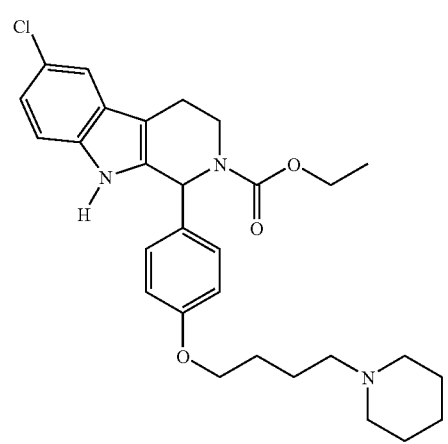
688 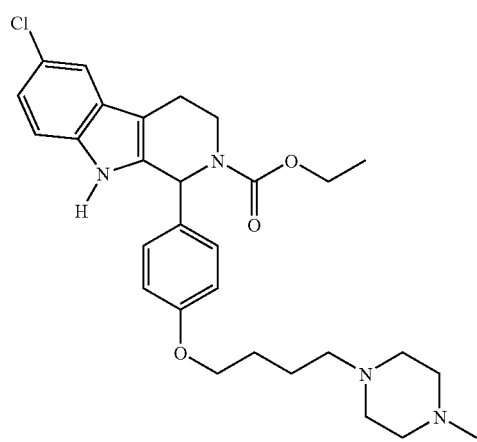
689 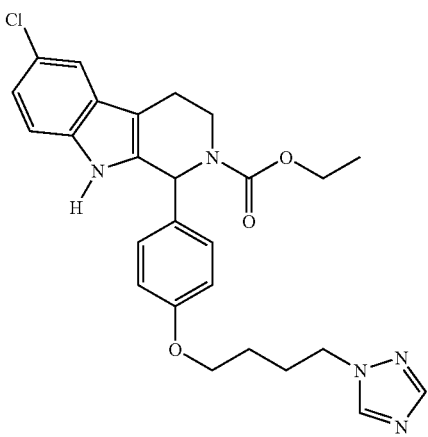
690 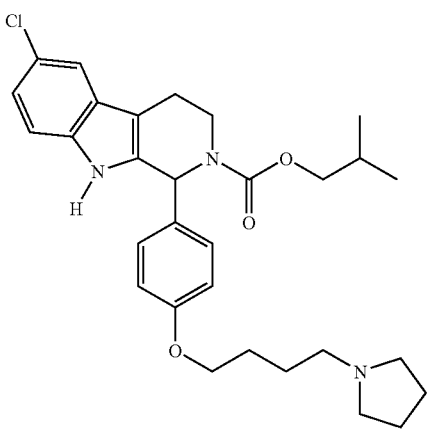
691 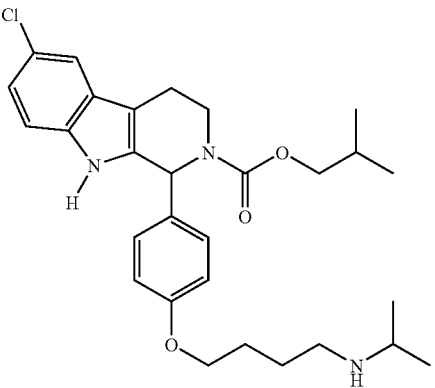
692

-continued
693
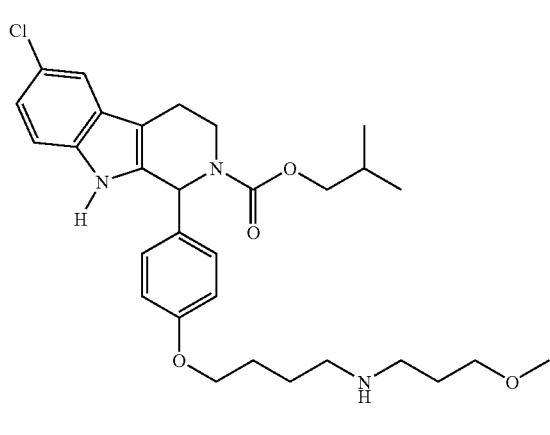
694
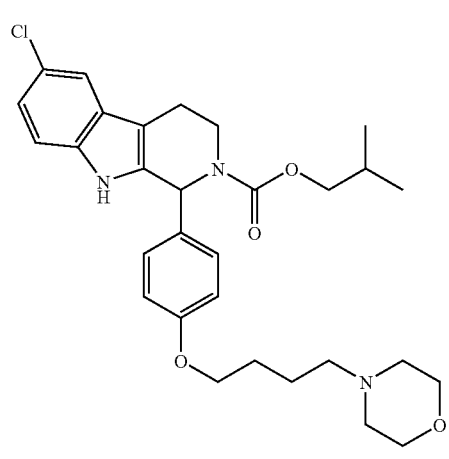
695
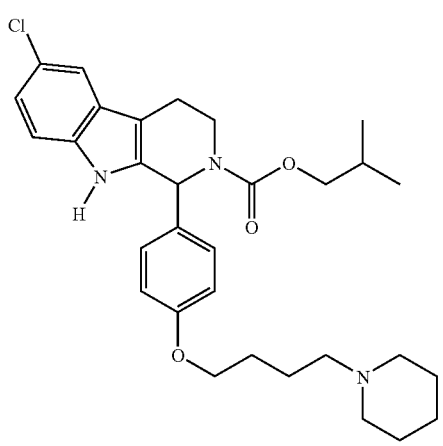
-continued
696
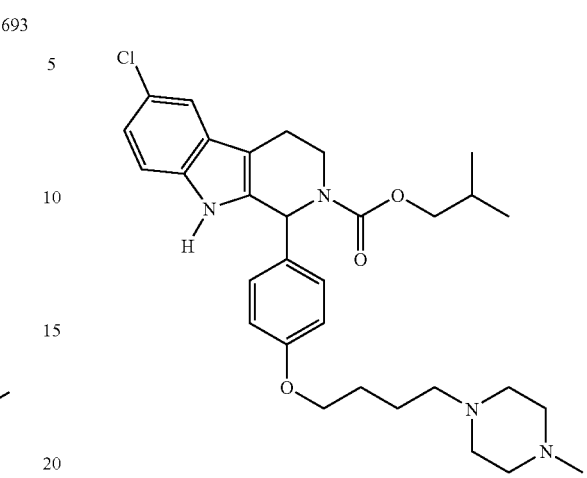
697
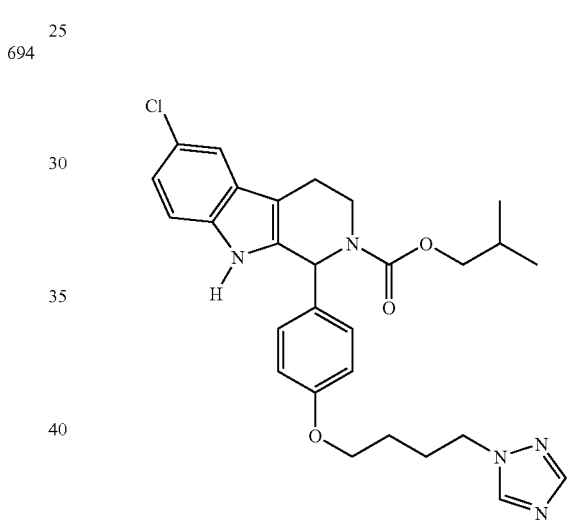
698
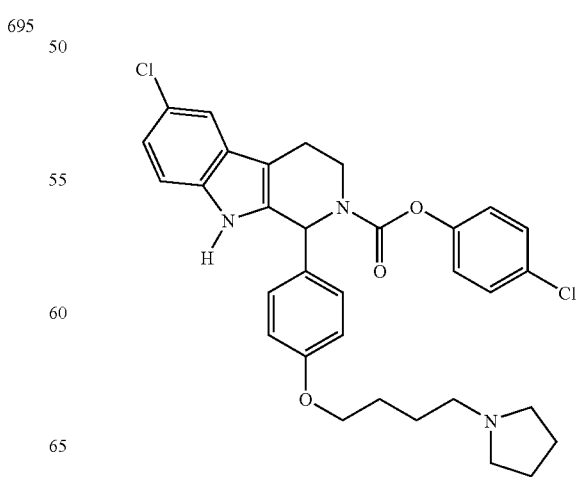

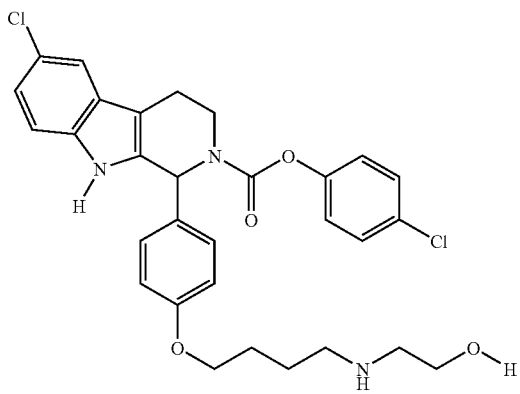
699
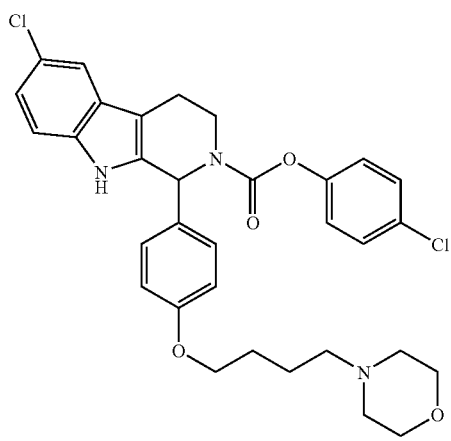
702
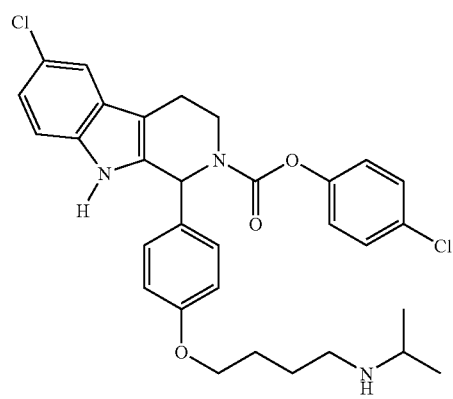
700
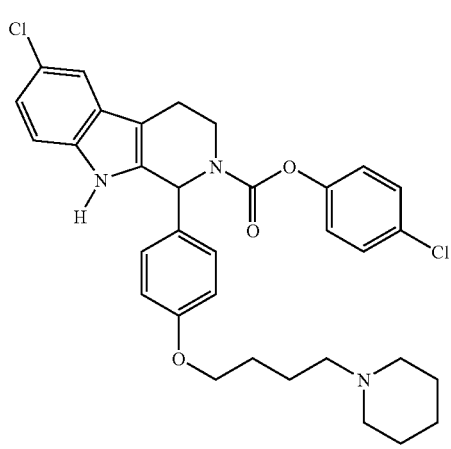
703
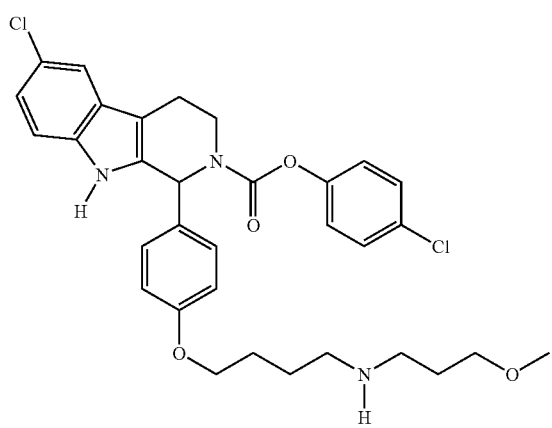
701
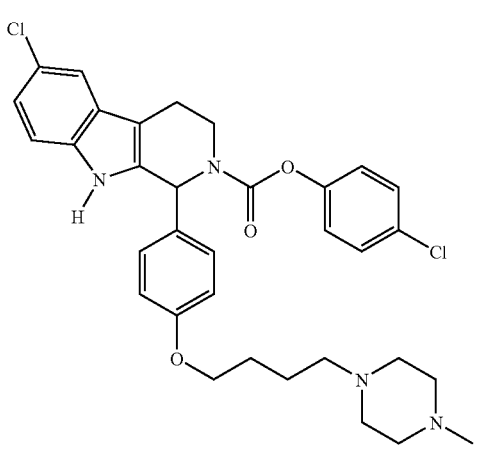
704

187
-continued
705
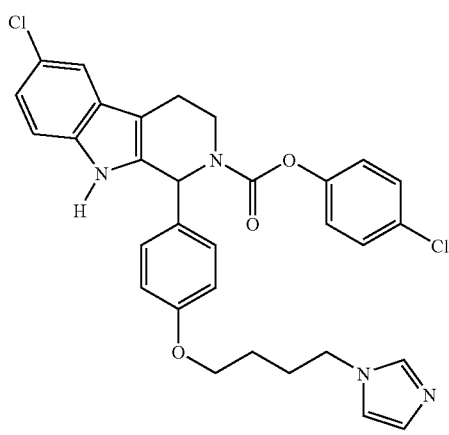
706
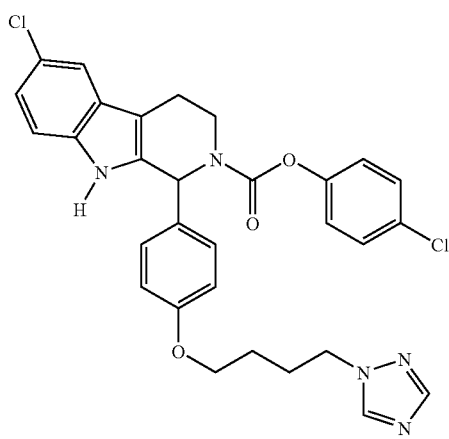
707
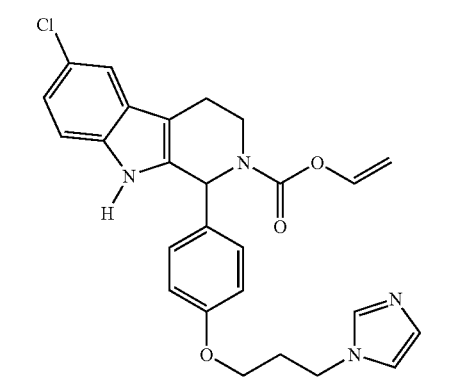
708
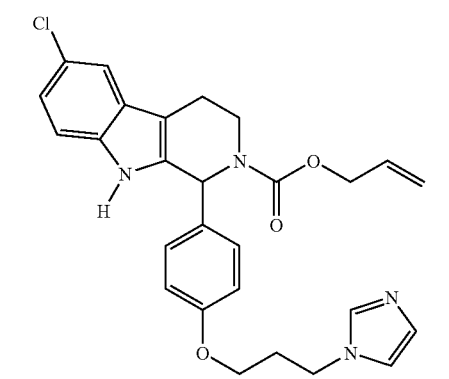
188
-continued
709
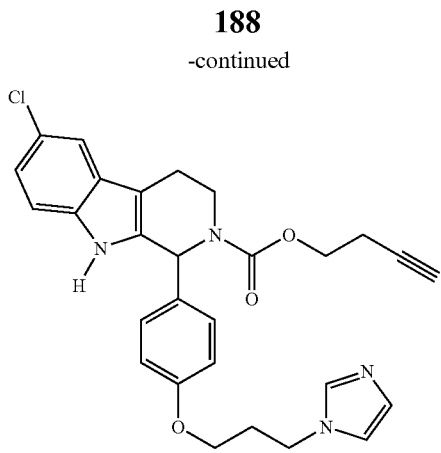
710
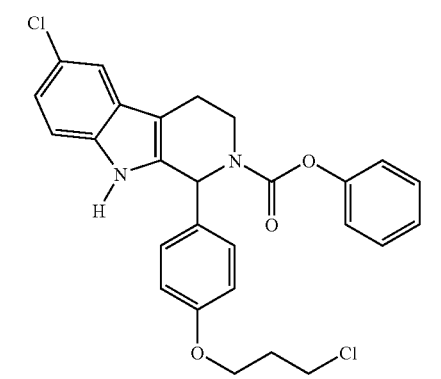
711
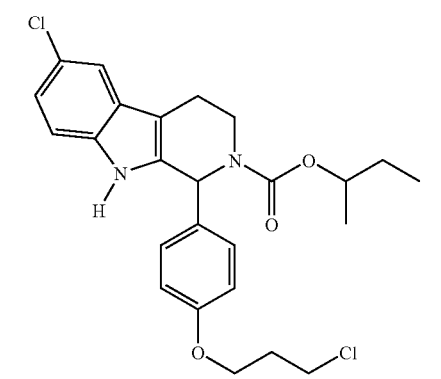
712
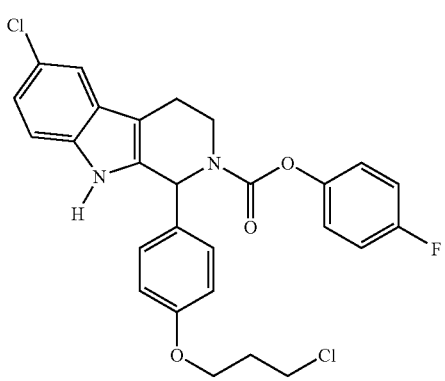

713
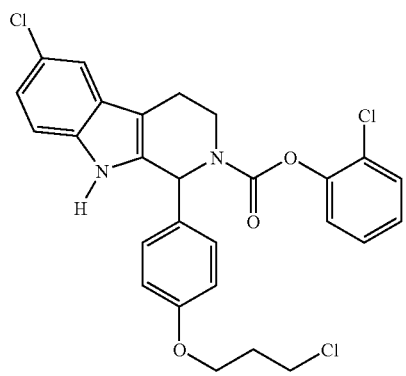
714
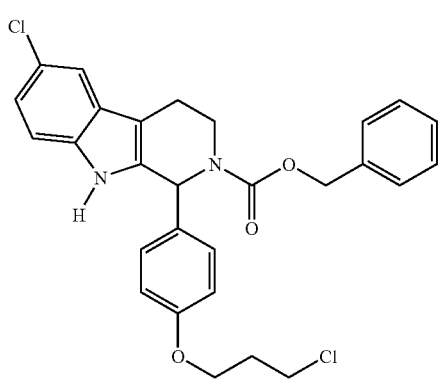
715
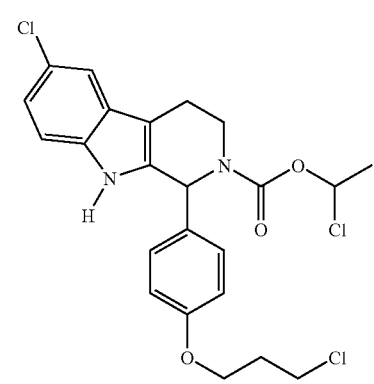
716
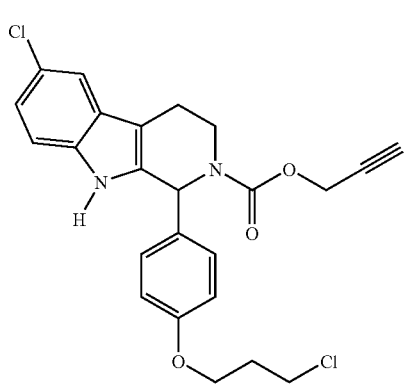
717
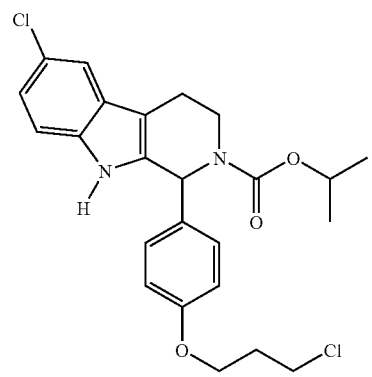
718
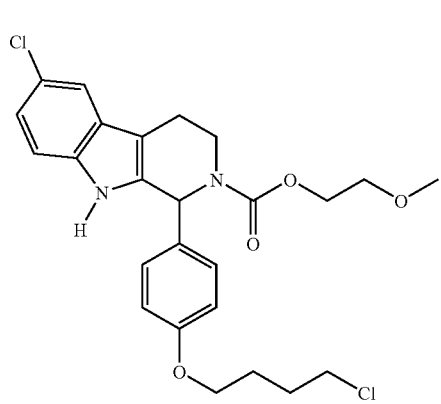
719
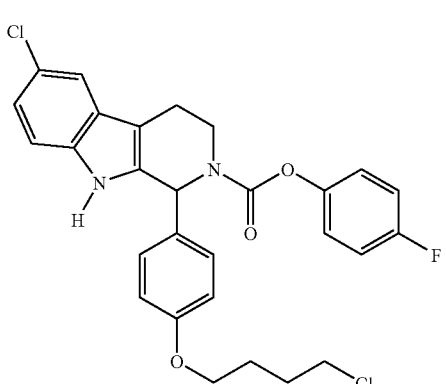
720
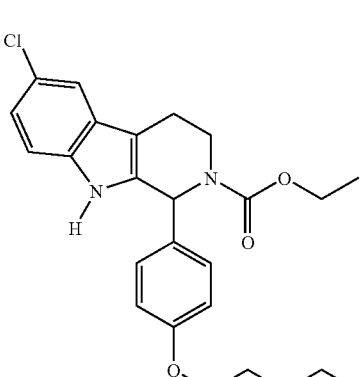

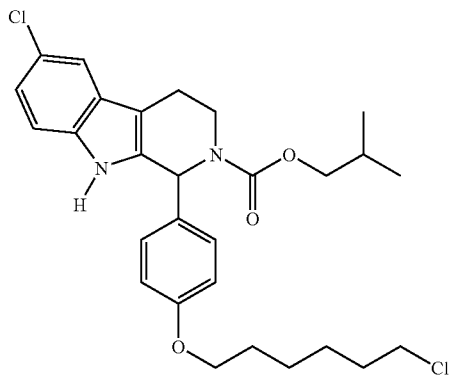
721
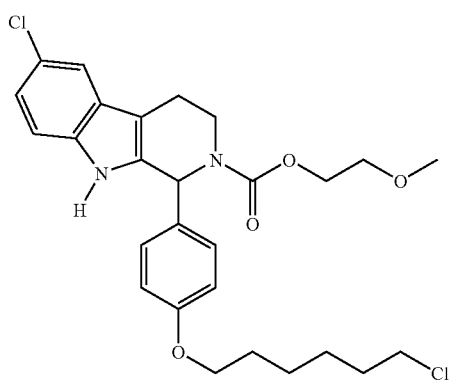
722
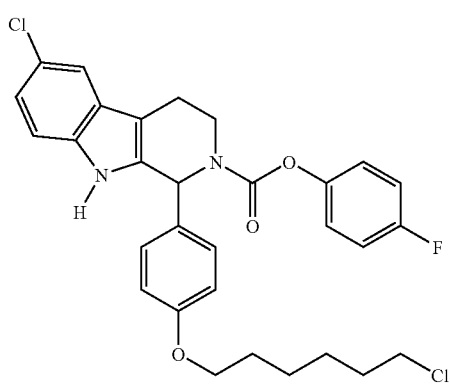
723
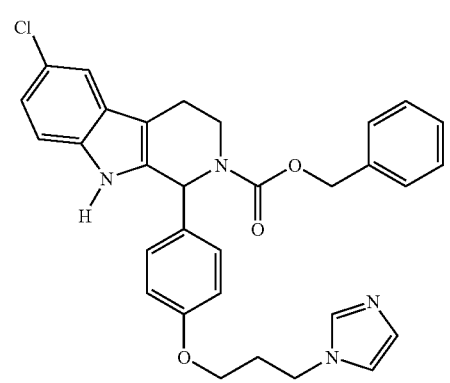
724
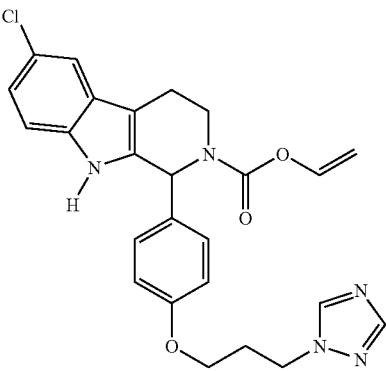
725
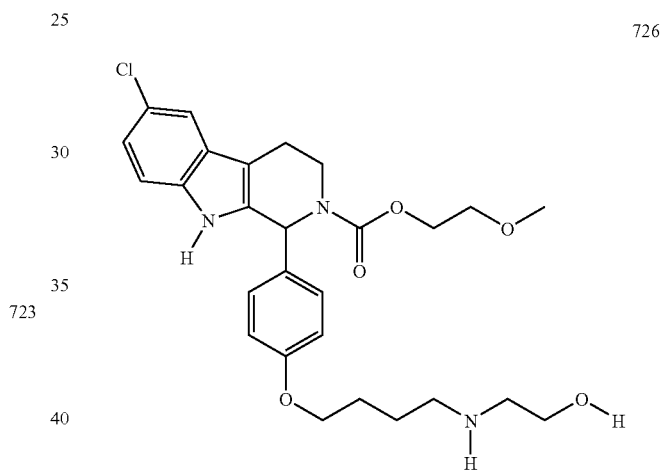
726
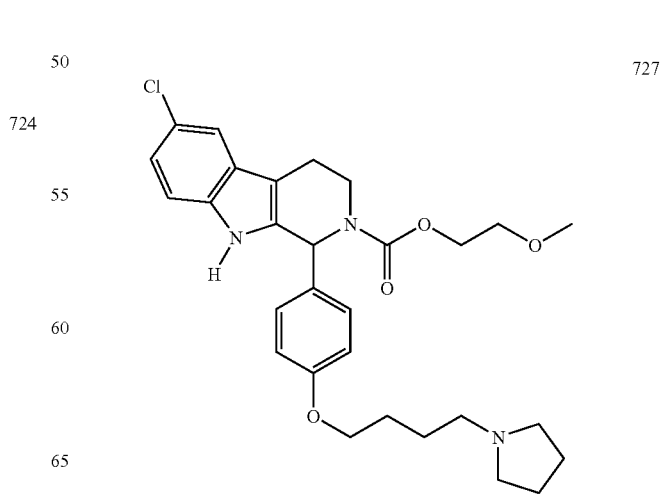
727

193
-continued
728
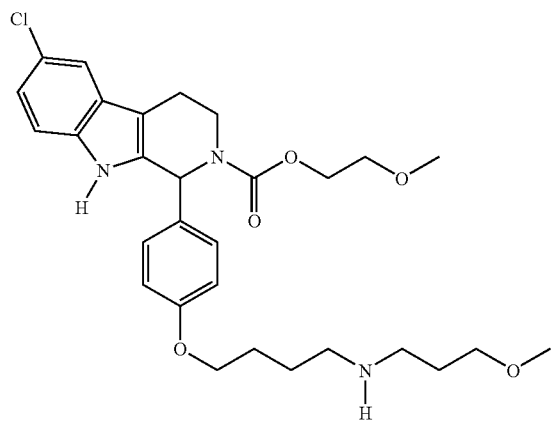
729
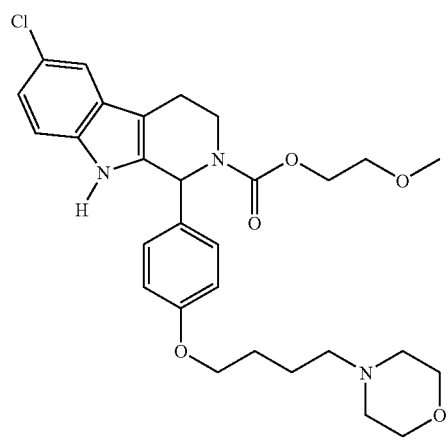
730
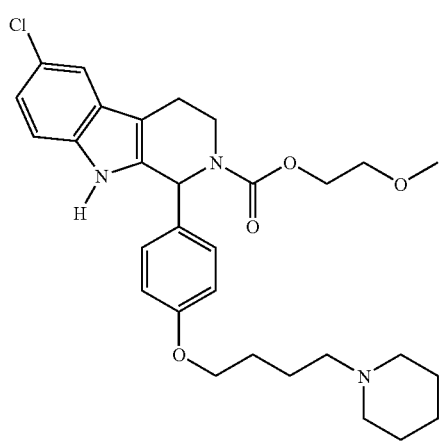
194
-continued
731
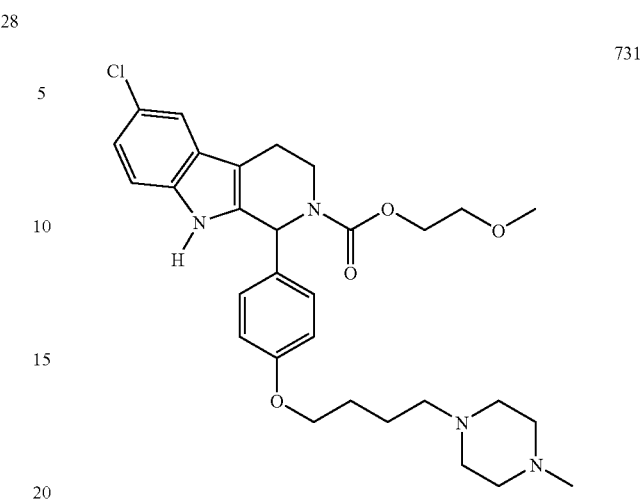
732
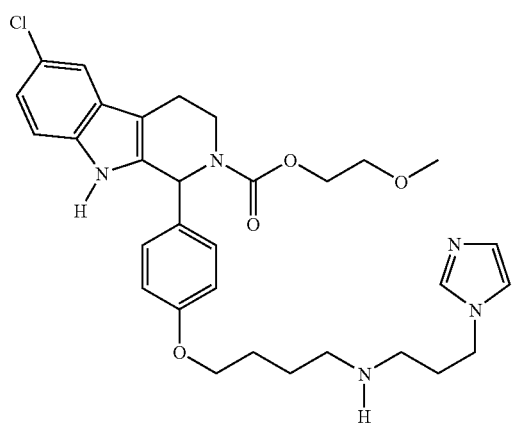
733
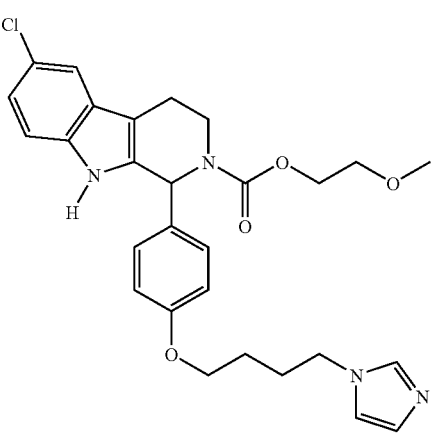

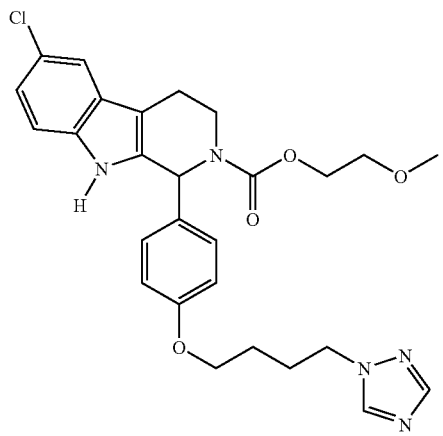
734
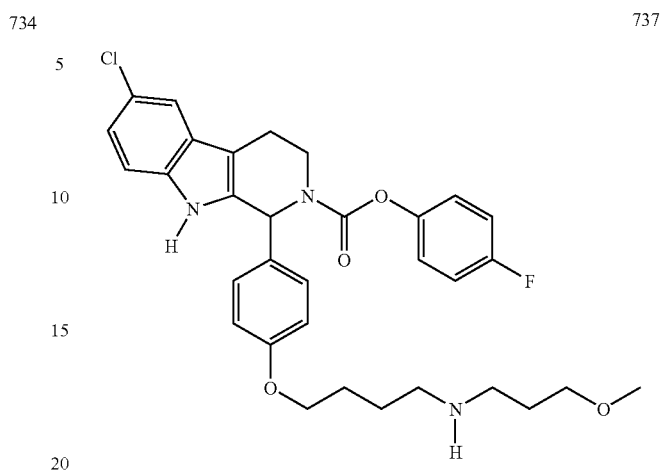
737
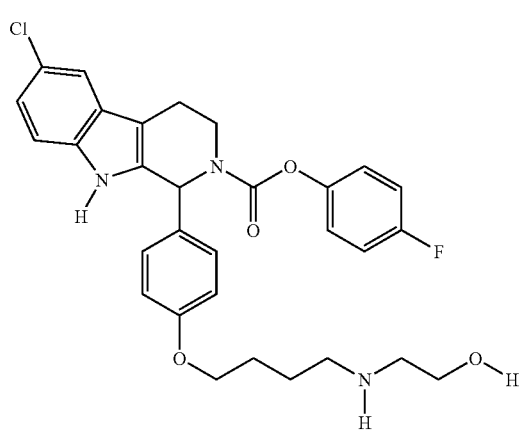
735
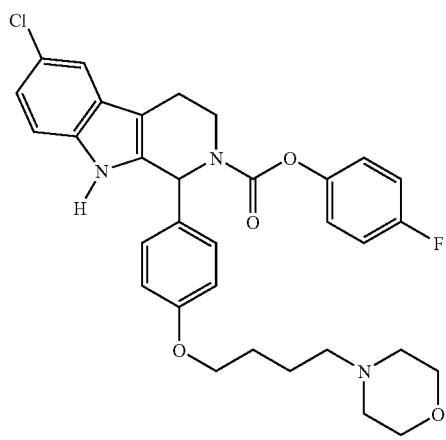
738
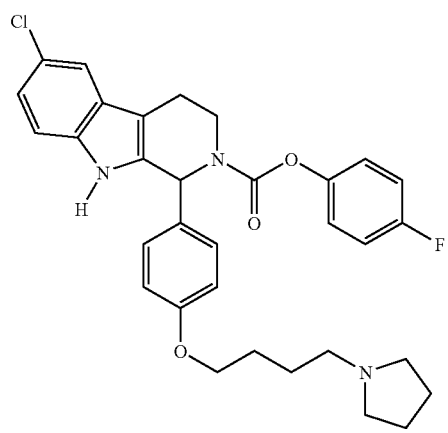
736
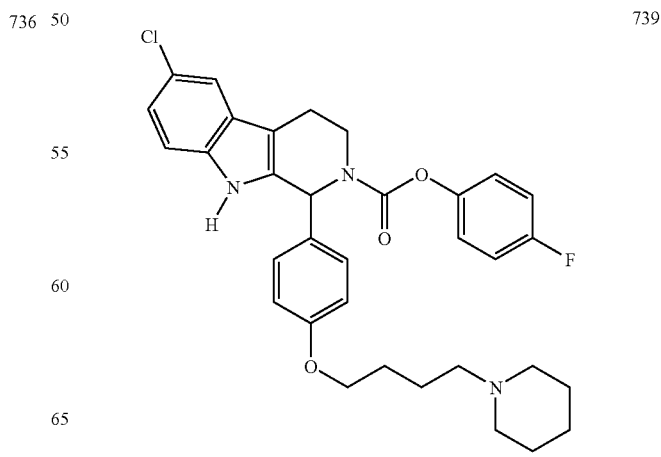
739

197
-continued
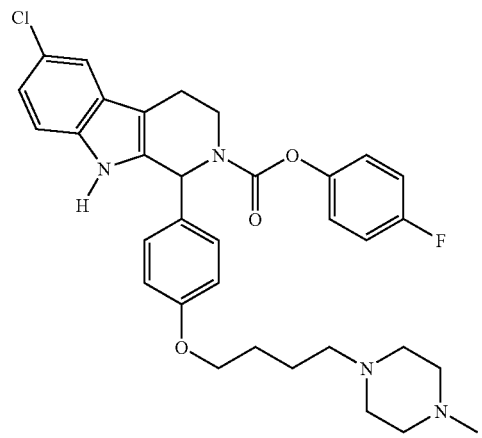
740
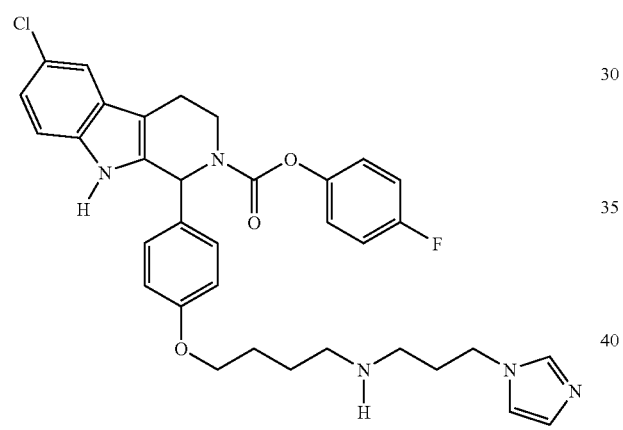
741
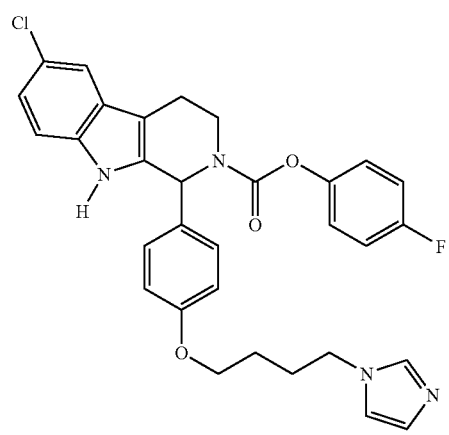
742
198
-continued
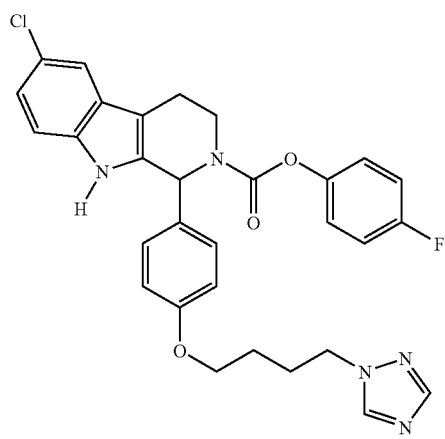
743
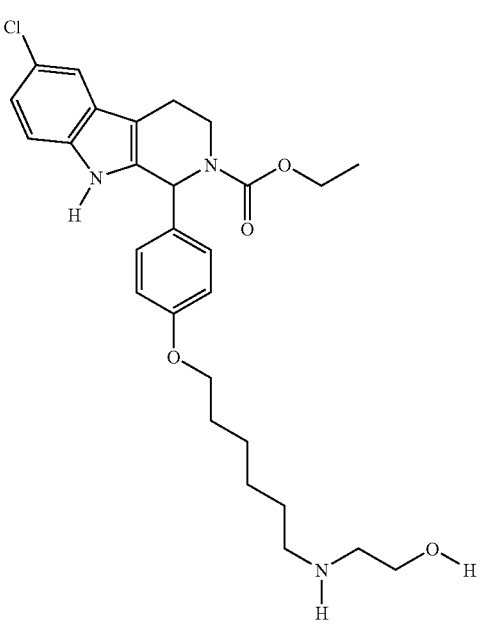
744
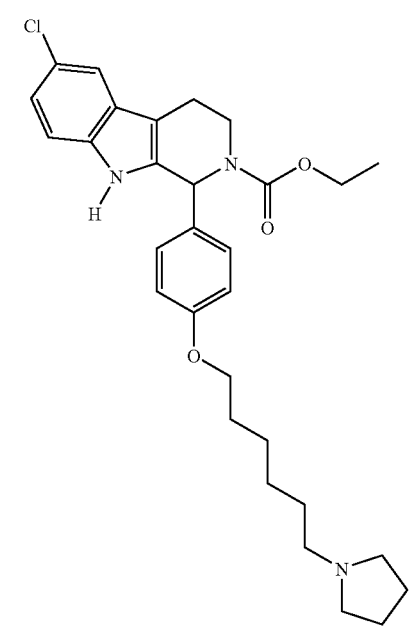
745

199
-continued
200
-continued
746
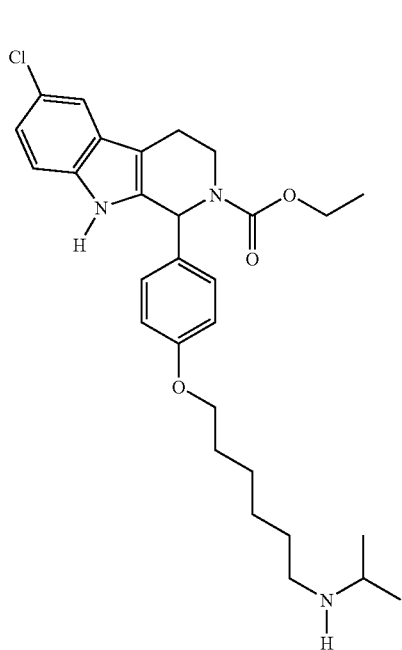
748
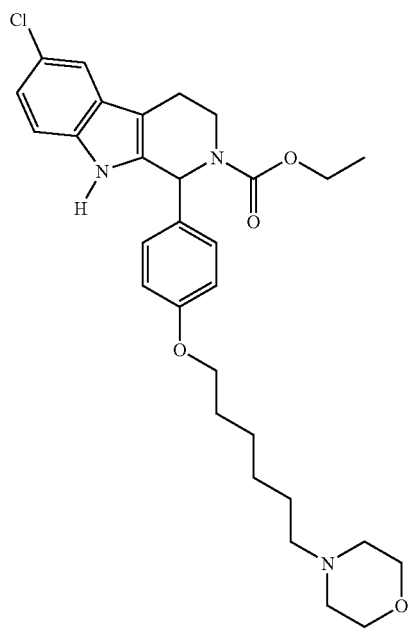
747
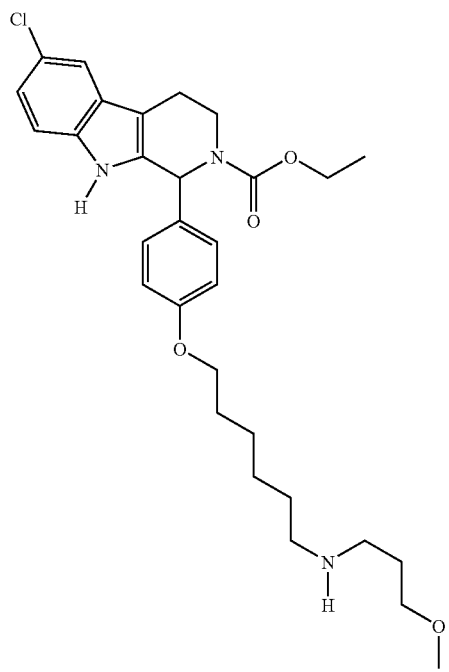
749
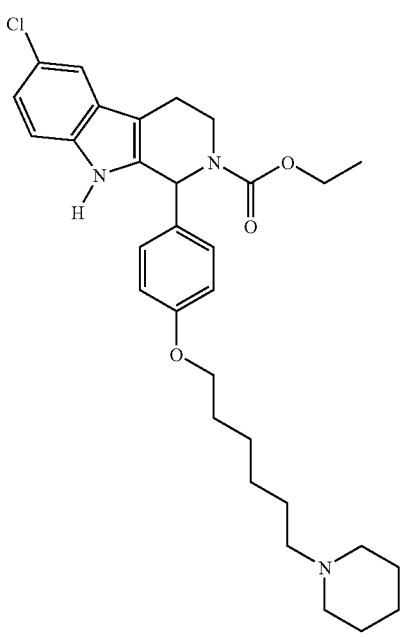

201
-continued
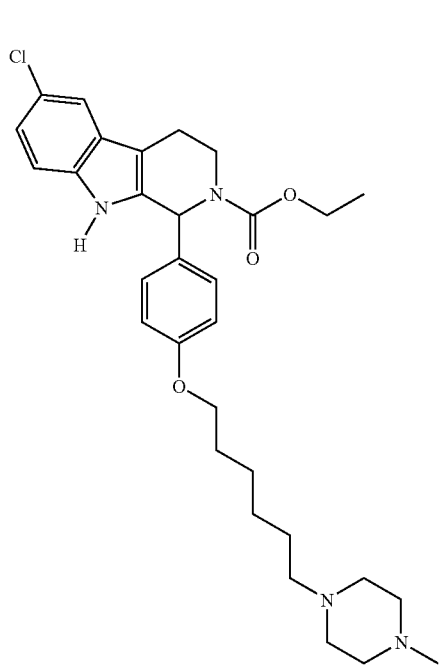
750
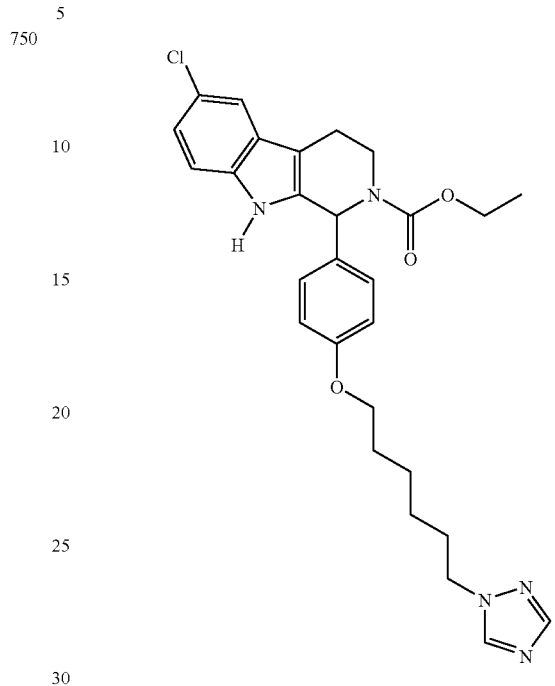
752
202
-continued
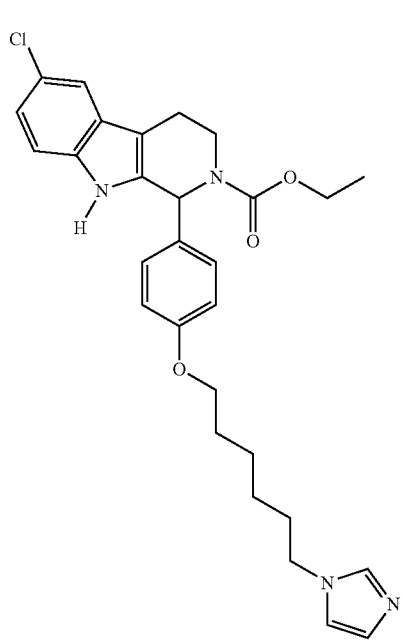
751
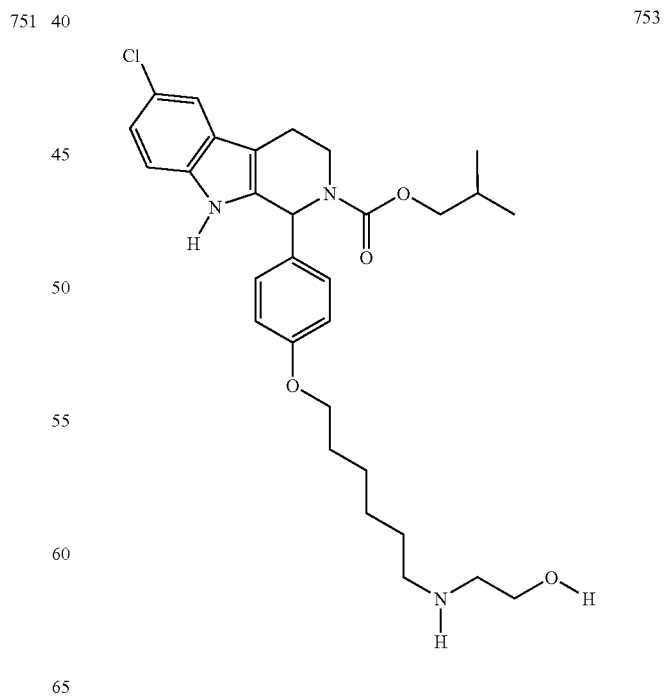
753

203
-continued
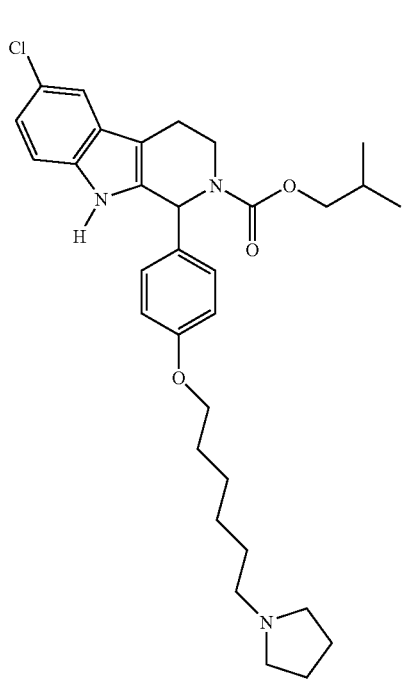
754
204
-continued
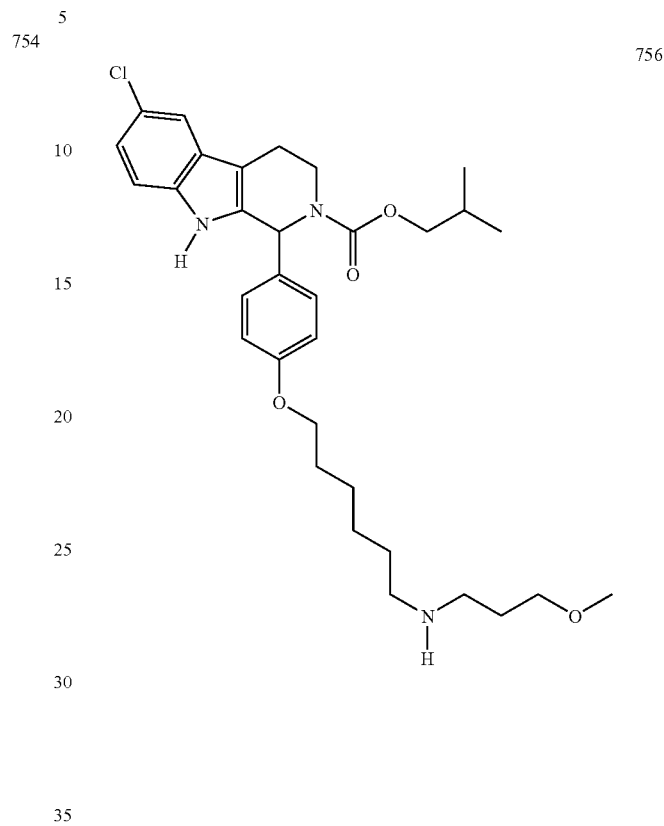
756
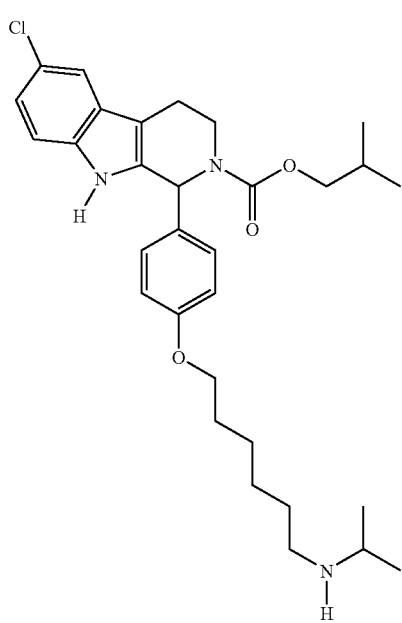
755
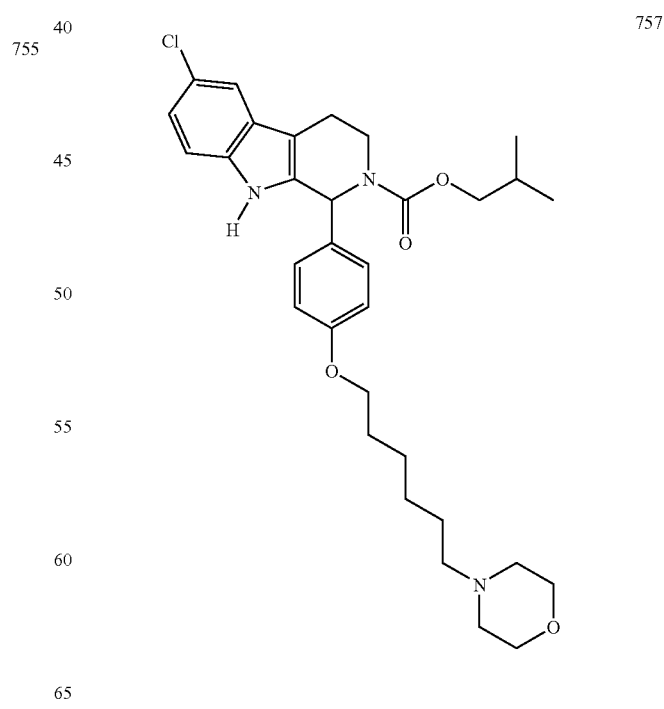
757

205
-continued
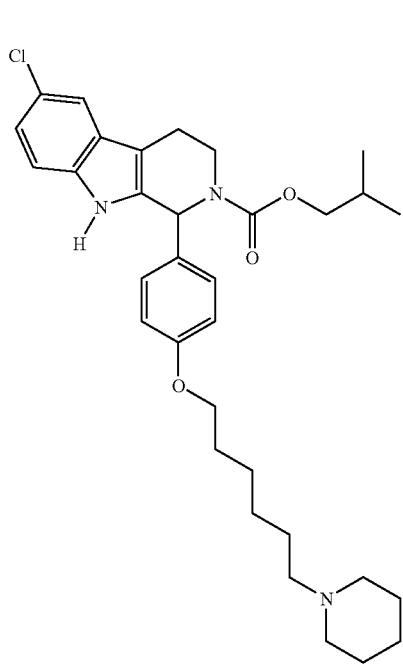
758
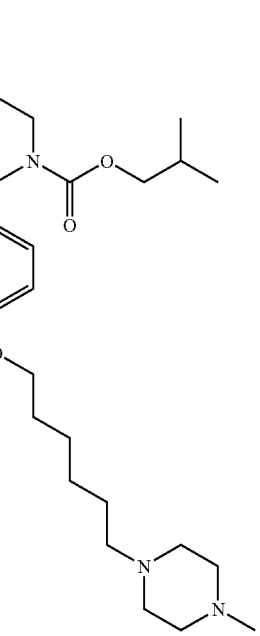
759
206
-continued
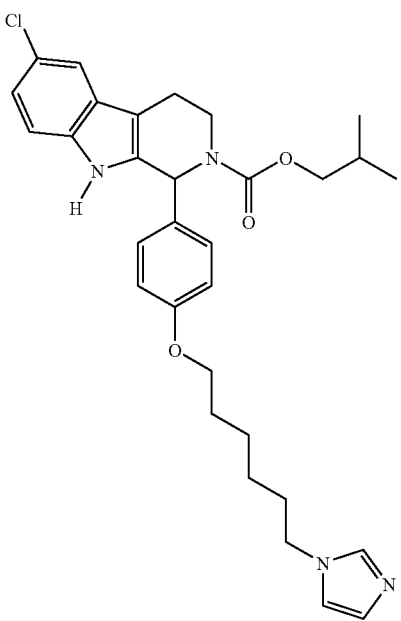
760
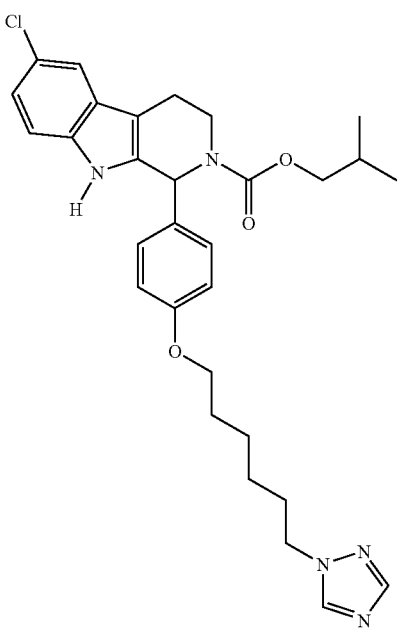
761

207
-continued
762
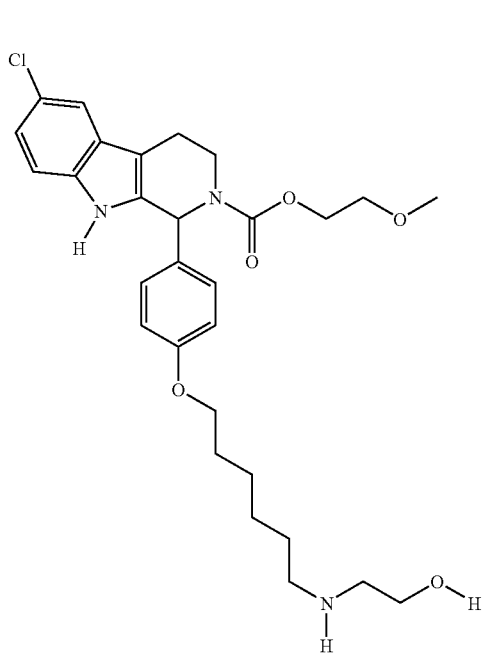
763
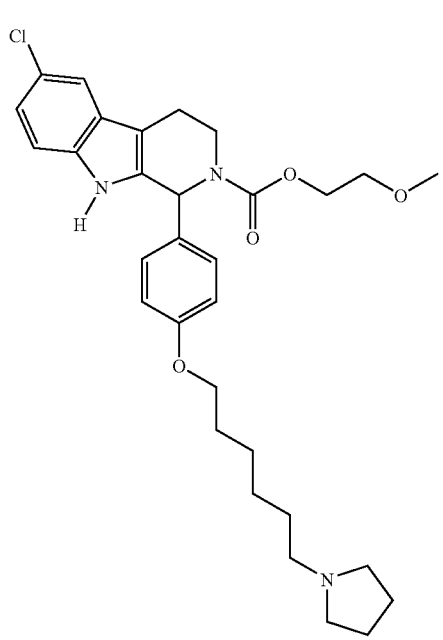
208
-continued
764
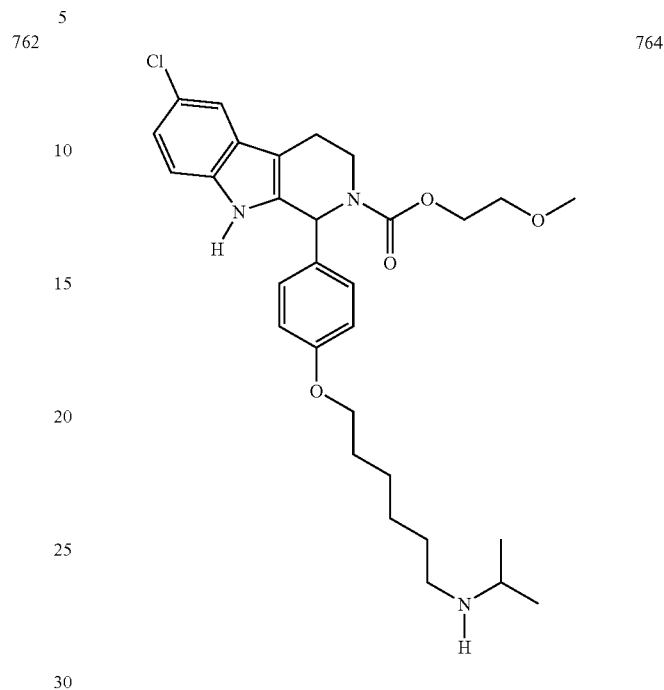
765
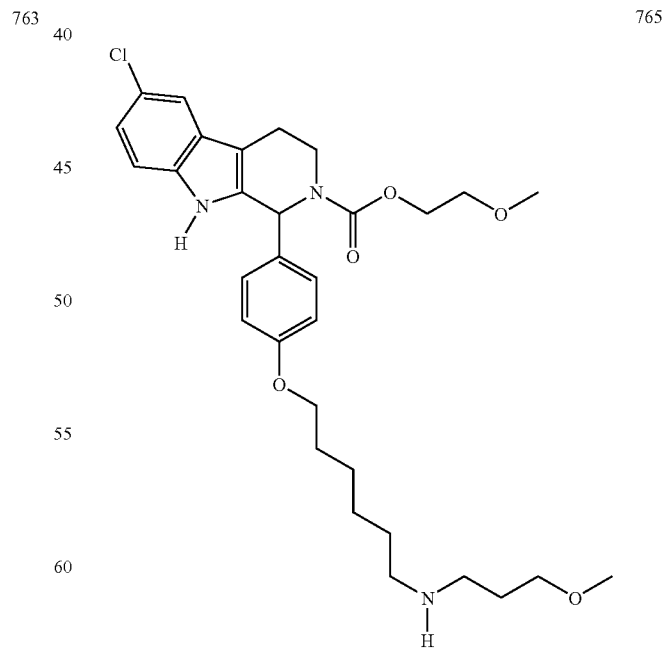

-continued
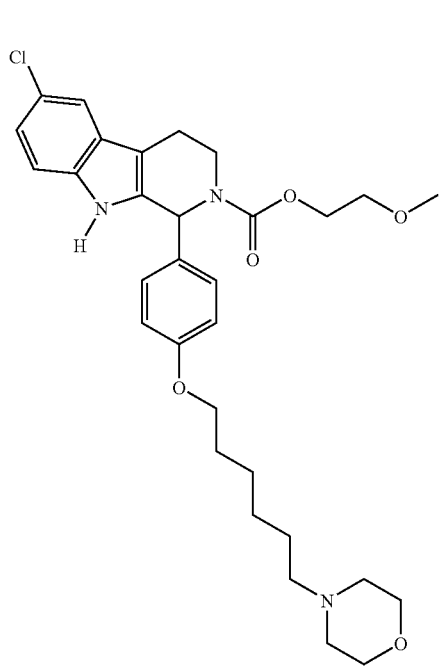
766
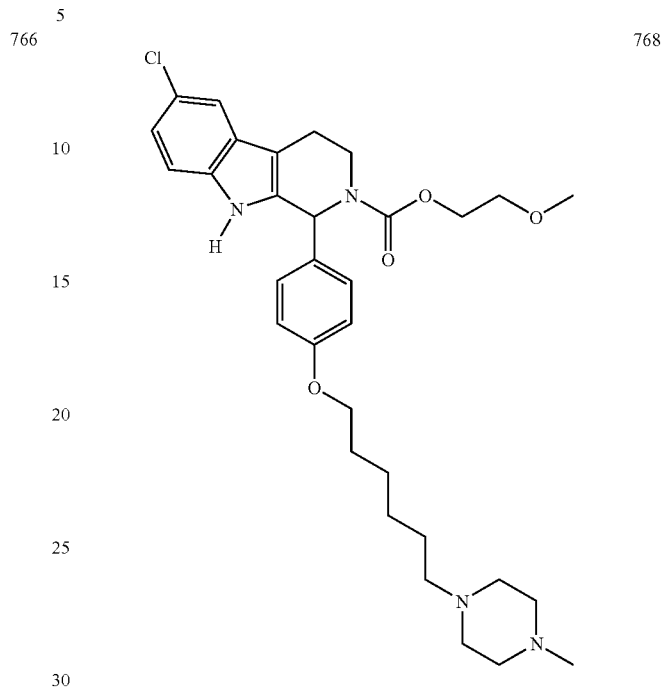
768
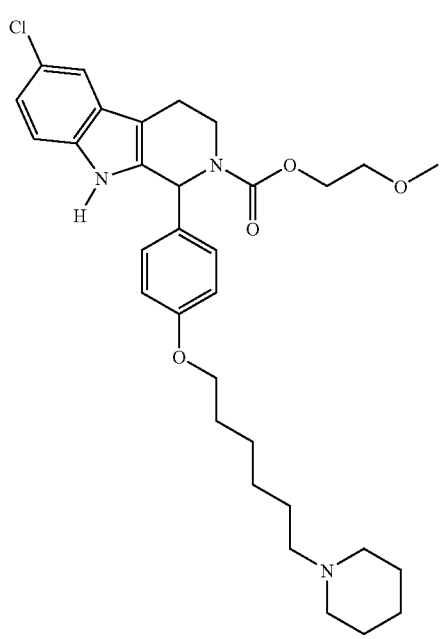
767
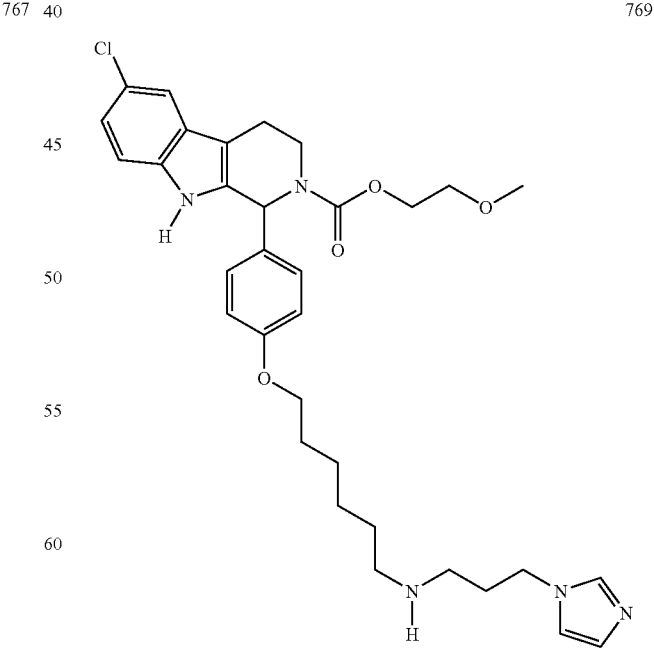
769

211
-continued
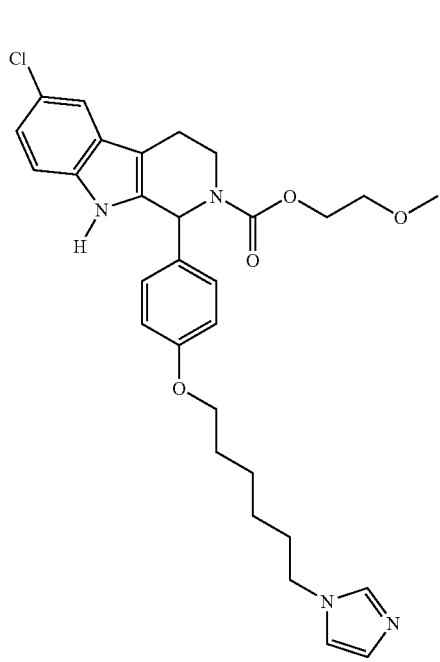
770
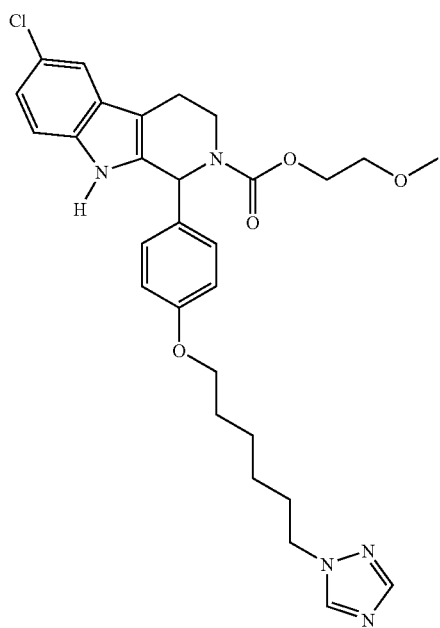
771
212
-continued
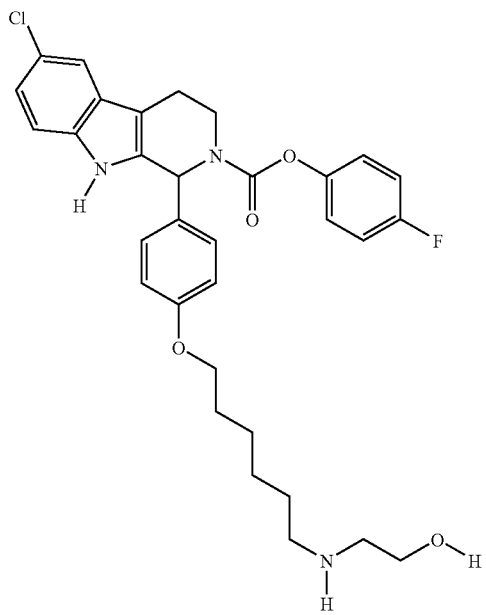
772
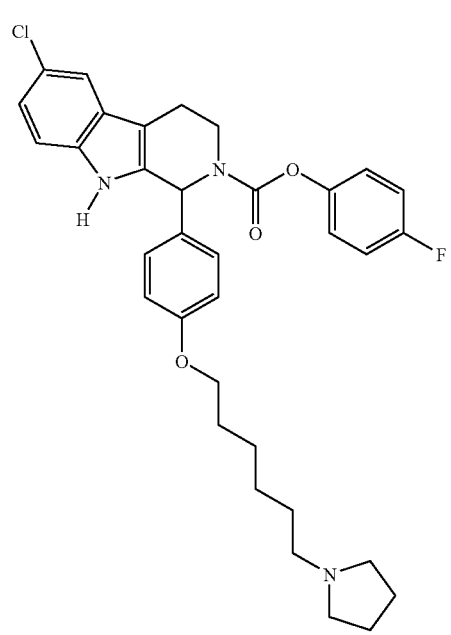
773

213
-continued
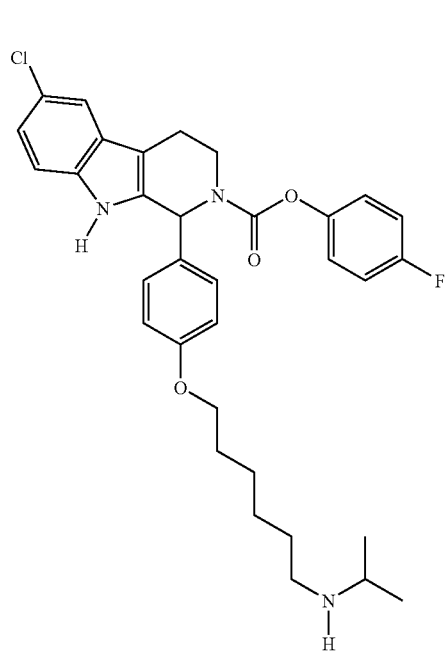
774
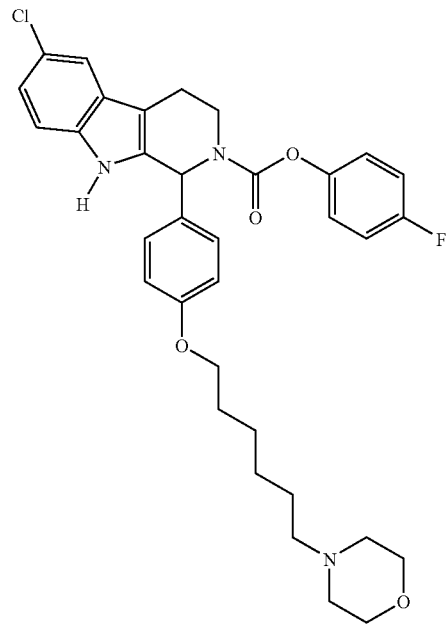
214
-continued
776
775
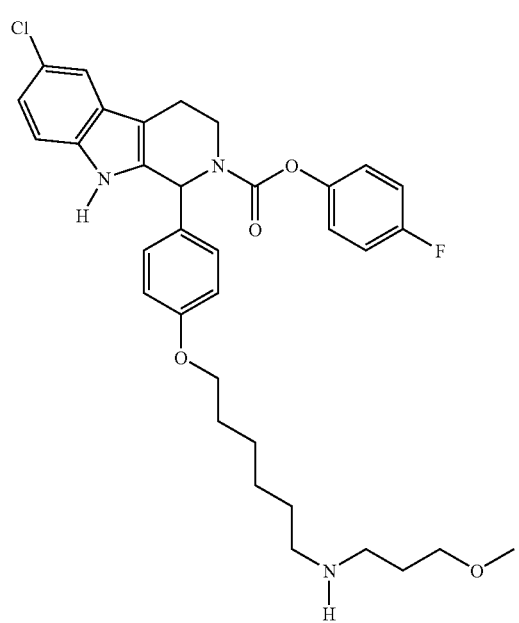
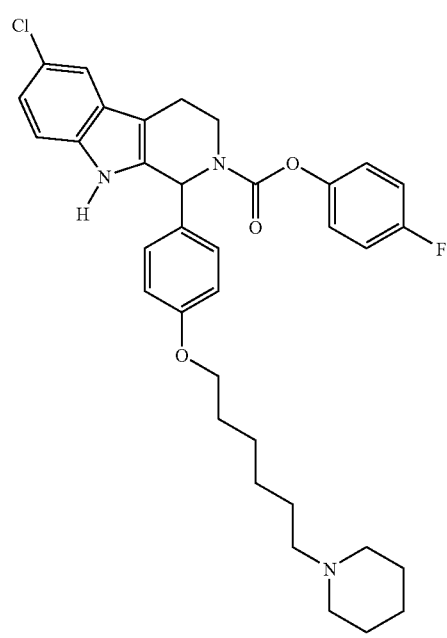
777

215
-continued
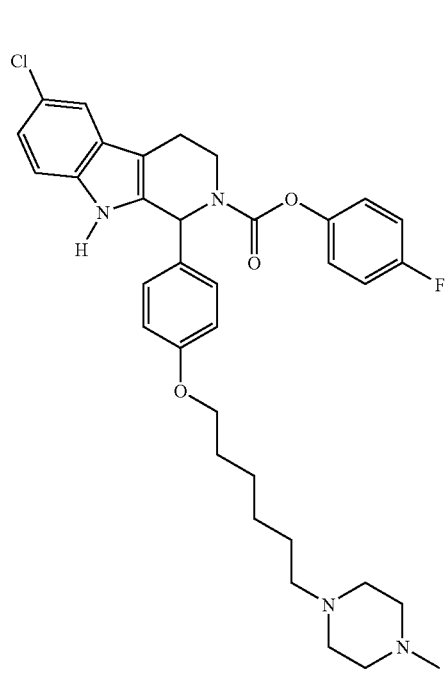
778
216
-continued
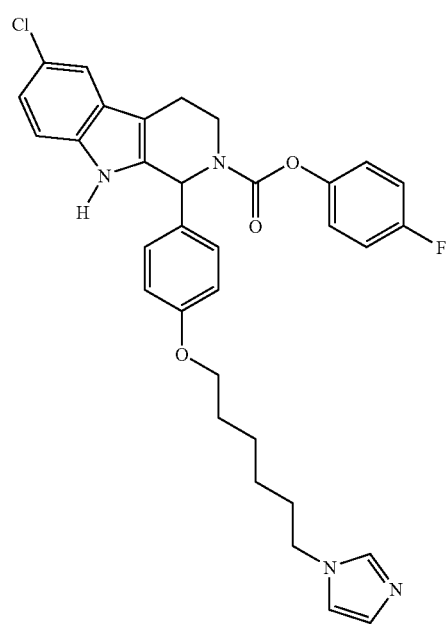
780
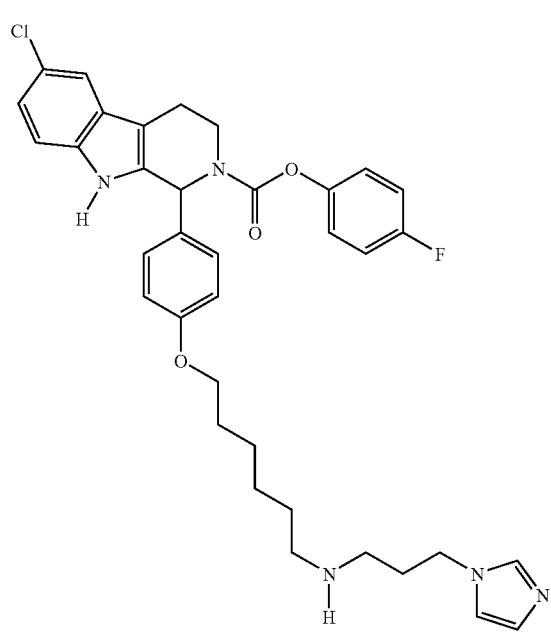
779
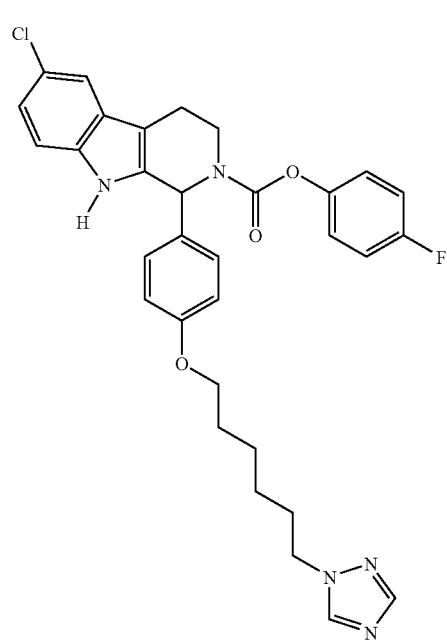
781

217
-continued
782
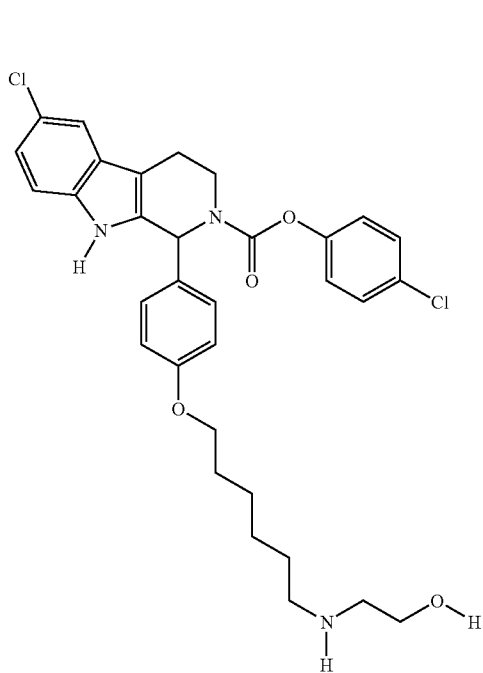
783
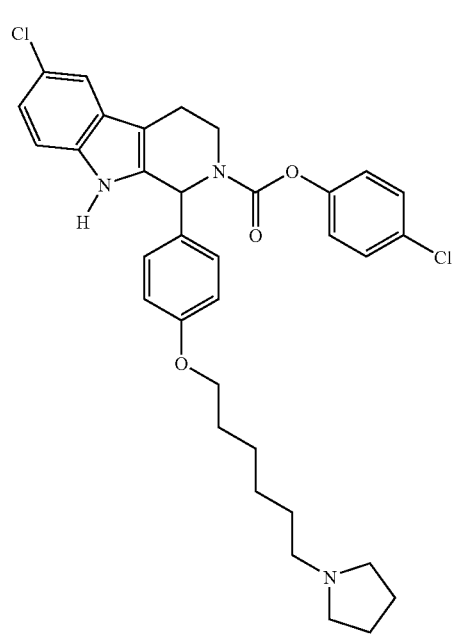
218
-continued
784
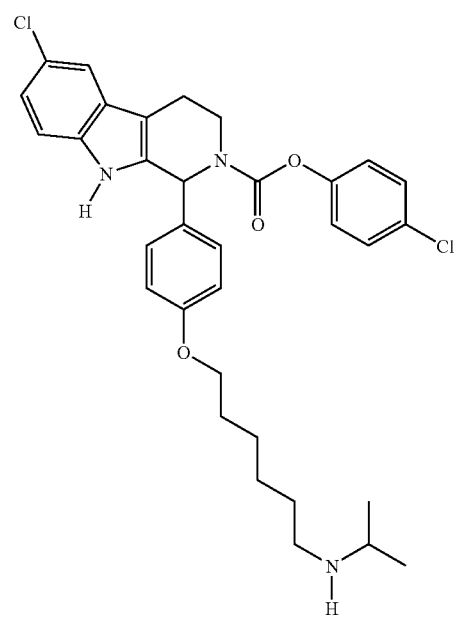
785

219
-continued
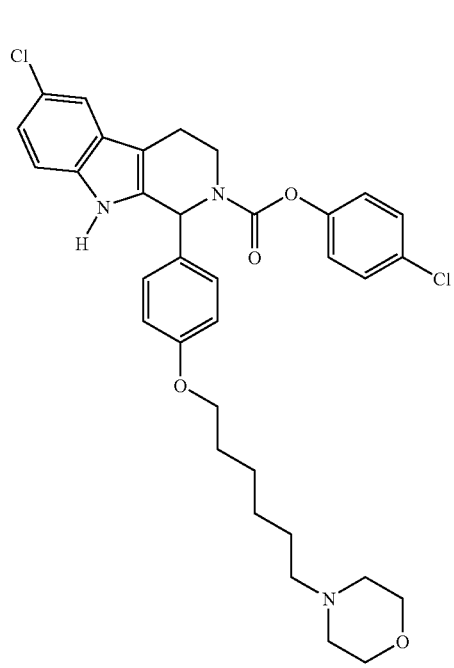
786
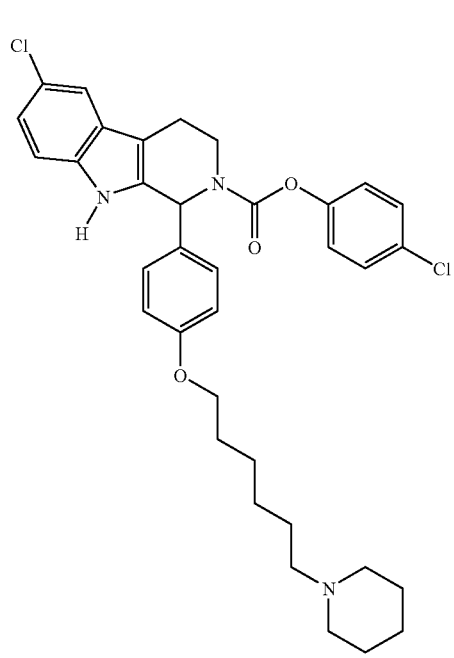
787
220
-continued
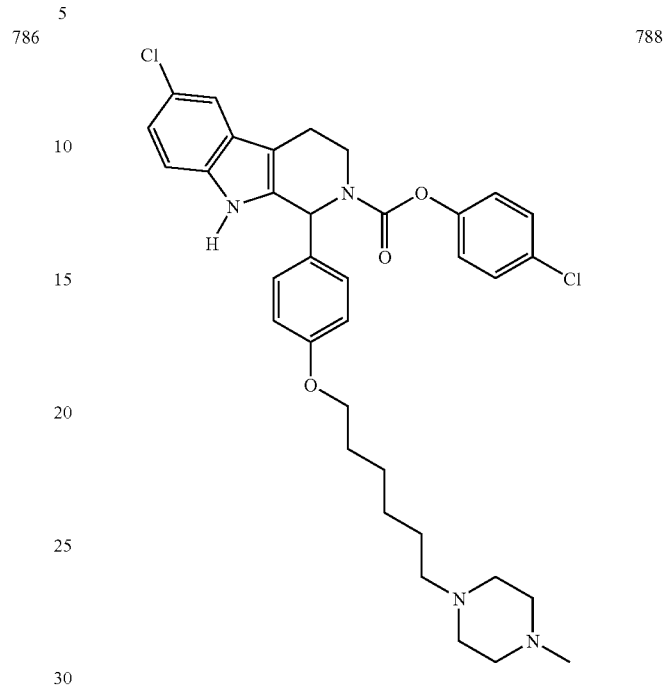
788
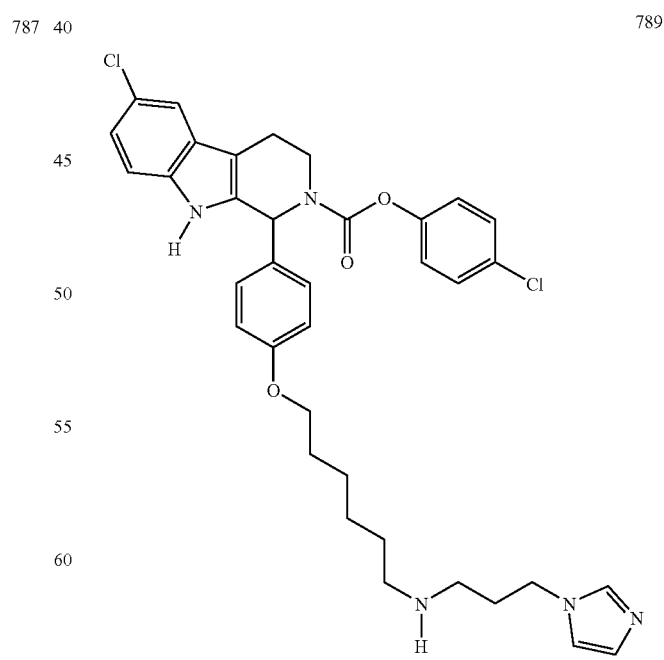
789

221
-continued
790
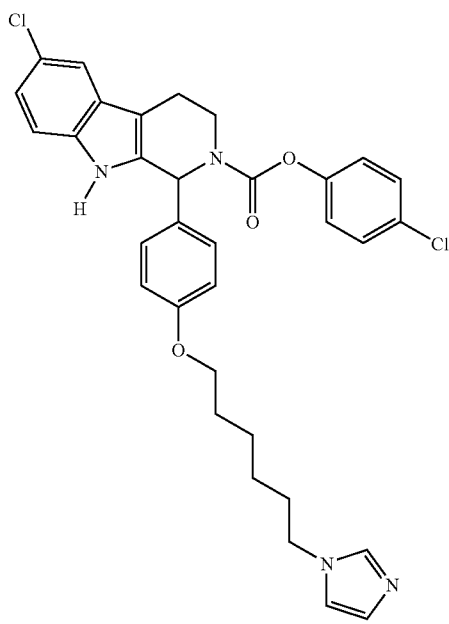
791
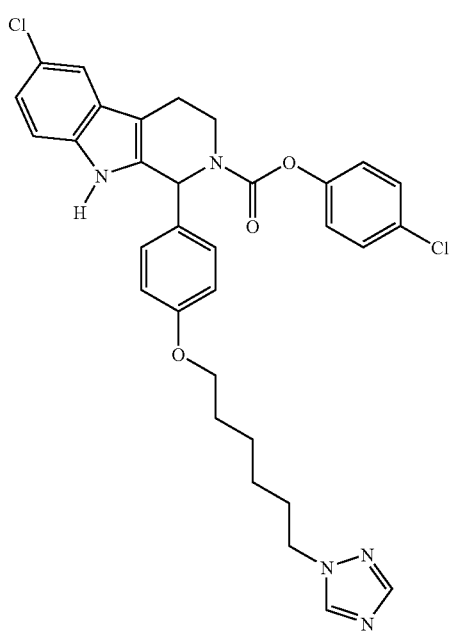
792
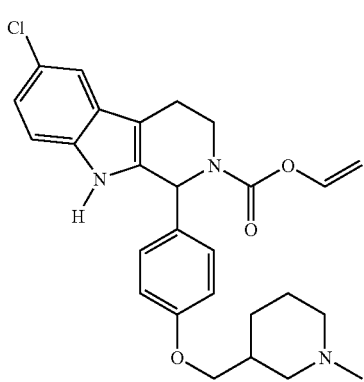
222
-continued
793
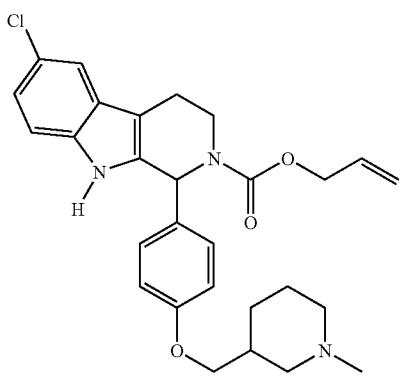
794
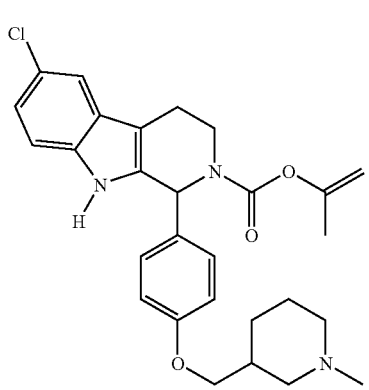
795
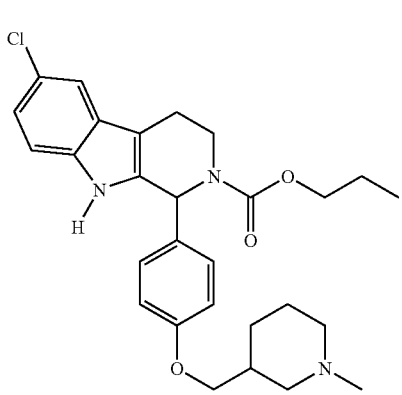

223
-continued
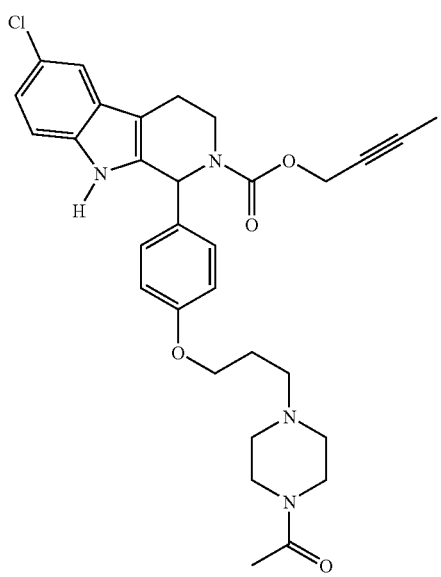
796
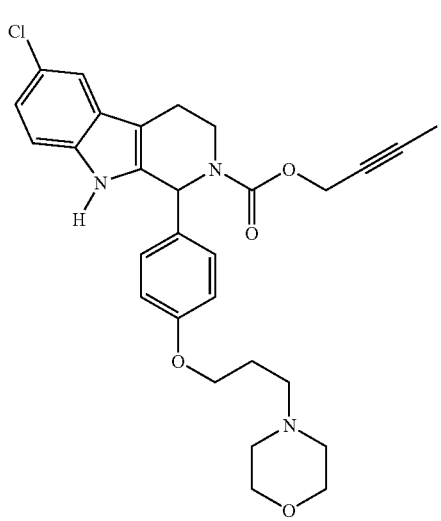
797
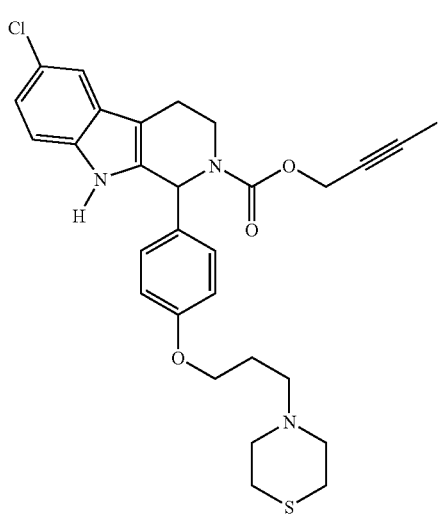
798
224
-continued
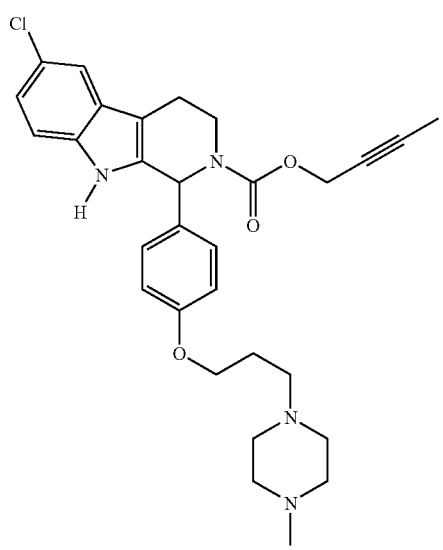
799
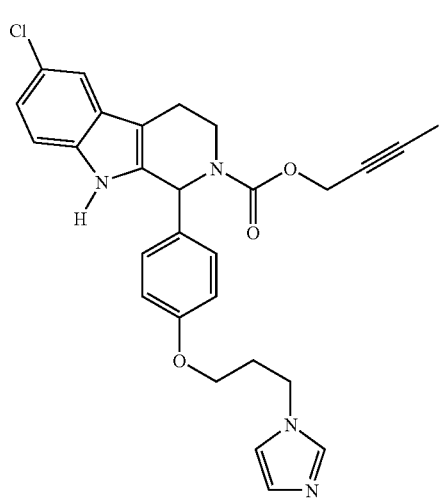
800
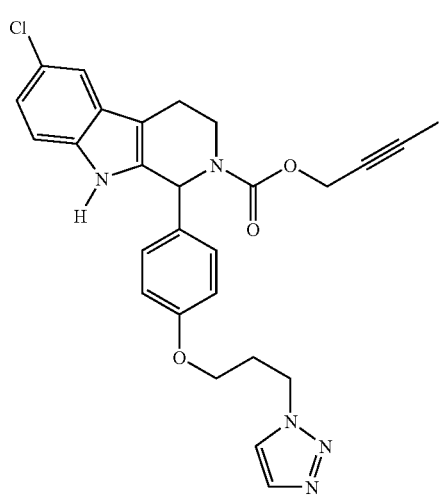
801

225
-continued
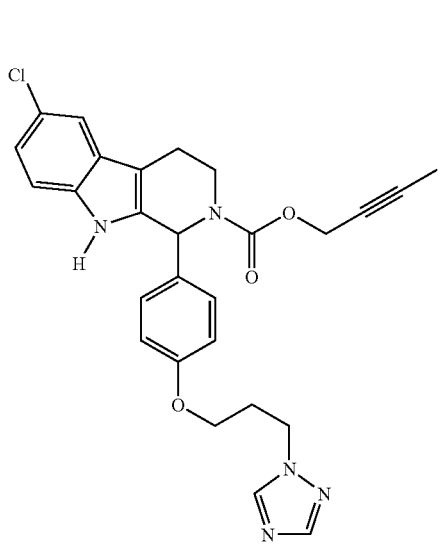
802
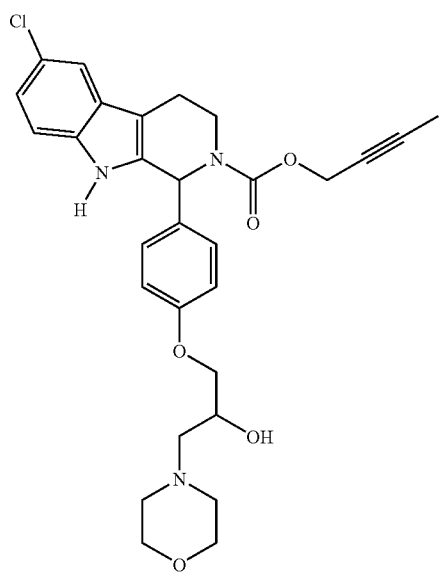
226
-continued
804
803
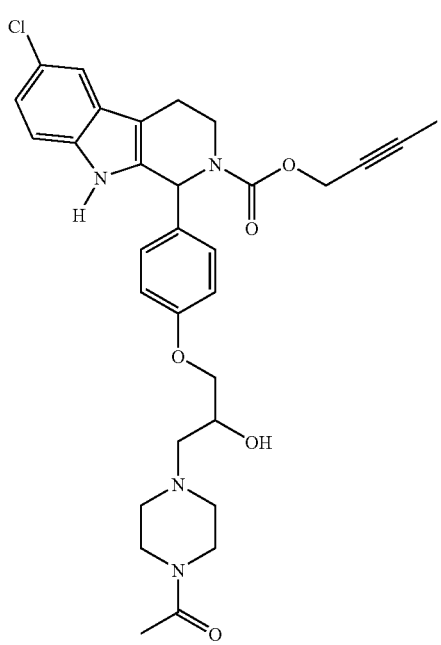
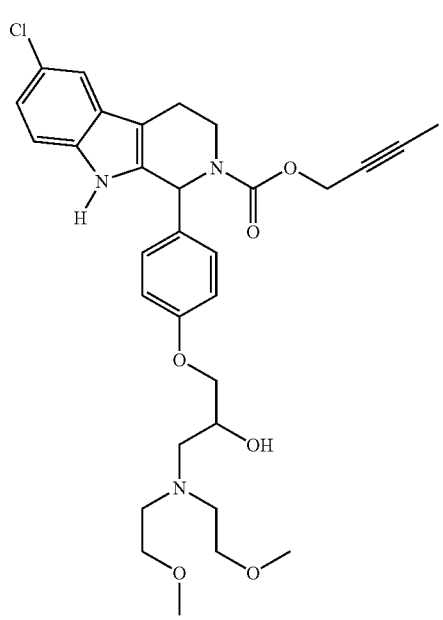
805

227
-continued
806
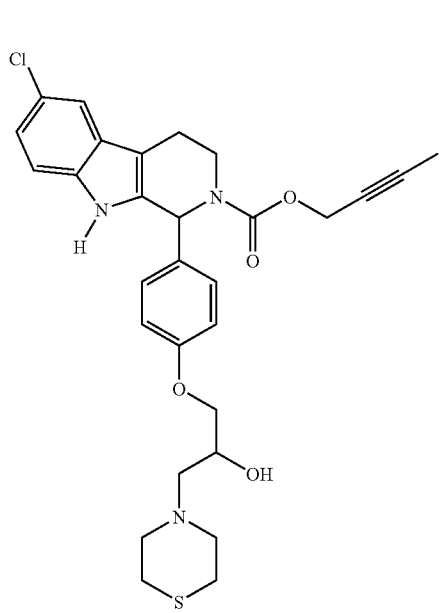
807
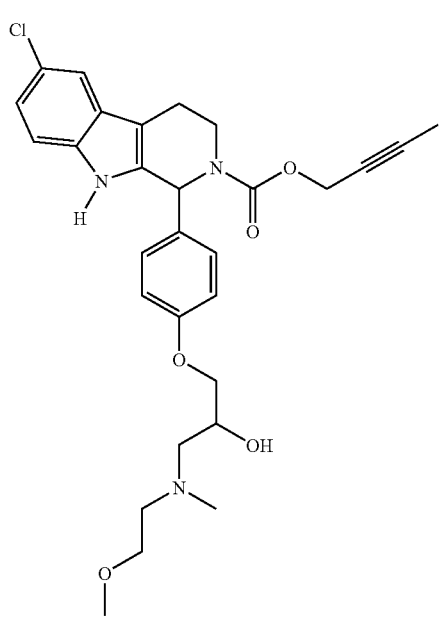
228
-continued
808
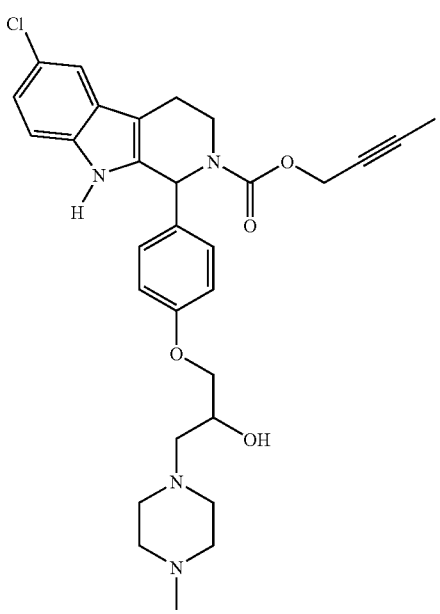
809
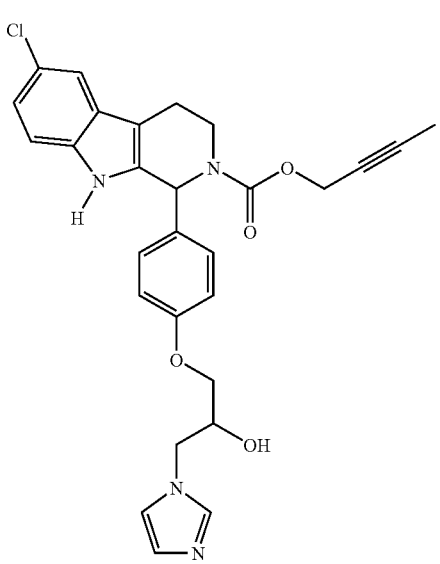

229
-continued
810
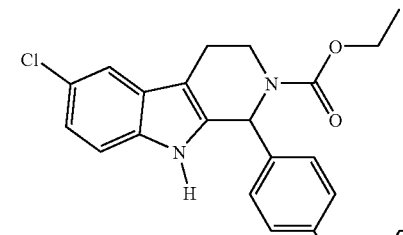
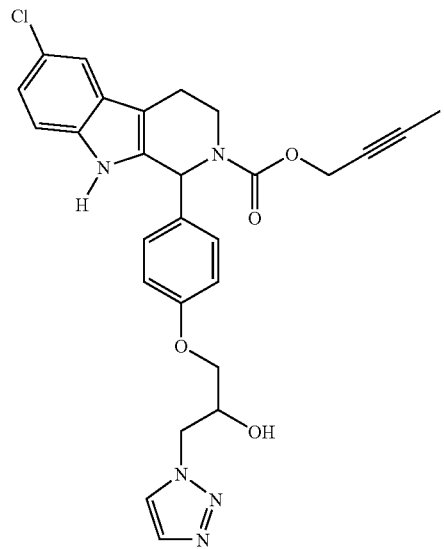
813
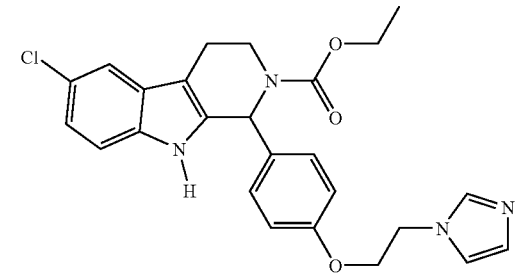
814
811
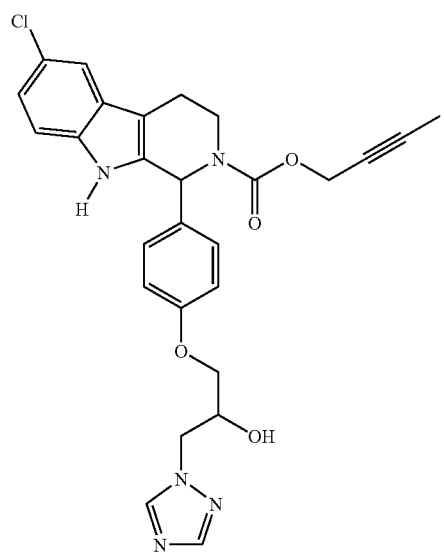
815
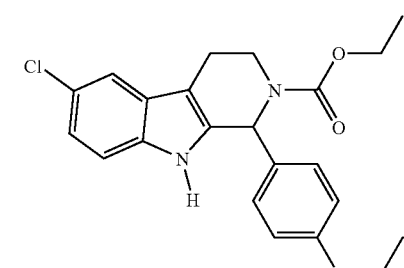
816
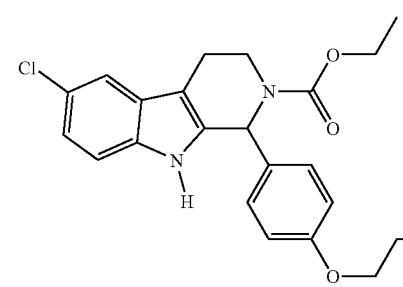
812
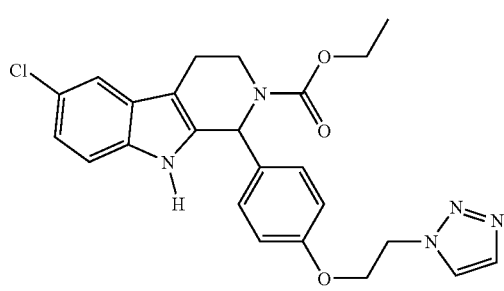
817
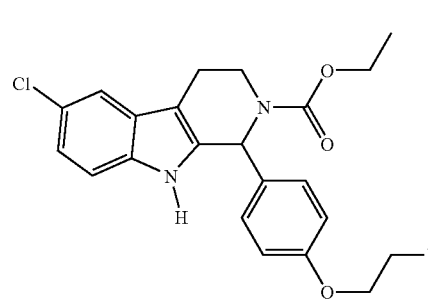

-continued
818
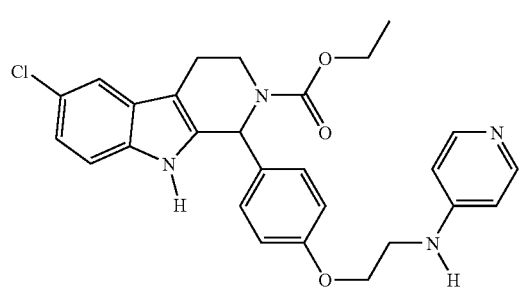
819
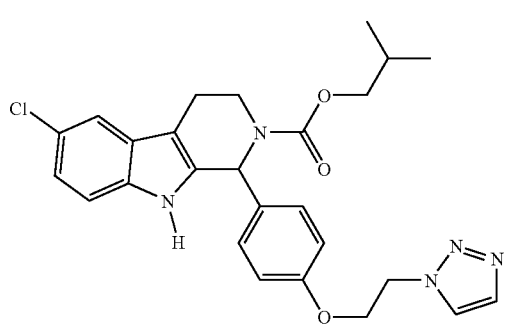
820
821
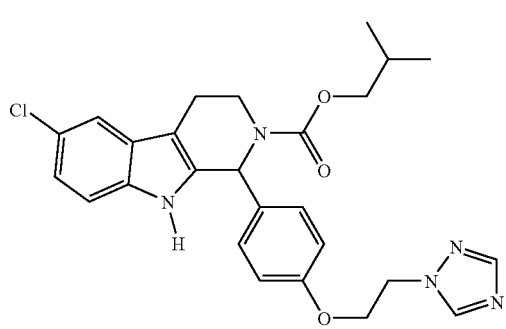
822
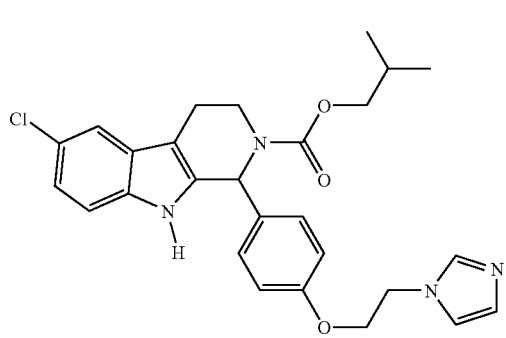
-continued
823
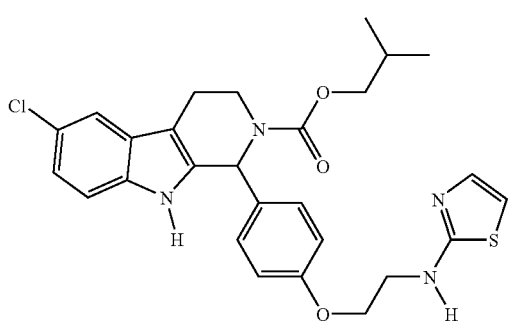
824
825
826
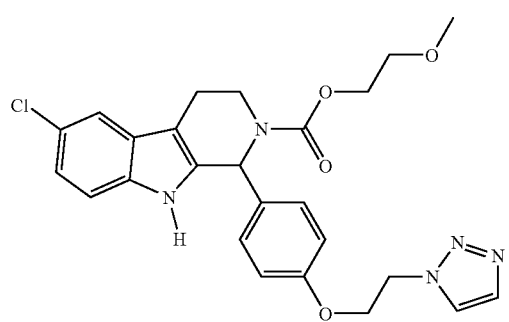
827

828
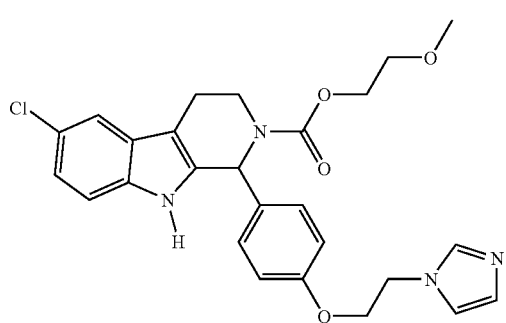
829
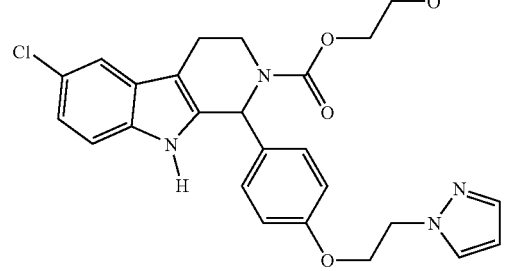
830
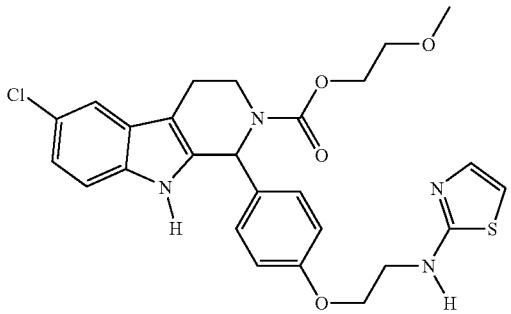
831
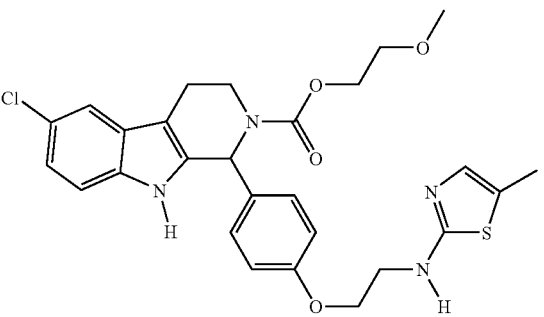
832
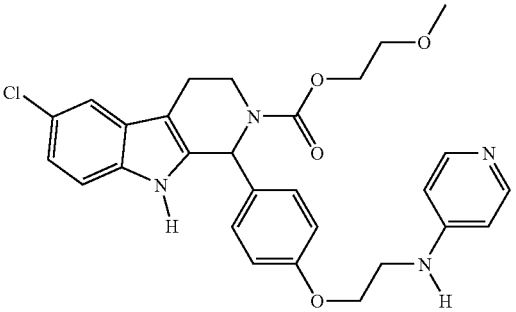
833
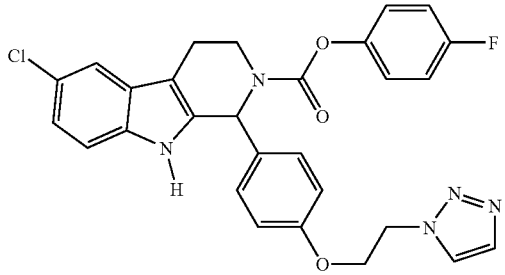
834
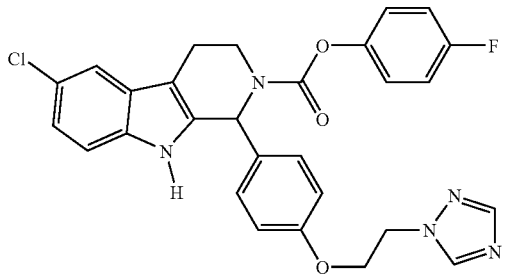
835
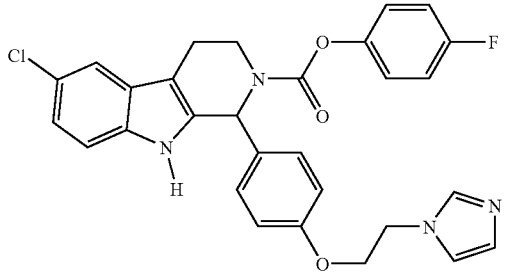
836
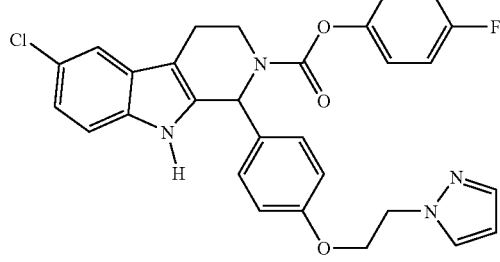
837
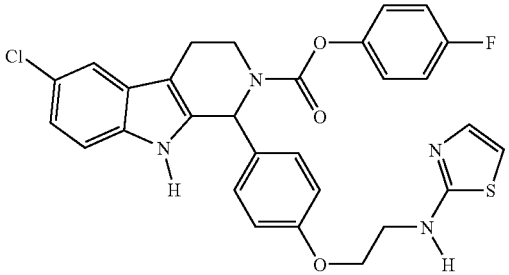

235
-continued
838
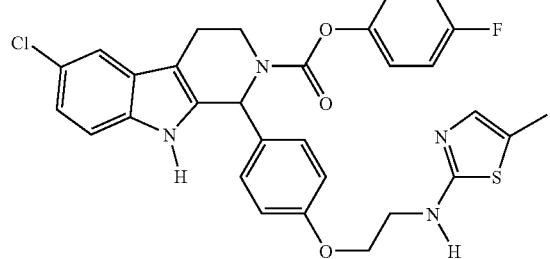
839
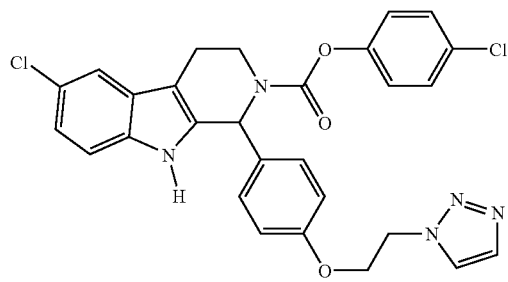
840
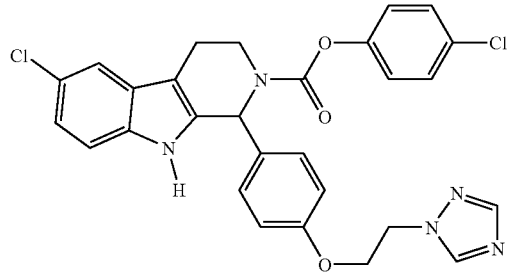
841
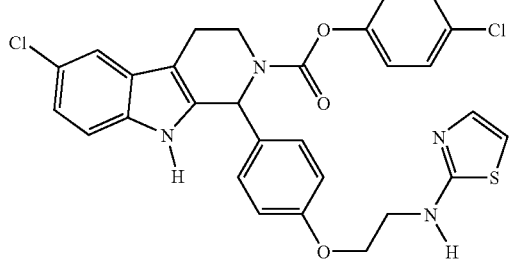
842
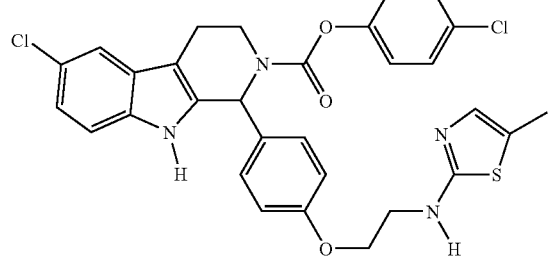
236
-continued
843
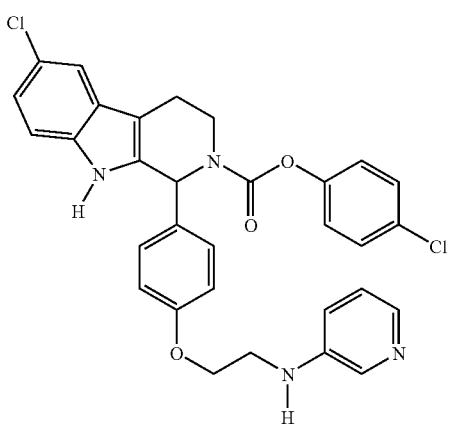
844
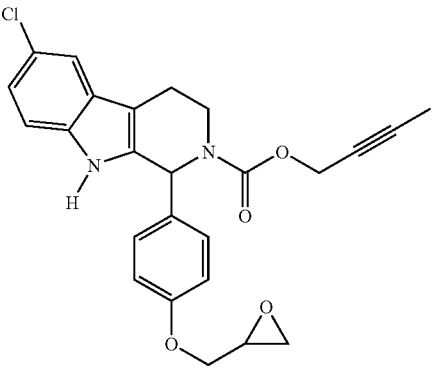
845
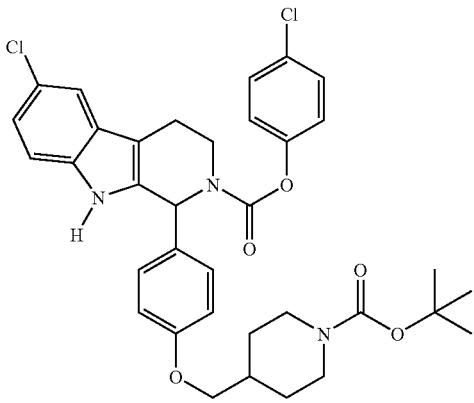
846
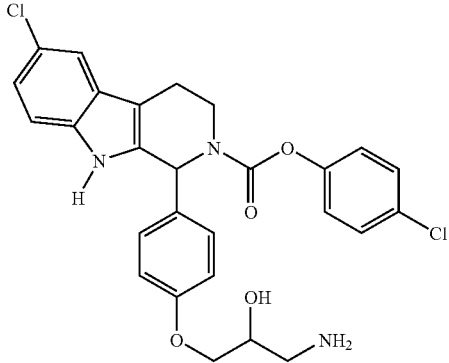

847 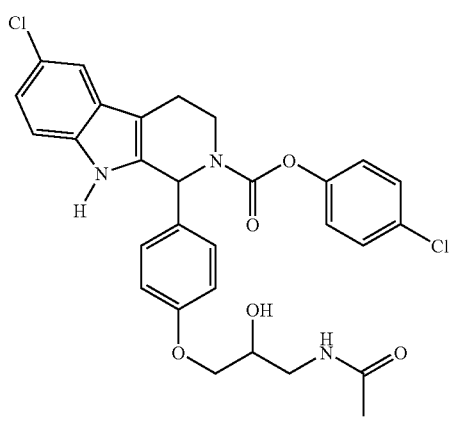
848 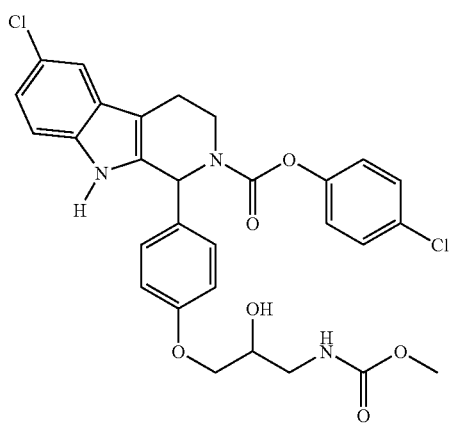
849 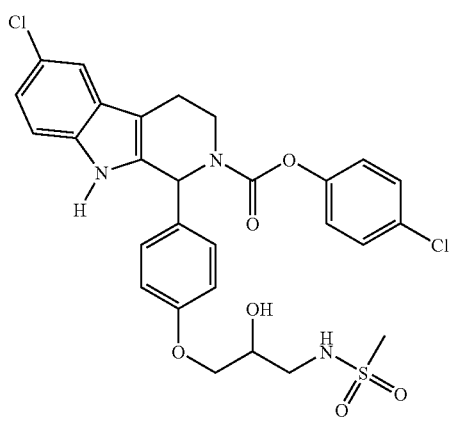
850 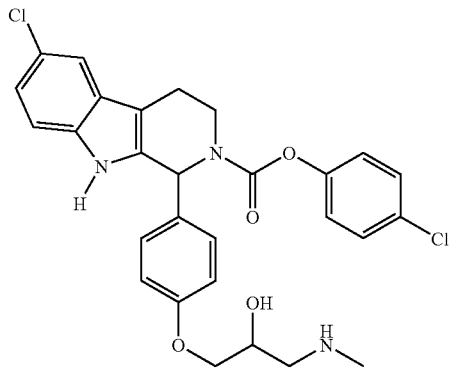
851 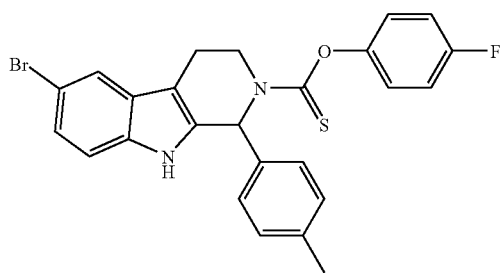
852 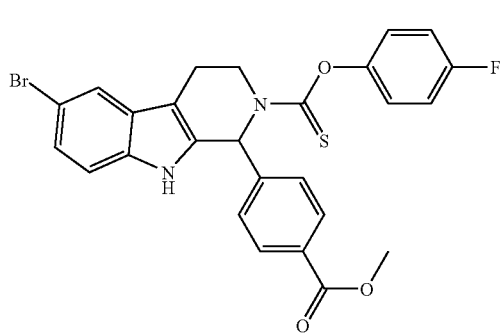
853
854
855

239
-continued
856
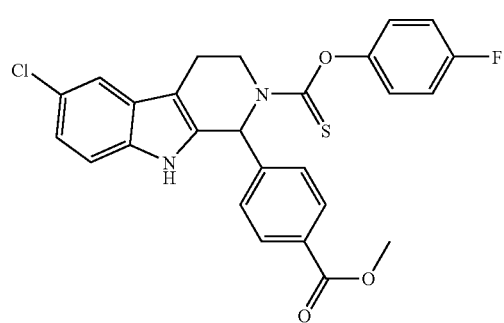
857
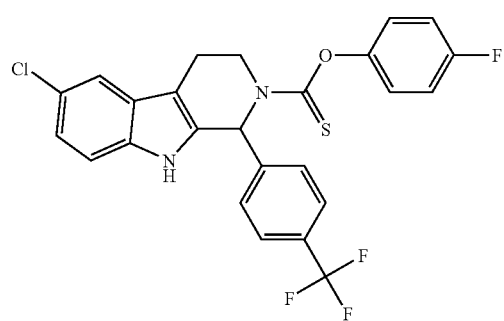
858
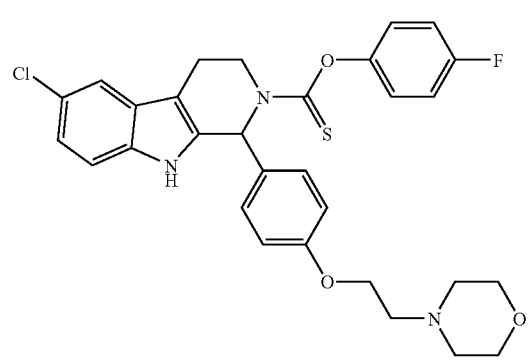
859
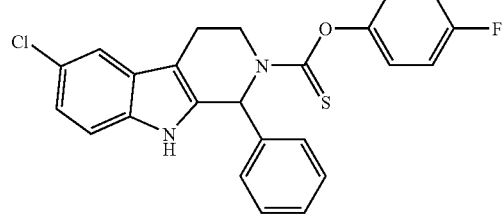
860
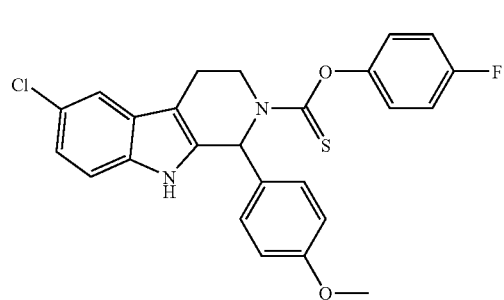
240
-continued
861
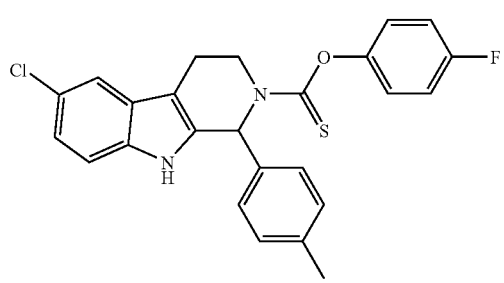
862
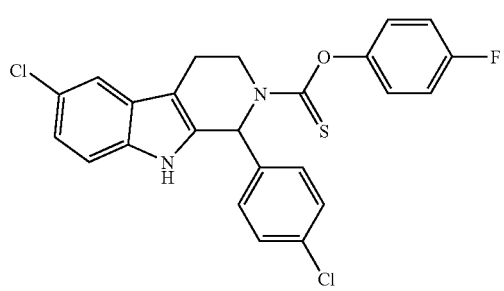
863
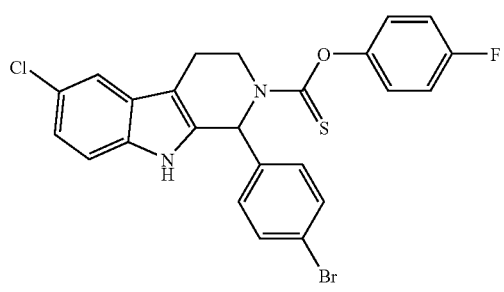
864
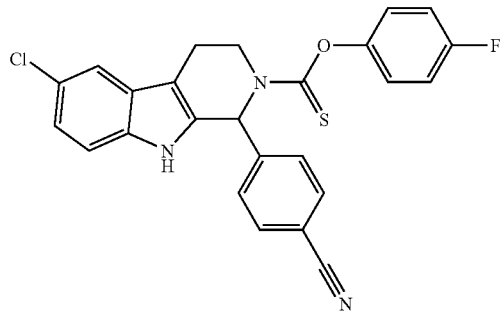
865
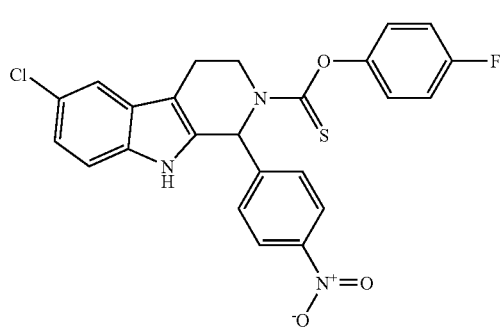

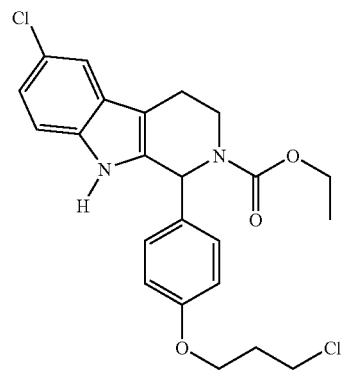
866
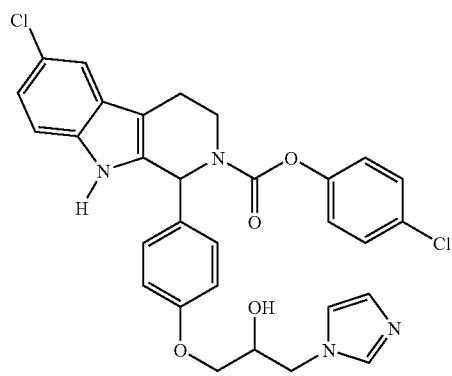
867
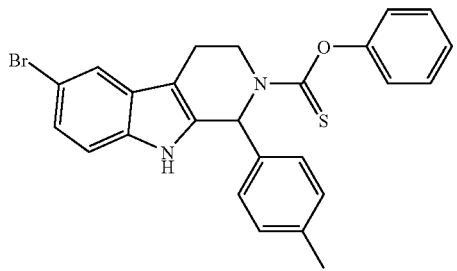
868
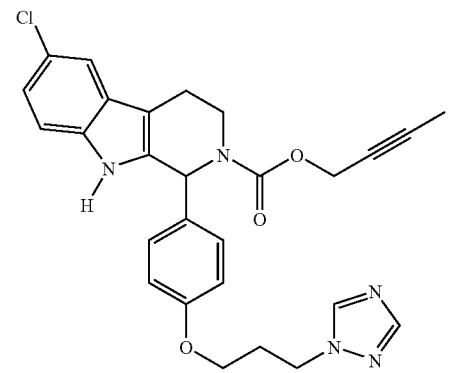
869
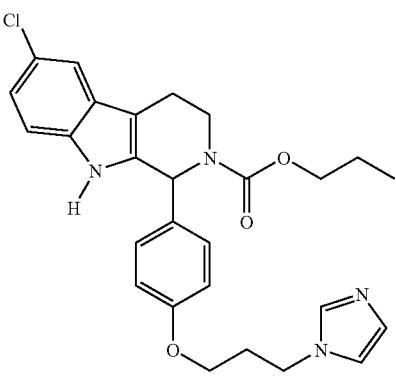
870
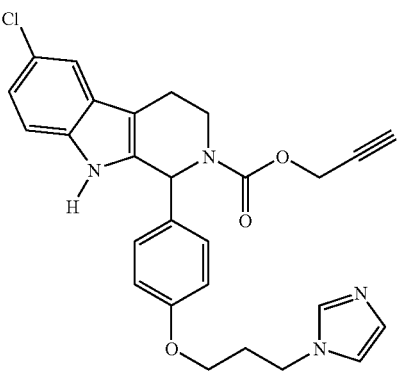
871
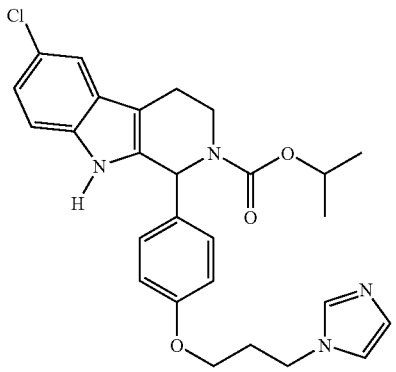
872
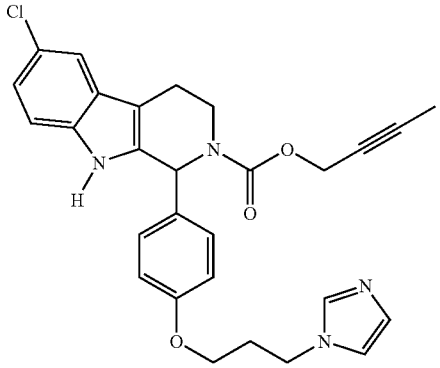
873

| 243 -continued | | 244 -continued | |
|---|---|---|---|
| 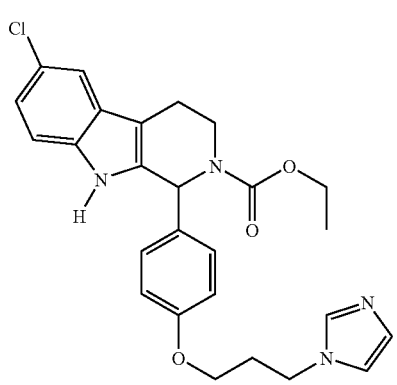 | 874 | 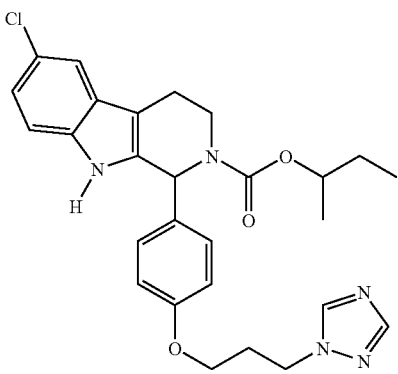 | 878 |
| 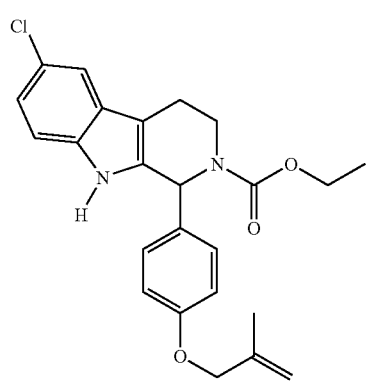 | 875 | 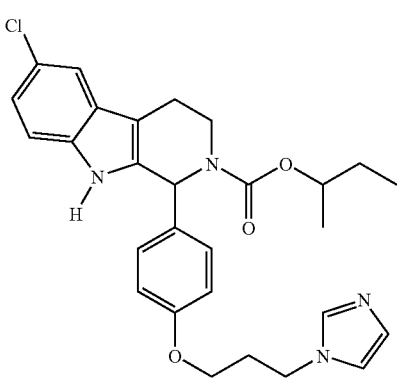 | 879 |
| 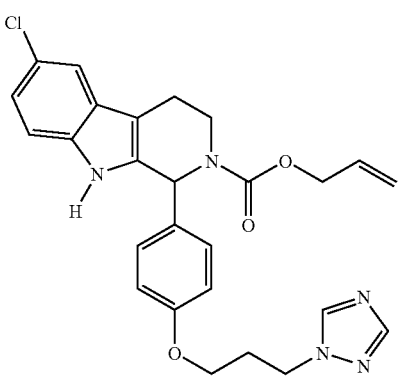 | 876 | 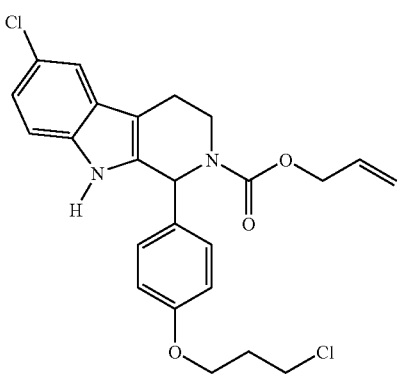 | 880 |
| 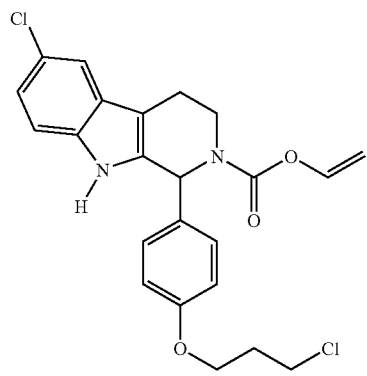 | 877 | 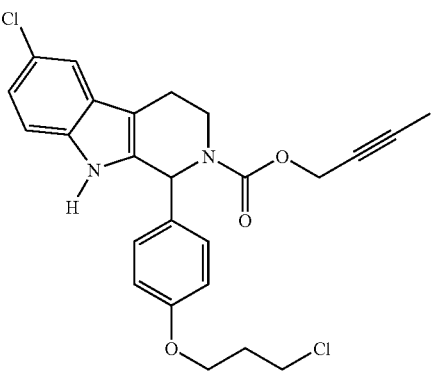 | 881 |

| | |
|---|---|
| 882 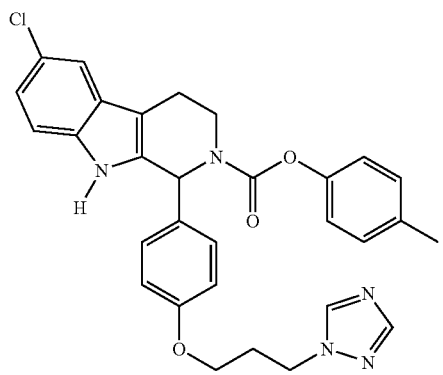 | 886 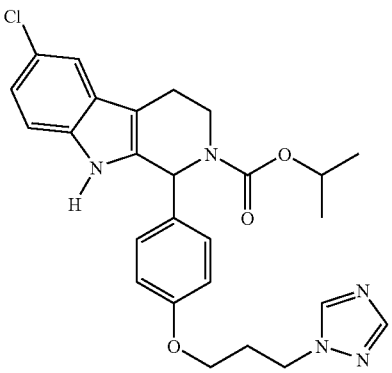 |
| 883 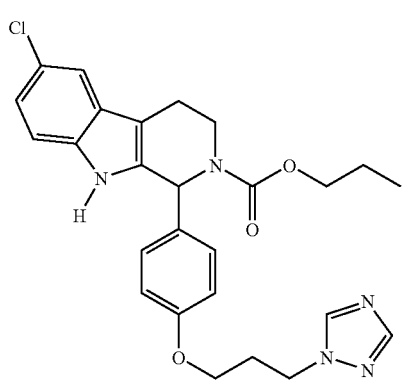 | 887 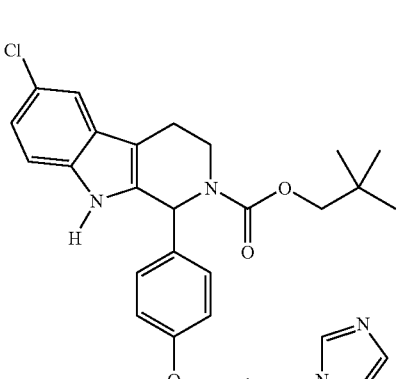 |
| 884 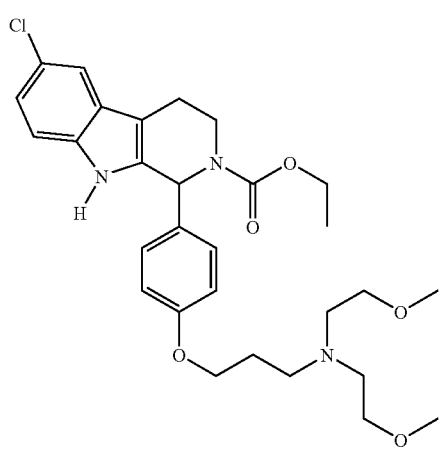 | 888 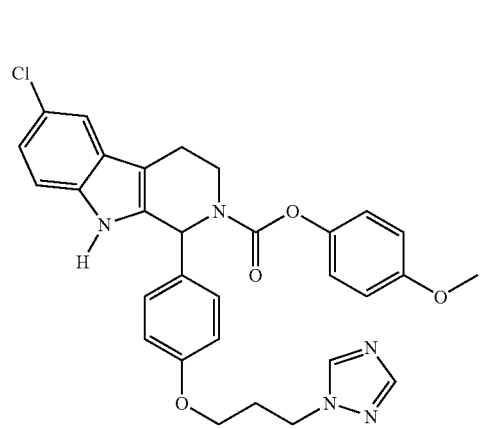 |
| 885 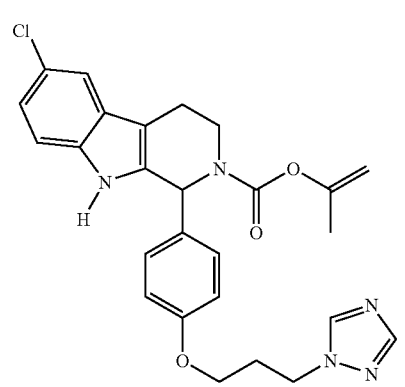 | 889 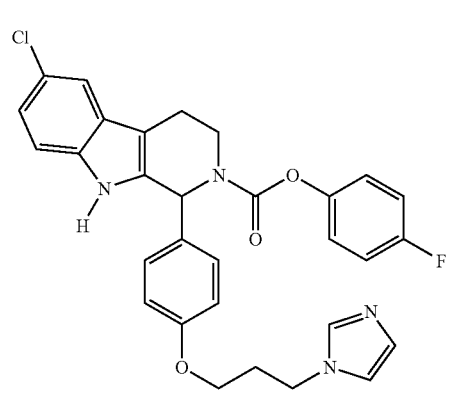 |

247
-continued
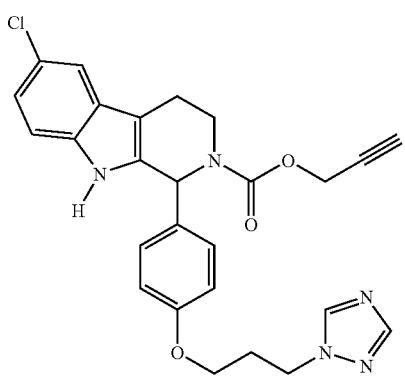
890
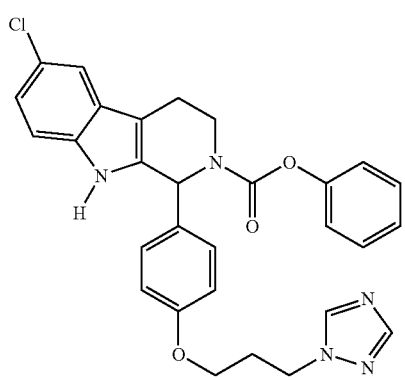
891
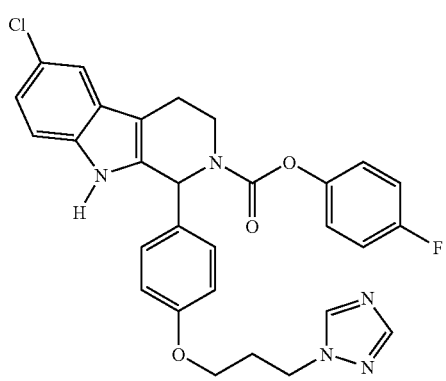
892
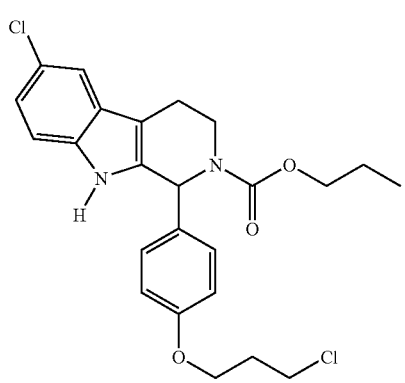
893
248
-continued
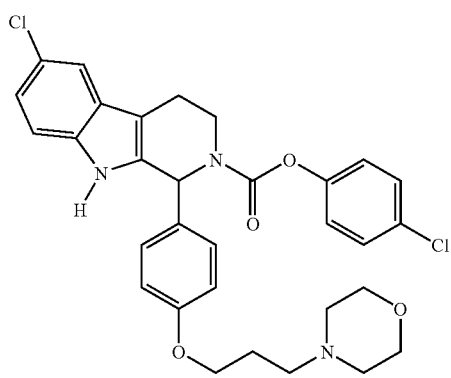
894
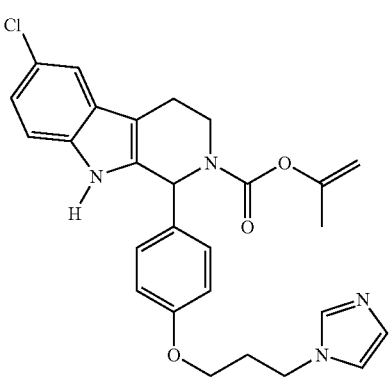
895
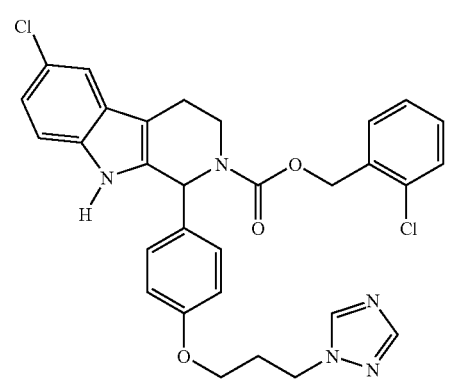
896
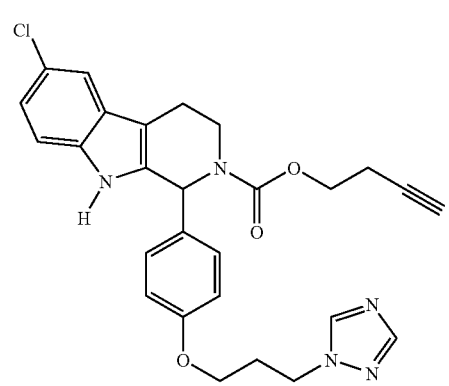
897

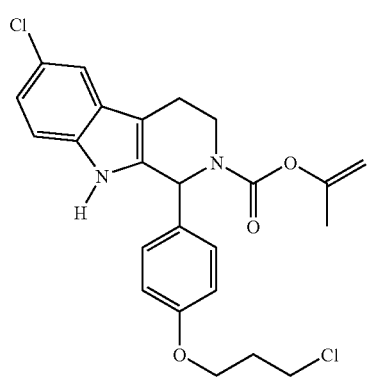
898
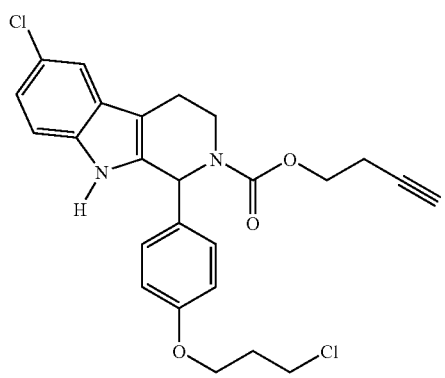
902
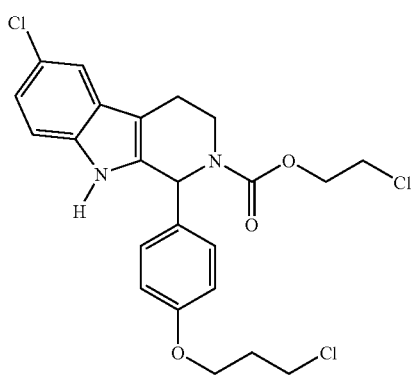
899
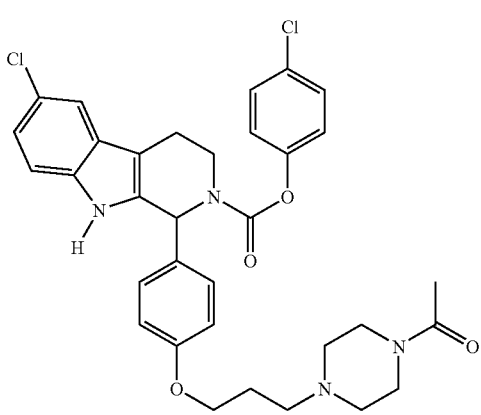
903
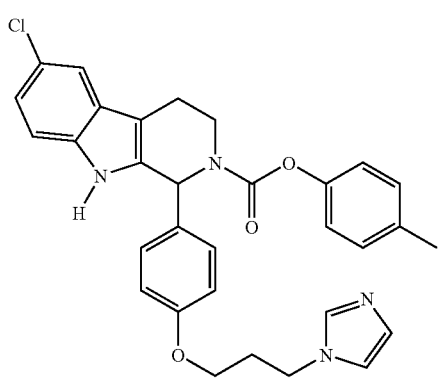
900
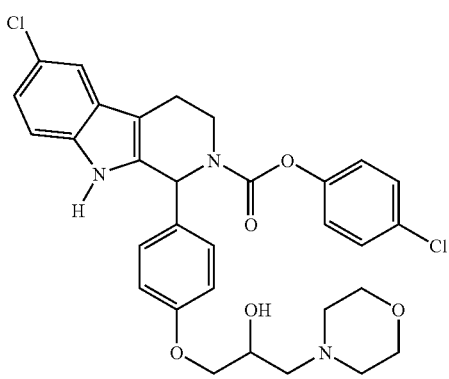
904
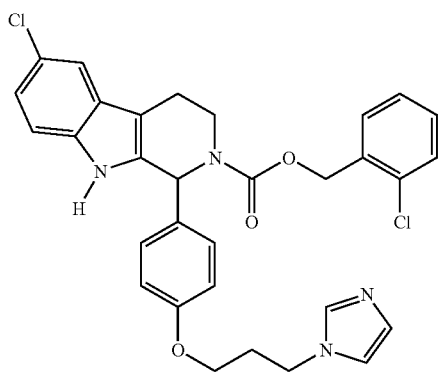
901
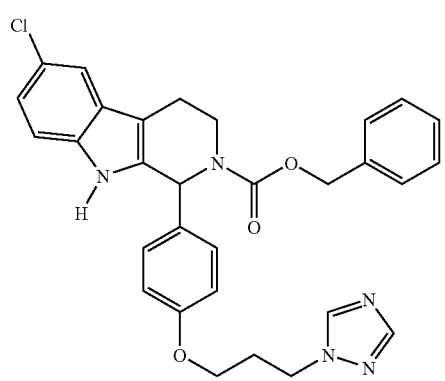
905

251
-continued
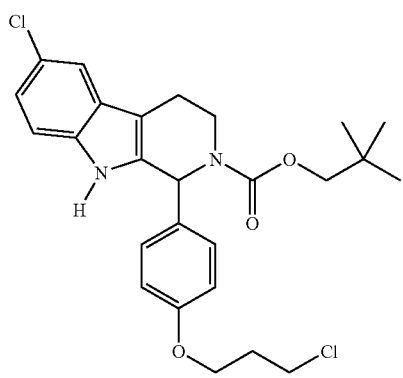
906
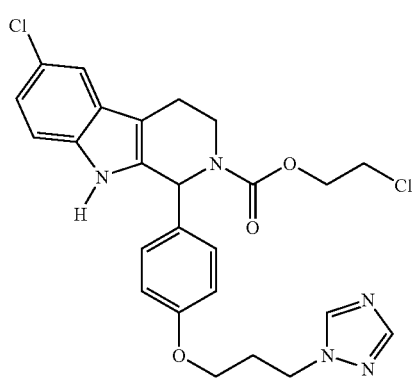
907
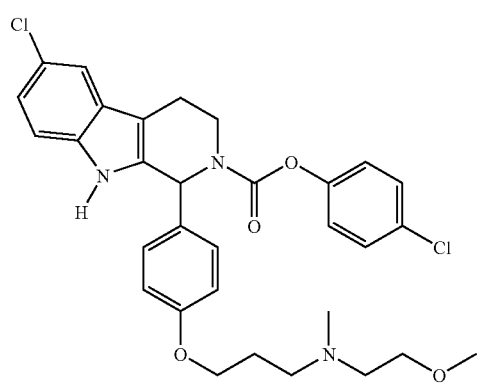
908
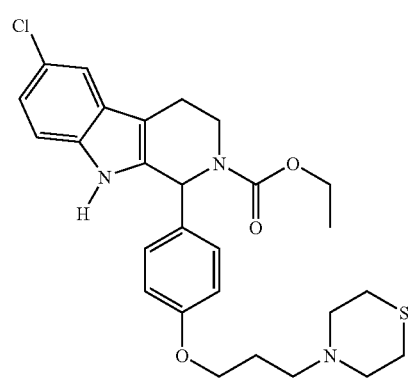
909
252
-continued
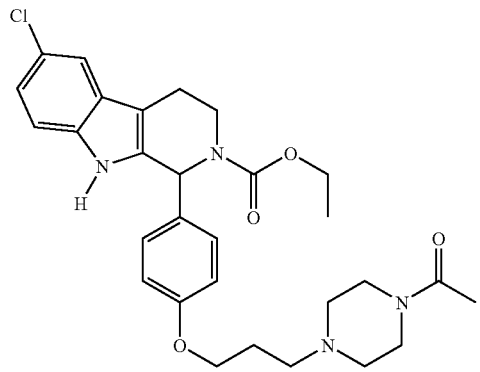
910
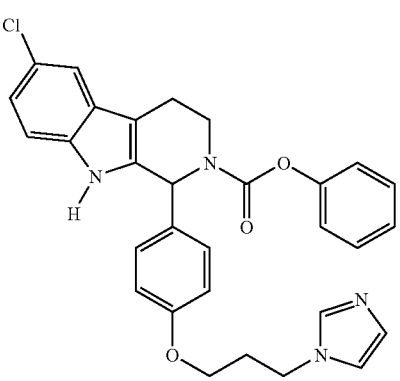
911
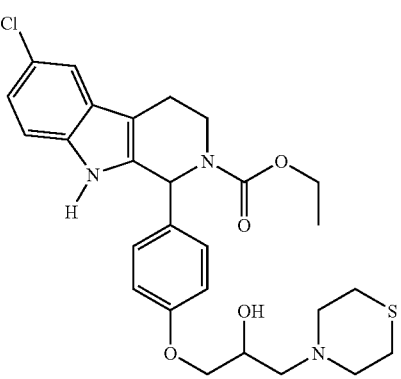
912
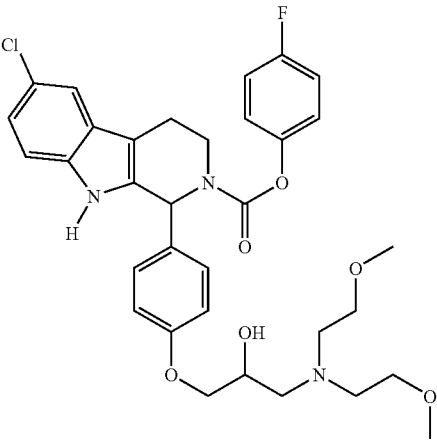
913

914
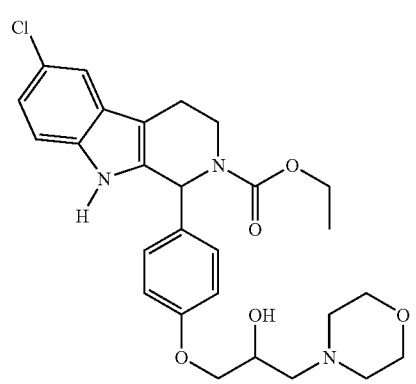
915
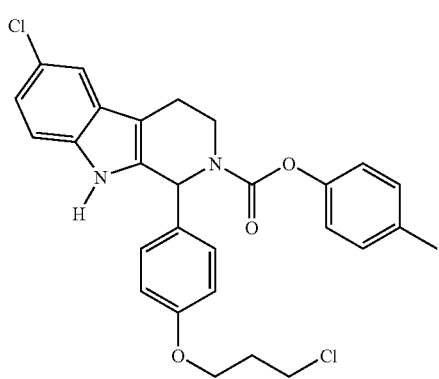
916
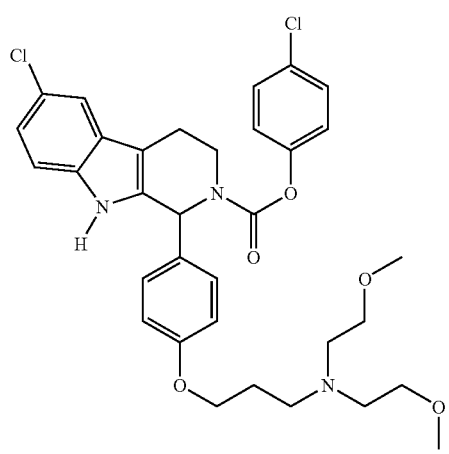
917
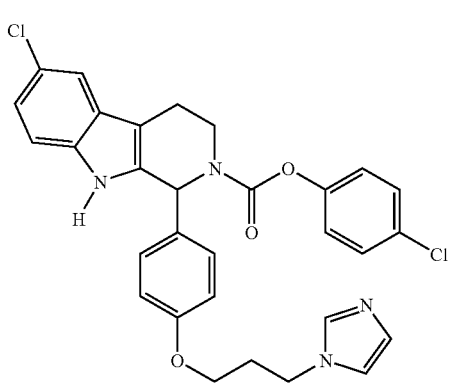
918
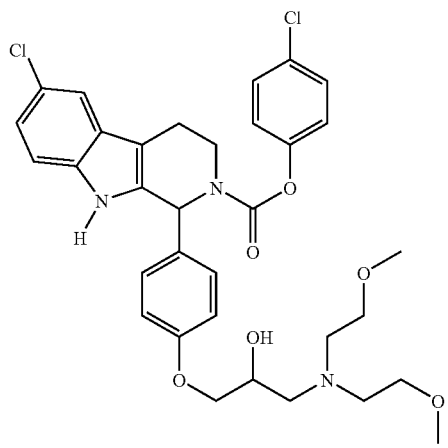
919
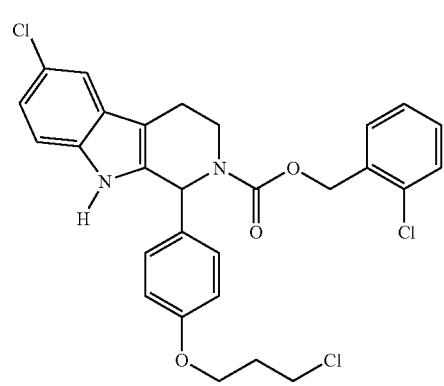
920
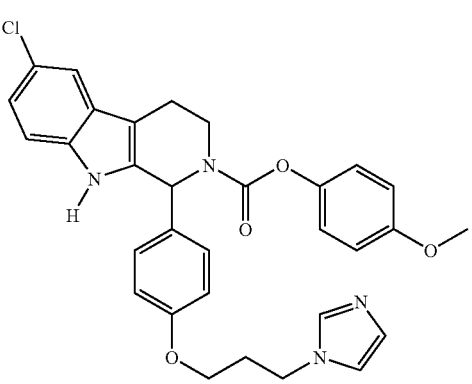
921
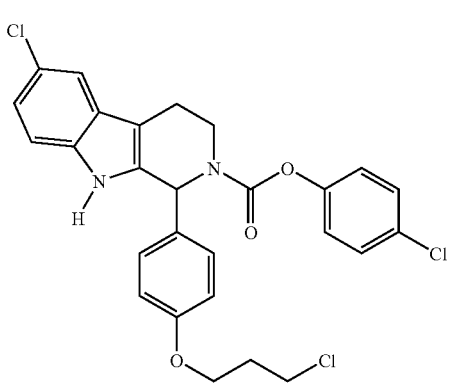

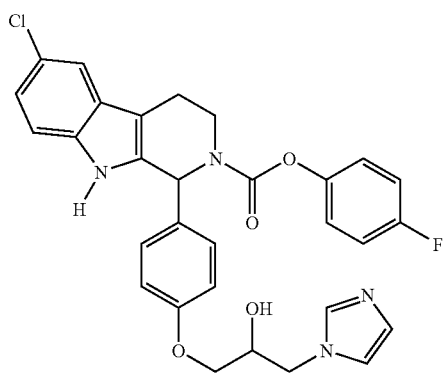
922
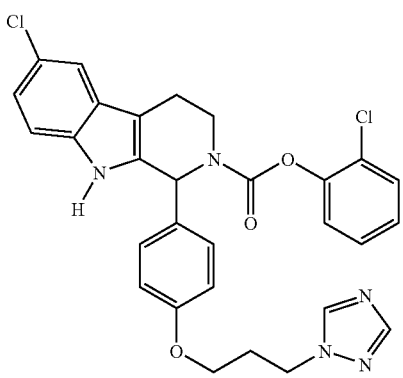
926
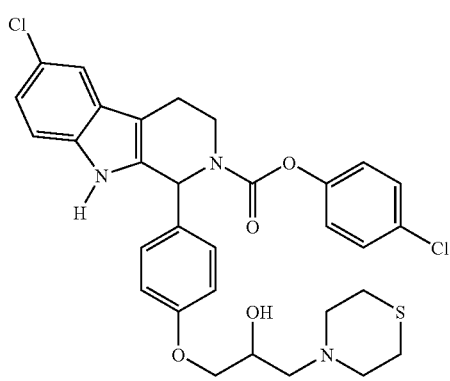
923
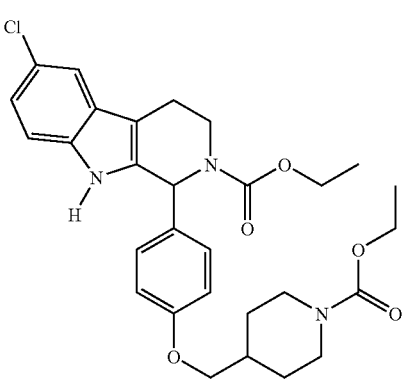
927
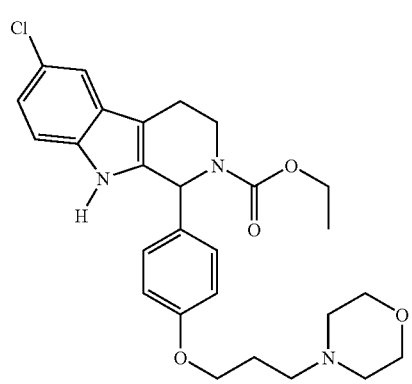
924
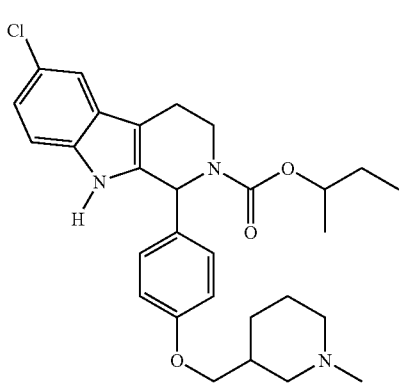
928
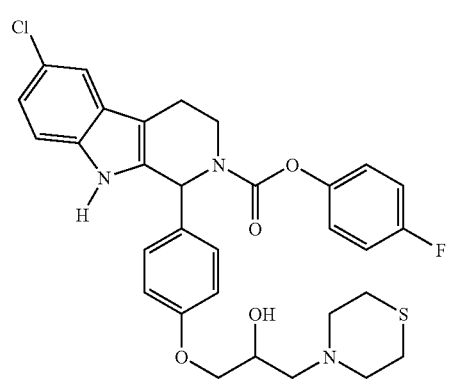
925
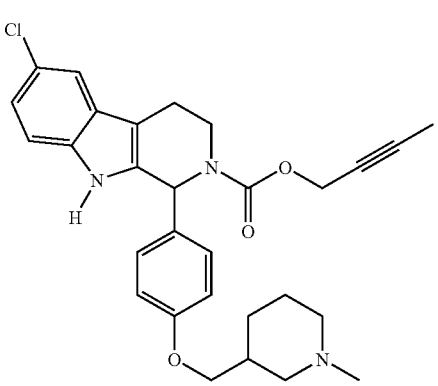
929

257
-continued
930
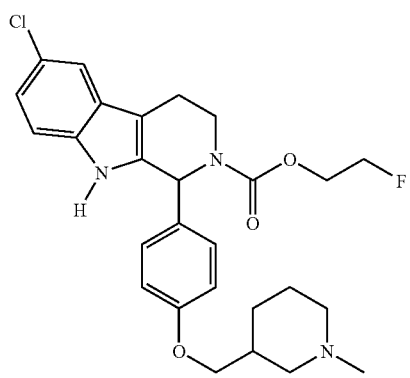
931
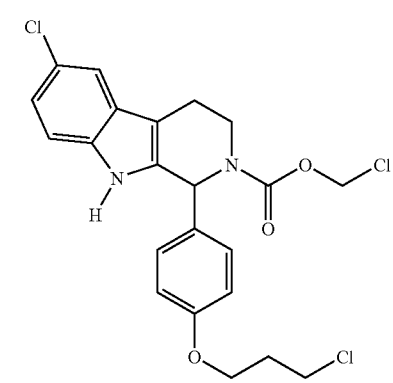
932
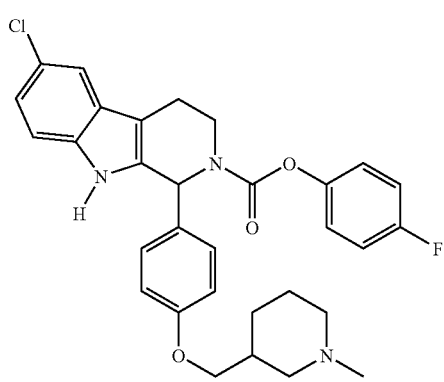
933
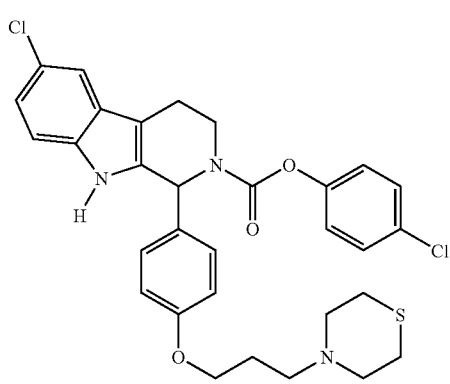
258
-continued
934
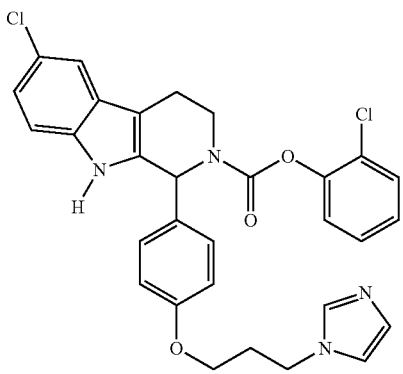
935
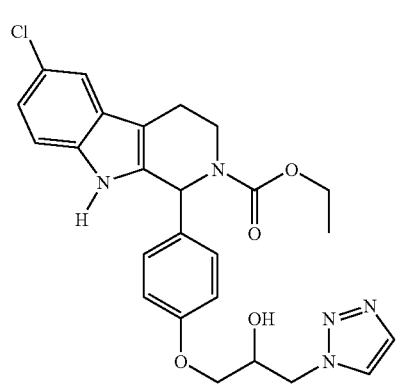
936
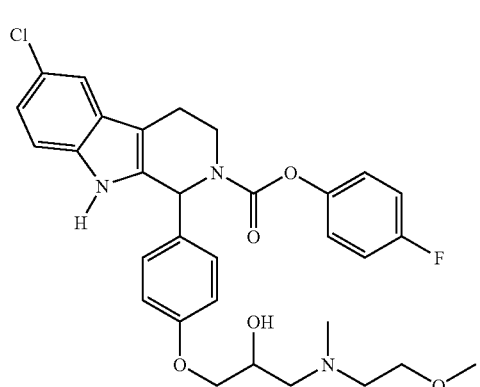
937
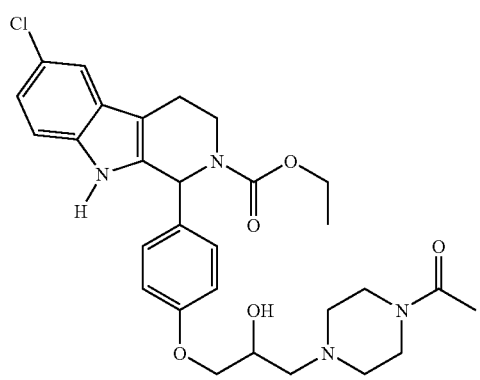

259
-continued
938
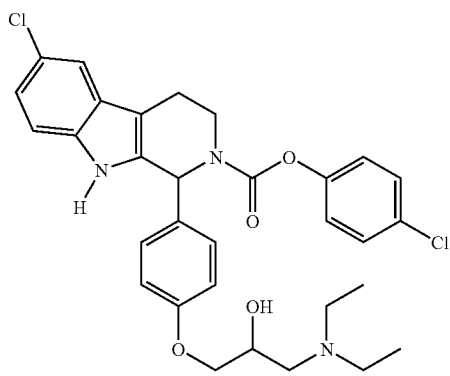
939
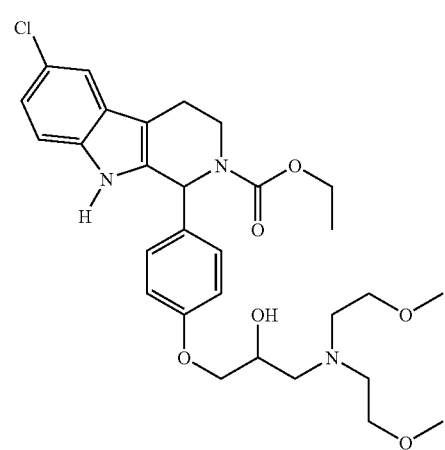
940
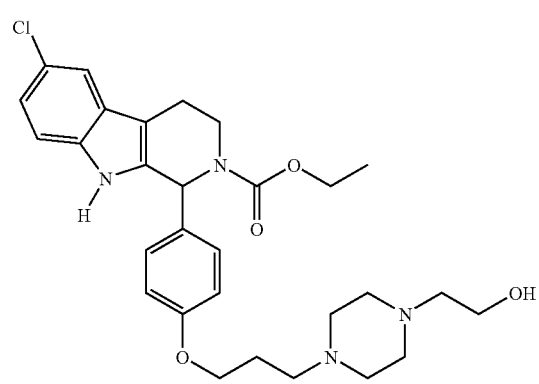
941
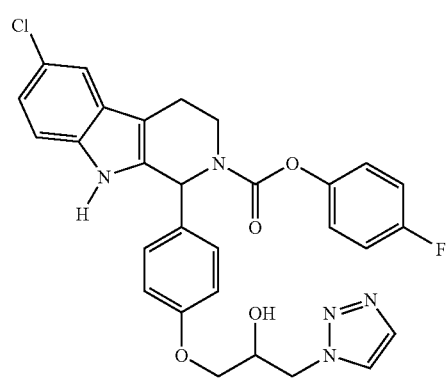
260
-continued
942
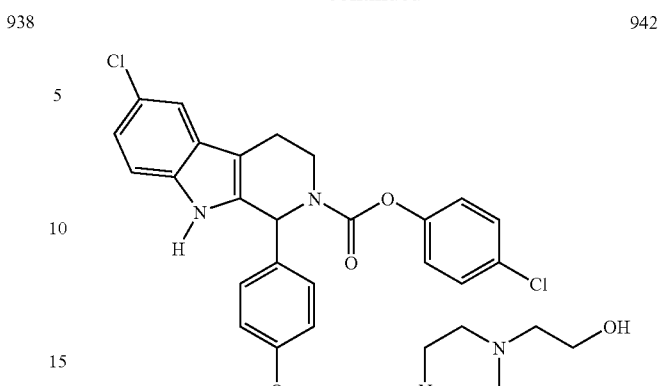
943
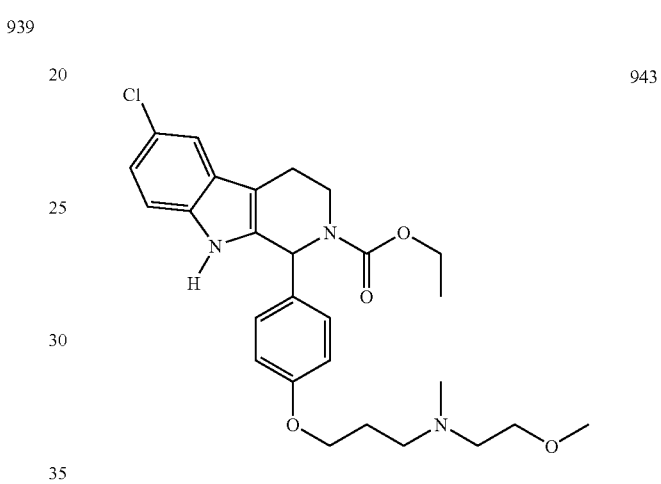
944
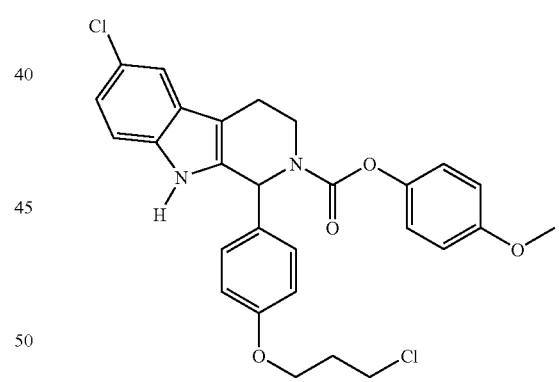
945
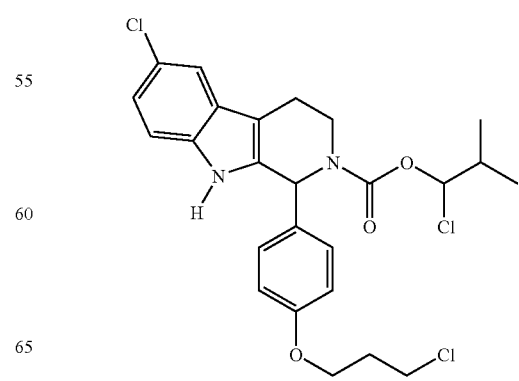

946
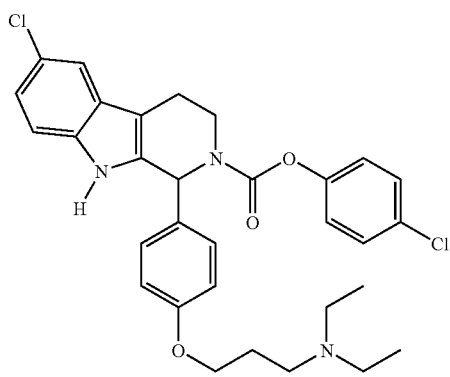
947
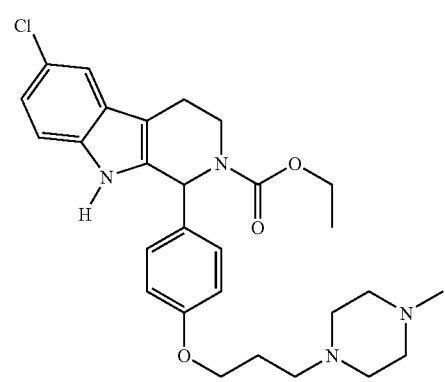
948
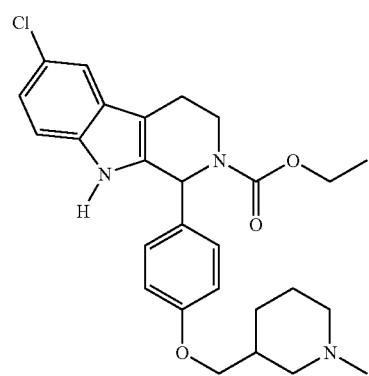
949
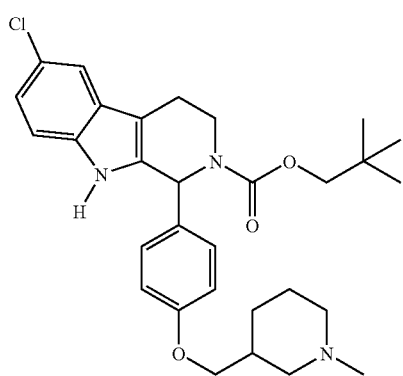
950
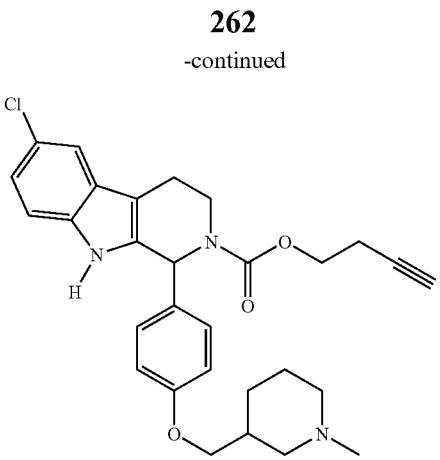
951
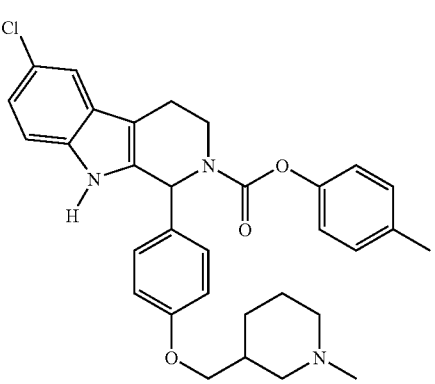
952
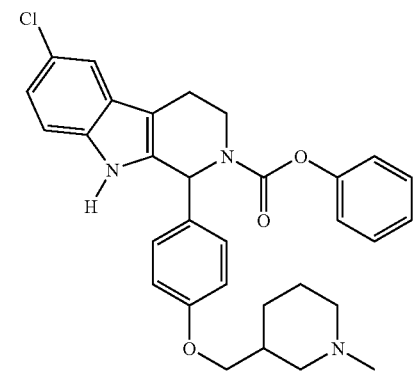
953
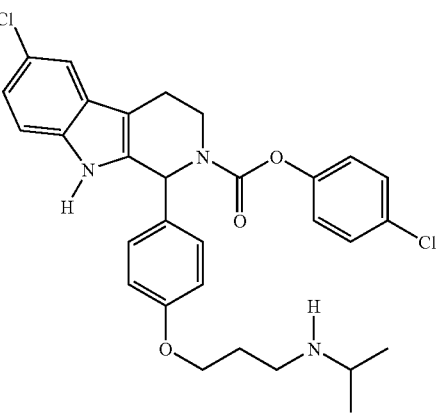

954
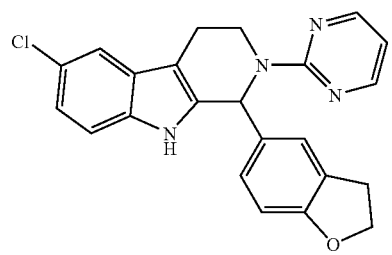
955
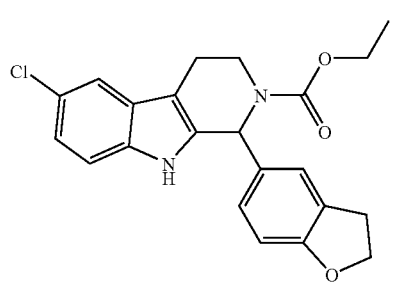
956
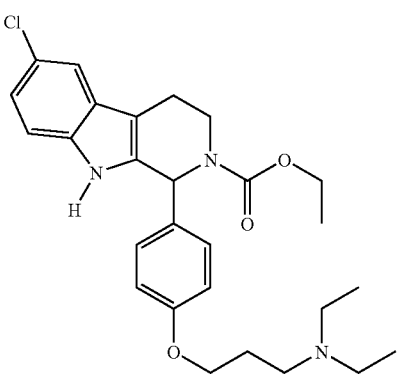
957
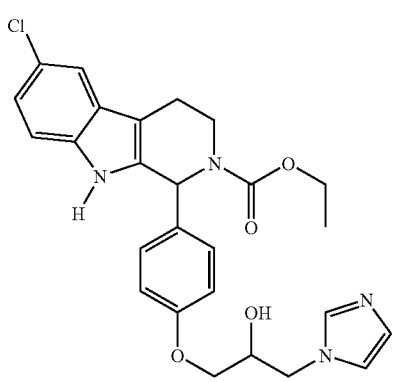
958
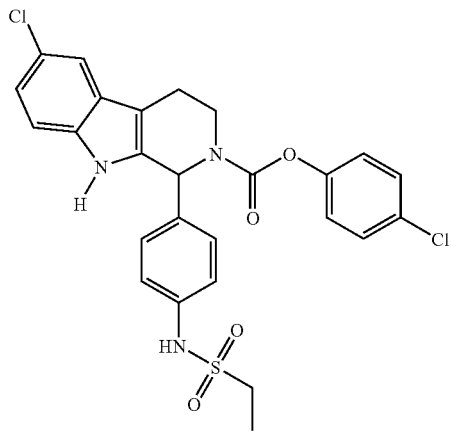
959
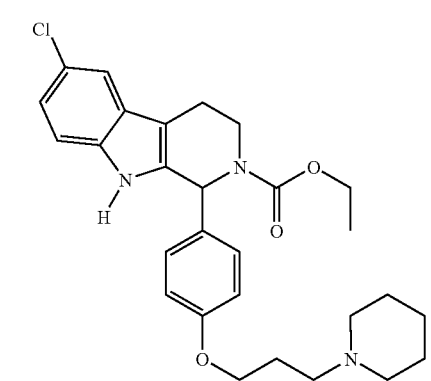
960
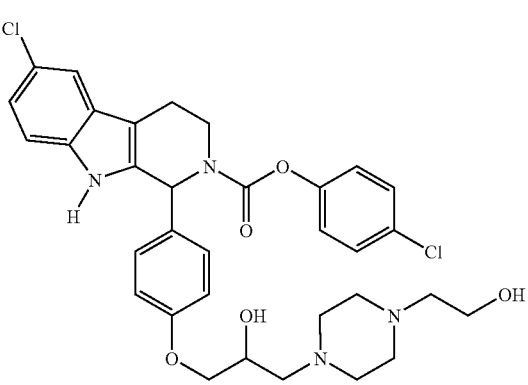
961
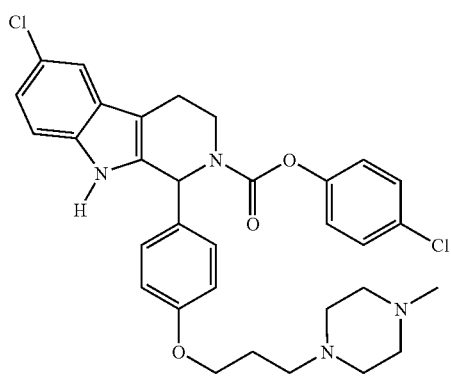

265
-continued
962
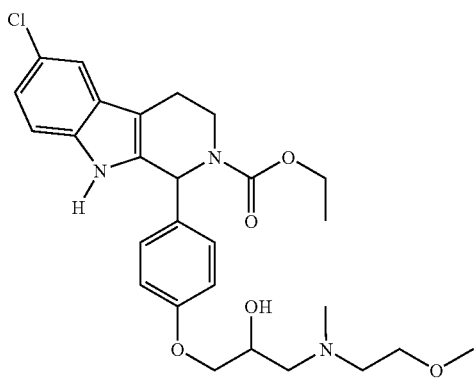
963
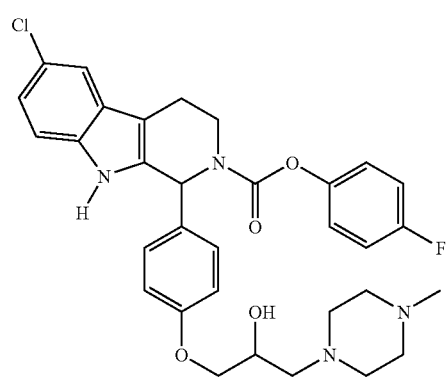
964
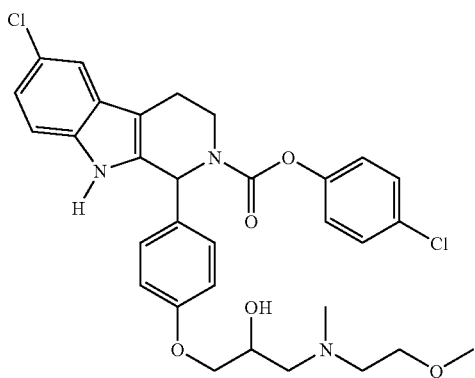
965
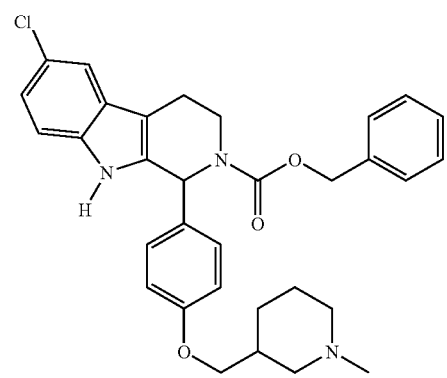
266
-continued
966
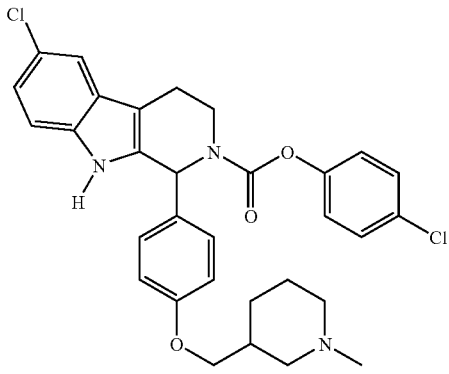
967
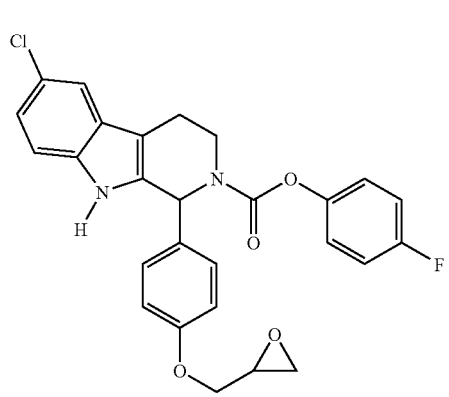
968
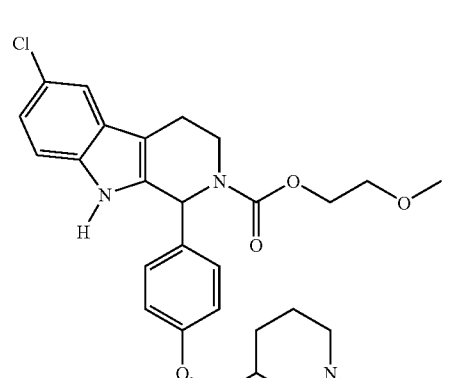
969
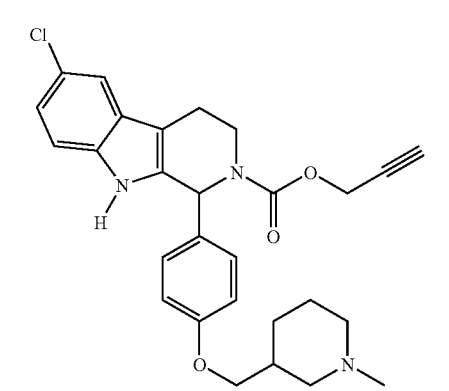

267
-continued
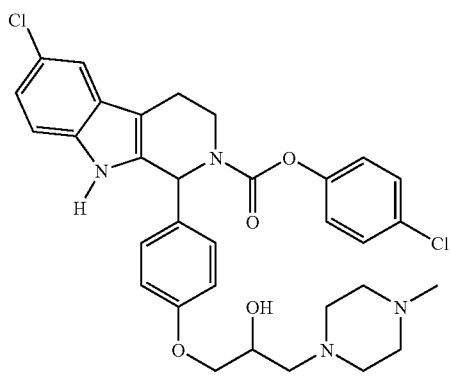
970
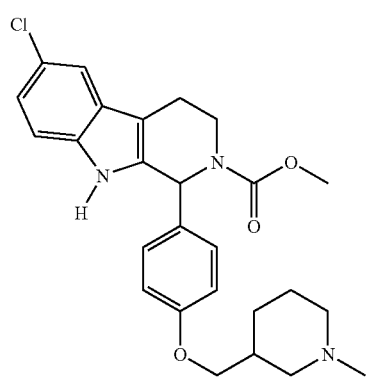
971
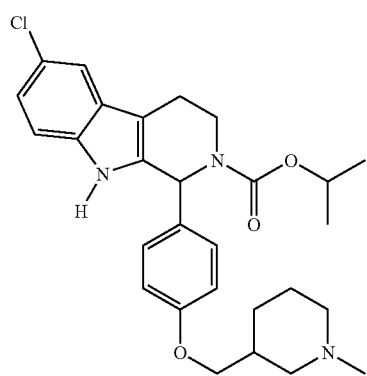
972
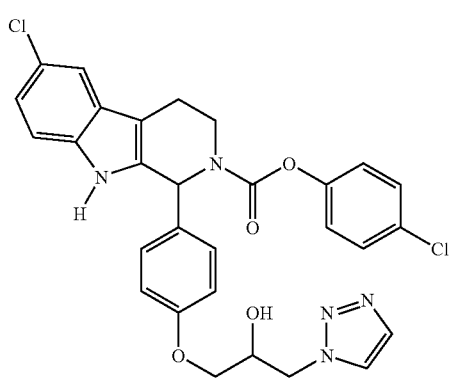
973
268
-continued
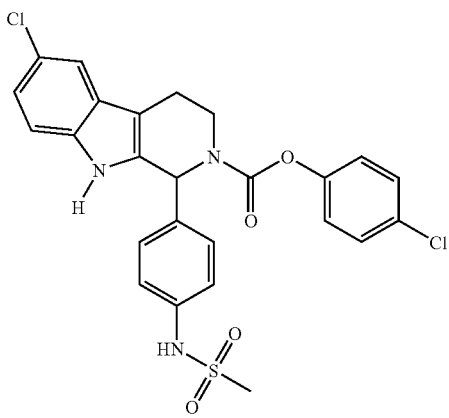
974
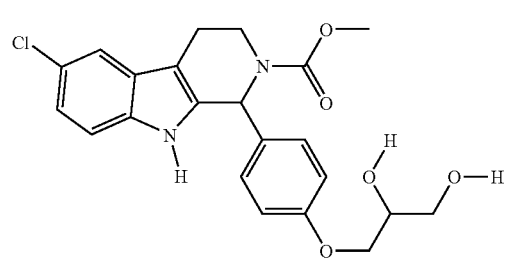
975
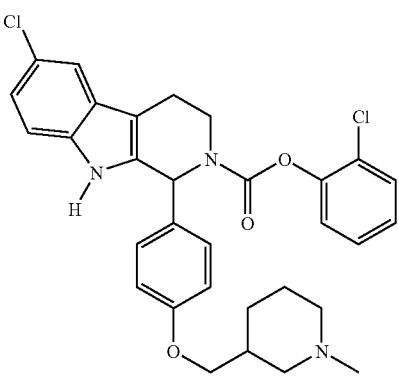
976
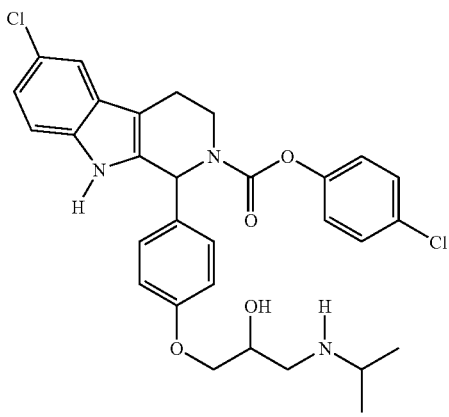
977

978 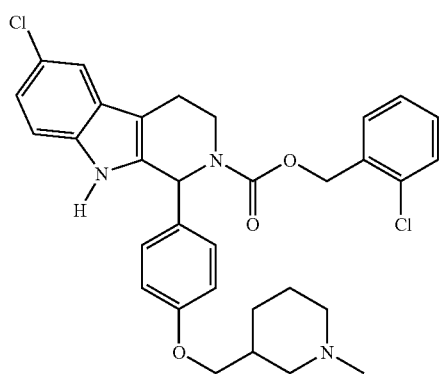
979 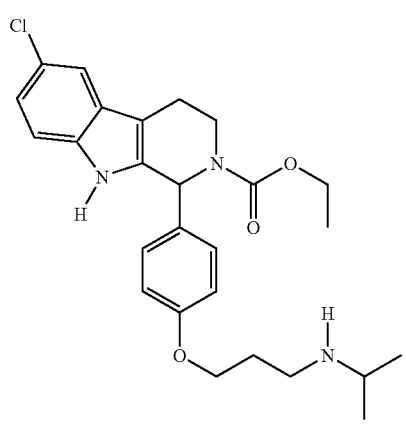
980 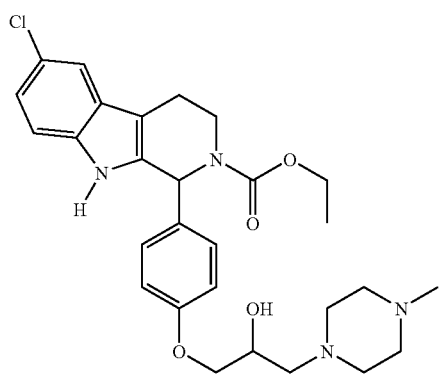
981 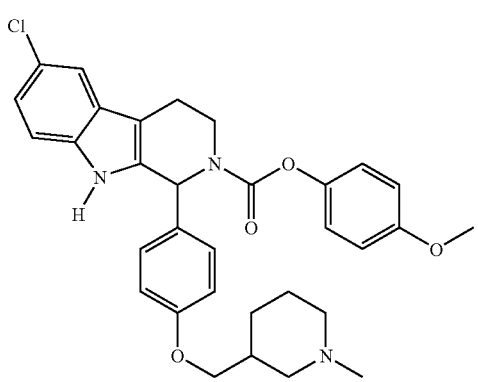
982 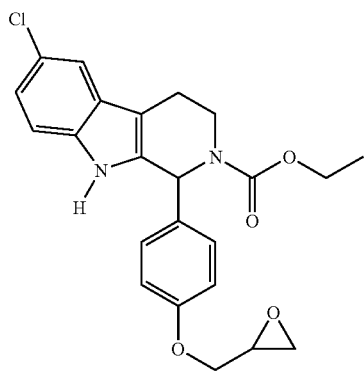
983 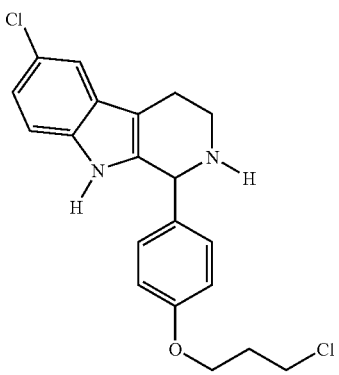
984 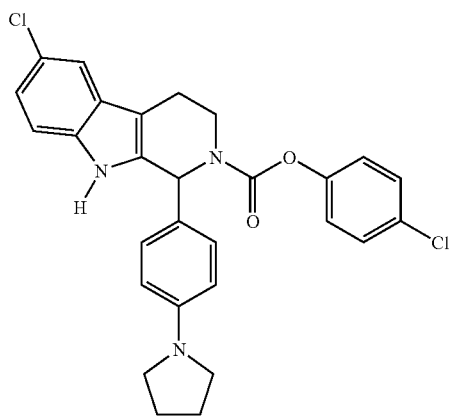
985 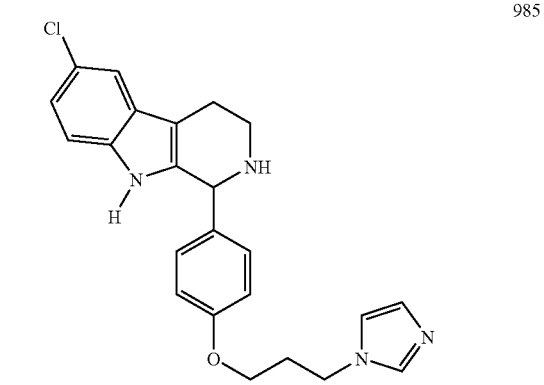

271
-continued
986
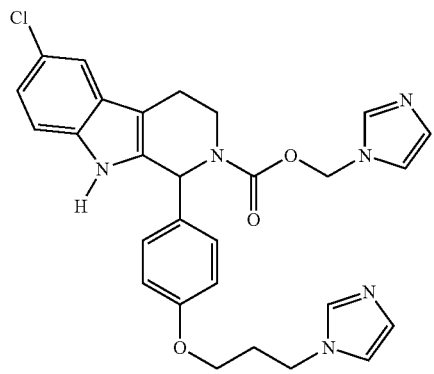
987
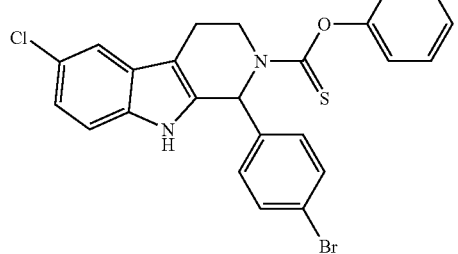
988
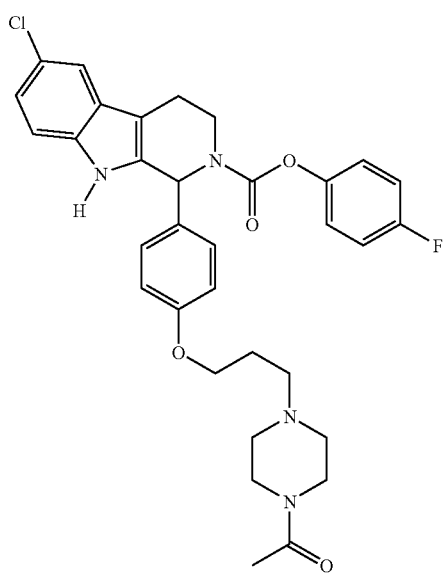
272
-continued
989
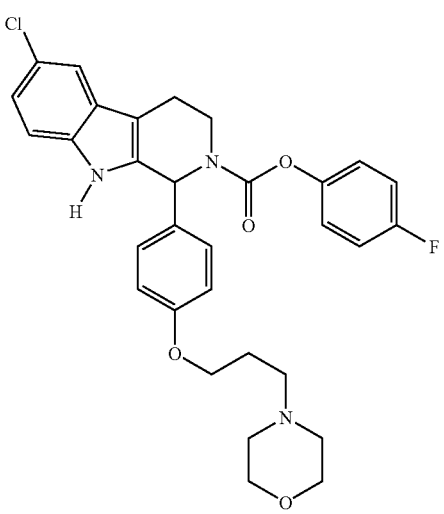
990
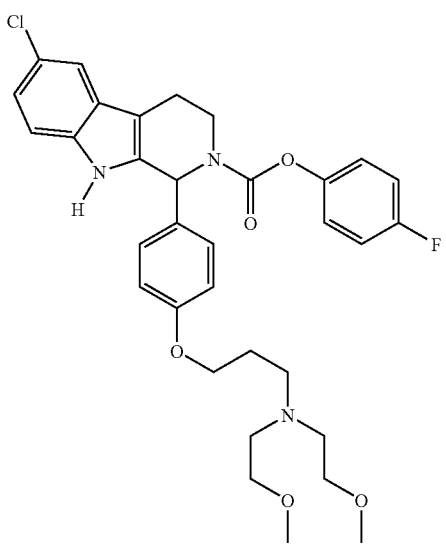
991
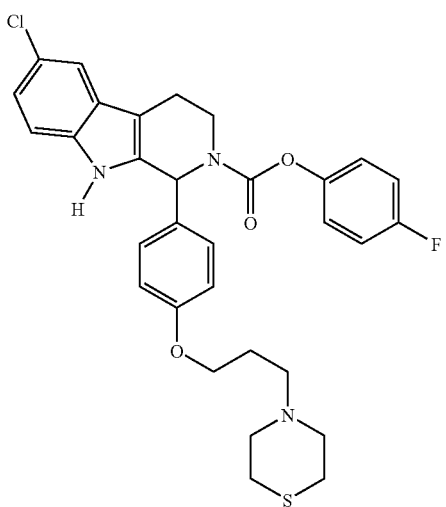

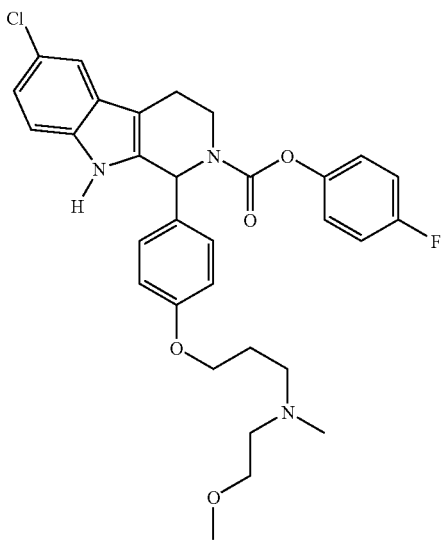

992

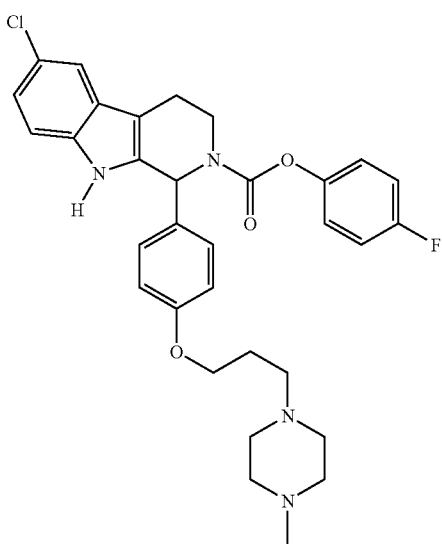

993

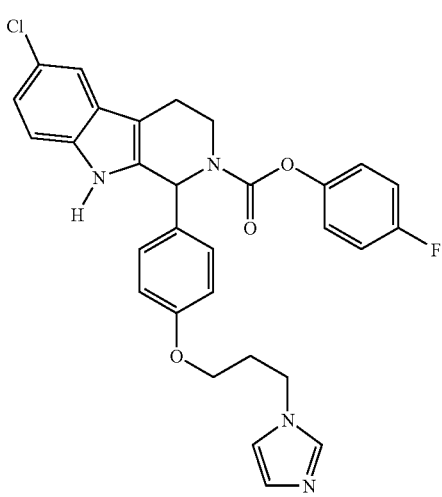

994

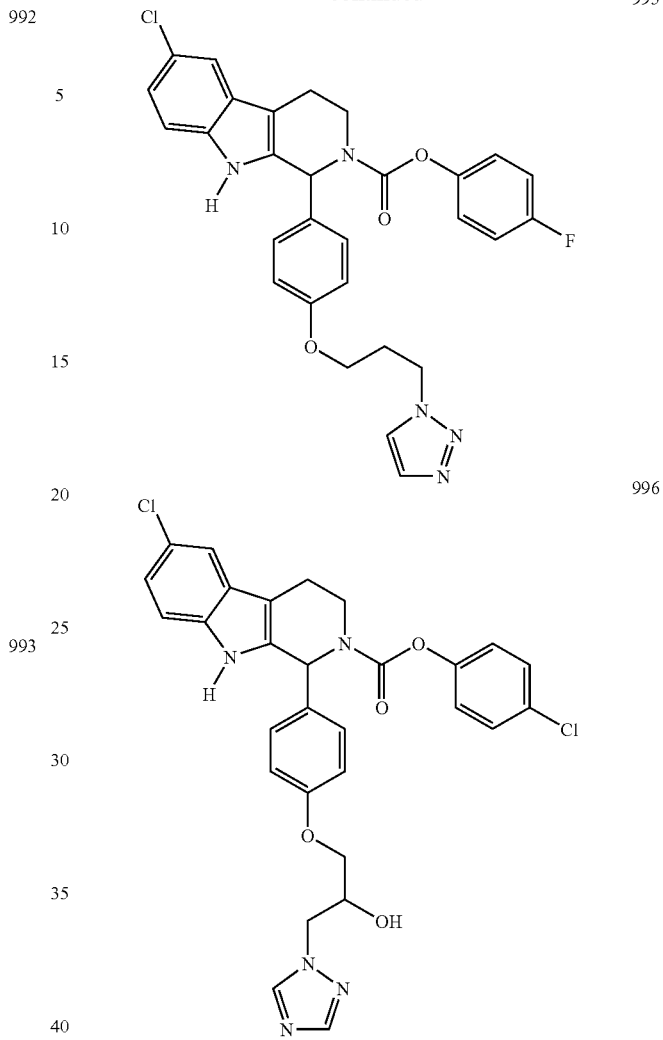

In certain embodiments, preferred compounds include those with an $EC_{50}$ in the VEGF ELISA assay described in Example 2 of less than about 2 uM, more preferably between about 2 uM and about 0.04 uM (200 nM to 40 nM); more preferably from about 0.04 uM to about 0.008 uM to (40 nM to 8 nM); and more preferably less than about 0.008 uM (<8 nM). Particularly preferred compounds are Compound Nos: 2, 4, 5, 7, 8, 10, 11, 12, 17, 23, 25, 81, 102, 112, 140, 328, 329, 330, 331, 332, 355, 816, 817, 818, 823, 824, 825, 830, 831, 832, 837, 838, 841, 842, 843, and regioisomers thereof. In one embodiment, the preferred compounds of the invention form a racemic mixture, and in another embodiment the compounds of the invention are the (R), (S), (R,R), (S,S), (R,S), (S,R) isomer, in an enantiomerically pure composition. More preferably, the compounds of the invention are the (S) isomers, in an enantiomerically pure composition.

The above compounds are listed only to provide examples that may be used in the methods of the invention. Based upon the instant disclosure, the skilled artisan would recognize other compounds intended to be included within the scope of the presently claimed invention that would be useful in the methods recited herein.

B. Preparation of Compounds of the Invention

Compounds of the invention may be produced in any manner known in the art. By way of example, compounds of the invention may be prepared according to the following general schemes. More specifically, Scheme I may be used to make compounds of Formula I. Scheme Ia can be used when in conjunction with Scheme I when $R_2$ is a —$CH_2$-furanyl group. Alternatively, for asymmetric synthesis when $R_2$ is hydrogen or hydroxyl, Scheme Ib may be used.
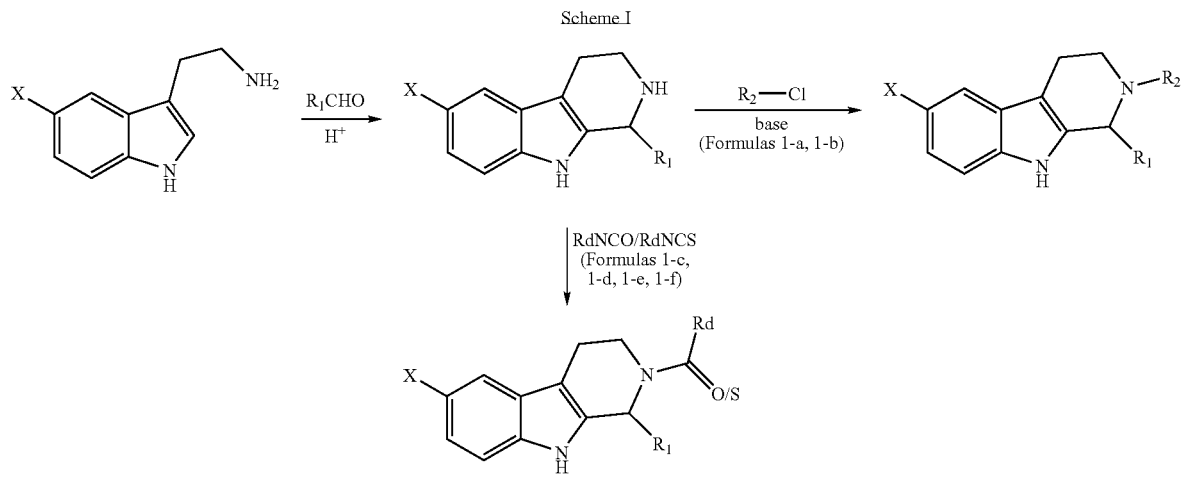
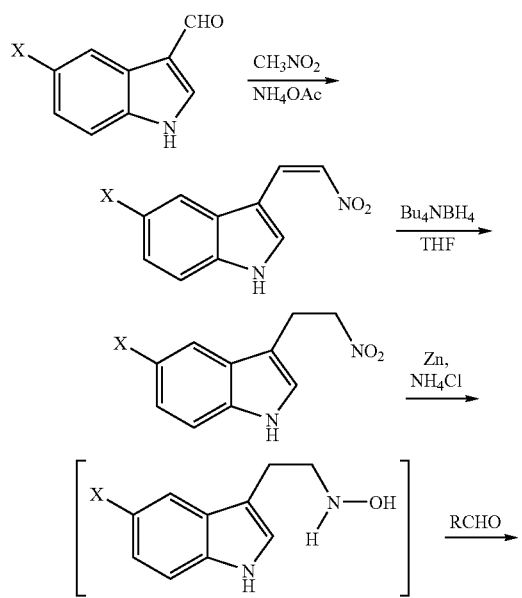
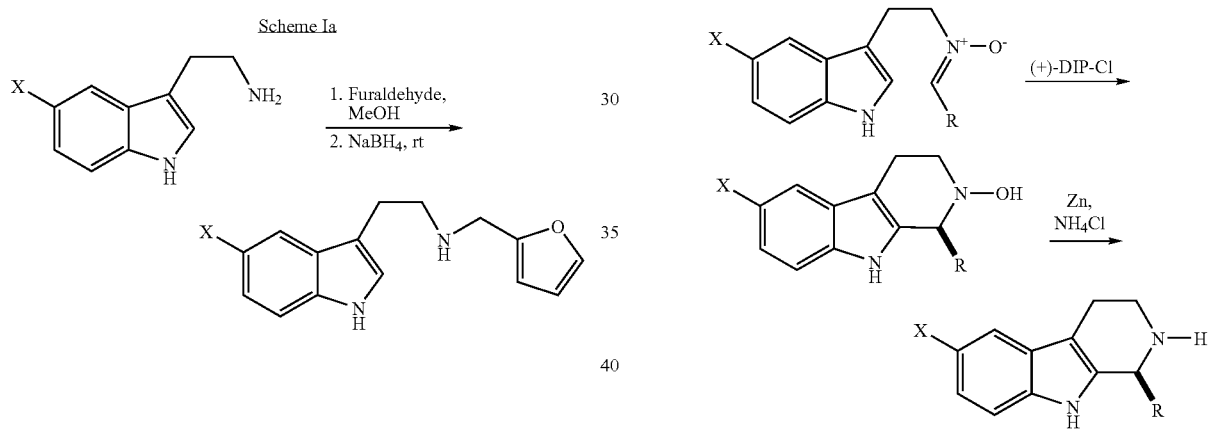
Scheme II can be used to prepare compounds of Formula I-h.
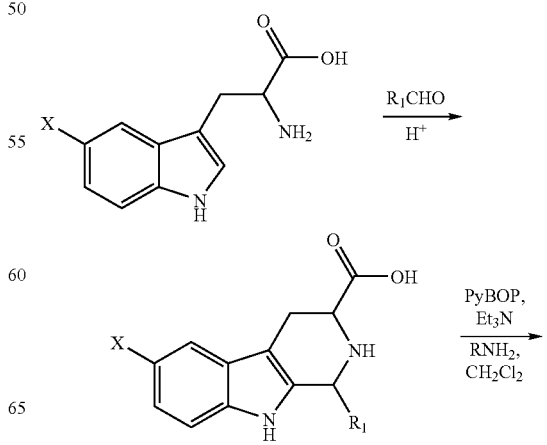

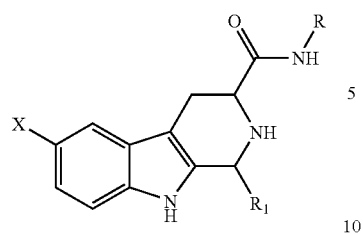

Schemes IIIa or IIIb can be used to prepare compounds of Formula I-i.

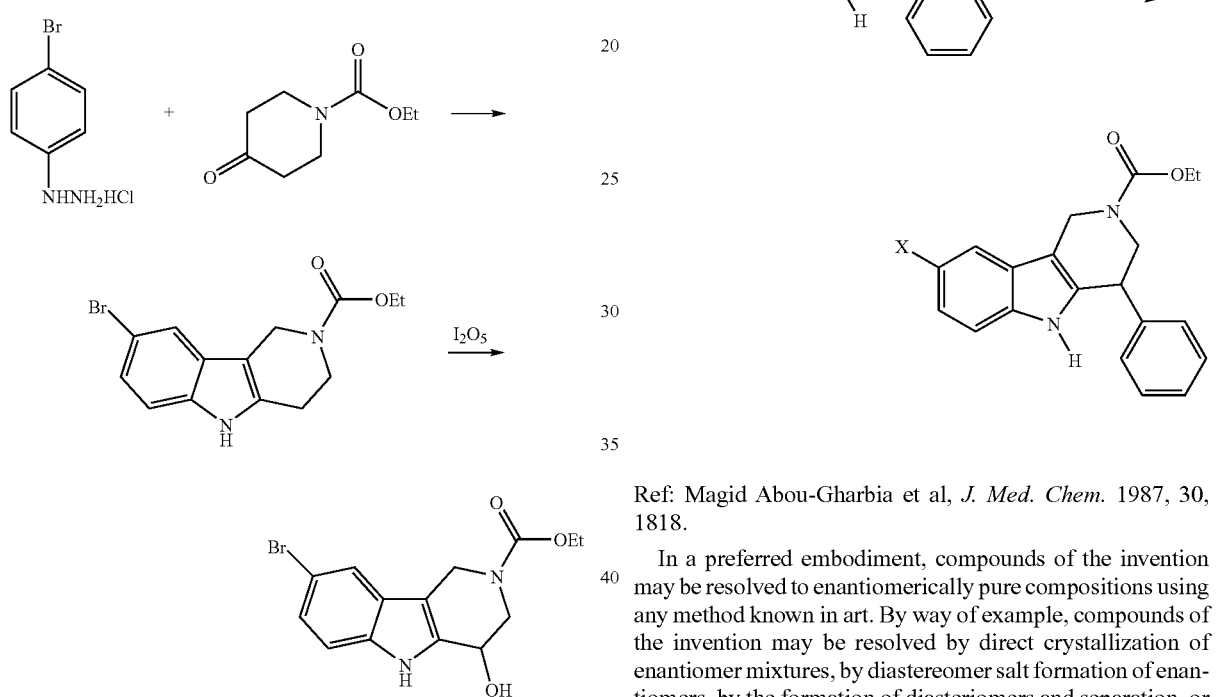

Ref: *Chem. Pharm. Bull.* 1987, 4700.

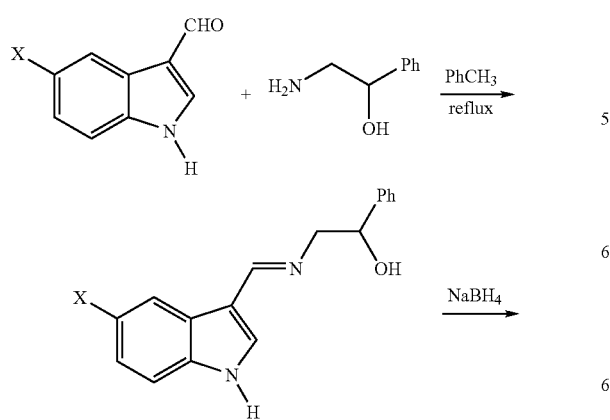

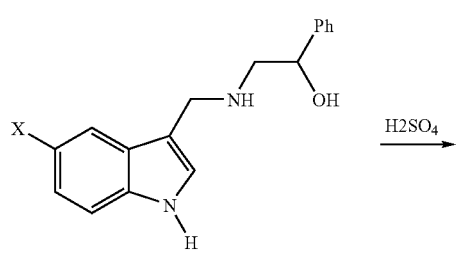

Ref: Magid Abou-Gharbia et al, *J. Med. Chem.* 1987, 30, 1818.

In a preferred embodiment, compounds of the invention may be resolved to enantiomerically pure compositions using any method known in art. By way of example, compounds of the invention may be resolved by direct crystallization of enantiomer mixtures, by diastereomer salt formation of enantiomers, by the formation of diasteriomers and separation, or by enzymatic resolution.

In a preferred embodiment, compounds of the invention may be resolved through crystallization using, e.g., N-acetyl-L-phenylalanine to obtain the (S) isomer, or N-acetyl-D-phenylalanine to obtain the (R) isomer, in a manner similar to that illustrated in Scheme IV.

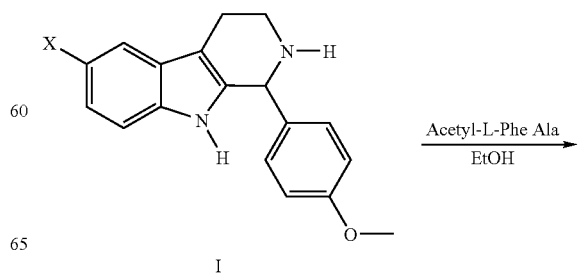

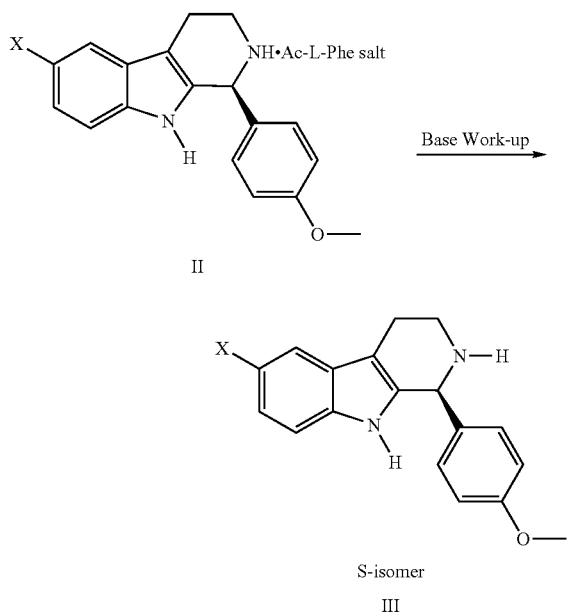

S-isomer
III

In certain embodiments, exemplary methods of Scheme I for preparing preferred compounds of Formula I involve the formation of free amine Pictet-Spengler reaction products/intermediates, as described below in Procedure-I.

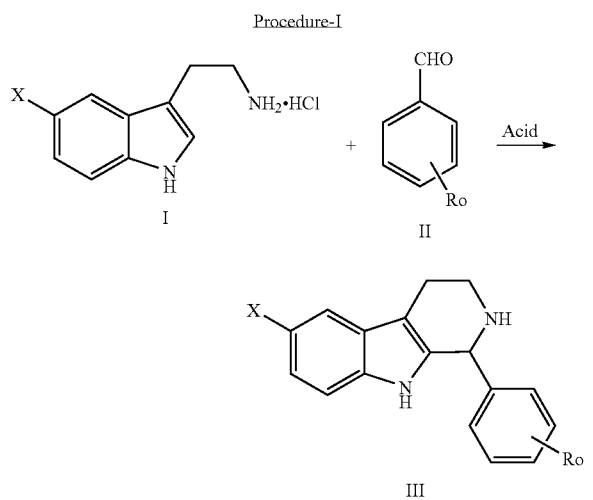

In one embodiment, Procedure-I may involve adding a desired Aldehyde (II) to a suspension of 5-substituted tryptamine. HCl (I) in 0.1N sulfuric acid. The solution may then be stirred at about 110° C.-120° C. in a closed reaction vessel until the reaction is sufficient to complete, e.g., for about 15 minutes to about 20 hours. After completion of the reaction, the reaction mixture may be cooled to room temperature and the precipitated salt may be filtered. The filtered residue may then be washed with ether, EtOAc or a mixture of DCM and DMF and dried to give the product (III) as acid salt. Alternatively, a desired Aldehyde (II) may be added to a suspension of 5-substituted tryptamine. HCl (I) in acetic acid and refluxed until the reaction is sufficiently complete, e.g., for about 15 minutes to about 20 hours. After completion of the reaction, the reaction mixture may be cooled to room temperature and the acid salt may be filtered. The filtered residue may then be washed with acetic acid followed by DCM and dried to give the product (III) as acid salt. The free amine(III) may be obtained by extraction with EtOAc and washing with aqueous ammonium hydroxide or 1M aq. sodium hydroxide.

The free amine, or its salt, may then be used to form other preferred compounds of Formula I, such as carbamate analogs (Formula I-c, Procedure-II), amide analogs, including N-acetyl analogs (Formula I-c, Procedure-IIIa and Procedure-IIIb), urea and thiourea analogs (Formula I-e and I-f, Procedure-IV and Procedure-V respectively), sulfoxide analogs (Formula I-g, Procedure-VI), and pyrimidine analogs (Procedure-VII).

More particularly, Procedure-II may be used to synthesize carbamate analogs of free amines(III), or their salts.

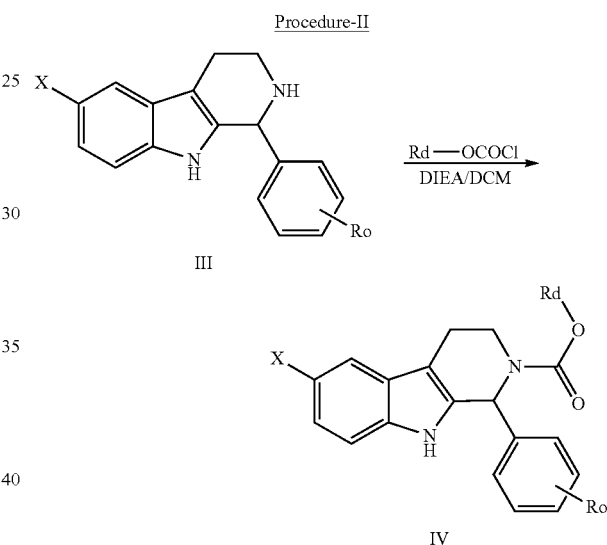

In accordance with Procedure-II, diisopropylethylamine (DIEA) may be added to the free amine(III), or its acid salt in dichloromethane (DCM), followed by slow addition of substituted chloroformate. The reaction mixture may be stirred at room temperature for about 1 to 20 hours. The solvent may then be evaporated and the crude product may either be purified by HPLC or silica gel column chromatography.

Procedure-IIIa may be used to synthesize amide analogs of free amine(III), or their salts.

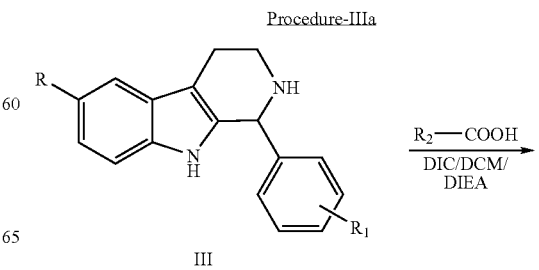

-continued

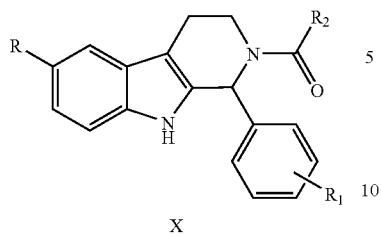

X

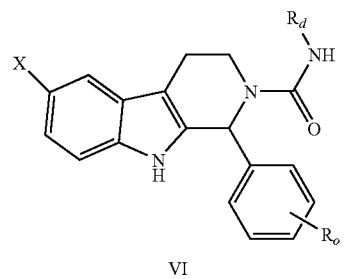

VI

In accordance with Procedure-IIIa, a 15 min pre-stirred mixture of an $R_2$-acid and diisopropyl carbodiimide (DIC) may be added to the free amine(III), or its acid salt in DCM and DIEA. The reaction mixture may be stirring for about 1 h. The solvents may then be evaporated and the crude product purified by HPLC.

Alternatively, Procedure-IIIb may be used to synthesize N-acetyl analogs of free amines (III), or their salts.

In accordance with Procedure-IV, DIEA and $R_2$-isocyanate may be added to the free amine(III), or its acid salt in DCM. The reaction mixture may be refluxed for about 1.5 h. The solvents may then be evaporated and the crude product purified by HPLC.

Procedure-V may be used to synthesize thiourea analogs of free amines(III), or their salts.

Procedure-IIIb

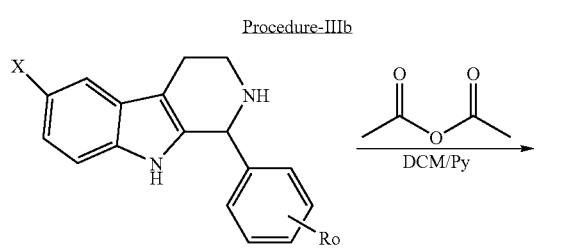

III

Procedure-V

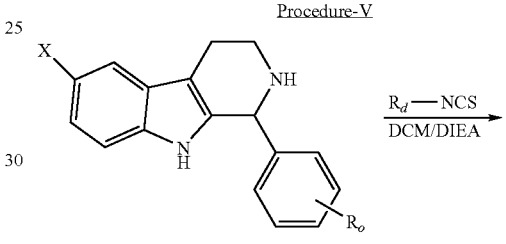

III

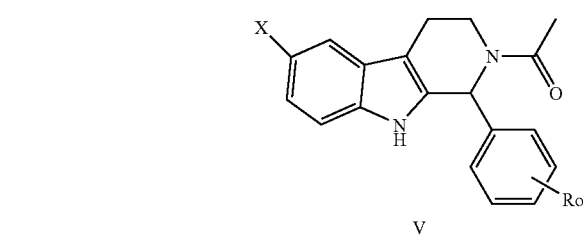

V

VIII

In accordance with Procedure-IIIb, pyridine may be added to the free amine(III), or its acid salt in DCM, followed by acetic anhydride. The reaction mixture may be stirred at room temperature for about 8 to 20 hours. The solvents may then be evaporated and the crude product was purified by HPLC.

Procedure-IV may be used to synthesize urea analogs of free amines(III), or their salts.

In accordance with Procedure-V, DIEA and $R_2$-isothiocyanate may be added to the free amine(III), or its acid salt in DCM. The reaction mixture may be refluxed for about 12 h. The solvents may then be evaporated and the crude product purified by HPLC.

Procedure-VI may be used to synthesize sulfonyl analogs of free amines(III), or their salts.

Procedure-IV

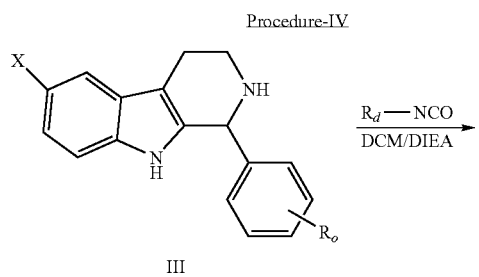

III

Procedure-VI

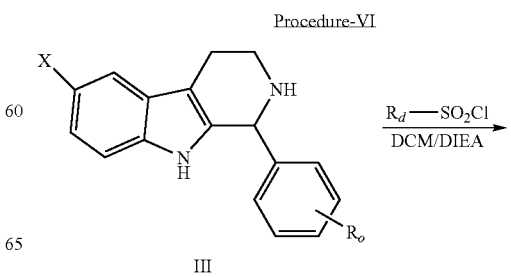

III

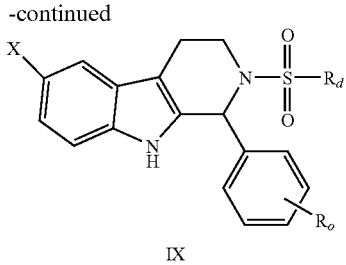

In accordance with Procedure-VI, DIEA and $R_2$-sulfonyl-chloride may be added to the free amine(III), or its acid salt in DCM. The reaction mixture may be stirred at room temperature for about 12 h. The solvents may then be evaporated and the crude product purified by HPLC.

Procedure-VII may be used to synthesize pyrimidine analogs of free amines(III), or their salts.

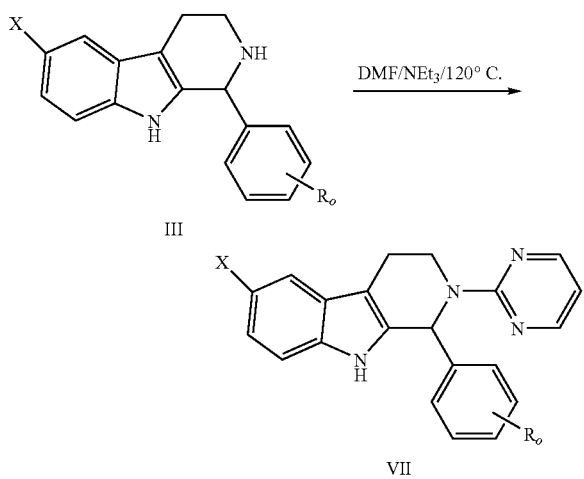

In accordance with Procedure-VII, triethylamine and 2-bromopyrimidine in N,N-dimethylformamide (DMF) may be added to the free amine(III), or its acid salt in DCM. The reaction mixture may be heated to about 120° C. for about 12 h. The solvents may then be evaporated and the crude product purified by HPLC.

These and other reaction methodologies may be useful in preparing the compounds of the invention, as recognized by one of skill in the art. Various modifications to the above schemes and procedures will be apparent to one of skill in the art, and the invention is not limited specifically by the method of preparing the compounds of the invention.

C. Methods of the Invention

In another aspect of the invention, methods are provided for the inhibition of VEGF production, the inhibition of angiogenesis, and/or the treatment of cancer, diabetic retinopathy, rheumatoid arthritis, psoriasis, atherosclerosis, chronic inflammation, other chronic inflammation-related diseases and disorders, obesity, or exudative macular degeneration using the compounds described herein.

In one embodiment, the invention is directed to methods for inhibiting VEGF production comprising administering a VEGF-expression inhibiting amount of at least one compound of the invention to a subject in need thereof.

In another embodiment, methods for inhibiting angiogenesis are provided comprising administering an anti-angiogenic amount of at least one compound of the invention to a subject in need thereof.

In yet another embodiment, methods for treating cancer, diabetic retinopathy, rheumatoid arthritis, psoriasis, atherosclerosis, chronic inflammation, other chronic inflammation-related diseases and disorders, obesity, or exudative macular degeneration are provided comprising administering a therapeutically effective amount of at least one compound of the invention to a subject in need thereof.

In yet a further embodiment, the cancers which can be treated by administering a therapeutically effective amount of at least one compound of the invention to a subject in need thereof include solid tumor cancers. Solid tumor cancers that can be treated by the present invention include solid tumor carcinomas and solid tumor sarcomas. Solid tumor carcinomas include, but are not limited to, pediatric solid tumors, such as Wilms tumor and neuroblastoma, and carcinomas of the epidermis, such as malignant melanomas, as well as lung cancers, cervical cancers, colon cancers and renal cancers. Solid tumor sarcomas include, but are not limited to, fibrosarcomas. The methods of treating cancer can further include the administration of one or more additional cancer agents.

In yet another embodiment of the invention, methods for treating a solid tumor cancer by slowing tumorigenesis at a pre-vascular stage are provided, comprising administering a therapeutically effective amount of at least one compound of the invention to a subject in need thereof, either alone or together with one or more additional cancer agents.

In another embodiment of the invention, methods for treating a solid tumor cancer by blocking VEGF mRNA translation are provided, comprising administering a therapeutically effective amount of at least one compound of the invention to a subject in need thereof, either alone or together with one or more additional cancer agents.

In yet another embodiment of the invention methods for treating a solid tumor cancer by reducing tumor VEGF levels are provided, comprising administering a therapeutically effective amount of at least one compound of the invention to a subject in need thereof, either alone or together with one or more additional cancer agents.

In yet a further embodiment of the invention, methods for treating a solid tumor cancer by reducing perivascularly sequestered VEGF are provided, comprising administering a therapeutically effective amount of at least one compound of the invention to a subject in need thereof, either alone or together with one or more additional cancer agents. In this aspect, reduced perivascularly sequestered VEGF is an in situ comparison of perivascular VEGF of tumors treated with the compound of the invention and tumors not treated with the compound of the invention. In a preferred aspect, reduced perivascularly sequestered VEGF is compared with levels of perivascular VEGF in tumors treated with antibodies to VEGF.

Without intending to be limited by theory, it is believed that the methods of the present invention act through a combination of mechanisms that modulate the activity of VEGF. In this embodiment of the invention, methods for blocking VEGF mRNA translation are provided, comprising administering a therapeutically effective amount of at least one compound of the invention to a subject in need thereof.

In another embodiment of the invention, methods for slowing tumorigenesis at a pre-vascular stage are provided, comprising administering a therapeutically effective amount of at least one compound of the invention to a subject in need thereof, either alone or together with one or more additional cancer agents. The pre-vascular stage of tumorigenesis is clinically known as "carcinoma in situ" and tumors at this stage are characterized by their reliance on nearby blood vessels for oxygen and diffusion of nutrients, due to the tumors absence of its own vascular infrastructure. So, by slowing tumorigenesis at a pre-vascular stage, one is preventing the development of a vascular infrastructure in the tumor. In this embodiment of the invention, whether tumorigenesis has been slowed at the pre-vascular stage is determined by identifying whether the tumor has developed a vascular infrastructure. In a preferred aspect, growth is reduced in the treated tumors, as compared to the untreated tumors, by 90%, 80%, 70%, 60%, 50%, 40%, 30%, 20% or 10%.

In yet a further embodiment of the invention, methods for reducing perivascularly sequestered VEGF are provided, comprising administering a therapeutically effective amount of at least one compound of the invention to a subject in need thereof. In a preferred aspect, In yet an additional embodiment of the invention, methods of diagnosing cancer by measuring tumor and/or plasma levels of VEGF are provided. Tumor levels of VEGF can be measured using biopsy tissue, where plasma VEGF levels can be measured by taking blood. In humans, different tumors secrete different levels of VEGF. Standard ELISA procedures can be used to measure the amount of VEGF in the tumor or plasma. See, for example, Verheul, H. m. W. et al. (2000) Platelet and coagulation activation with vascular endothelial growth factor generation in soft tissue sacomas. Clim Cancer Res. 6:166. For tumors that do not secrete large amounts of VEGF into the plasma, the tumor VEGF concentration can be determined to diagnose the tumor progression. For tumors that do secrete large amount of VEGF into the plasma, plasma VEGF concentration can be determined to diagnose the tumor progression. After most known cancer treatments, VEGF levels are not affected, and therefore the plasma or tumor levels of VEGF do not predict efficacy of the treatment (i.e., progression of the cancer). Compounds of the present invention can affect VEGF levels, both in the plasma and tumor, and therefore measuring VEGF levels is an accurate way to predict the progression of the cancer when the methods of the present invention for treating cancer are used.

In yet another embodiment of the invention, methods for reducing tumor or plasma VEGF levels are provided, comprising administering a therapeutically effective amount of at least one compound of the invention to a subject in need thereof. In this embodiment, VEGF levels can be measured in a tumor not treated with the compounds of the present invention and the VEGF levels compared to the VEGF levels measured in a tumor treated with the compounds of the present invention, thereby showing that by treatment of tumors with the compounds of the present invention VEGF levels are reduced.

In yet another embodiment of the invention, methods for treating a solid tumor cancer are provided, comprising (a) measuring plasma VEGF levels, tumor VEGF levels, or both, and administering a therapeutically effective amount of at least one compound of the invention to a subject in need thereof. In an embodiment, a level of VEGF is measured to determine whether treatment with a compound of the present invention should be undertaken. In this aspect, treatment with a compound of the present invention is preferred and more effective as the VEGF levels increase.

In yet a further embodiment of the invention, methods for treating a solid tumor cancer are provided, comprising administering a therapeutically effective amount of at least one compound of the invention to a subject in need thereof, together with one or more additional cancer agents.

In preferred embodiments, the methods of the invention comprise administering a therapeutically effective amount of at least one compound of the invention, wherein the compound is an (5) isomer.

According to the methods of the invention, the compound(s) may be administered to the subject via any drug delivery route known in the art. Specific exemplary administration routes include oral, ocular, rectal, buccal, topical, nasal, ophthalmic, subcutaneous, intramuscular, intravenous (bolus and infusion), intracerebral, transdermal, and pulmonary.

The terms "VEGF-inhibiting amount", "anti-angiogenic amount", and "therapeutically effective amount", as used herein, refer to an amount of a pharmaceutical agent to treat, ameliorate, or prevent the identified disease or condition, or to exhibit a detectable therapeutic or inhibitory affect. The affect can be detected by, for example, the assays disclosed in the following examples. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $ED_{50}/LD_{50}$. Pharmaceutical compositions that exhibit large therapeutic indices are preferred. The data obtained from cell culture assays and animal studies may be used in formulating a range of dosage for human use. The dosage contained in such compositions is preferably within a range of circulating concentrations that include an $ED_{50}$ with little or no toxicity. The dosage may vary within this range depending upon the dosage form employed, sensitivity of the patient, and the route of administration.

More specifically, the concentration-biological effect relationships observed with regard to the compound(s) of the present invention indicate an initial target plasma concentration ranging from approximately 0.1 μg/mL to approximately 100 μg/mL, preferably from approximately 5 μg/mL to approximately 50 μg/mL, more preferably from approximately 5 μg/mL to approximately 10 μg/mL. To achieve such plasma concentrations, the compounds of the invention may be administered at doses that vary from 0.1 μg to 100,000 mg, depending upon the route of administration. Guidance as to particular dosages and methods of delivery is provided in the literature and is generally available to practitioners in the art. In general the dose will be in the range of about 1 mg/day to about 10 g/day, or about 0.1 g to about 3 g/day, or about 0.3 g to about 3 g/day, or about 0.5 g to about 2 g/day, in single, divided, or continuous doses for a patient weighing between about 40 to about 100 kg (which dose may be adjusted for patients above or below this weight range, particularly children under 40 kg).

The exact dosage will be determined by the practitioner, in light of factors related to the subject that requires treatment. Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

D. Metabolites of the Compounds of the Invention

Also falling within the scope of the present invention are the in vivo metabolic products of the compounds described herein. Such products may result for example from the oxidation, reduction, hydrolysis, amidation, esterification and the like of the administered compound, primarily due to enzymatic processes. Accordingly, the invention includes compounds produced by a process comprising contacting a compound of this invention with a mammalian tissue or a mammal for a period of time sufficient to yield a metabolic product thereof. Such products typically are identified by preparing a radio-labeled (e.g. $C^{14}$ or $H^3$) compound of the invention, administering it in a detectable dose (e.g., greater than about 0.5 mg/kg) to a mammal such as rat, mouse, guinea pig, monkey, or to man, allowing sufficient time for metabolism to occur (typically about 30 seconds to 30 hours), and isolating its conversion products from urine, blood or other biological samples. These products are easily isolated since they are labeled (others are isolated by the use of antibodies capable of binding epitopes surviving in the metabolite). The metabolite structures are determined in conventional fashion, e.g., by MS or NMR analysis. In general, analysis of metabolites may be done in the same way as conventional drug metabolism studies well-known to those skilled in the art. The conversion products, so long as they are not otherwise found in vivo, are useful in diagnostic assays for therapeutic dosing of the compounds of the invention even if they possess no biological activity of their own.

E. Pharmaceutical Compositions of the Invention

While it is possible for the compounds of the present invention to be administered neat, it may be preferable to formulate the compounds as pharmaceutical compositions. As such, in yet another aspect of the invention, pharmaceutical compositions useful in the methods of the invention are provided. The pharmaceutical compositions of the invention may be formulated with pharmaceutically acceptable excipients such as carriers, solvents, stabilizers, adjuvants, diluents, etc., depending upon the particular mode of administration and dosage form. The pharmaceutical compositions should generally be formulated to achieve a physiologically compatible pH, and may range from a pH of about 3 to a pH of about 11, preferably about pH 3 to about pH 7, depending on the formulation and route of administration. In alternative embodiments, it may be preferred that the pH is adjusted to a range from about pH 5.0 to about pH 8.0.

More particularly, the pharmaceutical compositions of the invention comprise a therapeutically or prophylactically effective amount of at least one compound of the present invention, together with one or more pharmaceutically acceptable excipients. Optionally, the pharmaceutical compositions of the invention may comprise a combination of compounds of the present invention, or may include a second active ingredient useful in the treatment of cancer, diabetic retinopathy, or exudative macular degeneration.

Formulations of the present invention, e.g., for parenteral or oral administration, are most typically solids, liquid solutions, emulsions or suspensions, while inhaleable formulations for pulmonary administration are generally liquids or powders, with powder formulations being generally preferred. A preferred pharmaceutical composition of the invention may also be formulated as a lyophilized solid that is reconstituted with a physiologically compatible solvent prior to administration. Alternative pharmaceutical compositions of the invention may be formulated as syrups, creams, ointments, tablets, and the like.

The term "pharmaceutically acceptable excipient" refers to an excipient for administration of a pharmaceutical agent, such as the compounds of the present invention. The term refers to any pharmaceutical excipient that may be administered without undue toxicity. Pharmaceutically acceptable excipients are determined in part by the particular composition being administered, as well as by the particular method used to administer the composition. Accordingly, there exists a wide variety of suitable formulations of pharmaceutical compositions of the present invention (see, e.g., Remington's Pharmaceutical Sciences).

Suitable excipients may be carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants such as ascorbic acid; chelating agents such as EDTA; carbohydrates such as dextrin, hydroxyalkylcellulose, hydroxyalkylmethylcellulose, stearic acid; liquids such as oils, water, saline, glycerol and ethanol; wetting or emulsifying agents; pH buffering substances; and the like. Liposomes are also included within the definition of pharmaceutically acceptable excipients.

The pharmaceutical compositions of the invention may be formulated in any form suitable for the intended method of administration. When intended for oral use for example, tablets, troches, lozenges, aqueous or oil suspensions, non-aqueous solutions, dispersible powders or granules (including micronized particles or nanoparticles), emulsions, hard or soft capsules, syrups or elixirs may be prepared. Compositions intended for oral use may be prepared according to any method known to the art for the manufacture of pharmaceutical compositions, and such compositions may contain one or more agents including sweetening agents, flavoring agents, coloring agents and preserving agents, in order to provide a palatable preparation.

Pharmaceutically acceptable excipients particularly suitable for use in conjunction with tablets include, for example, inert diluents, such as celluloses, calcium or sodium carbonate, lactose, calcium or sodium phosphate; disintegrating agents, such as croscarmellose sodium, cross-linked povidone, maize starch, or alginic acid; binding agents, such as povidone, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example celluloses, lactose, calcium phosphate or kaolin, or as soft gelatin capsules wherein the active ingredient is mixed with non-aqueous or oil medium, such as glycerin, propylene glycol, polyethylene glycol, peanut oil, liquid paraffin or olive oil.

In another embodiment, pharmaceutical compositions of the invention may be formulated as suspensions comprising a compound of the present invention in admixture with at least one pharmaceutically acceptable excipient suitable for the manufacture of a suspension. In yet another embodiment, pharmaceutical compositions of the invention may be formulated as dispersible powders and granules suitable for preparation of a suspension by the addition of suitable excipients.

Excipients suitable for use in connection with suspensions include suspending agents, such as sodium carboxymethylcellulose, methylcellulose, hydroxypropyl methylcelluose, sodium alginate, polyvinylpyrrolidone, gum tragacanth, gum acacia, dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycethanol), a condensation product of ethylene oxide with a partial ester derived from a fatty acid and a hexitol anhydride (e.g., polyoxyethylene sorbitan monooleate); and thickening agents, such as carbomer, beeswax, hard paraffin or cetyl alcohol. The suspensions may also contain one or more preservatives such as acetic acid, methyl and/or n-propyl p-hydroxy-benzoate; one or more coloring agents; one or more flavoring agents; and one or more sweetening agents such as sucrose or saccharin.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth; naturally occurring phosphatides, such as soybean lecithin, esters or partial esters derived from fatty acids; hexitol anhydrides, such as sorbitan monooleate; and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

Additionally, the pharmaceutical compositions of the invention may be in the form of a sterile injectable preparation, such as a sterile injectable aqueous emulsion or oleaginous suspension. This emulsion or suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,2-propane-diol. The sterile injectable preparation may also be prepared as a lyophilized powder. Among the acceptable vehicles and solvents that may be employed are water, Ringer's solution, and isotonic sodium chloride solution. In addition, sterile fixed oils may be employed as a solvent or suspending medium. For this purpose any bland fixed oil may be employed including synthetic mono- or diglycerides. In addition, fatty acids such as oleic acid may likewise be used in the preparation of injectables.

Generally, the compounds of the present invention useful in the methods of the present invention are substantially insoluble in water and are sparingly soluble in most pharmaceutically acceptable protic solvents and in vegetable oils. However, the compounds are generally soluble in medium chain fatty acids (e.g., caprylic and capric acids) or triglycerides and have high solubility in propylene glycol esters of medium chain fatty acids. Also contemplated in the invention are compounds which have been modified by substitutions or additions of chemical or biochemical moieties which make them more suitable for delivery (e.g., increase solubility, bioactivity, palatability, decrease adverse reactions, etc.), for example by esterification, glycosylation, PEGylation, etc.

In a preferred embodiment, the compounds of the present invention may be formulated for oral administration in a lipid-based formulation suitable for low solubility compounds. Lipid-based formulations can generally enhance the oral bioavailability of such compounds. As such, a preferred pharmaceutical composition of the invention comprises a therapeutically or prophylactically effective amount of a compound of the present invention, together with at least one pharmaceutically acceptable excipient selected from the group consisting of: medium chain fatty acids or propylene glycol esters thereof (e.g., propylene glycol esters of edible fatty acids such as caprylic and capric fatty acids) and pharmaceutically acceptable surfactants such as polyoxyl 40 hydrogenated castor oil.

In an alternative preferred embodiment, cyclodextrins may be added as aqueous solubility enhancers. Preferred cyclodextrins include hydroxypropyl, hydroxyethyl, glucosyl, maltosyl and maltotriosyl derivatives of $\alpha$-, $\beta$-, and $\gamma$-cyclodextrin. A particularly preferred cyclodextrin solubility enhancer is hydroxypropyl-$\beta$-cyclodextrin (HPBC), which may be added to any of the above-described compositions to further improve the aqueous solubility characteristics of the compounds of the present invention. In one embodiment, the composition comprises 0.1% to 20% hydroxypropyl-$\beta$-cyclodextrin, more preferably 1% to 15% hydroxypropyl-$\beta$-cyclodextrin, and even more preferably from 2.5% to 10% hydroxypropyl-$\beta$-cyclodextrin. The amount of solubility enhancer employed will depend on the amount of the compound of the present invention in the composition.

F. Combination Therapy

It is also possible to combine any compound of the present invention with one or more other active ingredients useful in the treatment of cancer, including compounds, in a unitary dosage form, or in separate dosage forms intended for simultaneous or sequential administration to a patient in need of treatment. When administered sequentially, the combination may be administered in two or more administrations. In an alternative embodiment, it is possible to administer one or more compounds of the present invention and one or more additional active ingredients by different routes.

The skilled artisan will recognize that a variety of active ingredients may be administered in combination with the compounds of the present invention that may act to augment or synergistically enhance the VEGF-inhibiting and/or anti-angiogenesis activity of the compounds of the invention.

More specifically, for methods involving the treatment of cancer, agents known in the art to be useful for treating cancer are provided. Such agents include, but are not limited to, radiation therapy, agents that cause DNA damage, agents that reduce the concentration or effect of a growth factor, agents that inhibit angiogenesis, paclitaxel, fluorouracil, CPT-11, a tyrosine kinase inhibitor, a COX-2 inhibitor, thalidomide, gemcitabine, squalamine, endostatin, angiostatin, AE-941, lenalidomide, medi-522, 2-methoxyestradiol, carboxyamidotriazole, combretastatin A4 phosphate, SU6668, SU11248, BMS-275291, COL-3, cilengitide, IMC-1121B, vatalanib, LY317615, VEGF Trap, ZD6474, halofuginone, hydrobromide, celecoxib, interferon alpha, interleukin-12, and antibodies capable of binding VEGF or a VEGF receptor, such as bevacizumab. VEGF receptors include VEGF receptor 1, VEGF receptor 2, and VEGF receptor 3. In another embodiment, the compounds of the present invention are used in combination with an agent that blocks the activity of a VEGF receptor. In yet another embodiment, the compounds of the present invention can be used in combination with agents that can block the VEGF signaling pathway. Treatment only with a factor that can block VEGF signaling may cause an increase in VEGF concentration. In such a case, including a compound of the present invention in the treatment protocol can prevent the subsequent increase in VEGF levels. Similarly, use of the compounds of the present invention in combination with an antibody is highly preferred. Antibodies are relatively large and may not cross tight barriers, allowing secreted VEGF to remain in areas such as the perivascular space. Post-transcriptional control of VEGF expression can prevent the tumor from retaining as much VEGF in the perivascular space, in the extracellular matrix, or in other spaces and vessels that have a physical barrier to antibodies.

According to the methods of the invention, the combination of active ingredients may be: (1) co-formulated and administered or delivered simultaneously in a combined formulation; (2) delivered by alternation or in parallel as separate formulations; or (3) by any other combination therapy regimen known in the art. When delivered in alternation therapy, the methods of the invention may comprise administering or delivering the active ingredients sequentially, e.g., in separate solution, emulsion, suspension, tablets, pills or capsules, or by different injections in separate syringes. In general, during alternation therapy, an effective dosage of each active ingredient is administered sequentially, i.e., serially, whereas in simultaneous therapy, effective dosages of two or more active ingredients are administered together. Various sequences of intermittent combination therapy may also be used.

To assist in understanding the present invention, the following Examples are included. The experiments relating to this invention should not, of course, be construed as specifically limiting the invention and such variations of the invention, now known or later developed, which would be within the purview of one skilled in the art are considered to fall within the scope of the invention as described herein and hereinafter claimed.

EXAMPLES

The present invention is described in more detail with reference to the following non-limiting examples, which are offered to more fully illustrate the invention, but are not to be construed as limiting the scope thereof. The examples illustrate the preparation of certain compounds of the invention, and the testing of these compounds in vitro and/or in vivo. Those of skill in the art will understand that the techniques described in these examples represent techniques described by the inventors to function well in the practice of the invention, and as such constitute preferred modes for the practice thereof. However, it should be appreciated that those of skill in the art should in light of the present disclosure, appreciate that many changes can be made in the specific methods that are disclosed and still obtain a like or similar result without departing from the spirit and scope of the invention.

Example 1

Preparation of Compounds of the Invention

Using the schemes and procedures described above in Section B, one may prepare certain compounds of the invention as follows. Other preferred compounds of the invention, such as those in Table 5 below, may be similarly prepared.

Example 1A

Compounds of Formula I, Scheme I

Certain compounds of Formula I may be prepared according to Scheme I using free amine products/intermediates, or their salts prepared in accordance with Procedure I. By way of example, certain free amines(III), or their salts are prepared using Procedure I. Table 4 illustrates certain free amines(III) or their salts, Intermediates 1-11.

TABLE 4

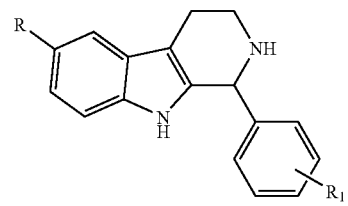

(III)

| Intermediate | R— of Free Amine (III) | $R_1$— of Free Amine (III) |
|---|---|---|
| 1 | Cl | 4-OMe |
| 2 | Cl | 2,3-difluoro |
| 3 | Cl | 4-Cl |
| 4 | Cl | 4-CN |
| 5 | Cl | 4-F |
| 6 | Cl | 4-iPr |
| 7 | Br | 4-Cl |
| 8 | Br | 4-Me |
| 9 | Br | 4-iPr |
| 10 | Br | 3-Cl |
| 11 | Br | 4-OMe |
| 12 | Cl | 4-(2-morpholine-4-yl-ethoxy) |

Intermediate-1:
This intermediate is prepared using Procedure-I with 5-chlorotryptamine.HCl (5.8 g, 25 mmol), p-anisaldehyde (6.13 mL, 50 mmol) and 0.1N sulfuric acid (60 mL) to give the title compound as an acid salt (6.1 g, 59%). ES-MS: 313 (M+H)⁺. Alternatively, this intermediate is prepared using Procedure-1B with 5-chlorotryptamine.HCl (20 g, 86.5 mmol), p-anisaldehyde (15.9 mL, 130 mmol) and acetic acid (250 mL) to give the title compound as an acid salt (25.8 g, 79%). ES-MS: 313 (M+H)⁺.

Intermediate-2:
This intermediate is prepared using Procedure-I with 5-chlorotryptamine.HCl (116 mg, 0.5 mmol), 2,3-difluoro benzaldehyde (109 µL, 1 mmol) and 0.1N sulfuric acid (2 mL) to give the title compound as an acid salt (158 mg, 75%). ES-MS: 319 (M+H)⁺

Intermediate-3:
This intermediate is prepared using Procedure-I with 5-chlorotryptamine.HCl (462 mg, 2 mmol), 4-chloro benzaldehyde (562 mg, 4 mmol) and 0.1N sulfuric acid (8 mL) to give the title compound as an acid salt (825 mg, 99%). ES-MS: 317 (M+H)⁺

Intermediate-4:
This intermediate is prepared using Procedure-I with 5-chlorotryptamine.HCl (462 mg, 2 mmol), 4-cyano benzaldehyde (525 mg, 4 mmol) and 0.1N sulfuric acid (8 mL) to give the title compound as an acid salt (810 mg, 100%). ES-MS: 308 (M+H)⁺

Intermediate-5:

This intermediate is prepared using Procedure-I with 5-chlorotryptamine.HCl (374 mg, 1.5 mmol), 4-fluoro benzaldehyde (322 μL, 3 mmol) and 0.1N sulfuric acid (4 mL) to give the title compound as an acid salt (250 mg, 42%). ES-MS: 301 (M+H)$^+$ Intermediate-6:

This intermediate is prepared using Procedure-I with 5-chlorotryptamine.HCl (1.15 g, 5 mmol), 4-isopropyl benzaldehyde (1.516 mL, 10 mmol) and 0.1N sulfuric acid (12 mL) to give the title compound as an acid salt (628 mg, 30%). ES-MS: 325 (M+H)$^+$ Intermediate-7:

This intermediate is prepared using Procedure-I with 5-bromotryptamine.HCl (551 mg, 2 mmol), 4-chloro benzaldehyde (562 mg, 4 mmol) and 0.1N sulfuric acid (8 mL) to give the title compound as an acid salt (330 mg, 36%). ES-MS: 363 (M+H)$^+$ Intermediate-8:

This intermediate is prepared using Procedure-I with 5-bromotryptamine.HCl (551 mg, 2 mmol), p-tolualdehyde (471 μL, 4 mmol) and 0.1N sulfuric acid (8 mL) to give the title compound as hydrogen sulfate salt (257 mg, 29%). ES-MS: 341 (M+H)$^+$. Alternatively, this intermediate is prepared using Procedure-1B with 5-bromotryptamine.HCl (10 g, 36.3 mmol), p-tolualdehyde (6.41 mL, 54.5 mmol) and acetic acid (120 mL) to give the title compound as acetate salt (14.5 g, 100%). ES-MS: 341 (M+H)$^+$ Intermediate-9 (Compound 112)

This product/intermediate is prepared using Procedure-I with 5-bromotryptamine.HCl (551 mg, 2 mmol), 4-isopropyl benzaldehyde (606 μL, 4 mmol) and 0.1N sulfuric acid (8 mL) to give the title compound as hydrogen sulfate salt (329 mg, 35%). ES-MS: 369 (M+H)$^+$. Alternatively, this intermediate is prepared using Procedure-1B with 5-bromotryptamine.HCl (10 g, 36.3 mmol), 4-isopropyl benzaldehyde (8.24 mL, 54.5 mmol) and acetic acid (120 mL) to give the title compound as acetate salt (13 g, 77%). ES-MS: 369 (M+H)$^+$ Intermediate-10:

This intermediate is prepared using Procedure-I with 5-bromotryptamine.HCl (551 mg, 2 mmol), 3-chloro benzaldehyde (453 μL, 4 mmol) and 0.1N sulfuric acid (8 mL) to give the title compound as an acid salt (662 mg, 72%). ES-MS: 361 (M+H)$^+$ Intermediate-11:

This intermediate is prepared using Procedure-I with 5-bromotryptamine.HCl (551 mg, 2 mmol), p-anisaldehyde (491 μL, 4 mmol) and 0.1N sulfuric acid (8 mL) to give the title compound as an acid salt (611 mg, 67%). ES-MS: 357 (M+H)$^+$ Intermediate-12:

The 4-(2-Morpholin-4-yl-ethoxy)-benzaldehyde reaction intermediate is prepared by combining 4-hydroxybenzaldehyde (1.2 g, 10.0 mmol), 4-(2-chloroethyl)-morpholine hydrochloride (2.0 g, 11.0 mmol), potassium carbonate (4.1 g, 30.0 mmol), and potassium iodide (170 mg, 1 mmol) in 100 ml of acetone and heating to reflux with stirring. After all the 4-hydroxybenzaldehyde is consumed (48 hours by LC/MS), the solids are filtered and the solvent is removed in vacuo. The yield is 4.1 g.

Then Intermediate 12 is prepared in accordance with Procedure-IB. Thus, 5-Chlorotryptamine hydrochloride (231 mg, 1.0 mmol) is combined with 4-(2-Morpholin-4-yl-ethoxy)-benzaldehyde (565 mg, ~1.2 mmol) in 3 mL of glacial acetic acid. The suspension is heated to about 120° C. for 10 minutes with constant cooling and a max power of 300W using the CEM Explorer microwave system. Acetonitrile (2 mL) is added to the cooled reaction mixture, and the solid is filtered and washed with 1 mL of acetonitrile to produce the acetic acid salt of Intermediate 12 (6-Chloro-1-[4-(2-morpholin-4-yl-ethoxy)-phenyl]-2,3,4,9-tetrahydro-1H-β-carboline) (179 mg, 34%).

Intermediates 1-12 may then be used to prepare compounds of the invention according to Procedures II through VII as follows.

Compound 2:

This product is prepared by Procedure-II using the Intermediate-1 (3 g, 9.6 mmol), ethyl chloroformate (1.37 mL, 14.4 mmol) and DIEA (2.5 mL, 14.4 mmol) in dichloromethane (70 mL) to give the title compound as white powder (1.56 g, 42%). ES-MS: 385 (M+H)$^+$.

Compound 4:

This product is prepared by Procedure-II using the Intermediate-7 (72 mg, 0.2 mmol), ethyl chloroformate (29 μL, 0.3 mmol) and DIEA (52 μL, 0.3 mmol) in dichloromethane (2 mL) to give the title compound as white powder (37 mg, 43%). ES-MS: 435 (M+H)$^+$.

Compound 5:

This product is prepared by the Procedure-II using the Intermediate-2 (50 mg, 0.16 mmol), ethyl chloroformate (23 μL, 0.24 mmol) and DIEA (42 μL, 0.24 mmol) in dichloromethane (2 mL) to give the title compound as white powder (25 mg, 41%). ES-MS: 391 (M+H)$^+$.

Compound 7:

This product is prepared by the Procedure-II using the Intermediate-9 (74 mg, 0.2 mmol), ethyl chloroformate (29 μL, 0.3 mmol) and DIEA (52 μL, 0.3 mmol) in dichloromethane (2 mL) to give the title compound as white powder (34 mg, 38%). ES-MS: 441 (M+H)$^+$.

Compound 8:

This product is prepared by the Procedure-II using the Intermediate-8 (72 mg, 0.2 mmol), ethyl chloroformate (29 μL, 0.3 mmol) and DIEA (52 μL, 0.3 mmol) in dichloromethane (2 mL) to give the title compound as white powder (39 mg, 47%). ES-MS: 413 (M+H)$^+$.

Compound 10:

This product is prepared by the Procedure-II using the Intermediate-1 acetate (10.5 g, 28.2 mmol), 4-chlorophenyl chloroformate (4.74 mL, 33.8 mmol) and DIEA (9.8 mL, 56.4 mmol) in dichloromethane (300 mL) to give the title compound as white powder (10.2 g, 78%). ES-MS: 467 (M+H)$^+$.

Compound 11:

This product is prepared by the Procedure-II using the Intermediate-3 (63 mg, 0.2 mmol), ethyl chloroformate (29 μL, 0.3 mmol) and DIEA (52 μL, 0.3 mmol) in dichloromethane (2 mL) to give the title compound as white powder (31 mg, 40%). ES-MS: 389 (M+H)$^+$.

Compound 12:

This product is prepared by the Procedure-II using the Intermediate-4 (31 mg, 0.1 mmol), 2-chloroethyl chloroformate (16 μL, 0.15 mmol) and DIEA (26 μL, 0.15 mmol) in dichloromethane (2 mL) to give the title compound as white powder (22 mg, 53%). ES-MS: 414 (M+H)$^+$.

Compound 17:

This product is prepared by the Procedure-II using the Intermediate-1 (47 mg, 0.15 mmol), 4-methylphenyl chloroformate (33 μL, 0.23 mmol) and DIEA (39 μL, 0.23 mmol) in dichloromethane (2 mL) to give the title compound as white powder (34 mg, 51%). ES-MS: 447 (M+H)$^+$.

Compound 23:

This product is prepared by the Procedure-II using the Intermediate-5 (30 mg, 0.1 mmol), ethyl chloroformate (14 μL, 0.15 mmol) and DIEA (26 μL, 0.15 mmol) in dichloromethane (2 mL) to give the title compound as white powder (21 mg, 56%). ES-MS: 373 (M+H)$^+$.

Compound 25:

This product is prepared by the Procedure-VII using the Intermediate-9 (74 mg, 0.2 mmol), 2-bromopyrimidine (48 mg, 0.3 mmol) and triethylamine (42 µL, 0.3 mmol) in DMF (2 mL) to give the title compound (42 mg, 47%). ES-MS: 447 (M+H)$^+$.

Compound 102:

This product is prepared by the Procedure-IIIb using the Intermediate-9 (74 mg, 0.2 mmol), acetic anhydride (47 µL, 0.5 mmol) and pyridine (41 µL, 0.5 mmol) in dichloromethane (2 mL) to give the title compound as white powder (31 mg, 38%). ES-MS: 411 (M+H)$^+$.

Compound 140:

This product is prepared by the Procedure-IV using the Intermediate-10 (72 mg, 0.2 mmol), cyclohexyl isocyanate (26 µL, 0.2 mmol) and DIEA (37 µL, 0.21 mmol) in dichloromethane (2 mL) to give the title compound as white powder (51 mg, 53%). ES-MS: 486 (M+H)$^+$.

Compound 166:

This product is prepared by the Procedure-Ma using its free amine intermediate (141 mg, 0.5 mmol), Boc-L-Alanine (105 mg, 0.6 mmol), DIC (94 µL, 0.6 mmol), DIEA (105 µL, 0.6 mmol) and dichloromethane (4 mL) to give the title compound (105 mg, 46%). ES-MS: 420 (M+H)$^+$.

Compound 225:

This product is prepared by the Procedure-VI using its free amine intermediate (78 mg, 0.2 mmol), methyl sulfonylchloride (16 µL, 0.2 mmol) and DIEA (37 µL, 0.21 mmol) and dichloromethane (2 mL) to give the title compound (32 mg, 34%). ES-MS: 461 (M+H)$^+$.

Compound 242:

This product is prepared by the Procedure-V using its free amine intermediate (59 mg, 0.2 mmol), cyclohexyl isothiocyanate (29 µL, 0.2 mmol), DIEA (35 µL, 0.2 mmol) and dichloromethane (4 mL) to give the title compound (52 mg, 60%). ES-MS: 438 (M+H)$^+$.

Compound 279:

This product is prepared by generating Intermediate 12 (6-Chloro-1-[4-(2-morpholin-4-yl-ethoxy)-phenyl]-2,3,4,9-tetrahydro-1H-β-carboline) using Procedure-I. Intermediate 12 is then used to generate Compound 279 (6-Chloro-1-[4-(2-morpholin-4-yl-ethoxy)-phenyl]-1,3,4,9-tetrahydro-b-carboline-2-carboxylic acid ethyl ester) using Procedure-II.

In accordance with Procedure-II, Intermediate 12 (82 mg, 0.20 mmol), ethyl chloroformate (24 mg, 21 µL, 0.22 mmol), and diisopropylethylamine (175 µL, 1.00 mmol) are dissolved in methylene chloride (2 mL) and stirred at room temperature for 15 minutes to form Compound 279. The solvent is removed under a stream of nitrogen. The crude mixture is purified by preparative reversed phase HPLC on a C-18 column using a gradient of acetonitrile in water buffered with 0.2% trifluoroacetic acid (TFA). The TFA salt of Compound 279 (3.7 mg, 3%) is isolated as a yellow solid. The same procedure may be applied for other carbamate formation reactions according to Procedure-II.

Compound 320:

This product/intermediate is prepared using Procedure-I with 5-benzyloxy tryptamine.HCl (100 mg, 0.33 mmol), pyridine-3-carboxaldehyde (62 µL, 0.66 mmol) and 0.1N sulfuric acid (2 mL) to give the title compound as dihydrogen sulfate salt (64 mg, 55%). ES-MS: 356 (M+H)$^+$ Compound 329:

This product is prepared by the Procedure-VII using the Intermediate-11 (71 mg, 0.2 mmol), 2-bromopyrimidine (48 mg, 0.3 mmol) and triethylamine (42 µL, 0.3 mmol) in DMF (2 mL) to give the title compound (41 mg, 49%). ES-MS: 434 (M+H)$^+$.

Compound 330:

This product is prepared by the Procedure-II using the Intermediate-6 (65 mg, 0.2 mmol), 2-fluoroethyl chloroformate (38 µL, 0.3 mmol) and DIEA (70 µL, 0.4 mmol) in dichloromethane (2 mL) to give the title compound as white powder (34 mg, 41%). ES-MS: 415 (M+H)$^+$.

Compound 332:

This product is prepared by the Procedure-II using the Intermediate-7 (36 mg, 0.1 mmol), 4-methoxyphenyl chloroformate (22 µL, 0.15 mmol) and DIEA (26 µL, 0.15 mmol) in dichloromethane (2 mL) to give the title compound as white powder (41 mg, 81%). ES-MS: 511 (M+H)$^+$.

Example 1B

Certain Starting Materials, Scheme Ia

Scheme Ia can be used when in conjunction with Scheme I (above) to generate starting materials when $R_2$ is a —$CH_2$-furanyl group, as follows.

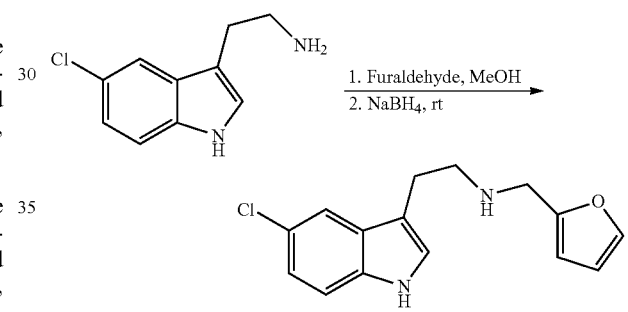

2-furaldehyde (0.05 mL, 1.1 eq) is added to a solution of 5-chlorotryptamine (114 mg, 0.586 mmol) in 2 mL of MeOH. The reaction mixture is stirred at room temperature for about 1 hour. NaBH$_4$ (110 mg, 5 eq) is added slowly. The reaction mixture is stirred at room temperature for about 30 min. MeOH is evaporated and the residue is partitioned between water and methylene chloride. The organic layer is separated and dried over K$_2$CO$_3$. The collected organic layer is concentrated to give 134.9 mg of viscous oil (84%).

Example 1C

Compounds of Formula I, Scheme Ib

Alternatively, certain compounds of Formula I may be prepared according to Scheme Ib as follows.

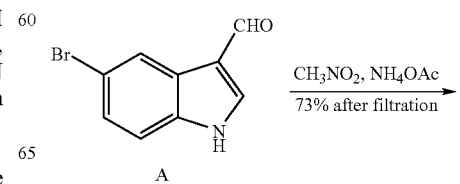

A

-continued

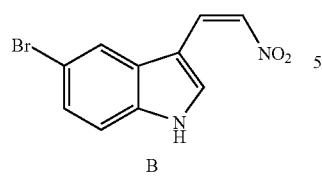

B

A suspension of reaction material A (8.05 g, 35.9 mmol) and CH$_3$COONH$_4$ (4.15 g, 1.5 eq) in 60 mL of CH$_3$NO$_2$ is refluxed in oil bath at about 110° C. After about 30 minutes, the reaction mixture is cooled with ice-bath. The precipitated solid is filtered and washed with water (3×100 mL), followed by hexane (2×50 mL) to give crude indole product B. The collected solid is dried under vacuum at about 40° C. for about 30 min to give 6.97 g of brown solid (73%).

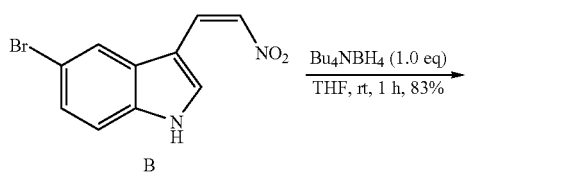

C

A solution of indole product B (12.32 g, 46.1 mmol) in THF (130 mL) is then treated with a solution of tetrabutylammonium borohydride (11.9 g, 1 eq) in 75 mL of THF slowly for about 60 minutes at about −5° C. The reaction is stirred at room temperature for about 1 hour and diluted with dichloromethane (200 mL). The organic layer is washed with water twice and brine. The combined organic layers are dried and evaporated under vacuum. The residue is purified on silica gel to give 10.28 g of solid C (83%).

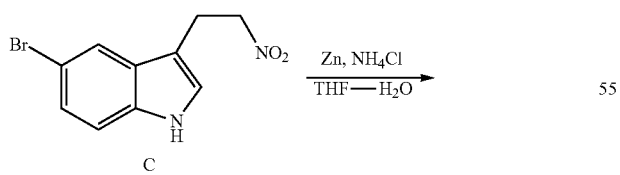

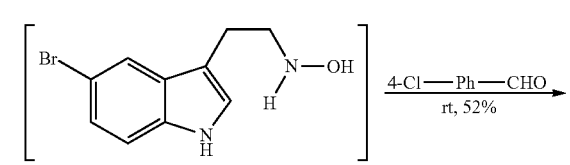

-continued

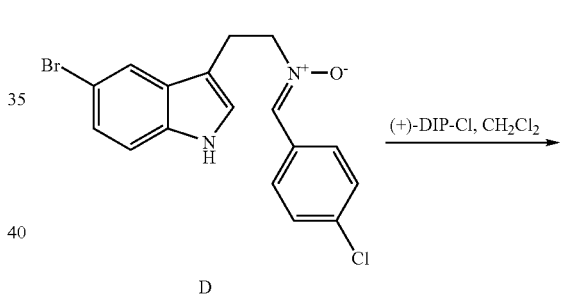

D

Ammonium chloride (9.9 mL of aqueous solution (100 mg/mL), 2 eq) and Zn (725 mg, 1.2 eq) are then added to a solution of indole product C (2.49 g, 9.24 mmol) in 161 mL of THF. The reaction mixture is stirred at room temperature for about 10 min and Zn (725 mg, 1.2 eq) is then added. After about 30 min, additional Zn (967 mg, 1.6 eq) is added and stirred for about 2 hours, followed by the addition of further Zn (845 mg, 1.4 eq). After stirring at room temperature for about 15 min, Zn is filtered off and the residue is concentrated and dissolved in THF. The resulting solution is then treated with p-chlorobenzaldehyde (0.7 eq) and stirred at room temperature for about 15 hours. The reaction mixture is concentrated under vacuum and purified on silica gel to give 953.5 mg of the desired nitrone product D.

D

E (+)-DIP-Cl (6.93 mL, 2 eq, 85.8 mg/mL in CH$_2$Cl$_2$) is then added to a solution of nitrone product D (350 mg, 0.93 mmol) in 60 mL of dichloromethane. The reaction mixture is stirred at about −78° C. for about 10 days and quenched with a mixture of 10% NaHCO$_3$ (7 mL) and 10 mL of water. The aqueous layer is extracted with dichloromethane three times. Combined organic layers are concentrated and purified on silica gel to give the desired hydroxylamine product E (>98% ee).

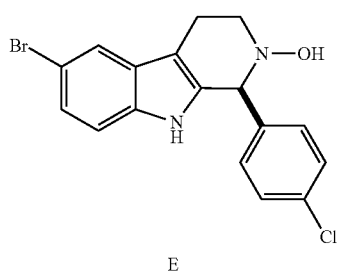

E

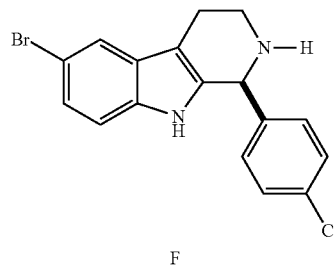

F

Water (11.5 mL), NH$_4$Cl (2.5 mL, 5 eq) and Zn (908 mg, 15 eq) are then added to a solution of hydroxylamine product E (0.927 mmol) in THF (28 mL). The reaction mixture is stirred at room temperature for about 1 day. Additional THF (10 mL), NH$_4$Cl (5 mL, 10 eq) and Zn (1.8 g, 30 eq) are then added and stirred for about another 21 hours. Again, THF (10 mL), NH4Cl (5 mL, 10 eq) and Zn (1.8 g, 30 eq) are added and stirred for about another 20 hours. The reaction mixture is then filtered through celite and washed with MC. The collected dichloromethane layer is washed with water and brine. The organic layer is dried and concentrated to give a boron complex of beta-carboline. This product is dissolved in 20 mL of THF. This solution is loaded into prepacked cation exchange resin (preconditioned with MeOH and THF) and washed with THF. The combined THF solution is concentrated to give 390 mg of free amine. The solid is then washed with ether and hexane consecutively to yield 130 mg of the enantiomerically pure compound F.

Example 1D

Compounds of Formula I, Scheme II

Compounds of Formula I-h may be prepared according to Scheme II as follows.

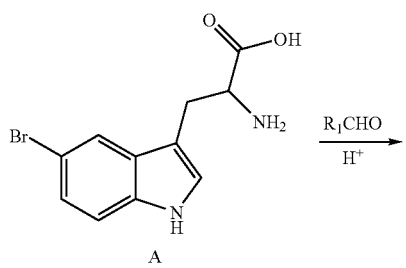

A

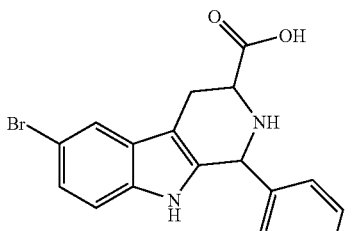

B

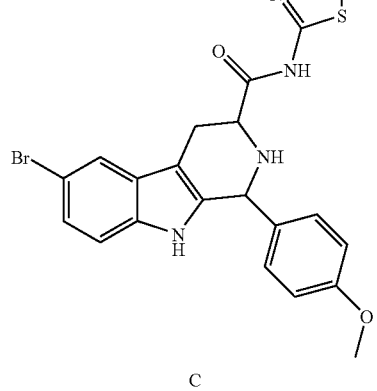

C p-anisaldehyde (2.16 g, 15.9 mmol, 1.93 mL) is added to a suspension of 5-Bromotryptophan A (3 g, 10.6 mmol) in 100 mL of Acetic acid at room temperature. The reaction mixture is then heated to reflux at about 125° C. in silicon oil bath and maintained at that temperature for about 3 hours 20 minutes. The resultant solution is concentrated under vacuum. The residue is triturated with dichloromethane, diethyl ether and hexane to yield a powdery brown solid. The acetic salts of the intermediate product B is collected and washed with hexane three times.

The intermediate product B is suspended (70 mg, 0.174 mmol) in 2 mL of dichloromethane, and triethylamine (52.8 mg, 0.522 mmol), 5-methyl-2-aminothiazole (37.6 mg, 0.26 mmol) and PyBOP (135.8 mg, 0.26 mmol) is added to the suspension. The reaction mixture is stirred at room temperature for about 6 hour and quenched with sat. NaHCO$_3$ solution. The aqueous layer is extracted with dichloromethane. The combined organic layers are dried over K$_2$CO$_3$ and concentrated. Purification on silica gel with 40% ethyl acetate in hexane yields 8.1 mg of the desired amide C. LCMS [MH$^+$] 498, Rt=2.54.

Example 1E

Compounds of Formula I, Scheme III

Compounds of Formula I-i may be prepared according to Scheme III as follows.

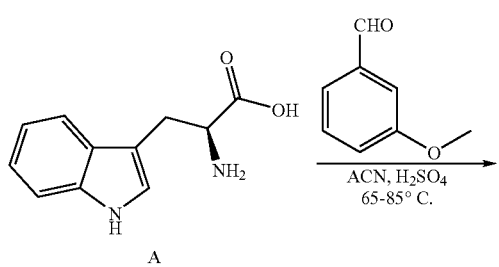

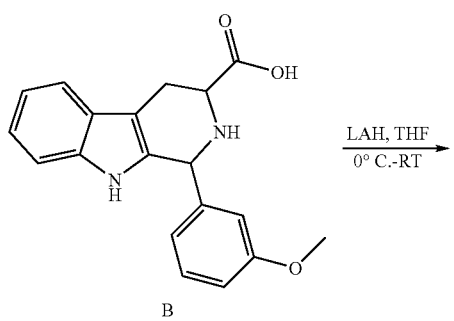

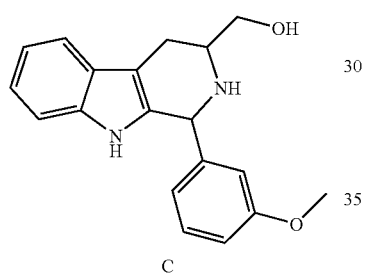

Tryptophan A (1.0 g, 5.0 mmol) and 3-methoxybenzaldehyde (670 µL, 5.5 mmol) are suspended/dissolved in acetonitrile (100 mL) and concentrated sulfuric acid (100 µL) is added. The reaction is heated to reflux until all the aldehyde was consumed (overnight). The solvent was removed in vacuo and the residue was dissolved in 5 mL of ethanol. The product was precipitated out with ether, filtered, and washed with 10 mL of ether. The desired β-carboline product/intermediate B (1-(3-Methoxy-phenyl)-2,3,4,9-tetrahydro-1H-β-carboline-3-carboxylic acid) is isolated as a beige solid (1.2 g, 76%). LC/MS RT=2.33 min. M/Z+323, 100%.

The β-carboline product/intermediate B (200 mg, 0.62 mmol) is then dissolved in 5 mL of dry THF and cooled to about 0° C. Lithium aluminum hydride (LAH) solution (1.2 mL, 1.0M in ether, 1.2 mmol) is added to the cooled reaction mixture under nitrogen. After the addition is complete (about 10 minutes), the reaction is allowed to warm to room temperature for about 4 hours. The reaction mixture is then cooled back to 0° C., and saturated sodium sulfate solution (750 µL) is added and the mixture stirred for about 5 minutes at 0° C. The reaction mixture is then filtered and washed with THF (100 mL). The solvent is removed in vacuo, and the crude product purified by preparative HPLC. The product C ([1-(3-Methoxy-phenyl)-2,3,4,9-tetrahydro-1H-b-carbolin-3-yl]-methanol) is isolated as a white solid (106 mg, 55%). LC/MS RT=2.25 min. M/Z+309, 100%.

Example 1F

Chemical Resolution of Compounds of the Invention

Compounds of the invention may optionally be chemical resolved to enantiomerically pure compositions, preferably enantiomerically pure (S) isomer compositions as follows.

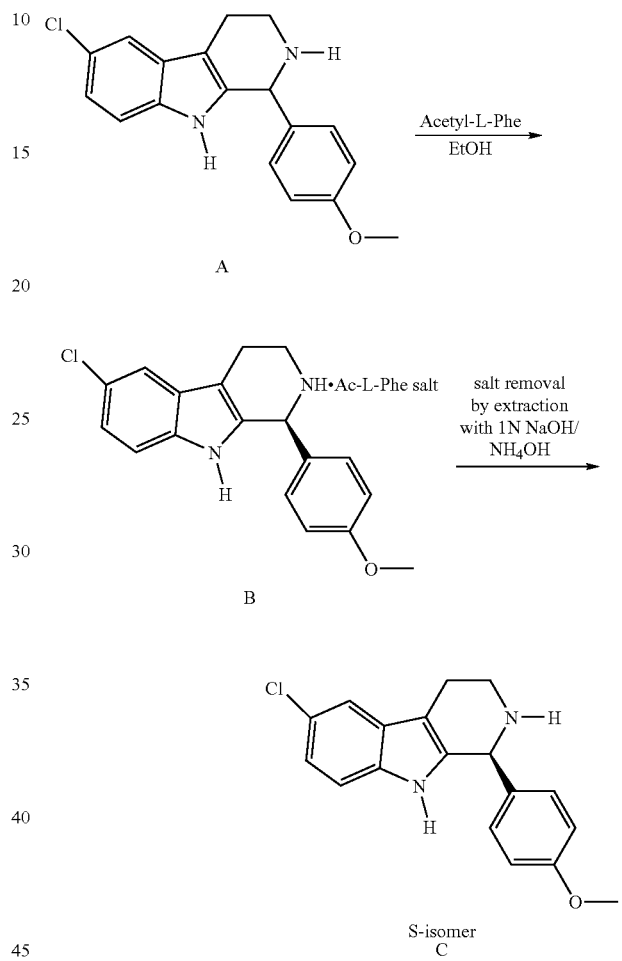

The racemic amine A (18.21 g, 58.2 mmol) is mixed with N-acetyl-L-phenylalanine (12.05 g, 58.2 mmol) in EtOH (1.28 L) and refluxed to get a clear solution. The solution is then allowed to cool to room temperature. After overnight standing, the precipitated solid is filtered and washed with EtOH (200 mL) to give the salt B (16.4 g). The salt B is taken in EtOAc (500 mL) and washed with aqueous 1N NaOH (300 mL×2) or NH₄OH (200 mL×2), dried and evaporated to give the S-isomer of the free amine C (7.4 g). The R-isomer is prepared by similar procedure using N-acetyl-D-phenylalanine.

Example 1G

Further Exemplary Compounds of the Invention

By way of further non-limiting example, the following compounds (Table 5) may be prepared by similar methodology to that described above, as will be recognized by one of skill in the art.

TABLE 5
| Compound | NMR | Mass Spec (LCMS) | Reten. Time (min) |
|---|---|---|---|
| 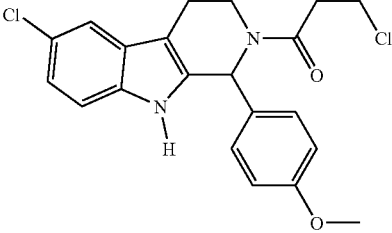 367 | (CDCl3, 400 MHz), δ 8.16 (s, 1H), 7.48 (s, 1H), 7.22 (d, J = 8.8 Hz, 1H), 7.19 (d, J = 8.8 Hz, 2H), 7.13 (d, J = 8.8 Hz, 1H), 6.94 (s, 1H), 6.80 (d, J = 8.8 Hz, 2H), 3.92-3.91 (m, 1H), 3.86 (t, J = 7.2 Hz, 2H), 3.77 (s, 3H), 3.46-3.39 (m, 1H), 3.11-3.09 (m, 1H), 2.91-2.83 (m, 3H) | 402.8 | 4.37 |
| 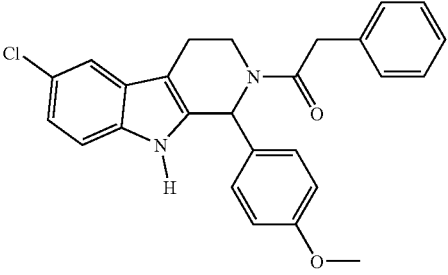 368 | (CDCl3, 400 MHz), δ 8.29 (s, 1H), 7.47-7.09 (m, 10H), 6.98 (s, 1H), 6.77 (d, J = 8.8 Hz, 2H), 3.93 (dd, J = 13.6 Hz and 4.8 Hz, 1H), 3.82-3.80 (m, 2H), 3.77 (s, 3H), 3.38-3.30 (m, 1H), 2.69-2.65 (m, 1H), 2.53-2.45 (m, 1H) | 430.9 | 4.79 |
| 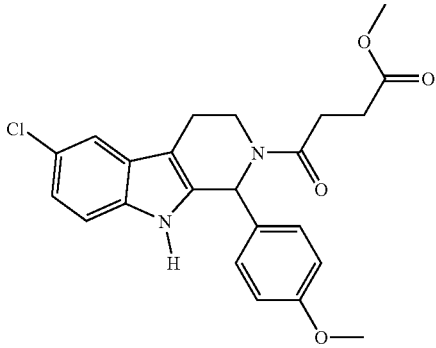 369 | (CDCl3, 400 MHz), δ 8.21 (s, 1H), 7.46 (s, 1H), 7.22 (d, J = 8.4 Hz, 1H), 7.17 (d, J = 8.4 Hz, 2H), 7.12 (dd, J = 8.4 Hz and 2.0 Hz, 1H), 6.92 (s, 1H), 6.77 (d, J = 8.4 Hz, 2H), 3.94 (dd, J = 13.2 Hz and 4.4 Hz, 1H), 3.76 (s, 3H), 3.65 (s, 3H), 3.43-3.35 (m, 1H), 2.87-2.62 (m, 6H) | 427.0 | 4.06 |
| 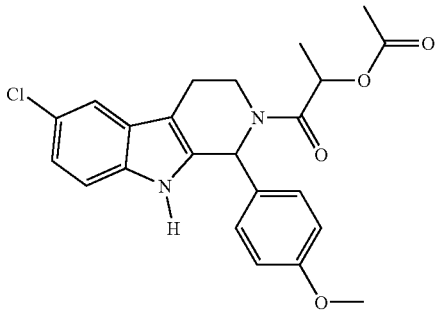 370 | (CDCl3, 400 MHz), δ 8.23, 8.12 (s, 1H), 7.48, 7.42 (d, J = 1.6 Hz, 1.2 Hz, 1H), 7.22-7.10 (m, 4H), 6.94, 6.88 (s, 1H), 6.79 (d, J = 8.8 Hz, 2H), 5.48-5.45 (m, 1H), 3.96-3.80 (m, 1H), 3.77 (s, 3H), 3.47-3.36 (m, 1H), 3.08-2.77 (m, 2H), 2.14, 2.09 (s, 3H), 1.48, 1.41 (d, J = 6.8 Hz, 6.4 Hz, 3H) | 427.0 | 3.99 |

TABLE 5-continued
| Compound | NMR | Mass Spec (LCMS) | Reten. Time (min) |
|---|---|---|---|
| 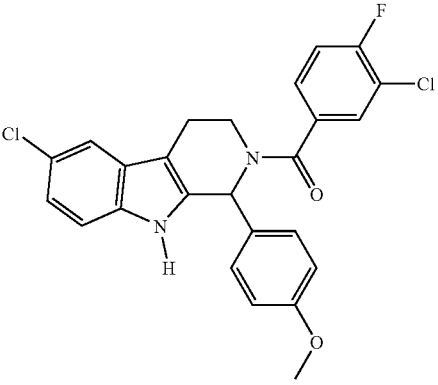 371 | (CDCl3, 400 MHz), δ 7.87 (s, 1H), 7.51 (s, 1H), 7.47 (dd, J = 6.8 Hz and 1.6 Hz, 1H), 7.30-7.15 (m, 6H), 6.98 (b, 1H), 6.76 (d, J = 8.8 Hz, 2H), 3.80 (s, 3H), 3.77-3.74 (m, 1H), 3.49-3.39 (m, 1H), 2.93-2.82 (m, 2H) | 469.0 | 5.27 |
| 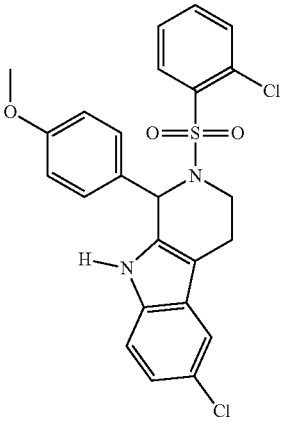 372 | (CDCl3, 400 MHz), δ 8.07 (dd, J = 7.6 Hz and 1.2 Hz, 1H), 7.74 (s, 1H), 7.45-7.32 (m, 4H), 7.18 (d, J = 8.4 Hz, 1H), 7.12 (dd, J = 8.8 Hz and 2.0 Hz, 1H), 7.07 (d, J = 8.4 Hz, 2H), 6.76 (d, J = 8.8 Hz, 2H), 6.35 (s, 1H), 3.97 (dd, J = 14.8 Hz and 5.2 Hz, 1H), 3.77 (s, 3H), 3.49-3.41 (m, 1H), 2.67 (dd, J = 15.6 Hz and 3.2 Hz, 1H), 2.57-2.53 (m, 1H) | 486.9 | 4.96 |
| 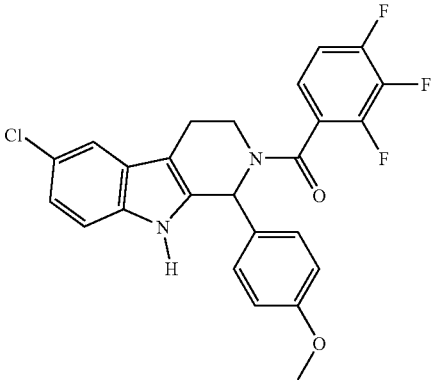 373 | (CDCl3, 400 MHz), δ 7.95 (s, 1H), 7.48 (s, 1H), 7.30 (d, J = 8.4 Hz, 2H), 7.23 (d, J = 8.8 Hz, 1H), 7.16 (dd, J = 8.8 Hz and 1.6 Hz, 1H), 7.05 (b, 3H), 6.86 (d, J = 8.4 Hz, 2H), 3.80 (s, 3H), 3.61 (dd, J = 13.6 Hz and 5.2 Hz, 1H), 3.52-3.44 (m, 1H), 2.91-2.88 (m, 1H), 2.78 (dd, J = 15.2 Hz and 3.2 Hz, 1H) | 470.8 | 5.01 |

TABLE 5-continued

| Compound | NMR | Mass Spec (LCMS) | Reten. Time (min) |
|---|---|---|---|
| 374 | (CDCl3, 400 MHz), δ 8.09 (s, 1H), 7.45 (s, 1H), 7.21-7.17 (m, 4H), 7.12 (d, J = 8.8 Hz, 1H), 6.98 (s, 1H), 6.91 (d, J = 4 Hz, 1H), 6.80 (s, 1H), 6.79 (d, J = 8.4 Hz, 2H), 3.99 (s, 2H), 3.96 (d, J = 4.4 Hz, 1H), 3.77 (s, 3H), 3.43-3.38 (m, 1H), 2.77-2.63 (m, 2H) | 436.9 | 4.66 |
| 375 | (CDCl3, 400 MHz), δ 8.19, 8.16 (s, 1H), 7.48, 8.42 (s, 1H), 7.24-7.09 (m, 6H), 6.94 (t, J = 7.8 Hz, 2H), 6.85 (t, J = 8.2 Hz, 2H), 6.77 (d, J = 8.4 Hz, 1H), 6.72 (d, J = 8.4 Hz, 1H), 5.09-4.98 (m, 1H), 4.39-4.17 (m, 1H), 3.77, 3.75 (s, 3H), 3.41-3.28 (m, 1H), 3.02-2.65 (m, 2H), 1.61-1.59 (m, 3H) | 461 | 4.92 |
| 376 | (CDCl3, 400 MHz), δ 8.39 (s, 1H), 7.48 (s, 1H), 7.23 (d, J = 8.4 Hz, 1H), 7.19 (d, J = 8.4 Hz, 2H), 7.13 (dd, J = 8.8 Hz and 1.6 Hz, 1H), 6.89 (s, 1H), 6.77 (d, J = 8.4 Hz, 2H), 4.17 (q, J = 12.8 Hz, 2H), 3.88 (d, J = 10 Hz, 1H), 3.75 (s, 3H), 3.41 (s, 3H), 3.38-3.34 (m, 1H), 2.95-2.81 (m, 2H) | 385 | 3.79 |
| 389 | (CD3OD, 400 MHz), δ 7.48-7.46 (m, 4H), 7.35 (b, 1H), 7.23 (d, J = 8.8 Hz, 1H), 7.07 (dd, J = 8.8 Hz and 2.0 Hz, 1H), 6.46 (b, 1H), 4.35-4.14 (m, 5H), 3.52-3.47 (m, 2H), 3.22-3.19 (m, 7H), 2.98-2.93 (m, 3H), 2.89 (s, 6H), 2.67-2.63 (m, 5H), 2.06-1.96 (m, 2H), 1.31 (t, J = 7.2 Hz, 3H) | 538.3 | 4.29 |

TABLE 5-continued

| Compound | NMR | Mass Spec (LCMS) | Reten. Time (min) |
|---|---|---|---|
| 393 | (DMSO, 400 MHz), δ 11.00 (s, 1H), 8.47 (s, 2H), 7.67 (s, 1H), 7.26 (d, J = 8.4 Hz, 1H), 7.19 (dd, J = 8.8 Hz and 2.0 Hz, 1H), 6.26 (b, 1H), 4.25 (b, 1H), 4.11 (t, J = 6.8 Hz, 2H), 3.22-3.17 (m, 1H), 2.86-2.81 (m, 1H), 2.77-2.66 (m, 1H), 2.50 (b, 3H), 1.21 (t, J = 6.8 Hz, 3H) | 447.1 | 6.55 |
| 394 | (CD3OD, 400 MHz), δ 8.43-8.41 (m, 4H), 7.63 (d, J = 1.2 Hz, 1H), 7.22 (d, J = 8.8 Hz, 1H), 7.19 (dd, J = 8.4 Hz and 1.6 Hz, 1H), 7.04 (s, 1H), 6.67 (t, J = 4.8 Hz, 1H), 5.01 (dd, J = 14.0 Hz and 3.6 Hz, 1H), 3.29-3.26 (m, 1H), 3.21 (s, 6H), 2.91-2.86 (m, 2H) | 450.1 | 5.48 |
| 410 | (DMSO, 400 MHz), δ 11.15, 11.05 (b, 1H), 7.53 (d, J = 1.6 Hz, 1H), 7.29 (d, J = 8.8 Hz, 1H), 7.20-7.18 (m, 6H), 7.06 (dd, J = 8.8 Hz and 2 Hz, 1H), 6.93 (d, J = 7.2 Hz, 2H), 6.45-6.37 (m, 1H), 4.30 (b, 1H), 3.72 (s, 3H), 3.18 (b, 1H), 2.82 (b, 2H) | 451.3 | 3.99 |
| 416 HCl salt | (CD3OD, 400 MHz), δ 10.98 (b, 1H), 7.49 (d, J = 2.0 Hz, 1H), 7.34-7.30 (m, 5H), 7.25-7.21 (m, 1H), 7.13 (dd, J = 8.8 Hz and 2.0 Hz, 1H), 4.81-4.79 (m, 1H), 3.82-3.76 (m, 1H), 3.54-3.49 (m, 1H), 3.11-3.07 (m, 2H), 2.91-2.87 (m, 2H), 2.59-2.55 (m, 1H), 2.24-2.20 (m, 1H) | 311.1 | 4.39 |
| 420 | (CD3OD, 400 MHz), δ 7.61 (s, 1H), 7.46 (d, J = 8.0 Hz, 2H), 7.38 (d, J = 8.0 Hz, 2H), 7.19 (s, 2H), 6.47 (s, 1H), 4.32-4.19 (m, 5H), 3.62 (t, J = 3.9 Hz, 2H), 3.42 (s, 1H), 3.19-3.10 (m, 3H), 2.29-2.76 (m, 2H), 1.30 (s, 3H) | 486.6 | 3.45 |

TABLE 5-continued
| Compound | NMR | Mass Spec (LCMS) | Reten. Time (min) |
|---|---|---|---|
| 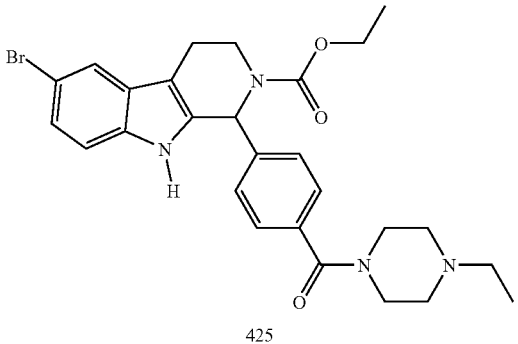 [SMILES: CCOC(=O)N1CCc2c([nH]c3ccc(Br)cc23)C1c1ccc(C(=O)N2CCN(CC)CC2)cc1] 425 | (CD3OD, 400 MHz), δ 7.63 (s, 1H), 7.49 (d, J = 8.4 Hz, 2H), 7.42 (d, J = 8.4 Hz, 2H), 7.19 (s, 2H), 6.49 (b, 1H), 4.34-4.19 (m, 4H), 3.60 (b, 4H), 3.29-3.17 (m, 6H), 2.89-2.75 (m, 2H), 1.36 (t, J = 7.2 Hz, 3H), 1.30 (b, 3H) | 539.2 | 3.11 |
| 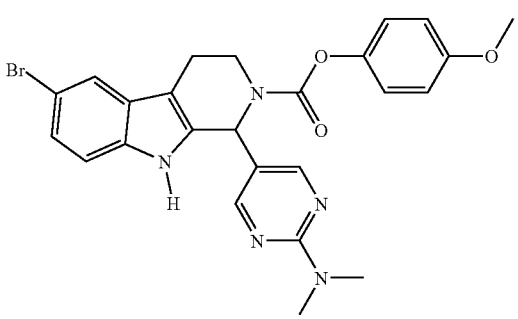 431 | (CDCl3, 400 MHz), δ 8.56 (b, 1H), 8.40 (b, 2H), 7.68 (s, 1H), 7.28 (d, J = 2.0 Hz, 1H), 7.14 (d, J = 8.4 Hz, 1H), 7.00 (d, J = 8.2 Hz, 2H), 6.80 (d, J = 8.4 Hz, 2H), 6.48-6.38 (m, 1H), 4.55-4.52 (m, 1H), 3.81-3.74 (m, 4H), 3.24 (s, 6H), 3.00-2.91 (m, 1H), 2.88-2.84 (m, 1H) | 522.2 | 5.05 |
| 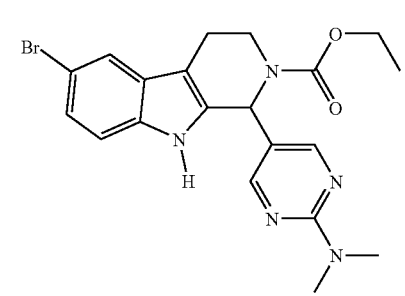 435 | (DMSO, 400 MHz), δ 11.00 (s, 1H), 8.14 (s, 2H), 7.64 (s, 1H), 7.23 (d, J = 8.4 Hz, 1H), 7.18 (d, J = 8.8 Hz, 1H), 6.14 (s, 1H), 4.23 (b, 1H), 4.11-4.08 (m, 2H), 3.14-3.10 (m, 1H), 3.08 (s, 6H), 2.81-2.77 (m, 1H), 2.70-2.66 (m, 1H), 1.21 (t, J = 6.8 Hz, 3H) | 444.3 | 3.95 |
| 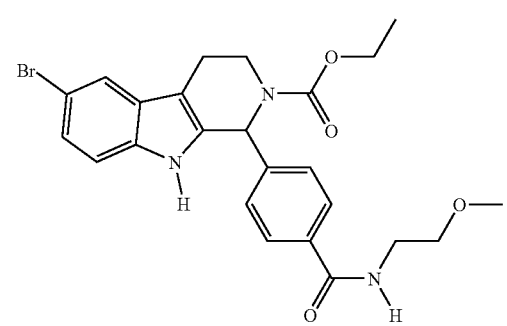 438 | (CD3OD, 400 MHz), δ 7.79 (d, J = 8.4 Hz, 2H), 7.63 (s, 1H), 7.37 (d, J = 8.4 Hz, 2H), 7.20 (s, 2H), 6.51 (b, 1H), 4.32-4.22 (m, 3H), 3.54 (s, 3H), 3.36 (s, 2H), 3.30 (s, 2H), 3.21-3.11 (m, 1H), 2.90-2.77 (m, 2H), 1.32 (s, 3H) | 500.1 | 4.35 |

TABLE 5-continued

| Compound | NMR | Mass Spec (LCMS) | Reten. Time (min) |
|---|---|---|---|
| 439 | (CDCl3, 400 MHz), δ 7.98, 7.81 (s, 1H), 7.42 (s, 1H), 7.21 (d, J = 8.4 Hz, 1H), 7.11 (d, J = 8.4 Hz, 1H), 5.40-5.23 (m, 3H), 4.55-4.35 (m, 1H), 4.20-4.11 (m, 2H), 3.24-3.13 (m, 1H), 2.79-2.63 (m, 2H), 2.22 (d, J = 6.8 Hz, 2H), 2.08 (b, 2H), 1.89-1.81 (m, 2H), 1.30 (b, 3H), 0.97 (b, 3H) | 361.2 | 5.95 |
| 441 | (CD3OD, 400 MHz), δ 7.47 (d, J = 1.6 Hz, 1H), 7.43 (d, J = 7.6 Hz, 2H), 7.37 (d, J = 8.0 Hz, 2H), 7.24 (d, J = 8.8 Hz, 1H), 7.06 (dd, J = 8.4 Hz and 1.6 Hz, 1H), 6.49 (b, 1H), 4.35-4.21 (m, 3H), 3.83 (s, 4H), 3.19-3.10 (m, 1H), 2.90-2.79 (m, 2H), 1.57 (b, 6H), 1.32 (s, 3H) | 482.1 | 5.11 |
| 442 | (CDCl3, 400 MHz), δ 8.48-8.09 (m, 1H), 7.44-7.42 (m, 1H), 7.24 (t, J = 9 Hz, 1H), 7.11-7.09 (m, 1H), 5.59-5.40 (m, 1H), 4.54-4.34 (m, 1H), 4.21-4.18 (m, 2H), 3.23-3.13 (m, 1H), 2.87-2.81 (m, 2H), 2.76-263 (m, 1H), 2.17 (s, 3H), 2.12-1.90 (m, 2H), 1.42-1.24 (m, 6H) | 367.1 | 2.92 |
| 443 | (CD3OD, 400 MHz), δ 8.62 (d, J = 4.4 Hz, 2H), 8.59 (s, 2H), 7.84 (s, 1H), 7.43-7.39 (m, 2H), 7.24 (s, 1H), 6.88 (t, J = 8.0 Hz, 1H), 5.24-5.20 (m, 1H), 3.47-3.44 (m, 1H), 3.16 (s, 3H), 3.11-3.05 (m, 2H) | 436.2 | 5.25 |

TABLE 5-continued
| Compound | NMR | Mass Spec (LCMS) | Reten. Time (min) |
|---|---|---|---|
| 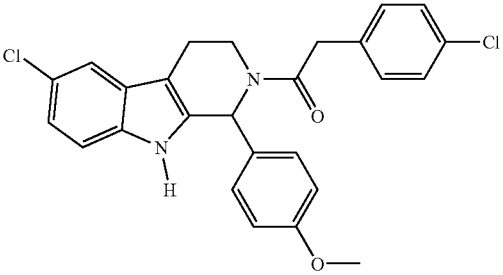 447 | (CDCl3, 400 MHz), δ 8.12 (s, 1H), 7.45 (s, 1H), 7.26 (d, J = 8 Hz, 2H), 7.18 (d, J = 8.8 Hz, 2H), 7.14-7.12 (m, 4H), 6.97 (s, 1H), 6.78 (d, J = 8.8 Hz, 2H), 3.89 (dd, J = 14 Hz and 1.2 Hz, 1H), 3.80-3.78 (m, 5H), 3.41-3.33 (m, 1H), 2.73 (dd, J = 15.2 Hz and 3.2 Hz, 1H), 2.64-2.60 (m, 1H) | 464.9 | 5.11 |
| 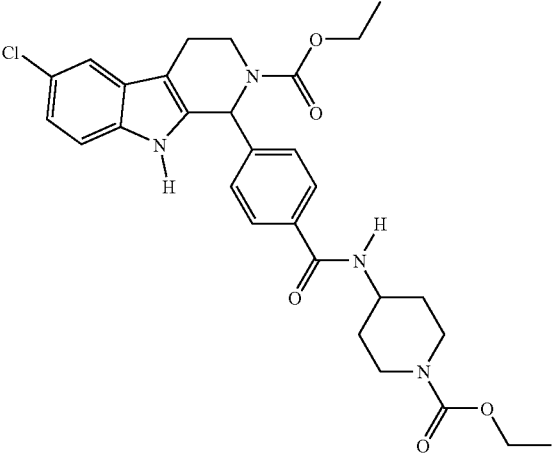 453 | (CD3OD, 400 MHz), δ 7.78 (d, J = 8.0 Hz, 2H), 7.47 (d, J = 1.6 Hz, 1H), 7.37 (d, J = 8.0 Hz, 2H), 7.24 (d, J = 8.4 Hz, 1H), 7.06 (dd, J = 8.8 Hz and 1.6 Hz, 1H), 6.49 (b, 1H), 4.31-4.05 (m, 8H), 3.20-3.11 (m, 1H), 3.00-2.77 (m, 4H), 1.94-1.90 (m, 2H), 1.54-1.45 (m, 2H), 1.31 (b, 3H), 1.25 (t, J = 7.2 Hz, 3H) | 553.1 | 6.13 |
| 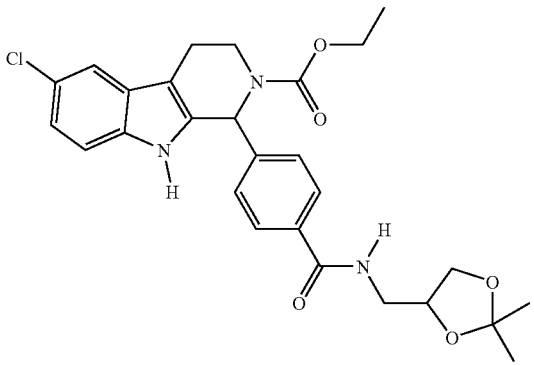 461 | (CD3OD, 400 MHz), δ 7.80 (d, J = 8.0 Hz, 2H), 7.48 (d, J = 1.6 Hz, 1H), 7.38 (d, J = 8.4 Hz, 2H), 7.25 (d, J = 8.8 Hz, 1H), 7.07 (dd, J = 8.4 Hz and 1.6 Hz, 1H), 6.49 (b, 1H), 4.31-4.21 (m, 4H), 4.06 (t, J = 8.4 Hz, 1H), 3.74 (t, J = 8.0 Hz, 1H), 3.51 (d, J = 5.2 Hz, 2H), 3.21-3.11 (m, 1H), 2.90-2.79 (m, 2H), 2.26 (s, 1H), 1.39 (s, 3H), 1.32 (s, 6H) | 454.3 | 5.98 |

TABLE 5-continued

| Compound | NMR | Mass Spec (LCMS) | Reten. Time (min) |
|---|---|---|---|
| 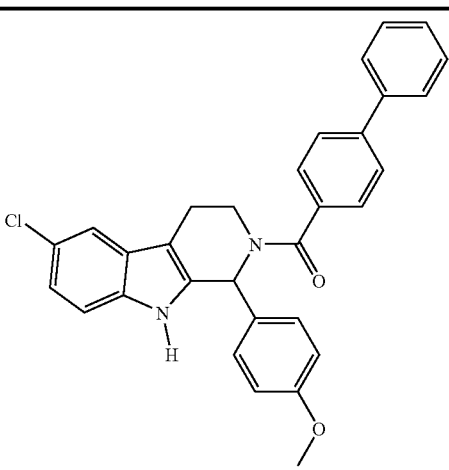<br>464 | (CDCl3, 400 MHz), δ 8.29 (b, 1H), 7.64 (d, J = 8.0 Hz, 2H), 7.61 (d, J = 7.2 Hz, 2H), 7.50-7.45 (m, 5H), 7.39 (d, J = 7.6 Hz, 1H), 7.33 (d, J = 7.6 Hz, 2H), 7.19 (d, J = 8.8 Hz, 1H), 7.14 (dd, J = 8.4 Hz and 1.6 Hz, 1H), 7.08 (s, 1H), 6.84 (d, J = 8 Hz, 2H), 3.87 (d, J = 9.2 Hz, 1H), 3.79 (s, 3H), 3.45-3.40 (m, 1H), 2.96-2.94 (m, 1H), 2.80-2.76 (m, 1H) | 493.0 | 5.71 |
| 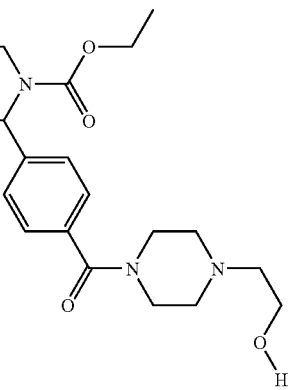<br>466 | (CD3OD, 400 MHz), δ 7.63 (s, 1H), 7.48 (d, J = 8.4 Hz, 2H), 7.42 (d, J = 8.0 Hz, 2H), 7.20 (s, 2H), 6.49 (b, 1H), 4.33-4.22 (b, 3H), 3.89 (t, J = 5.2 Hz, 2H), 3.50 (b, 4H), 3.21-3.11 (m, 2H), 2.91-2.78 (m, 2H), 1.31 (s, 3H) | 555.2 | 3.14 |
| 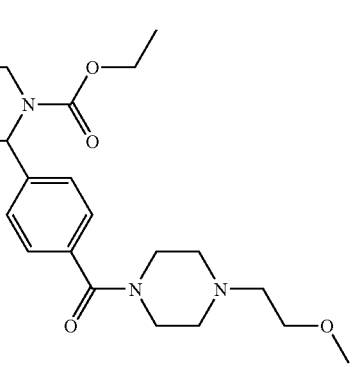<br>469 | (CD3OD, 400 MHz), δ 7.47 (d, J = 2.0 Hz, 1H), 7.39 (s, 4H), 7.23 (d, J = 8.8 Hz, 1H), 7.06 (dd, J = 8.4 Hz and 2.0 Hz, 1H), 6.49 (b, 1H), 4.35-4.21 (m, 3H), 3.75 (b, 2H), 3.53 (t, J = 5.4 Hz, 2H), 3.44 (b, 2H), 3.26-3.30 (m, 4H), 3.22-3.13 (m, 1H), 2.89-2.78 (m, 2H), 2.60 (t, J = 5.4 Hz, 4H), 2.46 (b, 2H), 1.32 (s, 3H) | 525.2 | 5.07 |
| 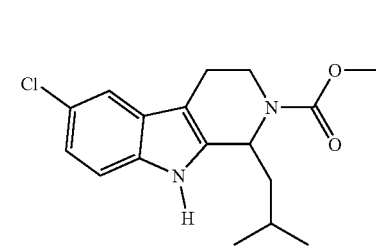<br>472 | (CDCl3, 400 MHz), δ 7.80, 7.75 (s, 1H), 7.43, 7.41 (s, 1H), 7.21 (d, J = 8.4 Hz, 1H), 7.10 (d, J = 8.0 Hz, 1H), 5.43, 5.27 (d, J = 7.2 Hz, 1H), 4.51-4.30 (m, 1H), 4.21-4.10 (m, 2H), 3.18 (q, J = 12.8 Hz, 1H), 2.82-2.76 (m, 1H), 2.64-2.61 (m, 1H), 1.82-1.76 (m, 2H), 1.55-1.53 (m, 1H), 1.29-1.24 (m, 3H), 1.08 (b, 3H), 0.98 (d, J = 6.8 Hz, 3H) | 335.3 | 5.52 |

TABLE 5-continued

| Compound | NMR | Mass Spec (LCMS) | Reten. Time (min) |
|---|---|---|---|
| 473 | (CD3OD, 400 MHz), δ 7.47 (d, J = 2.0 Hz, 1H), 7.39 (s, 4H), 7.23 (d, J = 8.8 Hz, 1H), 7.05 (dd, J = 8.4 Hz and 2.0 Hz, 1H), 6.49 (b, 1H), 4.32-4.20 (m, 3H), 3.76 (b, 2H), 3.46 (b, 2H), 3.21-3.13 (m, 1H), 2.90-2.78 (m, 2H), 2.54 (b, 2H), 2.49-2.43 (m, 4H), 1.32 (b, 3H), 1.10 (t, J = 7.2 Hz, 3H) | 495.3 | 4.68 |
| 474 | ((CD3OD, 400 MHz), δ 7.61 (s, 1H), 7.44 (d, J = 8.0 Hz, 2H), 7.35 (d, J = 8.0 Hz, 2H), 7.20-7.16 (m, 2H), 6.45 (b, 1H), 4.28-4.14 (m, 3H), 4.11 (s, 2H), 3.47 (s, 4H), 3.26 (s, 4H), 3.19-3.12 (m, 1H), 2.91 (s, 3H), 2.88-2.79 (m, 2H), 1.30 (s, 3H) | 511.2 | 4.99 |
| 477 HCl salt | (CD3OD, 400 MHz), δ 7.48 (d, J = 1.6 Hz, 1H), 7.34 (d, J = 8.4 Hz, 1H), 7.12 (dd, J = 8.8 Hz and 2.0 Hz, 1H), 4.68 (s, 1H), 3.77-3.72 (m, 1H), 3.47-3.44 (m, 1H), 3.10-3.03 (m, 2H), 2.65-2.61 (m, 1H), 1.25 (d, J = 7.2 Hz, 3H), 0.96 (d, J = 7.2 Hz, 3H) | 249.1 | 3.67 |
| 478 | CD3OD, 400 MHz), δ 7.63 (s, 1H), 7.48 (d, J = 8.0 Hz, 2H), 7.42 (d, J = 8.0 Hz, 2H), 7.20 (s, 2H), 6.49 (b, 1H), 4.32-4.21 (m, 3H), 3.50 (b, 4H), 3.21-3.15 (m, 3H), 2.92 (s, 3H), 2.90-2.73 (m, 2H), 1.32 (s, 3H) | 525.1 | 3.25 |

TABLE 5-continued
| Compound | NMR | Mass Spec (LCMS) | Reten. Time (min) |
|---|---|---|---|
| 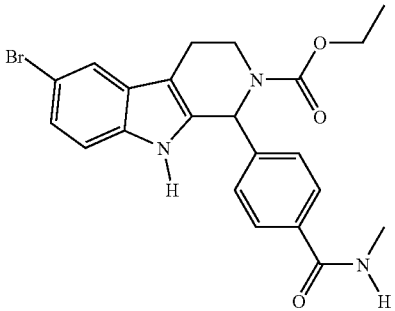 480 | (CD3OD, 400 MHz), δ 7.78 (d, J = 8.0 Hz, 2H), 7.63 (s, 1H), 7.37 (d, J = 8.4 Hz, 2H), 7.20 (s, 2H), 6.49 (b, 1H), 4.31-4.22 (m, 3H), 3.19-3.11 (m, 1H), 2.90 (s, 3H), 2.86-2.77 (m, 2H), 1.32 (s, 3H) | 456.1 | 4.26 |
| 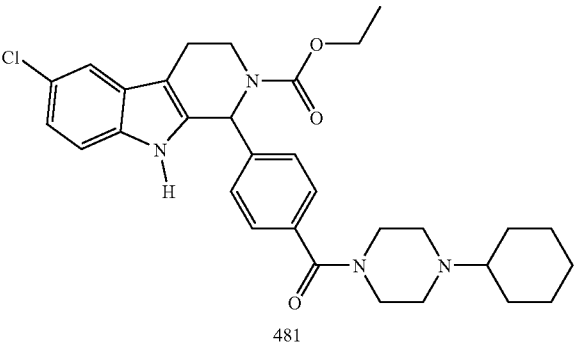 481 | (CD3OD, 400 MHz), δ 7.48 (d, J = 2 Hz, 1H), 7.41-7.36 (m, 4H), 7.23 (d, J = 8.4 Hz, 1H), 7.06 (dd, J = 8.8 Hz and 2.0 Hz, 1H), 6.49 (b, 1H), 4.35-4.21 (m, 3H), 3.64 (b, 2H), 3.45 (b, 2H), 3.20-3.11 (m, 1H), 2.92-2.78 (m, 2H), 2.68 (b, 2H), 2.55 (b, 2H), 1.92-1.80 (m, 4H), 1.66-1.62 (m, 1H), 1.32-1.22 (m, 8H) | 549.3 | 5.29 |
| 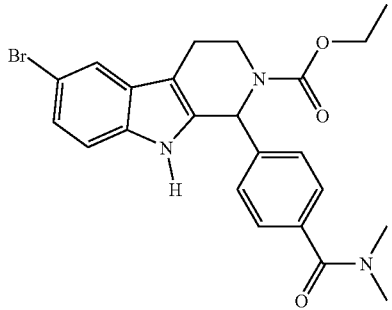 483 | (CD3OD, 400 MHz), δ 7.63 (s, 1H), 7.41 (d, J = 8.4 Hz, 2H), 7.37 (d, J = 8.0 Hz, 2H), 7.19 (s, 2H), 6.49 (b, 1H), 4.35-4.22 (m, 3H), 3.22-3.13 (m, 1H), 3.08 (s, 3H), 2.98 (s, 3H), 2.89-2.77 (m, 2H), 1.32 (s, 3H) | 470.1 | 4.46 |
| 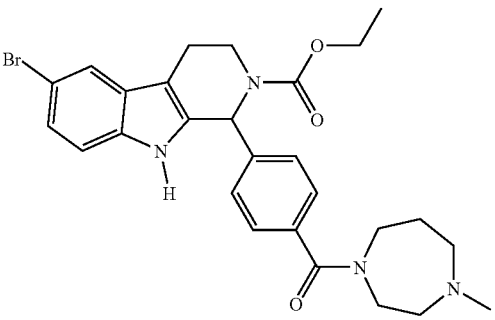 484 | (CD3OD, 400 MHz), δ 7.63 (s, 1H), 7.48 (d, J = 7.2 Hz, 2H), 7.40 (d, J = 8.0 Hz, 2H), 7.20 (s, 2H), 6.49 (b, 1H), 4.35-4.22 (m, 4H), 3.82-3.50 (m, 6H), 3.45 (b, 1H), 3.21-3.11 (m, 1H), 3.00-2.78 (m, 5H), 2.25-2.15 (m, 2H), 1.32 (s, 3H) | 539.2 | 3.02 |

TABLE 5-continued
| Compound | NMR | Mass Spec (LCMS) | Reten. Time (min) |
|---|---|---|---|
| 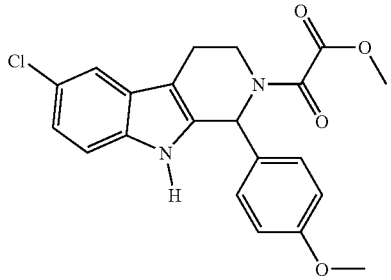 485 | (CDCl3, 400 MHz), δ 8.06 7.98 (s, 1H), 7.50, 7.49 (s, 1H), 7.22 (d, J = 6.0 Hz, 1H), 7.21 (d, J = 6.4 Hz, 2H), 7.15 (dd, J = 8.8 Hz and 1.6 Hz, 1H), 6.81 (d, J = 8.4 Hz, 2H), 6.77 (s, 1H), 3.91 (s, 3H), 3.77 (s, 3H), 3.72 (d, J = 5.2 Hz, 1H), 3.51-3.43 (m, 1H), 3.02-2.96 (m, 1H), 2.86-2.81 (m, 1H) | 398.9 | 4.18 |
| 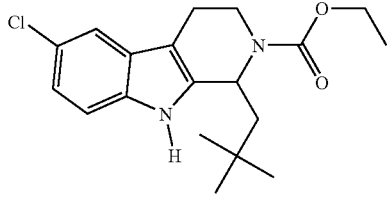 486 | (CDCl3, 400 MHz), δ 7.77, 7.70 (s, 1H), 7.42, 7.39 (s, 1H), 7.20 (dd, J = 8.4 Hz and 1.6 Hz, 1H), 7.09 (d, J = 8.0 Hz, 1H), 5.52-5.36 (m, 1H), 4.44-4.17 (m, 3H), 3.28-3.20 (m, 1H), 2.88-2.77 (m, 1H), 2.60 (d, J = 15.2 Hz, 1H), 2.05-1.88 (m, 1H), 1.58-1.54 (m, 1H), 1.30-1.26 (m, 3H), 1.04 (d, J = 2 Hz, 9H) | 349.1 | 6.03 |
| 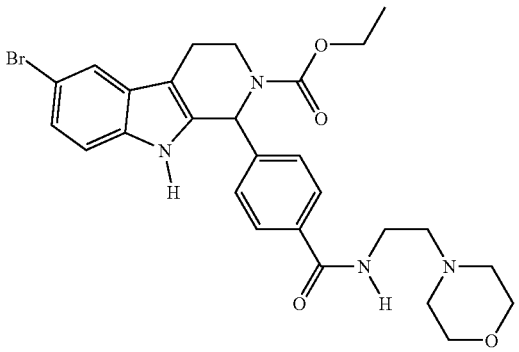 488 | (CD3OD, 400 MHz), δ 7.85 (d, J = 8.0 Hz, 2H), 7.64 (s, 1H), 7.41 (d, J = 8.4 Hz, 2H), 7.20 (s, 2H), 6.52 (b, 1H), 4.33-4.22 (b, 3H), 4.07 (b, 2H), 3.77 (t, J = 5.6 Hz, 4H), 3.65 (b, 2H), 3.39 (t, J = 5.6 Hz, 2H), 3.21-3.11 (m, 3H), 2.91-2.78 (m, 2H), 1.32 (s, 3H) | 555.2 | 3.34 |
| 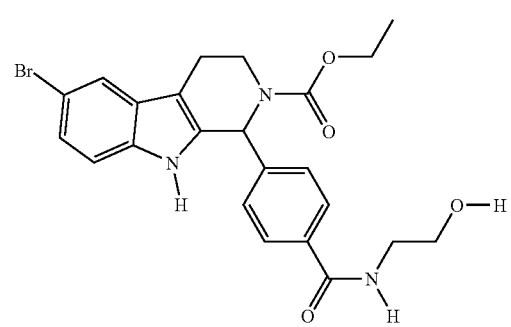 490 | (CD3OD, 400 MHz), δ 7.81 (d, J = 8.4 Hz, 2H), 7.63 (s, 1H), 7.37 (d, J = 8.0 Hz, 2H), 7.20 (s, 2H), 6.51 (b, 1H), 4.32-4.22 (m, 3H), 3.69 (t, J = 5.8 Hz, 2H), 3.48 (t, J = 5.6 Hz, 2H), 3.21-3.11 (m, 1H), 2.90-2.77 (m, 2H), 1.32 (s, 3H) | 486.1 | 3.80 |

TABLE 5-continued

| Compound | NMR | Mass Spec (LCMS) | Reten. Time (min) |
|---|---|---|---|
| 492 | (CD3OD, 400 MHz), δ 7.47 (s, 1H), 7.41-7.38 (m, 4H), 7.23 (d, J = 8.8 Hz, 1H), 7.06 (dd, J = 8.8 Hz and 1.6 Hz, 1H), 6.49 (b, 1H), 4.35-4.21 (m, 3H), 3.73-3.62 (m, 6H), 3.44 (b, 2H), 3.19-3.10 (m, 1H), 2.91-2.78 (m, 2H), 1.32 (b, 3H) | 468 | 5.52 |
| 494 | (DMSO, 400 MHz), δ 11.19 (b, 1H), 8.49 (b, 1H), 7.81 (d, J = 8.0 Hz, 2H), 7.51 (d, J = 1.6 Hz, 1H), 7.30 (d, J = 8.4 Hz, 2H), 7.29 (d, J = 14.0 Hz, 1H), 7.07 (dd, J = 8.4 Hz and 1.6 Hz, 1H), 6.39 (b, 1H), 4.21-4.16 (m, 3H), 3.93 (t, J = 6.4 Hz, 1H), 3.74 (q, J = 6.8 Hz, 1H), 3.59 (q, J = 6.8 Hz, 1H), 3.28 (s, 2H), 3.08-3.01 (m, 1H), 2.81-2.70 (m, 2H), 1.91-1.79 (m, 3H), 1.59-1.52 (m, 1H), 1.21 (s, 3H) | 482.2 | 5.74 |
| 496 | (CD3OD, 400 MHz), δ 11.05 (s, 1H), 8.09 (s, 2H), 7.64 (s, 1H), 7.32 (b, 1H), 7.24 (d, J = 8.4 Hz, 1H), 7.17 (dd, J = 8.8 Hz and 2.0 Hz, 1H), 6.24 (s, 1H), 4.22 (b, 1H), 4.12-4.09 (m, 2H), 3.15-3.09 (m, 1H), 2.83-2.65 (m, 5H), 1.21 (t, J = 6.8 Hz, 3H) | 430.2 | 3.65 |
| 497 HCl salt | (CD3OD, 400 MHz), δ 7.49 (d, J = 1.6 Hz, 1H), 7.34 (d, J = 8.8 Hz, 1H), 7.13 (dd, J = 8.8 Hz and 2.0 Hz, 1H), 3.77-3.72 (m, 1H), 3.52-3.45 (m, 1H), 3.15-3.01 (m, 2H), 2.80-2.74 (m, 2H), 2.60-2.52 (m, 1H), 2.27-2.20 (m, 4H) | 281.0 | 3.84 |

TABLE 5-continued

| Compound | NMR | Mass Spec (LCMS) | Reten. Time (min) |
|---|---|---|---|
| 498 | (CDCl3, 400 MHz), δ 8.35 (b, 1H), 7.51 (s, 1H), 7.32-7.26 (m, 4H), 7.20 (d, J = 8.4 Hz, 1H), 7.13 (dd, J = 8.8 Hz and 2.4 Hz, 1H), 6.39 (b, 1H), 4.25-4.21 (m, 2H), 3.80 (b, 2H), 3.47 (b, 2H), 3.16-3.10 (m, 1H), 2.96-2.88 (m, 3H), 2.79-2.75 (m, 1H), 2.54-2.36 (m, 6H), 1.32 (s, 3H) | 481.4 | 4.81 |
| 499 | (DMSO, 400 MHz), δ 10.86 (s, 1H), 8.17 (s, 1H), 8.03 (d, J = 7.6 Hz, 1H), 7.81 (t, J = 8.0 Hz, 1H), 7.65 (d, J = 8.4 Hz, 1H), 7.50 (b, 2H), 7.26 (d, J = 8.4 Hz, 1H), 7.02 (d, J = 8.8 Hz, 1H), 6.24 (s, 1H), 4.35 (b, 1H), 4.09-4.05 (m, 2H), 3.61-3.49 (m, 1H), 2.78-2.65 (m, 2H), 1.45 (t, J = 6.8 Hz, 3H) | 423.3 | 5.15 |
| 503 | (CD3OD, 400 MHz), δ 8.33 (s, 2H), 7.67 (s, 1H), 7.23 (s, 2H), 7.05 (d, J = 8.4 Hz, 2H), 6.91 (d, J = 8.8 Hz, 2H), 6.54-6.38 (m, 1H), 4.52 (b, 1H), 3.78 (s, 3H), 3.36-3.34 (m, 1H), 2.99 (s, 3H), 2.92-2.88 (m, 2H) | 508.2 | 5.72 |
| 504 | (CDCl3, 400 MHz), δ 7.88-7.77 (m, 1H), 7.43 (d, J = 8.0 Hz, 1H), 7.23 (d, J = 8.8 Hz, 1H), 7.11 (d, J = 8.8 Hz 1H), 5.70-7.68 (m, 2H), 5.19-4.97 (m, 1H), 4.60-4.38 (m, 1H), 4.19-4.07 (m, 2H), 2.82-2.80 (m, 1H), 2.68-2.64 (m, 1H), 2.29-1.84 (m, 6H), 1.55-1.46 (m, 1H), 1.36-1.24 (m, 3H) | 359.1 | 5.65 |

TABLE 5-continued
| Compound | NMR | Mass Spec (LCMS) | Reten. Time (min) |
|---|---|---|---|
| 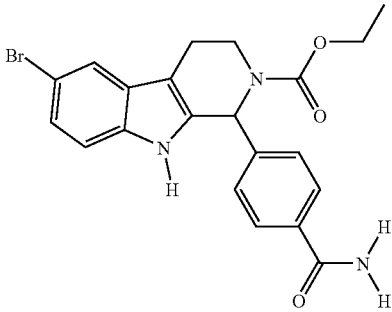 505 | (CD3OD, 400 MHz), δ 7.84 (d, J = 8.0 Hz, 2H), 7.63 (s, 1H), 7.38 (d, J = 8.0 Hz, 2H), 7.20 (s, 2H), 6.49 (b, 1H), 4.31-4.22 (m, 3H), 3.19-3.11 (m, 1H), 2.89-2.77 (m, 2H), 1.32 (s, 3H) | 442.0 | 4.06 |
| 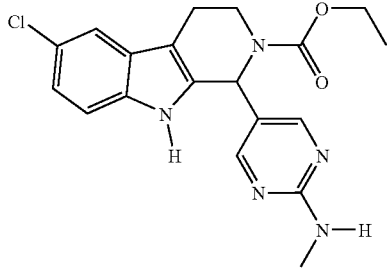 506 | (CD3OD, 400 MHz), δ 8.44 (s, 2H), 7.67 (d, J = 2.0 Hz, 1H), 7.44 (d, J = 8.8 Hz, 1H), 7.28 (dd, J = 8.8 Hz and 2.0 Hz, 1H), 6.52 (s, 1H), 4.58-4.55 (m, 1H), 4.43-4.40 (m, 2H), 3.41-3.31 (m, 1H), 3.15 (s, 3H), 3.03-3.01 (m, 2H), 1.32 (b, 3H) | 386.3 | 5.32 |
| 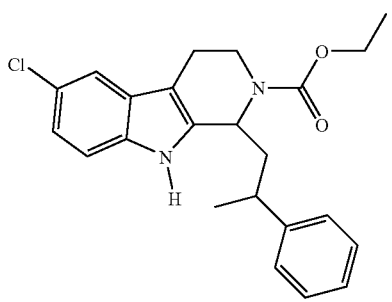 508 | (CDCl3, 400 MHz), δ 7.66 (d, J = 24.8 Hz, 1H), 7.39-6.89 (m, 8H), 5.44-5.02 (m, 1H), 4.49-4.10 (m, 3H), 3.23-2.94 (m, 2H), 2.83-2.74 (m, 1H), 2.64-2.58 (m, 1H), 2.26-1.98 (m, 2H), 1.47-1.26 (m, 6H) | 397.1 | 5.97 |
| 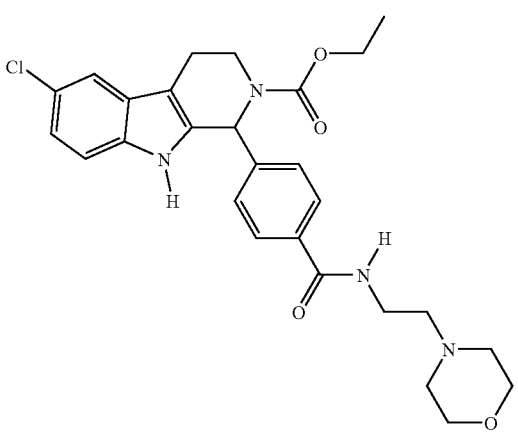 509 | (CD3OD, 400 MHz), δ 7.80 (d, J = 8.4 Hz, 2H), 7.47 (d, J = 1.6 Hz, 1H), 7.38 (d, J = 8.0 Hz, 2H), 7.24 (d, J = 8.8 Hz, 1H), 7.07 (dd, J = 8.0 Hz and 1.6 Hz, 1H), 6.49 (b, 1H), 4.35-4.21 (m, 3H), 3.69 (t, J = 4.6 Hz, 4H), 3.53 (t, J = 6.8 Hz, 2H), 3.19-3.10 (m, 1H), 2.90-2.78 (m, 2H), 2.59 (t, J = 6.6 Hz, 4H), 2.53 (s, 2H), 1.32 (s, 3H) | 511.4 | 5.05 |

TABLE 5-continued
| Compound | NMR | Mass Spec (LCMS) | Reten. Time (min) |
|---|---|---|---|
| 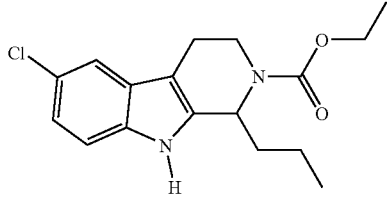 510 | (CDCl3, 400 MHz), δ 8.09, 7.83 (s, 1H), 7.42 (s, 1H), 7.21 (d, J = 8.4 Hz, 1H), 7.09 (dd, J = 8.4 Hz and 1.2 Hz, 1H), 5.33-5.21 (m, 1H), 4.50-4.34 (m,1H), 4.21-4.10 (m, 2H), 3.19-3.17 (m, 1H), 2.77-2.74 (m, 1H), 2.67-2.61 (m, 1H), 1.81 (s, 2H), 1.52 (s, 2H), 1.29-1.23 (m, 3H), 0.96 (s, 3H) | 321.4 | 5.19 |
| 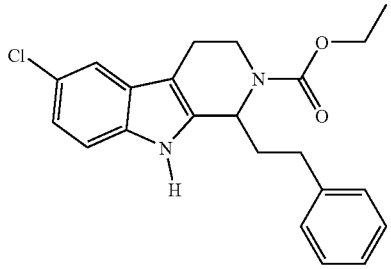 511 | (CDCl3, 400 MHz), δ 7.73-7.52 (m, 1H), 7.47 (s, 1H), 7.42-7.18 (m, 6H), 7.09 (dd, J = 8.8 Hz and 2.0 Hz, 1H), 5.41-5.26 (m, 1H), 4.56-4.32 (m, 1H), 4.23-4.10 (m, 2H), 3.21 (b, 1H), 2.85-2.72 (m, 3H), 2.65 (d, J = 14.2 Hz, 1H), 2.23-2.10 (m, 2H), 1.38 (b, 3H) | 383.1 | 5.75 |
| 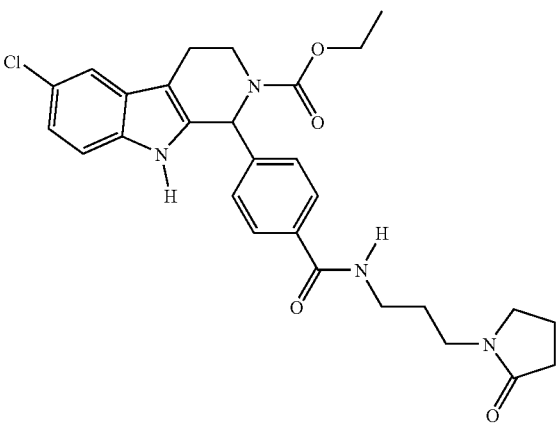 512 | (CD3OD, 400 MHz), δ 7.80 (d, J = 8.4 Hz, 2H), 7.47 (d, J = 1.6 Hz, 1H), 7.37 (d, J = 8.0 Hz, 2H), 7.24 (d, J = 8.8 Hz, 1H), 7.06 (dd, J = 8.8 Hz and 2.0 Hz, 1H), 6.50 (b, 1H), 4.32-4.21 (m, 3H), 3.47 (t, J = 7.2 Hz, 2H), 3.38-3.34 (m, 4H), 3.19-3.10 (m, 1H), 2.89-2.78 (m, 2H), 2.39 (t, J = 8.4 Hz, 2H), 2.09-2.00 (m, 2H), 1.86-1.80 (m, 2H), 1.32 (b, 3H) | 523.1 | 5.69 |
| 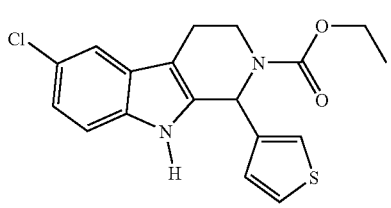 513 | (CDCl3, 400 MHz), δ 7.81 (s, 1H), 7.51 (d, J = 6.8 Hz, 1H), 7.29 (dd, J = 12.0 Hz and 2.8 Hz, 1H), 7.21 (d, J = 8.4 Hz, 1H), 7.13 (dd, J = 8.4 Hz and 2.0 Hz, 1H), 7.12-7.08 (m, 1H), 7.07 (s, 1H), 6.50 (b, 1H), 4.49-4.21 (m, 3H), 3.17-3.09 (m, 1H), 2.91-2.85 (m, 1H), 2.77-2.73 (m, 1H), 1.39 (s, 3H) | 361.1 | 5.12 |

TABLE 5-continued
| Compound | NMR | Mass Spec (LCMS) | Reten. Time (min) |
|---|---|---|---|
| 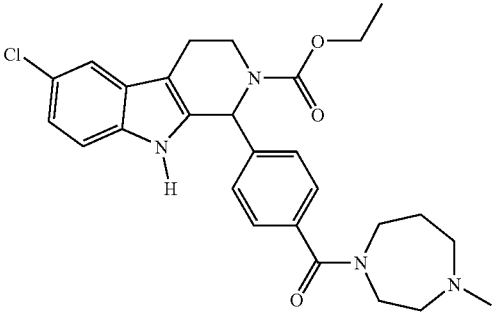 514 | (CD3OD, 400 MHz), δ 7.47 (d, J = 2.0 Hz, 1H), 7.46-7.37 (m, 4H), 7.23 (d, J = 8.4 Hz, 1H), 7.06 (dd, J = 8.8 Hz and 2.0 Hz, 1H), 6.49 (b, 1H), 4.35-4.21 (m, 3H), 3.77-3.69 (m, 2H), 3.55-3.45 (m, 2H), 3.20-3.11 (m, 1H), 2.90-2.78 (m, 3H), 2.67-2.55 (m, 3H), 2.39-2.31 (m, 3H), 2.01-1.95 (m, 1H), 1.82-1.79 (m, 1H), 1.32 (s, 3H) | 495.3 | 4.67 |
| 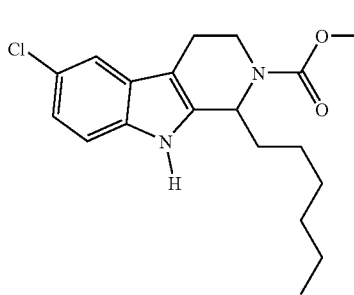 515 | (CDCl3, 400 MHz), δ 7.92, 7.82 (s, 1H), 7.42 (s, 1H), 7.22 (dd, J = 8.4 Hz and 1.2 Hz, 1H), 7.10 (d, J = 8.8 Hz, 1H), 5.31, 5.19 (s, 1H), 4.52, 4.32 (d, J = 10.8 Hz, 1H), 4.20-4.12 (m, 2H), 3.19-3.12 (m, 1H), 2.81-2.62 (m, 2H), 1.81 (d, J = 6.8 Hz, 2H), 1.48-22 (m, 12H), 0.88 (s, 3H) | 363.5 | 6.34 |
| 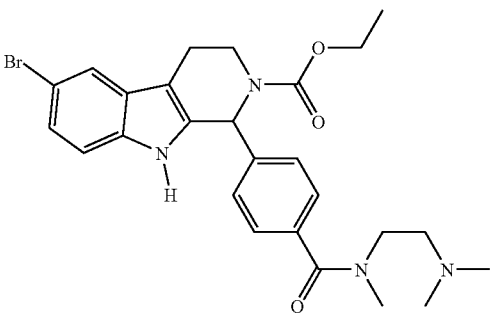 516 | (CD3OD, 400 MHz), δ 7.63 (s, 1H), 7.50 (d, J = 8.0 Hz, 2H), 7.40 (d, J = 8.0 Hz, 2H), 7.20 (s, 2H), 6.49 (b, 1H), 4.30-4.20 (m, 3H), 3.89 (s, 2H), 3.45 (b, 2H), 3.20-3.10 (m, 1H), 3.03-3.01 (m, 9H), 2.91-2.80 (m, 2H), 1.32 (s, 3H) | 527.1 | 3.16 |
| 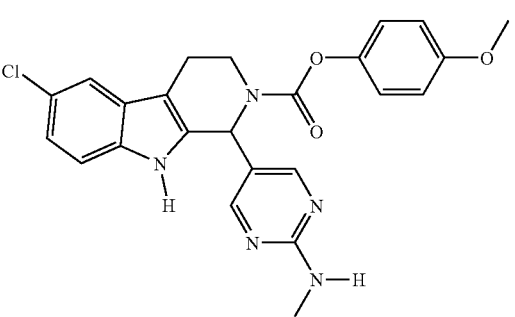 517 | (CD3OD, 400 MHz), δ 8.27 (s, 2H), 7.52 (d, J = 2 Hz, 1H), 7.27 (d, J = 8.8 Hz, 1H), 7.17 (d, J = 8.8 Hz, 1H), 7.10 (dd, J = 8.8 Hz and 2.4 Hz, 1H), 7.05 (d, J = 8.8 Hz, 2H), 6.95 (d, J = 9.2 Hz, 2H), 6.92 (s, 1H), 6.58-6.38 (m, 1H), 4.52 (b, 1H), 3.80 (s, 1H), 3.79 (s, 3H), 3.31-3.30 (m, 1H), 2.95 (s, 3H), 2.92-2.88 (m, 1H) | 464.2 | 5.86 |

TABLE 5-continued
| Compound | NMR | Mass Spec (LCMS) | Reten. Time (min) |
|---|---|---|---|
| 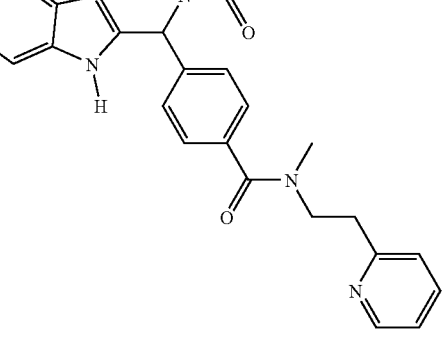 518 | (CD3OD, 400 MHz), δ 8.49, 8.29 (d, J = 4.4 Hz, 2.8 Hz, 1H), 7.82, 7.70 (t, J = 2.0 Hz, 1H), 7.46 (s, 1H), 7.38-7.23 (m, 5H), 7.15 (d, J = 7.6 Hz, 1H), 7.07 (d, J = 8.4 Hz, 1H), 6.98 (d, J = 6.8 Hz, 1H), 6.46 (b, 1H), 4.35-4.21 (m, 3H), 3.88 (t, J = 7.0 Hz, 1H), 3.71-3.67 (m, 1H), 3.20-3.11 (m, 3H), 3.01-2.80 (m, 4H), 1.32 (s, 3H) | 517.6 | 5.03 |
| 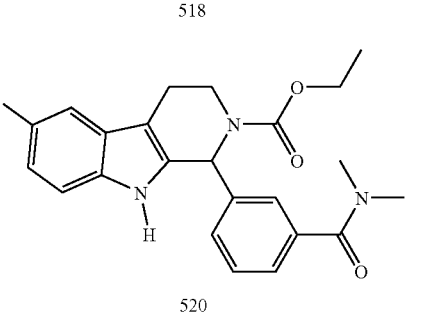 520 | (DMSO, 400 MHz), δ 11.15 (s, 1H), 7.51 (d, J = 2.0 Hz, 1H), 7.42 (t, J = 7.6 Hz, 1H), 7.35 (d, J = 7.6 Hz, 1H), 7.30 (d, J = 8.8 Hz, 2H), 7.16 (s, 1H), 7.06 (dd, J = 8.4 Hz and 2.0 Hz, 1H), 6.36 (b, 1H), 4.18-4.10 (m, 3H), 3.09-3.00 (m, 1H), 2.91-2.64 (m, 8H), 1.21 (t, J = 6.6 Hz, 3H) | 426.2 | 4.29 |
| 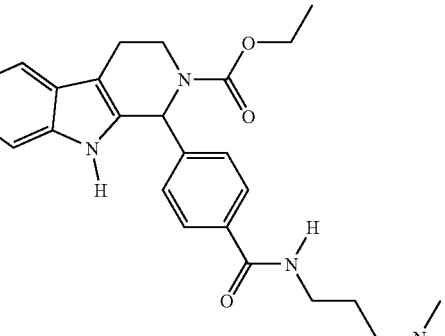 521 | (CD3OD, 400 MHz), δ 7.81 (d, J = 8.4 Hz, 2H), 7.47 (d, J = 1.6 Hz, 1H), 7.39 (d, J = 8.4 Hz, 2H), 7.24 (d, J = 8.4 Hz, 1H), 7.07 (dd, J = 8.4 Hz and 2.0 Hz, 1H), 6.50 (b, 1H), 4.35-4.29 (m, 3H), 3.70-3.60 (m, 1H), 3.51-3.47 (m, 2H), 3.37-3.29 (m, 1H), 3.19-3.11 (m, 2H), 2.92 (s, 3H), 2.88-2.78 (m, 2H), 2.51-2.41 (m, 1H), 2.29-2.20 (m, 1H), 2.17-2.00 (m, 2H), 1.89-1.78 (m, 2H), 1.32 (s, 3H) | 509.4 | 4.99 |
| 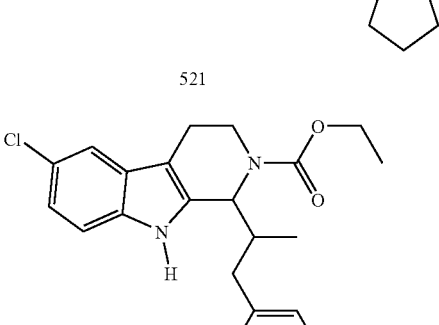 523 | (CDCl3, 400 MHz), δ 7.91, 7.72 (s, 1H), 7.50-7.43 (s, 1H), 7.22-7.06 (m, 6H), 5.28-5.19 (m, 1H), 4.64-4.45 (m, 1H), 4.20 (b, 2H), 3.27-3.10 (m, 2H), 2.91-2.72 (m, 2H), 2.70-2.66 (m, 1H), 2.49-2.28 (m, 2H), 1.38-1.24 (m, 9H), 1.01, 0.96 (d, J = 6.8 Hz, 3H) | 439.0 | 6.11 |

TABLE 5-continued
| Compound | NMR | Mass Spec (LCMS) | Reten. Time (min) |
|---|---|---|---|
| 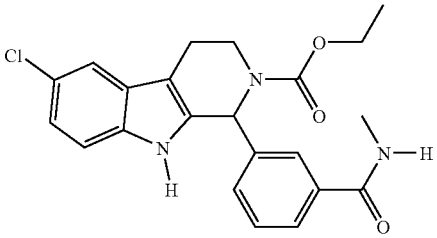 524 | (DMSO, 400 MHz), δ 11.10 (s, 1H), 8.42 (s, 1H), 7.75 (d, J = 7.2 Hz, 1H), 7.67 (s, 1H), 7.51 (d, J = 1.6 Hz, 1H), 7.43 (t, J = 7.2 Hz, 1H), 7.35 (d, J = 8.0 Hz, 1H), 7.29 (d, J = 8.4 Hz, 1H), 7.06 (dd, J = 8.8 Hz and 2.4 Hz, 1H), 6.39 (b, 1H), 4.13-4.09 (m, 3H), 3.10-3.04 (m, 1H), 2.81-2.72 (m, 5H), 1.21 (s, 3H) | 412.1 | 4.13 |
| 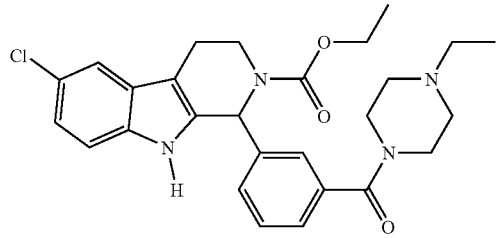 525 | (CD3OD, 400 MHz), δ 7.53-7.46 (m, 4H), 7.29 (b, 1H), 7.25 (d, J = 8.8 Hz, 1H), 7.08 (dd, J = 8.8 Hz and 2.08 Hz, 1H), 6.49 (b, 1H), 4.34-4.23 (m, 3H), 3.53-3.42 (m, 2H), 3.18-3.12 (m, 5H), 2.91-2.74 (m, 3H), 1.32 (t, J = 7.2 Hz, 6H) | 4.95.3 | 3.46 |
| 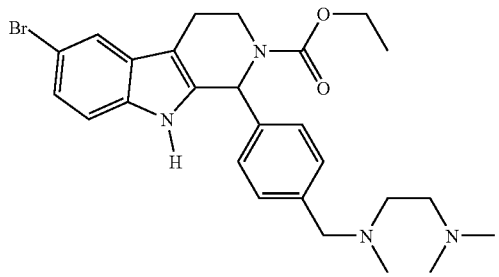 526 | (CD3OD, 400 MHz), δ 7.63 (s, 1H), 7.51 (d, J = 8.0 Hz, 2H), 7.41 (d, J = 8.4 Hz, 2H), 7.19 (d, J = 1.2 Hz, 2H), 6.46 (b, 1H), 4.31 (s, 2H), 4.23-4.20 (m, 3H), 3.62-3.50 (m, 4H), 3.19-3.11 (m, 1H), 2.92 (s, 6H), 2.87-2.81 (m, 2H), 2.76 (s, 3H), 1.31 (s, 3H) | 513.2 | 4.43 |
| 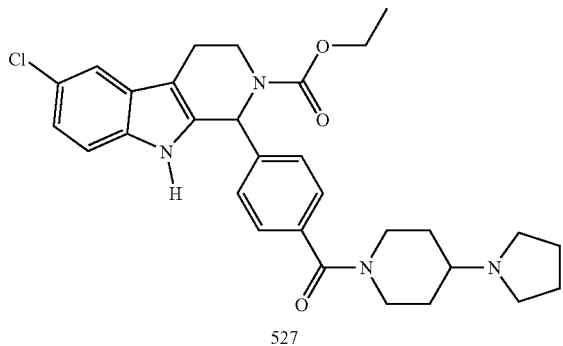 [SMILES: CCOC(=O)N1CCc2c([nH]c3ccc(Cl)cc23)C1c1ccc(C(=O)N2CCC(N3CCCC3)CC2)cc1] 527 | (CD3OD, 400 MHz), δ 7.47 (d, J = 2 Hz, 1H), 7.46-7.37 (m, 4H), 7.24 (d, J = 8.8 Hz, 1H), 7.07 (d, J = 8.8 Hz and 2.0 Hz, 1H), 6.49 (b, 1H), 4.75 (b, 1H), 4.35-4.21 (m, 3H), 3.85 (b, 1H), 3.64 (b, 2H), 3.45-3.37 (m, 1H), 3.19-3.12 (m, 4H), 2.91-2.80 (m, 3H), 2.28-2.00 (m, 6H), 2.12-2.05 (m, 2H), 1.61 (b, 2H), 1.32 (s, 3H) | 535.3 | 4.94 |

TABLE 5-continued

| Compound | NMR | Mass Spec (LCMS) | Reten. Time (min) |
|---|---|---|---|
| 528 | (CDCl3, 400 MHz), δ 7.89-7.69 (m, 1H), 7.43 (b, 1H), 7.33-7.30 (m, 2H), 7.20-7.06 (m, 4H), 5.29-5.19 (m, 1H), 4.64-4.45 (m, 1H), 4.20 (b, 2H), 3.27-3.10 (m, 2H), 2.91-2.72 (m, 2H), 2.70-2.66 (m, 1H), 2.50 (b, 2H), 2.29 (b, 1H), 1.32-1.31 (m, 12H), 1.02, 0.90 (d, J = 6.8 Hz, 3H) | 453.0 | 6.30 |
| 529 | (CD3OD, 400 MHz), δ 7.52-7.45 (m, 4H), 7.31 (b, 1H), 7.25 (d, J = 8.4 Hz, 1H), 7.08 (dd, J = 8.4 Hz and 2.0 Hz, 1H), 6.48 (b, 1H), 4.34-4.23 (m, 3H), 3.45 (b, 3H), 3.23-3.13 (m, 4H), 2.92-2.80 (m, 5H), 1.32 (s, 3H) | 481.3 | 3.43 |
| 531 | (CD3OD, 400 MHz), δ 7.48 (d, J = 1.6 Hz, 1H), 7.43 (d, J = 8.4 Hz, 2H), 7.40 (d, J = 8.4 Hz, 2H), 7.24 (d, J = 8.4 Hz, 1H), 7.07 (dd, J = 8.4 Hz and 2.0 Hz, 1H), 6.50 (b, 1H), 4.35-4.29 (m, 3H), 3.90 (b, 1H), 3.52-3.47 (m, 3H), 3.20-3.16 (m, 2H), 3.01 (t, J = 12.0 Hz, 2H), 2.91-2.79 (m, 3H), 2.20 (b, 1H), 2.00-1.97 (m, 3H), 1.82-1.71 (m, 6H), 1.56-1.48 (m, 1H), 1.32 (b, 3H) | 549.6 | 5.21 |
| HCl salt 532 | (DMSO, 400 MHz), δ 11.39 (s, 1H), 9.80 (b, 1H), 9.40 (b, 1H), 7.52 (d, J = 1.6 Hz, 1H), 7.48 (s, 1H), 7.37-7.31 (m, 4H), 7.25-7.19 (m, 1H), 7.00 (dd, J = 8.8 Hz and 2 Hz, 1H), 4.76 (d, J = 5.6 Hz, 1H), 3.61-3.53 (m, 1H), 3.25-3.20 (m, 1H), 2.94-2.92 (m, 2H), 2.13-1.97 (m, 1H), 1.35, 1.24 (d, J = 6.8 Hz, 3H) | 325.3 | 4.75 |

TABLE 5-continued

| Compound | NMR | Mass Spec (LCMS) | Reten. Time (min) |
|---|---|---|---|
| 533 | (CD3OD, 400 MHz), δ 8.99 (s, 1H), 7.80 (d, J = 8.0 Hz, 2H), 7.71 (d, J = 1.2 Hz, 1H), 7.57 (s, 1H), 7.47 (d, J = 1.6 Hz, 1H), 7.39 (d, J = 8.0 Hz, 2H), 7.24 (d, J = 8.4 Hz, 1H), 7.07 (d, J = 8.0 Hz, 1H), 6.51 (b, 1H), 4.32 (t, J = 4.8 Hz, 3H), 4.23-4.21 (m, 2H), 3.43 (t, J = 6.4 Hz, 2H), 3.20-3.11 (m, 1H), 2.91-2.78 (m, 2H), 2.23-2.17 (m, 2H), 1.32 (b, 3H) | 506.2 | 4.96 |
| 534 | (CD3OD, 400 MHz), δ 7.79 (d, J = 8.4 Hz, 2H), 7.48 (s, 1H), 7.38 (d, J = 8.0 Hz, 2H), 7.25 (d, J = 8.8 Hz, 1H), 7.07 (dd, J = 8.4 Hz and 2.0 Hz, 1H), 6.51 (b, 1H), 4.35-4.21 (m, 3H), 3.67 (t, J = 4.6 Hz, 4H), 3.41 (q, J = 4.8 Hz, 2H), 3.20-3.11 (m, 1H), 2.91-2.79 (m, 2H), 2.62 (s, 1H), 2.46-2.42 (m, 5H), 1.83-1.79 (m, 2H), 1.32 (s, 3H) | 525.2 | 4.76 |
| 535 | (CD3OD, 400 MHz), δ 7.62 (s, 1H), 7.49 (d, J = 8.0 Hz, 2H), 7.39 (d, J = 8.4 Hz, 2H), 7.19 (s, 2H), 6.48 (s, 1H), 4.27-4.18 (m, 5H), 3.87 (t, J = 4.6 Hz, 4H), 3.47 (t, J = 6.8 Hz, 2H), 3.34-3.30 (m, 2H), 3.16-3.12 (m, 5H), 2.89-2.75 (m, 2H), 1.30 (s, 3H) | 541.2 | 3.51 |
| 541 | (CD3OD, 400 MHz), δ 7.60 (s, 1H), 7.51 (d, J = 8.0 Hz, 2H), 7.40 (d, J = 8.0 Hz, 2H), 7.21-7.16 (m, 2H), 6.46 (b, 1H), 4.41 (s, 2H), 4.28-4.19 (m, 3H), 3.79-3.74 (m, 4H), 3.51-3.49 (m, 4H), 3.19-3.11 (m, 1H), 2.95 (s, 3H), 2.88-2.75 (m, 2H), 2.30 (s, 2H), 1.30 (s, 3H) | 525.2 | 4.42 |

TABLE 5-continued

| Compound | NMR | Mass Spec (LCMS) | Reten. Time (min) |
|---|---|---|---|
| 542 | (CD3OD, 400 MHz), δ 7.84 (d, J = 8.0 Hz, 2H), 7.47 (d, J = 2.0 Hz, 1H), 7.37 (d, J = 8.4 Hz, 2H), 7.24 (d, J = 8.4 Hz, 1H), 7.06 (dd, J = 8.4 Hz and 2.0 Hz, 1H), 6.49 (b, 1H), 4.35-4.16 (m, 3H), 3.21-3.10 (m, 1H), 2.90-2.71 (m, 2H), 1.32 (b, 3H) | 398.1 | 3.95 |
| 547 | (CDCl3, 400 MHz), δ 7.92-7.77 (m, 1H), 7.42-7.39 (m, 8H), 7.26-7.21 (m, 1H), 7.10 (d, J = 8.4 Hz, 1H), 5.16-4.97 (m, 1H), 4.56-4.36 (m, 1H), 4.19-4.11 (m, 2H), 3.27-3.19 (m, 1H), 2.78-2.63 (m, 2H), 1.90 (d, J = 5.6 Hz, 1H), 1.74 (b, 1H), 1.49-1.26 (m, 4H), 1.10-0.91 (m, 6H) | 335.2 | 5.45 |
| 552 | (CD3OD, 400 MHz), δ 7.82 (s, 1H), 7.80 (s, 1H), 7.55-7.48 (m, 3H), 7.23 (d, J = 8.4 Hz, 1H), 7.07 (dd, J = 8.4 Hz and 2.0 Hz, 1H), 6.49 (b, 1H), 4.33-4.21 (m, 3H), 4.05 (b, 2H), 3.5-3.73 (m, 4H), 3.61 (b, 2H), 3.37 (t, J = 5.8 Hz, 2H), 3.25-3.17 (m, 3H), 2.92-2.80 (m, 2H), 1.32 (s, 3H) | 511.3 | 3.56 |
| 553 | (CDCl3, 400 MHz), δ 8.01, 7.91 (s, 1H), 7.43 (s, 1H), 7.23 (d, J = 8.4 Hz, 1H), 7.11 (d, J = 7.2 Hz, 1H), 6.71 (d, J = 7.6 Hz, 1H), 6.63 (s, 1H), 6.57 (d, J = 7.6 Hz, 1H), 5.92 (s, 2H), 5.18-5.07 (m, 1H), 4.63-4.41 (m, 1H), 4.30-4.11 (m, 2H), 3.36-3.31 (m, 1H), 2.91-2.83 (m, 2H), 2.70-2.61 (m, 1H), 2.38-2.15 (m, 2H), 1.38-1.30 (m, 3H), 1.09-1.01 (m, 3H) | 440.9 | 5.75 |
| 556 | (CD3OD, 400 MHz), δ 7.76 (s, 1H), 7.75 (s, 1H), 7.52-7.43 (m, 2H), 7.23 (d, J = 8.4 Hz, 1H), 7.06 (d, J = 7.6 Hz, 1H), 6.47 (b, 1H), 4.30-4.21 (m, 3H), 3.52 (s, 4H), 3.33 (s, 3H), 3.26-3.18 (m, 1H), 2.91-2.80 (m, 2H), 1.32 (s, 3H) | 456.1 | 4.21 |

TABLE 5-continued
| Compound | NMR | Mass Spec (LCMS) | Reten. Time (min) |
|---|---|---|---|
| 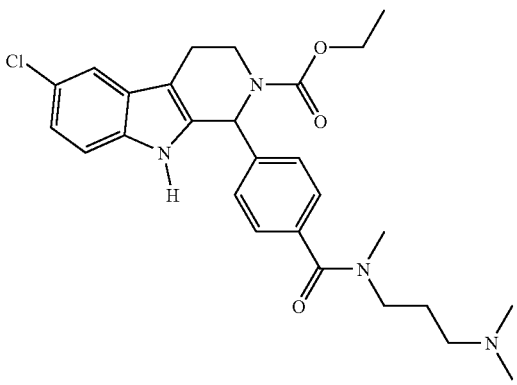 558 | (CD3OD, 400 MHz), δ 7.48 (s, 1H), 7.46 (d, J = 8.8 Hz, 2H), 7.40 (d, J = 7.6 Hz, 2H), 7.24 (d, J = 8.4 Hz, 1H), 7.07 (d, J = 8.0 Hz, 1H), 6.49 (b, 1H), 4.35-4.21 (m, 3H), 3.64-3.61 (m, 2H), 3.20-3.11 (m, 3H), 3.01 (s, 3H), 2.93 (s, 5H), 2.89-2.78 (m, 3H), 2.12-2.05 (m, 2H), 1.32 (s, 3H) | 497.2 | 4.69 |
| 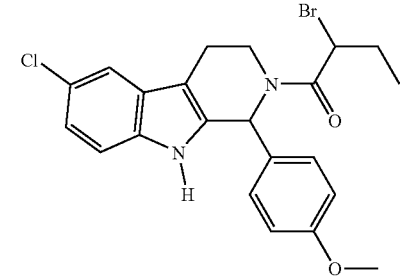 559 | (CDCl3, 400 MHz), δ 8.17, 8.00 (s, 1H), 7.50 (s, 1H), 7.23-7.13 (m, 4H), 6.97, 6.92 (s, 1H), 6.80 (d, J = 8.4 Hz, 2H), 4.43, 4.34 (t, J = 7.0 Hz, 1H), 4.04-3.98 (m, 1H), 3.77 (s, 3H), 3.47-3.41 (m, 1H), 3.25-2.81 (m, 2H), 2.23-2.06 (m, 2H), 1.02 (t, J = 6.2 Hz, 3H) | 460.8 | 4.96 |
| 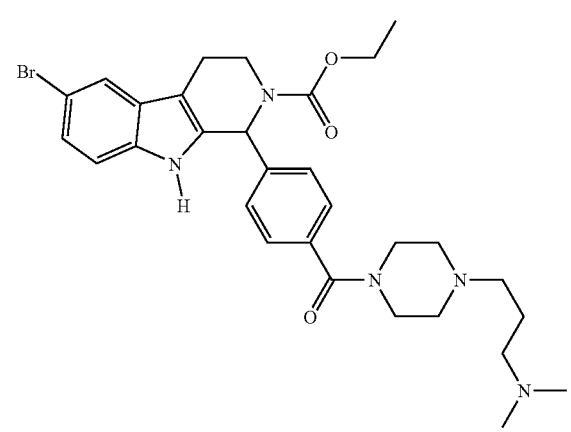 560 | (DMSO, 300 MHz), δ 7.63 (s, 1H), 7.49 (d, J = 6.3 Hz, 2H), 7.42 (d, J = 6.0 Hz, 2H), 7.20 (s, 2H), 6.49 (s, 1H), 4.32-4.21 (m, 3H), 3.85 (b, 4H), 3.39-3.30 (m, 3H), 3.26-3.15 (m, 5H), 2.92-2.73 (m, 9H), 2.26-2.20 (m, 2H), 1.31 (s, 3H) | 596.3 | 4.45 |

TABLE 5-continued

| Compound | NMR | Mass Spec (LCMS) | Reten. Time (min) |
|---|---|---|---|
| 561 | (CD3OD, 400 MHz), δ 7.52 (d, J = 8.4 Hz, 2H), 7.47 (s, 1H), 7.39-7.36 (m, 2H), 7.24 (d, J = 8.8 Hz, 1H), 7.06 (dd, J = 8.4 Hz and 1.6 Hz, 1H), 6.49 (b, 1H), 4.45-4.23 (m, 4H), 3.84-3.45 (m, 4H), 3.20-3.12 (m, 1H), 2.91-2.78 (m, 2H), 2.25-2.10 (m, 1H), 1.98-1.89 (m, 4H), 1.32 (s, 3H) | 509.2 | 5.18 |
| 562 | (CD3OD, 400 MHz), δ 7.52-7.45 (m, 4H), 7.32 (b, 1H), 7.25 (d, J = 8.4 Hz, 1H), 7.08 (dd, J = 8.4 Hz and 1.6 Hz, 1H), 6.49 (b, 1H), 4.34-4.23 (m, 4H), 3.69 (s, 3H), 3.31-3.30 (m, 8H), 3.21-3.12 (m, 3H), 2.91-2.74 (m, 2H), 1.32 (s, 3H) | 525.3 | 3.52 |
| 563 | (CD3OD, 400 MHz), δ 7.51-7.48 (m, 3H), 7.40 (d, J = 8.0 Hz, 2H), 7.24 (d, J = 8.8 Hz, 1H), 7.07 (dd, J = 8.4 Hz and 1.2 Hz, 1H), 6.49 (b, 1H), 4.35-4.21 (m, 3H), 3.89 (b, 2H), 3.45 (b, 2H), 3.19-3.10 (m, 1H), 3.05-3.01 (m, 9H), 2.91-2.78 (m, 2H), 1.32 (b, 3H) | 483.1 | 4.96 |
| 565 | (CD3OD, 400 MHz), δ 7.47 (d, J = 1.6 Hz 2H), 7.35 (d, J = 8.4 Hz, 1H), 7.12 (dd, J = 8.4 Hz and J = 2.0 Hz, 1H), 4.87 (s, 1H), 3.75-3.72 (m, 1H), 3.50-3.47 (m, 1H), 3.09-3.03 (m, 2H), 2.22 (dd, J = 15.6 Hz and J = 2.4 Hz, 1H), 1.84 (dd, J = 15.6 Hz and 8.4 Hz, 1H), 1.17 (s, 9H) | 276.9 | 4.00 |

TABLE 5-continued

| Compound | NMR | Mass Spec (LCMS) | Reten. Time (min) |
|---|---|---|---|
| 567 | (CD3OD, 400 MHz), δ 7.48 (d, J = 1.6 Hz, 1H), 7.41-7.32 (m, 3H), 7.23 (d, J = 8.4 Hz, 2H), 7.07 (dd, J = 8.4 Hz and 2.0 Hz, 1H), 6.46 (b, 1H), 4.32-4.17 (m, 3H), 3.80 (s, 2H), 3.67 (t, J = 5.0 Hz, 2H), 3.39 (s, 3H), 3.30-15 (m, 6H), 2.88-2.83 (m, 6H), 1.32 (s, 3H) | 511.4 | 4.71 |
| 568 HCl salt | (DMSO, 400 MHz), δ 11.39 (d, J = 2.8 Hz, 1H), 9.75 (s, 1H), 9.34 (s, 1H), 7.53 (s, 1H), 7.36 (dd, J = 8.4 Hz and 4.0 Hz, 1H), 7.10 (dd, J = 8.8 Hz and 2.0 Hz, 1H), 4.82-4.71 (m, 1H), 3.62-3.56 (m, 1H), 3.14 (b, 1H), 3.00-2.83 (m, 2H), 2.35-2.23 (m, 1H), 2.18-1.82 (m, 4H), 1.34 (q, J = 6.4 Hz, 3H) | 295.0 | 4.14 |

Example 2

Assay to Evaluate Affect on Hypoxia-Inducible Endogenous VEGF Expression

The ability of the compounds of the invention to modulate hypoxia-inducible endogenous VEGF expression may be analyzed as follows. VEGF protein levels may be monitored by an ELISA assay (R&D Systems). Briefly, HeLa cells may be cultured for 24-48 hours under hypoxic conditions (1% $O_2$, 5% $CO_2$, balanced with nitrogen) in the presence or absence of a compound of the invention. The conditioned media may then be assayed by ELISA, and the concentration of VEGF calculated from the standard ELISA curve of each assay.

A dose-response analysis may be performed using the ELISA assay and conditions described above. The conditions for the dose-response ELISA are analogous to those described above. A series of, e.g., seven different concentrations may be analyzed. In parallel, a dose-response cytotoxicity assay may be performed using Cell Titer Glo (Promega) under the same conditions as the ELISA to ensure that the inhibition of VEGF expression was not due to the cytotoxicity. Dose-response curves may be plotted using percentage inhibition versus concentration of the compound, and $EC_{50}$ and $CC_{50}$ values may be generated for each compound with the maximal inhibition set as 100% and the minimal inhibition as 0%. Preferred compounds of the invention will have an $EC_{50}$ of less than 50, preferably less than 10, more preferably less than 2, even more preferably less than 0.5, and even more preferably less than 0.01.

FIG. 1 shows the ability of a typical compound of the invention, Compound No. 7, to inhibit endogenous VEGF production in tumor cells under hypoxic conditions. The ELISA $EC_{50}$ is 0.0025 μM, while its $CC_{50}$ (50% cytotoxicity) is greater than 0.2 μM. The $EC_{50}$ for a series of preferred compounds of the invention is provided in Table 5.

TABLE 5

| Compound | LCMS [M + H] | LCMS Retention Time (min) | ELISA EC50 μM |
|---|---|---|---|
| 1 | 391.20 | 3.67 | **** |
| 2 | 385.28 | 4.01 | ***** |
| 3 | 479.18 | 4.35 | ***** |
| 4 | 435.23 | 4.28 | ***** |
| 5 | 391.28 | 4.05 | ***** |
| 6 | 425.28 | 4.07 | ***** |
| 7 | 443.28 | 4.61 | ***** |
| # 8 | 415.26 | 4.25 | ***** |
| 9 | 431.25 | 4.07 | ***** |
| # 10 | 467.15 | 4.51 | ***** |
| 11 | 389.24 | 4.24 | ***** |
| 12 | 414.31 | 3.94 | ***** |
| 13 | 411.24 | 4.89 | ***** |
| 14 | 397.22 | 4.57 | ***** |
| 15 | 457.3 | 4.24 | ***** |
| 16 | 435.19 | 4.47 | ***** |
| 17 | 447.14 | 4.44 | ***** |
| 18 | 431.14 | 4.55 | ***** |
| 19 | 437.26 | 4.54 | ***** |
| 20 | 389.24 | 4.22 | ***** |
| 21 | 391.28 | 4.04 | ***** |
| 22 | 425.28 | 4.11 | ***** |
| 23 | 373.23 | 4.04 | ***** |
| 24 | 411.24 | 4.8 | ***** |
| 25 | 449.23 | 4.03 | ***** |
| 26 | 437.15 | 4.52 | ***** |
| 27 | 399.25 | 4.11 | ***** |
| 28 | 399.19 | 4.2 | ***** |
| 29 | 435.09 | 4.14 | ***** |
| 30 | 413.22 | 4.42 | ***** |
| 31 | 423.17 | 4.32 | ***** |
| 32 | 467.25 | 4.26 | ***** |
| 33 | 457.15 | 4.29 | ***** |
| 34 | 383.19 | 4.42 | ***** |
| 35 | 425.28 | 4.14 | ***** |
| 36 | 383.2 | 4.37 | ***** |
| 37 | 423.3 | 4.24 | ***** |
| 38 | 355.24 | 4.07 | ***** |

TABLE 5-continued

| Compound | LCMS [M + H] | LCMS Retention Time (min) | ELISA EC50 μM |
|---|---|---|---|
| 39 | 391.28 | 4.12 | ***** |
| 40 | 403.15 | 4.45 | ***** |
| 41 | 449.11 | 4.59 | ***** |
| 42 | 383.19 | 4.44 | ***** |
| 43 | 371.31 | 3.89 | ***** |
| 44 | 479.18 | 4.35 | ***** |
| 45 | 394.16 | 4.09 | ***** |
| 46 | 421.19 | 4.22 | **** |
| 47 | 449.07 | 4.54 | **** |
| 48 | 403.32 | 4.2 | **** |
| 49 | 403.15 | 4.51 | **** |
| 50 | 405.18 | 3.81 | **** |
| 51 | 373.23 | 4.11 | **** |
| 52 | 355.3 | 4.07 | **** |
| 53 | 375.26 | 3.92 | **** |
| 54 | 435.23 | 4.3 | **** |
| 55 | 425.27 | 4.26 | **** |
| 56 | 414.14 | 4.19 | **** |
| 57 | 399.19 | 4.2 | **** |
| 58 | 469.22 | 4.32 | **** |
| 59 | 444.12 | 4.12 | **** |
| 60 | 433.17 | 4.27 | **** |
| 61 | 419.28 | 4.04 | **** |
| 62 | 409.14 | 4.22 | **** |
| 63 | 435.09 | 4.16 | **** |
| 64 | 435.12 | 4.27 | **** |
| 65 | 387.2 | 3.95 | **** |
| 66 | 414.17 | 4.24 | **** |
| 67 | 429.3 | 4.47 | **** |
| 68 | 359.19 | 3.89 | **** |
| 69 | 449.08 | 4.55 | **** |
| 70 | 375.25 | 4.19 | **** |
| 71 | 394.16 | 4.12 | **** |
| 72 | 403.15 | 4.49 | **** |
| 73 | 381.09 | 3.59 | **** |
| #74 | 400.15 | 4.05 | **** |
| 75 | 387.22 | 4.29 | **** |
| 76 | 449.26 | 4.3 | **** |
| 77 | 391.28 | 4.19 | **** |
| 78 | 435.12 | 4.24 | **** |
| 79 | 437.19 | 4.49 | **** |
| 80 | 437.2 | 3.84 | **** |
| 81 | 375.03 | 3.57 | **** |
| 82 | 391.28 | 4.05 | **** |
| 83 | 425.28 | 4.16 | **** |
| 84 | 359.22 | 3.95 | **** |
| 85 | 437.15 | 4.44 | **** |
| 86 | 399.19 | 4.22 | **** |
| 87 | 403.15 | 4.44 | **** |
| 88 | 399.19 | 4.17 | **** |
| 89 | 434.07 | 4.04 | **** |
| 90 | 387.23 | 4.26 | **** |
| 91 | 369.27 | 4.17 | **** |
| 92 | 377.29 | 4.04 | **** |
| 93 | 435.23 | 4.29 | **** |
| 94 | 369.17 | 4.24 | **** |
| 95 | 449.06 | 4.51 | **** |
| 96 | 341.27 | 3.89 | **** |
| 97 | 387.19 | 4.2 | **** |
| 98 | 405.18 | 3.79 | **** |
| 99 | 469.22 | 4.29 | **** |
| 100 | 461.32 | 4.61 | **** |
| 101 | 369.17 | 4.26 | **** |
| 102 | 413.28 | 4.02 | **** |
| 103 | 407.1 | 4.05 | **** |
| 104 | 375.27 | 4.11 | **** |
| 105 | 387.21 | 4.19 | **** |
| 106 | 373.18 | 4.04 | **** |
| 107 | 385.28 | 4.02 | **** |
| 108 | 359.16 | 3.92 | **** |
| 109 | 369.34 | 4.16 | **** |
| 110 | 374.24 | 3.07 | **** |
| 111 | 386.19 | 3.89 | **** |
| 112 | 369.27 | 2.63 | **** |
| 113 | 399.13 | 4.01 | **** |
| 114 | 389.3 | 4.05 | **** |
| 115 | 435.13 | 4.14 | **** |
| 116 | 407.16 | 4.09 | **** |
| 117 | 419.28 | 4.05 | **** |
| 118 | 366.29 | 3.79 | **** |
| 119 | 521.19 | 4.16 | **** |
| 120 | 380.31 | 3.92 | **** |
| 121 | 403.32 | 4.27 | **** |
| 122 | 383.31 | 4.37 | **** |
| 123 | 319.2 | 2.19 | **** |
| 124 | 351.14 | 2.53 | *** |
| 125 | 409.3 | 4.14 | *** |
| 126 | 423.3 | 3.95 | *** |
| 127 | 371.31 | 3.9 | *** |
| 128 | 371.31 | 3.62 | *** |
| 129 | 449.13 | 3.81 | *** |
| 130 | 401.23 | 3.56 | *** |
| 131 | 385.22 | 3.74 | *** |
| 132 | 363.06 | 2.31 | *** |
| 133 | 385.15 | 3.86 | *** |
| 134 | 377.3 | 4.04 | *** |
| 135 | 397.15 | 2.42 | *** |
| 136 | 443.33 | 4.11 | *** |
| 137 | 361.07 | 2.53 | *** |
| 138 | 345.07 | 3.15 | *** |
| 139 | 400.27 | 4.01 | *** |
| 140 | 488.23 | 4.36 | *** |
| 141 | 425.21 | 4.37 | *** |
| 142 | 462.15 | 4.11 | *** |
| 143 | 369.23 | 3.74 | *** |
| 144 | 415.33 | 3.84 | *** |
| 145 | 361.3 | 4.39 | *** |
| 146 | 400.21 | 3.81 | *** |
| 147 | 438.21 | 3.97 | *** |
| 148 | 469.01 | 4.42 | *** |
| 149 | 425.25 | 4.24 | *** |
| 150 | 504.2 | 4.68 | *** |
| 151 | 397.01 | 2.44 | *** |
| 152 | 369.21 | 3.59 | *** |
| 153 | 372.21 | 2.36 | *** |
| 154 | 377.29 | 3.97 | *** |
| 155 | 363.11 | 2.32 | *** |
| 156 | 341.21 | 2.46 | *** |
| 157 | 407.14 | 1.78 | *** |
| 158 | 428.11 | 3.85 | *** |
| 159 | 351.13 | 2.47 | *** |
| 160 | 450.15 | 3.95 | *** |
| 161 | 363.05 | 2.32 | *** |
| 162 | 325.26 | 2.66 | *** |
| 163 | 319.2 | 2.24 | *** |
| 164 | 462.19 | 3.87 | *** |
| 165 | 371.31 | 3.65 | *** |
| 166 | 354.28 (-Boc) | 3.95 | *** |
| 167 | 432.16 | 3.87 | *** |
| 168 | 351.08 | 2.4 | *** |
| 169 | 385.35 | 4.09 | *** |
| 170 | 351.07 | 2.51 | *** |
| 171 | 363.09 | 2.68 | ** |
| 172 | 384.21 | 3.52 | ** |
| 173 | 319.2 | 2.24 | ** |
| 174 | N/A | 2.38 | ** |
| 175 | 443.33 | 4.09 | ** |
| 176 | 417.30 | 2.77 | ** |
| 177 | 398.17 | 3.67 | ** |
| 178 | 363.11 | 2.31 | ** |
| 179 | 450.14 | 3.89 | ** |
| 180 | 421.19 | 2.65 | ** |
| 181 | 363.15 | 2.46 | ** |
| 182 | 419.14 | 4.14 | ** |
| 183 | 389.29 | 4.14 | ** |
| 184 | 431.27 | 4.1 | ** |
| 185 | 328.02 | 2.41 | ** |
| 186 | 462.19 | 3.81 | ** |
| 187 | 443.28 | 3.99 | ** |
| 188 | 446.19 | 3.81 | ** |
| 189 | 405.19 | 3.8 | ** |
| 190 | 317.16 | 2.7 | ** |
| 191 | 369.23 | 3.89 | ** |
| 192 | 495.28 | 4.89 | ** |

TABLE 5-continued

| Compound | LCMS [M + H] | LCMS Retention Time (min) | ELISA EC50 μM |
|---|---|---|---|
| 193 | 297.2 | 2.53 | ** |
| 194 | 319.21 | 2.19 | ** |
| 195 | 494.25 | 2.79 | ** |
| 196 | 419.22 | 4.09 | ** |
| 197 | 317.16 | 2.41 | ** |
| 198 | 317.08 | 2.53 | ** |
| 199 | 448.24 | 3.95 | ** |
| 200 | 363.09 | 2.45 | ** |
| 201 | 365.09 | 2.36 | ** |
| 202 | 464.2 | 4.32 | ** |
| 203 | 301.18 | 2.27 | ** |
| 204 | 429.23 | 3.57 | ** |
| 205 | 301.15 | 2.27 | ** |
| 206 | 476.3 | 4.33 | ** |
| 207 | 395.17 | 2.55 | ** |
| 208 | 367.36 | 2.72 | ** |
| 209 | 353.33 | 3.97 | ** |
| 210 | 313.21 | 2.33 | ** |
| 211 | 415.26 | 4.07 | ** |
| 212 | 389.2 | 2.88 | ** |
| 213 | 407.1 | 2.46 | ** |
| 214 | 357.07 | 2.48 | ** |
| 215 | 319.23 | 2.24 | ** |
| 216 | 283.1 | 2.41 | ** |
| 217 | 418.17 | 3.62 | ** |
| 218 | 435.23 | 3.77 | ** |
| 220 | 308.23 | 2.37 | ** |
| 221 | 460.29 | 4.05 | ** |
| 222 | 365.11 | 2.52 | ** |
| 223 | 441.02 | 2.6 | ** |
| 224 | 341.27 | 2.6 | ** |
| 225 | 467.25 | 4.18 | ** |
| 226 | 369.34 | 4.01 | ** |
| 227 | 327.16 | 2.26 | ** |
| 228 | 369.34 | 2.64 | ** |
| 229 | 373.29 | 4.04 | * |
| 230 | 401.23 | 3.2 | * |
| 231 | 313.12 | 2.43 | * |
| 232 | 433.25 | 2.73 | * |
| 233 | 430.38 (-Boc) | 4.34 | * |
| 234 | 351.17 | 2.4 | * |
| 235 | 351.25 | 3.79 | * |
| 236 | 379.35 | 2.74 | * |
| 237 | 439.11 | 4.41 | * |
| 238 | 479.24 | 3.77 | * |
| 239 | 328.16 | 2.35 | * |
| 240 | 307.27 | 3.87 | * |
| 241 | 523.19 | 3.7 | * |
| 242 | 438.27 | 4.14 | * |
| 243 | 323.20 | 3.49 | * |
| 244 | 512 | 2.27 | * |
| 245 | 485 | 2.62 | * |
| 246 | 498 | 2.54 | * |
| 247 | 471 | 2.36 | * |
| 248 | 283.23 | 2.24 | * |
| 249 | 339.17 | 3.07 | * |
| 250 | 355.30 | 3.57 | * |
| 251 | 297.26 | 2.26 | * |
| 252 | 341.21 | 2.44 | * |
| 253 | 301.27 | 2.29 | * |
| 254 | 301.25 | 2.27 | * |
| 255 | 281.31 | 2.2 | * |
| 256 | 345.2 | 2.26 | * |
| 257 | 335.21 | 2.34 | * |
| 258 | 459.27 | 3.72 | * |
| 259 | 479.24 | 3.52 | * |
| 260 | 287.26 | 2.36 | * |
| 261 | 287.26 | 2.56 | * |
| 262 | 380.24 | 3.92 | * |
| 263 | 503.50 | 3.20 | * |
| 264 | 369.36 | 2.52 | * |
| 265 | 355.26 | 2.54 | * |
| 266 | 355.26 | 2.42 | * |
| 267 | 370.22 | 3.61 | * |
| 268 | 355.26 | 2.42 | * |
| 269 | 355.27 | 2.37 | * |
| 270 | 370.23 | 3.19 | * |
| 271 | 369.34 | 2.62 | * |
| 272 | 374.31 | 2.90 | * |
| 273 | 492.25 | 2.76 | * |
| 274 | 451.30 | 3.17 | * |
| 275 | 374.31 | 2.61 | * |
| 276 | 374.31 | 2.72 | * |
| 277 | 349.28 | 1.5 | * |
| 278 | 457.28 | 4.11 | * |
| 279 |  |  | ***** |
| 280 | 407.10 | 3.92 | * |
| 281 | 508.15 | 4.74 | * |
| 282 | 507.08 | 4.42 | * |
| 283 | 422.32 | 3.86 | * |
| 284 | 373.29 | 4.01 | * |
| 285 | 385.24 | 2.25 | * |
| 286 | 297.2 | 2.52 | * |
| 287 | 289.22 | 2.48 | * |
| 288 | 461.26 | 2.57 | * |
| 289 | 380.29 | 3.82 | * |
| 290 | 396.27 | 3.60 | * |
| 291 | 299.17 | 2.43 | * |
| 292 | 385.18 | 2.6 | * |
| 293 | 413.22 | 3.8 | * |
| 294 | 340.25 | 2.27 | * |
| 295 | 404.34 | 3.84 | * |
| 296 | 299.17 | 2.23 | * |
| 297 | 326.24 | 2.4 | * |
| 298 | 235.13 | 2.18 | * |
| 299 | 351.16 | 2.62 | * |
| 300 | 401 | 2.57 | * |
| 301 | 313.21 | 2.35 | * |
| 302 | 398.28 | 3.74 | * |
| 303 | 355.22 | 2.58 | * |
| 304 | 440.32 | 4.09 | * |
| 305 | 341.08 | 2.48 | * |
| 306 | 364.3 | 3.65 | * |
| 307 | 350.32 | 3.35 | * |
| 308 | 432.27 | 3.92 | * |
| 309 | 474.26 | 3.02 | **** |
| 310 | 289.03 | 2.35 | * |
| 311 | 345.19 | 2.58 | * |
| 312 | 420.28 | 4.12 | * |
| 313 | 279.28 | 2.18 | * |
| 314 | 293.24 | 2.20 | * |
| 315 | 297.26 | 2.17 | * |
| 316 | 472.26 | 3.85 | * |
| 317 | 428.25 | 3.95 | * |
| 318 | 309 | 2.25 | * |
| 319 | 284.09 | 2.1 | * |
| 320 | 356.21 | 2.37 | * |
| 321 | 279.2 | 2.1 | * |
| 322 | 279.2 | 1.76 | * |
| 323 | 309.23 | 1.82 | * |
| 324 | 280.19 | 1.76 | * |
| 325 | 279.2 | 1.76 | * |
| 326 | 263.17 | 1.93 | * |
| 327 | 343.18 | 2.33 | * |
| 328 | ~0.005 | 4.16 | * |
| 329 | 0.0036 | 4.26 | * |
| 330 | 0.0047 | 4.24 | * |
| 331 | ~0.010 | 2.94 | * |
| #332 | ~0.010 | 4 | * |
| 333 | 410.27 | 3.64 | ** |
| 334 | 426.24 | 3.39 | * |
| 335 | 466.23 | 4.64 | *** |
| 336 | 438.31 | 4.31 | ** |
| 337 | 454.24 | 4.63 | *** |
| 338 | 474.32 | 4.33 | ** |
| 339 | 412.3 | 3.83 | * |
| 340 | 446.33 | 4.49 | * |
| 341 | 447.26 | 4.25 | *** |
| 342 | 371.31 | 3.88 | *** |
| 343 | 371.31 | 3.61 | * |
| 344 | 459.31 | 4.91 | **** |
| 345 | 383.35 | 4.44 | **** |
| 346 | 587 | 4.04 | **** |
| 347 | 451.16 | 3.93 | ***** |

TABLE 5-continued

| Compound | LCMS [M + H] | LCMS Retention Time (min) | ELISA EC50 μM |
|---|---|---|---|
| 348 | 479.28 | 4.13 | ***** |
| 349 | 481.21 | 3.74 | **** |
| 350 | 462.17 | 3.66 | ***** |
| 351 | 471.17 | 3.93 | **** |
| 352 | 403.29 | 3.98 | **** |
| 353 | 497.16 | 3.94 | ***** |
| 354 | 525.2 | 4.19 | ***** |
| 355 | 511.21 | 3.81 | ***** |
| 356 | 490.3 | 3.93 | ** |
| 357 | 534.23 | 3.93 | *** |
| 358 | 433.2 | 3.45 | *** |
| 359 | 511.25 | 3.64 | *** |
| 360 | 516 | 3.82 | **** |
| 361 | 474.26 | 3.02 | **** |
| 362 | 427 | 4.2 | ***** |
| 363 | 412.4 | 1.80 | * |
| 364 | 484.3 | 2.49 | ***** |
| 365 | 457.3 | 4.06 | *** |
| 366 | 553.3 | 4.42 | * |
| 367 | 402.8 | 4.37 | **** |
| 368 | 430.9 | 4.79 | ** |
| 369 | 427.0 | 4.06 | ** |
| 370 | 427.0 | 3.99 | ***** |
| 371 | 469.0 | 5.27 | *** |
| 372 | 486.9 | 4.96 | * |
| 373 | 470.8 | 5.01 | *** |
| 374 | 436.9 | 4.66 | *** |
| 375 | 461 | 4.92 | ** |
| 376 | 385 | 3.79 | ** |
| 377 | | | * |
| 378 | | | * |
| 379 | | | * |
| 380 | | | * |
| 381 | | | * |
| 382 | | | * |
| 383 | 417.2 | 4.93 | ***** |
| 384 | 403.22 | 4.65 | ***** |
| 385 | 509.51 | 2.57 | **** |
| 386 | 465.26 | 2.52 | ***** |
| 387 | 465.26 | 2.52 | ***** |
| 388 | 495.4 | 3.94 | ***** |
| 389 | 538.3 | 4.29 | ***** |
| 390 | 480.5 | 3.23 | ***** |
| 391 | 562.55 | 3.63 | ***** |
| 392 | 443.4 | 3.88 | ***** |
| 393 | 447.1 | 6.55 | ***** |
| 394 | 450.1 | 5.48 | ***** |
| 395 | 481.32 | 3.51 | ***** |
| 396 | 411.3 | 3.99 | ***** |
| 397 | 535.3 | 4.29 | ***** |
| 398 | 481.3 | 4.23 | ***** |
| 399 | 429.3 | 3.81 | ***** |
| 400 | 493.3 | 4.43 | ***** |
| 401 | 451.3 | 3.99 | ***** |
| 402 | 494.4 | 3.71 | ***** |
| 403 | 479.3 | 4.23 | ***** |
| 404 | 473.6 | 3.78 | ***** |
| 405 | 551.17 | 4.58 | ***** |
| 406 | 425.4 | 4.13 | ***** |
| 407 | 457.4 | 4.04 | ***** |
| 408 | 425.4 | 4.09 | ***** |
| 409 | 477.4 | 4.18 | ***** |
| 410 | 451.3 | 3.99 | ***** |
| 411 | 443.4 | 3.86 | ***** |
| 412 | 473.4 | 4.23 | ***** |
| 413 | 459.3 | 4.16 | ***** |
| 414 | 439.4 | 4.31 | ***** |
| 415 | 637.64 | 2.82 | ***** |
| 416 | 311.1 | 4.39 | ***** |
| 417 | 562.47 | 4.15 | ***** |
| 418 | 511.3 | 4.13 | ***** |
| 419 | 491.4 | 3.98 | ***** |
| 420 | 486.6 | 3.45 | ***** |
| 421 | 553.30 | 4.05 | ***** |
| 422 | 359.29 | 4.17 | ***** |
| 423 | 447.4 | 3.56 | ***** |
| 424 | 594.2 [M − H] | 4.58 | ***** |
| 425 | 539.2 | 3.11 | ***** |
| 426 | 535.27 | 4.29 | ***** |
| 427 | 554.3 | 4.45 | ***** |
| 428 | 563.55 | 4.64 | ***** |
| 429 | 564.42 | 2.77 | ***** |
| 430 | 431.3 | 3.41 | ***** |
| 431 | 522.2 | 5.05 | ***** |
| 432 | 489.4 | 4.14 | ***** |
| 433 | 578.44 | 2.82 | ***** |
| 434 | 467.18 | 4.11 | ***** |
| 435 | 444.3 | 3.95 | ***** |
| 436 | 477.4 | 3.93 | ***** |
| 437 | 543.4 | 3.92 | ***** |
| 438 | 500.1 | 4.35 | ***** |
| 439 | 361.2 | 5.95 | ***** |
| 440 | 536.43 | 3.95 | ***** |
| 441 | 482.1 | 5.11 | **** |
| 442 | 367.1 | 2.92 | **** |
| 443 | 436.2 | 5.25 | **** |
| 444 | 455.28 | 3.73 | **** |
| 445 | 478 | 3.67 | **** |
| 446 | 383.3 | 4.10 | **** |
| 447 | 464.9 | 5.11 | **** |
| 448 | 501.27 | 3.65 | **** |
| 449 | 482.24 | 2.62 | **** |
| 450 | 587 | 4.04 | **** |
| 451 | 644.3 [M − H] | 4.80 | **** |
| 452 | 439.3 | 3.56 | **** |
| 453 | 553.1 | 6.13 | **** |
| 454 | 579.3 | 2.75 | **** |
| 455 | 583 | 3.84 | **** |
| 456 | 474.3 | 2.44 | **** |
| 457 | 455 | 3.4 | **** |
| 458 | 456.3 | 2.51 | **** |
| 459 | 470.3 | 2.61 | **** |
| 460 | 509.30 | 4.16 | **** |
| 461 | 454.3 | 5.98 | **** |
| 462 | 580.56 | 2.85 | **** |
| 463 | 495.44 | 4.13 | **** |
| 464 | 493.0 | 5.71 | **** |
| 465 | 507.4 | 3.98 | **** |
| 466 | 555.2 | 3.14 | **** |
| 467 | 524.2 | 4.02 | **** |
| 468 | 582.2 | 2.81 | **** |
| 469 | 525.2 | 5.07 | **** |
| 470 | 554.3 | 3.90 | **** |
| 471 | 620.18 | 3.85 | **** |
| 472 | 335.3 | 5.52 | **** |
| 473 | 495.3 | 4.68 | *** |
| 474 | 511.2 | 4.99 | *** |
| 475 | 483 | 3.87 | *** |
| 476 | 400 | 3.45 | *** |
| 477 | 249.1 | 3.67 | *** |
| 478 | 525.1 | 3.25 | *** |
| 479 | 538.3 | 2.76 | *** |
| 480 | 456.1 | 4.26 | *** |
| 481 | 549.3 | 5.29 | *** |
| 482 | 522.3 | 3.95 | *** |
| 483 | 470.1 | 4.46 | *** |
| 484 | 539.2 | 3.02 | *** |
| 485 | 398.9 | 4.18 | *** |
| 486 | 349.1 | 6.03 | *** |
| 487 | 505 | 3.66 | *** |
| 488 | 555.2 | 3.34 | *** |
| 489 | 538.3 | 4.15 | *** |
| 490 | 486.1 | 3.80 | *** |
| 491 | 537.31 | 2.64 | *** |
| 492 | 468 | 5.52 | *** |
| 493 | 504.3 | 2.68 | *** |
| 494 | 482.2 | 5.74 | *** |
| 495 | 403.3 | 4.16 | *** |
| 496 | 430.2 | 3.65 | *** |
| 497 | 281.0 | 3.84 | *** |
| 498 | 481.4 | 4.81 | *** |
| 499 | 423.3 | 5.15 | *** |
| 500 | 506.29 | 3.85 | *** |
| 501 | 534.3 | 2.68 | *** |

TABLE 5-continued

| Compound | LCMS [M + H] | LCMS Retention Time (min) | ELISA EC50 μM |
|---|---|---|---|
| 502 | 518.3 | 2.76 | *** |
| 503 | 508.2 | 5.72 | *** |
| 504 | 359.1 | 5.65 | *** |
| 505 | 442.0 | 4.06 | *** |
| 506 | 386.3 | 5.32 | *** |
| 507 | 450 | 3.19 | *** |
| 508 | 397.1 | 5.97 | *** |
| 509 | 511.4 | 5.05 | *** |
| 510 | 321.4 | 5.19 | *** |
| 511 | 383.1 | 5.75 | *** |
| 512 | 523.1 | 5.69 | *** |
| 513 | 361.1 | 5.12 | *** |
| 514 | 495.3 | 4.67 | *** |
| 515 | 363.5 | 6.34 | ** |
| 516 | 527.1 | 3.16 | ** |
| 517 | 464.2 | 5.86 | ** |
| 518 | 517.6 | 5.03 | ** |
| 519 | 527.2 | 3.88 | ** |
| 520 | 426.2 | 4.29 | ** |
| 521 | 509.4 | 4.99 | ** |
| 522 | 383.3 | 4.10 | ** |
| 523 | 439.0 | 6.11 | ** |
| 524 | 412.1 | 4.13 | ** |
| 525 | 4.95.3 | 3.46 | ** |
| 526 | 513.2 | 4.43 | ** |
| 527 | 535.3 | 4.94 | ** |
| 528 | 453.0 | 6.30 | ** |
| 529 | 481.3 | 3.43 | ** |
| 530 | 466.28 | 3.21 | ** |
| 531 | 549.6 | 5.21 | ** |
| 532 | 325.3 | 4.75 | ** |
| 533 | 506.2 | 4.96 | ** |
| 534 | 525.2 | 4.76 | ** |
| 535 | 541.2 | 3.51 | ** |
| 536 | 482.29 | 3.29 | ** |
| 537 | 476.3 | 2.51 | ** |
| 538 | 516.37 | 3.49 | ** |
| 539 | 337.3 [M − H] | 2.14 | ** |
| 540 | 428.28 | 3.43 | ** |
| 541 | 525.2 | 4.42 | ** |
| 542 | 398.1 | 3.95 | ** |
| 543 | 466.34 | 3.29 | ** |
| 544 | 723.58 | 3.92 | ***** |
| 545 | 466.31 | 3.28 | ** |
| 546 | 426.3 | 2.26 | ** |
| 547 | 335.2 | 5.45 | ** |
| 548 | 516.37 | 3.46 | ** |
| 549 | 414 | 2.89 | ** |
| 550 | 496 | 4.58 | ** |
| 551 | 544.5 | 2.78 | ** |
| 552 | 511.3 | 3.56 | ** |
| 553 | 440.9 | 5.75 | ** |
| 554 | 482.32 | 3.41 | ** |
| 555 | 372 | 2.89 | ** |
| 556 | 456.1 | 4.21 | ** |
| 557 | 538.4 | 3.71 | ** |
| 558 | 497.2 | 4.69 | ** |
| 559 | 460.8 | 4.96 | ** |
| 560 | 596.3 | 4.45 | * |
| 561 | 509.2 | 5.18 | * |
| 562 | 525.3 | 3.52 | * |
| 563 | 483.1 | 4.96 | * |
| 564 | 432 | 2.18 | * |
| 565 | 276.9 | 4.00 | * |
| 566 | 384.4 | 1.73 | * |
| 567 | 511.4 | 4.71 | * |
| 568 | 295.0 | 4.14 | * |
| 569 | 480.21 | 3.50 | ***** |
| 570 | 549.22 | 4.59 | ***** |
| 571 | 497.13 | 3.50 | ** |
| 572 | 525.29 | 4.14 | ***** |
| 573 | 341.34 | 2.14 | **** |
| 574 | 427.37 | 2.23 | * |
| 575 | 437.33 | 3.16 | ** |
| 576 | 575.43 | 3.71 | *** |
| 577 | 453.28 | 3.34 | *** |
| 578 | 610.45 | 3.94 | *** |
| 579 | 481.32 | 3.51 | ***** |
| 580 | 495.29 | 3.64 | ***** |
| 581 | 465.43 | 3.64 | * |
| 582 | 516.34 | 3.31 | * |
| 583 | 512.26 | 3.39 | *** |
| 584 | 466.37 | 3.34 | *** |
| 585 | 516.33 | 3.46 | *** |
| 586 | 387.27 | 2.13 | ***** |
| 587 | 467.29 | 3.66 | *** |
| 588 | 455.26 | 3.69 | *** |
| 589 | 471.3 | 3.83 | *** |
| 590 | 495.31 | 3.64 | **** |
| 591 | 541.35 | 3.73 | ***** |
| 592 | 523.42 | 3.58 | ***** |
| 593 | 541.38 | 3.69 | **** |
| 594 | 505.38 | 3.83 | *** |
| 595 | 431.21 | 4.01 | **** |
| 596 | 431.24 | 3.99 | ***** |
| 597 | 445.24 | 4.19 | ***** |
| 598 | 459.24 | 4.36 | ***** |
| 599 | 513.17 | 4.19 | **** |
| 600 | 479.23 | 3.99 | ***** |
| 601 | 504.21 | 3.79 | **** |
| 602 | 493.2 | 4.18 | **** |
| 603 | 513.16 | 4.19 | **** |
| 604 | 446.18 | 2.86 | * |
| 605 | 503.23 | 3.84 | ***** |
| 606 | 461.19 | 3.46 | *** |
| 607 | 442.25 | 3.46 | *** |
| 608 | 489.2 | 3.72 | *** |
| 609 | 433.27 | 3.98 | ** |
| 610 | | | **** |
| 611 | | | ** |
| 612 | 491.23 | 3.56 | *** |
| 613 | 513.14 | 4.18 | **** |
| 614 | 463 | 3.88 | ** |
| 615 | 381 | 3.48 | *** |
| 616 | 540 | 4.17 | ** |
| 617 | 621.57 | 4.13 | **** |
| 618 | 493.6 | 2.63 | ***** |
| 619 | 521.6 | 2.80 | ***** |
| 620 | 445.5 | 3.23 | **** |
| 621 | 459.5 | 3.40 | ***** |
| 622 | 459.5 | 3.38 | ***** |
| 623 | 473.5 | 3.57 | ***** |
| 624 | 479.5 | 3.28 | **** |
| 625 | 507.6 | 3.53 | ***** |
| 626 | 493.6 | 3.48 | **** |
| 627 | 511.6 | 3.53 | ***** |
| 628 | 527.4 | 3.62 | *** |
| 629 | 527.5 | 3.72 | ***** |
| 630 | 573.5 | 3.75 | ***** |
| 631 | 507.6 | 3.65 | ***** |
| 632 | 538.6 | 3.53 | **** |
| 633 | 443.5 | 3.32 | ***** |
| 634 | 457.6 | 3.30 | ***** |
| 635 | 523.6 | 3.47 | **** |
| 636 | 463.6 | 3.12 | ***** |
| 637 | 621.62 | 2.77 | ***** |
| 638 | 580.56 | 2.80 | ***** |
| 639 | 496.54 | 3.28 | ***** |
| 640 | 552.64 | 2.48 | **** |
| 641 | 445.55 | 4.13 | ***** |
| 642 | 381.49 | 3.97 | ***** |
| 643 | 397.47 | 3.95 | ***** |
| 644 | 395.45 | 3.78 | ***** |
| 645 | 521.15 | 4.17 | ***** |
| 646 | 531.11 | 4.58 | **** |
| 647 | 505.18 | 4.7 | ***** |
| 648 | 437.19 | 4.15 | **** |
| 649 | 477.21 | 4.1 | ***** |
| 650 | 487.18 | 4.3 | **** |
| 651 | 548.3 | 2.53 | **** |
| 652 | 419.23 | 4.15 | **** |
| 653 | 449.24 | 4.12 | **** |
| 654 | 433.26 | 4.3 | ***** |
| 655 | 453.19 | 4.33 | **** |

TABLE 5-continued

| Compound | LCMS [M + H] | LCMS Retention Time (min) | ELISA EC50 μM |
|---|---|---|---|
| 656 | 444.17 | 4.02 | ***** |
| 657 | 464.22 | 4.08 | ***** |
| 658 | 461.6 | 4.30 | ***** |
| 659 | 489.7 | 4.78 | ***** |
| 660 | 543.7 | 4.92 | ***** |
| 661 | 459.5 | 3.63 | ***** |
| 662 | 471.5 | 3.87 | ***** |
| 663 | 491.6 | 3.63 | ***** |
| 664 | 507.6 | 3.80 | ***** |
| 665 | 485.6 | 3.85 | **** |
| 666 | 485.6 | 3.83 | ***** |
| 667 | 486.6 | 3.95 | ***** |
| 668 | 503.6 | 3.58 | ***** |
| 669 | 521.6 | 3.88 | ***** |
| 670 | 521.6 | 4.02 | ***** |
| 671 | 501.6 | 4.13 | ***** |
| 672 | 501.6 | 4.10 | ***** |
| 673 | 539.6 | 4.02 | |
| 674 | 555.6 | 4.13 | **** |
| 675 | 555.6 | 4.22 | **** |
| 676 | 535.6 | 4.05 | **** |
| 677 | 535.6 | 4.15 | **** |
| 678 | 551.6 | 3.98 | *** |
| 679 | 487.6 | 3.93 | **** |
| 680 | 599.5 | 4.27 | ***** |
| 681 | 566.6 | 4.02 | **** |
| 682 | 496.5 | 2.13 | ** |
| 683 | 486.5 | 2.03 | *** |
| 684 | 484.6 | 2.67 | *** |
| 685 | 514.6 | 2.15 | *** |
| 686 | 512.6 | 2.12 | **** |
| 687 | 510.6 | 2.13 | *** |
| 688 | 525.6 | 1.85 | *** |
| 689 | 494.5 | 3.12 | *** |
| 690 | 524.6 | 2.32 | *** |
| 691 | 514.6 | 2.23 | *** |
| 692 | 512.6 | 2.35 | *** |
| 693 | 542.6 | 2.35 | **** |
| 694 | 540.6 | 2.27 | **** |
| 695 | 538.6 | 2.35 | **** |
| 696 | 553.6 | 2.07 | *** |
| 697 | 522.6 | 3.95 | ***** |
| 698 | 578.5 | 2.43 | **** |
| 699 | 568.5 | 2.35 | **** |
| 700 | 566.6 | 2.45 | **** |
| 701 | 596.6 | 2.47 | **** |
| 702 | 594.6 | 2.43 | **** |
| 703 | 592.6 | 2.48 | **** |
| 704 | 607.6 | 2.20 | *** |
| 705 | 575.5 | 2.47 | **** |
| 706 | 576.5 | 3.58 | ***** |
| 707 | 477.51 | 2.77 | ***** |
| 708 | 491.53 | 2.73 | ***** |
| 709 | 503.55 | 2.68 | ***** |
| 710 | 495.45 | 4.42 | ***** |
| 711 | 475.51 | 4.62 | ***** |
| 712 | 513.50 | 4.42 | ***** |
| 713 | 529.46 | 4.62 | **** |
| 714 | 509.51 | 4.43 | ***** |
| 715 | 482.46 | 4.28 | ***** |
| 716 | 457.47 | 4.05 | **** |
| 717 | 459.59 | 4.33 | ***** |
| 718 | 491.5 | 4.10 | ***** |
| 719 | 527.5 | 4.47 | ***** |
| 720 | 489.5 | 4.75 | ***** |
| 721 | 517.5 | 4.26 | ***** |
| 722 | 519.5 | 3.84 | ***** |
| 723 | 555.4 | 4.09 (non polar) | ***** |
| 724 | 541.54 | 2.90 | ***** |
| 725 | 478.47 | 3.58 | ***** |
| 726 | 516.5 | 2.67 | ** |
| 727 | 526.5 | 2.78 | **** |
| 728 | 544.5 | 2.80 | *** |
| 729 | 542.5 | 2.72 | ***** |
| 730 | 540.5 | 2.83 | **** |
| 731 | 555.6 | 2.43 | *** |
| 732 | 580.6 | 2.40 | *** |
| 733 | 523.5 | 2.78 | ***** |
| 734 | 524.5 | 3.40 | ***** |
| 735 | 552.5 | 2.98 | ***** |
| 736 | 562.5 | 3.15 | ***** |
| 737 | 580.6 | 3.17 | **** |
| 738 | 578.5 | 3.02 | ***** |
| 739 | 576.6 | 3.17 | ***** |
| 740 | 591.6 | 2.75 | *** |
| 741 | 616.5 | 2.62 | *** |
| 742 | 559.5 | 3.13 | ***** |
| 743 | 560.5 | 3.83 | ***** |
| 744 | 514.6 | 2.80 | ***** |
| 745 | 524.6 | 2.92 | ***** |
| 746 | 512.5 | 2.93 | ***** |
| 747 | 542.6 | 2.93 | ***** |
| 748 | 540.5 | 2.85 | ***** |
| 749 | 538.6 | 2.93 | ***** |
| 750 | 553.6 | 2.55 | ***** |
| 751 | 521.5 | 2.92 | **** |
| 752 | 522.5 | 3.87 | ***** |
| 753 | 542.6 | 2.98 | **** |
| 754 | 552.6 | | ***** |
| 755 | 540.6 | 3.17 | **** |
| 756 | 570.6 | 3.17 | **** |
| 757 | 568.6 | 3.07 | ***** |
| 758 | 566.6 | 3.17 | *** |
| 759 | 581.6 | 2.78 | *** |
| 760 | 549.6 | 3.13 | ***** |
| 761 | 550.5 | 4.17 | ***** |
| 762 | 544.5 | 2.68 | **** |
| 763 | 554.5 | 2.77 | ***** |
| 764 | 542.6 | 2.78 | **** |
| 765 | 572.5 | 2.75 | **** |
| 766 | 570.6 | 2.70 | ***** |
| 767 | 568.6 | 2.82 | **** |
| 768 | 583.6 | 2.47 | **** |
| 769 | 608.6 | 2.38 | *** |
| 770 | 551.5 | 2.73 | ***** |
| 771 | 552.5 | 3.65 | ***** |
| 772 | 580.5 | 3.03 | ***** |
| 773 | 590.6 | 3.12 | ***** |
| 774 | 578.5 | 3.12 | **** |
| 775 | 608.6 | 3.05 | ***** |
| 776 | 606.5 | 3.05 | ***** |
| 777 | 604.6 | 3.12 | ***** |
| 778 | 619.6 | 2.77 | ***** |
| 779 | 644.5 | 2.63 | *** |
| 780 | 587.5 | 3.10 | ***** |
| 781 | 588.5 | 4.05 | ***** |
| 782 | 596.5 | 3.10 | ***** |
| 783 | 606.5 | 3.18 | ***** |
| 784 | 594.5 | 3.27 | ***** |
| 785 | 624.5 | 3.22 | ***** |
| 786 | 622.5 | 3.12 | ***** |
| 787 | 620.5 | 3.20 | ***** |
| 788 | 635.6 | 2.85 | **** |
| 789 | 660.5 | 2.68 | *** |
| 790 | 603.5 | 3.22 | ***** |
| 791 | 604.5 | 4.25 | ***** |
| 792 | 480.50 | 2.98 | ***** |
| 793 | 494.50 | 2.97 | **** |
| 794 | 494.50 | 2.97 | *** |
| 795 | 496.48 | 2.97 | **** |
| 796 | 563.50 | 2.41 | **** |
| 797 | 522.48 | 2.50 | ***** |
| 798 | 538.48 | 2.92 | ***** |
| 799 | 535.49 | 2.35 | *** |
| 800 | 503.40 | 2.52 | **** |
| 801 | 504.43 | 3.42 | ***** |
| 802 | 504.42 | 3.37 | ***** |
| 803 | 579.48 | 2.42 | **** |
| 804 | 538.48 | 2.43 | ***** |
| 805 | 584.50 | 2.52 | ***** |
| 806 | 554.40 | 2.47 | ***** |
| 807 | 540.47 | 2.50 | ***** |
| 808 | 551.48 | 2.33 | **** |
| 809 | 516.45 | 2.47 | ***** |

TABLE 5-continued

| Compound | LCMS [M + H] | LCMS Retention Time (min) | ELISA EC50 μM |
|---|---|---|---|
| 810 | 520.40 | 3.21 | ***** |
| 811 | 520.40 | 3.12 | ***** |
| 812 | 466.4 | 3.27 | ***** |
| 813 | 466.4 | 3.18 | ***** |
| 814 | 465.4 | 2.38 | ***** |
| 815 | 465.4 | 3.45 | ***** |
| # 816 | 497.4 | 2.70 | ***** |
| # 817 | 511.4 | 2.62 | ***** |
| # 818 | 491.4 | 2.43 | **** |
| 819 | 494.4 | 3.53 | ***** |
| 820 | 494.4 | 3.47 | **** |
| 821 | 493.4 | 2.55 | **** |
| 822 | 493.4 | 3.73 | ***** |
| # 823 | 525.4 | 2.95 | ***** |
| # 824 | 539.4 | 2.83 | ***** |
| # 825 | 519.4 | 2.58 | * |
| 826 | 496.4 | 3.07 | *** |
| 827 | 496.4 | 2.98 | **** |
| 828 | 495.4 | 2.32 | *** |
| 829 | 495.4 | 3.28 | *** |
| # 830 | 527.4 | 2.53 | ***** |
| # 831 | 541.4 | 2.50 | ***** |
| # 832 | 521.4 | 2.35 | |
| 833 | 532.4 | 3.50 | *** |
| 834 | 532.4 | 3.42 | **** |
| 835 | 531.4 | 2.57 | *** |
| 836 | 531.4 | 3.67 | **** |
| # 837 | 563.4 | 2.93 | ***** |
| # 838 | 577.4 | 2.82 | ***** |
| 839 | 548.3 | 3.63 | **** |
| 840 | 548.3 | 3.58 | **** |
| # 841 | 579.3 | 3.08 | ***** |
| # 842 | 593.3 | 2.95 | ***** |
| # 843 | 573.4 | 2.75 | ***** |
| 844 | 451.91 | 3.58 | *** |
| 845 | 648.48 | 4.45 | *** |
| 846 | 526.45 | 2.57 | *** |
| 847 | 568.37 | 3.40 | **** |
| 848 | 585.30 | 3.57 | ***** |
| 849 | 604.37 | 3.52 | **** |
| 850 | 540.39 | 2.60 | *** |
| 851 | 495.06 | 4.37 | ***** |
| 852 | 539.08 | 4.17 | ***** |
| 853 | 549.09 | 4.38 | ***** |
| 854 | 523.17 | 4.73 | ***** |
| 855 | 455.19 | 4.15 | **** |
| 856 | 495.18 | 4.10 | ***** |
| 857 | 505.16 | 4.30 | ***** |
| 858 | 566.3 | 2.57 | ***** |
| 859 | 437.22 | 4.15 | ***** |
| 860 | 467.2 | 4.13 | ***** |
| 861 | 451.12 | 4.10 | **** |
| 862 | 471.17 | 4.32 | ***** |
| 863 | 514.55 | 4.38 | ***** |
| 864 | 462.28 | 4.00 | **** |
| 865 | 482.13 | 4.08 | **** |
| 866 | 447.37 | 4.04 | ***** |
| 867 | 577.43 | 2.85 | **** |
| 868 | 477.14 | 4.37 | ***** |
| 869 | 504.53 | 3.62 | ***** |
| 870 | 493.55 | 2.80 | ***** |
| 871 | 489.54 | 2.72 | ***** |
| 872 | 493.55 | 2.80 | ***** |
| 873 | 503.54 | 2.73 | ***** |
| 874 | 479.2 | 2.74 | ***** |
| 875 | 425.52 | 4.27 | ***** |
| 876 | 492.52 | 3.57 | ***** |
| 877 | 489.54 | 2.72 | ***** |
| 878 | 508.55 | 3.82 | ***** |
| 879 | 507.55 | 2.90 | ***** |
| 880 | 459.49 | 4.24 | ***** |
| 881 | 471.45 | 4.22 | ***** |
| 882 | 542.51 | 3.87 | ***** |
| 883 | 494.50 | 3.67 | ***** |
| 884 | 544.27 | 2.79 | ***** |
| 885 | 490.54 | 3.54 | ***** |
| 886 | 494.57 | 3.68 | ***** |
| 887 | 521.62 | 2.93 | ***** |
| 888 | 558.54 | 3.70 | ***** |
| 889 | 545.55 | 2.93 | ***** |
| 890 | 490.49 | 3.48 | ***** |
| 891 | 528.49 | 3.69 | ***** |
| 892 | 546.50 | 3.75 | ***** |
| 893 | 461.49 | 4.36 | ***** |
| 894 | 580.47 | 2.72 | ***** |
| 895 | 491.51 | 2.77 | ***** |
| 896 | 576.49 | 4.00 | ***** |
| 897 | 504.51 | 3.52 | ***** |
| 898 | 457.53 | 4.25 | ***** |
| 899 | 481.37 | 4.17 | ***** |
| 900 | 541.55 | 3.00 | ***** |
| 901 | 575.54 | 2.98 | ***** |
| 902 | 471.49 | 4.12 | ***** |
| 903 | 621.39 | 2.72 | ***** |
| 904 | 596.54 | 2.85 | ***** |
| 905 | 542.54 | 3.78 | ***** |
| 906 | 489.53 | 4.82 | ***** |
| 907 | 514.47 | 3.54 | ***** |
| 908 | 582.43 | 2.79 | ***** |
| 909 | 514.21 | 2.75 | ***** |
| 910 | 539.45 | 3.97 | ***** |
| 911 | 527.54 | 2.88 | ***** |
| 912 | 530.53 | 2.67 | ***** |
| 913 | 626.6 | 2.88 | ***** |
| 914 | 514.55 | 2.60 | ***** |
| 915 | 509.56 | 4.63 | ***** |
| 916 | 626.40 | 2.82 | ***** |
| 917 | 561.46 | 2.95 | ***** |
| 918 | 642.56 | 2.85 | ***** |
| 919 | 543.45 | 4.82 | ***** |
| 920 | 557.57 | 2.87 | ***** |
| 921 | 527.39 | 4.52 | ***** |
| 922 | 561.53 | 2.85 | ***** |
| 923 | 612.51 | 2.92 | ***** |
| 924 | 498.20 | 2.71 | ***** |
| 925 | 596.54 | 2.88 | ***** |
| 926 | 5.62 | 3.85 | ***** |
| 927 | 540.65 | 4.25 | ***** |
| 928 | 510.52 | 3.10 | ***** |
| 929 | 506.46 | 2.95 | ***** |
| 930 | 500.48 | 2.83 | ***** |
| 931 | 467.39 | 4.17 | ***** |
| 932 | 548.49 | 3.17 | ***** |
| 933 | 596.37 | 2.79 | ***** |
| 934 | 561.53 | 2.95 | ***** |
| 935 | 496.54 | 3.37 | ***** |
| 936 | 582.6 | 2.83 | ***** |
| 937 | 555.61 | 2.55 | ***** |
| 938 | 582.53 | 2.85 | ***** |
| 939 | 560.63 | 2.68 | ***** |
| 940 | 541.43 | 2.45 | ***** |
| 941 | 562.55 | 3.63 | ***** |
| 942 | 623.35 | 2.73 | **** |
| 943 | 499 | 2.72 | **** |
| 944 | 525.56 | 4.36 | **** |
| 945 | 509.43 | 4.73 | **** |
| 946 | 566.53 | 2.77 | **** |
| 947 | 510 | 2.44 | **** |
| 948 | 482.47 | 2.88 | **** |
| 949 | 524.55 | 3.22 | **** |
| 950 | 506.46 | 2.87 | **** |
| 951 | 544.53 | 3.27 | **** |
| 952 | 530.53 | 3.12 | **** |
| 953 | 552.46 | 2.90 | **** |
| 954 | 403 | 4.11 | **** |
| 955 | 397 | 3.9 | **** |
| 956 | 484.55 | 2.42 | **** |
| 957 | 495.52 | 2.62 | **** |
| 958 | 542.36 | 3.84 | **** |
| 959 | 496.24 | 2.81 | **** |
| 960 | 639.57 | 2.70 | **** |
| 961 | 593.52 | 2.64 | **** |
| 962 | 516.59 | 2.65 | **** |
| 963 | 593.61 | 2.72 | **** |

TABLE 5-continued

| Compound | LCMS [M + H] | LCMS Retention Time (min) | ELISA EC50 µM |
|---|---|---|---|
| 964 | 598.55 | 2.83 | **** |
| 965 | 544.53 | 3.15 | **** |
| 966 | 564.45 | 3.32 | **** |
| 967 | 491.57 | 4.00 | **** |
| 968 | 512.51 | 2.73 | **** |
| 969 | 492.46 | 2.90 | **** |
| 970 | 609.54 | 2.72 | **** |
| 971 | 468.46 | 2.78 | **** |
| 972 | 496.47 | 3.02 | **** |
| 973 | 578.47 | 3.80 | **** |
| 974 | 528.34 | 3.79 | *** |
| 975 | 431.5 | 3.10 | *** |
| 976 | 564.46 | 3.23 | *** |
| 977 | 568.53 | 2.85 | *** |
| 978 | 578.45 | 3.30 | *** |
| 979 | 470.55 | 2.45 | *** |
| 980 | 527.61 | 2.50 | *** |
| 981 | 560.51 | 3.12 | *** |
| 982 | 425.60 | 3.78 | *** |
| 983 | 375.37 | 2.27 | *** |
| 984 | 5.06.19 | 3.97 | ** |
| 985 | 407.31 | 1.82 | * |
| 986 | 531.56 | 2.17 | * |
| 987 | 497.1 | 4.4 | ***** |
| 988 | 605.62 | 2.52 | ***** |
| 989 | 564.61 | 2.55 | ***** |
| 990 | 610.62 | 2.67 | ***** |
| 991 | 580.58 | 2.60 | *** |
| 992 | 566.61 | 2.60 | *** |
| 993 | 577.61 | 2.45 | ***** |
| 994 | 545.54 | 2.57 | ***** |
| 995 | 546.57 | 3.53 | ***** |
| 996 | 578.46 | 3.71 | ***** |

(S) Isomer prepared and tested.
Wherein:
1 star, >1 uM (1000 nM)
2 stars, 0.2 to 1 uM (200 nM to 1000 nM)
3 stars, 0.04 uM to 0.2 uM (40 nM to 200 nM)
4 stars, 0.008 uM to 0.04 uM (8 nM to 40 nM)
5 stars, <0.008 uM (<8 nM)

Example 3

Compounds of the Invention Inhibit VEGF Expression and Tumor Growth, and Inhibit angiogenesis, in an In Vivo Tumor Growth PD Model Compounds of the invention also show activity in the following pharmacodynamic model that assesses tumor VEGF levels. Briefly, HT1080 cells (a human fibrosarcoma cell line) may be implanted subcutaneously in nude mice. After seven days, mice may be administrated compounds orally at a desired dosage range, e.g., 200 mg/kg/day, for seven days. The tumors may then be excised from mice, weighed and homogenized in Tris-HCl buffer containing proteinase inhibitors. Moulder et al., *Cancer Res.* 61(24):8887-95 (2001). Tumor VEGF levels are subsequently measured using a human VEGF ELISA kit (R&D System). Protein concentrations of the homogenates are measured with a Bio-Rad Protein assay kit and tumor VEGF levels are normalized to the protein concentrations.

Figure 2:
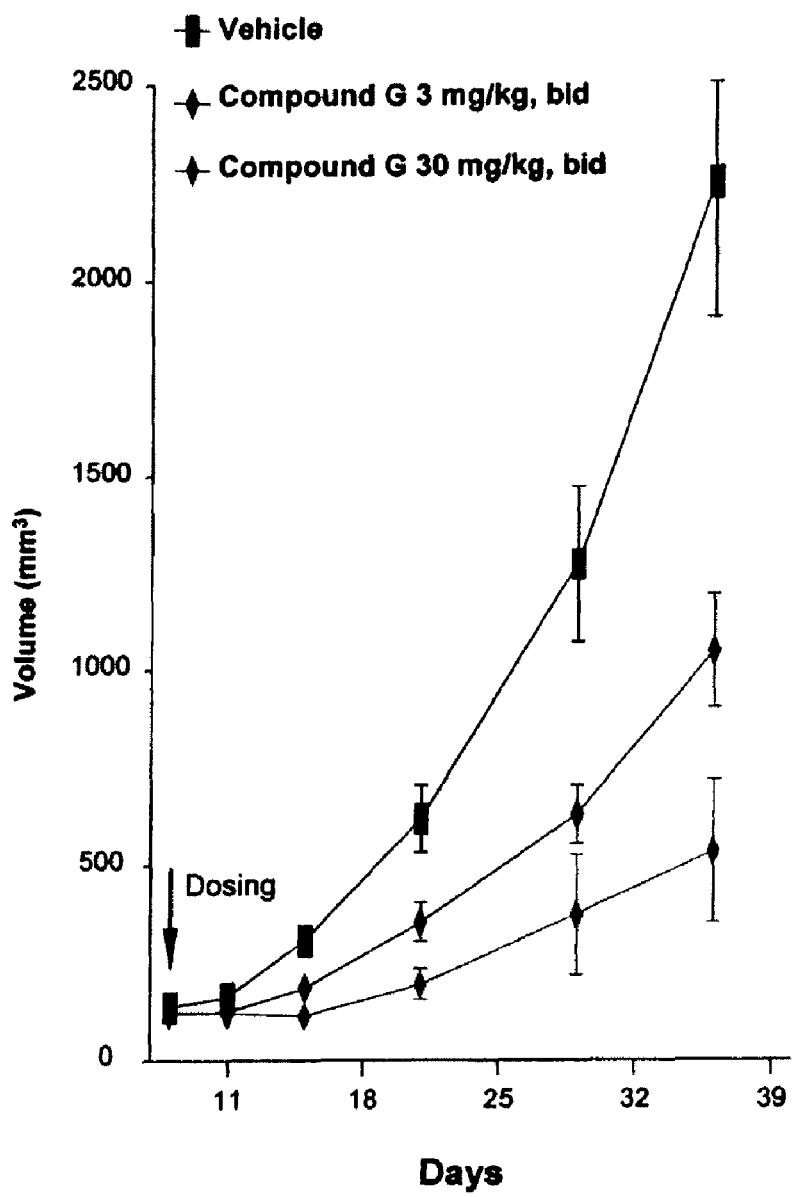
FIG. 2 illustrates inhibition of lung cancer tumor growth by a certain compound of the invention.
Figure 3:
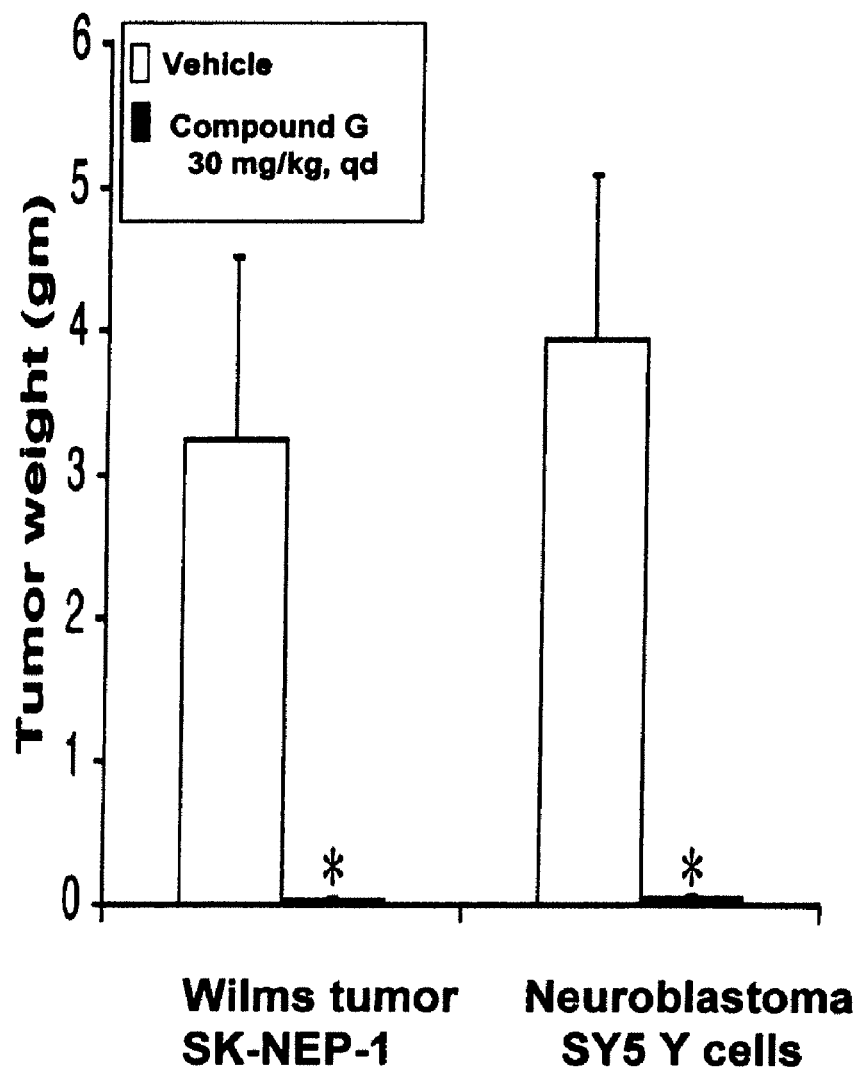
FIG. 3 illustrates inhibition of Wilms and neuroblastoma tumor growth by a certain compound of the invention.
Figure 4:
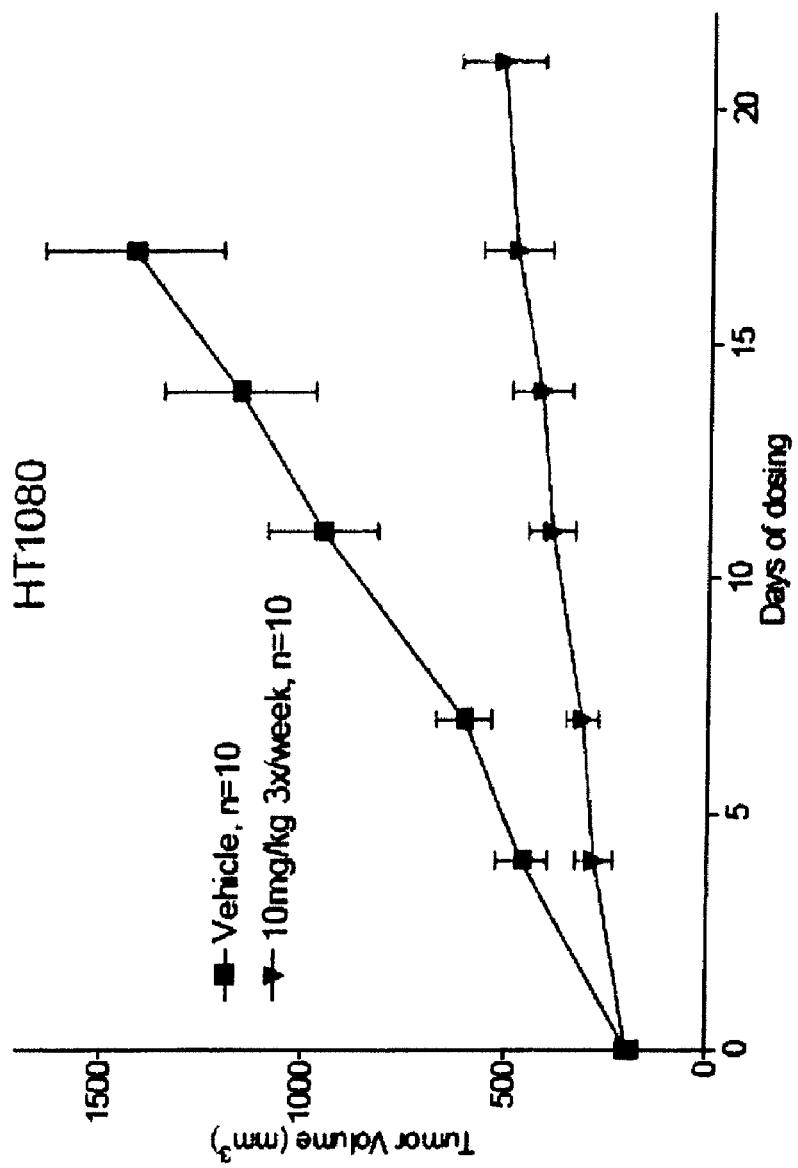
FIG. 4 illustrates inhibition of fibrosarcoma tumor growth by a certain compound of the invention.
Figure 5:
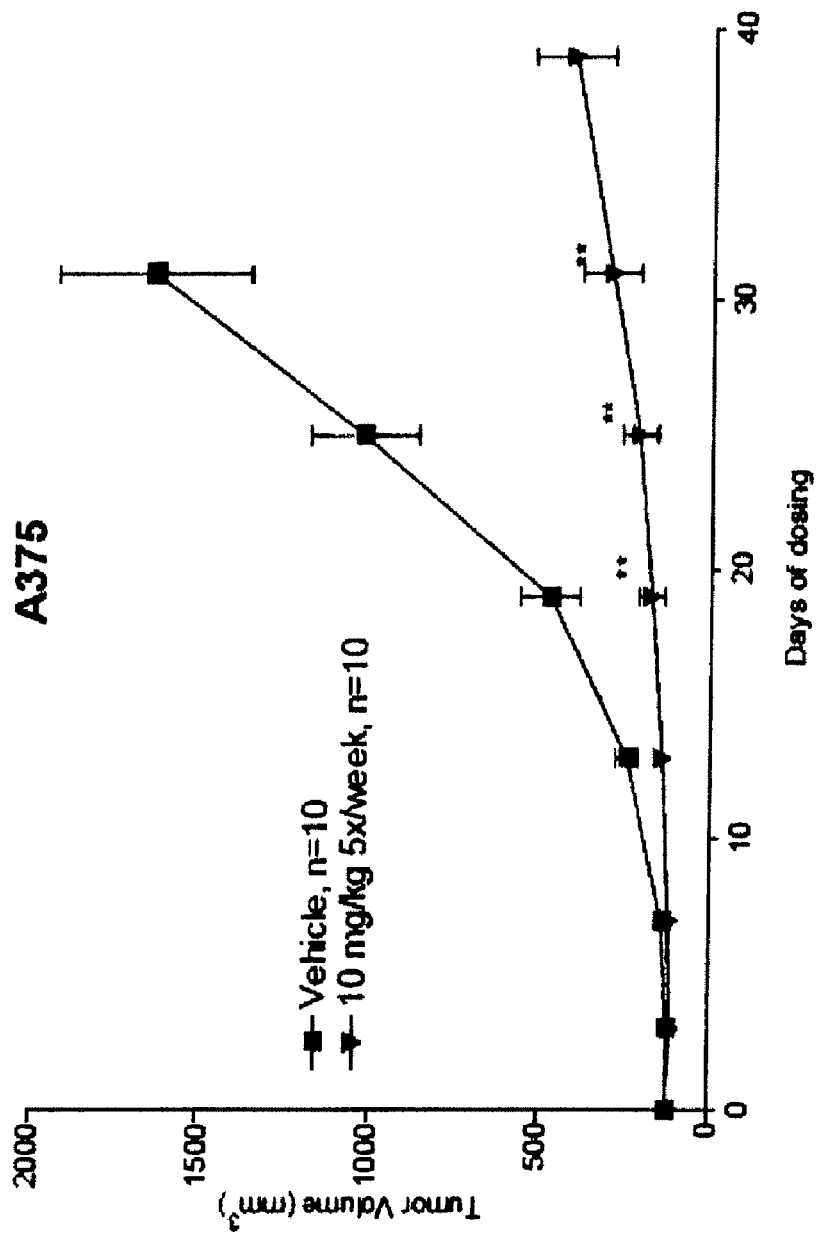
FIG. 5 illustrates inhibition of malignant melanoma tumor growth by a certain compound of the invention.
Figure 6:
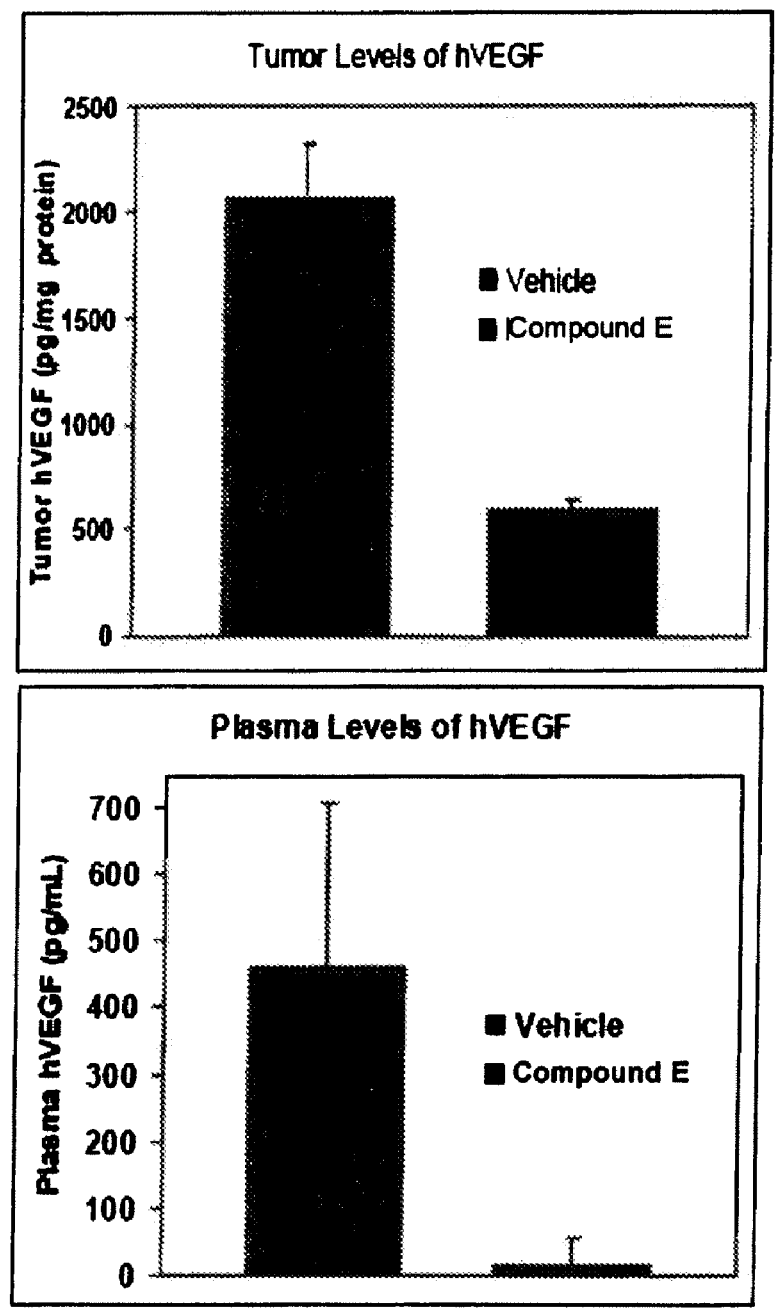
FIG. 6 illustrates inhibition of VEGF expression in a fibrosarcoma tumor by a certain compound of the invention.
Figure 7:
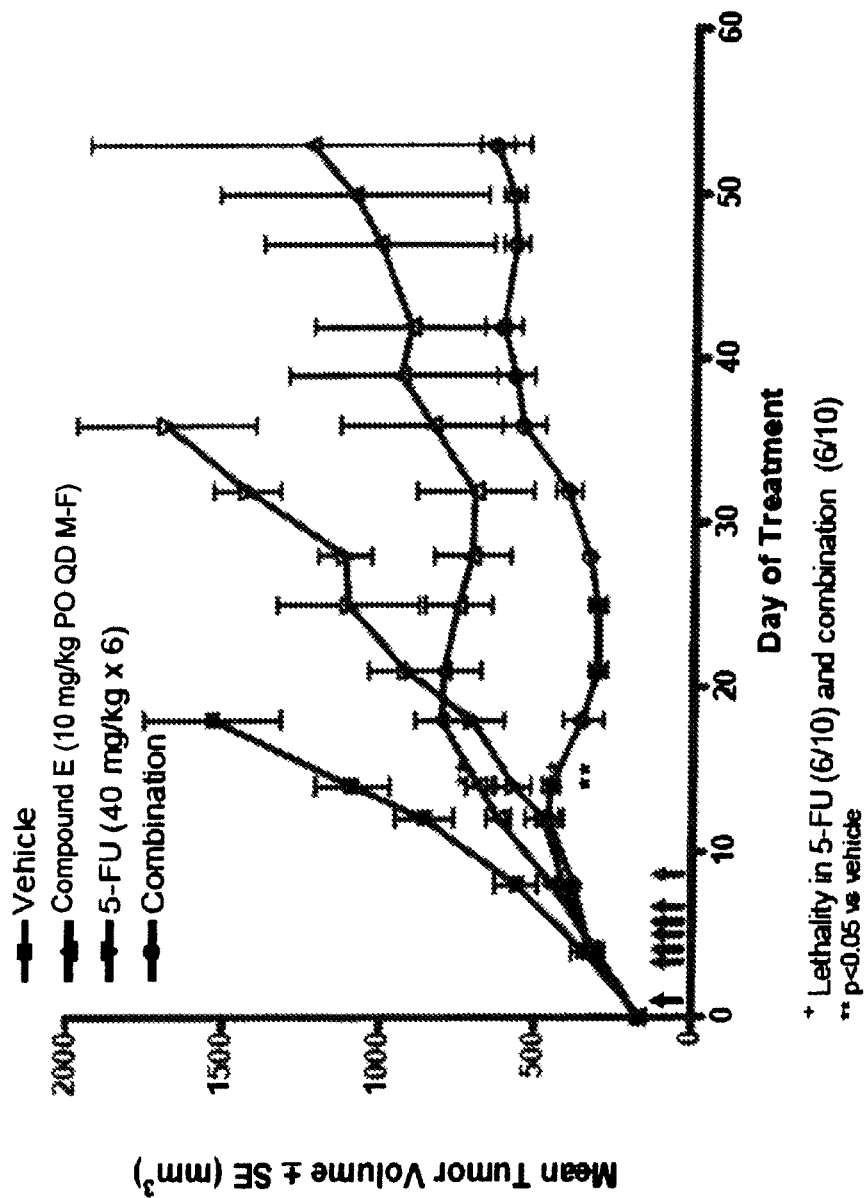
FIG. 7 illustrates inhibition of colon cancer tumor growth by a certain compound of the invention, either alone or in combination with 5-FU (fluorouracil).
Figure 8:
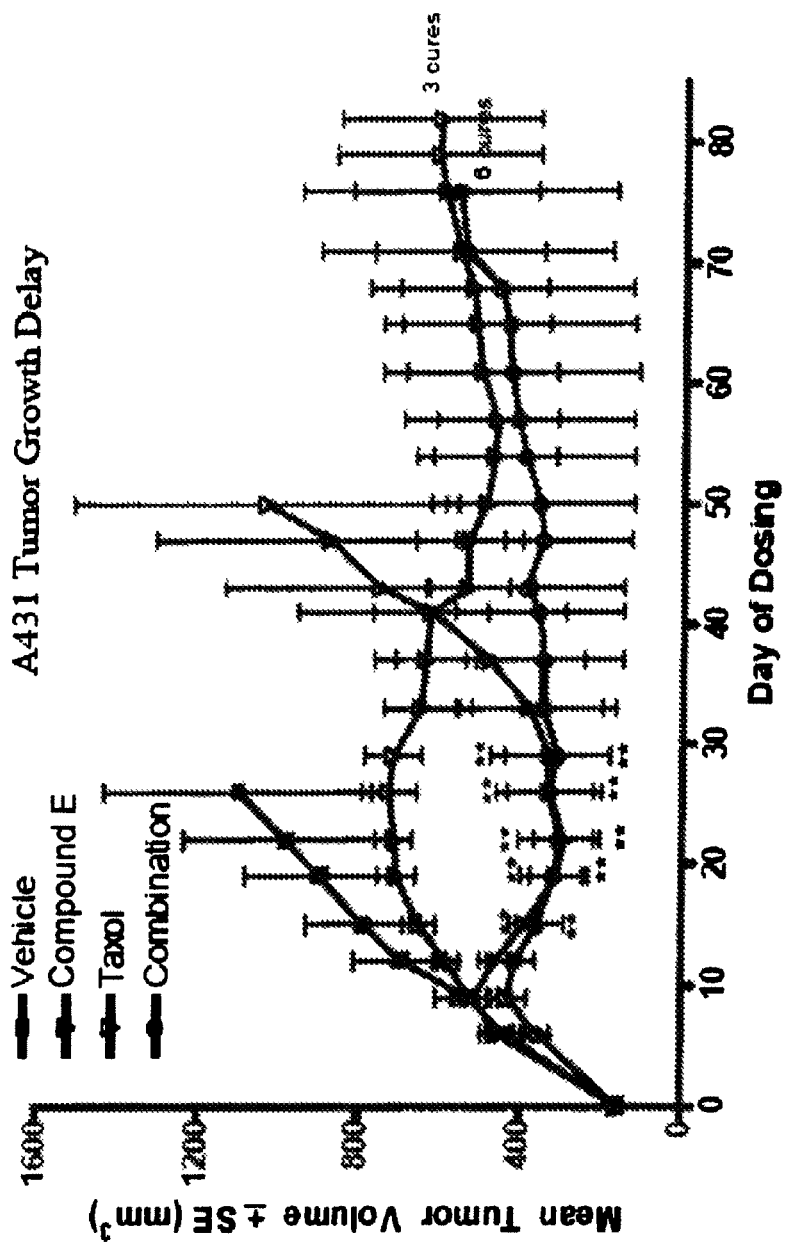
FIG. 8 illustrates inhibition of cervical cancer tumor growth by a certain compound of the invention, either alone or in combination with Taxol (paclitaxel).
Figure 9:
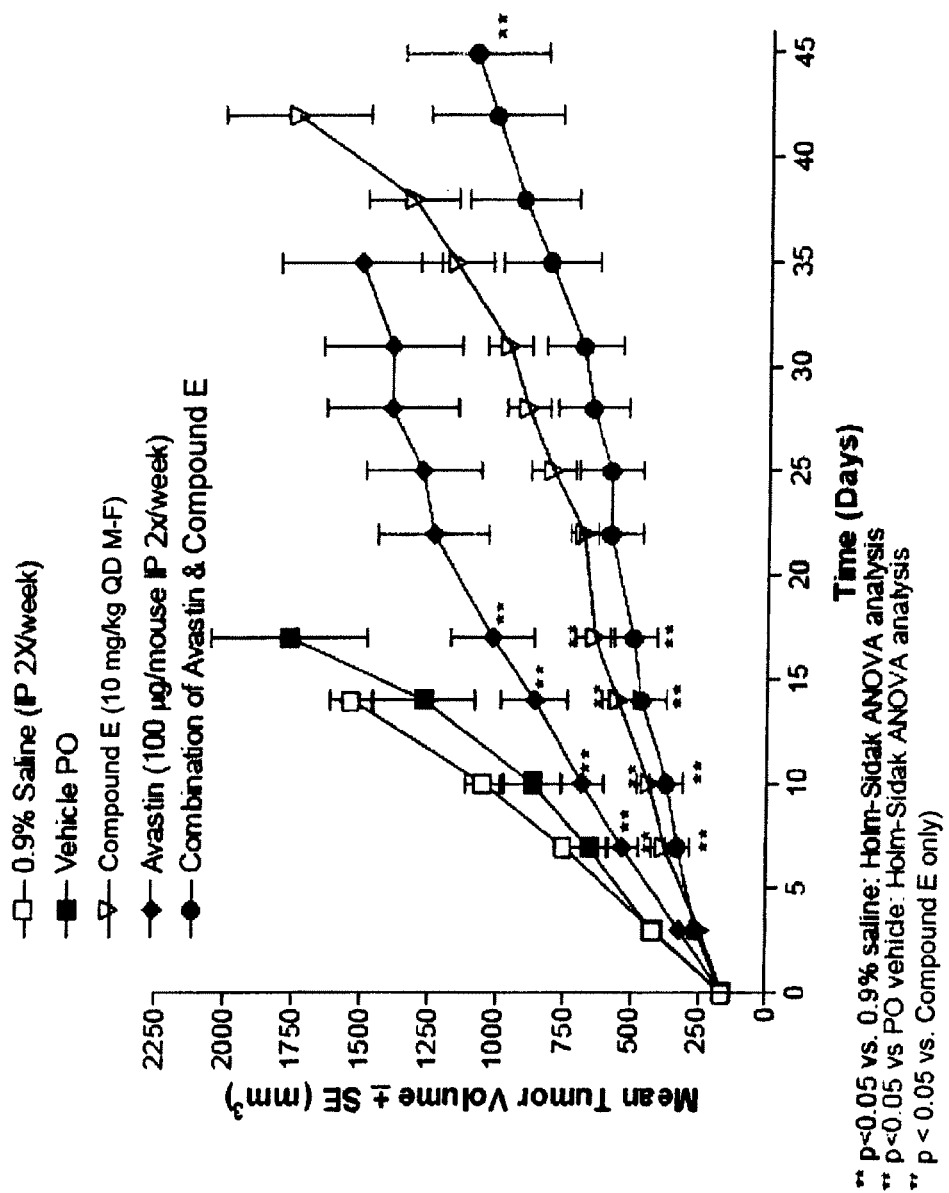
FIG. 9 illustrates inhibition of fibrosarcoma tumor growth by a certain compound of the invention, either alone or in combination with Avastin (bevacizumab, an antibody to VEGF).
Figure 10:
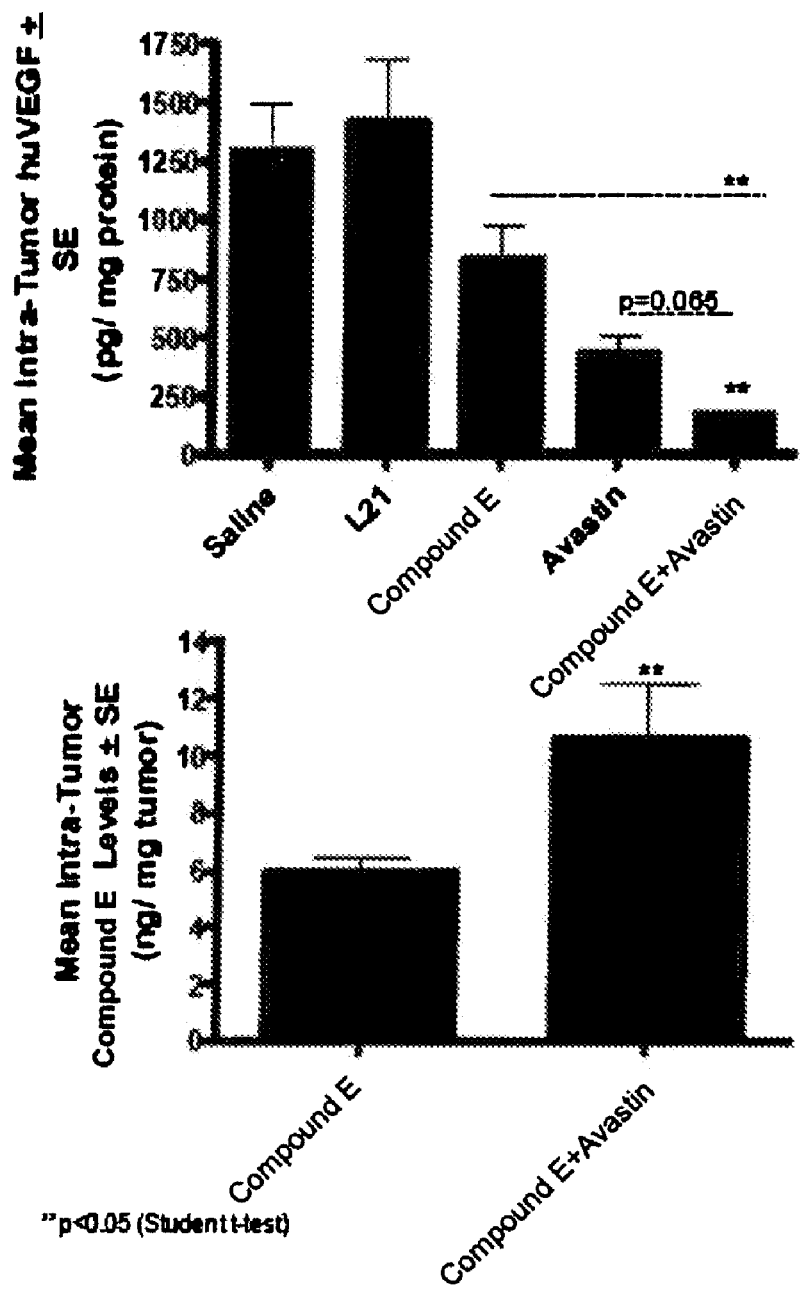
FIG. 10 illustrates inhibition of tumor and plasma VEGF expression in a fibrosarcoma tumor by a certain compound of the invention, either alone or in combination with Avastin.

Preferred compounds of the invention, when used for one week on a 100 mm$^3$ tumor, will generally inhibit tumor growth by at least 50%, as compared to the vehicle-treated control groups. In similarly conducted experiments, compounds of the invention are shown to reduce lung cancer tumor growth (at a dosage of 3 mg/kg, twice a day, or 30 mg/kg, twice a day) (FIG. 2), Wilms and neuroblastoma tumor growth (at a dosage of 30 mg/kg, once a day) (FIG. 3), fibrosarcoma tumor growth (at a dosage of 10 mg/kg 3×/week) (FIG. 4), and human skin malignant melanoma (at a dosage of 10 mg/kg 5×/week) (FIG. 5) as compared to vehicle. Furthermore, the compounds of the invention are shown to reduce VEGF plasma and tumor levels in fibrosarcoma tumors as compared to vehicle (at a dosage of 10 mg/kg 3×/week) (FIG. 6). The compounds of the invention also inhibit tumor growth when administered together with other cancer agents, such as 5-FU (fluorouracil) in a colon cancer tumor (FIG. 7), taxol (paclitaxel) in a human cervical carcinoma (FIG. 8), and Avastin (bevacizumab) (FIG. 9). Furthermore, as shown in FIG. 10, the compounds of the invention also reduce tumor and plasma VEGF levels when administered together with another cancer agent (such as Avastin).

Figure 11:
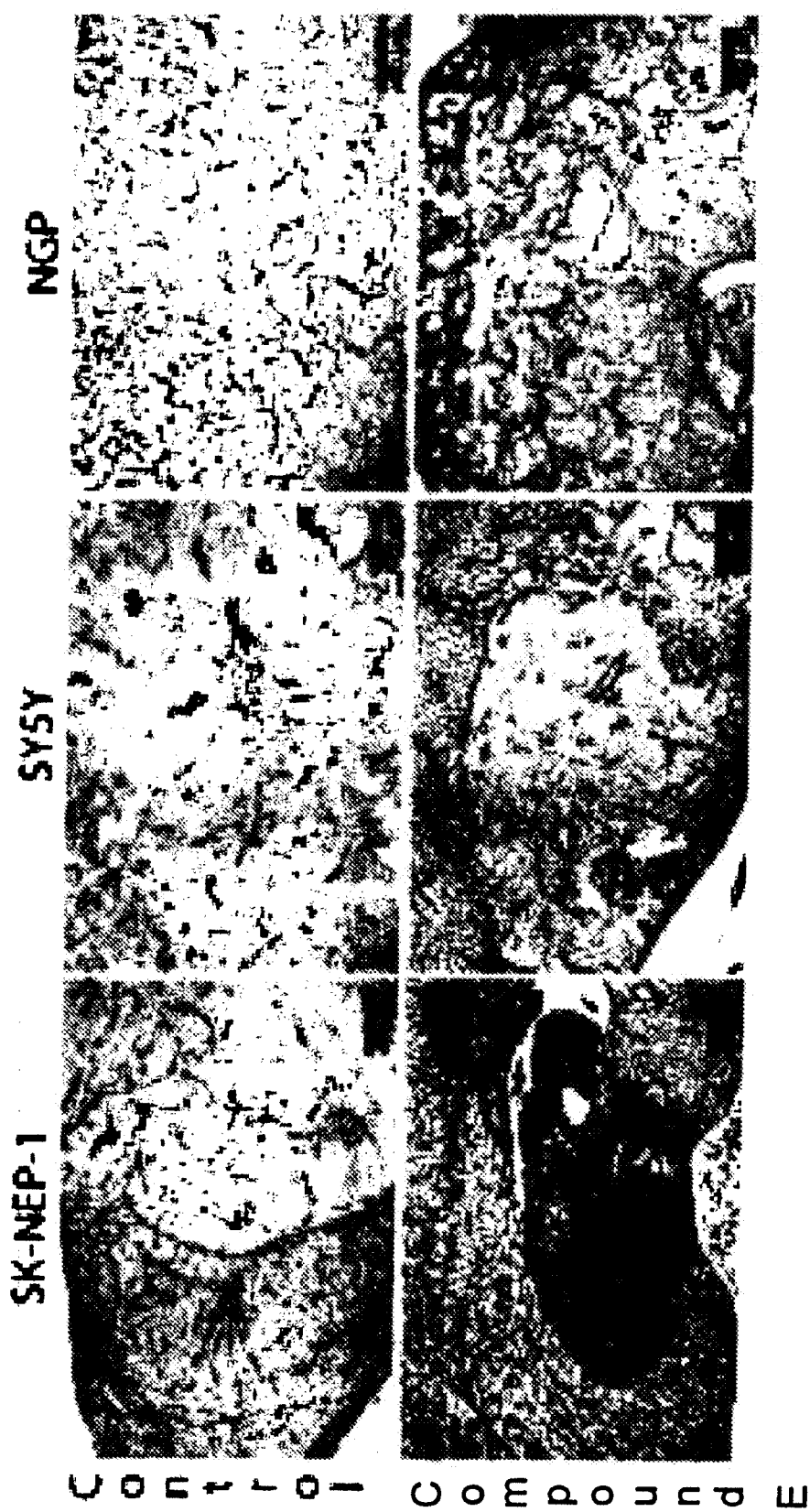
FIG. 11 illustrates inhibition of angiogenesis by a certain compound of the invention.

The tumors excised from the mice can also be used in immunochemistry experiments to determine levels of angiogenesis. As seen in FIG. 11, when antibodies to Collagen IV are used, angiogenesis is shown to be inhibited by the administration of a compound of the invention in Wilms tumor (SK-NEP-1) and neuroblastoma (SY5Y and NGP) tumors.

Example 4

Compounds of the Invention Do Not Affect VEGF mRNA Levels

Human solid tumor cells are treated with various concentrations of a compound of the present invention or a control under hypoxic conditions. Actinomycin D blocks transcription and is used as a control. Total RNA is isolated using the RNeasy kit (Qiagen, Inc., Valencia, Calif., USA) or an acid-guanidinium thiocyanate-phenol-chloroform based method (Chomczynski, P. and Sacchi, N., Anal. Biochem. 162: 156 (1987), hereby incorporated by reference).

Figure 12:
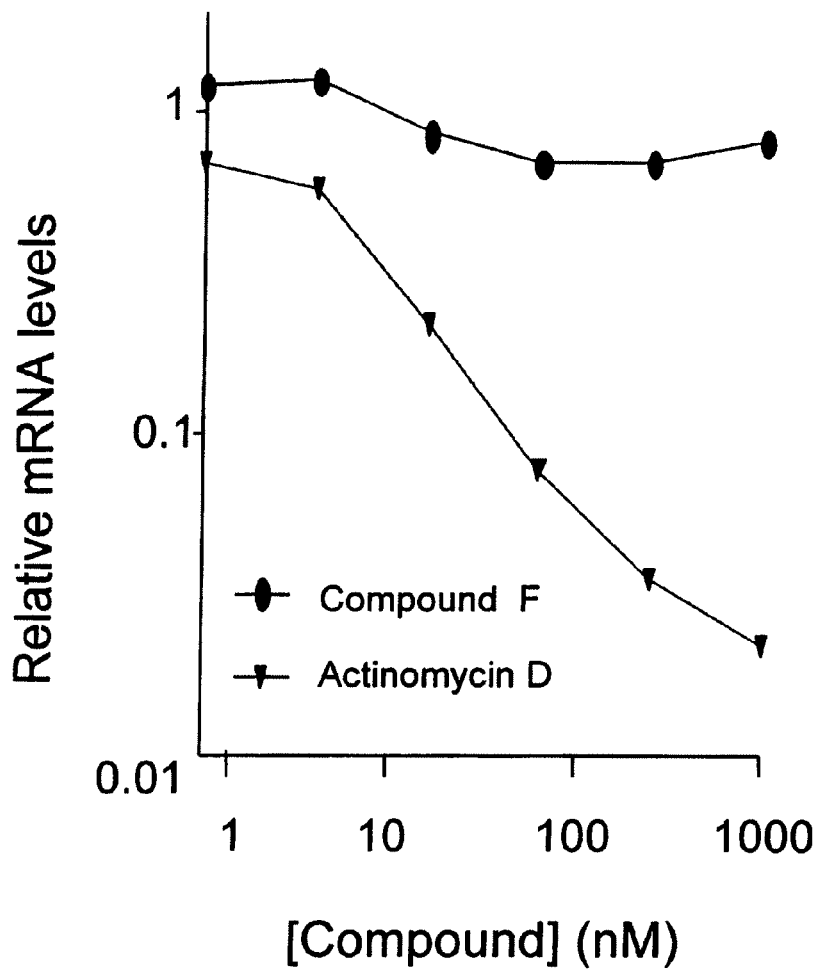
FIG. 12 illustrates that a certain compound of the invention does not affect VEGF mRNA levels under hypoxic conditions.

Concentration of total RNA can be determined using the RiboGreen® fluorescent dye (Molecular Probes, Inc., Eugene, Oreg., USA) with the VersaFluor Fluorometer System (BioRad, Hercules, Calif., USA). Quality and integrity of total RNA can be assessed on 1% formaldehyde-agarose gels. First-strand cDNA was synthesized using 1 µg of total RNA (DNase-treated) in a 20 µl reverse transcriptase reaction mixture (Leclerc G J, Barredo J C, Clin. Cancer Res. 2001, 7:942-951, which is hereby incorporated by reference). A region of the VEGF mRNA is amplified using PCR primers. The cDNA amplified fragment (approximately 300 basepairs) is cloned into a vector such as the pCR2.1-TOPO vector (Invitrogen, Carlsbad, Calif., USA) to generate a plasmid. Serial ten-fold dilutions (104 to 109 molecules) of this plasmid are used as a reference molecule for the standard curve calculation (see Figure X). All Real-Time PCR reactions are performed in a 25 µl mixture containing 1/20 volume of cDNA preparation (1 µl), 1×SYBR Green buffer (PE Applied Biosystems, Foster City, Calif., USA), 4 mM MgCl2, 0.2 µM of each VEGF primer used above, 0.2 mM dNTPs mix and 0.025 Unit of AmpliTaq Gold® thermostable DNA polymerase (Applied Biosystems, Foster City, Calif., USA). Real-Time quantitations are performed using the BIO-RAD iCycler iQ system (BioRad, Hercules, Calif., USA). The fluorescence threshold value can be calculated using the iCycle iQ system software. Using similar methodologies, the data shown in FIG. 12 was obtained, and shows that a compound of the present invention does not affect VEGF mRNA levels

Example 5

Compounds of the Invention Do Not Affect the Activity of PDE5

The compounds of the invention are tested to assess their affect on phosphodiesterase 5 (PDE5) activity. The affect on PDE5 activity is determined using the High-Efficiency Fluorescence Polarization Assay (HEFP) kit from Molecular Devices. The HEFP assay measures the activity of PDE-5 by using fluorescein-labeled derivatives of cGMP as a substrate. When hydrolyzed by PDE-5, fluorescein-labeled cGMP derivatives are able to bind to a binding reagent. The cGMP substrate:binding reagent complex results in a highly polarized fluorescent state.

Figure 13:
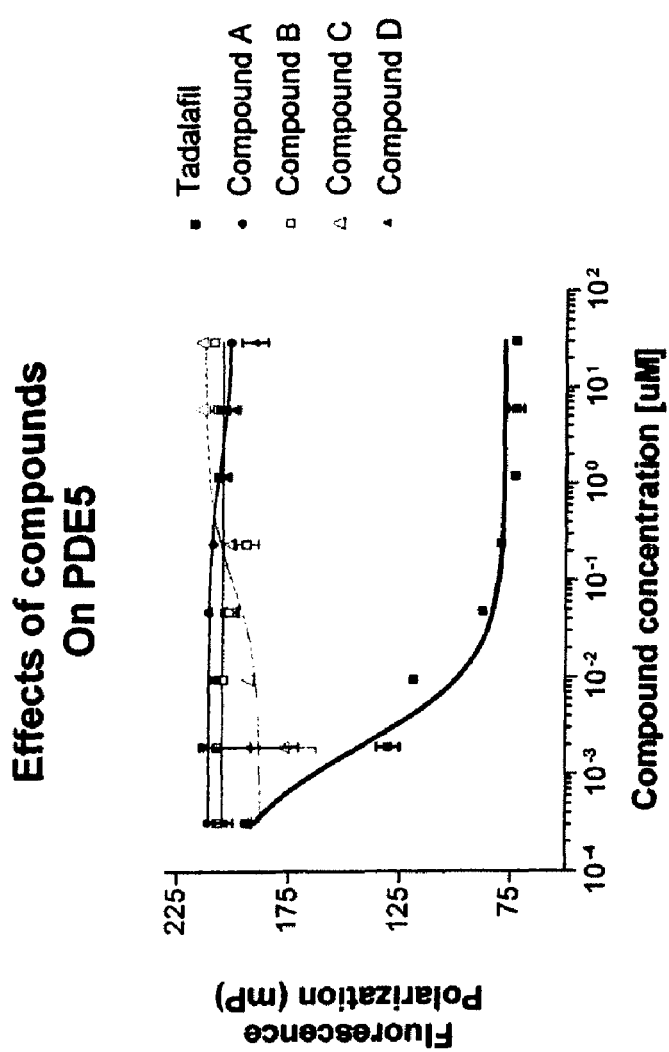
FIG. 13 illustrates that the activity of phosphdiesterase 5 (PDE-5) is not affected by certain compounds of the invention.

FIG. 13 shows the results of the compounds of the invention on PDE-5 activity. After combining recombinant PDE5 (CalBioChem) and the cGMP substrate, the mixture is incubated at room temperature for 45 minutes in the presence or absence of compounds or a positive control (Tadalafil). The reaction is stopped upon addition of the binding reagent. Fluorescence polarization is determined on a Viewlux using a setting recommended by the manufacturer. As is evident from FIG. 13, the compounds of the invention do not inhibit the activity of PDE-5 in comparison to the positive control.

All publications and patent applications cited herein are incorporated by reference to the same extent as if each individual publication or patent application was specifically and individually indicated to be incorporated by reference.

Although certain embodiments have been described in detail above, those having ordinary skill in the art will clearly understand that many modifications are possible in the embodiments without departing from the teachings thereof. All such modifications are intended to be encompassed within the claims of the invention.

What is claimed:

1. A method for treating a solid tumor cancer comprising administering a therapeutically effective amount of a compound of formula:

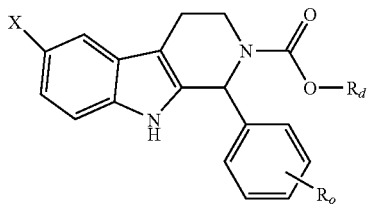

or a pharmaceutically acceptable salt, racemate or stereoisomer of said compound, to a subject in need thereof; wherein:

X is halogen;
$R_o$ is halogen, substituted or unsubstituted $C_1$ to $C_8$ alkyl or $OR_a$;
$R_a$ is H or $C_1$ to $C_8$ alkyl optionally substituted with one or more substituents independently selected from hydroxyl and halogen; and
$R_d$ is phenyl substituted with one or more alkoxy or halogen substituents,
wherein the compound inhibits VEGF production in a HT1080 solid tumor grown in a nude mouse, inhibits HT1080 solid tumor growth in a nude mouse or inhibits angiogenesis in a HT1080 solid tumor grown in a nude mouse.

2. The method of claim 1, wherein the compound has the formula:

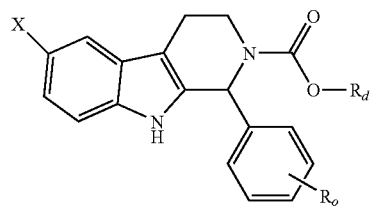

or a pharmaceutically acceptable salt, racemate or stereoisomer thereof, wherein, X is halogen;
$R_o$ is $OR_a$;
$R_a$ is H or $C_1$ to $C_8$ alkyl optionally substituted with one or more substituents independently selected from hydroxyl and halogen; and
$R_d$ is phenyl substituted with one or more alkoxy or halogen substituents.

3. The method of claim 1, wherein the compound has the formula:

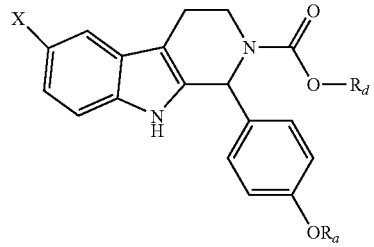

or a pharmaceutically acceptable salt, racemate or stereoisomer thereof, wherein, X is halogen;
$R_a$ is H or $C_1$ to $C_8$ alkyl optionally substituted with one or more substituents independently selected from hydroxyl and halogen; and
$R_d$ is phenyl substituted with one or more halogen substituents.

4. The method of claim 1, wherein the compound has the formula:

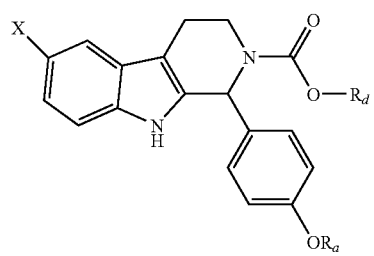

or a pharmaceutically acceptable salt, racemate or stereoisomer thereof, wherein, X is halogen;
$R_a$ is $C_1$ to $C_8$ alkyl optionally substituted with one or more substituents independently selected from hydroxyl and halogen; and
$R_d$ is phenyl substituted at the para position with a halogen substituent.

5. The method of claim 4, wherein X is chloro.

6. The method of claim 5, wherein $R_d$ is phenyl substituted at the para position with chloro.

7. The method of claim 6, wherein $R_a$ is unsubstituted $C_1$ to $C_8$ alkyl.

8. The method of claim 6, wherein $R_a$ is $C_1$ to $C_8$ alkyl substituted with one or more hydroxyl substituents.

9. The method of claim 1 or 2, wherein said compound has a chiral carbon at the point of attachment of the $R_a$ substituted phenyl and said compound is an (S) isomer at said chiral carbon.

10. The method of any of claims 3-8, wherein said compound has a chiral carbon at the point of attachment of the $OR_a$ substituted phenyl and said compound is an (S) isomer at said chiral carbon.

11. The method of claim 1, wherein the compound has an $EC_{50}$ of less than 50 nM for inhibiting hypoxia-induced VEGF expression in cultured HeLa cells.

12. The method of claim 1, wherein the compound inhibits VEGF production in a HT1080 solid tumor grown in a nude mouse.

13. The method of claim 1, wherein the compound inhibits HT1080 solid tumor growth in a nude mouse.

14. The method of claim 1, wherein the compound inhibits angiogenesis in a HT1080 solid tumor grown in a nude mouse.

15. A method for treating a solid tumor cancer comprising administering a therapeutically effective amount of a compound to a subject having a solid tumor cancer, wherein said compound is

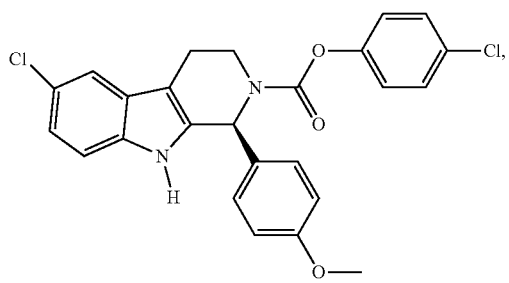 [SMILES: COc1ccc([C@H]2c3[nH]c4ccc(Cl)cc4c3CCN2C(=O)Oc2ccc(Cl)cc2)cc1]

or a pharmaceutically acceptable salt thereof, wherein the compound inhibits VEGF production in a HT 1080 solid tumor grown in a nude mouse, inhibits HT1080 solid tumor growth in a nude mouse or inhibits angiogenesis in a HT 1080 solid tumor grown in a nude mouse.

16. The method as in claim 1 or 15, wherein said compound is administered simultaneously or sequentially with one or more additional agents useful in the treatment of cancer.

17. The method of claim 16, wherein said one or more additional agents useful in the treatment of cancer is selected from the group consisting of paclitaxel, fluorouracil, irinotecan, thalidomide, gemcitabine, squalamine, endostatin, angiostatin, neovastat, lenalidomide, vitaxin, 2-methoxyestradiol, carboxyamidotriazole, combretastatin A4 phosphate, 5-[1,2-Dihydro-2-oxo-3H-indol-3-ylidene)methyl]-2,4-dimethyl-1H-pyrrole-3-propanoic acid, sunitinib malate, rebimastat, metastat, cilengitide, ramucirumab, vatalanib, enzastaurin, aflibercept, vandetanib, halofuginone hydrobromide, celecoxib, interferon alpha, interleukin-12, and bevacizumab.

18. The method of claim 17, wherein said one or more additional agents are selected from bevacizumab, paclitaxel and fluorouracil.

19. The method as in claim 1 or 15, wherein the solid tumor cancer is selected from the group consisting of a solid tumor carcinoma and a solid tumor sarcoma.

20. The method as in claim 1 or 15, wherein the solid tumor cancer is selected from the group consisting of a pediatric solid tumor, a carcinoma of the epidermis, a cervical carcinoma, a cervical cancer, a colon carcinoma, a colon cancer, a lung carcinoma, a lung cancer, a renal carcinoma and a renal cancer.

21. The method as in claim 1 or 15, wherein the solid tumor cancer is selected from a group consisting of a Wilms tumor, a neuroblastoma and a malignant melanoma.

* * * * *